(12) United States Patent
Lunde Robertsen et al.

(10) Patent No.: US 12,123,042 B2
(45) Date of Patent: Oct. 22, 2024

(54) PRODUCTION OF STEVIOL GLYCOSIDES IN RECOMBINANT HOSTS

(71) Applicant: EVOLVA SA, Reinach (CH)

(72) Inventors: Helene Lunde Robertsen, Horsholm (DK); Iben Nordmark Andersen, Vedbaek (DK); Adam Matthew Takos, Valby (DK); Swee Chuang Lim Hallwyl, Vallensbaek Strand (DK); Francesca Ambri, Hillerod (DK); Manuel Quiros Asensio, Soborg (DK); Michael Dalgaard Mikkelsen, Vaerlose (DK); Jens Houghton-Larsen, Birkerod (DK); Veronique Douchin, Birkerod (DK); Jane Dannow Dyekjaer, Frederiksberg (DK); Simon Carlsen, Copenhagen (DK); Nina Nicoline Rasmussen, Hvidovre (DK); Esben Halkjaer Hansen, Frederiksberg (DK)

(73) Assignee: Danstar Ferment AG, Schweiz (CH)

( * ) Notice: Subject to any disclaimer, the term of this patent is extended or adjusted under 35 U.S.C. 154(b) by 38 days.

(21) Appl. No.: 17/899,069

(22) Filed: Aug. 30, 2022

(65) Prior Publication Data
US 2023/0212630 A1    Jul. 6, 2023

Related U.S. Application Data

(60) Continuation of application No. 16/801,200, filed on Feb. 26, 2020, now Pat. No. 11,466,302, which is a division of application No. 15/506,196, filed as application No. PCT/EP2015/070620 on Sep. 5, 2015, now Pat. No. 10,612,064.

(60) Provisional application No. 62/148,585, filed on Apr. 16, 2015, provisional application No. 62/117,396, filed on Feb. 17, 2015, provisional application No. 62/103,547, filed on Jan. 14, 2015, provisional application No. 62/048,178, filed on Sep. 9, 2014.

(51) Int. Cl.
| | |
|---|---|
| *C12P 19/56* | (2006.01) |
| *A23L 27/30* | (2016.01) |
| *C07H 15/256* | (2006.01) |
| *C12N 9/02* | (2006.01) |
| *C12N 9/10* | (2006.01) |
| *C12N 9/88* | (2006.01) |
| *C12N 9/90* | (2006.01) |
| *C12N 15/52* | (2006.01) |

(52) U.S. Cl.
CPC .............. *C12P 19/56* (2013.01); *A23L 27/36* (2016.08); *C07H 15/256* (2013.01); *C12N 9/0042* (2013.01); *C12N 9/0073* (2013.01); *C12N 9/1085* (2013.01); *C12N 9/88* (2013.01); *C12N 9/90* (2013.01); *C12N 15/52* (2013.01); *C12Y 106/02004* (2013.01); *C12Y 114/13078* (2013.01); *C12Y 114/13079* (2013.01); *C12Y 205/01029* (2013.01); *C12Y 402/03019* (2013.01); *C12Y 505/01013* (2013.01); *A23V 2002/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,590,160 A | 5/1986 | Nishihashi et al. |
| 5,198,360 A | 3/1993 | Ballou |
| 5,204,253 A | 4/1993 | Sanford et al. |
| 5,306,862 A | 4/1994 | Chappell et al. |
| 5,460,949 A | 10/1995 | Saunders et al. |
| 5,538,880 A | 7/1996 | Lundquist et al. |
| 6,013,863 A | 1/2000 | Lundquist et al. |
| 6,215,051 B1 | 4/2001 | Yu et al. |
| 6,255,557 B1 | 7/2001 | Brandle |
| 6,284,493 B1 | 9/2001 | Roth |
| 6,284,506 B1 | 9/2001 | Hoshino et al. |
| 6,329,571 B1 | 12/2001 | Hiei |
| 6,586,202 B2 | 7/2003 | Hoshino et al. |
| 6,660,507 B2 | 12/2003 | Cheng et al. |
| 6,806,076 B1 | 10/2004 | Miyake et al. |
| 6,969,595 B2 | 11/2005 | Brzostowicz et al. |
| 7,034,140 B2 | 4/2006 | Bramucci et al. |
| 7,056,717 B2 | 6/2006 | Cheng et al. |
| 7,098,000 B2 | 8/2006 | Cheng et al. |
| 7,129,392 B2 | 10/2006 | Hahn et al. |
| 7,132,268 B2 | 11/2006 | Miyake et al. |
| 7,172,886 B2 | 2/2007 | Keasling et al. |
| 7,183,089 B2 | 2/2007 | Keasling et al. |

(Continued)

FOREIGN PATENT DOCUMENTS

| | | |
|---|---|---|
| CN | 101314776 | 12/2008 |
| CN | 101720910 | 6/2010 |

(Continued)

OTHER PUBLICATIONS

Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.

(Continued)

*Primary Examiner* — Hope A Robinson
(74) *Attorney, Agent, or Firm* — McDonnell Boehnen Hulbert & Berghoff LLP

(57) ABSTRACT

The invention relates to recombinant microorganisms and methods for producing steviol glycosides and steviol glycoside precursors.

13 Claims, 20 Drawing Sheets
Specification includes a Sequence Listing.

(56) References Cited

U.S. PATENT DOCUMENTS

| | | |
|---|---|---|
| 7,186,891 B1 | 3/2007 | Chappell et al. |
| 7,208,298 B2 | 4/2007 | Miyake et al. |
| 7,335,815 B2 | 2/2008 | Boronat et al. |
| 7,364,885 B2 | 4/2008 | Miyake et al. |
| 7,422,884 B2 | 9/2008 | Bai et al. |
| 7,514,597 B2 | 4/2009 | Nakamura et al. |
| 7,569,389 B2 | 9/2009 | Feldmann et al. |
| 7,692,065 B2 | 4/2010 | Harper et al. |
| 7,838,287 B2 | 11/2010 | Goldsmith et al. |
| 7,923,541 B2 | 4/2011 | Yang et al. |
| 7,927,851 B2 | 4/2011 | Brandle et al. |
| 9,441,233 B2 | 9/2016 | Apuya et al. |
| 9,562,251 B2 | 2/2017 | Kishore et al. |
| 9,957,539 B2 | 5/2018 | Ono et al. |
| 9,957,540 B2 | 5/2018 | Mikkelsen et al. |
| 10,364,450 B2 | 7/2019 | Olsson et al. |
| 10,805,514 B2 | 10/2020 | Olsson et al. |
| 10,947,515 B2 | 3/2021 | Boer et al. |
| 2002/0142408 A1 | 10/2002 | DiCosimo et al. |
| 2003/0033626 A1 | 2/2003 | Hahn et al. |
| 2003/0148416 A1 | 8/2003 | Berry et al. |
| 2003/0148479 A1 | 8/2003 | Keasling et al. |
| 2003/0190734 A1 | 10/2003 | Hoshino et al. |
| 2003/0219798 A1 | 11/2003 | Gokarn et al. |
| 2004/0010815 A1 | 1/2004 | Lange et al. |
| 2004/0072311 A1 | 4/2004 | DiCosimo et al. |
| 2004/0078846 A1 | 4/2004 | Desouza et al. |
| 2004/0176570 A1 | 9/2004 | Bacher et al. |
| 2004/0194162 A1 | 9/2004 | Hahn et al. |
| 2005/0003474 A1 | 1/2005 | Desouza et al. |
| 2005/0032169 A1 | 2/2005 | Miyake et al. |
| 2006/0014264 A1 | 1/2006 | Sauer et al. |
| 2006/0079476 A1 | 4/2006 | Keasling et al. |
| 2006/0083838 A1 | 4/2006 | Jackson et al. |
| 2007/0004000 A1 | 1/2007 | Miyake et al. |
| 2007/0039067 A1* | 2/2007 | Feldmann ............ C07K 14/415 536/23.6 |
| 2007/0077616 A1 | 4/2007 | Keasling et al. |
| 2007/0099261 A1 | 5/2007 | Keasling et al. |
| 2007/0118916 A1 | 5/2007 | Puzio et al. |
| 2007/0128311 A1 | 6/2007 | Prakash et al. |
| 2007/0166782 A1 | 7/2007 | Keasling et al. |
| 2007/0202579 A1 | 8/2007 | Berry et al. |
| 2007/0238157 A1 | 10/2007 | Millis et al. |
| 2007/0238159 A1 | 10/2007 | Millis et al. |
| 2007/0238160 A1 | 10/2007 | Millis et al. |
| 2007/0254354 A1 | 11/2007 | Millis et al. |
| 2007/0269857 A1 | 11/2007 | Miyake et al. |
| 2007/0286850 A1 | 12/2007 | Bai et al. |
| 2008/0064063 A1 | 3/2008 | Brandle et al. |
| 2008/0081358 A1 | 4/2008 | Vittanen et al. |
| 2008/0131926 A1 | 6/2008 | Miyake et al. |
| 2008/0216397 A1 | 9/2008 | Busby et al. |
| 2008/0261280 A1 | 10/2008 | Hahn et al. |
| 2008/0271205 A1 | 10/2008 | Yamaguchi et al. |
| 2008/0286870 A1 | 11/2008 | Vittanen et al. |
| 2008/0292775 A1 | 11/2008 | Prakash et al. |
| 2008/0318227 A1 | 12/2008 | Bacher et al. |
| 2009/0004724 A1 | 1/2009 | Keasling et al. |
| 2009/0047718 A1 | 2/2009 | Blaschek et al. |
| 2009/0055974 A1 | 2/2009 | Tanksley et al. |
| 2009/0074935 A1 | 3/2009 | Lee |
| 2009/0143308 A1 | 6/2009 | Monk et al. |
| 2009/0286262 A1 | 11/2009 | Slack |
| 2009/0298706 A1 | 12/2009 | Lee et al. |
| 2010/0112156 A1 | 5/2010 | Abelyan et al. |
| 2010/0120096 A1 | 5/2010 | Kitaoka et al. |
| 2010/0221801 A1 | 9/2010 | Van Dyk |
| 2010/0297722 A1 | 11/2010 | Anterola et al. |
| 2010/0316782 A1 | 12/2010 | Shi et al. |
| 2011/0087011 A1 | 4/2011 | Chiang et al. |
| 2011/0092684 A1 | 4/2011 | Abelyan et al. |
| 2011/0126318 A1 | 5/2011 | Allen et al. |
| 2011/0160311 A1 | 6/2011 | Prakash et al. |
| 2012/0021111 A1 | 1/2012 | Pfister et al. |
| 2012/0083593 A1 | 4/2012 | Liu et al. |
| 2012/0164678 A1 | 6/2012 | Stephanopoulos et al. |
| 2012/0178169 A1 | 7/2012 | Voytas et al. |
| 2013/0137138 A1 | 5/2013 | Hansen |
| 2013/0171328 A1 | 7/2013 | Kishore et al. |
| 2014/0329281 A1 | 11/2014 | Houghton-Larsen et al. |
| 2015/0159188 A1 | 6/2015 | Ono et al. |
| 2015/0342234 A1 | 12/2015 | Hicks et al. |
| 2020/0392552 A1 | 12/2020 | Robertsen et al. |
| 2021/0147815 A1 | 5/2021 | Boer et al. |
| 2023/0212630 A1* | 7/2023 | Lunde Robertson ........................ C07H 15/256 435/211 |

FOREIGN PATENT DOCUMENTS

| | | |
|---|---|---|
| CN | 102216313 | 10/2011 |
| CN | 102559528 | 7/2012 |
| CN | 103397064 | 11/2013 |
| CN | 104845990 | 8/2015 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 5910-001408 | 6/1984 |
| JP | 3-277275 | 12/1991 |
| JP | 05-115298 | 5/1993 |
| JP | 2005185101 | 7/2005 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | 2009/140394 | 11/2009 |
| WO | WO 2010/021001 | 2/2010 |
| WO | WO 2010/038911 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | 2011/140329 | 11/2011 |
| WO | 2011/151326 | 12/2011 |
| WO | 2011/153378 | 12/2011 |
| WO | WO 2011/153144 | 12/2011 |
| WO | WO 2012/075030 | 6/2012 |

(56) References Cited

FOREIGN PATENT DOCUMENTS

| WO | 2013/022989 | 2/2013 |
|---|---|---|
| WO | WO 2013/019050 | 2/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |
| WO | 2014/191580 | 12/2014 |
| WO | 2014/191581 | 12/2014 |
| WO | 2015/011209 | 1/2015 |
| WO | WO 2015007748 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015051454 | 4/2015 |
| WO | WO 2015/132411 | 9/2015 |
| WO | WO 2016/023844 | 2/2016 |
| WO | WO 2016/038095 | 3/2016 |
| WO | WO 2016/120486 | 8/2016 |
| WO | WO 2017/025362 | 2/2017 |
| WO | WO 2018083338 | 5/2018 |

OTHER PUBLICATIONS

Chen, "Summary on Study of Stevioside," China Pharmacist, vol. 10, No. 6, p. 598-599 (2007).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Giaever & Nislow, "The yeast deletion collection: a decade of functional genomics," Genetics 197(2):451-65 (Jun. 2014).
Piirainen et al., "Glycoengineering of yeasts from the perspective of glycosylation efficiency," N Biotechnol. 31 (6):532-7 (Dec. 2014).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Xu et al., "Generation of hepatitis B virus PreS2-S antigen in Hansenula polymorpha," Virol Sin. 29(6):403-9 (Dec. 2014).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Wilhelm et al., "Defining transcribed regions using RNA-seq," Nature Protocols 5:255-66 (2010).
GenBank Accession No. AEE36246, dated Oct. 6, 2014 (3 pages).
GenBank Accession No. CAG41604, dated Feb. 6, 2015 (2 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. Q9UVY5.1, dated Apr. 1, 2015 (3 pages).
International Preliminary Report on Patentability from the International Bureau for International Application PCT/EP2016/068259; mailed Feb. 13, 2018 (pp. 1-11).
International Search Report and Written Opinion of the International Searching Authority for International Application No. PCT/EP2017/061775; mailed Sep. 6, 2017, pp. 1-17.
International Search Report of the International Searching Authority for International Application No. PCT/EP2017/061774; mailed Aug. 30, 2017, pp. 1-20.
Written Opinion of the International Searching Authority for International Application No. PCT/EP2017/061774; mailed Aug. 30, 2017, pp. 1-13.

Third-Party Submission under 37 CFR 1.290 for U.S. Appl. No. 13/701,406, dated Mar. 7, 2014 (238 pages).
Patent Examination Report No. 1 issued by IP Australia for Australian Application No. 2011261394, dated Jan. 15, 2015.
Response to Patent Examination Report No. 1 issued by IP Australia for Australian Application No. 2011261394, dated Feb. 5, 2015.
Patent Examination Report No. 2 issued by IP Australia for Australian Application No. 2011261394, dated Feb. 23, 2015.
Notice of Acceptance issued by IP Australia for Australian Application No. 2011261394, dated Aug. 13, 2015 (pp. 1-3).
Office Action for Canadian Patent Application No. 2,802,627, mailed Dec. 15, 2015 (pp. 1-5).
English Translation on Response to First Office Action issued by the State Intellectual Property Office of People's Republic of China for CN Application No. 201180038475.4, dated Apr. 8, 2014.
English Translation of Second Office Action issued by the State Intellectual Property Office of People's Republic of China for Chinese Application No. 201180038475.4, dated Aug. 13, 2014.
English Translation of Response to Second Office Action issued by the State Intellectual Property Office of People's Republic of China for CN Application No. 201180038475.4, dated Oct. 28, 2014.
English Translation of Third Office Action issued by the State Intellectual Property Office of People's Republic of China for Chinese Application No. 201180038475.4, dated Mar. 3, 2015.
Notification of Grant of Patent Application issued by the State Intellectual Property Office of People's Republic of China for Chinese Application No. 201180038475.4, dated Dec. 1, 2015 (pp. 1-5). English translation included.
Response to Extended Search Report and Opinion issued by the European Patent Office for European Application No. 11790428.4, dated Jul. 16, 2014.
Communication pursuant to Rule 114(2) EPC for European Application No. 11790428.4, dated Nov. 28, 2014.
Examination Report issued by the European Patent Office for European Application No. 11790428.4, dated Dec. 1, 2014.
Response to Examination Report issued by the European Patent Office for European Application No. 11790428.4, dated Jun. 1, 2015 (16 pages).
English Translation of Notification of Reasons for Refusal of Japanese Application No. 2013-513355, dated Aug. 4, 2015 (pp. 1-10).
Examination Report issued by the Intellectual Property Corporation of Malaysia for Malaysian Application No. PI 2012005201, dated Jul. 31, 2014.
Response to Examination Report issued by the Intellectual Property Corporation of Malaysian for MY Application No. PI 2012005201, dated Sep. 18, 2014.
Response to First Examination Report issued by the Intellectual Property Office of New Zealand for New Zealand Application No. 604915, dated Jan. 17, 2014.
Further Examination Report issued by the Intellectual Property Office of New Zealand for New Zealand Application No. 604915, dated Feb. 3, 2014.
Response to Further Examination Report issued by the Intellectual Property Office of New Zealand for New Zealand Application No. 604915, dated May 27, 2014.
Further Examination Report issued by the Intellectual Property Office of New Zealand for New Zealand Application No. 604915, dated Jun. 18, 2014.
Response to Further Examination Report issued by the Intellectual Property Office of New Zealand for New Zealand Application No. 604915, dated Sep. 15, 2014.
Notice of Acceptance issued by the Intellectual Property Office of New Zealand for New Zealand Application No. 604915, dated Oct. 7, 2014 (1 page).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).

(56) References Cited

OTHER PUBLICATIONS

International Preliminary Report on Patentability issued by the International Bureau for International Application No. PCT/US2011/038967, dated Dec. 4, 2012 (13 pages).
Extended European Search Report and Opinion issued by the European Patent Office for European Application No. 11790428.4, dated Dec. 20, 2013.
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
Jones et al., "UGT73C6 and UGT78D1, Glycosyltransferases Involved in Flavonol Glycoside Biosynthesis in *Arabidopsis thaliana*\*," J. Biol. Chem., vol. 278, No. 45, pp. 43910-43918 (2003).
Popenberger et al., Heterologous Expression of *Arabidopsis* UDP-Glucosyltransferases in *Saccharomyces cerevisiae* for Production ofZearalenone-4-0-Glucoside, Appl. Environ. Microbial., vol. 72, pp. 4404-4410 (2006).
Wang et al., "Glycosylation and Glycosyltransferase of Small Molecular Compounds of Plant," China Academic Journal, vol. 44-5, 997-1003 (2008).
Broun et al., "Catalytic plasticity of fatty acid modification enzymes underlying chemical diversity of plant lipids," Science, vol. 282: 1315-1317 (1998).
Cheng, "Food Biotechnology," Inner Mongolia Science and Technology Press (2008). (Book).
Devos et al., "Practical limits of function prediction," Proteins: Structure, Function, and Genetics, vol. 41: 98-107 (2000).
Seffernick et al., "Melamine deaminase and Atrazine chlorohydrolase: 98 percent identical but functionally different," J. Bacterial., vol. 183 (8): 2405-2410 (2001).
Whisstock et al., "Prediction of protein function from protein sequence," Q. Rev. Biophysics., vol. 36 (3): 307-340 (2003).
Witkowski et al., "Conversion of b-ketoacyl synthase to a Malonyl Decarboxylase by replacement of the active cysteine with glutamine," Biochemistry, vol. 38: 11643-11650 (1999).
Pearson, et al., "Improved tools for biological sequence comparison," Proc Natl Acad Sci. 85(8):2444-8 (1988).
Liu et al., "Functional and Biochemical Characterization of *Escherichia coli* Sugar Efflux Transporters," JBC, 274 (33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
Uniprot Accession No. Q75183, dated Jul. 5, 2004 (pp. 1-2).
Uniprot Accession No. Q75183, dated Jul. 22, 2008 (pp. 1-4).
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).

Van Ooyen et al., "Heterologous protein production in the yeast *Kluyveromyces lactis*," FEMS Yeast Res. 6 (3):381-92 (May 2006).
Vazquez De Aldana et al., "Nucleotide sequence of the exo-1,3-beta-glucanase-encoding gene, EXG1, of the yeast *Saccharomyces cerevisiae*, " Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73 (13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583 (20):3303-9 (2009).
Yadav et al., "A review on the improvement of stevia [*Stevia rebaudiana* (Bertoni)]," Can J Plant Sci. 91:1-27 (2011).
Yao et al., "A genetic linkage map for Stevia rebaudiana," Genome 42:657-61 (1999).
Yang et al., Base substitution mutations in uridinediphosphate-dependent glycosyltransferase 76G1 gene of Stevia rebaudiana causes the low levels of rebaudioside A: mutations in UGT76G1, a key gene of steviol glycosides synthesis, Plant Physiol Biochem. 80:220-5 (2014).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14): e115 (Aug. 2004).
Zhu et al., "A multi-omic map of the lipid-producing yeast *Rhodosporidium toruloides*," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).

(56) References Cited

OTHER PUBLICATIONS

EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Jewett et al. " An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin Stevia rebaudiana (Bertoni)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast Rhodosporidium toruloides Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2): 123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "Stevia rebaudiana (Bert.) Bertoni—A Review," Indian Journal of Natural Products and Resources 1 (3):267-86 (2010).
Madhav et al., "Functional and structural variation of uridine diphosphate glycosyltransferase (UGT) gene of Stevia rebaudiana-UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from *Scoparia dulcis* L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4, 11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol.143 (3):212-23 (2007).
Bateman et al., "Pfam 3.1: 1313 multiple alignments and profile HMMs match the majority of proteins," Nucleic Acids Res. 27(1):260-2 (Jan. 1999).

(56) References Cited

OTHER PUBLICATIONS

Bay & Turner, "Diversity and evolution of the small multidrug resistance protein family," BMC Evol. Biol. 9:140 (Jun. 2009).
Brachmann et al., "Designer deletion strains derived from *Saccharomyces cerevisiae* S288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31 (13): 3497-500 (Jul. 2003).
Del Sorbo et al., "Fungal transporters involved in efflux of natural toxic compounds and fungicides," Fungal. Genet. Biol. 30(1):1-15 (Jun. 2000).
Diener et al., "*Arabidopsis* ALF5, a multidrug efflux transporter gene family member, confers resistance to toxins," Plant Cell 13(7):1625-38 (Jul. 2001).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. NP_197872.1, dated Jan. 22, 2014 (2 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. NM_116512, dated Jan. 22, 2014 (3 pages).
GenBank Accession No. NP_194183, dated Jan. 22, 2014 (4 pages).
GenBank Accession No. NP_195399, dated Jan. 22, 2014 (3 pages).
GenBank Accession No. AAS07253.1, dated Jan. 31, 2004 (3 pages).
Guo et al., "Protein tolerance to random amino acid change", Proceedings of the National Academy of Sciences USA, vol. 101, No. 25, pp. 9205-9210 (2004).
Ni et al., "Outer membrane mutation effects on UDP-glucose permeability and whole-cell catalysis rate," Appl Microbiol Biotechnol. 73(2):384-93 (2006).

Prisic et al., "Synergistic substrate inhibition of ent-copalyl diphosphate synthase: a potential feed-forward inhibition mechanism limiting gibberellin metabolism," Plant Physiol. 144(1):445-54 (2007).
Ünligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
Abraham & Bhat, "Permeabilization of baker's yeast with N-lauroyl sarcosine," J Ind Microbial Biotechnol. 35 (8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31 (10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42 (4):2827-37 (2010).
Bankar et al., "Environmental and industrial applications of Yarrowia lipolytica," Appl Microbiol Biotechnol. 84 (5):847-65 (Oct. 2009).
Baykov et al., "A malachite green procedure for orthophosphate determination and its use in alkaline phosphatase based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis, " Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the Arabidopsis DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen & Geuns, "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in *Saccharomyces cerevisiae*," Microb Cell Fact. 5:20 (2006).
Chen et al., "MolProbity: all-atom structure validation for macromolecular crystallography," Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol. 16(4):378-84 (2005).
Chow & Palecek, "Enzyme encapsulation in permeabilized *Saccharomyces cerevisiae* cells," Biotechnol Prog. 20 (2):449-56 (2004).
Correa et al., "Genetic mapping of 1,3-beta-glucanase-encoding genes in *Saccharomyces cerevisiae*," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28 (5):637-46 (2003).

(56) References Cited

OTHER PUBLICATIONS

Dubois & Stephenson "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
EMBOSS Needle results for Pairwise Sequence Alignment of UGT91D1 and UGT91D2; dated Apr. 4, 2016, 2 pages.
Estrada De Martin et al., "Ice2p is important for the distribution and structure of the cortical ER network in *Saccharomyces cerevisiae*," J Cell Sci. 118(Pt 1):65-77 (Oct. 2006).
Fernandez et al., "Activation of chitin synthetase in permeabilized cells of a *Saccharomyces cerevisiae* mutant lacking proteinase B," J Bacteriol. 152(3):1255-64 (1982).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Gietz & Schiestl, "High-efficiency yeast transformation using the LiAc/SS carrier DNA/PEG method," Nat Protoc. 2 (1):31-4 (2007).
Girvan et al., "Flavocytochrome P450 BM3 mutant W1046A is a NADH-dependent fatty acid hydroxylase: Implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Jansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
English Translation of First Office Action issued by the State Intellectual Property Office of People's Republic of China for CN Application No. 201180038475.4, dated Nov. 21, 2013.

First Examination Report issued by the Intellectual Property Office of New Zealand for New Zealand Application No. 604915, dated Sep. 2, 2013.
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in Escherichia coli and *Saccharomyces cerevisiae*," Gene 25(2-3):179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for bligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient In a novel glycosylation enzyme for anthocyanin biosynthesis, UDP-glucose:anthocyanidin 3-O-glucoside-2''-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).
Riesmeier et al., "Isolation and characterization of a sucrose carrier cDNA from spinach by functional expression in yeast," EMBO J. 11(13):4705-13 (Dec. 1992).
Rodríguez-Concepción & Boronat, "Elucidation of the methylerythritol phosphate pathway for isoprenoid biosynthesis in bacteria and plastids. A metabolic milestone achieved through genomics," Plant Physiol. 130 (3):1079-89 (Nov. 2002).
Saier Jr et al., "The major facilitator superfamily," J. Mol. Microbiol. Biotechnol. 1(2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).

(56) References Cited

OTHER PUBLICATIONS

Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
First Examination Report issued by the Intellectual Property Office of New Zealand for New Zealand Application No. 700097, dated Oct. 6, 2014 (pp. 1-2).
Notice of Acceptance issued by the Intellectual Property Office of New Zealand for New Zealand Application No. 700097, dated Oct. 7, 2015 (1 page).
First Examination Report issued by the Intellectual Property Office of New Zealand for New Zealand Application No. 708078, dated May 28, 2015 (pp. 1-3).
Search Report issued by the Intellectual Property Office of Singapore for Singaporean Application No. 201208854-8, dated Nov. 3, 2014.
Written Opinion issued by the Intellectual Property Office of Singapore for Singaporean Application No. 201208854-8, dated Nov. 3, 2014.
Non-Final Office Action for U.S. Appl. No. 14/237,540, mailed Dec. 30, 2015 (pp. 1-19).
Final Office Action issued in U.S. Appl. No. 14/237,540; mailed Jul. 8, 2016, pp. 1-19.
International Preliminary Report on Patentability issued by the International Bureau for International Application No. PCT/US2012/050021, dated Feb. 11, 2014.
English Translation of First Office Action and Search Report issued by the State Intellectual Property Office of People's Republic of China for Chinese Application No. 201280038853.3, dated Feb. 16, 2015.
English Translation of Second Office Action and Search Report issued by the State Intellectual Property Office of People's Republic of China for Chinese Application No. 201280038853.3, dated Jan. 11, 2016.
Communication pursuant to Rules 161(1) and 162 (EPC) issued by the European Patent Office for European Application No. 12750513.9, dated Mar. 14, 2014.
Response to Communication pursuant to Rules 161(1) and 162 (EPC) issued by the European Patent Office for European Application No. 12750513.9, dated Aug. 4, 2014.
Examination Report issued by the European Patent Office for European Application No. 12750513.9, dated Nov. 26, 2014.
Response to Examination Report issued by the European Patent Office for European Application No. 12750513.9, dated Mar. 25, 2015.
Extended European Search Report issued in EP 15193074.0; dated Feb. 12, 2016, pp. 1-9.
Statement of Facts and Arguments In Support Of Opposition for EP Application No. 12750513.9; mailed Feb. 28, 2017 pp. 1-24.
Communication of Notice of Opposition against EP Application No. 12750513.9; mailed Mar. 6, 2017 pp. 1-8.
Sequence alignment between the sequence of Uniprot database entry Q75183 version 31, updated Jul. 22, 2008 and SEQ ID No: 152 (from European Patent No. 2742142) as cited in Notice of Opposition against EP Application No. 12750513.9; mailed Mar. 6, 2017; pp. 1-2.
International Search Report from the International Searching Authority for International Application No. PCT/ EP2014/052363, mailed Sep. 22, 2014 (12 pages).
Written Opinion of the International Searching Authority for International Application No. PCT/EP2014/052363, mailed Sep. 22, 2014 (10 pages).
International Preliminary Report on Patentability issued by the International Bureau for International Application No. PCT/EP2014/052363, dated Aug. 11, 2015. (11 pages).
Non-Final Office Action for U.S. Appl. No. 14/761,629, mailed Mar. 21, 2017 (pp. 1-19).
International Search Report by the International Searching Authority for International Application No. PCT/EP2014/052675, mailed Apr. 23, 2014 (5 pages).
Written Opinion of the International Searching Authority for International Application No. PCT/EP2014/052675, mailed Apr. 23, 2014 (7 pages).
International Preliminary Report on Patentability issued by the International Bureau for International Application No. PCT/EP2014/052675, dated Aug. 11, 2015 (8 pages).
Communication pursuant to Rules 161(1) and 162 EPC for European Application No. 14704558.7, dated Sep. 18, 2015 (2 pages).
International Search Report of the International Searching Authority for International Application No. PCT/EP2013/075587, mailed Feb. 20, 2014 (pp. 1-5).
Written Opinion of the International Searching Authority for International Application No. PCT/EP2013/075587, mailed Feb. 20, 2014 (pp. 1-9).
International Preliminary Report on Patentability from the International Bureau for International Application No. PCT/EP2013/075587, dated Jun. 9, 2015 (pp. 1-10).
Final Office Action for U.S. Appl. No. 14/648,747, mailed Sep. 6, 2017 (pp. 1-19).
Third Party Observation in EP Application No. 13801569.8; mailed Oct. 23, 2017, pp. 1-6.
Third Party Submission in U.S. Appl. No. 14/648,747; dated Mar. 28, 2016, pp. 1-231.
Non-Final Office Action for U.S. Appl. No. 14/648,747, mailed Mar. 23, 2017, pp. 1-20.
Third Party Observation in EP Application No. 13801569.8; mailed Apr. 26, 2017. pp. 1-5.
Invitation to Pay Additional Fees and, Where Applicable, Protest Fee by the International Searching Authority for International Application No. PCT/EP2015/070620, mailed Nov. 27, 2015 (pp. 1-14).
International Search Report by the International Searching Authority for International Application No. PCT/ EP2015/070620; mailed Mar. 29, 2016, pp. 1-10.
Written Opinion of the International Searching Authority for International Application No. PCT/EP2015/070620; mailed Mar. 29, 2016, pp. 1-24.
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
International Preliminary Report on Patentability from the International Bureau for International Application PCTEP2015/068314; mailed Feb. 14, 2017 (pp. 1-10).
International Search Report and Written Opinion of the International Searching Authority for International Application No. PCT/EP2015/052007; mailed Jul. 4, 2016, pp. 1-24.
International Search Report and Written Opinion of the International Searching Authority for International Application No. PCT/EP2016/068259; mailed Jan. 24, 2017, pp. 1-18.
International Search Report and Written Opinion of International Search Authority for International Application No. PCTEP2016/080516; mailed Mar. 15, 2017, pp. 1-22.
International Search Report and Written Opinion of International Search Authority for International Application No. PCTEP2017/059028; mailed Jun. 27, 2017, pp. 1-15.

(56) References Cited

OTHER PUBLICATIONS

Saier, "Families of transmembrane sugar transport proteins," Mol Microbiol., 35(4):699-710 (2000).
Final Office Action for U.S. Appl. No. 14/761,629, mailed Aug. 11, 2017 (pp. 1-16).
English Translation of First Office Action issued by the State Intellectual Property Office of People's Republic of China for CN Application No. 201180038475.4, dated Nov. 21, 2013 (2 pages).
Bruyn et al., "Metabolic engineering of *Escherichia coli* into a versatile glycosylation platform: production of bio-active quercetin glycosides," Microb Cell Fact., 14:138 (2015).
Bruyn et al., "Development of an in vivo glucosylation platform by coupling production to growth: production of phenolic glucosides by a glycosyltransferase of Vitis vinifera," Biotechnol Bioeng., 112(8):1594-603 (2015).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65 (0):1257-69 (2013).
Daran et al., "Genetic and biochemical characterization of the UGP1 gene encoding the UDP-glucose byrophosphorylase from *Saccharomyces cerevisiae*," Eur J Biochem. 233(2):520-30 (1995).
Duetz, "Microtiter plates as mini-bioreactors: miniaturization of fermentation methods," Trends Microbiol 15 (10):469-75 (2007).
François et al., "Reserve carbohydrates metabolism in the yeast *Saccharomyces cerevisiae*," FEMS Microbiol Rev., 25(1):125-45 (2001).
Garber et al., "Computational methods for transcriptome annotation and quantification using RNA-seq," Nat Methods 8(6):469-77 (2011).
Gloster, "Advances in understanding glycosyltransferases from a structural perspective," Curr Opin Struct Biol. 28:131-41 (2014).
Husar et al., Overexpression of the UGT73C6 alters brassinosteriod glucoside formation in *Arabidopsis thaliana*, BMC Plant Biology, 11:1-14 (2011).
Kawai et al., "Transformation of *Saccharomyces cerevisiae* and other fungi: methods and possible underlying mechanism," Bioeng Bugs. 1(6):395-403 (2010).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Lin et al., "Arrestin-related ubiquitin-ligase adaptors regulate endocytosis and protein turnover at the cell surface," Cell 135(4):714-25 (2008).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Mao et al., "Produce steviol glycosides in engineered yeast", 2015 Synthetic Biology: Engineering, Evolution & Design (SEED), Poster Abstract (Jun. 2015).
Nagalakshmi et al., "The transcriptional landscape of the yeast genome defined by RNA sequencing," Science 320 (5881 ): 1344-9 (2008).
Nagatoshi et al., "UGT75L6 and UGT94E5 mediate sequential glucosylation of crocetin to crocin in Gardenia iasminoides", FEBS Letters, 586:1055-1061 (2012).
Nikko et al. "Arrestin-like proteins mediate ubiquitination and endocytosis of the yeast metal transporter Smf1," EMBO Rep. 9(12):1216-21 (2008).

Nikko & Pelham, "Arrestin-mediated endocytosis of yeast plasma membrane transporters," Traffic 10(12):1856-67 (2009).
Ohta et al., MassBank Accession No. FU000299 (May 2016).
Ohta et al., MassBank Accession No. FU000332 (May 2016).
Olsson et al., "Microbial production of next-generation stevia sweeteners," Microbial Cell Factories, 15:1-14 (2016).
Partow et al., "Characterization of different promoters for designing a new expression vector in *Saccharomyces cerevisiae*," Yeast 27:955-64 (2010).
Robinson & Oshlack et al., "A scaling normalization method for differential expression analysis of RNA-seq data," Genome Bioi. 11(3):R25 (2010).
Saier Jr et al., "The transporter classification database," Nucl. Acids Res., 42(1):D251-258 (2014).
Song et al., "The Aspergillus fumigatus 1-29 damage resistance protein family coordinately regulates ergosterol biosynthesis and azole susceptibility," MBIO, 7:1-13 (2016).
Tiwari et al., "Plant secondary metabolism linked glycosyltransferases: An update on expaning knowledge and scopes", Biotechnology Advances, 34:714-739 (May 2016).
Wang et al., "Pathway mining-based integration of critical enzyme parts for de novo biosynthesis of steviolglycoside sweetener in *Escherichia coli*", Cell Research, 26:258-261 (Sep. 2015).
Wang et al., "Efficient enzymatic production of rebaudioside A from stevioside", Bioscience, Biotechnology, and Biochemistry, 80:67-73 (Aug. 2015).
Wang et al., "RNA-Seq: a revolutionary tool for transcriptomics," Nat Rev Genet. 10(1):57-63 (2009).
Wang et al., "Design and construction of artificial biological systems for complex natural products biosynthesis," Chinese Journal of Biotechnology, 29(8):1146-60 (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
International Search Report and Written Opinion of the International Searching Authority for International Application No. PCT/EP2017/078473; mailed Jan. 25, 2018, pp. 1-16.
Non-Final Office Action for U.S. Appl. No. 14/764,898, mailed Mar. 30, 2017 (pp. 1-17).
International Preliminary Report on Patentability from the International Bureau for International Application PCT/EP2015/070620; mailed Mar. 14, 2017 (pp. 1-25).
Third Party Submission in U.S. Appl. No. 15/506,196; dated Mar. 9, 2018 pp. 1-68.
Non-Final Office Action for U.S. Appl. No. 15/506,196, mailed Sep. 17, 2018 (pp. 1-8).
Final Office Action for U.S. Appl. No. 15/506,196, mailed Feb. 21, 2019 (pp. 1-10).
Non-Final Office Action for U.S. Appl. No. 15/506,196, mailed Jun. 19, 2019 (pp. 1-10).
International Preliminary Report on Patentability from the International Bureau for International Application PCT/EP2015/052007; mailed Aug. 1, 2017 (pp. 1-16).
International Search Report and Written Opinion of International Search Authority for International Application No. PCT/EP2017/055589; mailed May 12, 2017, pp. 1-18.
Third party submission in European Patent Application No. 15762581.5 dated Aug. 29, 2019 (300 pages).

\* cited by examiner

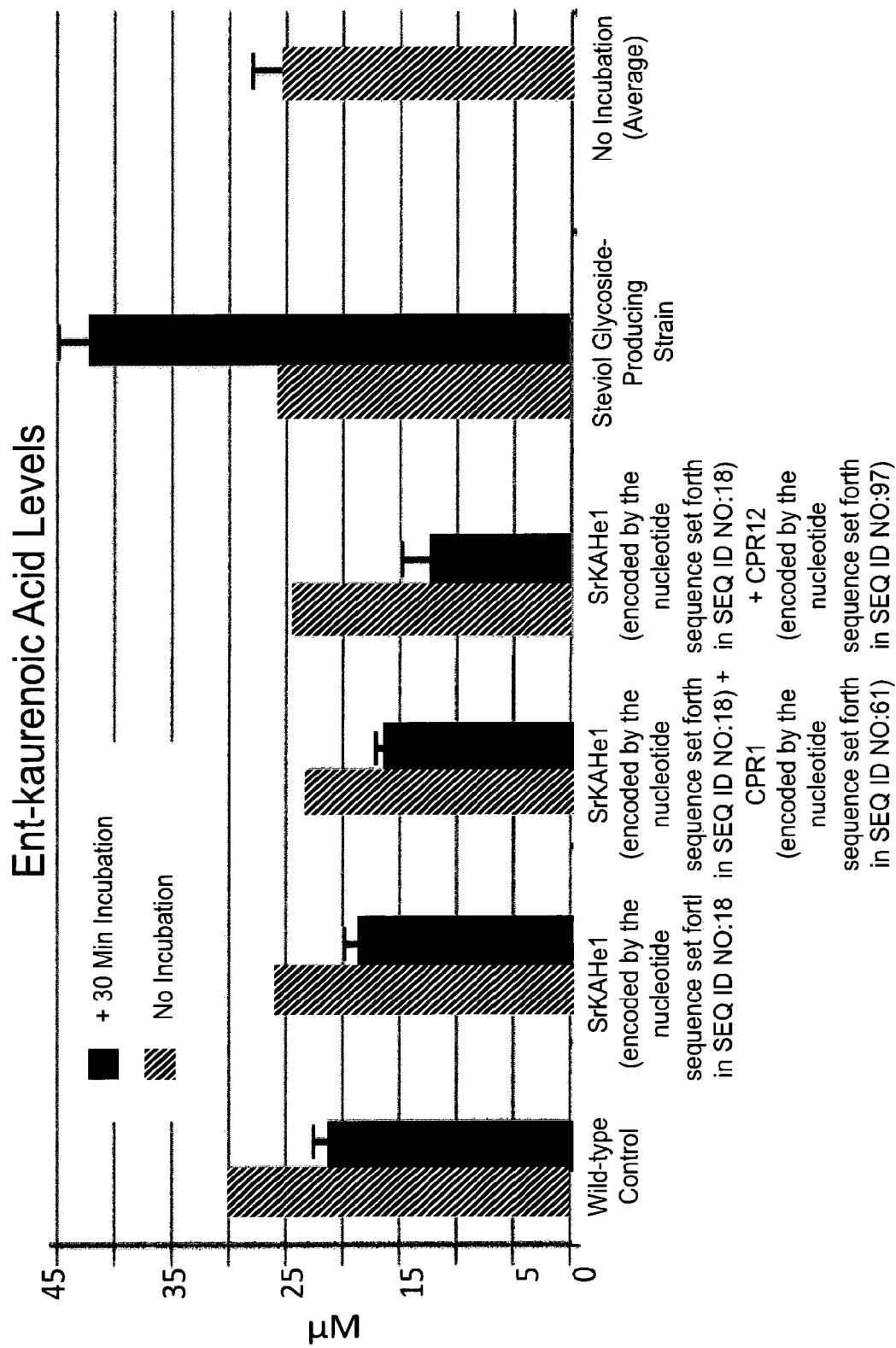

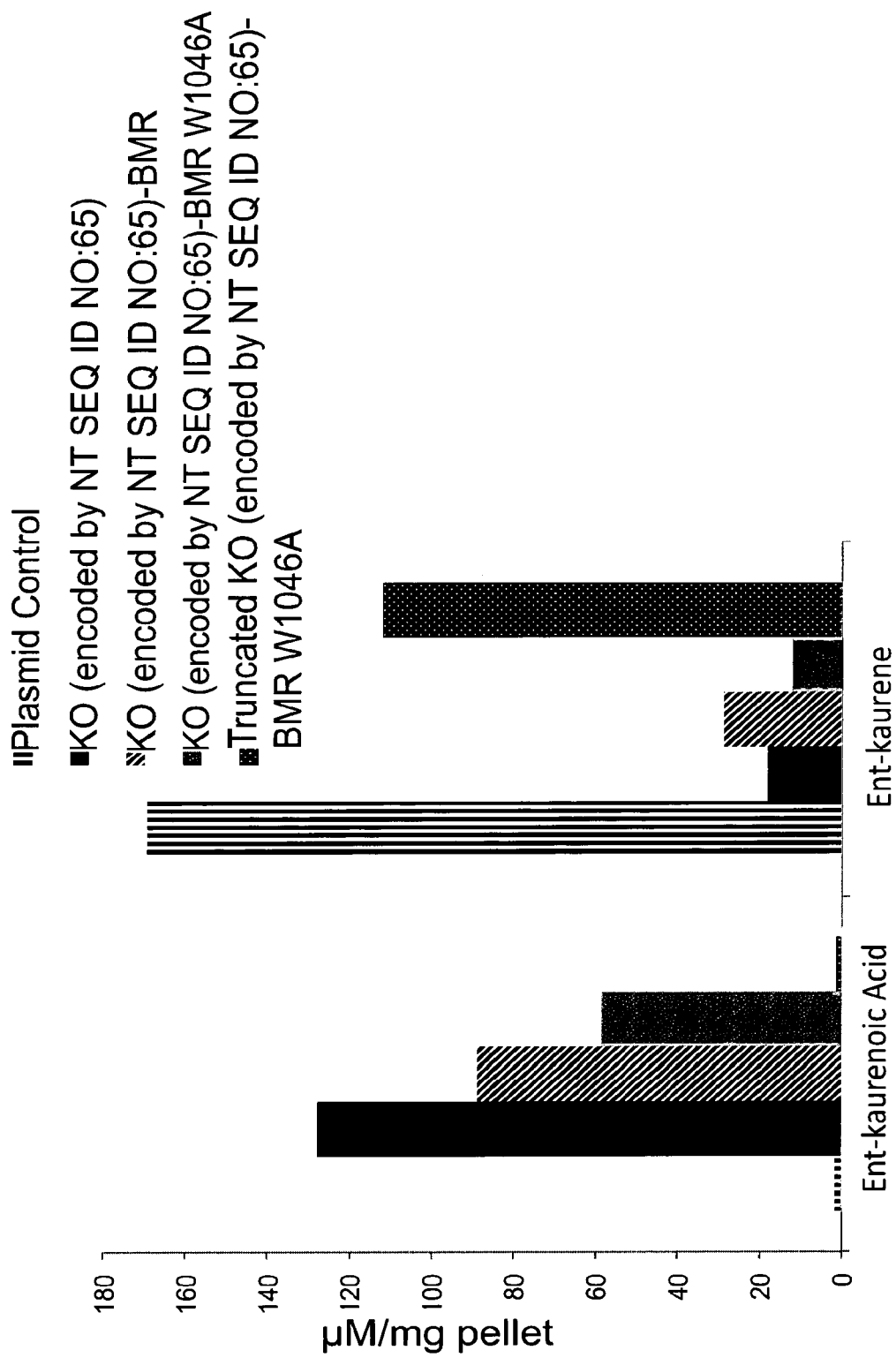

PRODUCTION OF STEVIOL GLYCOSIDES IN RECOMBINANT HOSTS

This application is a continuation of U.S. patent application Ser. No. 16/801,200, filed Feb. 26, 2020 (now U.S. Pat. No. 11,466,302), which is a divisional of Ser. No. 15/506,196, filed on Feb. 23, 2017 (now U.S. Pat. No. 10,612,064), which is a U.S. national phase of International Application No. PCT/EP2015/070620 filed Sep. 9, 2015, which claims the benefit of U.S. Provisional Application No. 62/048,178 filed on Sep. 9, 2014, U.S. Provisional Application No. 62/103,547, filed on Jan. 14, 2015, U.S. Provisional Application No. 62/117,396, filed on Dec. 17, 2015, and U.S. Provisional Application No. 62/148,585, filed on Apr. 16, 2015. The entire disclosure contents of these applications are herewith incorporated by reference in their entirety into the present application.

REFERENCE TO AN ELECTRONIC SEQUENCE LISTING

The instant application contains a Sequence Listing that has been submitted electronically and which is hereby incorporated by reference in its entirety. The Sequence Listing was created on Jan. 17, 2023, is named "14-830-US-CON.xml" and is 255 kilobytes in size.

BACKGROUND OF THE INVENTION

Field of the Invention

This disclosure relates to recombinant production of steviol glycosides and steviol glycoside precursors in recombinant hosts. In particular, this disclosure relates to production of steviol glycosides comprising steviol-13-O-glucoside (13-SMG), steviol-1,2-bioside, steviol-1,3-bioside, steviol-19-O-glucoside (19-SMG), stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, or isomers thereof in recombinant hosts.

Description of Related Art

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine, and sucralose. Stevia extract is a natural sweetener that can be isolated and extracted from a perennial shrub, *Stevia rebaudiana*. *Stevia* is commonly grown in South America and Asia for commercial production of *stevia* extract. *Stevia* extract, purified to various degrees, is used commercially as a high intensity sweetener in foods and in blends or alone as a tabletop sweetener.

Chemical structures for several steviol glycosides are shown in FIG. 1, including the diterpene steviol and various steviol glycosides. Extracts of the *Stevia* plant generally comprise steviol glycosides that contribute to the sweet flavor, although the amount of each steviol glycoside often varies, inter alia, among different production batches.

As recovery and purification of steviol glycosides from the *Stevia* plant have proven to be labor intensive and inefficient, there remains a need for a recombinant production system that can accumulate high yields of desired steviol glycosides, such as RebD and RebM. There also remains a need for improved production of steviol glycosides in recombinant hosts for commercial uses.

SUMMARY OF THE INVENTION

It is against the above background that the present invention provides certain advantages and advancements over the prior art.

Although this invention disclosed herein is not limited to specific advantages or functionalities, the invention provides a recombinant host comprising one or more of:
(a) a gene encoding an ent-kaurene oxidase (KO) polypeptide;
(b) a gene encoding a cytochrome P450 reductase (CPR) polypeptide; and/or
(c) a gene encoding an ent-kaurenoic acid hydroxylase (KAH) polypeptide;
wherein at least one of the genes is a recombinant gene; and
wherein the recombinant host is capable of producing a steviol glycoside precursor.

The invention also provides a recombinant host comprising:
(a) a gene encoding a geranylgeranyl diphosphate synthase (GGPPS) polypeptide;
(b) a gene encoding an ent-copalyl diphosphate synthase (CDPS) polypeptide;
(c) a gene encoding an ent-kaurene synthase (KS) polypeptide
(d) a gene encoding an ent-kaurene oxidase (KO) polypeptide;
(e) a gene encoding a cytochrome P450 reductase (CPR) polypeptide; and
(f) a gene encoding an ent-kaurenoic acid hydroxylase (KAH) polypeptide;
wherein at least one of the genes is a recombinant gene; and
wherein the recombinant host is capable of producing steviol.

In one aspect of the recombinant hosts disclosed herein,
(a) the KO polypeptide comprises a KO polypeptide having at least 60% identity to an amino acid sequence set forth in SEQ ID NO:72 or SEQ ID NO:75; 65% identity to an amino acid sequence set forth in SEQ ID NO:54; at least 70% identity to an amino acid sequence set forth in SEQ ID NO: 70, SEQ ID NO:71, or SEQ ID NO:79; at least 40% identity to an amino acid sequence set forth in SEQ ID NO:77; or at least 50% identity to an amino acid sequence set forth in SEQ ID NO:78;
(b) the CPR polypeptide comprises a CPR polypeptide having at least 70% identity to an amino acid sequences set forth in SEQ ID NO:69, SEQ ID NO:74, SEQ ID NO:76, or SEQ ID NO:87; at least 80% identity to an amino acid sequence set forth in SEQ ID NO:73; at least 85% identity to an amino acid sequence set forth in SEQ ID NO:22; at least 65% identity to an amino acid sequence set forth in SEQ ID NO:28; or at least 50% identity to an amino acid sequence set forth in SEQ ID NO:98; and/or
(c) the KAH polypeptide comprises a KAH polypeptide having at least 40% identity to an amino acid sequence set forth in SEQ ID NO:82; at least 50% identity to an amino acid sequence set forth in SEQ ID NO:91; or at least 60% identity to an amino acid sequence set forth in SEQ ID NO:68.

The invention further provides a recombinant host comprising one or more of:
  (a) a gene encoding a KO polypeptide having at least 60% identity to an amino acid sequence set forth in SEQ ID NO:75;
  (b) a gene encoding a KAH polypeptide having at least 40% identity to an amino acid sequence set forth in SEQ ID NO:82; and/or
  (c) a gene encoding a CPR polypeptide having at least 50% identity to an amino acid sequence set forth in SEQ ID NO:98;
  wherein at least one of the genes is a recombinant gene; and
  wherein the recombinant host is capable of producing a steviol glycoside precursor.

The invention further provides a recombinant host comprising one or more of:
  (a) a gene encoding a KO polypeptide having at least 70% identity to an amino acid sequence set forth in SEQ ID NO:70;
  (b) a gene encoding a KAH polypeptide having at least 40% identity to an amino acid sequence set forth in SEQ ID NO:82; and/or
  (c) a gene encoding a CPR polypeptide having at least 50% identity to an amino acid sequence set forth in SEQ ID NO:98;
  wherein at least one of the genes is a recombinant gene; and
  wherein the recombinant host is capable of producing a steviol glycoside precursor.

In one aspect of the recombinant hosts disclosed herein, the host further comprises a gene encoding a KO polypeptide having at least 65% identity to an amino acid sequence set forth in SEQ ID NO:54.

In another aspect of the recombinant hosts disclosed herein, the recombinant host further comprises a gene encoding a KAH polypeptide having at least 60% identity to an amino acid sequence set forth in SEQ ID NO:68.

In another aspect of the recombinant hosts disclosed herein, the recombinant host further comprises a gene encoding a KO polypeptide having at least 70% identity to an amino acid sequence set forth in SEQ ID NO:79.

In one aspect of the recombinant hosts disclosed herein, the host further comprises one or more of:
  (a) a gene encoding a geranylgeranyl diphosphate synthase (GGPPS) polypeptide;
  (b) a gene encoding an ent-copalyl diphosphate synthase (CDPS) polypeptide; and/or
  (c) a gene encoding an ent-kaurene synthase (KS) polypeptide;
  wherein at least one of the genes is a recombinant gene; and
  wherein the recombinant host is capable of producing a steviol glycoside precursor.

In some aspects of the recombinant hosts disclosed herein,
  (a) the GGPPS polypeptide comprises a polypeptide having at least 70% identity to an amino acid sequence set forth in SEQ ID NO:49;
  (b) the CDPS polypeptide comprises a polypeptide having at least 70% identity to an amino acid sequence set forth in SEQ ID NO:37; and/or
  (c) the KS polypeptide comprises a polypeptide having at least 40% identity to an amino acid sequence set forth in SEQ ID NO:6.

In one aspect of the recombinant hosts disclosed herein, the recombinant host further comprises a gene encoding an endoplasmic reticulum membrane polypeptide.

In another aspect of the recombinant hosts disclosed herein, the endoplasmic reticulum membrane polypeptide comprises an Inheritance of cortical ER protein 2 (ICE2) polypeptide having at least 50% identity to the amino acid sequence set forth in SEQ ID NO:114.

In one aspect of the recombinant host disclosed herein, the KO polypeptide is a fusion construct.

In another aspect, the fusion construct comprises a polypeptide having at least 60% identity to an amino acid sequence set forth in SEQ ID NO:118 or SEQ ID NO:120.

In another aspect, the fusion construct has at least 50% identity to an amino acid sequence set forth in SEQ ID NO:100, SEQ ID NO:102, SEQ ID NO:104, SEQ ID NO:106, SEQ ID NO:108, SEQ ID NO:110, or SEQ ID NO:112.

In one aspect of the recombinant hosts disclosed herein, the host further comprises one or more of:
  (a) a gene encoding a UGT85C polypeptide;
  (b) a gene encoding a UGT76G polypeptide;
  (c) a gene encoding a UGT74G1 polypeptide;
  (d) a gene encoding a UGT91D2 functional homolog polypeptide; and/or
  (e) a gene encoding an EUGT11 polypeptide;
  wherein at least one of the genes is a recombinant gene; and
  wherein the host is capable of producing a steviol glycoside.

In some aspects of the recombinant hosts disclosed herein,
  (a) the UGT85C2 polypeptide comprises a polypeptide having at least 55% identity to an amino acid sequence set forth in SEQ ID NO:30;
  (b) the UGT76G1 polypeptide comprises a polypeptide having at least 50% identity to an amino acid sequence set forth in SEQ ID NO:83;
  (c) the UGT74G1 polypeptide comprises a polypeptide having at least 55% identity to an amino acid sequence set forth in SEQ ID NO:29;
  (d) the UGT91D2 functional homolog polypeptide comprises a UGT91D2 polypeptide having 90% or greater identity to the amino acid sequence set forth in SEQ ID NO:84 or a UGT91D2e-b polypeptide having 90% or greater identity to the amino acid sequence set forth in SEQ ID NO:88; and/or
  (e) the EUGT11 polypeptide comprises a polypeptide having at least 65% identity to an amino acid sequence set forth in SEQ ID NO:86.

In some aspects, the recombinant hosts disclosed herein comprise a plant cell, a mammalian cell, an insect cell, a fungal cell, or a bacterial cell.

In one aspect, the bacterial cell comprises *Escherichia* bacteria cells, for example, *Escherichia coli* cells; *Lactobacillus* bacteria cells; *Lactococcus* bacteria cells; *Corynebacterium* bacteria cells; *Acetobacter* bacteria cells; *Acinetobacter* bacteria cells; or *Pseudomonas* bacterial cells.

In one aspect, the fungal cell comprises a yeast cell.

In one aspect, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Han-*

*senula polymorpha, Candida boidinii, Arxula adeninivorans, Xanthophyllomyces dendrorhous*, or *Candida albicans* species.

In one aspect, the yeast cell is a Saccharomycete.

In one aspect, the yeast cell is a cell from the *Saccharomyces cerevisiae* species.

The invention further provides a method of producing a steviol glycoside or a steviol glycoside precursor, comprising:
(a) growing a recombinant host disclosed herein in a culture medium, under conditions in which any of the genes disclosed herein are expressed;
wherein the steviol glycoside or the steviol glycoside precursor is synthesized by said host; and/or
(b) optionally quantifying the steviol glycoside or the steviol glycoside precursor; and/or
(c) optionally isolating the steviol glycoside or the steviol glycoside precursor.

In some aspects, the steviol glycoside comprises steviol-13-O-glucoside (13-SMG), steviol-1,2-bioside, steviol-1,3-bioside, steviol-19-O-glucoside (19-SMG), stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, di-glycosylated steviol, tri-glycosylated steviol, tetra-glycosylated steviol, penta-glycosylated steviol, hexa-glycosylated steviol, hepta-glycosylated steviol, or isomers thereof.

In some aspects, the steviol glycoside or steviol glycoside precursor produced by the recombinant hosts or methods disclosed herein accumulates to a detectable concentration when cultured under said conditions.

In some aspects, the steviol glycoside or steviol glycoside precursor produced by the recombinant hosts or methods disclosed herein has an undetectable concentration of *stevia* plant-derived contaminants.

In some aspects, the steviol glycoside or steviol glycoside precursor produced by the recombinant hosts or methods disclosed herein has a steviol glycoside composition enriched for RebD or RebM relative to the steviol glycoside composition of a wild-type *Stevia* plant.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 15B shows levels of ent-kaurenoic acid following 30 min incubation of ent-kaurenoic acid with microsomal protein prepared from *S. cerevisiae* strains expressing SrKAHe1 (encoded by the nucleotide sequence set forth in SEQ ID NO:18) alone or in combination with CPR1 (encoded by the nucleotide sequence set forth in SEQ ID NO:61) or CPR12 (encoded by the nucleotide sequence set forth in SEQ ID NO:97). Results are shown in μM as an average of three biological replicates. Control reactions comprised the microsomal protein described above but were not incubated for 30 min prior to measurement of ent-kaurenoic acid levels. See Example 9.

FIG. 16D shows levels of ent-kaurenoic acid or ent-kaurene accumulated by a steviol glycoside-producing *S. cerevisiae* strain expressing the KO encoded by the nucleotide sequence set forth in SEQ ID NO:65, a fusion construct of the KO encoded by the nucleotide sequence set forth in SEQ ID NO:65 and BMR (SEQ ID NO:107, SEQ ID NO:108), a fusion construct of the KO encoded by the nucleotide sequence set forth in SEQ ID NO:65 and BMR W1046A (SEQ ID NO:109, SEQ ID NO:110), a fusion construct of a truncated KO encoded by the nucleotide sequence set forth in SEQ ID NO:65 and BMR W1046A (SEQ ID NO:111, SEQ ID NO:112), or a plasmid control. See Example 10.

DETAILED DESCRIPTION OF THE INVENTION

Figure 1:
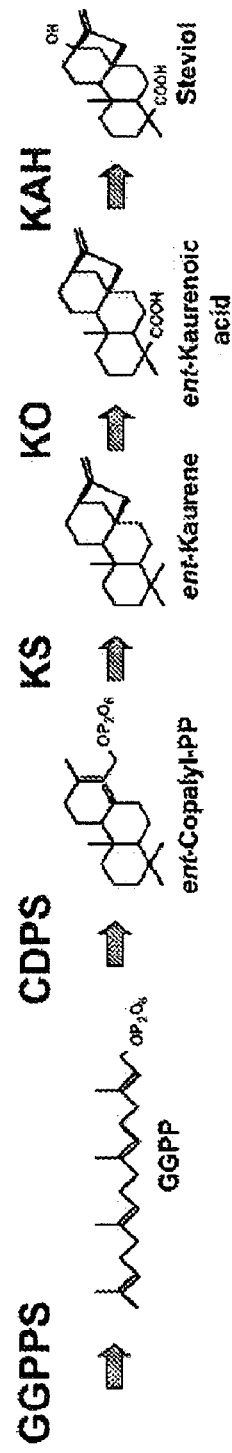
FIG. 1 shows a schematic of the engineered biosynthetic pathway for producing steviol in yeast from geranylgeranyl diphosphate using geranylgeranyl diphosphate synthase (GGPPS), ent-copalyl diphosphate synthase (CDPS), ent-kaurene synthase (KS), ent-kaurene oxidase (KO), and ent-kaurenoic acid hydroxylase (KAH) polypeptides.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, CA).

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in *S. cerevisiae*.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to *S. cerevisiae*, including, but not limited to *S. cerevisiae* strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, *Genetics* 190:841-54. In some embodiments, an endogenous yeast gene is deleted. See, e.g., Giaever & Nislow, 2014, *Genetics* 197(2):451-65. As used herein, the terms "deletion," "deleted," "knockout," and "knocked out" can be used interchangeably to refer to an endogenous gene that has been manipulated to no longer be expressed in an organism, including, but not limited to, *S. cerevisiae*.

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, *Ann. Rev. Genetics* 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

Figure 2:
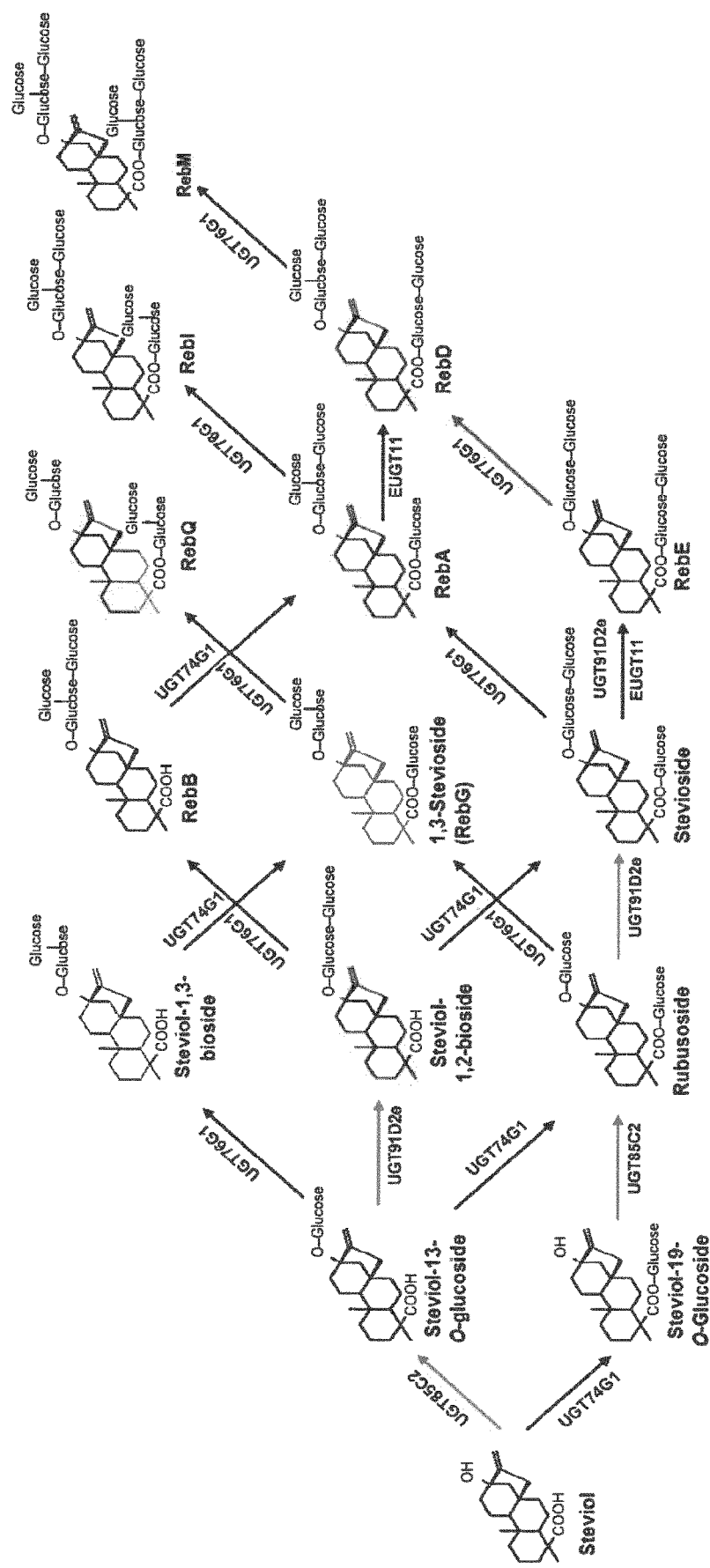
FIG. 2 shows representative steviol glycoside glycosylation reactions catalyzed by suitable uridine 5'-diphospho (UDP) glycosyl transferases (UGT) enzymes and chemical structures for several steviol glycoside compounds.

As used herein, the term "steviol glycoside" refers to Rebaudioside A (RebA) (CAS #58543-16-1), Rebaudioside B (RebB) (CAS #58543-17-2), Rebaudioside C (RebC) (CAS #63550-99-2), Rebaudioside D (RebD) (CAS #63279-13-0), Rebaudioside E (RebE) (CAS #63279-14-1), Rebaudioside F (RebF) (CAS #438045-89-7), Rebaudioside M (RebM) (CAS #1220616-44-3), Rubusoside (CAS #63849-39-4), Dulcoside A (CAS #64432-06-0), Rebaudioside I (RebI) (MassBank Record: FU000332), Rebaudioside Q (RebQ), 1,2-Stevioside (CAS #57817-89-7), 1,3-Stevioside (RebG), 1,2-bioside (MassBank Record: FU000299), 1,3-bioside, Steviol-13-O-glucoside (13-SMG), Steviol-19-O-glucoside (19-SMG), a tri-glucosylated steviol glycoside, a tetra-glucosylated steviol glycoside, a penta-glucosylated steviol glycoside, a hexa-glucosylated steviol glycoside, a hepta-glucosylated steviol glycoside, and isomers thereof. See FIG. 2; see also, Steviol Glycosides Chemical and Technical Assessment 69th JECFA, 2007, prepared by Harriet Wallin, Food Agric. Org.

As used herein, the terms "steviol glycoside precursor" and "steviol glycoside precursor compound" are used to refer to intermediate compounds in the steviol glycoside biosynthetic pathway. Steviol glycoside precursors include, but are not limited to, geranylgeranyl diphosphate (GGPP), ent-copalyl-diphosphate, ent-kaurene, ent-kaurenol, ent-kaurenal, ent-kaurenoic acid, and steviol. See FIG. 1. In some embodiments, steviol glycoside precursors are themselves steviol glycoside compounds. For example, 19-SMG, rubusoside, stevioside, and RebE are steviol glycoside precursors of RebM. See FIG. 2. Steviol glycosides and/or steviol glycoside precursors can be produced in vivo (i.e., in a recombinant host), in vitro (i.e., enzymatically), or by whole cell bioconversion. As used herein, the terms "produce" and "accumulate" can be used interchangeably to describe synthesis of steviol glycosides and steviol glycoside precursors in vivo, in vitro, or by whole cell bioconversion.

As used herein, the term "di-glycosylated steviol" can be used to refer to a steviol molecule comprising two sugar moieties, such as glucose or N-acetylglucosamine (GlcNAc). Non-limiting examples of di-glycosylated steviol molecules include steviol-1,3-bioside, steviol-1,2-bioside, rubusoside, a steviol molecule comprising two glucose moieties, a steviol molecule comprising one glucose moiety and one GlcNAc moiety, and isomers thereof.

As used herein, the term "tri-glycosylated steviol" can be used to refer to a steviol molecule comprising three sugar moieties, such as glucose or GlcNAc. Non-limiting examples of tri-glycosylated steviol molecules include RebB, RebG, stevioside, a steviol molecule comprising two glucose moieties and one GlcNAc moiety, and isomers thereof.

As used herein, the term "tetra-glycosylated steviol" can be used to refer to a steviol molecule comprising four sugar moieties, such as glucose or GlcNAc. Non-limiting examples of tetra-glycosylated steviol molecules include RebA, RebE, RebQ, a steviol molecule comprising four glucose moieties, a steviol molecule comprising three glucose moieties and one GlcNAc moiety, and isomers thereof.

As used herein, the term "penta-glycosylated steviol" can be used to refer to a steviol molecule comprising five sugar moieties, such as glucose or GlcNAc. Non-limiting examples of penta-glycosylated steviol molecules include RebD, a steviol molecule comprising five glucose moieties, a steviol molecule comprising four glucose moieties and one GlcNAc moiety, and isomers thereof.

As used herein, the term "hexa-glycosylated steviol" can be used to refer to a steviol molecule comprising six sugar moieties, such as glucose or GlcNAc. Non-limiting examples of hexa-glycosylated steviol molecules include RebM, a steviol molecule comprising six glucose moieties, a steviol molecule comprising five glucose moieties and one GlcNAc moiety, and isomers thereof.

As used herein, the term "hepta-glycosylated steviol" can be used to refer to a steviol molecule comprising seven sugar moieties, such as glucose or GlcNAc. Non-limiting examples of hepta-glycosylated steviol molecules include a steviol molecule comprising seven glucose moieties and isomers thereof.

As used herein, the term "glycosylated ent-kaurenoic acid" can be used to refer to an ent-kaurenoic acid molecule comprising sugar moieties, such as glucose or GlcNAc. Non-limiting examples of glycosylated ent-kaurenoic acid molecules include ent-kaurenoic acid molecule comprising two glucose moieties and one GlcNAc moiety, an ent-kaurenoic acid molecule comprising three glucose moieties, an ent-kaurenoic acid molecule comprising one glucose moiety and one GlcNAc moiety, an ent-kaurenoic acid molecule comprising two glucose moieties, and isomers thereof.

As used herein, the term "glycosylated ent-kaurenol" can be used to refer to an ent-kaurenol molecule comprising sugar moieties, such as glucose or GlcNAc. Non-limiting examples of glycosylated ent-kaurenol molecules include an ent-kaurenol molecule comprising three glucose moieties, an ent-kaurenol molecule comprising one glucose moiety and one GlcNAc moiety, an ent-kaurenol molecule comprising two glucose moieties, and isomers thereof.

Recombinant steviol glycoside-producing *Saccharomyces cerevisiae* (*S. cerevisiae*) strains are described in WO 2011/153378, WO 2013/022989, WO 2014/122227, and WO 2014/122328. Methods of producing steviol glycosides in recombinant hosts, by whole cell bioconversion, and in vitro are also described in WO 2011/153378, WO 2013/022989, WO 2014/122227, and WO 2014/122328.

In some embodiments, steviol glycosides and/or steviol glycoside precursors are produced in vivo through expression of one or more enzymes involved in the steviol glycoside biosynthetic pathway in a recombinant host. For example, a steviol-producing recombinant host expressing one or more of a gene encoding a GGPPS polypeptide, a gene encoding a CDPS polypeptide, a gene encoding a KS polypeptide, a gene encoding a KO polypeptide, a gene encoding a KAH polypeptide, a gene encoding a CPR polypeptide, and a gene encoding a UGT polypeptide can produce a steviol glycoside and/or steviol glycoside precursors in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

In another example, a recombinant host expressing a gene encoding a GGPPS polypeptide, a gene encoding a CDPS polypeptide, a gene encoding a KS polypeptide, a gene encoding a KO polypeptide, a gene encoding a KAH polypeptide, and a gene encoding a CPR polypeptide can produce steviol in vivo. See, e.g., FIG. 1. The skilled worker will appreciate that one or more of these genes can be endogenous to the host provided that at least one (and in some embodiments, all) of these genes is a recombinant gene introduced into the recombinant host.

In another example, a steviol-producing recombinant host expressing a gene encoding a GGPPS polypeptide, a gene encoding a CDPS polypeptide, a gene encoding a KS polypeptide, a gene encoding a KO polypeptide, a gene encoding a KAH polypeptide, a gene encoding a CPR polypeptide, and one or more of a gene encoding a UGT polypeptide can produce a steviol glycoside in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

Non-limiting examples of KS polypeptides are set forth in SEQ ID NOs:1-4 and SEQ ID NO:6. Non-limiting examples of KO polypeptides are set forth in SEQ ID NOs:7-10, 54, 70-72, 75, and 77-79. Non-limiting examples of KAH polypeptides are set forth in SEQ ID NOs:13-17, 68, 82, and 91. Non-limiting examples of CPR polypeptides are set forth in SEQ ID NOs:20-22, 28, 69, 73, 74, 76, 87, and 98. Non-limiting examples of CDPS polypeptides are set forth in SEQ ID NOs:33-39. Non-limiting examples of CDPS-KS polypeptides are set forth in SEQ ID NOs:40-42. Non-limiting examples of GGPPS polypeptides are set forth in SEQ ID NOs:43-50.

In some embodiments, a recombinant host comprises a nucleic acid encoding a UGT85C2 polypeptide (SEQ ID NO:32), a nucleic acid encoding a UGT76G1 polypeptide (SEQ ID NO:83), a nucleic acid encoding a UGT74G1 polypeptide (SEQ ID NO:29), a nucleic acid encoding a UGT91D2 polypeptide, and/or a nucleic acid encoding a EUGT11 polypeptide (SEQ ID NO:86). In some aspects, the UGT91D2 polypeptide can be a UGT91D2e polypeptide (SEQ ID NO:84) or a UGT91D2e-b polypeptide (SEQ ID NO:88). The skilled worker will appreciate that expression of these genes may be necessary to produce a particular steviol glycoside but that one or more of these genes can be endogenous to the host provided that at least one (and in some embodiments, all) of these genes is a recombinant gene introduced into the recombinant host. In a particular embodiment, a steviol-producing recombinant microorganism comprises exogenous nucleic acids encoding UGT85C2, UGT76G1, or UGT91D2 polypeptides. In another particular embodiment, a steviol-producing recombinant microorganism comprises exogenous nucleic acids encoding UGT85C2, UGT76G1, UGT74G1, and UGT91D2 polypeptides. In yet another particular embodiment, a steviol-producing recombinant microorganism comprises exogenous nucleic acids encoding UGT85C2, UGT76G1, UGT74G1, and EUGT11 polypeptides. In yet another particular embodiment, a steviol-producing recombinant microorganism comprises the exogenous nucleic acids encoding UGT85C2, UGT76G1, UGT74G1, UGT91D2 (including inter alia 91D2e, 91D2m, 91D2e-b, and functional homologs thereof), and EUGT11 polypeptides.

In certain embodiments, the steviol glycoside is RebA, RebB, RebD, and/or RebM. RebA can be synthesized in a steviol-producing recombinant microorganism expressing UGT85C2, UGT76G1, UGT74G1, and UGT91D2. RebB can be synthesized in a steviol-producing recombinant microorganism expressing UGT85C2, UGT76G1, and UGT91D2. RebD can be synthesized in a steviol-producing recombinant microorganism expressing UGT85C2, UGT76G1 UGT74G1, and UGT91D2 and/or EUGT11. RebM can be synthesized in a steviol-producing recombinant microorganism expressing UGT85C2, UGT76G1, UGT74G1, and UGT91D2 and/or EUGT11 (see FIG. 2).

In some embodiments, steviol glycosides and/or steviol glycoside precursors are produced through contact of a steviol glycoside precursor with one or more enzymes involved in the steviol glycoside pathway in vitro. For example, contacting steviol with a UGT polypeptide can result in production of a steviol glycoside in vitro. In some embodiments, a steviol glycoside precursor is produced through contact of an upstream steviol glycoside precursor with one or more enzymes involved in the steviol glycoside pathway in vitro. For example, contacting ent-kaurenoic acid with a KAH enzyme can result in production of steviol in vitro.

In some embodiments, a steviol glycoside or steviol glycoside precursor is produced by whole cell bioconversion. For whole cell bioconversion to occur, a host cell expressing one or more enzymes involved in the steviol glycoside pathway takes up and modifies a steviol glycoside precursor in the cell; following modification in vivo, a steviol glycoside remains in the cell and/or is excreted into the culture medium. For example, a host cell expressing a gene encoding a UGT polypeptide can take up steviol and glycosylate steviol in the cell; following glycosylation in vivo, a steviol glycoside can be excreted into the culture medium. In some embodiments, the cell is permeabilized to take up a substrate to be modified or to excrete a modified product.

In some embodiments, steviol, one or more steviol glycoside precursors, and/or one or more steviol glycosides are produced by co-culturing of two or more hosts. In some embodiments, one or more hosts, each expressing one or more enzymes involved in the steviol glycoside pathway, produce steviol, one or more steviol glycoside precursors, and/or one or more steviol glycosides. For example, a host comprising a GGPPS, a CDPS, a KO, a KS, a KAH, and/or a CPR and a host comprising one or more UGTs produce one or more steviol glycosides.

In some embodiments, a steviol glycoside or steviol glycoside precursor composition produced in vivo, in vitro, or by whole cell bioconversion comprises less contaminants than a *stevia* extract from, inter alia, a *stevia* plant. Contaminants include plant-derived compounds that contribute to off-flavors. Potential contaminants include pigments, lipids, proteins, phenolics, saccharides, spathulenol and other sesquiterpenes, labdane diterpenes, monoterpenes, decanoic acid, 8,11,14-eicosatrienoic add, 2-methyloctadecane, pentacosane, octacosane, tetracosane, octadecanol, stigmasterol, β-sitosterol, α-amyrin, β-amyrin, lupeol, β-amryin acetate, pentacyclic triterpenes, centauredin, quercitin, epi-alpha-cadinol, carophyllenes and derivatives, beta-pinene, beta-sitosterol, and gibberellin.

As used herein, the terms "detectable amount," "detectable concentration," "measurable amount," and "measurable concentration" refer to a level of steviol glycosides measured in AUC, $\mu M/OD_{600}$, mg/L, $\mu M$, or mM. Steviol glycoside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in a steviol glycoside or steviol glycoside precursor composition.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides and/or steviol glycoside precursors. In some embodiments, "and/or" is used to refer to production of steviol glycosides, wherein one or more steviol glycosides are produced. In some embodiments, "and/or" is used to refer to production of steviol glycosides, wherein one or more steviol glycosides are produced through one or more of the following steps: culturing a recombinant microorganism, synthesizing one or more steviol glycosides in a recombinant microorganism, and/or isolating one or more steviol glycosides.

In some embodiments, the nucleotide sequence of a nucleic acid encoding a KO polypeptide is set forth in SEQ ID NO: 55, SEQ ID NO:56, SEQ ID NO:57, SEQ ID NO:58, SEQ ID NO:59, or SEQ ID NO:60, SEQ ID NO:63, SEQ ID NO:64, or SEQ ID NO:65. In some aspects, the nucleic acid encoding the KO polypeptide has at least 70% identity to the nucleotide sequence set forth in SEQ ID NO:55, SEQ ID NO:57, SEQ ID NO:59 or SEQ ID NO:60, at least 80% identity to the nucleotide sequence set forth in SEQ ID NO:56 or SEQ ID NO:58, at least 95% identity to the nucleotide sequence set forth in SEQ ID NO:63, or at least 75% identity to the nucleotide sequence set forth in SEQ ID NO:64 or SEQ ID NO:65. In some embodiments, the amino acid sequence of a KO enzyme is set forth in SEQ ID NO:54, SEQ ID NO:70, SEQ ID NO:71, SEQ ID NO:72, SEQ ID NO:75, SEQ ID NO:77, SEQ ID NO:78, OR SEQ ID NO:79. In some embodiments, a host cell comprises one or more copies of one or more nucleic acids encoding a KO polypeptide.

In some embodiments, expression of a KO gene set forth in SEQ ID NO:55 or SEQ ID NO:56 in a RebB-producing S. cerevisiae strain results in higher production of RebB compared to expression of SrKO1 (SEQ ID NO:59, SEQ ID NO:79) in a RebB-producing S. cerevisiae strain. See Example 3.

In some embodiments, expression of a KO gene set forth in SEQ ID NO:55, SEQ ID NO:56, or SEQ ID NO:57 in an S. cerevisiae strain capable of producing RebB with a functional KO results in production of ent-kaurenoic acid. See Example 3.

As used herein, the terms "ent-kaurenoic acid hydroxylase" and "steviol synthase" can be used interchangeably and be abbreviated "KAH." In some embodiments, the nucleotide sequence of a nucleic acid encoding a KAH enzyme is set forth in SEQ ID NO:18, SEQ ID NO:80, SEQ ID NO:81, SEQ ID NO:90, or SEQ ID NO:96. In some aspects, the nucleic acid encoding the KAH polypeptide has at least 75% identity to a nucleotide sequence set forth in SEQ ID NO:80; or at least 70% identity to a nucleotide sequence set forth in SEQ ID NO:18, SEQ ID NO:81, SEQ ID NO:90, or SEQ ID NO:96. In some embodiments, the amino acid sequence of a KAH enzyme is set forth in SEQ ID NO:68, SEQ ID NO:82, or SEQ ID NO:91. In some embodiments, a host cell comprises one or more copies of one or more nucleic acids encoding a KAH enzyme.

In some embodiments, one or more copies of SrKAHe1 (SEQ ID NO:18, SEQ ID NO:68) are expressed in an S. cerevisiae strain. For example, in some embodiments, two copies of SrKAHe1 (SEQ ID NO:18, SEQ ID NO:68) are expressed in an S. cerevisiae strain.

In some embodiments, the nucleotide sequence of a nucleic acid encoding a KAH enzyme is set forth in SEQ ID NO:80. The nucleic acid of SEQ ID NO:80 encodes a KAH with an amino acid sequence set forth in SEQ ID NO:82. A version of SEQ ID NO:80 codon-optimized for expression in S. cerevisiae is set forth in SEQ ID NO:81. In some embodiments, a host cell comprises one or more copies of one or more nucleic acids encoding a KAH enzyme. See Example 7.

In some embodiments, SrKAHe1 (SEQ ID NO:18, SEQ ID NO:68) and either the KAH encoded by the nucleotide sequence set forth in SEQ ID NO:80 or the KAH encoded by the codon-optimized nucleotide sequence set forth in SEQ ID NO:81 are co-expressed in a steviol glycoside-producing S. cerevisiae strain. In some embodiments, co-expression of SrKAHe1 (SEQ ID NO:18, SEQ ID NO:68) and either the KAH encoded by the nucleotide sequence set forth in SEQ ID NO:80 or the KAH encoded by the codon-optimized nucleotide sequence set forth in SEQ ID NO:81 in a steviol glycoside-producing strain results in higher production of steviol glycosides compared to a control steviol glycoside-producing strain or a steviol glycoside producing strain overexpressing SrKAHe1. See Example 7 and Table 6. In some aspects, overexpressing SrKAHe1 results in production of 85.5 µM 13-SMG, expression of SrKAHe1 and the KAH encoded by the nucleotide set forth in SEQ ID NO:80 results in production of 153.8 µM 13-SMG, and expression of SrKAHe1 and the KAH encoded by the nucleotide set forth in SEQ ID NO:81 results in production of 130.5 µM 13-SMG.

In some embodiments, a KO gene is expressed in a steviol glycoside-producing S. cerevisiae strain that further overexpresses SrKAHe1 (SEQ ID NO:18, SEQ ID NO:68). In some embodiments, expression of a KO gene of SEQ ID NO:55, SEQ ID NO:56, SEQ ID NO:57, SEQ ID NO:58, SEQ ID NO:59, or SEQ ID NO:60, SEQ ID NO:65 in a steviol glycoside-producing S. cerevisiae strain overexpressing SrKAHe1 results in higher expression of steviol glycosides compared to a control steviol-glycoside producing strain or a steviol glycoside-producing strain overexpressing SrKAHe1 (SEQ ID NO:18, SEQ ID NO:68). See Example 4.

In some embodiments, expression of a KO gene of SEQ ID NO:55, SEQ ID NO:56, SEQ ID NO:57, or SEQ ID NO:60 in a steviol glycoside-producing S. cerevisiae strain overexpressing SrKAHe1 (SEQ ID NO:18, SEQ ID NO:68) results in higher levels of glycosylated ent-kaurenoic acid compared to a control S. cerevisiae strain. See Example 4.

In some embodiments, expression of a KO gene of SEQ ID NO:55, SEQ ID NO:56, SEQ ID NO:57, SEQ ID NO:59, or SEQ ID NO:60 in a steviol glycoside-producing S. cerevisiae strain overexpressing SrKAHe1 (SEQ ID NO:18, SEQ ID NO:68) results in improved metabolic conversion of a glycosylated ent-kaurenol intermediate compound relative to a control S. cerevisiae strain or a steviol glycoside-producing *S. cerevisiae* strain overexpressing SrKAHe1 (SEQ ID NO:18, SEQ ID NO:68). See Example 4.

In some embodiments, a KAH is a *Prunus* KAH, such as a *Prunus avium, Prunus mume,* or *Prunus persica* KAH. In some embodiments, a KAH is a KAH of the CYP72A219 or CYP71A219-like family. In some embodiments, the nucleotide sequence of a nucleic acid encoding a KAH enzyme is set forth in SEQ ID NO:90 or SEQ ID NO:96. The nucleic acids of SEQ ID NO:90 and SEQ ID NO:96 encode a KAH from *Prunus avium* with an amino acid sequence set forth in SEQ ID NO:91. In some embodiments, a KAH polypeptide is a polypeptide with an amino acid sequence set forth in SEQ ID NO:92, SEQ ID NO:93, SEQ ID NO:94, or SEQ ID NO:95. In some embodiments, a KAH polypeptide is a KAH polypeptide with at least 50% sequence identity to an amino acid sequence set forth in SEQ ID NO:91, SEQ ID NO:92, SEQ ID NO:93, SEQ ID NO:94, or SEQ ID NO:95. In some embodiments, expression of a gene encoding a polypeptide having at least 50% sequence identity to an amino acid sequence set forth in SEQ ID NO:91, SEQ ID NO:92, SEQ ID NO:93, SEQ ID NO:94, or SEQ ID NO:95 in a recombinant host results in production of a steviol glycoside or steviol glycoside precursor, such as 13-SMG and/or rubusoside. See Example 8.

In some embodiments, the nucleotide sequence of the nucleic acid encoding a CPR enzyme is set forth in SEQ ID NO:23, SEQ ID NO:51, SEQ ID NO:61, SEQ ID NO:62, SEQ ID NO:66, SEQ ID NO:67, or SEQ ID NO:97. In some aspects, the nucleic acid encoding the CPR polypeptide has at least 75% identity to the nucleotide sequence set forth in SEQ ID NO:23, SEQ ID NO:61, or SEQ ID NO:62, or at least 70% identity to the nucleotide sequence set forth in SEQ ID NO:24, SEQ ID NO:66, SEQ ID NO:67, SEQ ID NO:51, or SEQ ID NO:97. In some embodiments, the amino acid sequence of the CPR enzyme is set forth in SEQ ID NO:22, SEQ ID NO:28, SEQ ID NO:69, SEQ ID NO:73, SEQ ID NO:74, or SEQ ID NO:76, SEQ ID NO:87, or SEQ ID NO:98. In some embodiments, a host cell comprises one or more copies of one or more nucleic acids encoding a CPR enzyme.

In a non-limiting example, SrKAHe1 is activated by the *S. cerevisiae* CPR encoded by gene NCP1 (YHR042VV). Enhanced activation of the KAH encoded by SrKAHe1 is observed when the *Arabidopsis thaliana* CPR encoded by the gene ATR2 (SEQ ID NO:51) or the *S. rebaudiana* CPR encoded by the genes CPR7 (SEQ ID NO:23) or CPR8 (SEQ ID NO:24, SEQ ID NO:28) are co-expressed in a recombinant cell. Amino acid sequences of the *A. thaliana* polypeptides ATR1 and ATR2 are set forth in SEQ ID NO:25 and SEQ ID NO:26, respectively. The *S. rebaudiana* polypeptides CPR7 and CPR8 are set forth in SEQ ID NO:27 and SEQ ID NO:28, respectively.

In some embodiments, expression of CPR1 (SEQ ID NO:61, SEQ ID NO:76) or of CPR7 in the steviol glycoside-producing *S. cerevisiae* strain co-expressing *S. rebaudiana* CPR8 (SEQ ID NO:24, SEQ ID NO:28) and *A. thaliana* ATR2 (SEQ ID NO:51) results in higher levels of RebM compared to a control steviol glycoside-producing *S. cerevisiae* strain expressing *S. rebaudiana* CPR8 (SEQ ID NO:24, SEQ ID NO:28) and *A. thaliana* ATR2 (SEQ ID NO:51). In some embodiments, expression of the CPR set forth in SEQ ID NO:62 in a steviol glycoside-producing *S. cerevisiae* strain overexpressing SrKAHe1 (SEQ ID NO:18, SEQ ID NO:68) results in higher levels of RebM compared to a steviol glycoside-producing *S. cerevisiae* strain that does not express the nucleic acid set forth in SEQ ID NO:62 or overexpress SrKAHe1. See Example 5.

In some embodiments, co-expression of SrKO1 (SEQ ID NO:59, SEQ ID NO:79) and a CPR gene of SEQ ID NO:66 or SEQ ID NO:77 in a RebB-producing strain results in higher production of 13-SMG and RebB than co-expression of a KO gene of SEQ ID NO:63 or SEQ ID NO:64 and a CPR gene of SEQ ID NO:66 or SEQ ID NO:77. See Example 6.

In some embodiments, CPR1 (SEQ ID NO:61, SEQ ID NO:76) or CPR12 (SEQ ID NO:97, SEQ ID NO:98) activates cytochrome c. In some embodiments, CPR1 (SEQ ID NO:61, SEQ ID NO:76) or CPR12 (SEQ ID NO:97, SEQ ID NO:98) in the presence of SrKAHe1 (SEQ ID NO:18, SEQ ID NO:68) activate cytochrome c. In some embodiments, CPR1 (SEQ ID NO:61, SEQ ID NO:76) or CPR12 (SEQ ID NO:97, SEQ ID NO:98) regulate conversion of ent-kaurenoic acid to steviol. In some embodiments, CPR1 (SEQ ID NO:61, SEQ ID NO:76) or CPR12 (SEQ ID NO:97, SEQ ID NO:98) in combination with SrKAHe1 (SEQ ID NO:18, SEQ ID NO:68) convert ent-kaurenoic acid to steviol. In some embodiments, steviol production is detected upon incubation of ent-kaurenoic acid with microsomal protein prepared from *S. cerevisiae* strains expressing CPR1 (SEQ ID NO:61, SEQ ID NO:76) or CPR12 (SEQ ID NO:97, SEQ ID NO:98) in combination with SrKAHe1 (SEQ ID NO:18, SEQ ID NO:68). In some embodiments, expression of CPR1 (SEQ ID NO:61, SEQ ID NO:76) or CPR12 (SEQ ID NO:97, SEQ ID NO:98) in a recombinant host results in production of a steviol glycoside or steviol glycoside precursor. See Example 9.

In some embodiments, a steviol glycoside-producing strain expresses a fusion construct comprising a KO and the NADPH-dependent P450 oxidoreductase domain of CYP102A1, referred to herein as "BMR." The codon-optimized nucleotide sequence encoding the BMR polypeptide is set forth in SEQ ID NO:117; the BMR amino acid sequence is set forth in SEQ ID NO:118. In some embodiments, BMR is a mutant BMR, including, but not limited to a BMR W1046A mutant (SEQ ID NO:119, SEQ ID NO:120). The BMR mutant can be specific for NADH. In some embodiments, the KO-BMR fusion construct comprises a linker (SEQ ID NO:121, SEQ ID NO:122). In some embodiments, the KO of the fusion construct is SrKO1 (SEQ ID NO:59, SEQ ID NO:79) or the KO encoded by the nucleotide sequence set forth in SEQ ID NO:65 (corresponding to the amino acid sequence set forth in SEQ ID NO:75). In some embodiments, the KO of the fusion construct is a truncated KO. Exemplary KO-BMR fusion constructs are set forth in SEQ ID NOs:99-112. See Example 10.

In some embodiments, expression of SrKO1-BMR fusion constructs (SEQ ID NOs:99-106) in a steviol glycoside-producing strain results in an increase in ent-kaurenoic acid, 13-SMG, and RebB levels, compared to expression of SrKO1 (SEQ ID NO:59, SEQ ID NO:79) in a steviol glycoside-producing strain. In some embodiments, expression of a fusion construct (SEQ ID NO:107, SEQ ID NO:108) in a steviol glycoside-producing strain results in greater conversion of ent-kaurene to ent-kaurenoic acid and greater conversion of ent-kaurenoic acid to 13-SMG, compared to expression of the KO encoded by the nucleotide sequence set forth in SEQ ID NO:65 in a steviol glycoside-producing strain. In some embodiments, expression of a fusion construct comprising the KO encoded by the nucleotide sequence set forth in SEQ ID NO:65 and the W1046A mutant BMR (SEQ ID NO:109, SEQ ID NO:110) results in increased ent-kaurenoic acid levels. See FIG. 16 (B and D) and Example 10.

In some embodiments, a steviol glycoside-producing strain comprises inheritance of cortical ER protein 2 (ICE2; SEQ ID NO:113, SEQ ID NO:114). ICE2 is also referred to as YIL090W. In some aspects, ICE2 is overexpressed. ICE2 can be expressed in a strain comprising CPR1 (SEQ ID NO:61, SEQ ID NO:76) and/or CPR12 (SEQ ID NO:97, SEQ ID NO:98). In some embodiments, a steviol glycoside-producing strain comprises two copies of ICE2. In some embodiments, expression of ICE2 increases ent-kaurene metabolism (resulting in decreased accumulation of ent-kaurene, ent-kaurenol, ent-kaurenal, and ent-kaurenol glycosides), resulting in increased accumulation of steviol glycosides, compared to a control strain. See Table 10 and Example 11.

In some embodiments, expression of the KO encoded by nucleotide sequence set forth in SEQ ID NO:56 in a steviol glycoside-producing strain cultivated by fermentation results in a lower accumulation of ent-kaurene compounds, compared to a control steviol glycoside-producing strain. In some aspects, higher levels of ent-kaurenoic acid and steviol glycosides result, as compared to a control strain. In some embodiments, expression of the KAH encoded by nucleotide sequence set forth in SEQ ID NO:80, the KO encoded by nucleotide sequence set forth in SEQ ID NO:56, and the KO encoded by nucleotide sequence set forth in SEQ ID NO:65 in a steviol glycoside-producing strain cultivated by fermentation results in decreased accumulation of ent-kaurene, ent-kaurenol, ent-kaurenal, ent-kaurenol glycosides, ent-kaurenoic acid, and ent-kaurenoic acid glycosides and increased production of steviol glycosides, as compared to a control strain. In some embodiments, expression of CPR12 (SEQ ID NO:97, SEQ ID NO:98), the KAH encoded by nucleotide sequence set forth in SEQ ID NO:80, and the KO encoded by nucleotide sequence set forth in SEQ ID NO:56 cultivated by fermentation results in decreased ent-kaurene, ent-kaurenol, ent-kaurenal, ent-kaurenol glycosides, ent-kaurenoic acid, and ent-kaurenoic acid glycosides accumulation and higher levels of steviol glycosides, as compared to a control strain. See Table 12 and Example 12.

Functional Homologs

Functional homologs of the polypeptides described above are also suitable for use in producing steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol glycoside biosynthesis polypeptides. Sequence analysis can involve BLAST, Reciprocal BLAST, or PSI-BLAST analysis of non-redundant databases using a KO, KAH, or CPR amino acid sequence as the reference sequence. Amino acid sequence is, in some instances, deduced from the nucleotide sequence. Those polypeptides in the database that have greater than 40% sequence identity are candidates for further evaluation for suitability as a steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol glycoside biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.*, 26:320-322 (1998); Sonnhammer et al., Proteins, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol in a recombinant host include functional homologs of KO, KAH, and CPR.

Methods to modify the substrate specificity of, for example, KO, KAH, or CPR, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, *Phytochemistry* 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine % identity of a candidate nucleic acid or amino acid sequence to a reference sequence, the sequences are aligned using ClustalW, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional KO, KAH, or CPR proteins can include additional amino acids that are not involved in the enzymatic activities carried out by the enzymes. In some embodiments, KO, KAH, or CPR proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins. In some embodiments, a nucleic acid sequence encoding a KO, KAH, or CPR polypeptide can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, CT). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a KO polypeptide is altered by domain swapping. See Example 10.

Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. In such cases, a nucleic acid that overexpresses the polypeptide or gene product may be included in a recombinant construct that is transformed into the strain. Alternatively, mutagenesis can be used to generate mutants in genes for which it is desired to increase or enhance function.

Host Microorganisms

Recombinant hosts can be used to express polypeptides for the producing steviol glycosides, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a steviol glycoside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a defined temperature(s) for a desired period of time. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

Carbon sources of use in the instant method include any molecule that can be metabolized by the recombinant host cell to facilitate growth and/or production of the steviol glycosides. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After the recombinant microorganism has been grown in culture for the desired period of time, steviol and/or one or more steviol glycosides can then be recovered from the culture using various techniques known in the art. In some embodiments, a permeabilizing agent can be added to aid the feedstock entering into the host and product getting out. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC. See also, WO 2009/140394.

It will be appreciated that the various genes and modules discussed herein can be present in two or more recombinant hosts rather than a single host. When a plurality of recombinant hosts is used, they can be grown in a mixed culture to accumulate steviol and/or steviol glycosides.

Alternatively, the two or more hosts each can be grown in a separate culture medium and the product of the first culture medium, e.g., steviol, can be introduced into second culture medium to be converted into a subsequent intermediate, or into an end product such as, for example, RebA. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis, Rhodoturula mucilaginosa, Phaffia rhodozyma, Xanthophyllomyces dendrorhous, Fusarium fujikuroi/Gibberella fujikuroi, Candida utilis, Candida glabrata, Candida albicans,* and *Yarrowia lipolytica*.

In some embodiments, a microorganism can be a prokaryote such as *Escherichia* bacteria cells, for example, *Escherichia coli* cells; *Lactobacillus* bacteria cells; *Lactococcus* bacteria cells; *Corynebacterium* bacteria cells; *Acetobacter* bacteria cells; *Acinetobacter* bacteria cells; or *Pseudomonas* bacterial cells.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii,* or *S. cerevisiae*.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a cyanobacterial cell such as *Blakeslea trispora, Dunaliella salina, Haematococcus pluvialis, Chlorella* sp., *Undaria pinnatifida,* Sargassum, *Laminaria japonica, Scenedesmus almeriensis*.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger,* and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing steviol glycosides.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella,* and *Phanerochaete* spp.

*Agaricus, Gibberella,* and *Phanerochaete* spp. can be useful because they are known to produce large amounts of isoprenoids in culture. Thus, the terpene precursors for producing large amounts of steviol glycosides are already produced by endogenous genes. Thus, modules comprising recombinant genes for steviol glycoside biosynthesis polypeptides can be introduced into species from such genera without the necessity of introducing mevalonate or MEP pathway genes.

*Arxula adeninivorans (Blastobotrys adeninivorans)*

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorgamism. *Yarrowia lipolytica* can accumulate lipid content to approximately 40% of its dry cell weight and is a model organism for lipid accumulation and remobilization. See e.g., Nicaud, 2012, *Yeast* 29(10):409-18; Beopoulos et al., 2009, *Biochimie* 91(6):692-6; Bankar et al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4): 1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

Steviol Glycoside Compositions

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD or RebM) and have a consistent taste profile. As used herein, the term "enriched" is used to describe a steviol glycoside composition with an increased proportion of a particular steviol glycoside, compared to a steviol glycoside composition (extract) from a *stevia* plant. Thus, the recombinant hosts described herein can facilitate the production of compositions that are tailored to meet the sweetening profile desired for a given food product and that have a proportion of each steviol glycoside that is consistent from batch to batch. In some embodiments, hosts described herein do not produce or produce a reduced amount of undesired plant by-products found in *Stevia* extracts. Thus, steviol glycoside compositions produced by the recombinant hosts described herein are distinguishable from compositions derived from *Stevia* plants.

The amount of an individual steviol glycoside (e.g., RebA, RebB, RebD, or RebM) accumulated can be from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of an individual steviol glycoside can exceed 7,000 mg/L. The amount of a combination of steviol glycosides (e.g., RebA, RebB, RebD, or RebM) accumulated can be from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of steviol glycosides can exceed 7,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing a steviol glycoside precursor, while a second microorganism comprises steviol glycoside biosynthesis genes. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., steviol, can be introduced into second culture medium to be converted into a subsequent intermediate, or into an end product such as RebA. The product produced by the second, or final microorganism is then recovered. It will also be appreciated that in some embodiments, a recombinant microorganism is grown using nutrient sources other than a culture medium and utilizing a system other than a fermenter.

Steviol glycosides and compositions obtained by the methods disclosed herein can be used to make food products, dietary supplements and sweetener compositions. See, e.g., WO 2011/153378, WO 2013/022989, WO 2014/122227, and WO 2014/122328.

For example, substantially pure steviol or steviol glycoside such as RebM or RebD can be included in food products such as ice cream, carbonated beverages, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately, each producing a specific steviol or steviol glycoside, recovering the steviol or steviol glycoside in substantially pure form from each microorganism and then combining the compounds to obtain a mixture comprising each compound in the desired proportion. The recombinant microorganisms described herein permit more precise and consistent mixtures to be obtained compared to current *Stevia* products.

In another alternative, a substantially pure steviol or steviol glycoside can be incorporated into a food product along with other sweeteners, e.g. saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. 2007/0128311. In some embodiments, the steviol or steviol glycoside may be provided with a flavor (e.g., citrus) as a flavor modulator.

Compositions produced by a recombinant microorganism described herein can be incorporated into food products. For example, a steviol glycoside composition produced by a recombinant microorganism can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism can be incorporated into a baked good (e.g., a biscuit) such that the food product has a maximum of 300 mg steviol glycoside/kg food on a dry weight basis. A steviol glycoside composition produced by a recombinant microorganism can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism can be incorporated into a bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis. In some embodiments, a steviol glycoside composition produced herein is a component of a pharmaceutical composition. See, e.g., Steviol Glycosides Chemical and Technical Assessment 69th JECFA, 2007, prepared by Harriet Wallin, Food Agric. Org.; EFSA Panel on Food Additives and Nutrient Sources added to Food (ANS), "Scientific Opinion on the safety of steviol glycosides for the proposed uses as a food additive," 2010, *EFSA Journal* 8(4):1537; U.S. Food and Drug Administration GRAS Notice 323; U.S Food and Drug Administration GRAS Notice 329; WO 2011/037959; WO 2010/146463; WO 2011/046423; and WO 2011/056834.

For example, such a steviol glycoside composition can have from 90-99 weight % RebA and an undetectable amount of *stevia* plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a RebB-enriched composition having greater than 3 weight % RebB and be incorporated into the food product such that the amount of RebB in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebB-enriched composition has an undetectable amount of *stevia* plant-derived contaminants.

Such a steviol glycoside composition can be a RebD-enriched composition having greater than 3 weight % RebD and be incorporated into the food product such that the amount of RebD in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebD-enriched composition has an undetectable amount of *stevia* plant-derived contaminants.

Such a steviol glycoside composition can be a RebE-enriched composition having greater than 3 weight % RebE and be incorporated into the food product such that the amount of RebE in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebE-enriched composition has an undetectable amount of *stevia* plant-derived contaminants.

Such a steviol glycoside composition can be a RebM-enriched composition having greater than 3 weight % RebM and be incorporated into the food product such that the amount of RebM in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebM-enriched composition has an undetectable amount of *stevia* plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for RebA, RebB, RebD, RebE, or RebM, can be package in a sachet, for example, at from 10,000 to 30,000 mg steviol glycoside/kg product on a dry weight basis, for tabletop use. In some embodiments, a steviol glycoside produced in vitro, in vivo, or by whole cell bioconversion The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1. LC-MS Analytical Procedures

Three LC-MS procedures were used herein. In the first method used for Examples 2-6, LC-MS analyses were performed using an Ultimate 3000 UPLC system (Dionex) fitted with a Waters Acquity UPLC® BEH shield RP18 column (2.1×50 mm, 1.7 µm particles, 130 Å pore size) connected to a TSQ Quantum Access (ThermoFisher Scientific) triple quadropole mass spectrometer with a heated electrospray ion (HESI) source. Elution was carried out using a mobile phase of eluent B (MeCN with 0.1% formic acid) and eluent A (water with 0.1% formic acid) by increasing the gradient from 25% to 47% B from min 0.0 to 4.0, increasing 47% to 100% B from min 4.0 to 5.0, and holding 100% B from min 5.0 to 6.5. The flow rate was 0.4 mL/min and the column temperature 35° C. Steviol glycosides were detected using SIM (Single Ion Monitoring) with the following m/z-traces.

TABLE 1A

LC-MS analytical information for Steviol Glycosides.

| Description | Exact Mass | m/z trace (Da) | compound (typical $t_R$ in min) |
|---|---|---|---|
| Steviol + 1 Glucose | [M + H]⁺ 481.2796<br>[M + Na]⁺ 503.2615 | 481.2 ± 0.5<br>503.1 ± 0.5 | 19-SMG (2.29), 13-SMG (3.5) |
| Steviol + 2 Glucose | [M + Na]⁺ 665.3149 | 665 ± 0.5 | Rubusoside (2.52)<br>Steviol-1,2-bioside (2.92)<br>Steviol-1,3-bioside (2.28) |
| Steviol + 3 Glucose | [M + Na]⁺ 827.3677 | 827.4 ± 0.5 | 1,2-Stevioside (2.01)<br>1,3-Stevioside (2.39)<br>Rebaudioside B (2.88) |
| Steviol + 4 Glucose | [M + Na]⁺ 989.4200 | 989.4 ± 0.5 | Rebaudioside A (2.0) |
| Steviol + 5 Glucose | [M + Na]⁺ 1151.4728 | 1151.4 ± 0.5 | Rebaudioside D (1.1) |
| Steviol + 6 Glucose | [M + Na]⁺ 1313.5257 | 1313.5 ± 0.5 | Rebaudioside M (1.3) |

In the second method used for Examples 7, 8, and 10, LC-MS analyses were performed on Waters ACQUITY UPLC (Waters Corporation, Milford, MA) with coupled to a Waters ACQUITY ESI (electrospray ionization)-TQD triple quadropole mass spectrometer. Compound separation was achieved on Waters ACQUITY UPLC® BEH C18 column (2.1×50 mm, 1.7 µm particles, 130 Å pore size) equipped with ACQUITY UPLC BEH C18 VanGuard pre-column (130 Å, 1.7 µm, 2.1 mm×5 mm) by using a gradient of the two mobile phases: A (Water with 0.1% formic acid) and B (Acetonitrile with 0.1% formic acid) increasing B from 20% to 50% between 0.3 to 2.0 min up to 100% at 2.01 min, holding to 100% for 0.6 min, and re-equilibrating for 0.6 min. The flow rate was 0.6 mL/min, and the column temperature was 55° C. The MS acquisition was in negative ion-mode using SIM mode (Single Ion Monitoring). Steviol glycoside quantification was done by comparison with authentic standards.

TABLE 1B

MS analytical information for Steviol Glycosides.

| Compound | m/z trace (Da) | Retention time (min) |
|---|---|---|
| RebE | 965.42 | 1.06 |
| RebD | 1127.48 | 1.09 |
| RebM | 1289.53 | 1.15 |
| RebA | 965.42 | 1.43 |
| 1,3-Stevioside | 803.37 | 1.60 |
| Rubusoside | 641.32 | 1.67 |
| RebB | 803.37 | 1.76 |
| 1,2-bioside | 641.32 | 1.77 |
| 13-SMG | 479.26 | 2.04 |

In the third method used for Example 9, LC-MS analyses were performed on Waters ACQUITY UPLC (Waters Corporation, Milford, MA) using a Waters Acquity UPLC® BEH C18 column (2.1×50 mm, 1.7 µm particles, 130 Å) coupled to a Waters single quadropole mass spectrometer (SQD), equipped with an ESI and operated in negative mode. Compound separation was achieved by a gradient of the two mobile phases: A (water with 0.1% formic acid) and B (acetonitrile with 0.1% formic acid) by increasing from 60% to 100% B between 0.3 to 2.5 min, holding 100% B for 0.1 min, and re-equilibrating for 0.2 min. The flow rate was 0.6 mL/min, and the column temperature was set at 55° C. Steviol or ent-kaurenoic acid was monitored using SIM (Single Ion Monitoring) and quantified by comparing with authentic standards.

TABLE 1C

MS analytical information for steviol and ent-kaurenoic acid.

| Compound | m/z trace (Da) | Retention time (min) |
|---|---|---|
| Steviol | 317.21 | 0.61 |
| Ent-kaurenoic acid | 301.001 | 1.46 |

Example 2. Construction of Steviol Glycoside-Producing and RebB-Producing Yeast Strains Steviol glycoside-producing *S. cerevisiae* strains were constructed as described in WO 2011/153378, WO 2013/022989, WO 2014/122227, and WO 2014/122328. For example, a yeast strain comprising a recombinant gene encoding a Synechococcus sp. GGPPS (SEQ ID NO:49) polypeptide, a recombinant gene encoding a truncated *Zea mays* CDPS (SEQ ID NO:37) polypeptide, a recombinant gene encoding an *A. thaliana* KS (SEQ ID NO:6) polypeptide, a recombinant gene encoding an *S. rebaudiana* KO (SEQ ID NO:59, SEQ ID NO:79) polypeptide, a recombinant gene encoding an *A. thaliana* ATR2 (SEQ ID NO:51, SEQ ID NO:87) polypeptide, a recombinant gene encoding an *O. sativa* EUGT11 (SEQ ID NO:86) polypeptide, a recombinant gene encoding an SrKAHe1 (SEQ ID NO:18, SEQ ID NO:68) polypeptide, a recombinant gene encoding an *S. rebaudiana* CPR8 (SEQ ID NO:24, SEQ ID NO:28) polypeptide, a recombinant gene encoding an *S. rebaudiana* UGT85C2 (SEQ ID NO:30) polypeptide, a recombinant gene encoding an *S. rebaudiana* UGT74G1 (SEQ ID NO:29) polypeptide, a recombinant gene encoding an *S. rebaudiana* UGT76G1 (SEQ ID NO:2) polypeptide, and a recombinant gene encoding an *S. rebaudiana* UGT91D2 variant, UGT91D2e-b (SEQ ID NO:88), polypeptide accumulated steviol glycosides.

The UGT91D2e-b variant of UGT91D2 (SEQ ID NO:5 from PCT/US2012/050021) includes a substitution of a methionine for leucine at position 211 and a substitution of an alanine for valine at position 286. Additional variants can include variants (except T144S, M152L, L213F, S364P, and G384C variants) described in Table 14 and Example 11 of the PCT/US2012/050021. GeneArt codon-optimized sequence encoding a *S. rebaudiana* UGT91D2e-b with the amino acid modifications L211M and V286A (SEQ ID NO:88 for amino acid sequence; codon optimized nucleotide sequence is set forth in SEQ ID NO:89) and expressed from the native yeast TDH3 promoter and followed by the native yeast CYC1 terminator.

Cells were grown in Synthetic Complete (SC) medium at 30° C. for 5 days with shaking (400 rpm for deep wells and 200 rpm for 15 mL Falcon growth tubes) prior to harvest. Culture samples (without cell removal) were heated in the presence of DMSO for detection of total glycoside levels with LC-MS. The strain accumulated total amounts of RebD of over 2500 mg/L, total amounts of RebM of over 2500 mg/L, and total amounts of RebA of over 700 mg/L. See WO 2014/122227.

A separate S. cerevisiae strain was constructed to accumulate RebB. This strain comprised a recombinant gene encoding a Synechococcus sp. GGPPS (SEQ ID NO:49) polypeptide, a recombinant gene encoding a truncated Z. mays CDPS (SEQ ID NO:37) polypeptide, a recombinant gene encoding an A. thaliana KS (SEQ ID NO:6) polypeptide, a recombinant gene encoding an S. rebaudiana KO (SEQ ID NO:59, SEQ ID NO:79) polypeptide, a recombinant gene encoding an A. thaliana ATR2 (SEQ ID NO:51, SEQ ID NO:87) polypeptide, a recombinant gene encoding an O. sativa EUGT11 (SEQ ID NO:86) polypeptide, a recombinant gene encoding an SrKAHe1 (SEQ ID NO:18, SEQ ID NO:68) polypeptide, a recombinant gene encoding an S. rebaudiana CPR8 (SEQ ID NO:24, SEQ ID NO:28) polypeptide, a recombinant gene encoding an S. rebaudiana UGT85C2 (SEQ ID NO:30) polypeptide, a recombinant gene encoding an S. rebaudiana UGT76G1 (SEQ ID NO:2) polypeptide, and a recombinant gene encoding an S. rebaudiana UGT91D2 variant, UGT91D2e-b (SEQ ID NO:88), polypeptide accumulated steviol glycosides.

Example 3. Steviol Glycoside Production in Yeast Strains Expressing KO Genes

To determine whether increased levels of ent-kaurenoic acid improve steviol glycoside production, the activity of KO genes from various species were analyzed. Putative KO genes were identified using the NCBI Basic Local Alignment Sequence Search Tool (BLAST). Genes encoding KO polypeptides were cloned and expressed the RebB-producing S. cerevisiae strain described in Example 2, which was modified to lack KO genes. Thus, RebB was only accumulated upon expression of a functional KO.

Figure 3:
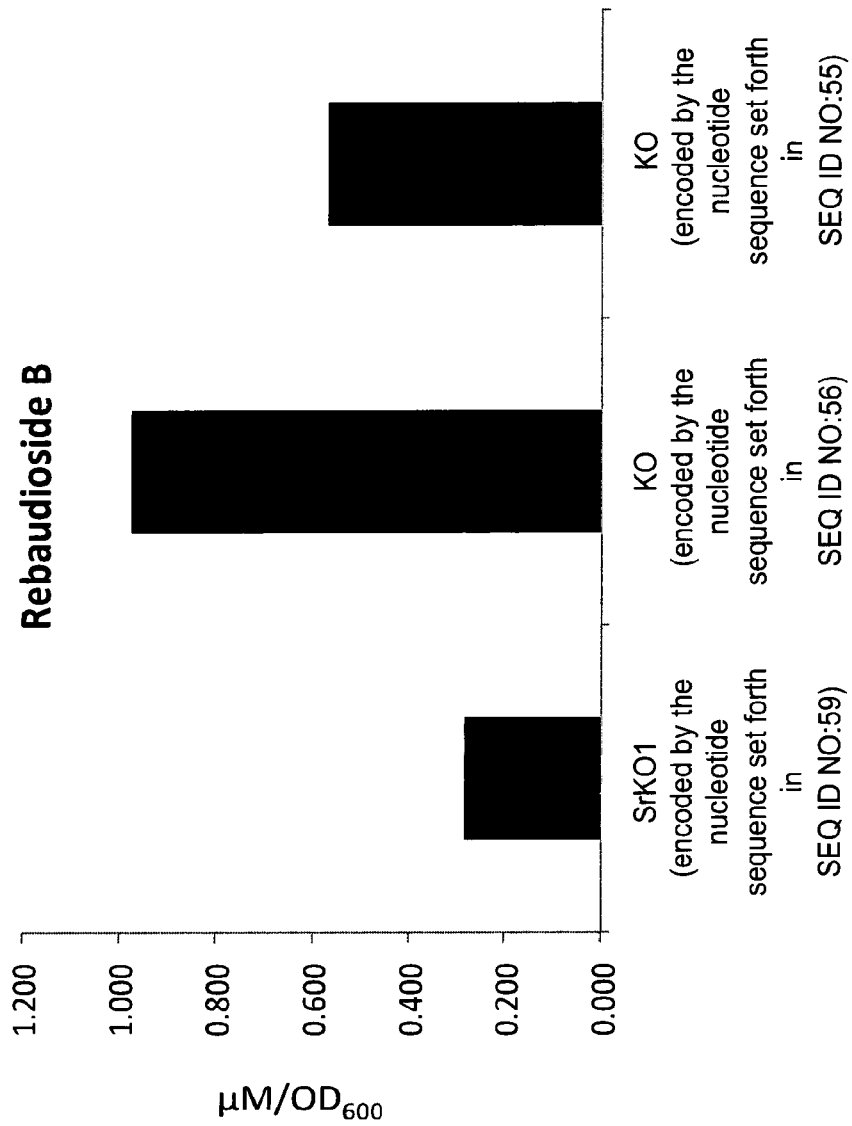
FIG. 3 shows Rebaudioside B (RebB) production in a steviol glycoside-producing *S. cerevisiae* strain individually expressing *S. rebaudiana* KO1 (SrKO1) encoded by the nucleotide sequence set forth in SEQ ID NO:59, the KO encoded by the codon-optimized nucleotide sequence set forth in SEQ ID NO:55, or the KO encoded by the nucleotide sequence set forth in SEQ ID NO:56. RebB production was measured by liquid chromatography-mass spectrometry (LC-MS) analysis as $\mu M/OD_{600}$ of individual cultures. See Example 3.

Two KO polypeptides identified by the amino acid sequences set forth in SEQ ID NO:54 (nucleotide sequence set forth in SEQ ID NO:55) and SEQ ID NO:75 (nucleotide sequences set forth in SEQ ID NO:56) were found to accumulate higher levels of RebB than SrKO1 (nucleotide sequence set forth in SEQ ID NO:59, amino acid sequences set forth in SEQ ID NO:79) in the RebB-producing strain. RebB levels ($\mu M/OD_{600}$) are shown in FIG. 3.

Figure 4:
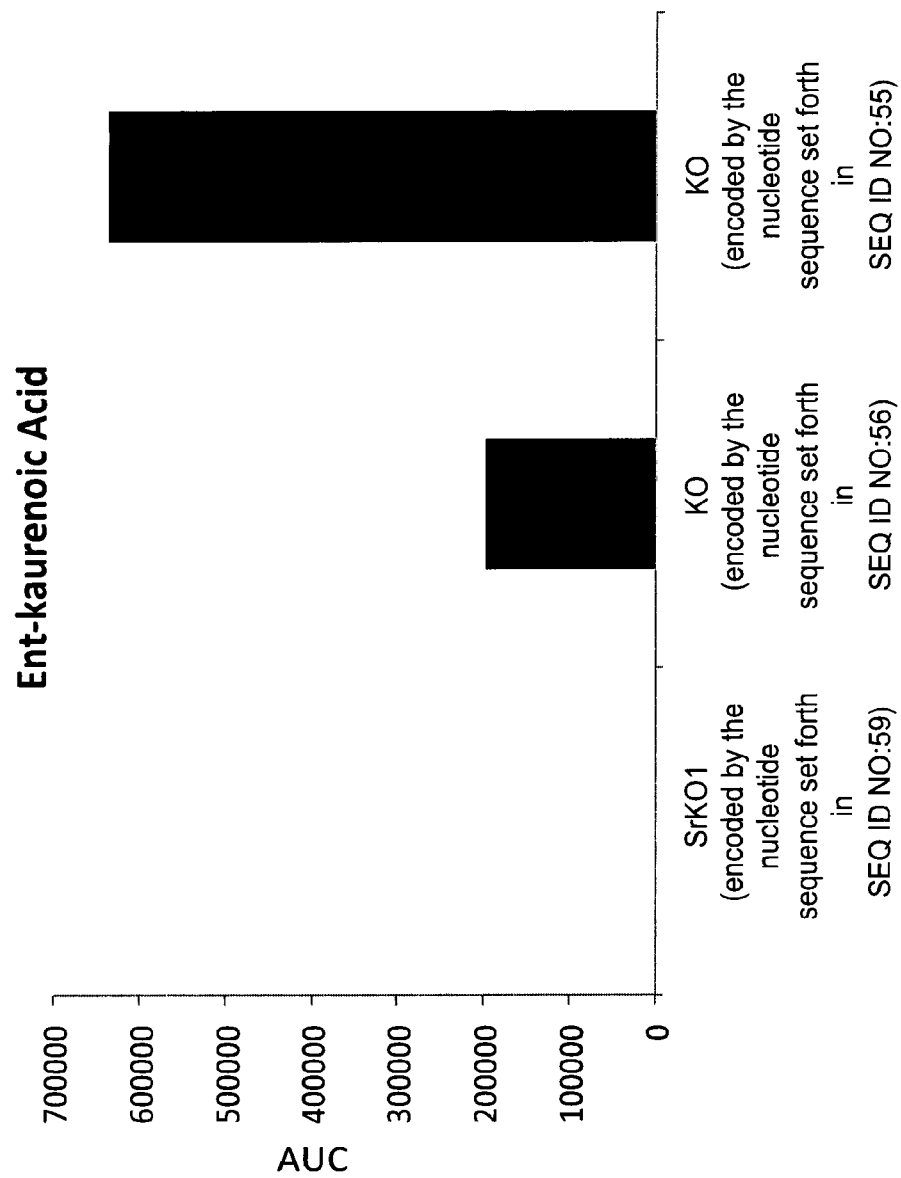
FIG. 4 shows production of ent-kaurenoic acid in steviol glycoside-producing *S. cerevisiae* strains individually expressing SrKO1 encoded by the nucleotide sequence set forth in SEQ ID NO:59, the KO encoded by the codon-optimized nucleotide sequence set forth in SEQ ID NO:55, or the KO encoded by the nucleotide sequence set forth in SEQ ID NO:56, as measured by LC-MS analysis of culture samples. Ent-kaurenoic acid levels were calculated as the Area under Curve (AUC) of LC-MS peaks corresponding to ent-kaurenoic acid. See Example 3.

Expression of genes (SEQ ID NO:55 or SEQ ID NO:56) encoding KO polypeptides in an S. cerevisiae steviol glycoside-producing strain also resulted in accumulation of ent-kaurenoic acid (FIG. 4). Expression of a gene encoding a codon-optimized KO polypeptide (SEQ ID NO:57) and a gene encoding the KO polypeptide set forth in SEQ ID NO:70 also resulted in accumulation of ent-kaurenoic acid. However, expression of SrKO1 (SEQ ID NO:59, SEQ ID NO:79) did not result in measurable levels of ent-kaurenoic acid. Thus, the KO polypeptides encoded by nucleotide sequences set forth in SEQ ID NOs: 55-57 more efficiently converted ent-kaurene, ent-kaurenol, and/or ent-kaurenal to ent-kaurenoic acid in S. cerevisiae, as compared to the SrKO1 polypeptide encoded by nucleotide sequence set forth in SEQ ID NO:59.

Example 4. Steviol Glycoside Production in Yeast Strains Expressing KO Genes and Further Overexpressing SrKAHe1

Cloned KO genes were individually expressed in a steviol glycoside-producing S. cerevisiae strain. The S. cerevisiae strain described in Example 2, which expresses SrKO1 (SEQ ID NO:59, SEQ ID NO:79), was modified to comprise overexpress SrKAHe1 (SEQ ID NO:18, SEQ ID NO:68). The coding sequences of the KO genes tested, as well as their corresponding amino acid sequences, are set forth in Table 2. The sequences set forth in SEQ ID NOs: 55, 57, 58, 59, and 60 were codon-optimized for expression in S. cerevisiae.

TABLE 2

KO Genes Expressed in Steviol Glycoside-Producing S. cerevisiae strain that Further Overexpresses SrKAHe1.

| KO Nucleotide Sequence | Corresponding KO Amino Acid Sequence |
| --- | --- |
| SEQ ID NO: 55 | SEQ ID NO: 54 |
| SEQ ID NO: 56 | SEQ ID NO: 75 |
| SEQ ID NO: 57 | SEQ ID NO: 70 |
| SEQ ID NO: 58 | SEQ ID NO: 71 |
| SEQ ID NO: 59 | SEQ ID NO: 79 |
| SEQ ID NQ: 60 | SEQ ID NO: 72 |

Figure 5:
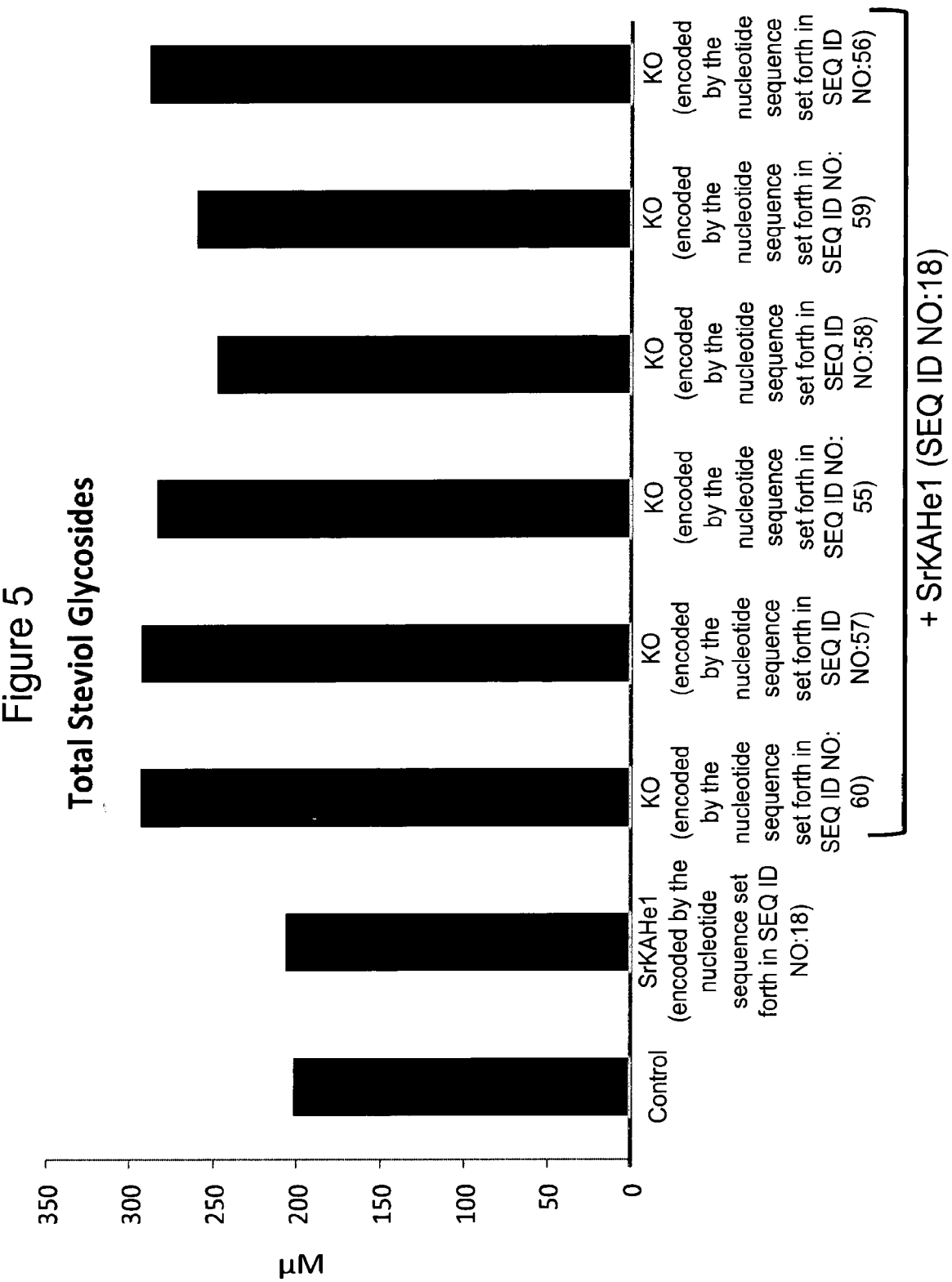
FIG. 5 shows production of total (extracellular plus intracellular) steviol glycosides in a steviol glycoside-producing *S. cerevisiae* strain overexpressing *S. rebaudiana* KAHe1 (SrKAHe1; encoded by the nucleotide sequence set forth in SEQ ID NO:18) or in a steviol glycoside-producing *S. cerevisiae* stain co-expressing SrKAHe1 (encoded by the nucleotide sequence set forth in SEQ ID NO:18) and a KO encoded by the nucleotide sequences set forth in any one of SEQ ID NOs: 55-60, compared to a control strain that does not overexpress SrKAHe1 or express a KO encoded by the nucleotide sequence set forth in any one of SEQ ID NOs: 55-60. Production of total steviol glycosides was quantified by comparison to a standard curve. Values plotted on the y-axis in $\mu M$ are an average of three biological replicates. See Example 4.
Figure 6:
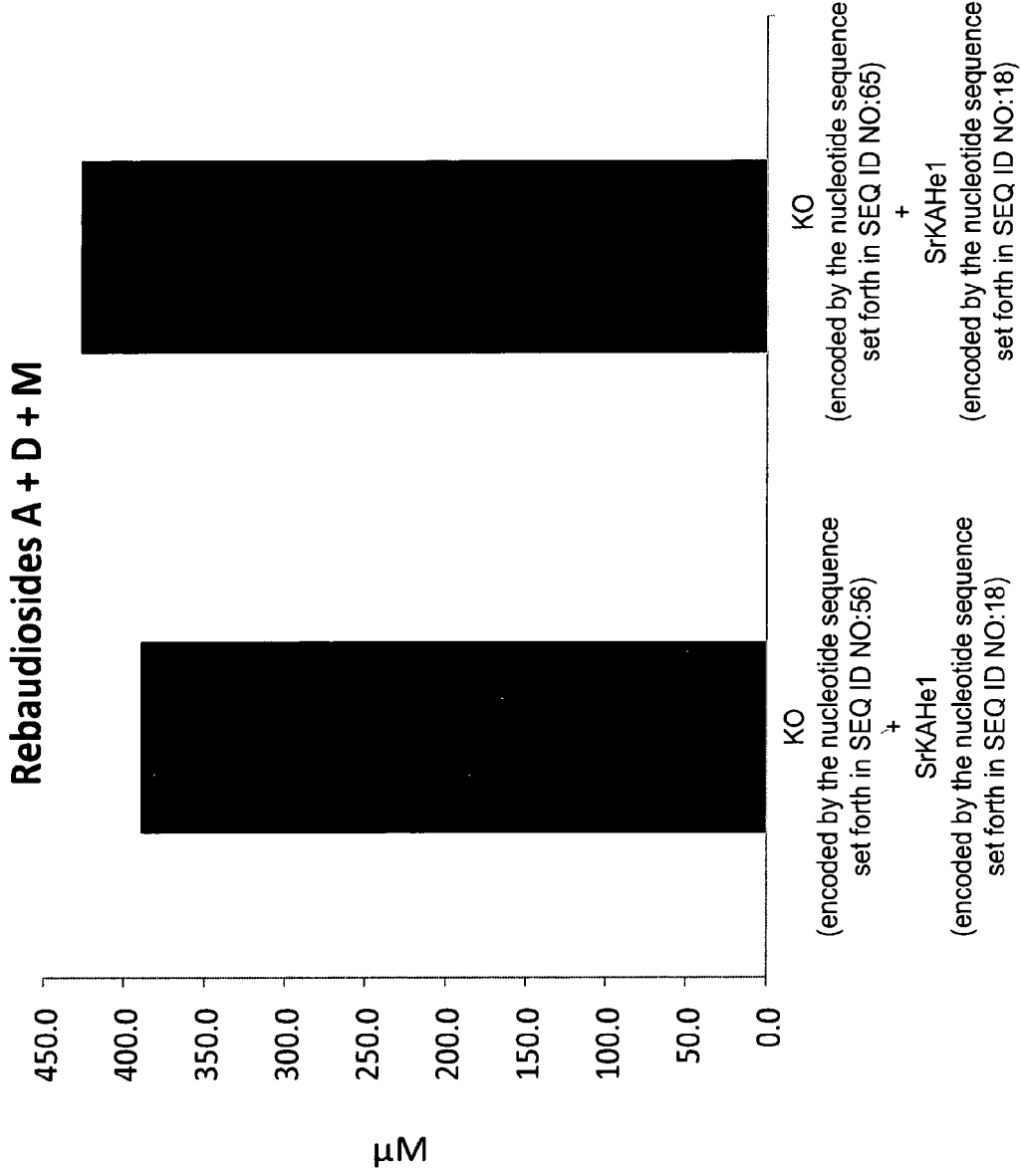
FIG. 6 shows production of Rebaudioside A (RebA), Rebaudioside D (RebD), and Rebaudioside M (RebM) in a steviol glycoside-producing *S. cerevisiae* strain overexpressing SrKAHe1 (encoded by the nucleotide sequence set forth in SEQ ID NO:18) and further expressing either the KO encoded by the nucleotide sequence set forth in SEQ ID NO:56 or the KO encoded by the nucleotide sequence set forth in SEQ ID NO:65. Production of RebA+RebD+RebM was measured in $\mu M$. See Example 4.

S. cerevisiae strains co-expressing any of the heterologous nucleic acids encoding a KO enzyme of Table 2 and further overexprssing SrKAHe1 (SEQ ID NO:18, SEQ ID NO:68) accumulated higher levels of steviol glycosides than the control S. cerevisiae strain (not expressing a KO of Table 2) or a steviol glycoside-producing S. cerevisiae strain only overexpressing SrKAHe1, as shown in FIG. 5. A steviol glycoside-producing S. cerevisiae strain expressing a codon-optimized version of SEQ ID NO:56, identified herein as SEQ ID NO:65, and overexpressing SrKAHe1 accumulated higher levels of steviol glycosides (RebA, RebD, and RebM) than the steviol glycoside-producing S. cerevisiae strain co-expressing the nucleic acid set forth in SEQ ID NO:56 and SrKAHe1 (FIG. 6).

Figure 7:
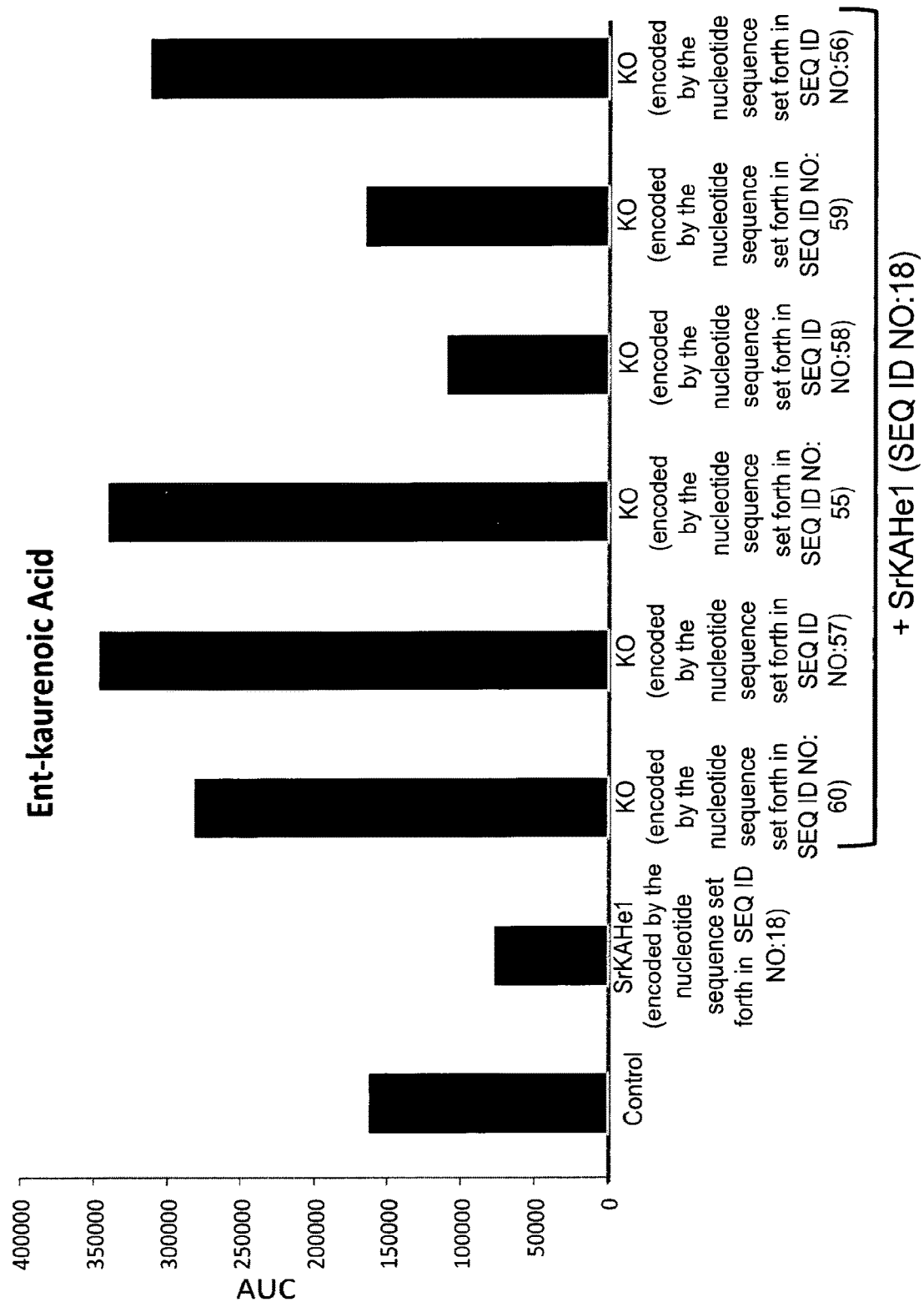
FIG. 7 shows production of glycosylated ent-kaurenoic acid in a steviol glycoside-producing *S. cerevisiae* strain overexpressing SrKAHe1 (encoded by the nucleotide sequence set forth in SEQ ID NO:18) or in a steviol glycoside-producing strain coexpressing SrKAHe1 (encoded by the nucleotide sequence set forth in SEQ ID NO:18) and a KO encoded by the nucleotide sequences set forth in any one of SEQ ID NOs: 55-60). Values were calculated as the AUC of LC-MS peaks corresponding to glycosylated ent-kaurenoic acid and as an average of three biological replicates. See Example 4.

Additionally, S. cerevisiae strains co-expressing a nucleic acid set forth in SEQ ID NO:55, SEQ ID NO:56, SEQ ID NO:57, or SEQ ID NO:60 and further overexpressing SrKAHe1 accumulated higher levels of glycosylated ent-kaurenoic acid than the control S. cerevisiae strain not expressing a KO of Table 2 (FIG. 7).

Figure 8:
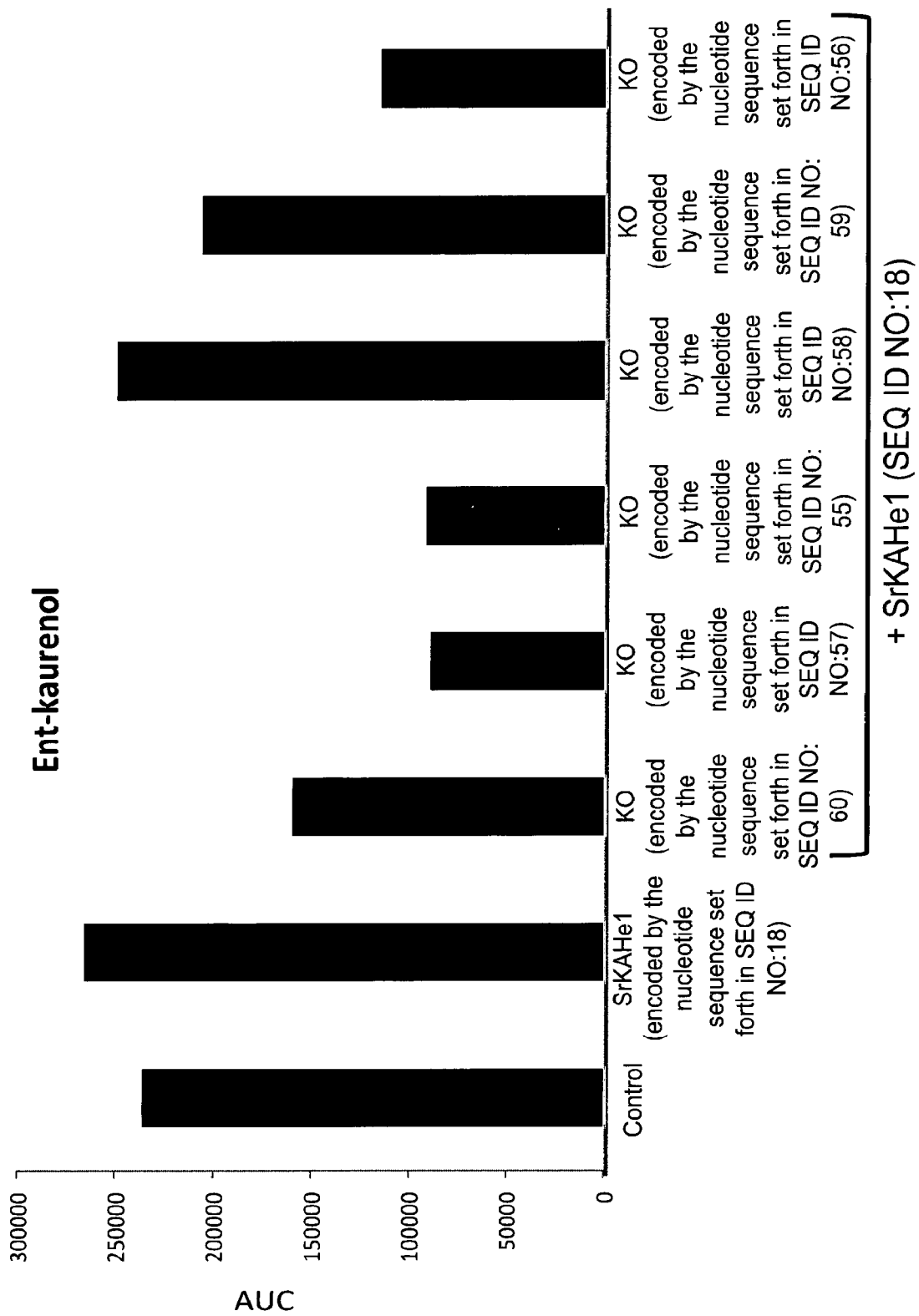
FIG. 8 shows production of glycosylated ent-kaurenol in a steviol glycoside-producing *S. cerevisiae* strain overexpressing SrKAHe1 (encoded by the nucleotide sequence set forth in SEQ ID NO:18) or in a steviol glycoside-producing *S. cerevisiae* strain co-expressing SrKAHe1 (encoded by the nucleotide sequence set forth in SEQ ID NO:18) and a KO encoded by the nucleotide sequence set forth in SEQ ID NOs: 55-60). Values plotted on the y-axis were calculated as the AUC of LC-MS peaks corresponding to glycosylated ent-kaurenol. See Example 4.

As well, S. cerevisiae strains co-expressing a nucleic acid set forth in SEQ ID NO:55, SEQ ID NO:56, SEQ ID NO:57, SEQ ID NO:59, or SEQ ID NO:60 and further overexpressing SrKAHe1 demonstrated improved metabolic conversion of intermediate compound, ent-kaurenol, which, in turn, resulted in reduced accumulation of glycosylated ent-kaurenol, relative to the control S. cerevisiae strain not expressing a KO of Table 2 or the steviol glycoside-producing S. cerevisiae strain only overexpressing SrKAHe1, as shown in FIG. 8. The control S. cerevisiae strain and the steviol glycoside-producing S. cerevisiae strain only overexpressing SrKAHe1 each accumulated higher levels of glycosylated ent-kaurenol than did S. cerevisiae strains expressing a nucleic acid set forth in SEQ ID NO:55, SEQ ID NO:56, SEQ ID NO:57, SEQ ID NO:59, or SEQ ID NO:60 and further overexpressing SrKAHe1.

Example 5. Steviol Glycoside Production in Yeast Strains Expressing CPR Genes

Cloned CPR genes were individually expressed in a steviol glycoside-producing *S. cerevisiae* strain. The steviol glycoside-producing *S. cerevisiae* strain described in Example 2, which expresses *S. rebaudiana* CPR8 (SEQ ID NO:24, SEQ ID NO:28) and *A. thaliana* ATR2 (SEQ ID NO:51), was modified to co-express a nucleic acid encoding a CPR of Table 3. The coding sequences of the CPR genes tested, as well as their corresponding amino acid sequences, are set forth in Table 3.

TABLE 3

CPR Genes Tested in Combination with CPR8 and ATR2.

| Gene | Nucleotide Sequence | Amino Acid Sequence |
|---|---|---|
| *S. rebaudiana* CPR1 | SEQ ID NO: 61 | SEQ ID NO: 76 |
| *S. rebaudiana* CPR7 | SEQ ID NO: 23 | SEQ ID NO: 69 |
| CPR4497 | SEQ ID NO: 62 | SEQ ID NO: 74 |

Figure 9:
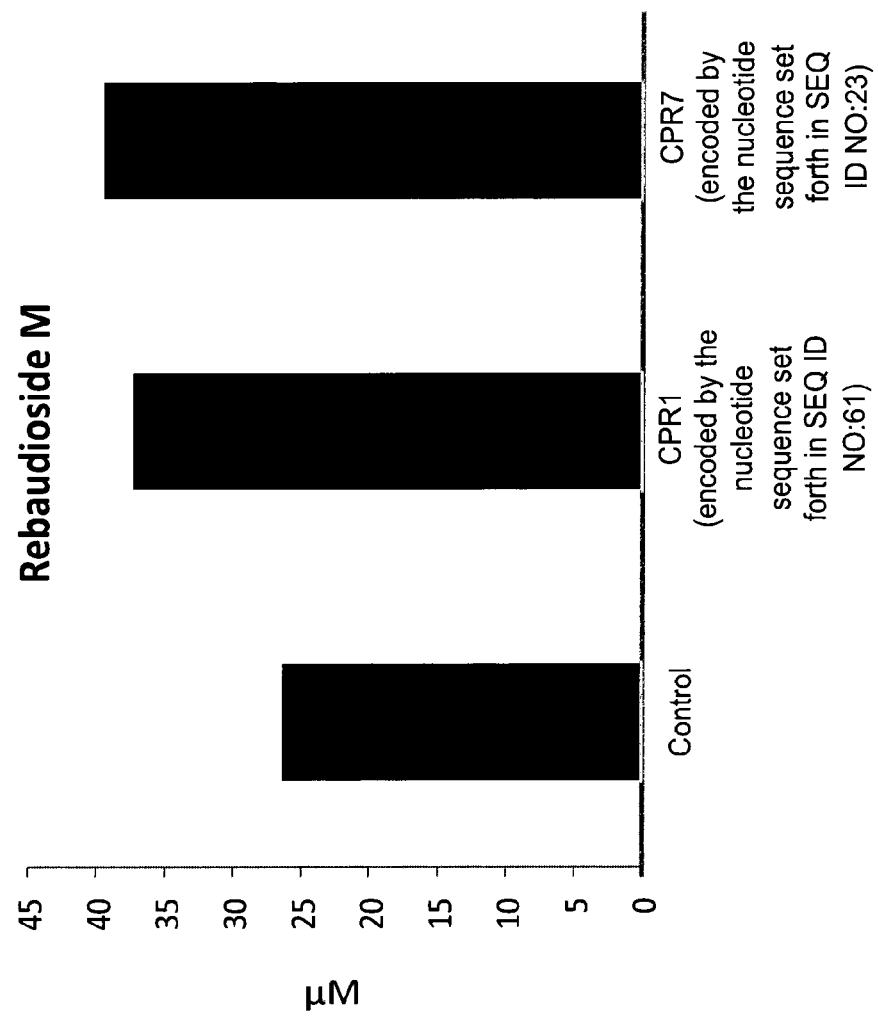
FIG. 9 shows Rebaudioside M (RebM) production in a steviol glycoside-producing *S. cerevisiae* strain expressing CPR1 (encoded by the codon-optimized nucleotide sequence set forth in SEQ ID NO:61) or CPR7 (encoded by the nucleotide sequence set forth in SEQ ID NO:23). Values plotted on the y-axis were measured in μM. See Example 5.
Figure 10:
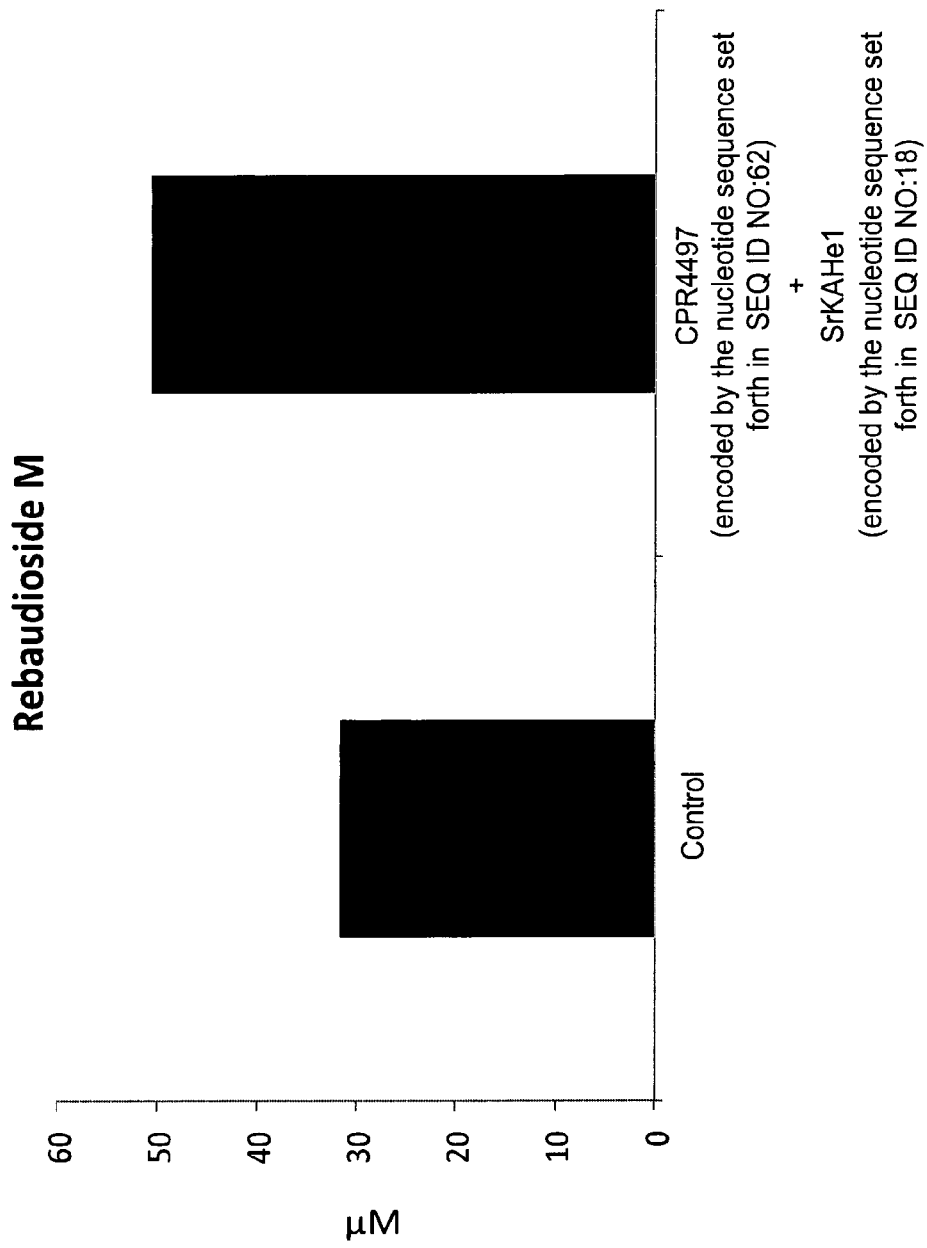
FIG. 10 shows Rebaudioside M (RebM) production in a steviol glycoside-producing *S. cerevisiae* strain overexpressing SrKAHe1 (encoded by the codon-optimized nucleotide sequence set forth in SEQ ID NO:18) and further expressing CPR4497 encoded by the nucleotide sequence set forth in SEQ ID NO:62. Values plotted on the y-axis indicate μM concentration of RebM. See Example 5.

As shown in FIG. 9, expression of CPR1 (SEQ ID NO:61, SEQ ID NO:76) or of CPR7 (SEQ ID NO:23, SEQ ID NO:69) in the steviol glycoside-producing *S. cerevisiae* strain already expressing *S. rebaudiana* CPR8 (SEQ ID NO:24, SEQ ID NO:28) and *A. thaliana* ATR2 (SEQ ID NO:51) resulted in higher levels of RebM than those accumulated by the control steviol glycoside-producing *S. cerevisiae* strain not expressing CPR1 or CPR7. As well, a steviol glycoside-producing *S. cerevisiae* strain expressing the nucleic acid set forth in SEQ ID NO:62 and overexpressing SrKAHe1 (SEQ ID NO:18, SEQ ID NO:68) accumulated higher levels of RebM than those accumulated by the control steviol glycoside-producing *S. cerevisiae* strain that only overexpressed SrKAHe1 (FIG. 10).

Example 6. Steviol Glycoside Production in Yeast Strains Co-Expressing KO and CPR Genes Steviol glycoside production was tested in the RebB-producing *S. cerevisiae* strain described in Example 2, which was modified to co-express a KO gene of Table 4 and a CPR of Table 5.

TABLE 4

KO Genes Tested in Combination with CPR Genes.

| Gene | Nucleotide Sequence | Amino Acid Sequence |
|---|---|---|
| SrKO1 | SEQ ID NO: 59 | SEQ ID NO: 79 |
| Codon-optimized KO | SEQ ID NO: 63 | SEQ ID NO: 77 |
| Codon-optimized KO | SEQ ID NO: 64 | SEQ ID NO: 78 |

TABLE 5

CPR Genes Tested in Combination with KO Genes.

| Nucleotide Sequence | Amino Acid Sequence |
|---|---|
| SEQ ID NO: 66 | SEQ ID NO: 73 |
| SEQ ID NO: 67 | SEQ ID NO: 22 |

Figure 12:
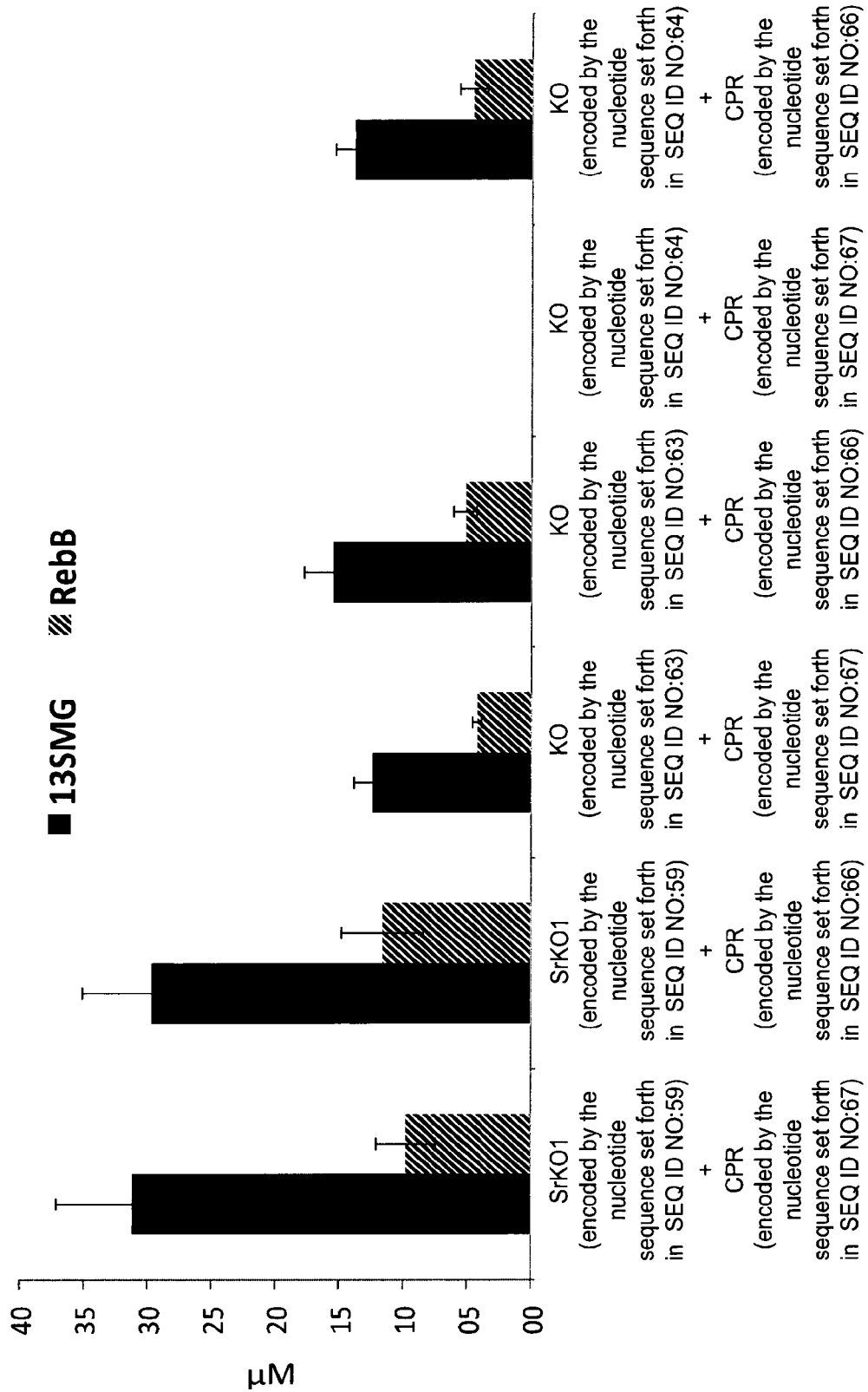
FIG. 12 shows steviol-13-O-glucoside (13-SMG) and Rebaudioside B (RebB) production in a steviol glycoside-producing *S. cerevisiae* strain co-expressing a KO and a CPR. The KO was selected from SrKO1 (encoded by the codon-optimized nucleotide sequence set forth in SEQ ID NO:59), the KO encoded by the codon-optimized nucleotide sequence set forth in SEQ ID NO:63, or the KO encoded by the codon-optimized nucleotide sequence set forth in SEQ ID NO:64. The cytochrome P450 reductase (CPR) polypeptide was selected from the CPR encoded by the codon-optimized nucleotide sequence set forth in SEQ ID NO:66 or the CPR encoded by the codon-optimized nucleotide sequence set forth in SEQ ID NO:67. Values displayed on the y-axis are μM concentrations of the indicated steviol glycosides. See Example 6.

As shown in FIG. 12, co-expression of SrKO1 (SEQ ID NO:59, SEQ ID NO:79) and either of the CPR genes of Table 5 in the RebB-producing strain resulted in higher production of 13-SMG and RebB than co-expression of a nucleic acid set forth in SEQ ID NO:63 or SEQ ID NO:64 and either of the cytochrome P450 genes of Table 5.

Example 7. Steviol Glycoside Production in Yeast Strains Expressing KAH Genes

Figure 11A:
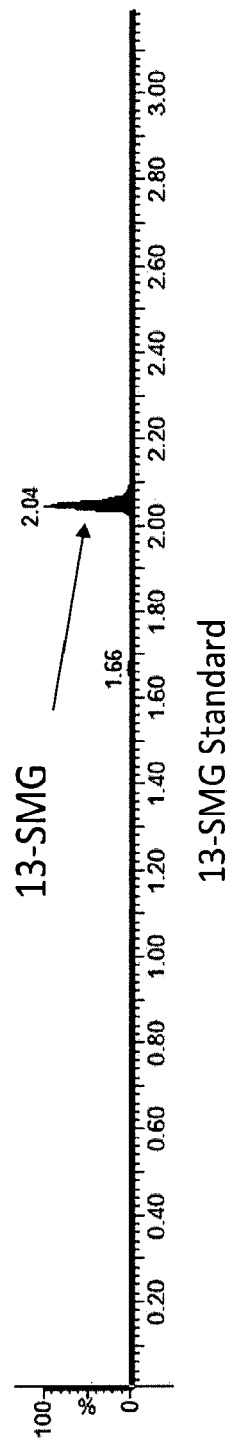
FIG. 11A shows an LC-MS chromatogram of a steviol-13-O-glucoside (13-SMG) standard.
Figure 11B:
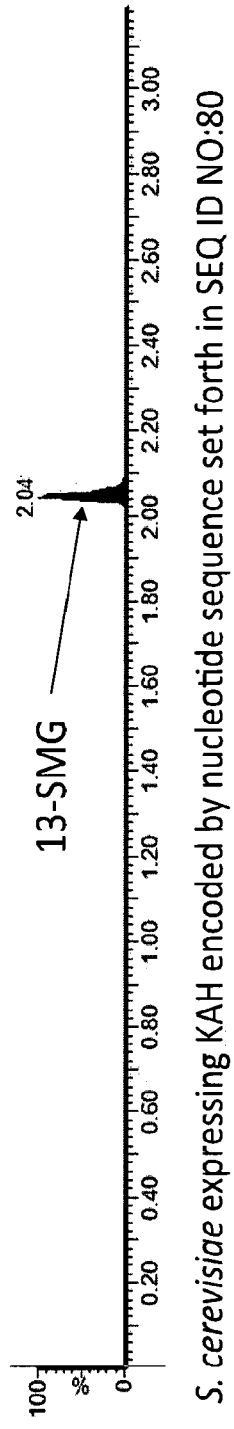
FIG. 11B shows production of 13-SMG by a steviol glycoside-producing *S. cerevisiae* strain expressing the KAH encoded by the nucleotide sequence set forth in SEQ ID NO:80 (amino acid sequence set forth in SEQ ID NO:82). See Example 7.

Candidate KAH enzymes were cloned and expressed in an *S. cerevisiae* strain engineered to accumulate 13-SMG. The 13-SMG-producing *S. cerevisiae* strain comprised a recombinant gene encoding a Synechococcus sp. GGPPS7 polypeptide (SEQ ID NO:49), a recombinant gene encoding a truncated *Z. mays* CDPS polypeptide (SEQ ID NO:37), a recombinant gene encoding an *A. thaliana* KS polypeptide (SEQ ID NO:6), SrKO1 (SEQ ID NO:59, SEQ ID NO:79), CPR8 (SEQ ID NO:24, SEQ ID NO:28), the KO encoded by the nucleotide sequence set forth in SEQ ID NO:56 (amino acid sequence set forth in SEQ ID NO:75), and UGT85C2 (SEQ ID NO:30) chromosomally integrated in separate expression cassettes (FIG. 11B). The strain lacked SrKAHe1 (SEQ ID NO:18, SEQ ID NO:68); thus, 13-SMG was only accumulated upon transformation of the *S. cerevisiae* strain with a functional KAH (FIG. 11B).

Transformants were grown in SC-URA medium for 4 days and extracted with 1:1 with DMSO at 80° C. for 10 min. The extracts were analyzed by LC-MS (method 2 of Example 1). *S. cerevisiae* transformed with the nucleic acid set forth in SEQ ID NO:80 accumulated 13-SMG (FIG. 11B). Thus, the protein encoded by SEQ ID NO:80, set forth in SEQ ID NO:82, is a KAH.

Figure 13:
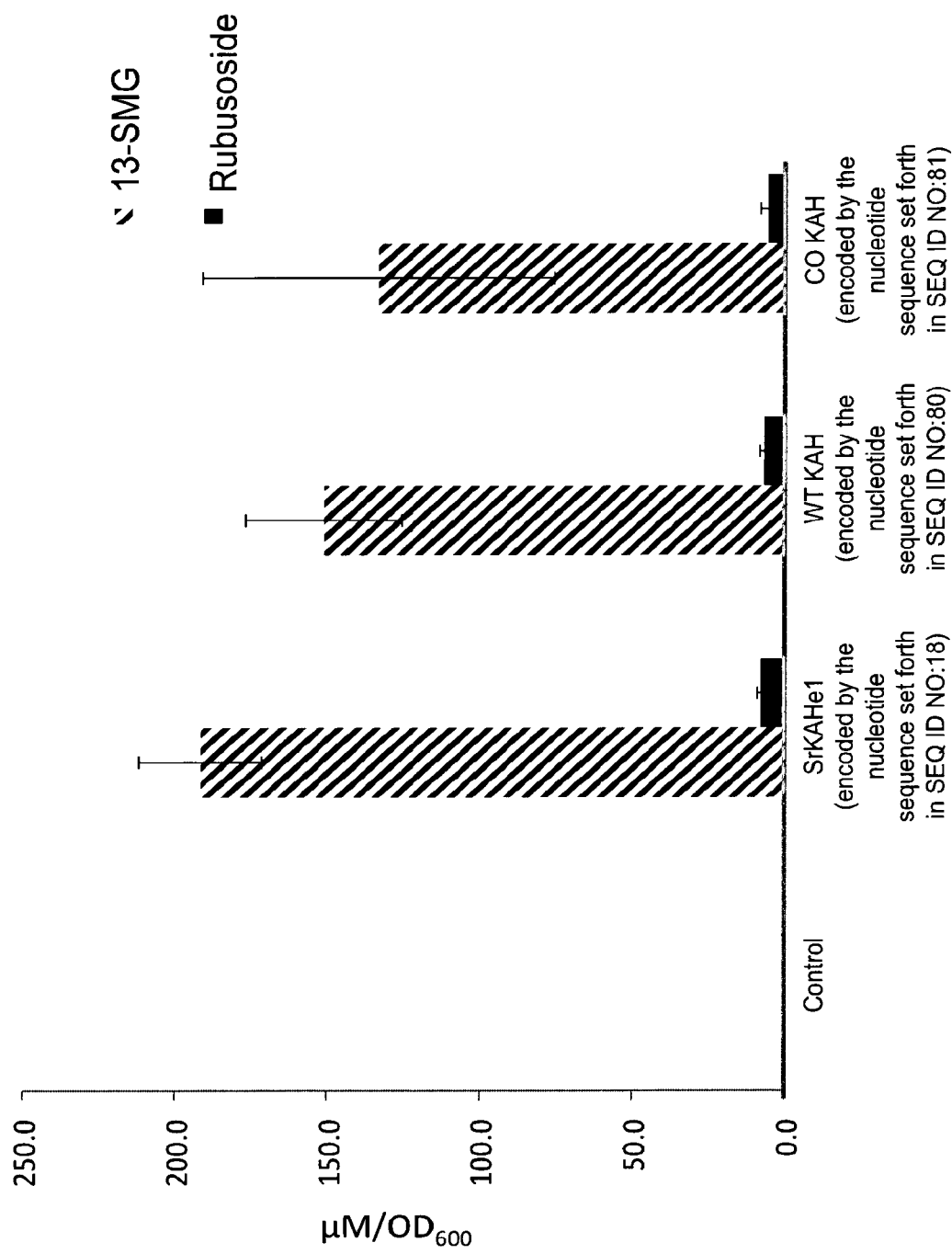
FIG. 13 shows production of steviol-13-O-glucoside (13-SMG) and rubusoside in a steviol glycoside-producing *S. cerevisiae* strain expressing SrKAHe1 (encoded by the nucleotide sequence set forth in SEQ ID NO:18), the KAH encoded by the nucleotide sequence set forth in SEQ ID NO:80, or the KAH encoded by the codon-optimized nucleotide sequence set forth in SEQ ID NO:81. Values displayed in the y-axis are μM concentrations of 13-SMG and rubusoside, averaged over eight biological replicates and normalized to $OD_{600}$ measured using a plate reader. Error bars are ± the respective standard deviation. See Example 7.

The KAH encoded by the nucleotide sequence set forth in SEQ ID NO:80 was codon-optimized for expression in yeast (SEQ ID NO:81) and expressed in the above-described 13-SMG-producing *S. cerevisiae* strain. Similar to expression of SrKAHe1 (SEQ ID NO:18) or the KAH encoded by the nucleotide sequence set forth in SEQ ID NO:80, expression of the codon-optimized nucleotide sequence set forth in SEQ ID NO:81 resulted in production of 13-SMG plus rubusoside (FIG. 13).

The KAHs encoded by the nucleotide sequence set forth in SEQ ID NO:80 and the codon-optimized nucleotide sequence set forth in SEQ ID NO:81 were also individually expressed in a steviol glycoside-producing strain, as described in Example 2, which expresses SrKAHe1. Production of 13-SMG was increased upon overexpression of SrKAHe1 (SEQ ID NO:18), of the KAH encoded by the nucleotide sequence set forth in SEQ ID NO:80, or of the KAH encoded by the codon-optimized nucleotide sequence set forth in SEQ ID NO:81, as compared to a control strain not expressing the KAH encoded by the nucleotide sequence set forth in SEQ ID NO:80, the KAH encoded by the codon-optimized nucleotide sequence set forth in SEQ ID NO:81, or overexpressing SrKAHe1. See Table 6. Expression of either the KAH encoded by the nucleotide sequence set forth in SEQ ID NO:80 or the KAH encoded by the codon-optimized nucleotide sequence set forth in SEQ ID NO:81 resulted in higher steviol glycoside production (13-SMG+1,2-bioside+rubusoside+RebB+RebA+RebD+RebM) than either the control strain or the *S. cerevisiae* strain overexpressing SrKAHe1 (SEQ ID NO:18). See Table 6.

TABLE 6

Quantification of Steviol Glycosides Accumulated by Yeast Expressing KAH Genes.

| | Control (μM) | Overexpression of SrKAHe1 (encoded by the nucleotide set forth in SEQ ID NO: 18) (μM) | SrKAHe1 + KAH (encoded by the nucleotide set forth in SEQ ID NO: 80) (μM) | SrKAHe1 + KAH (encoded by the nucleotide sequence set forth in SEQ ID NO: 81) (μM) |
|---|---|---|---|---|
| 13-SMG | 67.6 | 85.5 | 153.8 | 130.5 |
| Steviol-1,2-bioside | 0.4 | 0.3 | 0.4 | 0.4 |
| Rubusoside | 1.2 | 1.0 | 1.4 | 1.1 |
| RebB | 8.6 | 7.6 | 9.6 | 9.6 |
| RebA | 30.7 | 26.0 | 26.8 | 28.7 |
| RebD | 36.2 | 27.6 | 32.9 | 36.5 |
| RebM | 138.3 | 118.9 | 100.0 | 90.3 |
| Sum | 282.7 | 266.2 | 324.0 | 296.7 |

Example 8. Steviol Glycoside Production in Yeast Strain Expressing KAH Gene of the CYP72A219 Family A nucleic acid of SEQ ID NO:90, which was codon-optimized for expression in S. cerevisiae and encodes the polypeptide of SEQ ID NO:91, was cloned and expressed in an S. cerevisiae strain described in Example 7, which was engineered to accumulate 13-SMG. The 13-SMG-producing S. cerevisiae strain comprised a recombinant gene encoding a Synechococcus sp. GGPPS7 polypeptide (SEQ ID NO:49), a recombinant gene encoding a truncated Z. mays CDPS polypeptide (SEQ ID NO:37), a recombinant gene encoding an A. thaliana KS polypeptide (SEQ ID NO:6), SrKO1 (SEQ ID NO:59, SEQ ID NO:79), CPR8 (SEQ ID NO:24, SEQ ID NO:28), the KO encoded by the nucleotide sequence set forth in SEQ ID NO:56 (amino acid sequence set forth in SEQ ID NO:75), and UGT85C2 (SEQ ID NO:30) chromosomally integrated in separate expression cassettes.

Transformants were grown in SC-URA medium for 4 days and extracted 1:1 with DMSO at 80° C. for 10 min. The extracts were analyzed by LC-MS (method 2 of Example 1). S. cerevisiae transformed with the nucleic acid set forth in SEQ ID NO:90 accumulated 13-SMG as well as rubusoside (Table 7). Thus, the protein encoded by the nucleic acid sequence of SEQ ID NO:90, set forth in SEQ ID NO:91, is a KAH.

TABLE 7

Quantification of Steviol Glycosides Accumulated by Yeast Expressing the KAH encoded by the Nucleotide Sequence Set Forth in SEQ ID NO: 90 (Amino Acid Sequence Set Forth in SEQ ID NO: 91).

| | 13-SMG (μM) | Rubusoside (μM) |
|---|---|---|
| KAH (encoded by the nucleotide sequence set forth in SEQ ID NO: 90) | 4.3 ± 0.1 | 0.2 ± 0.0 |

Example 9. Determination of CPR1 and CPR12 Activity

Activity of CPR1 and CPR12 were measured using an in vitro microsomal assay. Microsomes were prepared by a modified version of the method taught by Pompon et al., "Yeast expression of animal and plant P450s in optimized redox environments," Methods Enzymol. 272:51-64 (1996). S. cerevisiae cells were sedimented for 10 min at 4° C. The pellets were washed with 10 mL TEK buffer (50 mM Tris-HCl (pH 7.5), 1 mM EDTA, 100 mM KCl.) The cells were sedimented again for 10 min at 4° C., and the pellets were resuspended in 1-3 mL of TES2 buffer (50 mM Tri-HCl (pH 7.5) 1 mM EDTA, 600 mM sorbitol). Glass beads (425-600 microns) were added to the samples, and the cells were broken vigorously by shaking and vortexing for 5 min at 4° C. The supernatant was collected, and the beads were washed several times with TES2 buffer. The washes were combined with the supernatant, and the samples were centrifuged for 15 min at 4° C. to remove unbroken cells and glass beads. Samples were then ultracentrifuged for 1 h at 4° C. The pellets were washed twice with TES buffer (50 mM Tris-HCl (pH 7.5), 1 mM EDTA, 600 mM sorbitol, 1% (w/V) BSA, 5 mM DTT), and once with TEG buffer (50 mM Tris-HCl (pH 7.5), 1 mM EDTA, 30% (V/V) glycerol). The samples were resuspended in 1-3 mL TEG, and the pellets were homogenized.

Wild-type control microsomal protein was prepared as described above from wild-type S. cerevisiae cells that did not comprise a heterologous KAH or CPR. Microsomal protein was also prepared from S. cerevisiae cells expressing i) SrKAHe1 (SEQ ID NO:18, SEQ ID NO:68), ii) SrKAHe1 (SEQ ID NO:18, SEQ ID NO:68) and CPR1 (SEQ ID NO:61, SEQ ID NO:76), or iii) SrKAHe1 (SEQ ID NO:18, SEQ ID NO:68) and CPR12 (SEQ ID NO:97, SEQ ID NO:98) from a genetic construct integrated at the chromosome level. Microsomal protein from a steviol glycoside-producing strain was prepared from S. cerevisiae cells expressing the genes described in Example 2 and additionally comprising codon-optimized CPR1 from S. rebaudiana (SEQ ID NO:61 corresponding to amino acid sequence SEQ ID NO:76) as well as the KO encoded by SEQ ID NO:75).

CPR1 and CPR12 activities were first determined using a cytochrome C reductase assay kit (Sigma-Aldrich; CY0100-1KT) to measure the ability of CPR1 or CPR12 to reduce cytochrome C in the presence of NADPH in vitro. Reduction of cytochrome C resulted in an increase in absorbance at 550 nm, which could quantified spectrophotometrically. Working solution was prepared by adding 9 mg cytochrome C to 20 mL assay buffer, and solution was stored at 25° C. until use. NADPH was diluted in $H_2O$ to a concentration of 0.85 mg/mL. Final reaction volumes were 1.1 mL (950 μL working solution (0.43 mg cytochrome C), 28 μL enzyme dilution buffer, 100 μL NADPH solution (0.085 mg NADPH), 20 μL cytochrome C oxidase inhibitor, 2 μL microsomal protein.) Blank samples did not comprise microsomal protein and were prepared with 950 μL working solution (0.43 mg cytochrome C), 30 μL enzyme dilution buffer, 100 μL NADPH solution (0.085 mg NADPH), and 20 μL cytochrome C oxidase inhibitor. The spectrophotometer was blanked with all components added to the reactions except for NADPH. The enzymatic reactions were initiated by addition of NADPH, the samples were thoroughly mixed by pipetting, and absorbance was measured at 550 nm for 70 s with 10 s intervals between reads. Two independent rate measurements were taken for each microsomal preparation, and rates were averaged for calculation of specific activity. After the reactions were completed, results were normalized to protein concentration, which was measured using a standard BCA assay (Thermo Scientific).

Units/mL was calculated using the following equation, where $\Delta A_{550}$/min represents the change in absorbance at 550 nm during the absorbance reading period, 1.1 represents the reaction volume in mL, and 21.1 represents the extinction coefficient for reduced cytochrome c:

$$\text{Units/mL} = (\Delta A_{550}/\text{min} \times \text{dilution factor} \times 1.1)/(21.1 \times \text{enzyme volume})$$

Figure 14:
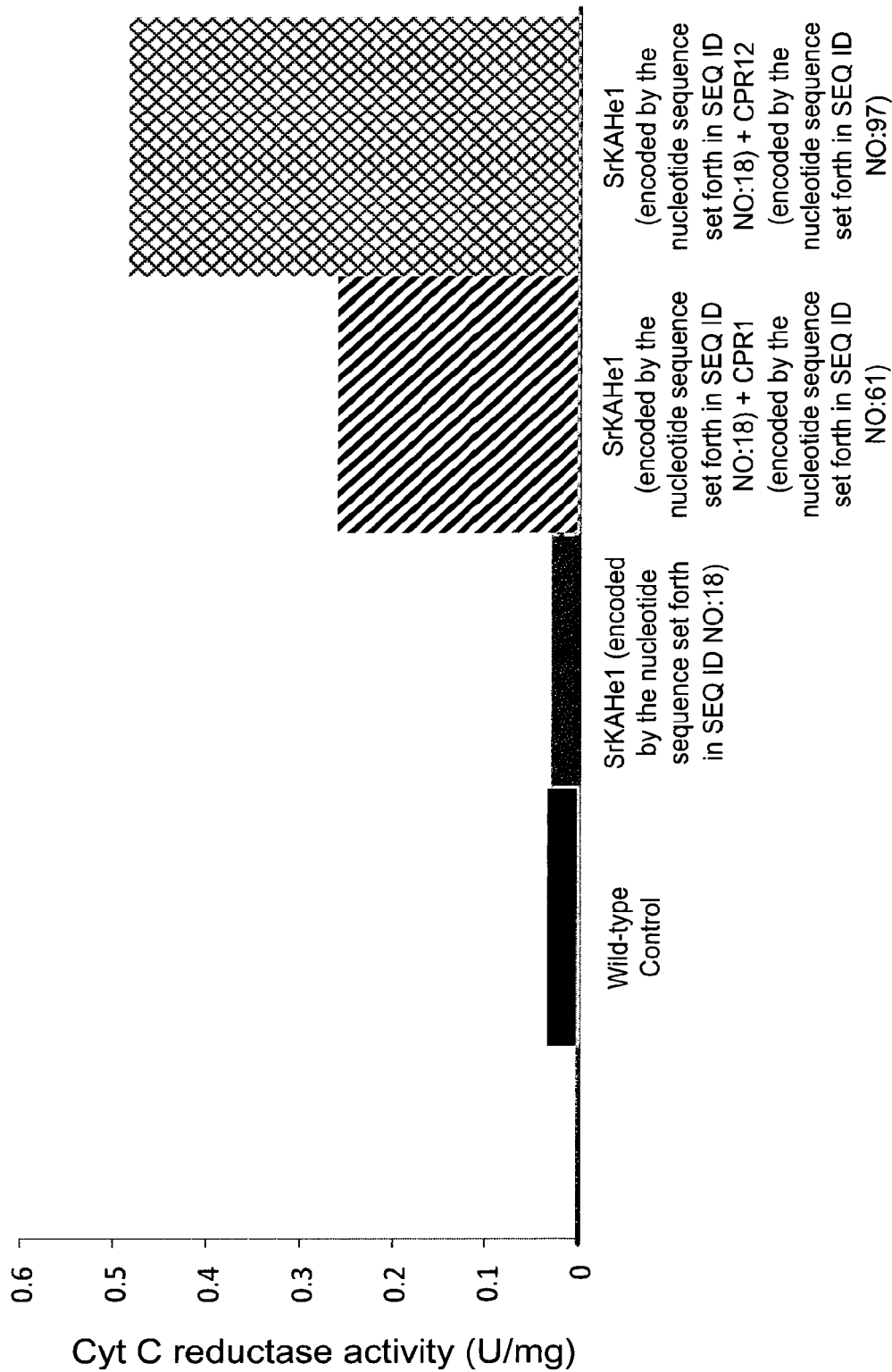
FIG. 14 shows cytochrome P450 reductase (CPR) polypeptide activity on cytochrome c upon incubation with microsomal protein prepared from *S. cerevisiae* strains expressing SrKAHe1 (encoded by the nucleotide sequence set forth in SEQ ID NO:18) alone or in combination with CPR1 (encoded by the nucleotide sequence set forth in SEQ ID NO:61) or CPR12 (encoded by the nucleotide sequence set forth in SEQ ID NO:97). Results are shown in U/mg as an average of two biological replicates. See Example 9.

The units/mL value of each sample was divided by its respective microsomal protein concentrations to calculate CPR activity in units/mg. FIG. 14 shows the activity measurements of the i) SrKAHe1 (SEQ ID NO:18, SEQ ID NO:68), ii) SrKAHe1 (SEQ ID NO:18, SEQ ID NO:68) and CPR1 (SEQ ID NO:61, SEQ ID NO:76), and iii) SrKAHe1 (SEQ ID NO:18, SEQ ID NO:68) and CPR12 (SEQ ID NO:97, SEQ ID NO:98) microsomal samples.

The microsomal preparation from the wild-type control showed only minimal CPR activity, reflecting the low activity of native NCP1 (YHR042VV). Likewise, the microsomal preparation from a yeast strain overexpressing KAHe1 did not demonstrate an increase in CPR activity. In contrast, microsomal preparation from strains expressing SrKAHe1 (SEQ ID NO:18, SEQ ID NO:68) and CPR1 (SEQ ID NO:61, SEQ ID NO:76) or SrKAHe1 (SEQ ID NO:18, SEQ ID NO:68) and CPR12 (SEQ ID NO:97, SEQ ID NO:98) demonstrated high CPR activity, with 7- and 14-fold higher activity, respectively, compared to the negative control (FIG. 14).

In a separate experiment, formation of steviol and consumption of ent-kaurenoic acid in microsomes, as prepared above, were measured. 33 μM ent-kaurenoic acid, 10 mM NADPH, and 10 μL of microsomal protein in 50 mM phosphate buffer (pH 7.5) were incubated for 30 min at 30° C. in a total reaction volume of 100 μL. Control reactions were extracted immediately after addition of all the reaction components, which were mixed on ice and aliquoted prior to incubation. Steviol and ent-kaurenoic acid levels were quantified using the second LC-MS procedure described in Example 1. For steviol quantification, the microsomal reactions were extracted with DMSO (1:1) at 80° C. for 10 min and submitted for LC-MS analysis after centrifugation. For ent-kaurenoic acid quantification the microsomes reactions were extracted with acetonitrile 1:4 (20% microsomal reaction and 80% acetonitrile) at 80° C. for 10 min and after centrifugation submitted for LC-MS analysis. The AUC values obtained for the ent-kaurenoic acid measurements were converted to concentrations using a standard curve.

Figure 15A:
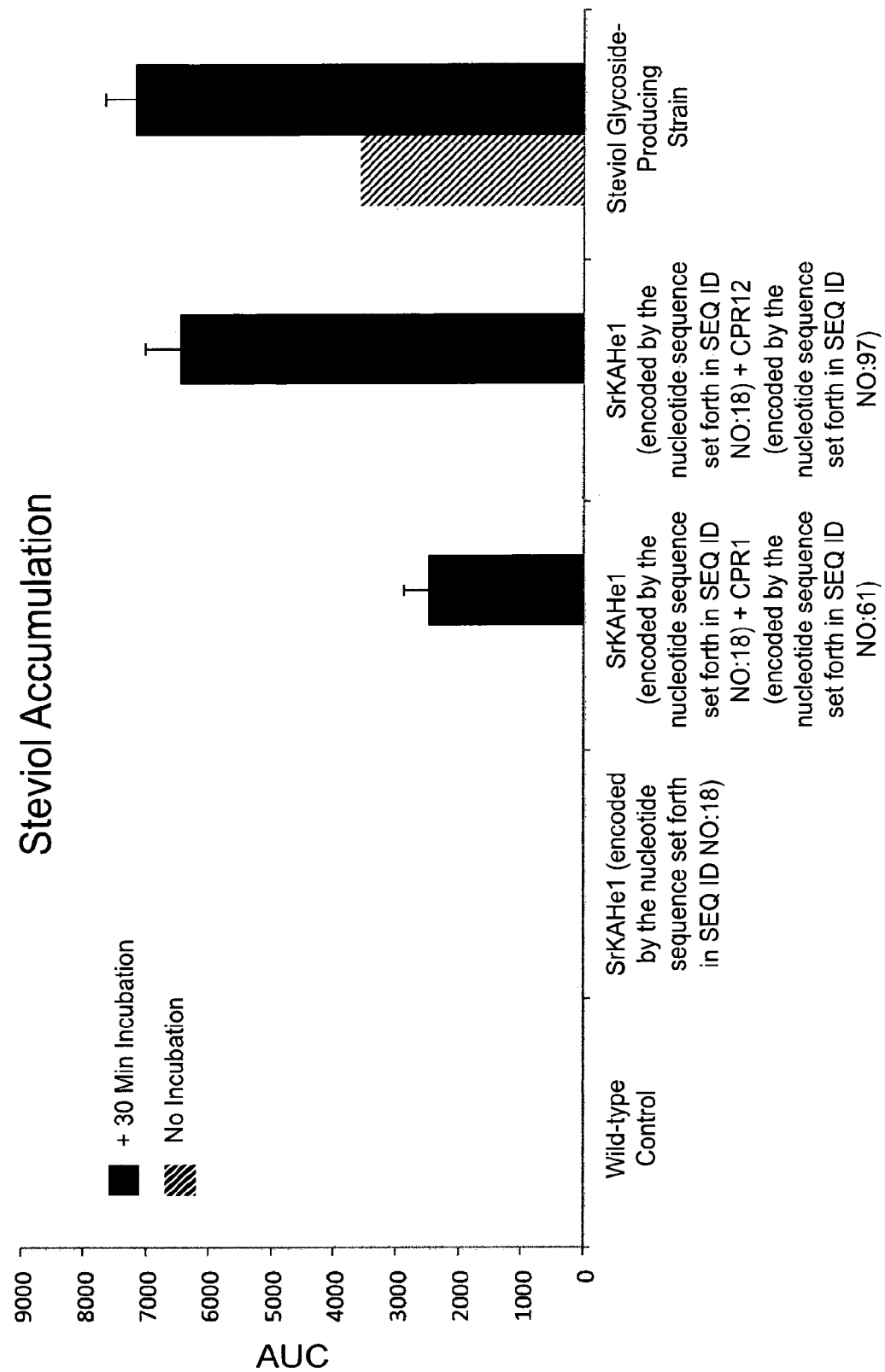
FIG. 15A shows steviol accumulation upon 30 min incubation of ent-kaurenoic acid with microsomal protein prepared from *S. cerevisiae* strains expressing SrKAHe1 (encoded by the nucleotide sequence set forth in SEQ ID NO:18) alone or in combination with CPR1 (encoded by the nucleotide sequence set forth in SEQ ID NO:61) or CPR12 (encoded by the nucleotide sequence set forth in SEQ ID NO:97). Results are shown in AUC as an average of three biological replicates. Control reactions comprised the microsomal protein described above, but these were not incubated for 30 min prior to measurement of steviol accumulation.

As shown in FIG. 15A, microsomal protein prepared from an S. cerevisiae strain expressing SrKAHe1 (SEQ ID NO:18, SEQ ID NO:68) and either CPR1 (SEQ ID NO:61, SEQ ID NO:76) or CPR12 (SEQ ID NO:97, SEQ ID NO:98) converted ent-kaurenoic acid to steviol during the 30 minute incubation period. The steviol level shown in FIG. 15A for the steviol-glycoside-producing strain control (extracted immediately with no 30 min incubation period) corresponds to steviol that was accumulated by the strain prior to microsomal preparation and that had co-purified with the microsomes. As shown in FIG. 15B, ent-kaurenoic acid levels decreased upon incubation with microsomal protein prepared from S. cerevisiae strains expressing SrKAHe1 (SEQ ID NO:18, SEQ ID NO:68) alone or in combination with CPR1 (SEQ ID NO:61, SEQ ID NO:76) or CPR12 (SEQ ID NO:97, SEQ ID NO:98). The increased ent-kaurenoic acid levels shown in FIG. 15B for the steviol glycoside-producing strain microsomal sample incubated for 30 min corresponds to ent-kaurenoic acid that was accumulated by the strain prior to microsomal preparation and to ent-kaurenoic acid accumulated from ent-kaurene that had co-purified with the microsomes. The levels of ent-kaurenoic acid shown in FIG. 15B were corrected for the dilution factor used.

Example 10. Steviol Glycoside Production in S. cerevisiae Strains Comprising Fusion Constructs Between a KO and a P450 Reductase Domain CYP102A1 (also referred to as $P450_{BM3}$; SEQ ID NO:115, SEQ ID NO:116) is a catalytically self-sufficient soluble enzyme from Bacillus megatarium. See, e.g., Whitehouse et al., 2012, Chem Soc Rev. 41(3):1218-60. Two domains are present in the CYP102A1 polypeptide chain: a P450 heme domain (BMP) and an NADPH-dependent P450 oxidoreductase domain (BMR). CYP102A1 utilizes nearly 100% of the reducing power of NADPH to produce a monooxygenated product. See, e.g., Yuan et al., 2009, Biochemistry 48(38):9140-6.

The BMR domain of CYP102A1 ("BMR"; codon-optimized nucleotide sequence set forth in SEQ ID NO:117, SEQ ID NO:118) was fused to SrKO1 (SEQ ID NO:59, SEQ ID NO:79) or a KO encoded by the nucleotide sequence set forth in SEQ ID NO:65 (amino acid sequence set forth in SEQ ID NO:75) with a linker (SEQ ID NO:121, SEQ ID NO:122), as described in Dodhia et al., 2006, J Biol Inorg Chem. 11(7):903-16. A wild-type version of the BMR domain of CYP102A1, as well as a W1046A mutant of the BMR domain (SEQ ID NO:119, SEQ ID NO:120), which has been found to switch the cofactor specificity of CYP102A1 from NADPH to NADH, were used. See, Girvan et al., 2011, Arch Biochem Biophys. 507(1):75-85. SrKO1 (SEQ ID NO:59, SEQ ID NO:79) and the KO encoded by the nucleotide sequence set forth in SEQ ID NO:65 were also truncated prior to fusion with the BMR domain of CYP102A1; these truncations were predicted by bioinformatics to result in loss of membrane anchors of the KO genes and in cytosolic versions of the KO-BMR fusion constructs. The KO-BMR fusion constructs analyzed are shown in Table 8.

TABLE 8

KO-BMR fusion constructs and sequences.

| Fusion Construct | Codon-Optimized Nucleotide Sequence | Amino Acid Sequence |
|---|---|---|
| SrKO1-BMR | SEQ ID NO: 99 | SEQ ID NO: 100 |
| SrKO1-BMR W1046A mutant | SEQ ID NO: 101 | SEQ ID NO: 102 |

TABLE 8-continued

KO-BMR fusion constructs and sequences.

| Fusion Construct | Codon-Optimized Nucleotide Sequence | Amino Acid Sequence |
|---|---|---|
| Truncated SrKO1-BMR | SEQ ID NO: 103 | SEQ ID NO: 104 |
| Truncated SrKO1-BMR W1046A mutant | SEQ ID NO: 105 | SEQ ID NO: 106 |
| KO (encoded by nucleotide sequence set forth in SEQ ID NO: 65)-BMR | SEQ ID NO: 107 | SEQ ID NO: 108 |
| KO (encoded by nucleotide sequence set forth in SEQ ID NO: 65)-BMR W1046A mutant | SEQ ID NO: 109 | SEQ ID NO: 110 |
| Truncated KO (encoded by nucleotide sequence set forth in SEQ ID NO: 65)-BMR W1046A mutant | SEQ ID NO: 111 | SEQ ID NO: 112 |

The KO-BMR fusion constructs were cloned and transformed in the RebB-producing strain described in Example 2, which was modified to not comprise any additional KO genes. Thus, steviol glycosides, including 13-SMG, 1,2-bioside, and RebB, were only accumulated upon expression of a functional KO. Three scrapes (1 µL loop of cells) from each transformation plate were resuspended in 200 µl nanopure H$_2$O. 70 µL were then transferred to 1 mL SC-URA in a 96 deep well plate and incubated at 30° C. for 5 days at 400 rpm. Biological triplicates were analyzed by LC-MS (method 2 of Example 1) to measure 13-SMG, 1,2-bioside, and RebB levels, and single samples were analyzed by LC-UV to measure ent-kaurene and ent-kaurenoic acid levels.

For LC-MS, 50 µL samples were mixed with 50 µL 100% DMSO and heated to 80° C. for 10 min. Subsequently, the samples were spun down at 4000 RCF for 10 min, and 85 µL of the resulting supernatant was transferred to an LC-MS plate. The LC-MS results were normalized by OD$_{600}$ of individual cultures, which was measured by a Wallac, 2104 EnVision (Perkin Elmer) plate reader.

LC-UV was conducted with an Agilent 1290 instrument comprising a variable wavelength detector (VWD), a thermostated column compartment (TCC), an autosampler, an autosampler cooling unit, and a binary pump and using SB-C18 rapid resolution high definition (RRHD) 2.1 mm×300 mm, 1.8 µm analytical columns (two 150 mm columns in series; column temperature of 65° C.). Steviol glycosides and steviol glycoside precursors were separated by a reversed phase C18 column followed by detection by UV absorbance at 210 mm. Quantification of steviol glycosides was done by comparing the peak area of each analyte to standards of RebA and applying a correction factor for species with differing molar absorptivities. Quantification of steviol glycoside precursors (such as kaurenoic acid, kaurenal, kaurenol, ent-kaurene, and geranylgeraniol) was done by comparing the peak area of each analyte to standards of kaurenoic acid and applying a correction factor for species with differing molar absorptivities. For LC-UV, 0.5 mL cultures were spun down, the supernatant was removed, and the wet weight of the pellets was calculated. The LC-UV results were normalized by pellet wet weight.

Figure 16A:
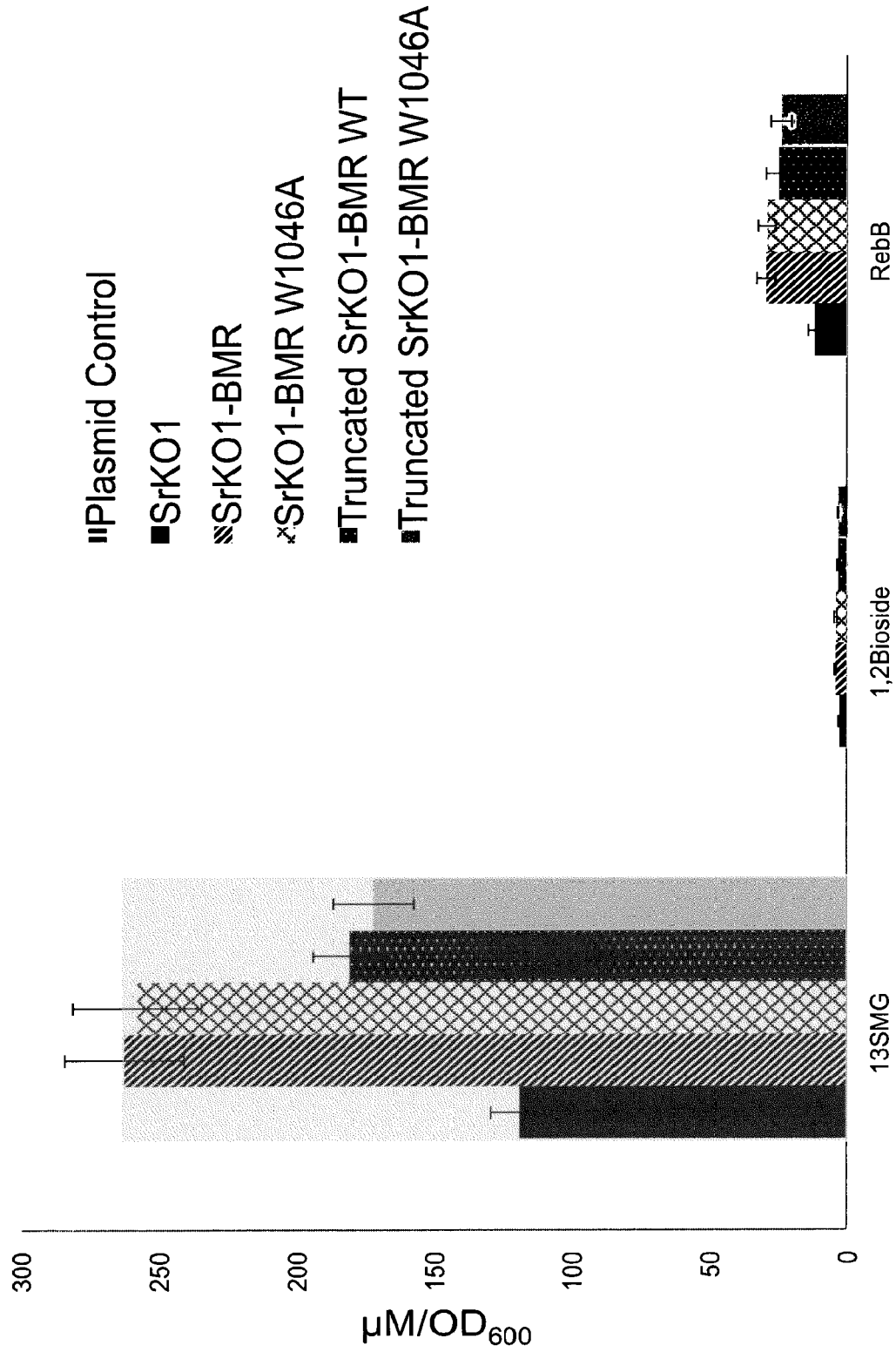
FIG. 16A shows levels of 13-SMG, 1,2-bioside, and RebB measured by LC-MS for a steviol glycoside-producing *S. cerevisiae* strain expressing SrKO1 (SEQ ID NO:59, SEQ ID NO:79), a fusion construct of SrKO1 and BMR (SEQ ID NO:99, SEQ ID NO:100), a fusion construct of SrKO1 and BMR W1046A (SEQ ID NO:101, SEQ ID NO:102), a fusion construct of truncated SrKO1 and BMR (SEQ ID NO:103, SEQ ID NO:104), a fusion construct of truncated SrKO1 and BMR W1046A (SEQ ID NO:105, SEQ ID NO:106), or a control plasmid.
Figure 16B:
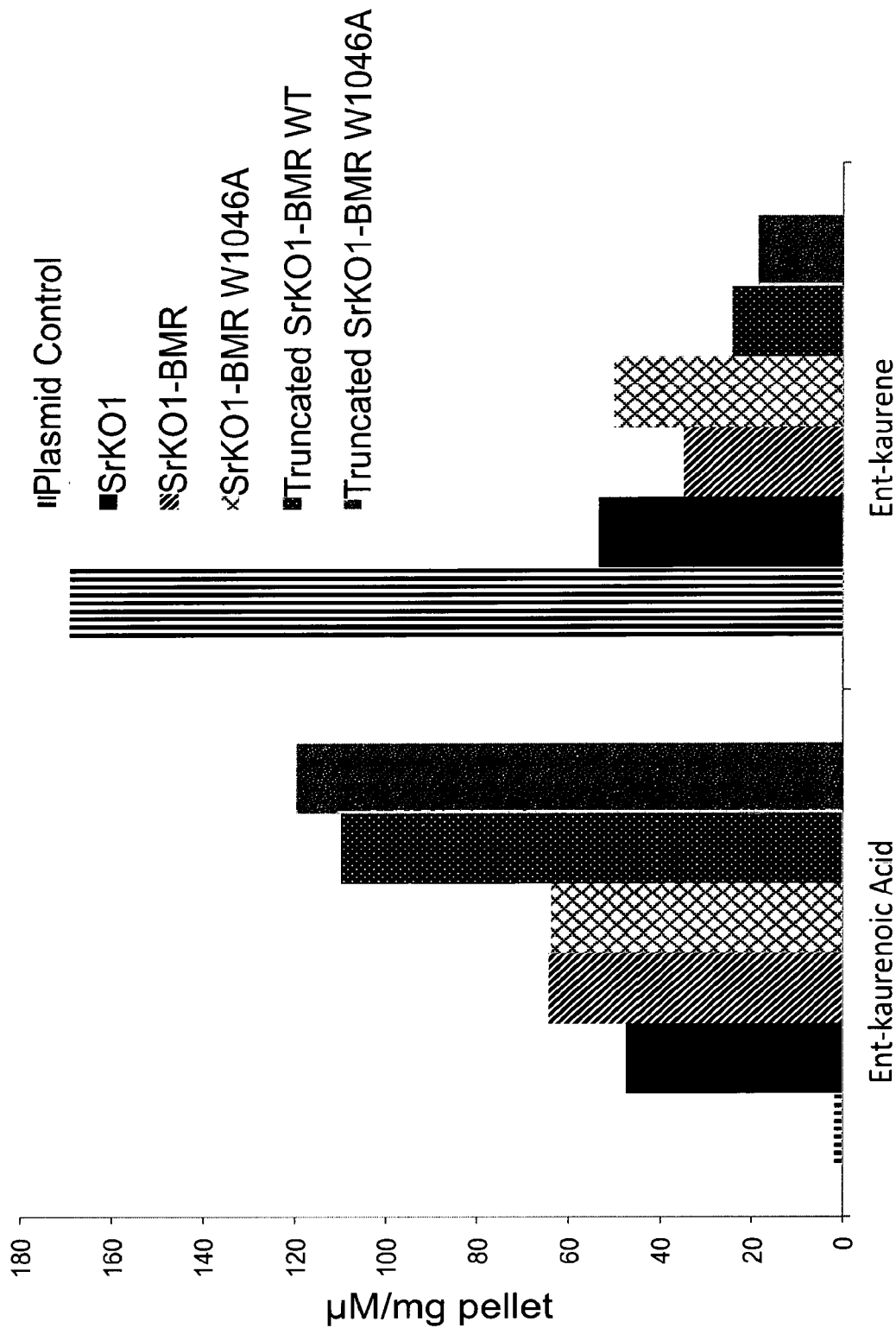
FIG. 16B shows levels of ent-kaurenoic acid and ent-kaurene measured by LC-UV for a steviol glycoside-producing *S. cerevisiae* strain expressing SrKO1 (SEQ ID NO:59, SEQ ID NO:79), a fusion construct of SrKO1 and BMR (SEQ ID NO:99, SEQ ID NO:100), a fusion construct of SrKO1 and BMR W1046A (SEQ ID NO:101, SEQ ID NO:102), a fusion construct of truncated SrKO1 and BMR (SEQ ID NO:103, SEQ ID NO:104), a fusion construct of truncated SrKO1 and BMR W1046A (SEQ ID NO:105, SEQ ID NO:106), or a control plasmid.

As shown in FIGS. 16B and 16D, the S. cerevisiae strain transformed with empty plasmid accumulated ent-kaurene. Transformation with a plasmid comprising SrKO1 (SEQ ID NO:59, SEQ ID NO:79) or with a plasmid comprising the KO gene having the nucleotide sequence set forth in SEQ ID NO:65 resulted in accumulation of 13-SMG, 1,2-bioside, and RebB (FIGS. 16A and 186C).

Expression of full-length SrKO1-BMR fusion constructs (wild type or W1046A mutant BMR; SEQ ID NOs:99-102), resulted in an increase in ent-kaurenoic acid, 13-SMG, and RebB, compared to expression of SrKO1 (SEQ ID NO:59, SEQ ID NO:79). See FIGS. 16A and 16B. Expression of truncated SrKO1-BMR fusion constructs (wild type or W1046A mutant BMR; SEQ ID NOs:103-106) resulted in an increase in ent-kaurenoic acid, compared to expression of SrKO1 (SEQ ID NO:59, SEQ ID NO:79) (FIG. 16B). Although the truncated SrKO1-BMR fusion constructs also increased steviol glycoside production, glycosylation activity was higher for the full-length SrKO1-BMR fusion constructs than for the truncated SrKO1-BMR fusion constructs (FIG. 16A).

Figure 16C:
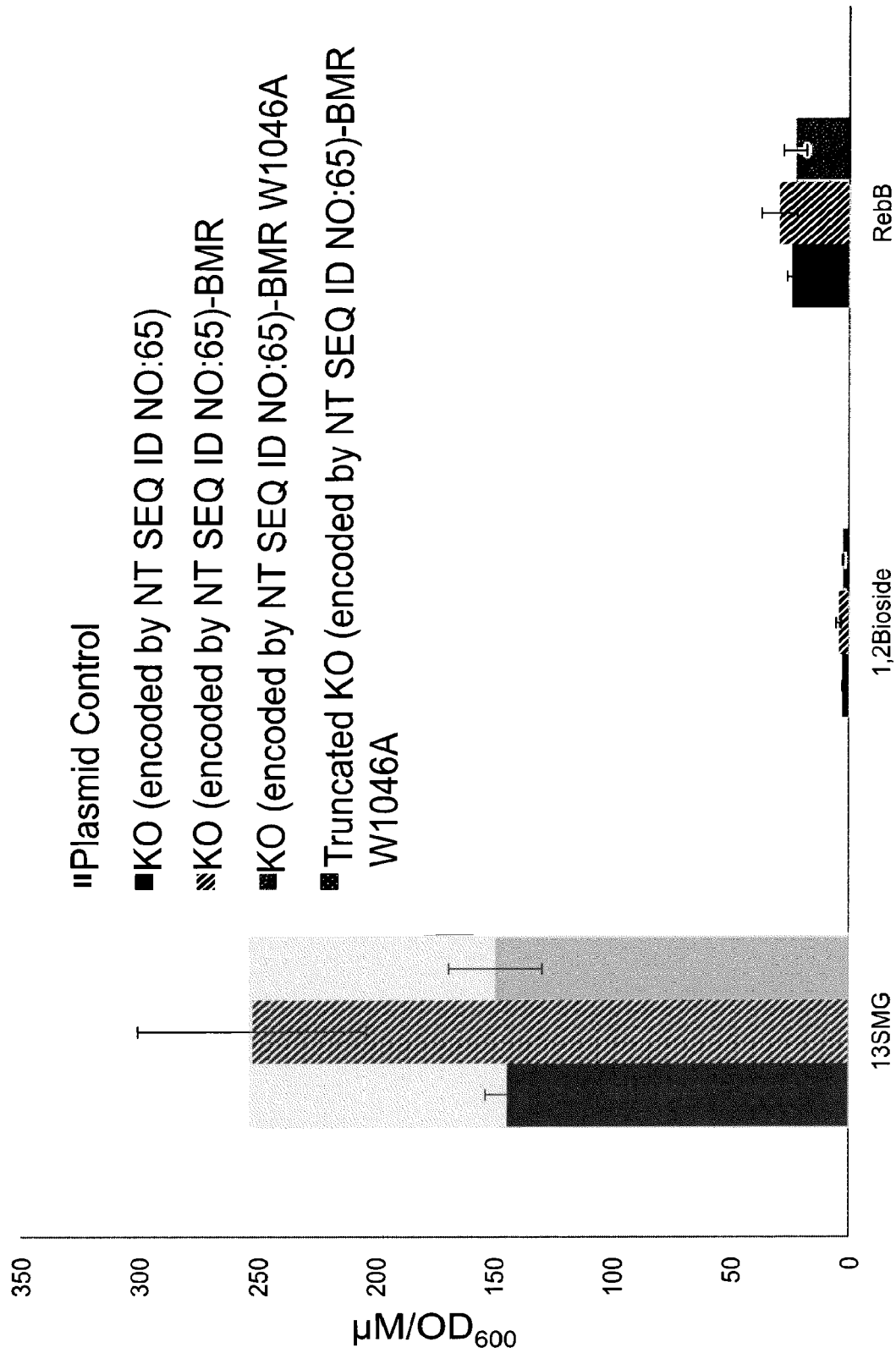
FIG. 16C shows levels of 13-SMG, 1,2-bioside, and RebB measured by LC-MS for a steviol glycoside-producing *S. cerevisiae* strain expressing the KO encoded by the nucleotide sequence set forth in SEQ ID NO:65, a fusion construct of the KO encoded by the nucleotide sequence set forth in SEQ ID NO:65 and BMR (SEQ ID NO:107, SEQ ID NO:108), a fusion construct of the KO encoded by the nucleotide sequence set forth in SEQ ID NO:65 and BMR W1046A (SEQ ID NO:109, SEQ ID NO:110), a fusion construct of a truncated KO encoded by the nucleotide sequence set forth in SEQ ID NO:65 and BMR W1046A (SEQ ID NO:111, SEQ ID NO:112), or a plasmid control.

Expression of a fusion construct comprising the KO encoded by the nucleotide sequence set forth in SEQ ID NO:65 and the wild type BMR (SEQ ID NO:107, SEQ ID NO:108) resulted in greater conversion of ent-kaurenoic acid to 13-SMG, compared to the KO encoded by the nucleotide sequence set forth in SEQ ID NO:65 (FIG. 16C). Expression of a fusion construct comprising the KO encoded by the nucleotide sequence set forth in SEQ ID NO:65 and the W1046A mutant BMR (SEQ ID NO:109, SEQ ID NO:110) resulted in decreases in ent-kaurenoic acid levels but glycosylation activity similar to that of the KO encoded by the nucleotide sequence set forth in SEQ ID NO:65 (FIG. 16C).

Example 11. Evaluation of Steviol Glycoside Pathway in S. cerevisiae Strain Comprising ICE2

ICE2 is an endoplasmic reticulum (ER) membrane protein involved in mechanisms such as ER zinc homeostasis and cytochrome P450 stability and/or activity. See, e.g., Estrada de Martin et al., 2005, J Cell Sci. 118(Pt 1):65-77 and Emmerstorfer et al., 2015, Biotechnol J. 10(4):623-35. ICE2 (SEQ ID NO:113, SEQ ID NO:114) was cloned and overexpressed in a steviol glycoside-producing S. cerevisiae strain comprising a recombinant gene encoding a Synechococcus sp. GGPPS polypeptide (SEQ ID NO:49), a recombinant gene encoding a truncated Z. mays CDPS polypeptide (SEQ ID NO:37), a recombinant gene encoding an A. thaliana KS polypeptide (SEQ ID NO:6), a recombinant gene encoding a recombinant S. rebaudiana KO polypeptide (SEQ ID NO:59, SEQ ID NO:79), a recombinant gene encoding an A. thaliana ATR2 polypeptide (SEQ ID NO:51, SEQ ID NO:87), a recombinant gene encoding an SrKAHe1 (SEQ ID NO:18, SEQ ID NO:68) polypeptide, a recombinant gene encoding an S. rebaudiana CPR8 polypeptide (SEQ ID NO:24, SEQ ID NO:28), a recombinant KAH gene encoded by the nucleotide sequence set forth in SEQ ID NO:81 (corresponding to the amino acid sequence set forth in SEQ ID NO:82), a recombinant KO gene encoded by the nucleotide sequence set forth in SEQ ID NO:56 (corresponding to the amino acid sequence set forth in SEQ ID NO:75), a recombinant KO gene encoded by the nucleotide sequence set forth in SEQ ID NO:65 (corresponding to the amino acid sequence set forth in SEQ ID NO:75), a recombinant gene encoding a UGT76G1 (SEQ ID NO:83) polypeptide, a recombinant gene encoding an S. rebaudiana UGT85C2 polypeptide (SEQ ID NO:30), a recombinant gene encoding an S. rebaudiana UGT74G1 polypeptide (SEQ ID NO:29), a recombinant gene encoding an EUGT11 (SEQ ID NO:86) polypeptide, a recombinant gene encoding a UGT91D2e (SEQ ID NO:84) polypeptide, and a recombinant gene encoding a CPR1 (SEQ ID NO:61, SEQ ID NO:76) polypeptide. Overexpression was performed by integration using the USER cloning system; see, e.g., Nour-Eldin et al., 2010, *Methods Mol Biol.* 643:185-200. Table 9 shows additional recombinant genes (ICE2 and/or CPR12) expressed in the above-described strain. The control strain did not comprise recombinant genes encoding ICE2 (SEQ ID NO:113, SEQ ID NO:114) or CPR12 (SEQ ID NO:97, SEQ ID NO:98) polypeptides.

TABLE 9

ICE2 steviol glycoside-producing strains.

| Strain | Sequences |
|---|---|
| ICE2 "strain A" | ICE2 (SEQ ID NO: 113, SEQ ID NO: 114) Overexpressed CPR1 (SEQ ID NO: 61, SEQ ID NO: 76) |
| ICE2 "strain B" | ICE2 (SEQ ID NO: 113, SEQ ID NO: 114) (2 copies) |
| ICE2 "strain C" | ICE2 (SEQ ID NO: 113, SEQ ID NO: 114) CPR12 (SEQ ID NO: 97, SEQ ID NO: 98) |

Fed-batch fermentation was carried out aerobically in 2 L fermenters at 30° C. with an approximate 16 h growth phase in minimal medium comprising glucose, ammonium sulfate, trace metals, vitamins, salts, and buffer followed by an approximate 110 h feeding phase with a glucose-comprising defined feed medium. A pH near 6.0 and glucose-limiting conditions were maintained. Whole culture samples (without cell removal) were analysed by the LC-UV method of Example 10 to determine levels of steviol glycosides and steviol pathway intermediates.

The following values were calculated based upon the measured levels of steviol glycosides and steviol glycoside precursors. "Total Flux" was calculated as a sum (in g/L RebD equivalents) of measured RebA, RebB, RebD, RebE, RebM, 13-SMG, rubusoside, steviol-1,2-bioside, di-glycosylated steviol, tri-glycosylated steviol, tetra-glycosylated steviol, penta-glycosylated steviol, hexa-glycosylated steviol, hepta-glycosylated steviol, copalol, ent-kaurenoic acid, glycosylated ent-kaurenoic acid, glycosylated ent-kaurenol, ent-kaurenal, geranylgeraniol, ent-kaurenal, and ent-kaurene levels. "Pre-steviol glycoside/flux" was calculated as (("total flux"–(geranylgeraniol+copalol+ent-kaurene+glycosylated ent-kaurenol+ent-kaurenol+ent-kaurenal+ent-kaurenoic acid+glycosylated ent-kaurenoic acid)/"total flux"). "KAH step/flux" was calculated as ((ent-kaurenoic acid+glycosylated ent-kaurenoic acid)/"total flux"). "KO step/flux" was calculated as ((ent-kaurene+glycosylated ent-kaurenol+ent-kaurenol+ent-kaurenal)/"total flux").

The pre-steviol glycoside/flux, KO step/flux, and KAH step/flux values are shown in Table 10 below. Decreased amounts of ent-kaurene, ent-kaurenol, ent-kaurenal, glycosylated ent-kaurenol and increased amounts of ent-kaurenoic acid and glycosylated ent-kaurenoic acid were observed in the strains comprising ICE2, as compared to the control steviol glycoside-producing strain. These effects were stronger in the presence of CPR1 and/or CPR12 (Table 10). Overexpression of two copies of ICE2 (ICE2 strain B) resulted decreased ent-kaurene, ent-kaurenol, ent-kaurenal, and ent-kaurenol glycoside levels and increased steviol glycoside levels, compared to the control strain, ICE2 strain A, or ICE2 strain C (Table 10). Steviol glycoside levels increased most in the steviol glycoside-producing strain comprising two copies of ICE2. Thus, ICE2 was found to improve cytochrome P450 function.

TABLE 10

Pre-steviol glycoside/flux, KO step/flux, and KAH step/flux values for steviol glycoside-producing strains comprising ICE2.

| Strain | Pre-Steviol Glycoside/Flux | KO step/Flux | KAH step/Flux |
|---|---|---|---|
| ICE2 "strain A" | 0.38 | 0.36 | 0.22 |
| ICE2 "strain B" | 0.43 | 0.42 | 0.10 |
| ICE2 "strain C" | 0.39 | 0.38 | 0.19 |
| Control | 0.41 | 0.48 | 0.08 |

Example 12. Steviol Glycoside Production by Fermentation of *S. cerevisiae* Strain Comprising CPR1 and CPR12

Steviol glycoside-producing *S. cerevisiae* strains comprising a recombinant gene encoding a Synechococcus sp. GGPPS polypeptide (SEQ ID NO:49), a recombinant gene encoding a truncated *Z. mays* CDPS polypeptide (SEQ ID NO:37), a recombinant gene encoding an *A. thaliana* KS polypeptide (SEQ ID NO:6), a recombinant gene encoding a recombinant *S. rebaudiana* KO polypeptide (SEQ ID NO:59, SEQ ID NO:79), a recombinant gene encoding an *A. thaliana* ATR2 polypeptide (SEQ ID NO:51, SEQ ID NO:87), a recombinant gene encoding an SrKAHe1 (SEQ ID NO:18, SEQ ID NO:68) polypeptide, a recombinant gene encoding an *S. rebaudiana* CPR8 polypeptide (SEQ ID NO:24, SEQ ID NO:28), a recombinant gene encoding a CPR1 (SEQ ID NO:61, SEQ ID NO:76) polypeptide, a recombinant gene encoding an SrKAHe1 (SEQ ID NO:18, SEQ ID NO:68) polypeptide, a recombinant KO gene encoded by the nucleotide sequence set forth in SEQ ID NO:56 (corresponding to the amino acid sequence set forth in SEQ ID NO:75), a recombinant gene encoding a UGT76G1 (SEQ ID NO:83) polypeptide, a recombinant gene encoding an *S. rebaudiana* UGT85C2 (SEQ ID NO:30) polypeptide, a recombinant gene encoding an *S. rebaudiana* UGT74G1 (SEQ ID NO:29) polypeptide, a recombinant gene encoding a UGT91D2e-b polypeptide (SEQ ID NO:88), and a recombinant gene encoding an EUGT11 (SEQ ID NO:86) polypeptide, as well as the recombinant genes shown in Table 11, which were genomically integrated into the strains, were cultivated by fermentation. Levels of steviol glycosides and steviol glycoside precursors were measured by LC-UV as described in Example 11. The pre-KO/flux, pre-KAH/flux, pre-steviol glycoside/flux values were calculated as described in Example 11.

TABLE 11

Recombinant genes also expressed in steviol glycoside-producing *S. cerevisiae* strain in Example 12.

| Strain | Genes |
|---|---|
| Example 12, Strain A | KO encoded by nucleotide sequence set forth in SEQ ID NO: 56 (corresponding to amino acid sequence set forth in SEQ ID NO: 75) |

TABLE 11-continued

Recombinant genes also expressed in steviol glycoside-producing *S. cerevisiae* strain in Example 12.

| Strain | Genes |
|---|---|
| Example 12, Strain B | KAH encoded by nucleotide sequence set forth in SEQ ID NO: 80 (corresponding to amino acid sequence set forth in SEQ ID NO: 82) KO encoded by nucleotide sequence set forth in SEQ ID NO: 56 (corresponding to amino acid sequence set forth in SEQ ID NO: 75) KO encoded by nucleotide sequence set forth in SEQ ID NO: 65 (corresponding to amino acid sequence set forth in SEQ ID NO: 75) |
| Example 12, Strain C | CPR12 (SEQ ID NO: 97, SEQ ID NO: 98) KAH encoded by nucleotide sequence set forth in SEQ ID NO: 80 (corresponding to amino acid sequence set forth in SEQ ID NO: 82) KO encoded by nucleotide sequence set forth in SEQ ID NO: 56 (corresponding to amino acid sequence set forth in SEQ ID NO: 75) |

The pre-steviol glycoside/flux, KO step/flux, and KAH step/flux values are shown in Table 12 below. In the strain comprising the KO encoded by nucleotide sequence set forth in SEQ ID NO:56 (strain A), lower accumulation of ent-kaurene, ent-kaurenol, ent-kaurnal, and ent-kaurenol glycosides resulted. Higher levels of ent-kaurenoic acid and steviol glycosides were also measured, as compared to the control strain. In the strain comprising the KAH encoded by nucleotide sequence set forth in SEQ ID NO:80, the KO encoded by nucleotide sequence set forth in SEQ ID NO:56 (corresponding to amino acid sequence set forth in SEQ ID NO:75), and the KO encoded by nucleotide sequence set forth in SEQ ID NO:65 (strain B), ent-kaurene, ent-kaurenol, ent-kaurenal, ent-kaurenol glycosides, and ent-kaurenoic acid accumulation decreased and accumulation of steviol glycosides increased, as compared to the control strain. In the strain comprising CPR12 (SEQ ID NO:97, SEQ ID NO:98), the KAH encoded by nucleotide sequence set forth in SEQ ID NO:80, and the KO encoded by nucleotide sequence set forth in SEQ ID NO:56 (strain C), ent-kaurenol, ent-kaurenal, ent-kaurenol glycosides, and ent-kaurenoic acid accumulation decreased and accumulation of steviol glycosides increased, as compared to the control. See Table 12. Thus, CPR12 was found to be a reductase protein that improves KAH and/or KO activity.

TABLE 12

Pre-steviol glycoside/flux, KO step/flux, and KAH step/flux values for steviol glycoside-producing strains of Example 12.

| Strain | Pre-Steviol Glycoside/Flux | KO step/Flux | KAH step/Flux |
|---|---|---|---|
| Example 12, Strain A | 0.48 | 0.28 | 0.22 |
| Example 12, Strain B | 0.64 | 0.18 | 0.12 |
| Example 12, Strain C | 0.55 | 0.24 | 0.12 |
| Control | 0.40 | 0.43 | 0.17 |

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 13

Sequences disclosed herein.

SEQ ID NO: 1

| | | | | | |
|---|---|---|---|---|---|
| MNLSLCIASP | LLTKSNRPAA | LSAIHTASTS | HGGQTNPTNL | IIDTTKERIQ | KQFKNVEISV 60 |
| SSYDTAWVAM | VPSPNSPKSP | CFPECLNWLI | NNQLNDGSWG | LVNHTHNHNH | PLLKDSLSST 120 |
| LACIVALKRW | NVGEDQINKG | LSFIESNLAS | ATEKSQPSPI | GFDIIFPGLL | EYAKNLDINL 180 |
| LSKQTDFSLM | LHKRELEQKR | CHSNEMDGYL | AYISEGLGNL | YDWNMVKKYQ | MKNGSVFNSP 240 |
| SATAAAFINH | QNPGCLNYLN | SLLDKFGNAV | PTVYPHDLFI | RLSMVDTIER | LGISHHFRVE 300 |
| IKNVLDETYR | CWVERDEQIF | MDVVTCALAF | RLLRINGYEV | SPDPLAEITN | ELALKDEYAA 360 |
| LETYHASHIL | YQEDLSSGKQ | ILKSADFLKE | IISTDSNRLS | KLIHKEVENA | LKFPINTGLE 420 |
| RINTRRNIQL | YNVDNTRILK | TTYHSSNISN | TDYLRLAVED | FYTCQSIYRE | ELKGLERWVV 480 |
| ENKLDQLKFA | RQKTAYCYFS | VAATLSSPEL | SDARISWAKN | GILTTVVDDF | FDIGGTIDEL 540 |
| TNLIQCVEKW | NVDVDKDCCS | EHVRILFLAL | KDAICWIGDE | AFKWQARDVT | SHVIQTWLEL 600 |
| MNSMLREAIW | TRDAYVPTLN | EYMENAYVSF | ALGPIVKPAI | YFVGPKLSEE | IVESSEYHNL 660 |

TABLE 13-continued

Sequences disclosed herein.

| | | | | | |
|---|---|---|---|---|---|
| FKLMSTQGRL | LNDIHSFKRE | FKEGKLNAVA | LHLSNGESGK | VEEEVVEEMM | MMIKNKRKEL 720 |
| MKLIFEENGS | IVPRACKDAF | WNMCHVLNFF | YANDDGFTGN | TILDTVKDII | YNPLVLVNEN 780 |
| EEQR | | | | | 784 |

SEQ ID NO: 2

| | | | | | |
|---|---|---|---|---|---|
| MNLSLCIASP | LLTKSSRPTA | LSAIHTASTS | HGGQTNPTNL | IIDTTKERIQ | KLFKNVEISV 60 |
| SSYDTAWVAM | VPSPNSPKSP | CFPECLNWLI | NNQLNDGSWG | LVNHTHNHNH | PLLKDSLSST 120 |
| LACIVALKRW | NVGEDQINKG | LSFIESNLAS | ATDKSQPSPI | GFDIIFPGLL | EYAKNLDINL 180 |
| LSKQTDFSLM | LHKRELEQKR | CHSNEIDGYL | AYISEGLGNL | YDWNMVKKYQ | MKNGSVFNSP 240 |
| SATAAAFINH | QNPGCLNYLN | SLLDKFGNAV | PTVYPLDLYI | RLSMVDTIER | LGISHHFRVE 300 |
| IKNVLDETYR | CWVERDEQIF | MDVVTCALAF | RLLRIHGYKV | SPDQLAEITN | ELAFKDEYAA 360 |
| LETYHASQIL | YQEDLSSGKQ | ILKSADFLKG | ILSTDSNRLS | KLIHKEVENA | LKFPINTGLE 420 |
| RINTRRNIQL | YNVDNTRILK | TTYHSSNISN | TYYLRLAVED | FYTCQSIYRE | ELKGLERWVV 480 |
| QNKLDQLKFA | RQKTAYCYFS | VAATLSSPEL | SDARISWAKN | GILTTVVDDF | FDIGGTIDEL 540 |
| TNLIQCVEKW | NVDVDKDCCS | EHVRILFLAL | KDAICWIGDE | AFKWQARDVT | SHVIQTWLEL 600 |
| MNSMLREAIW | TRDAYVPTLN | EYMENAYVSF | ALGPIVKPAI | YFVGPKLSEE | IVESSEYHNL 660 |
| FKLMSTQGRL | LNDIHSFKRE | FKEGKLNAVA | LHLSNGESGK | VEEEVVEEMM | MMIKNKRKEL 720 |
| MKLIFEENGS | IVPRACKDAF | WNMCHVLNFF | YANDDGFTGN | TILDTVKDII | YNPLVLVNEN 780 |
| EEQR | | | | | 784 |

SEQ ID NO: 3

| | | | | | |
|---|---|---|---|---|---|
| MAMPVKLTPA | SLSLKAVCCR | FSSGGHALRF | GSSLPCWRRT | PTQRSTSSST | TRPAAEVSSG 60 |
| KSKQHDQEAS | EATIRQQLQL | VDVLENMGIS | RHFAAEIKCI | LDRTYRSWLQ | RHEEIMLDTM 120 |
| TCAMAFRILR | LNGYNVSSDE | LYHVVEASGL | HNSLGGYLND | TRTLLELHKA | STVSISEDES 180 |
| ILDSIGSRSR | TLLREQLESG | GALRKPSLFK | EVEHALDGPF | YTTLDRLHHR | WNIENFNIIE 240 |
| QHMLETPYLS | NQHTSRDILA | LSIRDFSSSQ | FTYQQELQHL | ESWVKECRLD | QLQFARQKLA 300 |
| YFYLSAAGTM | FSPELSDART | LWAKNGVLTT | IVDDFFDVAG | SKEELENLVM | LVEMWDEHHK 360 |
| VEFYSEQVEI | IFSSIYDSVN | QLGEKASLVQ | DRSITKHLVE | IWLDLLKSMM | TEVEWRLSKY 420 |
| VPTEKEYMIN | ASLIFGLGPI | VLPALYFVGP | KISESIVKDP | EYDELFKLMS | TCGRLLNDVQ 480 |
| TFEREYNEGK | LNSVSLLVLH | GGPMSISDAK | RKLQKPIDTC | RRDLLSLVLR | EESVVPRPCK 540 |
| ELFWKMCKVC | YFFYSTTDGF | SSQVERAKEV | DAVINEPLKL | QGSHTLVSDV | 590 |

SEQ ID NO: 4

| | | | | | |
|---|---|---|---|---|---|
| MSCIRPWFCP | SSISATLTDP | ASKLVTGEFK | TTSLNFHGTK | ERIKKMFDKI | ELSVSSYDTA 60 |
| WVAMVPSPDC | PETPCFPECT | KWILENQLGD | GSWSLPHGNP | LLVKDALSST | LACILALKRW 120 |
| GIGEEQINKG | LRFIELNSAS | VTDNEQHKPI | GFDIIFPGMI | EYAKDLDLNL | PLKPTDINSM 180 |
| LHRRALELTS | GGGKNLEGRR | AYLAYVSEGI | GKLQDWEMAM | KYQRKNGSLF | NSPSTTAAAF 240 |
| IHIQDAECLH | YIRSLLQKFG | NAVPTIYPLD | IYARLSMVDA | LERLGIDRHF | RKERKFVLDE 300 |
| TYRFWLQGEE | EIFSDNATCA | LAFRILRLNG | YDVSLEDHFS | NSLGGYLKDS | GAALELYRAL 360 |
| QLSYPDESLL | EKQNSRTSYF | LKQGLSNVSL | CGDRLRKNII | GEVHDALNFP | DHANLQRLAI 420 |
| RRRIKHYATD | DTRILKTSYR | CSTIGNQDFL | KLAVEDFNIC | QSIQREEFKH | IERWVVERRL 480 |
| DKLKFARQKE | AYCYFSAAAT | LFAPELSDAR | MSWAKNGVLT | TVVDDFFDVG | GSEEELVNLI 540 |

TABLE 13-continued

Sequences disclosed herein.

| | | | | | |
|---|---|---|---|---|---|
| ELIERWDVNG | SADFCSEEVE | IIYSAIHSTI | SEIGDKSFGW | QGRDVKSHVI | KIWLDLLKSM 600 |
| LTEAQWSSNK | SVPTLDEYMT | TAHVSFALGP | IVLPALYFVG | PKLSEEVAGH | PELLNLYKVM 660 |
| STCGRLLNDW | RSFKRESEEG | KLNAISLYMI | HSGGASTEEE | TIEHFKGLID | SQRRQLLQLV 720 |
| LQEKDSIIPR | PCKDLFWNMI | KLLHTFYMKD | DGFTSNEMRN | VVKAIINEPI | SLDEL       775 |

SEQ ID NO: 5

```
cgtcagtcat caaggctaat tcgtcgcgag ttgctacgac gccgtttcgg ttgcttctgg   60
tttctttatg tctatcaacc ttcgctcctc cggttgttcg tctccgatct cagctacttt  120
ggaacgagga ttggactcag aagtacagac aagagctaac aatgtgagct tgagcaaac   180
aaaggagaag attaggaaga tgttggagaa agtggagctt tctgtttcgg cctacgatac  240
tagttgggta gcaatggttc catcaccgag ctcccaaaat gctccacttt tcccacagtg  300
tgtgaaatgg ttattggata tcaacatga agatggatct ggggacttg ataaccatga    360
ccatcaatct cttaagaagg atgtgttatc atctacactg gctagtatcc tcgcgttaaa  420
gaagtgggga attggtgaaa gacaaataaa caagggtctc cagtttattg agctgaattc  480
tgcattagtc actgatgaaa ccatacagaa accaacaggg tttgatatta tatttcctgg  540
gatgattaaa tatgctagag atttgaatct gacgattcca ttgggctcag aagtggtgga  600
tgacatgata cgaaaaagag atctggatct taaatgtgat agtgaaaagt tttcaaaggg  660
aagagaagca tatctggcct atgttttaga ggggacaaga aacctaaaag attgggattt  720
gatagtcaaa tatcaaagga aaaatgggtc actgtttgat tctccagcca caacagcagc  780
tgcttttact cagtttggga atgatggttg tctccgttat ctctgttctc tccttcagaa  840
attcgaggct gcagttcctt cagtttatcc atttgatcaa tatgcacgcc ttagtataat  900
tgtcactctt gaaagcttag gaattgatag agatttcaaa accgaaatca aaagcatatt  960
ggatgaaacc tatagatatt ggcttcgtgg ggatgaagaa atatgtttgg acttggccac 1020
ttgtgctttg gctttccgat tattgcttgc tcatggctat gatgtgtctt acgatccgct 1080
aaaaccattt gcagaagaat ctggtttctc tgatactttg gaaggatatg ttaagaatac 1140
gttttctgtg ttagaattat ttaaggctgc tcaaagttat ccacatgaat cagctttgaa 1200
gaagcagtgt tgttggacta acaatatct ggagatggaa ttgtccagct gggttaagac  1260
ctctgttcga gataaatacc tcaagaaaga ggtcgaggat gctcttgctt ttccctccta 1320
tgcaagccta gaaagatcag atcacaggag aaaaatactc aatggttctg ctgtggaaaa 1380
caccagagtt acaaaaacct catatcgttt gcacaatatt tgcacctctg atatcctgaa 1440
gttagctgtg gatgacttca atttctgcca gtccatacac cgtgaagaaa tgaacgtctc 1500
tgataggtgg attgtggaga atagattgca ggaactgaaa tttgccagac agaagctggc 1560
ttactgttat ttctctgggg ctgcaacttt atttttctcca gaactatctg atgctcgtat 1620
atcgtgggcc aaaggtggag tacttacaac ggttgtagac gacttctttg atgttggagg 1680
gtccaaagaa gaactggaaa acctcataca cttggtcgaa aagtgggatt tgaacggtgt 1740
tcctgagtac agctcagaac atgttgagat catattctca gttctaaggg acaccattct 1800
cgaaacagga gacaaagcat tcacctatca aggacgcaat gtgacacacc acattgtgaa 1860
aatttggttg gatctgctca gtctatgtt gagagaagcc gagtggtcca gtgacaagtc 1920
aacaccaagc ttgaaggatt acatggaaaa tgcgtacata tcatttgcat taggaccaat 1980
tgtcctccca gctacctatc tgatcggacc tccacttcca gagaagacag tcgatagcca 2040
```

TABLE 13-continued

Sequences disclosed herein.

```
ccaatataat cagctctaca agctcgtgag cactatgggt cgtcttctaa atgcacataca 2100
aggttttaag agagaaagcg cggaagggaa gctgaatgcg gtttcattgc acatgaaaca 2160
cgagagagac aatcgcagca aagaagtgat catagaatcg atgaaaggtt tagcagagag 2220
aaagagggaa gaattgcata agctagtttt ggaggagaaa ggaagtgtgg ttccaaggga 2280
atgcaaagaa gcgttcttga aaatgagcaa agtgttgaac ttattttaca ggaaggacga 2340
tggattcaca tcaaatgatc tgatgagtct tgttaaatca gtgatctacg agcctgttag 2400
cttacagaaa gaatetttaa cttgatccaa gttgatctgg caggtaaact cagtaaatga 2460
aaataagact ttggtcttct tctttgttgc ttcagaacaa gaagag          2506
```

SEQ ID NO: 6

```
MSINLRSSGC SSPISATLER GLDSEVQTRA NNVSFEQTKE KIRKMLEKVE LSVSAYDTSW   60
VAMVPSPSSQ NAPLFPQCVK WLLDNQHEDG SWGLDNHDHQ SLKKDVLSST LASILALKKW  120
GIGERQINKG LQFIELNSAL VTDETIQKPT GFDIIFPGMI KYARDLNLTI PLGSEVVDDM  180
IRKRDLDLKC DSEKFSKGRE AYLAYVLEGT RNLKDWDLIV KYQRKNGSLF DSPATTAAAF  240
TQFGNDGCLR YLCSLLQKFE AAVPSVYPFD QYARLSIIVT LESLGIDRDF KTEIKSILDE  300
TYRYWLRGDE EIGLDLATCA LAFRLLLAHG YDVSYDPLKP FAEESGFSDT LEGYVKNTFS  360
VLELFKAAQS YPHESALKKQ CCWTKQYLEM ELSSWVKTSV RDKYLKKEVE DALAFPSYAS  420
LERSDHRRKI LNGSAVENTR VTKTSYRLHN ICTSDILKLA VDDFNFCQSI HREEMERLDR  480
WIVENRLQEL KFARQKLAYC YFSGAATLFS PELSDARISW AKGGVLTTVV DDFFDVGGSK  540
EELENLIHLV EKWDLNGVPE YSSEHVEIIF SVLRDTILET GDKAFTYQGR NVTHHIVKIW  600
LDLLKSMLRE AEWSSDKSTP SLEDYMENAY ISFALGPIVL PATYLIGPPL PEKTVDSHQY  660
NQLYKLVSTM GRLLNDIQGF KRESAEGKLN AVSLHMKHER DNRSKEVIIE SMKGLAERKR  720
EELHKLVLEE KGSVVPRECK EAFLKMSKVL NLFYRKDDGF TSNDLMSLVK SVIYEPVSLQ  780
KESLT                                                             785
```

SEQ ID NO: 7

```
MDAVTGLLTV PATAITIGGT AVALAVALIF WYLKSYTSAR RSQSNHLPRV PEVPGVPLLG   60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRI                               513
```

SEQ ID NO: 8

```
MAFFSMISIL LGFVISSFIF IFFFKKLLSF SRKNMSEVST LPSVPVVPGF PVIGNLLQLK   60
EKKPHKTFTR WSEIYGPIYS IKMGSSSLIV LNSTETAKEA MVTRFSSIST RKLSNALTVL  120
TCDKSMVATS DYDDFHKLVK RCLLNGLLGA NAQKRKRHYR DALIENVSSK LHAHARDHPQ  180
EPVNFRAIFE HELFGVALKQ AFGKDVESIY VKELGVTLSK DEIFKVLVHD MMEGAIDVDW  240
RDFFPYLKWI PNKSFEARIQ QKHKRRLAVM NALIQDRLKQ NGSESDDDCY LNFLMSEAKT  300
```

TABLE 13-continued

Sequences disclosed herein.

| | |
|---|---|
| LTKEQIAILV WETIIETADT TLVTTEWAIY ELAKHPSVQD RLCKEIQNVC GGEKFKEEQL | 360 |
| SQVPYLNGVF HETLRKYSPA PLVPIRYAHE DTQIGGYHVP AGSEIAINIY GCNMDKKRWE | 420 |
| RPEDWWPERF LDDGKYETSD LHKTMAFGAG KRVCAGALQA SLMAGIAIGR LVQEFEWKLR | 480 |
| DGEEENVDTY GLTSQKLYPL MAIINPRRS | 509 |

SEQ ID NO: 9

| | |
|---|---|
| MSKSNSMNST SHETLFQQLV LGLDRMPLMD VHWLIYVAFG AWLCSYVIHV LSSSSTVKVP | 60 |
| VVGYRSVFEP TWLLRLRFVW EGGSIIGQGY NKFKDSIFQV RKLGTDIVII PPNYIDEVRK | 120 |
| LSQDKTRSVE PFINDFAGQY TRGMVFLQSD LQNRVIQQRL TPKLVSLTKV MKEELDYALT | 180 |
| KEMPDMKNDE WVEVDISSIM VRLISRISAR VFLGPEHCRN QEWLTTTAEY SESLFITGFI | 240 |
| LRVVPHILRP FIAPLLPSYR TLLRNVSSGR RVIGDIIRSQ QGDGNEDILS WMRDAATGEE | 300 |
| KQIDNIAQRM LILSLASIHT TAMTMTHAMY DLCACPEYIE PLRDEVKSVV GASGWDKTAL | 360 |
| NRFHKLDSFL KESQRFNPVF LLTFNRIYHQ SMTLSDGTNI PSGTRIAVPS HAMLQDSAHV | 420 |
| PGPTPPTEFD GFRYSKIRSD SNYAQKYLFS MTDSSNMAFG YGKYACPGRF YASNEMKLTL | 480 |
| AILLLQFEFK LPDGKGRPRN ITIDSDMIPD PRARLCVRKR SLRDE | 525 |

SEQ ID NO: 10

| | |
|---|---|
| MEDPTVLYAC LAIAVATFVV RWYRDPLRSI PTVGGSDLFI LSYIGALRWT RRGREILQEG | 60 |
| YDGYRGSTFK IAMLDRWIVI ANGPKLADEV RRRPDEELNF MDGLGAFVQT KYTLGEAIHN | 120 |
| DPYHVDIIRE KLTRGLPAVL PDVIEELTLA VRQYIPTEGD EWVSVNCSKA ARDIVARASN | 180 |
| RVFVGLPACR NQGYLDLAID FTLSVVKDRA IINMFPELLK PIVGRVVGNA TRNVRRAVPF | 240 |
| VAPLVEERRR LMEEYGEDWS EKPNDMLQWI MDEAASRDSS VKAIAERLLM VNFAAIHTSS | 300 |
| NTITHALYHL AEMPETLQPL REEIEPLVKE EGWTKAAMGK MWWLDSFLRE SQRYNGINIV | 360 |
| SLTRMADKDI TLSDGTFLPK GTLVAVPAYS THRDDAVYAD ALVFDPFRFS RMRAREGEGT | 420 |
| KHQFVNTSVE YVPFGHGKHA CPGRFFAANE LKAMLAYIVL NYDVKLPGDG KRPLNMYWGP | 480 |
| TVLPAPAGQV LFRKRQVSL | 499 |

SEQ ID NO: 11

| | |
|---|---|
| aaacaaagaa tgattcaagt tctaacaccg atccttctct tcctcatttt cttcgttttc | 60 |
| tggaaggttt acaagcacca gaaaaccaaa atcaatcttc caccgggaag cttcggatgg | 120 |
| ccatttctgg gcgaaactct ggcactccta cgtgcaggtt gggactcaga gccgagaga | 180 |
| tttgttcgtg aacggatcaa gaaacacgga agtcctctag tgtttaagac gtcgttgttt | 240 |
| ggcgaccgtt ttgcggtgtt gtgtggacct gccggaaaca agttcctgtt ctgcaacgag | 300 |
| aacaagctgg tggcgtcgtg gtggccggtt ccggtgagga agcttttcgg caagtctctg | 360 |
| ctcacgattc gtggtgatga agctaagtgg atgaggaaga tgttgttatc gtatctcggt | 420 |
| cctgatgctt tcgcaactca ttatgccgtc accatggacg tcgtcacccg tcggcatatc | 480 |
| gacgttcatt ggcgagggaa ggaagaggtg aacgtattcc aaaccgttaa gttatatgcc | 540 |
| tttgagcttg catgtcgttt attcatgaac ctagacgacc aaaccacat tgcaaaactc | 600 |
| ggttccttgt tcaacatttt cttgaaaggc atcattgagc ttccaatcga cgtcccaggg | 660 |
| acacgatttt atagctccaa aaaagcagca gcagctatca ggattgaact aaaaaaattg | 720 |
| attaaagcaa gaaaactgga actgaaagaa gggaaggcat catcttcaca agacctctta | 780 |
| tcacatttgc ttacatctcc agatgaaaat ggtatgtttt taaccgaaga agagattgta | 840 |

TABLE 13-continued

Sequences disclosed herein.

```
gacaacatct tgttactact ctttgcgggt catgatacct cggctctttc aatcactttg  900
ctcatgaaga ctcttggcga acattctgat gtttatgaca aggtgttaaa agagcaacta  960
gagatatcga agacgaaaga agcatgggag tccctgaaat ggaggacat acaaaagatc 1020
aaatactcct ggagtgttat atgtgaagtc atgagactaa atccacctgt tataggaacc 1080
tatagagagg cccttgtgga tattgattat gcgggttata ccatcccaa aggatggaag 1140
ctgcactgga gtgctgtatc gacacaaagg gacgaggcta actttgaaga cgtaacacgt 1200
tttgacccat cacggtttga aggcgcagga ccgactccat tcacctttgt tccgtttgga 1260
gggggcccta gaatgtgttt agggaaagaa tttgctcgat tggaagtact tgcgtttctt 1320
cacaatattg tcaccaattt caaatgggac ctgttgatac ctgatgagaa atagaatat 1380
gatcccatgg ctaccccagc aaagggggctt ccaattcgtc ttcatcccca tcaagtttga 1440
ttacttcaag catgaatcag tgatgtgaag gtaaaccata atggatctta ttggtagtta 1500
cagattatgt gttttatgg catgaagaag ttatgataaa taaaattgtg ttattctaca 1560
acttatgtaa tttgtgcctg taagtaactg aatctattaa tgttttatgt gacatgaaac 1620
ataaatgtat aattagtaaa ttttctgctc aaaaaaaaaa aaaaaaaaaa aaaaaaa    1678
```

SEQ ID NO: 12

```
MIQVLTPILL FLIFFVFWKV YKHQKTKINL PPGSFGWPFL GETLALLRAG WDSEPERFVR   60
ERIKKHGSPL VFKTSLFGDR FAVLCGPAGN KFLFCNENKL VASWWPVPVR KLFGKSLLTI  120
RGDEAKWMRK MLLSYLGPDA FATHYAVTMD VVTRRHIDVH WRGKEEVNVF QTVKLYAFEL  180
ACRLFMNLDD PNHIAKLGSL FNIFLKGIIE LPIDVPGTRF YSSKKAAAAI RIELKKLIKA  240
RKLELKEGKA SSSQDLLSHL LTSPDENGMF LTEEEIVDNI LLLLFAGHDT SALSITLLMK  300
TLGEHSDVYD KVLKEQLEIS KTKEAWESLK WEDIQKMKYS WSVICEVMRL NPPVIGTYRE  360
ALVDIDYAGY TIPKGWKLHW SAVSTQRDEA NFEDVTRFDP SRFEGAGPTP FTFVPFGGGP  420
RMCLGKEFAR LEVLAFLHNI VTNFKWDLLI PDEKIEYDPM ATPAKGLPIR LHPHQV     476
```

SEQ ID NO: 13

```
MGLFPLEDSY ALVFEGLAIT LALYYLLSFI YKTSKKTCTP PKASGEHPIT GHLNLLSGSS   60
GLPHLALASL ADRCGPIFTI RLGIRRVLVV SNWEIAKEIF TTHDLIVSNR PKYLAAKILG  120
FNYVSFSFAP YGPYWVGIRK IIATKLMSSS RLQKLQFVRV FELENSMKSI RESWKEKKDE  180
EGKVLVEMKK WFWELNMNIV LRTVAGKQYT GTVDDADAKR ISELFREWFH YTGRFVVGDA  240
FPPFLGWLDLG GYKKTMELVA SRLDSMVSKW LDEHRKKQAN DDKKEDMDFM DIMISMTEAN  300
SPLEGYGTDT IIKTTCMTLI VSGVDTTSIV LTWALSLLLN NRDTLKKAQE ELDMCVGKGR  360
QVNESDLVNL IYLEAVLKEA LRLYPAAFLG GPRAFLEDCT VAGYRIPKGT CLLINMWKLH  420
RDPNIWSDPC EFKPERFLTP NQKDVDVIGM DFELIPFGAG RRYCPGTRLA LQMLHIVLAT  480
LLQNFEMSTP NDAPVDMTAS VGMTNAKASP LEVLLSPRVK WS                   522
```

SEQ ID NO: 14

```
MIQVLTPILL FLIFFVFWKV YKHQKTKINL PPGSFGWPFL GETLALLRAG WDSEPERFVR   60
ERIKKHGSPL VFKTSLFGDR FAVLCGPAGN KFLFCNENKL VASWWPVPVR KLFGKSLLTI  120
RGDEAKWMRK MLLSYLGPDA FATHYAVTMD VVTRRHIDVH WRGKEEVNVF QTVKLYAFEL  180
ACRLFMNLDD PNHIAKLGSL FNIFLKGIIE LPIDVPGTRF YSSKKAAAAI RIELKKLIKA  240
RKLELKEGKA SSSQDLLSHL LTSPDENGMF LTEEEIVDNI LLLLFAGHDT SALSITLLMK  300
```

TABLE 13-continued

Sequences disclosed herein.

| | | | | | |
|---|---|---|---|---|---|
|TLGEHSDVYD|KVLKEQLEIS|KTKEAWESLK|WEDIQKMKYS|WSVICEVMRL|NPPVIGTYRE 360|
|ALVDIDYAGY|TIPKGWKLHW|SAVSTQRDEA|NFEDVTRFDP|SRFEGAGPTP|FTFVPFGGGP 420|
|RMCLGKEFAR|LEVLAFLHNI|VTNFKWDLLI|PDEKIEYDPM|ATPAKGLPIR|LHPHQV    476|

SEQ ID NO: 15

| | | | | | |
|---|---|---|---|---|---|
|MESLVVHTVN|AIWCIVIVGI|FSVGYHVYGR|AVVEQWRMRR|SLKLQGVKGP|PPSIFNGNVS  60|
|EMQRIQSEAK|HCSGDNIISH|DYSSSLFPHF|DHWRKQYGRI|YTYSTGLKQH|LYINHPEMVK 120|
|ELSQTNTLNL|GRITHITKRL|NPILGNGIIT|SNGPWAHQR|RIIAYEFTHD|KIKGMVGLMV 180|
|ESAMPMLNKW|EEMVKRGGEM|GCDIRVDEDL|KDVSADVIAK|ACFGSSFSKG|KAIFSMIRDL 240|
|LTAITKRSVL|FRFNGFTDMV|FGSKKHGDVD|IDALEMELES|SIWETVKERE|IECKDTHKKD 300|
|LMQLILEGAM|RSCDGNLWDK|SAYRRFVVDN|CKSIYFAGHD|STAVSVSWCL|MLLALNPSWQ 360|
|VKIRDEILSS|CKNGIPDAES|IPNLKTVTMV|IQETMRLYPP|APIVGREASK|DIRLGDLVVP 420|
|KGVCIWTLIP|ALHRDPEIWG|PDANDFKPER|FSEGISKACK|YPQSYIPFGL|GPRTCVGKNF 480|
|GMMEVKVLVS|LIVSKFSFTL|SPTYQHSPSH|KLLVEPQHGV|VIRVV|          525|

SEQ ID NO: 16

| | | | | | |
|---|---|---|---|---|---|
|MYFLLQYLNI|TTVGVFATLF|LSYCLLLWRS|RAGNKKIAPE|AAAAWPIIGH|LHLLAGGSHQ  60|
|LPHITLGNMA|DKYGPVFTIR|IGLHRAVVVS|SWEMAKEGST|ANDQVSSSRP|ELLASKLLGY 120|
|NYAMFGFSPY|GSYWREMRKI|ISLELLSNSR|LELLKDVRAS|EVVTSIKELY|KLWAEKKNES 180|
|GLVSVEMKQW|FGDLTLNVIL|RMVAGKRYFS|ASDASENKQA|QRCRRVFREF|FHLSGLFVVA 240|
|DAIPFLGWLD|WGRHEKTLKK|TAIEMDSIAQ|EWLEEHRRRK|DSGDDNSTQD|FMDVMQSVLD 300|
|GKNLGGYDAD|TINKATCLTL|ISGGSDTTVV|SLTWALSLVL|NNRDTLKKAQ|EELDIQVGKE 360|
|RLVNEQDISK|LVYLQAIVKE|TLRLYPPGPL|GGLRQFTEDC|TLGGYHVSKG|TRLIMNLSKI 420|
|QKDPRIWSDP|TEFQPERFLT|THKDVDPRGK|HFEFIPFGAG|RRACPGITFG|LQVLHLTLAS 480|
|FLHAFEFSTP|SNEQVNMRES|LGLTNMKSTP|LEVLISPRLS|SCSLYN|          526|

SEQ ID NO: 17

| | | | | | |
|---|---|---|---|---|---|
|MEPNFYLSLL|LLFVTFISLS|LFFIFYKQKS|PLNLPPGKMG|YPIIGESLEF|LSTGWKGHPE  60|
|KFIFDRMRKY|SSELFKTSIV|GESTVVCCGA|ASNKFLFSNE|NKLVTAWWPD|SVNKIFPTTS 120|
|LDSNLKEESI|KMRKLLPQFF|KPEALQRYVG|VMDVIAQRHF|VTHWDNKNEI|TVYPLAKRYT 180|
|FLLACRLFMS|VEDENHVAKF|SDPFQLIAAG|IISLPIDLPG|TPFNKAIKAS|NFIRKELIKI 240|
|IKQRRVDLAE|GTASPTQDIL|SHMLLTSDEN|GKSMNELNIA|DKILGLLIGG|HDTASVACTF 300|
|LVKYLGELPH|IYDKVYQEQM|EIAKSKPAGE|LLNWDDLKKM|KYSWNVACEV|MRLSPPLQGG 360|
|FREAITDFMF|NGFSIPKGWK|LYWSANSTHK|NAECFPMPEK|FDPTRFEGNG|PAPYTFVPFG 420|
|GGPRMCPGKE|YARLEILVFM|HNLVKRFKWE|KVIPDEKIIV|DPFPIPAKDL|PIRLYPHKA 479|

SEQ ID NO: 18

| | | | | | |
|---|---|---|---|---|---|
|atggaagcct|cttacctata|catttctatt|ttgcttttac|tggcatcata|cctgttcacc  60|
|actcaactta|gaaggaagag|cgctaatcta|ccaccaaccg|tgtttccatc|aataccaatc 120|
|attggacact|tatacttact|caaaaagcct|ctttatagaa|ctttagcaaa|aattgccgct 180|
|aagtacggac|caatactgca|attacaactc|ggctacagac|gtgttctggt|gatttcctca 240|
|ccatcagcag|cagaagagtg|ctttaccaat|aacgatgtaa|tcttcgcaaa|tagacctaag 300|
|acattgtttg|gcaaaatagt|gggtggaaca|tcccttggca|gttatcccta|cggcgatcaa 360|

TABLE 13-continued

Sequences disclosed herein.

```
tggcgtaatc taaggagagt agcttctatc gaaatcctat cagttcatag gttgaacgaa  420
tttcatgata tcagagtgga tgagaacaga ttgttaatta gaaaacttag aagttcatct  480
tctcctgtta ctcttataac agtcttttat gctctaacat tgaacgtcat tatgagaatg  540
atctctggca aaagatattt cgacagtggg gatagagaat ggaggagga aggtaagaga  600 tttcgagaaa tcttagacga aacgttgctt ctagccggtg cttctaatgt tggcgactac  660
ttaccaatat tgaactggtt gggagttaag tctcttgaaa agaaattgat cgctttgcag  720
aaaaagagag atgactttt ccaggggtttg attgaacagg ttagaaaatc tcgtggtgct  780
aaagtaggca aaggtagaaa aacgatgatc gaactcttat tatctttgca agagtcagaa  840
cctgagtact atacagatgc tatgataaga tcttttgtcc taggtctgct ggctgcaggt  900
agtgatactt cagcgggcac tatggaatgg gccatgagct tactggtcaa tcacccacat  960
gtattgaaga agctcaagc tgaaatcgat agagttatcg gtaataacag attgattgac 1020
gagtcagaca ttggaaatat ccctttacatc gggtgtatta tcaatgaaac tctaagactc 1080
tatccagcag ggccattgtt gttcccacat gaaagttctg ccgactgcgt tatttccggt 1140
tacaatatac ctagaggtac aatgttaatc gtaaaccaat gggcgattca tcacgatcct 1200
aaagtctggg atgatcctga aacctttaaa cctgaaagat ttcaaggatt agaaggaact 1260
agagatggtt tcaaacttat gccattcggt tctgggagaa gaggatgtcc aggtgaaggt 1320
ttggcaataa ggctgttagg gatgacacta ggctcagtga tccaatgttt tgattgggag 1380
agagtaggag atgagatggt tgacatgaca gaaggtttgg gtgtcacact tcctaaggcc 1440
gttccattag ttgccaaatg taagccacgt tccgaaatga ctaatctcct atccgaactt 1500
taa                                                              1503
```

SEQ ID NO: 19

```
MEASYLYISI LLLLASYLFT TQLRRKSANL PPTVFPSIPI IGHLYLLKKP LYRTLAKIAA   60

KYGPILQLQL GYRRVLVISS PSAAEECFTN NDVIFANRPK TLFGKIVGGT SLGSLSYGDQ  120

WRNLRRVASI EILSVHRLNE FHDIRVDENR LLIRKLRSSS SPVTLITVFY ALTLNVIMRM  180

ISGKRYFDSG DRELEEEGKR FREILDETLL LAGASNVGDY LPILNWLGVK SLEKKLIALQ  240

KKRDDFFQGL IEQVRKSRGA KVGKGRKTMI ELLLSLQESE PEYYTDAMIR SFVLGLLAAG  300

SDTSAGTMEW AMSLLVNHPH VLKKAQAEID RVIGNNRLID ESDIGNIPYI GCIINETLRL  360

YPAGPLLFPH ESSADCVISG YNIPRGTMLI VNQWAIHHDP KVWDDPETFK PERFQGLEGT  420

RDGFKLMPFG SGRRGCPGEG LAIRLLGMTL GSVIQCFDWE RVGDEMVDMT EGLGVTLPKA  480

VPLVAKCKPR SEMTNLLSEL                                             500
```

SEQ ID NO: 20

```
MQSDSVKVSP FDLVSAAMNG KAMEKLNASE SEDPTTLPAL KMLVENRELL TLFTTSFAVL   60

IGCLVFLMWR RSSSKKLVQD PVPQVIVVKK KEKESEVDDG KKKVSIFYGT QTGTAEGFAK  120

ALVEEAKVRY EKTSFKVIDL DDYAADDDEY EEKLKKESLA FFFLATYGDG EPTDNAANFY  180

KWFTEGDDKG EWLKKLQYGV FGLGNRQYEH FNKIAIVVDD KLTEMGAKRL VPVGLGDDDQ  240

CIEDDFTAWK ELVWPELDQL LRDEDDTSVT TPYTAAVLEY RVVYHDKPAD SYAEDQTHTN  300

GHVVHDAQHP SRSNVAFKKE LHTSQSDRSC THLEFDISHT GLSYETGDHV GVYSENLSEV  360

VDEALKLLGL SPDTYFSVHA DKEDGTPIGG ASLPPPFPPC TLRDALTRYA DVLSSPKKVA  420

LLALAAHASD PSEADRLKFL ASPAGKDEYA QWIVANQRSL LEVMQSFPSA KPPLGVFFAA  480
```

TABLE 13-continued

Sequences disclosed herein.

VAPRLQPRYY SISSSPKMSP NRIHVTCALV YETTPAGRIH RGLCSTWMKN AVPLTESPDC 540

SQASIFVRTS NFRLPVDPKV PVIMIGPGTG LAPFRGFLQE RLALKESGTE LGSSIFFFGC 600

RNRKVDFIYE DELNNFVETG ALSELIVAFS REGTAKEYVQ HKMSQKASDI WKLLSEGAYL 660

YVCGDAKGMA KDVHRTLHTI VQEQGSLDSS KAELYVKNLQ MSGRYLRDVW           710

SEQ ID NO: 21

MTSALYASDL FKQLKSIMGT DSLSDDVVLV IATTSLALVA GFVVLLWKKT TADRSGELKP  60

LMIPKSLMAK DEDDDLDLGS GKTRVSIFFG TQTGTAEGFA KALSEEIKAR YEKAAVKVID 120

LDDYAADDDQ YEEKLKKETL AFFCVATYGD GEPTDNAARF YKWFTEENER DIKLQQLAYG 180

VFALGNRQYE HFNKIGIVLD EELCKKGAKR LIEVGLGDDD QSIEDDFNAW KESLWSELDK 240

LLKDEDDKSV ATPYTAVIPE YRVVTHDPRF TTQKSMESNV ANGNTTIDIH HPCRVDVAVQ 300

KELHTHESDR SCIHLEFDIS RTGITYETGD HVGVYAENHV EIVEEAGKLL GHSLDLVFSI 360

HADKEDGSPL ESAVPPPFPG PCTLGTGLAR YADLLNPPRK SALVALAAYA TEPSEAEKLK 420

HLTSPDGKDE YSQWIVASQR SLLEVMAAFP SAKPPLGVFF AAIAPRLQPR YYSISSSPRL 480

APSRVHVTSA LVYGPTPTGR IHKGVCSTWM KNAVPAEKSH ECSGAPIFIR ASNFKLPSNP 540

STPIVMVGPG TGLAPFRGFL QERMALKEDG EELGSSLLFF GCRNRQMDFI YEDELNNFVD 600

QGVISELIMA FSREGAQKEY VQHKMMEKAA QVWDLIKEEG YLYVCGDAKG MARDVHRTLH 660

TIVQEQEGVS SSEAEAIVKK LQTEGRYLRD VW                              692

SEQ ID NO: 22

MAELDTLDIV VLGVIFLGTV AYFTKGKLWG VTKDPYANGF AAGGASKPGR TRNIVEAMEE  60

SGKNCVVFYG SQTGTAEDYA SRLAKEGSR FGLNTMIADL EDYDFDNLDT VPSDNIVMFV 120

LATYGEGEPT DNAVDFYEFI TGEDASFNEG NDPPLGNLNY VAFGLGNNTY EHYNSMVRNV 180

NKALEKLGAH RIGEAGEGDD GAGTMEEDFL AWKDPMWEAL AKKMGLEERE AVYEPIFAIN 240

ERDDLTPEAN EVYLGEPNKL HLEGTAKGPF NSHNPYIAPI AESYELFSAK DRNCLHMEID 300

ISGSNLKYET GDHIAIWPTN PGEEVNKFLD ILDLSGKQHS VVTVKALEPT AKVPFPNPTT 360

YDAILRYHLE ICAPVSRQFV STLAAFAPND DIKAEMNRLG SDKDYFHEKT GPHYYNIARF 420

LASVSKGEKW TKIPFSAFIE GLTKLQPRYY SISSSSLVQP KKISITAVVE SQQIPGRDDP 480

FRGVATNYLF ALKQKQNGDP NPAPFGQSYE LTGPRNKYDG IHVPVHVRHS NFKLPSDPGK 540

PIIMIGPGTG VAPFRGFVQE RAKQARDGVE VGKTLLFFGC RKSTEDFMYQ KEWQEYKEAL 600

GDKFEMITAF SREGSKKVYV QHRLKERSKE VSDLLSQKAY FYVCGDAAHM AREVNTVLAQ 660

IIAEGRGVSE AKGEEIVKNM RSANQYQVCS DFVTLHCKET TYANSELQED VWS         713

SEQ ID NO: 23 atgcaatcgg aatccgttga agcatcgacg attgatttga tgactgctgt tttgaaggac  60
acagtgatcg atacagcgaa cgcatctgat aacggagact caaagatgcc gccggcgttg 120
gcgatgatgt tcgaaattcg tgatctgttg ctgattttga ctacgtcagt tgctgttttg 180
gtcggatgtt tcgttgtttt ggtgtggaag agatcgtccg ggaagaagtc cggcaaggaa 240
ttggagccgc cgaagatcgt tgtgccgaag aggcggctgg agcaggaggt tgatgatggt 300
aagaagaagg ttacgatttt cttcggaaca caaactggaa cggctgaagg tttcgctaag 360
gcacttttcg aagaagcgaa agcgcgatat gaaaaggcag cgtttaaagt gattgatttg 420
gatgattatg ctgctgattt ggatgagtat gcagagaagc tgaagaagga aacatatgct 480

TABLE 13-continued

Sequences disclosed herein.

```
ttcttcttct tggctacata tggagatggt gagccaactg ataatgctgc caaattttat  540
aaatggttta etgagggaga cgagaaaggc gtttggcttc aaaaacttca atatggagta  600
tttggtcttg gcaacagaca atatgaacat ttcaacaaga ttggaatagt ggttgatgat  660
ggtctcaccg agcagggtgc aaaacgcatt gttcccgttg gtcttggaga cgacgatcaa  720
tcaattgaag acgattttc ggcatggaaa gagttagtgt ggcccgaatt ggatctattg  780
cttcgcgatg aagatgacaa agctgctgca actccttaca cagctgcaat ccctgaatac  840
cgcgtcgtat ttcatgacaa acccgatgcg ttttctgatg atcatactca aaccaatggt  900
catgctgttc atgatgctca acatccatgc agatccaatg tggctgttaa aaaagagctt  960
catactcctg aatccgatcg ttcatgcaca catcttgaat ttgacatttc tcacactgga 1020
ttatcttatg aaactgggga tcatgttggt gtatactgtg aaaacctaat tgaagtagtg 1080
gaagaagctg ggaaattgtt aggattatca acagatactt atttctcgtt acatattgat 1140
aacgaagatg gttcaccact tggtggacct tcattacaac ctccttttcc tccttgtact 1200
ttaagaaaag cattgactaa ttatgcagat ctgttaagct ctcccaaaaa gtcaactttg 1260
cttgctctag ctgctcatgc ttccgatccc actgaagctg atcgtttaag atttcttgca 1320
tctcgcgagg gcaaggatga atatgctgaa tgggttgttg caaaccaaag aagtcttctt 1380
gaagtcatgg aagctttccc gtcagctaga ccgccacttg gtgttttctt tgcagcggtt 1440
gcaccgcgtt tacagcctcg ttactactct atttcttcct ccccaaagat ggaaccaaac 1500
aggattcatg ttacttgcgc gttggtttat gaaaaaactc ccgcaggtcg tatccacaaa 1560
ggaatctgct caacctggat gaagaacgct gtacctttga ccgaaagtca agattgcagt 1620
tgggcaccga tttttgttag aacatcaaac ttcagacttc caattgaccc gaaagtcccg 1680
gttatcatga ttggtcctgg aaccggggttg gctccattta ggggttttct tcaagaaaga 1740
ttggctctta aagaatccgg aaccgaactc gggtcatcta ttttattctt cggttgtaga 1800
aaccgcaaag tggattacat atatgagaat gaactcaaca actttgttga aaatggtgcg 1860
cttttctgagc ttgatgttgc tttctcccgc gatggcccga cgaaagaata cgtgcaacat 1920
aaaatgaccc aaaaggcttc tgaaatatgg aatatgcttt ctgagggagc atatttatat 1980
gtatgtggtg atgctaaagg catggctaaa gatgtacacc gtacacttca caccattgtg 2040
caagaacagg gaagtttgga ctcgtctaaa gcggagttgt atgtgaagaa tctacaaatg 2100
tcaggaagat acctccgtga tgtttggtaa                                   2130
```

SEQ ID NO: 24

```
atgcaatcta actccgtgaa gatttcgccg cttgatctgg taactgcgct gtttagcggc   60
aaggttttgg acacatcgaa cgcatcggaa tcgggagaat ctgctatgct gccgactata  120
gcgatgatta tggagaatcg tgagctgttg atgatactca aacgtcggt tgctgtattg  180
atcggatgcg ttgtcgtttt ggtgtggcgg agatcgtcta cgaagaagtc ggcgttggag  240
ccaccggtga ttgtggttcc gaagagagtg caagaggagg aagttgatga tggtaagaag  300
aaagttacgg ttttcttcgg cacccaaact ggaacagctg aaggcttcgc taaggcactt  360
gttgaggaag ctaaagctcg atatgaaaag gctgtctttta agtaattga tttggatgat  420
tatgctgctg atgacgatga gtatgaggag aaactaaaga aagaatcttt ggccttttc  480
tttttggcta cgtatggaga tggtgagcca acagataatg ctgccagatt ttataaatgg  540
tttactgagg gagatgcgaa aggagaatgg cttaataagc ttcaatatgg agtatttggt  600
```

TABLE 13-continued

Sequences disclosed herein.

```
ttgggtaaca gacaatatga acatttaac aagatcgcaa aagtggttga tgatggtctt   660
gtagaacagg gtgcaaagcg tcttgttcct gttggacttg gagatgatga tcaatgtatt  720
gaagatgact tcaccgcatg gaaagagtta gtatggccgg agttggatca attacttcgt  780
gatgaggatg acacaactgt tgctactcca tacacagctg ctgttgcaga atatcgcgtt  840
gtttttcatg aaaaaccaga cgcgcttcct gaagattata gttatacaaa tggccatgct  900
gttcatgatg ctcaacatcc atgcagatcc aacgtggctg tcaaaaagga acttcatagt  960
cctgaatctg accggtcttg cactcatctt gaatttgaca tctcgaacac cggactatca 1020
tatgaaactg gggaccatgt tggagtttac tgtgaaaact gagtgaagt tgtgaatgat 1080
gctgaaagat tagtaggatt accaccagac acttactcct ccatccacac tgatagtgaa 1140
gacgggtcgc cacttggcgg agcctcattg ccgcctcctt tcccgccatg cactttaagg 1200
aaagcattga cgtgttatgc tgatgttttg agttctccca agaagtcggc tttgcttgca 1260
ctagctgctc atgccaccga tcccagtgaa gctgatagat tgaaatttct tgcatccccc 1320
gccgaaagg atgaatattc tcaatggata gttgcaagcc aaagaagtct ccttgaagtc 1380
atggaagcat tcccgtcagc taagccttca cttggtgttt tctttgcatc tgttgccccg 1440
cgcttacaac caagatacta ctctatttct tcctcaccca agatggcacc ggataggatt 1500
catgttacat gtgcattagt ctatgagaaa acacctgcag ccgcatcca caaggagtt 1560
tgttcaactt ggatgaagaa cgcagtgcct atgaccgaga gtcaagattg cagttgggcc 1620
ccaatatacg tccgaacatc caatttcaga ctaccatctg accctaaggt cccggttatc 1680
atgattggac ctggcactgg tttggctcct tttagaggtt tccttcaaga gcggttagct 1740
ttaaaggaag ccggaactga cctcggttta tccattttat tcttcggatg taggaatcgc 1800
aaagtggatt tcatatatga aaacgagctt aacaactttg tggagactgg tgctcttttct 1860
gagcttattg ttgctttctc ccgtgaaggc ccgactaagg aatatgtgca acacaagatg 1920
agtgagaagg cttcggatat ctggaacttg cttttctgaag gagcatattt atacgtatgt 1980
ggtgatgcca aaggcatggc caaagatgta catcgaaccc tccacacaat tgtgcaagaa 2040
cagggatctc ttgactcgtc aaaggcagaa ctctacgtga agaatctaca atgtcagga 2100
agatacctcc gtgacgtttg gtaa                                       2124
```

SEQ ID NO: 25

```
MTSALYASDL FKQLKSIMGT DSLSDDVVLV IATTSLALVA GFVVLLWKKT TADRSGELKP   60
LMIPKSLMAK DEDDDLDLGS GKTRVSIFFG TQTGTAEGFA KALSEEIKAR YEKAAVKVID  120
LDDYAADDDQ YEEKLKKETL AFFCVATYGD GEPTDNAARF YKWFTEENER DIKLQQLAYG  180
VFALGNRQYE HFNKIGIVLD EELCKKGAKR LIEVGLGDDD QSIEDDFNAW KESLWSELDK  240
LLKDEDDKSV ATPYTAVIPE YRVVTHDPRF TTQKSMESNV ANGNTTIDIH HPCRVDVAVQ  300
KELHTHESDR SCIHLEFDIS RTGITYETGD HVGVYAENHV EIVEEAGKLL GHSLDLVFSI  360
HADKEDGSPL ESAVPPPFPG PCTLGTGLAR YADLLNPPRK SALVALAAYA TEPSEAEKLK  420
HLTSPDGKDE YSQWIVASQR SLLEVMAAFP SAKPPLGVFF AAIAPRLQPR YYSISSSPRL  480
APSRVHVTSA LVYGPTPTGR IHKGVCSTWM KNAVPAEKSH ECSGAPIFIR ASNFKLPSNP  540
STPIVMVGPG TGLAPFRGFL QERMALKEDG EELGSSLLFF GCRNRQMDFI YEDELNNFVD  600
QGVISELIMA FSREGAQKEY VQHKMMEKAA QVWDLIKEEG YLYVCGDAKG MARDVHRTLH  660
TIVQEQEGVS SSEAEAIVKK LQTEGRYLRD VW                               692
```

TABLE 13-continued

Sequences disclosed herein.

SEQ ID NO: 26

```
MSSSSSSSTS MIDLMAAIIK GEPVIVSDPA NASAYESVAA ELSSMLIENR QFAMIVTTSI  60
AVLIGCIVML VWRRSGSGNS KRVEPLKPLV IKPREEEIDD GRKKVTIFFG TQTGTAEGFA 120
KALGEEAKAR YEKTRFKIVD LDDYAADDDE YEEKLKKEDV AFFFLATYGD GEPTDNAARF 180
YKWFTEGNDR GEWLKNLKYG VFGLGNRQYE HFNKVAKVVD DILVEQGAQR LVQVGLGDDD 240
QCIEDDFTAW REALWPELDT ILREEGDTAV ATPYTAAVLE YRVSIHDSED AKFNDITLAN 300
GNGYTVFDAQ HPYKANVAVK RELHTPESDR SCIHLEFDIA GSGLTMKLGD HVGVLCDNLS 360
ETVDEALRLL DMSPDTYFSL HAEKEDGTPI SSSLPPPFPP CNLRTALTRY ACLLSSPKKS 420
ALVALAAHAS DPTEAERLKH LASPAGKDEY SKWVVESQRS LLEVMAEFPS AKPPLGVFFA 480
GVAPRLQPRF YSISSSPKIA ETRIHVTCAL VYEKMPTGRI HKGVCSTWMK NAVPYEKSEK 540
LFLGRPIFVR QSNFKLPSDS KVPIIMIGPG TGLAPFRGFL QERLALVESG VELGPSVLFF 600
GCRNRRMDFI YEEELQRFVE SGALAELSVA FSREGPTKEY VQHKMMDKAS DIWNMISQGA 660
YLYVCGDAKG MARDVHRSLH TIAQEQGSMD STKAEGFVKN LQTSGRYLRD VW          712
```

SEQ ID NO: 27

```
MQSESVEAST IDLMTAVLKD TVIDTANASD NGDSKMPPAL AMMFEIRDLL LILTTSVAVL  60
VGCFVVLVWK RSSGKKSGKE LEPPKIVVPK RRLEQEVDDG KKKVTIFFGT QTGTAEGFAK 120
ALFEEEAKARY EKAAFKVIDL DDYAADLDEY AEKLKKETYA FFFLATYGDG EPTDNAAKFY 180
KWFTEGDEKG VWLQKLQYGV FGLGNRQYEH FNKIGIVVDD GLTEQGAKRI VPVGLGDDDQ 240
SIEDDFSAWK ELVWPELDLL LRDEDDKAAA TPYTAAIPEY RVVFHDKPDA FSDDHTQTNG 300
HAVHDAQHPC RSNVAVKKEL HTPESDRSCT HLEFDISHTG LSYETGDHVG VYCENLIEVV 360
EEAGKLLGLS TDTYFSLHID NEDGSPLGGP SLQPPFPPCT LRKALTNYAD LLSSPKKSTL 420
LALAAHASDP TEADRLRFLA SREGKDEYAE WVVANQRSLL EVMEAFPSAR PPLGVFFAAV 480
APRLQPRYYS ISSSPKMEPN RIHVTCALVY EKTPAGRIHK GICSTWMKNA VPLTESQDCS 540
WAPIFVRTSN FRLPIDPKVP VIMIGPGTGL APFRGFLQER LALKESGTEL GSSILFFGCR 600
NRKVDYIYEN ELNNFVENGA LSELDVAFSR DGPTKEYVQH KMTQKASEIW NMLSEGAYLY 660
VCGDAKGMAK DVHRTLHTIV QEQGSLDSSK AELYVKNLQM SGRYLRDVW              709
```

SEQ ID NO: 28

```
MQSNSVKISP LDLVTALFSG KVLDTSNASE SGESAMLPTI AMIMENRELL MILTTSVAVL  60
IGCVVVLVWR RSSTKKSALE PPVIVVPKRV QEEEVDDGKK KVTVFFGTQT GTAEGFAKAL 120
VEEEAKARYEK AVFKVIDLDD YAADDDEYEE KLKKESLAFF FLATYGDGEP TDNAARFYKW 180
FTEGDAKGEW LNKLQYGVFG LGNRQYEHFN KIAKVVDDGL VEQGAKRLVP VGLGDDDQCI 240
EDDFTAWKEL VWPELDQLLR DEDDTTVATP YTAAVAEYRV VFHEKPDALS EDYSYTNGHA 300
VHDAQHPCRS NVAVKKELHS PESDRSCTHL EFDISNTGLS YETGDHVGVY CENLSEVVND 360
AERLVGLPPD TYSSIHTDSE DGSPLGGASL PPPFPPCTLR KALTCYADVL SSPKKSALLA 420
LAAHATDPSE ADRLKFLASP AGKDEYSQWI VASQRSLLEV MEAFPSAKPS LGVFFASVAP 480
RLQPRYYSIS SSPKMAPDRI HVTCALVYEK TPAGRIHKGV CSTWMKNAVP MTESQDCSWA 540
PIYVRTSNFR LPSDPKVPVI MIGPGTGLAP FRGFLQERLA LKEAGTDLGL SILFFGCRNR 600
KVDFIYENEL NNFVETGALS ELIVAFSREG PTKEYVQHKM SEKASDIWNL LSEGAYLYVC 660
GDAKGMAKDV HRTLHTIVQE QGSLDSSKAE LYVKNLQMSG RYLRDVW                707
```

TABLE 13-continued

Sequences disclosed herein.

SEQ ID NO: 29

| | | | | | |
|---|---|---|---|---|---|
| MAEQQKIKKS | PHVLLIPFPL | QGHINPFIQF | GKRLISKGVK | ITLVTTIHTL | NSTLNHSNTT | 60
| TTSIEIQAIS | DGCDEGGFMS | AGESYLETFK | QVGSKSLADL | IKKLQSEGTT | IDAIIYDSMT | 120
| EWVLDVAIEF | GIDGGSFFTQ | ACVVNSLYYH | VHKGLISLPL | GETVSVPGFP | VLQRWETPLI | 180
| LQNHEQIQSP | WSQMLFGQFA | NIDQARWVFT | NSFYKLEEEV | IEWTRKIWNL | KVIGPTLPSM | 240
| YLDKRLDDDK | DNGFNLYKAN | HHECMNWLDD | KPKESVVYVA | FGSLVKHGPE | QVEEITRALI | 300
| DSDVNFLWVI | KHKEEGKLPE | NLSEVIKTGK | GLIVAWCKQL | DVLAHESVGC | FVTHCGFNST | 360
| LEAISLGVPV | VAMPQFSDQT | TNAKLLDEIL | GVGVRVKADE | NGIVRRGNLA | SCIKMIMEEE | 420
| RGVIIRKNAV | KWKDLAKVAV | HEGGSSDNDI | VEFVSELIKA | | | 460

SEQ ID NO: 30

| | | | | | |
|---|---|---|---|---|---|
| MDAMATTEKK | PHVIFIPFPA | QSHIKAMLKL | AQLLHHKGLQ | ITFVNTDFIH | NQFLESSGPH | 60
| CLDGAPGFRF | ETIPDGVSHS | PEASIPIRES | LLRSIETNFL | DRFIDLVTKL | PDPPTCIISD | 120
| GFLSVFTIDA | AKKLGIPVMM | YWTLAACGFM | GFYHIHSLIE | KGFAPLKDAS | YLTNGYLDTV | 180
| IDWVPGMEGI | RLKDFPLDWS | TDLNDKVLMF | TTEAPQRSHK | VSHHIFHTFD | ELEPSIIKTL | 240
| SLRYNHIYTI | GPLQLLLDQI | PEEKKQTGIT | SLHGYSLVKE | EPECFQWLQS | KEPNSVVYVN | 300
| FGSTTVMSLE | DMTEFGWGLA | NSNHYFLWII | RSNLVIGENA | VLPPELEEHI | KKRGFIASWC | 360
| SQEKVLKHPS | VGGFLTHCGW | GSTIESLSAG | VPMICWPYSW | DQLTNCRYIC | KEWEVGLEMG | 420
| TKVKRDEVKR | LVQELMGEGG | HKMRNKAKDW | KEKARIAIAP | NGSSSLNIDK | MVKEITVLAR | 480
| N | | | | | | 481

SEQ ID NO: 31

| | | | | | |
|---|---|---|---|---|---|
| atggatgcaa | tggctacaac | tgagaagaaa | ccacacgtca | tcttcatacc | atttccagca | 60
| caaagccaca | ttaaagccat | gctcaaacta | gcacaacttc | tccaccacaa | aggactccag | 120
| ataaccttcg | tcaacaccga | cttcatccac | aaccagtttc | ttgaatcatc | gggcccacat | 180
| tgtctagacg | gtgcaccggg | tttccggttc | gaaaccattc | cggatggtgt | ttctcacagt | 240
| ccggaagcga | gcatcccaat | cagagaatca | ctcttgagat | ccattgaaac | caacttcttg | 300
| gatcgtttca | ttgatcttgt | aaccaaactt | ccggatcctc | cgacttgtat | tatctcagat | 360
| gggttcttgt | cggttttcac | aattgacgct | gcaaaaaagc | ttggaattcc | ggtcatgatg | 420
| tattggacac | ttgctgcctg | tgggttcatg | gttttttacc | atattcattc | tctcattgag | 480
| aaaggatttg | caccacttaa | agatgcaagt | tacttgacaa | atgggtattt | ggacaccgtc | 540
| attgattggg | ttccgggaat | ggaaggcatc | cgtctcaagg | atttcccgct | ggactggagc | 600
| actgacctca | tgacaaagt | tttgatgttc | actacggaag | ctcctcaaag | gtcacacaag | 660
| gtttcacatc | atattttcca | cacgttcgat | gagttggagc | ctagtattat | aaaaactttg | 720
| tcattgaggt | ataatcacat | ttacaccatc | ggcccactgc | aattacttct | tgatcaaata | 780
| cccgaagaga | aaaagcaaac | tggaattacg | agtctccatg | gatacagttt | agtaaaagaa | 840
| gaaccagagt | gtttccagtg | gcttcagtct | aaagaaccaa | attccgtcgt | ttatgtaaat | 900
| tttggaagta | ctacagtaat | gtcttttagaa | gacatgacgg | aatttggttg | gggacttgct | 960
| aatagcaacc | attatttcct | ttggatcatc | cgatcaaact | tggtgatagg | ggaaaatgca | 1020
| gttttgcccc | ctgaacttga | ggaacatata | aagaaaagag | ctttattgc | tagctggtgt | 1080
| tcacaagaaa | aggtcttgaa | gcacccttcg | gttggagggt | tcttgactca | ttgtgggtgg | 1140

TABLE 13-continued

Sequences disclosed herein.

```
ggatcgacca tcgagagctt gtctgctggg gtgccaatga tatgctggcc ttattcgtgg 1200
gaccagctga ccaactgtag gtatatatgc aaagaatggg aggttgggct cgagatggga 1260
accaaagtga acgagatga agtcaagagg cttgtacaag agttgatggg agaaggaggt 1320
cacaaaatga ggaacaaggc taaagattgg aaagaaaagg ctcgcattgc aatagctcct 1380
aacggttcat cttctttgaa catagacaaa atggtcaagg aaatcaccgt gctagcaaga 1440
aactagttac aaagttgttt cacattgtgc tttctattta agatgtaact tgttctaat 1500 ttaatattgt ctagatgtat tgaaccataa gtttagttgg tctcaggaat tgattttaa 1560 tgaaataatg gtcattaggg gtgagt                                     1586
```

SEQ ID NO: 32

```
atggatgcaa tggcaactac tgagaaaaag cctcatgtga tcttcattcc atttcctgca   60
caatctcaca taaaggcaat gctaaagtta gcacaactat tacaccataa gggattacag  120
ataactttcg tgaataccga cttcatccat aatcaatttc tggaatctag tggccctcat  180
tgtttggacg gagccccagg gtttagattc gaaacaattc ctgacggtgt tcacattcc   240 ccagaggcct ccatcccaat aagagagagt ttactgaggt caatagaaac caacttttg   300 gatcgtttca ttgacttggt cacaaaactt ccagacccac caacttgcat aatctctgat  360
ggctttctgt cagtgtttac tatcgacgct gccaaaaagt tgggtatccc agttatgatg  420
tactggactc ttgctgcatg cggtttcatg ggtttctatc acatccattc tcttatcgaa  480
aagggttttg ctccactgaa agatgcatca tacttaacca acggctacct ggatactgtt  540
attgactggg taccaggtat ggaaggtata agacttaaag attttccttt ggattggtct  600 acagaccta atgataaagt attgatgttt actacagaag ctccacaaag atctcataag  660
gtttcacatc atatctttca cacctttgat gaattggaac catcaatcat caaaaccttg  720
tctctaagat acaatcatat ctacactatt ggtccattac aattacttct agatcaaatt  780
cctgaagaga aaaagcaaac tggtattaca tccttacacg gctactcttt agtgaaagag  840
gaaccagaat gttttcaatg gctacaaagt aaagagccta attctgtggt ctacgtcaac  900
ttcggaagta aacagtcat gtccttggaa gatatgactg aatttggttg gggccttgct  960
aattcaaatc attactttct atggattatc aggtccaatt tggtaatagg ggaaaacgcc 1020
gtattacctc cagaattgga ggaacacatc aaaagagag gtttcattgc ttcctggtgt 1080
tctcaggaaa aggtattgaa acatccttct gttggtggtt tccttactca ttgcggttgg 1140
ggctctacaa tcgaatcact aagtgcagga gttccaatga tttgttggcc atattcatgg 1200
gaccaactta caaattgtag gtatatctgt aaagagtggg aagttggatt agaaatggga 1260
acaaaggtta acgtgatga agtgaaaaga ttggttcagg agttgatggg ggaaggtggc 1320
cacaagatga gaaacaaggc caaagattgg aaggaaaaag ccagaattgc tattgctcct 1380
aacgggtcat cctctctaaa cattgataag atggtcaaag agattacagt cttagccaga 1440
aactaa                                                          1446
```

SEQ ID NO: 33

```
MKTGFISPAT VFHHRISPAT TFRHHLSPAT TNSTGIVALR DINFRCKAVS KEYSDLLQKD  60

EASFTKWDDD KVKDHLDTNK NLYPNDEIKE FVESVKAMFG SMNDGEINVS AYDTAWVALV 120

QDVDGSGSPQ FPSSLEWIAN NQLSDGSWGD HLLFSAHDRI INTLACVIAL TSWNVHPSKC 180

EKGLNFLREN ICKLEDENAE HMPIGFEVTF PSLIDIAKKL NIEVPEDTPA LKEIYARRDI 240
```

TABLE 13-continued

Sequences disclosed herein.

| | | | | | |
|---|---|---|---|---|---|
| KLTKIPMEVL | HKVPTTLLHS | LEGMPDLEWE | KLLKLQCKDG | SFLFSPSSTA | FALMQTKDEK 300 |
| CLQYLTNIVT | KFNGGVPNVY | PVDLFEHIWV | VDRLQRLGIA | RYFKSEIKDC | VEYINKYWTK 360 |
| NGICWARNTH | VQDIDDTAMG | FRVLRAHGYD | VTPDVFRQFE | KDGKFVCFAG | QSTQAVTGMF 420 |
| NVYRASQMLF | PGERILEDAK | KFSYNYLKEK | QSTNELLDKW | IIAKDLPGEV | GYALDIPWYA 480 |
| SLPRLETRYY | LEQYGGEDDV | WIGKTLYRMG | YVSNNTYLEM | AKLDYNNYVA | VLQLEWYTIQ 540 |
| QWYVDIGIEK | FESDNIKSVL | VSYYLAAASI | FEPERSKERI | AWAKTTILVD | KITSIFDSSQ 600 |
| SSKEDITAFI | DKFRNKSSSK | KHSINGEPWH | EVMVALKKTL | HGFALDALMT | HSQDIHPQLH 660 |
| QAWEMWLTKL | QDGVDVTAEL | MVQMINMTAG | RWVSKELLTH | PQYQRLSTVT | NSVCHDITKL 720 |
| HNFKENSTTV | DSKVQELVQL | VFSDTPDDLD | QDMKQTFLTV | MKTFYYKAWC | DPNTINDHIS 780 |
| KVFEIVI | | | | | 787 |

SEQ ID NO: 34

| | | | | | |
|---|---|---|---|---|---|
| MPDAHDAPPP | QIRQRTLVDE | ATQLLTESAE | DAWGEVSVSE | YETARLVAHA | TWLGGHATRV 60 |
| AFLLERQHED | GSWGPPGGYR | LVPTLSAVHA | LLTCLASPAQ | DHGVPHDRLL | RAVDAGLTAL 120 |
| RRLGTSDSPP | DTIAVELVIP | SLLEGIQHLL | DPAHPHSRPA | FSQHRGSLVC | PGGLDGRTLG 180 |
| ALRSHAAAGT | PVPGKVWHAS | ETLGLSTEAA | SHLQPAQGII | GGSAAATATW | LTRVAPSQQS 240 |
| DSARRYLEEL | QHRYSGPVPS | ITPITYFERA | WLLNNFAAAG | VPCEAPAALL | DSLEAALTPQ 300 |
| GAPAGAGLPP | DADDTAAVLL | ALATHGRGRR | PEVLMDYRTD | GYFQCFIGER | TPSISTNAHV 360 |
| LETLGHHVAQ | HPQDRARYGS | AMDTASAWLL | AAQKQDGSWL | DKWHASPYYA | TVCCTQALAA 420 |
| HASPATAPAR | QRAVRWVLAT | QRSDGGWGLW | HSTVEETAYA | LQILAPPSGG | GNIPVQQALT 480 |
| RGRARLCGAL | PLTPLWHDKD | LYTPVRVVRA | ARAAALYTTR | DLLLPPL | 527 |

SEQ ID NO: 35

| | | | | | |
|---|---|---|---|---|---|
| MNALSEHILS | ELRRLLSEMS | DGGSVGPSVY | DTAQALRFHG | NVTGRQDAYA | WLIAQQQADG 60 |
| GWGSADFPLF | RHAPTWAALL | ALQRADPLPG | AADAVQTATR | FLQRQPDPYA | HAVPEDAPIG 120 |
| AELILPQFCG | EAAWLLGGVA | FPRHPALLPL | RQACLVKLGA | VAMLPSGHPL | LHSWEAWGTS 180 |
| PTTACPDDDG | SIGISPAATA | AWRAQAVTRG | STPQVGRADA | YLQMASRATR | SGIEGVFPNV 240 |
| WPINVFEPCW | SLYTLHLAGL | FAHPALAEAV | RVIVAQLEAR | LGVHGLGPAL | HFAADADDTA 300 |
| VALCVLHLAG | RDPAVDALRH | FEIGELFVTF | PGERNASVST | NIHALHALRL | LGKPAAGASA 360 |
| YVEANRNPHG | LWDNEKWHVS | WLYPTAHAVA | ALAQGKPQWR | DERALAALLQ | AQRDDGGWGA 420 |
| GRGSTFEETA | YALFALHVMD | GSEEATGRRR | IAQVVARALE | WMLARHAAHG | LPQTPLWIGK 480 |
| ELYCPTRVVR | VAELAGLWLA | LRWGRRVLAE | GAGAAP | | 516 |

SEQ ID NO: 36

| | | | | | |
|---|---|---|---|---|---|
| gacctgacca | ccaccccccg | gccggcccctt | tcattctttc | cttactttct | tcctcctgct 60 |
| gctcttgccg | tttcagtgat | tattagctgc | tgtacgtgcg | tgcgtacatt | gttctctctg 120 |
| ctgacaccca | tacacgctgt | agcttctaca | cataccagtt | cgatcgcaag | ctatagcatg 180 |
| gggcttcaat | catcgcccat | gctgctgcca | gcgccgacgg | caacggcggc | cggcagcggg 240 |
| tcacagtggc | gcacggctgt | ggcgggtaat | ggtaactcgt | ttatcttctt | ctacacgtaa 300 |
| tctctattat | atacctagat | tttctccaca | ggcagatcag | attctttaca | cagctgtatt 360 |
| ctcaaaaaaa | actcatagaa | aaaaagaaa | aaactaaacc | aaaggagcga | cctcaacctg 420 |
| taccagtgcc | cctgctagca | gtagcttcgt | tctgtcccctt | ttttttcatt | tggatcctct 480 |

TABLE 13-continued

Sequences disclosed herein.

```
acataaatgc tgggtggtgg tgtcctttca cgcacacatc cgcagatagc gccccagcag  540
catttatgtg gggacgacgg ctctgaaatg aattactagt cagtttcatg cgtttcagtg  600
cgagtattat agtagtagat ctcttctccg atatatccgg ccaaaggaag aagagaagag  660
aaaccacaca tctcattctc aactagtagt agaaaagtaa aaacgtacta caagcgcaag  720
cgcaaagatg gttcttttcat cgtcttgcac aacagttcct cacctttctt cccttgcggt  780
cgttcaacta ggcccatgga gttcccgcat caagaagaag acggatacag tcgccgtccc  840
cgcggccgcc ggccggtgga ggagggcact ggcgcgggcc cagcacacca gcgaatccgc  900
cgccgtcgcc aaaggtacgg gtgatcgcta gctttgatag ctccaaatct gagcagcaaa  960
ttaaatagct aggtttgtaa cgcacgcacg catgcaggtt cgtccctaac gcccatcgtg 1020
agaaccgatg ccgaaagccg ccgcacgaga tggcctacgg acgacgacga cgctgagccg 1080
ctggtcgacg agatcagggc aatgctgacg tcgatgagcg acggggacat cagcgtgtcg 1140
gcgtacgaca ccgcctgggt gggtcttgtg cccaggctgg acggcggcga gggcccgcag 1200
ttcccggccg ccgtgcggtg gatccggaac aaccagctcc ccgacggctc gtggggcgac 1260
gcggccctgt tctccgcgta cgaccgcctg atcaacacgc tggcgtgcgt cgtcacgctc 1320
accaggtggt cgctggagcc cgagatgcgc ggcagaggta cgtaattact gtgtgctggc 1380
cgatcgagag aacacacgac ggcagtgtac ctcgacagaa acgggcgtt gctgaagact 1440 caagtgtgtg tgtgtgtgtg ttcacagggc tctctttcct cggccggaac atgtggaagc 1500
tagcgacgga ggacgaggag tccatgccga tagggttcga gctcgcgttc ccttctctca 1560
tcgaactagc caagagtctg ggcgtccacg acttcccgta cgaccaccag gctctgcagg 1620
gaatatactc gagcagggag atcaagatga agaggattcc taaggaagtg atgcacacgg 1680
ttcccacatc cattctccac agcctggaag ggatgcccgg gctagactgg gcgaagctgc 1740
tgaaactgca gtcgagcgac gggtccttcc tcttctctcc cgcggccacc gcgtacgctc 1800
tcatgaacac cggcgacgac aggtgcttca gctacatcga caggacagtc aagaaattca 1860
acggaggagg tacgcaagca gtagcgtaga tacatgggca tagcatgcat gcatgcaatg 1920
cagcgttgcc cactgcatgc gccttccttc cttccttctc gtctcttcaa cggttcgtct 1980
tctctcgccg tttctcgcag tgcccaacgt ctaccccgtg gaccttttcg agcacatatg 2040
ggctgtcgat cgcctggagc gtctcgggat ctcccgctac ttccagaaag agattgagca 2100
gtgcatggac tacgtgaaca ggcactggac tgaggacggg atctgctggg cgaggaactc 2160
cgacgtgaag gaggtggacg acacggccat ggctttccgc ctgctacggc tgcacggata 2220
cagcgtctcg ccaggtacgt aacaaacaca aaaaaaaaaa acgcgcagac aacagagatc 2280
gtcacgtcat acacacgcgt gtcctgaaca tttttcattt ggtctcccac ccatcgtacg 2340
taataataat aaaaaaaaac gtgcttctgc cctgcctgtg tacgtgtaga tgtgttcaag 2400
aacttcgaga aggacgggga gttcttcgcc ttcgtgggc agtcgaacca ggcggtgacg 2460
gggatgtaca acctcaacag ggcctcccag ataagcttcc cggggagga cgtcctgcac 2520 cgtgcagggg ctttctcgta cgagtttctc aggcggaaag aggccgaggg agcgctccgt 2580
gacaaatgga tcatatctaa ggacctgcct ggggaggtag tgtacaccct ggacttcct 2640 tggtatggga acctgccgcg cgtggaggcg agagactatc tggaacagta cggcggcggc 2700
gacgatgtct ggatcgggaa gacgctctac aggtagatag atcttttag ctattaattg 2760 gtttcagatc gaccagataa aatttgcatt attggttctt ttgatgcatg taattgaaag 2820
```

TABLE 13-continued

Sequences disclosed herein.

ccaataaata acctcagtat gcgtgatggc tgacttttgc attggcagga tgcctcttgt 2880
gaataacgat gtgtatcttg agctggctag gatggacttc aaccattgcc aagccctaca 2940
tcagcttgag tggcaaggcc tgaaaaggta tgtatgttac tatatatata cagcccggtt 3000
gttgagtttt ttttttattt tattttttc gcgattacca tttcttctcg atgcaaaata 3060
aatctgcaca gatcatcata tatatccttg atgatatata agggcttctc gtatatatat 3120
cttatcacct atatatacat aggtggtaca ctgagaaccg gctcatggat ttcggagtgg 3180
cgcaagagga tgctctgcga gcgtatttcc tggccgccgc ttccgtctac gagccgtgcc 3240
gagccgcgga gcggcttgcg tgggccagag cggcgatact tgccaacgcc gtctctaccc 3300
atctccgtaa cagcccctca ttcagagaac gcttggaaca ctccttgcgt tgccgcccca 3360
gtgaagaaac ggatggatca tggtaataag ctgatcgatg gaaattaaa aatttaagtt 3420 ttttttttct tttttgttgc cattatctga gaccaatgca atgtggtgca tatatatcca 3480
ggttcaactc atcaagtgga agtgacgctg ttcttgtgaa ggcagttctg cggcttaccg 3540
actcgttagc gcgagaagcg cagccgattc atggcggtga tccggaggac atcatccaca 3600
agctactgag atcagctgta agttaaacgt aacgttcaga agaagatttt ttttttttt 3660 tgcagttaac aagtactacg acatctatcg tttttgttca gcatgcacag tcatcctagc 3720
tactaatacc attattcttc tgtgaacttg tgtagtgggc tgaatgggtc agggagaagg 3780
cagatgcagc agacagcgtg tgtaatggat ccagtgctgt ggaacaagaa gggtcgcgca 3840
tggttcatga caagcaaacg tgtctgcttt tagctcgaat gatcgagatc agcgctgggc 3900
gagctgcagg tgaggctgcg agcgaagatg gtgaccgtcg gattatccag ctcactgggt 3960
ctatatgtga cagtctcaag cagaagatgc tagtatctca ggtatagcac atatatacta 4020
cagaaagttt gtgcgtagtt attatttccc tttttcatg tgacgaacat gatgacctga 4080
tgatgcatgt atatggcttc ataggacc ccgagaagaa cgaagagatg atgagccatg 4140
tcgatgacga attgaagctg cgtatacgag agttcgttca gtatcttctg agactcggtg 4200
agaagaaaac cggcagcagc gagacaaggc agacctttct gagcatcgtg aaaagctgtt 4260
actacgctgc tcactgcccg ccgcatgtgg tagacaggca tatttccaga gttattttg 4320 aacctgtttc cgccgcaaaa taatggtaat ggtagatgtg aatgtgatat ggagataaga 4380
gagagagaaa atgttgatag tggaaattgg cgttgatgtc gcctccacat tctttacgca 4440
aaagtagcgt ctgttttgga taaaaaaat ccagtttctg taaattatag aataaatcaa 4500
tcgctgtgtc ccaaactcta aatgttatt ctgtgaagta tggaataaat cggtcactat 4560
acctatcttg tggatgc 4577

SEQ ID NO: 37

MVLSSSCTTV PHLSSLAVVQ LGPWSSRIKK KTDTVAVPAA AGRWRRALAR AQHTSESAAV 60

AKGSSLTPIV RTDAESRRTR WPTDDDDAEP LVDEIRAMLT SMSDGDISVS AYDTAWVGLV 120

PRLDGGEGPQ FPAAVRWIRN NQLPDGSWGD AALFSAYDRL INTLACVVTL TRWSLEPEMR 180

GRGLSFLGRN MWKLATEDEE SMPIGFELAF PSLIELAKSL GVHDFPYDHQ ALQGIYSSRE 240

IKMKRIPKEV MHTVPTSILH SLEGMPGLDW AKLLKLQSSD GSFLFSPAAT AYALMNTGDD 300

RCFSYIDRTV KKFNGGVPNV YPVDLFEHIW AVDRLERLGI SRYFQKEIEQ CMDYVNRHWT 360

EDGICWARNS DVKEVDDTAM AFRLLRLHGY SVSPDVFKNF EKDGEFFAFV GQSNQAVTGM 420

YNLNRASQIS FPGEDVLHRA GAFSYEFLRR KEAEGALRDK WIISKDLPGE VVYTLDFPWY 480

TABLE 13-continued

Sequences disclosed herein.

| | | | | | |
|---|---|---|---|---|---|
| GNLPRVEARD | YLEQYGGGDD | VWIGKTLYRM | PLVNNDVYLE | LARMDFNHCQ | ALHQLEWQGL 540 |
| KRWYTENRLM | DFGVAQEDAL | RAYFLAAASV | YEPCRAAERL | AWARAAILAN | AVSTHLRNSP 600 |
| SFRERLEHSL | RCRPSEETDG | SWFNSSSGSD | AVLVKAVLRL | TDSLAREAQP | IHGGDPEDII 660 |
| HKLLRSAWAE | WVREKADAAD | SVCNGSSAVE | QEGSRMVHDK | QTCLLLARMI | EISAGRAAGE 720 |
| AASEDGDRRI | IQLTGSICDS | LKQKMLVSQD | PEKNEEMMSH | VDDELKLRIR | EFVQYLLRLG 780 |
| EKKTGSSETR | QTFLSIVKSC | YYAAHCPPHV | VDRHISRVIF | EPVSAAK | 827 |

SEQ ID NO: 38

| | | | | |
|---|---|---|---|---|
| cttcttcact | aaatacttag | acagagaaaa | cagagctttt | taaagccatg tctcttcagt 60 |
| atcatgttct | aaactccatt | ccaagtacaa | cctttctcag | ttctactaaa acaacaatat 120 |
| cttcttcttt | ccttaccatc | tcaggatctc | ctctcaatgt | cgctagagac aaatccagaa 180 |
| gcggttccat | acattgttca | aagcttcgaa | ctcaagaata | cattaattct caagaggttc 240 |
| aacatgattt | gcctctaata | catgagtggc | aacagcttca | aggagaagat gctcctcaga 300 |
| ttagtgttgg | aagtaatagt | aatgcattca | agaagcagt | gaagagtgtg aaaacgatct 360 |
| tgagaaacct | aacggacggg | gaaattacga | tatcggctta | cgatacagct tgggttgcat 420 |
| tgatcgatgc | cggagataaa | actccggcgt | tccctccgc | cgtgaaatgg atcgccgaga 480 |
| accaactttc | cgatggttct | tggggagatg | cgtatctctt | ctcttatcat gatcgtctca 540 |
| tcaataccct | tgcatgcgtc | gttgctctaa | gatcatggaa | tctctttcct catcaatgca 600 |
| acaaaggaat | cacgtttttc | cgggaaaata | ttgggaagct | agaagacgaa aatgatgagc 660 |
| atatgccaat | cggattcgaa | gtagcattcc | catcgttgct | tgagatagct cgaggaataa 720 |
| acattgatgt | accgtacgat | tctccggtct | taaaagatat | atacgccaag aaagagctaa 780 |
| agcttacaag | gataccaaaa | gagataatgc | acaagatacc | aacaacattg ttgcatagtt 840 |
| tggaggggat | gcgtgattta | gattgggaaa | agctcttgaa | acttcaatct caagacggat 900 |
| ctttcctctt | ctctccttcc | tctaccgctt | ttgcattcat | gcagacccga gacagtaact 960 |
| gcctcgagta | tttgcgaaat | gccgtcaaac | gtttcaatgg | aggagttccc aatgtctttc 1020 |
| ccgtggatct | tttcgagcac | atatggatag | tggatcggtt | acaacgttta gggatatcga 1080 |
| gatactttga | agaagagatt | aaagagtgtc | ttgactatgt | ccacagatat tggaccgaca 1140 |
| atggcatatg | ttgggctaga | tgttcccatg | tccaagacat | cgatgataca gccatggcat 1200 |
| ttaggctctt | aagacaacat | ggataccaag | tgtccgcaga | tgtattcaag aactttgaga 1260 |
| aagagggaga | gттттттcтgc | tttgtggggc | aatcaaacca | agcagtaacc ggtatgttca 1320 |
| acctataccg | ggcatcacaa | ttggcgtttc | caagggaaga | gatattgaaa acgccaaag 1380 |
| agтттттcтта | taattatctg | ctagaaaaac | gggagagaga | ggagttgatt gataagtgga 1440 |
| ttataatgaa | agacttacct | ggcgagattg | gtttgcgtt | agagattcca tggtacgcaa 1500 |
| gcttgcctcg | agtagagacg | agattctata | ttgatcaata | tggtggagaa aacgacgttt 1560 |
| ggattggcaa | gactctttat | aggatgccat | acgtgaacaa | tatggatat ctggaattag 1620 |
| caaaacaaga | ttacaacaat | tgccaagctc | agcatcagct | cgaatgggac atattccaaa 1680 |
| agtggtatga | agaaaatagg | ttaagtgagt | ggggtgtgcg | cagaagtgag cttctcgagt 1740 |
| gttactactt | agcggctgca | actatatttg | aatcagaaag | gtcacatgag agaatggttt 1800 |
| gggctaagtc | aagtgtattg | gttaaagcca | tttcttcttc | tttttgggaa tcctctgact 1860 |
| ccagaagaag | cttctccgat | cagtttcatg | aatacattgc | caatgctcga cgaagtgatc 1920 |

TABLE 13-continued

Sequences disclosed herein.

```
atcactttaa tgacaggaac atgagattgg accgaccagg atcggttcag gccagtcggc 1980
ttgccggagt gttaatcggg actttgaatc aaatgtcttt tgaccttttc atgtctcatg 2040
gccgtgacgt taacaatctc ctctatctat cgtggggaga ttggatggaa aaatggaaac 2100
tatatggaga tgaaggagaa ggagagctca tggtgaagat gataattcta atgaagaaca 2160
atgacctaac taacttcttc acccacactc acttcgttcg tctcgcggaa atcatcaatc 2220
gaatctgtct tcctcgccaa tacttaaagg caaggagaaa cgatgagaag gagaagacaa 2280
taaagagtat ggagaaggag atggggaaaa tggttgagtt agcattgtcg gagagtgaca 2340
catttcgtga cgtcagcatc acgtttcttg atgtagcaaa agcattttac tactttgctt 2400
tatgtggcga tcatctccaa actcacatct ccaaagtctt gtttcaaaaa gtctagtaac 2460
ctcatcatca tcatcgatcc attaacaatc agtggatcga tgtatccata gatgcgtgaa 2520
taatatttca tgtagagaag gagaacaaat tagatcatgt agggttatca             2570
```

SEQ ID NO: 39

```
MSLQYHVLNS IPSTTFLSST KTTISSSFLT ISGSPLNVAR DKSRSGSIHC SKLRTQEYIN  60
SQEVQHDLPL IHEWQQLQGE DAPQISVGSN SNAFKEAVKS VKTILRNLTD GEITISAYDT 120
AWVALIDAGD KTPAFPSAVK WIAENQLSDG SWGDAYLFSY HDRLINTLAC VVALRSWNLF 180
PHQCNKGITF FRENIGKLED ENDEHMPIGF EVAFPSLLEI ARGINIDVPY DSPVLKDIYA 240
KKELKLTRIP KEIMHKIPTT LLHSLEGMRD LDWEKLLKLQ SQDGSFLFSP SSTAFAFMQT 300
RDSNCLEYLR NAVKRFNGGV PNVFPVDLFE HIWIVDRLQR LGISRYFEEE IKECLDYVHR 360
YWTDNGICWA RCSHVQDIDD TAMAFRLLRQ HGYQVSADVF KNFEKEGEFF CFVGQSNQAV 420
TGMFNLYRAS QLAFPREEIL KNAKEFSYNY LLEKREREEL IDKWIIMKDL PGEIGFALEI 480
PWYASLPRVE TRFYIDQYGG ENDVWIGKTL YRMPYVNNNG YLELAKQDYN NCQAQHQLEW 540
DIFQKWYEEN RLSEWGVRRS ELLECYYLAA ATIFESERSH ERMVWAKSSV LVKAISSSFG 600
ESSDSRRSFS DQFHEYIANA RRSDHHFNDR NMRLDRPGSV QASRLAGVLI GTLNQMSFDL 660
FMSHGRDVNN LLYLSWGDWM EKWKLYGDEG EGELMVKMII LMKNNDLTNF FTHTHFVRLA 720
EIINRICLPR QYLKARRNDE KEKTIKSMEK EMGKMVELAL SESDTFRDVS ITFLDVAKAF 780
YYFALCGDHL QTHISKVLFQ KV                                         802
```

SEQ ID NO: 40

```
MEFDEPLVDE ARSLVQRTLQ DYDDRYGFGT MSCAAYDTAW VSLVTKTVDG RKQWLFPECF  60
EFLLETQSDA GGWEIGNSAP IDGILNTAAS LLALKRHVQT EQIIQPQHDH KDLAGRAERA 120
AASLRAQLAA LDVSTTEHVG FEIIVPAMLD PLEAEDPSLV FDFPARKPLM KIHDAKMSRF 180
RPEYLYGKQP MTALHSLEAF IGKIDFDKVR HHRTHGSMMG SPSSTAAYLM HASQWDGDSE 240
AYLRHVIKHA AGQGTGAVPS AFPSTHFESS WILTTLFRAG FSASHLACDE LNKLVEILEG 300
SFEKEGGAIG YAPGFQADVD DTAKTISTLA VLGRDATPRQ MIKVFEANTH FRTYPGERDP 360
SLTANCNALS ALLHQPDAAM YGSQIQKITK FVCDYWWKSD GKIKDKWNTC YLYPSVLLVE 420
VLVDLVSLLE QGKLPDVLDQ ELQYRVAITL FQACLRPLLD QDAEGSWNKS IEATAYGILI 480
LTEARRVCFF DRLSEPLNEA IRRGIAFADS MSGTEAQLNY IWIEKVSYAP ALLTKSYLLA 540
ARWAAKSPLG ASVGSSLWTP PREGLDKHVR LFHQAELFRS LPEWELRASM IEAALFTPLL 600
RAHRLDVFPR QDVGEDKYLD VVPFFWTAAN NRDRTYASTL FLYDMCFIAM LNFQLDEFME 660
ATAGILFRDH MDDLRQLIHD LLAEKTSPKS SGRSSQGTKD ADSGIEEDVS MSDSASDSQD 720
```

TABLE 13-continued

Sequences disclosed herein.

| | |
|---|---|
| RSPEYDLVFS ALSTFTKHVL QHPSIQSASV WDRKLLAREM KAYLLAHIQQ AEDSTPLSEL | 780 |
| KDVPQKTDVT RVSTSTTTFF NWVRTTSADH ISCPYSFHFV ACHLGAALSP KGSNGDCYPS | 840 |
| AGEKFLAAAV CRHLATMCRM YNDLGSAERD SDEGNLNSLD FPEFADSAGN GGIEIQKAAL | 900 |
| LRLAEFERDS YLEAFRRLQD ESNRVHGPAG GDEARLSRRR MAILEFFAQQ VDLYGQVYVI | 960 |
| RDISARIPKN EVEKKRKLDD AFN | 983 |

SEQ ID NO: 41

| | |
|---|---|
| MASSTLIQNR SCGVTSSMSS FQIFRGQPLR FPGTRTPAAV QCLKKRRCLR PTESVLESSP | 60 |
| GSGSYRIVTG PSGINPSSNG HLQEGSLTHR LPIPMEKSID NFQSTLYVSD IWSETLQRTE | 120 |
| CLLQVTENVQ MNEWIEEIRM YFRNMTLGEI SMSPYDTAWV ARVPALDGSH GPQFHRSLQW | 180 |
| IIDNQLPDGD WGEPSLFLGY DRVCNTLACV IALKTWGVGA QNVERGIQFL QSNIYKMEED | 240 |
| DANHMPIGFE IVFPAMMEDA KALGLDLPYD ATILQQISAE REKKMKKIPM AMVYKYPTTL | 300 |
| LHSLEGLHRE VDWNKLLQLQ SENGSFLYSP ASTACALMYT KDVKCFDYLN QLLIKFDHAC | 360 |
| PNVYPVDLFE RLWMVDRLQR LGISRYFERE IRDCLQYVYR YWKDCGIGWA SNSSVQDVDD | 420 |
| TAMAFRLLRT HGFDVKEDCF RQFFKDGEFF CFAGQSSQAV TGMFNLSRAS QTLFPGESLL | 480 |
| KKARTFSRNF LRTKHENNEC FDKWIITKDL AGEVEYNLTF PWYASLPRLE HRTYLDQYGI | 540 |
| DDIWIGKSLY KMPAVTNEVF LKLAKADFNM CQALHKKELE QVIKWNASCQ FRDLEFARQK | 600 |
| SVECYFAGAA TMFEPEMVQA RLVWARCCVL TTVLDDYFDH GTPVEELRVF VQAVRTWNPE | 660 |
| LINGLPEQAK ILFMGLYKTV NTIAEEAFMA QKRDVHHHLK HYWDKLITSA LKEAEWAESG | 720 |
| YVPTFDEYME VAEISVALEP IVCSTLFFAG HRLDEDVLDS YDYHLVMHLV NRVGRILNDI | 780 |
| QGMKREASQG KISSVQIYME EHPSVPSEAM AIAHLQELVD NSMQQLTYEV LRFTAVPKSC | 840 |
| KRIHLNMAKI MHAFYKDTDG FSSLTAMTGF VKKVLFEPVP E | 881 |

SEQ ID NO: 42

| | |
|---|---|
| MPGKIENGTP KDLKTGNDFV SAAKSLLDRA FKSHHSYYGL CSTSCQVYDT AWVAMIPKTR | 60 |
| DNVKQWLFPE CFHYLLKTQA ADGSWGSLPT TQTAGILDTA SAVLALLCHA QEPLQILDVS | 120 |
| PDEMGLRIEH GVTSLKRQLA VWNDVEDTNH IGVEFIIPAL LSMLEKELDV PSFEFPCRSI | 180 |
| LERMHGEKLG HFDLEQVYGK PSSLLHSLEA FLGKLDFDRL SHHLYHGSMM ASPSSTAAYL | 240 |
| IGATKWDDEA EDYLRHVMRN GAGHGNGGIS GTFPTTHFEC SWIIATLLKV GFTLKQIDGD | 300 |
| GLRGLSTILL EALRDENGVI GFAPRTADVD DTAKALLALS LVNQPVSPDI MIKVFEGKDH | 360 |
| FTTFGSERDP SLTSNLHVLL SLLKQSNLSQ YHPQILKTTL FTCRWWWGSD HCVKDKWNLS | 420 |
| HLYPTMLLVE AFTEVLHLID GGELSSLFDE SFKCKIGLSI FQAVLRIILT QDNDGSWRGY | 480 |
| REQTCYAILA LVQARHVCFF THMVDRLQSC VDRGFSWLKS CSFHSQDLTW TSKTAYEVGF | 540 |
| VAEAYKLAAL QSASLEVPAA TIGHSVTSAV PSSDLEKYMR LVRKTALFSP LDEWGLMASI | 600 |
| IESSFFVPLL QAQRVEIYPR DNIKVDEDKY LSIIPFTWVG CNNRSRTFAS NRWLYDMMYL | 660 |
| SLLGYQTDEY MEAVAGPVFG DVSLLHQTID KVIDNTMGNL ARANGTVHSG NGHQHESPNI | 720 |
| GQVEDTLTRF TNSVLNHKDV LNSSSSDQDT LRREFRTFMH AHITQIEDNS RFSKQASSDA | 780 |
| FSSPEQSYFQ WVNSTGGSHV ACAYSFAFSN CLMSANLLQG KDAFPSGTQK YLISSVMRHA | 840 |
| TNMCRMYNDF GSIARDNAER NVNSIHFPEF TLCNGTSQNL DERKERLLKI ATYEQGYLDR | 900 |
| ALEALERQSR DDAGDRAGSK DMRKLKIVKL FCDVTDLYDQ LYVIKDLSSS MK | 952 |

TABLE 13-continued

Sequences disclosed herein.

SEQ ID NO: 43

```
MALVNPTALF YGTSIRTRPT NLLNPTQKLR PVSSSSLPSF SSVSAILTEK HQSNPSENNN  60
LQTHLETPFN FDSYMLEKVN MVNEALDASV PLKDPIK1HE SMRYSLLAGG KRIRPMMCIA 120
ACEIVGGNIL NAMPAACAVE MIHTMSLVHD DLPCMDNDDF RRGKPISHKV YGEEMAVLTG 180
DALLSLSFEH IATATKGVSK DRIVRAIGEL ARSVGSEGLV AGQVVDILSE GADVGLDHLE 240
Y1HIHKTAML LESSVVIGAI MGGGSDQQ1E KLRKFARS1G LLFQVVDD1L DVTKSTEELG 300
KTAGKDLLTD KTTYPKLLGI EKSREFAEKL NKEAQEQLSG FDRRKAAPLI ALANYNAYRQ 360
N                                                                361
```

SEQ ID NO: 44

```
MAEQQISNLL SMFDASHASQ KLEITVQMMD TYHYRETPPD SSSSEGGSLS RYDERRVSLP  60
LSHNAASPDI VSQLCFSTAM SSELNHRWKS QRLKVADSPY NYILTLPSKG IRGAFIDSLN 120
VWLEVPEDET SVIKEVIGML HNSSLIIDDF QDNSPLRRGK PSTHTVFGPA QAINTATYVI 180
VKAIEKIQDI VGHDALADVT GTITTIFQGQ AMDLWWTANA IVPSIQEYLL MVNDKTGALF 240
RLSLELLALN SEASISDSAL ESLSSAVSLL GQYFQIRDDY MNLIDNKYTD QKGFCEDLDE 300
GKYSLTLIHA LQTDSSDLLT NILSMRRVQG KLTAQKRCWF WK                 342
```

SEQ ID NO: 45

```
MEKTKEKAER 1LLEPYRYLL QLPGKQVRSK LSQAFNHWLK VPEDKLQ1II EVTEMLHNAS  60
LLIDDIEDSS KLRRGFPVAH SIYGVPSVIN SANYVYFLGL EKVLTLDHPD AVKLFTRQLL 120
ELHQGQGLDI YWRDTYTCPT EEEYKAMVLQ KTGGLFGLAV GLMQLFSDYK EDLKPLLDTL 180
GLFFQIRDDY ANLHSKEYSE NKSFCEDLTE GKFSFPTIHA IWSRPESTQV QNILRQRTEN 240
IDIKKYCVQY LEDVGSFAYT RHTLRELEAK AYKQIEACGG NPSLVALVKH LSKMFTEENK 300
```

SEQ ID NO: 46

```
MARFYFLNAL LMVISLQSTT AFTPAKLAYP TTTTALNVAS AETSFSLDEY LASK1GP1ES  60
ALEASVKSRI PQTDKICESM AYSLMAGGKR IRPVLCIAAC EMFGGSQDVA MPTAVALEMI 120
HTMSLIHDDL PSMDNDDLRR GKPTNHVVFG EDVAILAGDS LLSTSFEHVA RETKGVSAEK 180
1VDVIARLGK SVGAEGLAGG QVMDLECEAK PGTTLDDLKW IHIHKTATLL QVAVASGAVL 240
GGATPEEVAA CELFAMNIGL AFQVADDILD VTASSEDLGK TAGKDEATDK TTYPKLLGLE 300
ESKAYARQLI DEAKESLAPF GDRAAPLLAI ADFIIDRKN                      339
```

SEQ ID NO: 47

```
MHLAPRRVPR GRRSPPDRVP ERQGALGRRR GAGSTGCARA AAGVHRRRGG GEADPSAAVH  60
RGWQAGGGTG LPDEVVSTAA ALEMFHAFAL IHDDIMDDSA TRRGSPTVHR ALADRLGAAL 120
DPDQAGQLGV STAILVGDLA LTWSDELLYA PLTPHRLAAV LPLVTAMRAE TVHGQYLDIT 180
SARRPGTDTS LALRIARYKT AAYTMERPLH IGAALAGARP ELLAGLSAYA LPAGEAFQLA 240
DDLLGVFGDP RRTGKPDLDD LRGGKHTVLV ALAREHATPE QRHTLDTLLG TPGLDRQGAS 300
RLRCVLVATG ARAEAERLIT ERRDQALTAL NALTLPPPLA EALARLTLGS TAHPA     355
```

SEQ ID NO: 48

```
MSYFDNYFNE IVNSVNDIIK SYISGDVPKL YEASYHLFTS GGKRLRPLIL TISSDLFGGQ  60
RERAYYAGAA IEVLHTFTLV HDDIMDQDNI RRGLPTVHVK YGLPLAILAG DLLHAKAFQL 120
LTQALRGLPS ETIIKAFDIF TRSIIIISEG QAVDMEFEDR IDIKEQEYLD MISRKTAALF 180
```

TABLE 13-continued

Sequences disclosed herein.

| | |
|---|---|
| SASSSIGALI AGANDNDVRL MSDFGTNLGI AFQIVDDILG LTADEKELGK PVFSDIREGK | 240 |
| KTILVIKTLE LCKEDEKKIV LKALGNKSAS KEELMSSADI IKKYSLDYAY NLAEKYYKNA | 300 |
| IDSLNQVSSK SDIPGKALKY LAEFT1RRRK | 330 |

SEQ ID NO: 49

| | |
|---|---|
| MVAQTFNLDT YLSQRQQQVE EALSAALVPA YPERIYEAMR YSLLAGGKRL RPILCLAACE | 60 |
| LAGGSVEQAM PTACALEMIH TMSLIHDDLP AMDNDDFRRG KPTNHKVFGE DIAILAGDAL | 120 |
| LAYAFEHIAS QTRGVPPQLV LQVIARIGHA VAATGLVGGQ VVDLESEGKA ISLETLEYIH | 180 |
| SHKTGALLEA SVVSGGILAG ADEELLARLS HYARDIGLAF QIVDDILDVT ATSEQLGKTA | 240 |
| GKDQAAAKAT YPSLLGLEAS RQKAEELIQS AKEALRPYGS QAEPLLALAD FITRRQH | 297 |

SEQ ID NO: 50

| | |
|---|---|
| MASVTLGSWI VVHHHNHHHP SSILTKSRSR SCPITLTKPI SFRSKRTVSS SSSIVSSSVV | 60 |
| TKEDNLRQSE PSSFDFMSYI ITKAELVNKA LDSAVPLREP LKIHEAMRYS LLAGGKRVRP | 120 |
| VLCIAACELV GGEESTAMPA ACAVEMIHTM SLIHDDLPCM DNDDLRRGKP TNHKVFGEDV | 180 |
| AVLAGDALLS FAFEHLASAT SSDVVSPVRV VRAVGELAKA IGTEGLVAGQ VVDISSEGLD | 240 |
| LNDVGLEHLE FIHLHKTAAL LEASAVLGAI VGGGSDDEIE RLRKFARCIG LLFQVVDDIL | 300 |
| DVTKSSKELG KTAGKDLIAD KLTYPKIMGL EKSREFAEKL NREARDQLLG FDSDKVAPLL | 360 |
| ALANYIAYRQ N | 371 |

SEQ ID NO: 51

| | |
|---|---|
| atgtcttcct cttcctcttc cagtacctct atgattgatt tgatggctgc tattattaaa | 60 |
| ggtgaaccag ttatcgtctc cgacccagca aatgcctctg cttatgaatc agttgctgca | 120 |
| gaattgtctt caatgttgat cgaaaacaga caattcgcca tgatcgtaac tacatcaatc | 180 |
| gctgttttga tcggttgtat tgtcatgttg gtatggagaa gatccggtag tggtaattct | 240 |
| aaaagagtcg aacctttgaa accattagta attaagccaa gagaagaaga aatagatgac | 300 |
| ggtagaaaga agttacaat attttcggt acccaaactg gtacagctga aggttttgca | 360 |
| aaagccttag gtgaagaagc taaggcaaga tacgaaaaga ctagattcaa gatagtcgat | 420 |
| ttggatgact atgccgctga tgacgatgaa tacgaagaaa agttgaagaa agaagatgtt | 480 |
| gcattttct ttttggcaac ctatggtgac ggtgaaccaa ctgacaatgc agccagattc | 540 |
| tacaaatggt ttacagaggg taatgatcgt ggtgaatggt tgaaaaactt aaagtacggt | 600 |
| gttttcggtt tgggtaacag acaatacgaa catttcaaca agttgcaaa ggttgtcgac | 660 |
| gatattttgg tcgaacaagg tgctcaaaga ttagtccaag taggtttggg tgacgatgac | 720 |
| caatgtatag aagatgactt tactgcctgg agagaagctt gtggcctga attagacaca | 780 |
| atcttgagag aagaaggtga caccgccgtt gctaccccat atactgctgc agtattagaa | 840 |
| tacagagttt ccatccatga tagtgaagac gcaaagttta tgatatcac tttggccaat | 900 |
| ggtaacggtt atacagtttt cgatgcacaa caccccttaca aagctaacgt tgcagtcaag | 960 |
| agagaattac atacaccaga atccgacaga agttgtatac acttggaatt tgatatcgct | 1020 |
| ggttccggtt taaccatgaa gttgggtgac catgtaggtg ttttatgcga caatttgtct | 1080 |
| gaaactgttg atgaagcatt gagattgttg gatatgtccc ctgacactta ttttagtttg | 1140 |
| cacgctgaaa aagaagatgg tacaccaatt tccagttctt taccacctcc attccctcca | 1200 |
| tgtaacttaa gaacagcctt gaccagatac gcttgcttgt tatcatcccc taaaaagtcc | 1260 |

TABLE 13-continued

Sequences disclosed herein.

| | | | | |
|---|---|---|---|---|
| gccttggttg | ctttagccgc | tcatgctagt | gatcctactg | aagcagaaag attgaaacac 1320 |
| ttagcatctc | cagccggtaa | agatgaatat | tcaaagtggg | tagttgaatc tcaaagatca 1380 |
| ttgttagaag | ttatggcaga | atttccatct | gccaagcctc | cattaggtgt cttctttgct 1440 |
| ggtgtagcac | ctagattgca | accaagattc | tactcaatca | gttcttcacc taagatcgct 1500 |
| gaaactagaa | ttcatgttac | atgtgcatta | gtctacgaaa | agatgccaac cggtagaatt 1560 |
| cacaagggtg | tatgctctac | ttggatgaaa | aatgctgttc | cttacgaaaa atcagaaaag 1620 |
| ttgttcttag | gtagaccaat | cttcgtaaga | caatcaaact | tcaagttgcc ttctgattca 1680 |
| aaggttccaa | taatcatgat | aggtcctggt | acaggtttag | ccccattcag aggtttcttg 1740 |
| caagaaagat | tggctttagt | tgaatctggt | gtcgaattag | gtccttcagt tttgttcttt 1800 |
| ggttgtagaa | acagaagaat | ggatttcatc | tatgaagaag | aattgcaaag attcgtcgaa 1860 |
| tctggtgcat | tggccgaatt | atctgtagct | tttcaagag | aaggtccaac taaggaatac 1920 |
| gttcaacata | agatgatgga | taaggcatcc | gacatatgga | acatgatcag tcaaggtgct 1980 |
| tatttgtacg | tttgcggtga | cgcaaagggt | atggccagag | atgtccatag atctttgcac 2040 |
| acaattgctc | aagaacaagg | ttccatggat | agtaccaaag | ctgaaggttt cgtaaagaac 2100 |
| ttacaaactt | ccggtagata | cttgagagat | gtctggtga | 2139 |

SEQ ID NO: 52

| | | | | |
|---|---|---|---|---|
| atggcggaac | aacaaaagat | caagaaatca | ccacacgttc | tactcatccc attccctta 60 |
| caaggccata | taaacccttt | catccagttt | ggcaaacgat | taatctccaa aggtgtcaaa 120 |
| acaacacttg | ttaccaccat | ccacacctta | aactcaaccc | taaaccacag taacaccacc 180 |
| accacctcca | tcgaaatcca | agcaatttcc | gatggttgtg | atgaaggcgg ttttatgagt 240 |
| gcaggagaat | catatttgga | aacattcaaa | caagttgggt | ctaaatcact agctgactta 300 |
| atcaagaagc | ttcaaagtga | aggaaccaca | attgatgcaa | tcatttatga ttctatgact 360 |
| gaatgggttt | tagatgttgc | aattgagttt | ggaatcgatg | gtggttcgtt tttcactcaa 420 |
| gcttgtgttg | taaacagctt | atattatcat | gttcataagg | gtttgatttc tttgccattg 480 |
| ggtgaaactg | tttcggttcc | tggatttcca | gtgcttcaac | ggtgggagac accgttaatt 540 |
| ttgcagaatc | atgagcaaat | acagagccct | tggtctcaga | tgttgtttgg tcagtttgct 600 |
| aatattgatc | aagcacgttg | ggtcttcaca | aatagttttt | acaagctcga ggaagaggta 660 |
| atagagtgga | cgagaaagat | atggaacttg | aaggtaatcg | gccaacact tccatccatg 720 |
| taccttgaca | aacgacttga | tgatgataaa | gataacggat | taatctcta caaagcaaac 780 |
| catcatgagt | gcatgaactg | gttagacgat | aagccaaagg | aatcagttgt ttacgtagca 840 |
| tttggtagcc | tggtgaaaca | tggacccgaa | caagtggaag | aaatcacacg gctttaata 900 |
| gatagtgatg | tcaacttctt | gtgggttatc | aaacataaag | aagagggaaa gctcccagaa 960 |
| aatctttcgg | aagtaataaa | aaccggaaag | ggtttgattg | tagcatggtg caaacaattg 1020 |
| gatgtgttag | cacacgaatc | agtaggatgc | tttgttacac | attgtgggtt caactcaact 1080 |
| cttgaagcaa | taagtcttgg | agtccccgtt | gttgcaatgc | ctcaattttc ggatcaaact 1140 |
| acaaatgcca | agcttctaga | tgaaattttg | ggtgttggag | ttagagttaa ggctgatgag 1200 |
| aatgggatag | tgagaagagg | aaatcttgcg | tcatgtatta | agatgattat ggaggaggaa 1260 |
| agaggagtaa | taatccgaaa | gaatgcggta | aaatggaagg | atttggctaa agtagccgtt 1320 |
| catgaaggtg | gtagctcaga | caatgatatt | gtcgaatttg | taagtgagct aattaaggct 1380 |

TABLE 13-continued

Sequences disclosed herein.

| | | | | |
|---|---|---|---|---|
| taaattttg | ttgctttgta | ttttatgtgt | tatggttttt | tgatttagat gtattcaatt 1440 |
| aatattgaat | cataactaaa | ttcaagatta | ttgtttgtaa | tattctttgt cctaaaattt 1500 |
| tgcgacttaa | aacctttagt | ttataaaaag | aaattagaaa | atactattgc acgga 1555 |

SEQ ID NO: 53

| | | | | |
|---|---|---|---|---|
| atggaaaaca | agaccgaaac | aacagttaga | cgtaggcgta | gaatcattct gtttccagta 60 |
| ccttttcaag | ggcacatcaa | tccaatacta | caactagcca | acgttttgta ctctaaaggt 120 |
| ttttctatta | caatctttca | caccaatttc | aacaaaccaa | aaacatccaa ttacccacat 180 |
| ttcacattca | gattcatact | tgataatgat | ccacaagatg | aacgtatttc aaacttacct 240 |
| acccacggtc | ctttagctgg | aatgagaatt | ccaatcatca | atgaacatgg tgccgatgag 300 |
| cttagaagag | aattagagtt | acttatgttg | gcatccgaag | aggacgagga agtctccttgt 360 |
| ctgattactg | acgctctatg | gtactttgcc | caatctgtgg | ctgatagttt gaatttgagg 420 |
| agattggtac | taatgacatc | cagtctgttt | aactttcacg | ctcatgttag tttaccacaa 480 |
| tttgacgaat | tgggatactt | ggaccctgat | gacaagacta | ggttagagga acaggcctct 540 |
| ggttttccta | tgttgaaagt | caaagatatc | aagtctgcct | attctaattg gcaaatcttg 600 |
| aaagagatct | taggaaagat | gatcaaacag | acaaaggctt | catctggagt gatttggaac 660 |
| agtttcaaag | agttagaaga | gtctgaattg | gagactgtaa | tcagagaaat tccagcacct 720 |
| tcattcctga | taccattacc | aaaacatttg | actgcttcct | cttcctcttt gttggatcat 780 |
| gacagaacag | ttttcaatg | gttggaccaa | caaccaccta | gttctgttt gtacgtgtca 840 |
| tttggtagta | cttctgaagt | cgatgaaaag | gacttccttg | aaatcgcaag aggcttagtc 900 |
| gatagtaagc | agtcattcct | ttgggtcgtg | cgtccaggtt | tcgtgaaagg ctcaacatgg 960 |
| gtcgaaccac | ttccagatgg | ttttctaggc | gaaagaggta | gaatagtcaa atgggttcct 1020 |
| caacaggaag | ttttagctca | tggcgctatt | ggggcattct | ggactcattc cggatggaat 1080 |
| tcaactttag | aatcagtatg | cgaaggggta | cctatgatct | tttcagattt tggtcttgat 1140 |
| caaccactga | acgcaagata | catgtctgat | gttttgaaag | tgggtgtata tctagaaaat 1200 |
| ggctgggaaa | ggggtgaaat | agctaatgca | ataagacgtg | ttatggttga tgaagagggg 1260 |
| gagtatatca | gacaaaacgc | aagagtgctg | aagcaaaagg | ccgacgtttc tctaatgaag 1320 |
| ggaggctctt | catacgaatc | cttagaatct | cttgtttcct | acatttcatc actgtaa 1377 |

SEQ ID NO: 54

| | | | | |
|---|---|---|---|---|
| MDGVIDMQTI | PLRTAIAIGG | TAVALVVALY | FWFLRSYASP | SHHSNHLPPV PEVPGVPVLG 60 |
| NLLQLKEKKP | YMTFTKWAEM | YGPIYSIRTG | ATSMVVVSSN | EIAKEVVVTR FPSISTRKLS 120 |
| YALKVLTEDK | SMVAMSDYHD | YHKTVKRH1L | TAVLGPNAQK | KFRAHRDTMM ENVSNELHAF 180 |
| FEKNPNQEVN | LRKIFQSQLF | GLAMKQALGK | DVESIYVKDL | ETTMKREEIF EVLVVDPMMG 240 |
| AIEVDWRDFF | PYLKWVPNKS | FENIIHRMYT | RREAVMKALI | QEHKKRIASG ENLNSYIDYL 300 |
| LSEAQTLTDK | QLLMSLWEPI | IESSDTTMVT | TEWAMYELAK | NPNMQDRLYE EIQSVCGSEK 360 |
| ITEENLSQLP | YLYAVFQETL | RKHCPVPIMP | LRYVHENTVL | GGYHVPAGTE VAINIYGCNM 420 |
| DKKVWENPEE | WNPERFLSEK | ESMDLYKTMA | FGGGKRVCAG | SLQAMVSICI GIGRLVQDFE 480 |
| WKLKDDAEED | VNTLGLTTQK | LHPLLALINP | RK | 512 |

TABLE 13-continued

Sequences disclosed herein.

SEQ ID NO: 55

| | | | | | |
|---|---|---|---|---|---|
| aagcttacta | gtaaaatgga | cggtgtcatc | gatatgcaaa | ccattccatt | gagaaccgct 60 |
| attgctattg | gtggtactgc | tgttgctttg | gttgttgcat | tatacttttg | gttcttgaga 120 |
| tcctacgctt | ccccatctca | tcattctaat | catttgccac | cagtacctga | agttccaggt 180 |
| gttccagttt | tgggtaattt | gttgcaattg | aaagaaaaaa | agccttacat | gaccttcacc 240 |
| aagtgggctg | aaatgtatgg | tccaatctac | tctattagaa | ctggtgctac | ttccatggtt 300 |
| gttgtctctt | ctaacgaaat | cgccaaagaa | gttgttgtta | ccagattccc | atctatctct 360 |
| accagaaaat | tgtcttacgc | cttgaaggtt | ttgaccgaag | ataagtctat | ggttgccatg 420 |
| tctgattatc | acgattacca | taagaccgtc | aagagacata | ttttgactgc | tgttttgggt 480 |
| ccaaacgccc | aaaaaaagtt | tagagcacat | agagacacca | tgatggaaaa | cgtttccaat 540 |
| gaattgcatg | ccttcttcga | aaagaaccca | aatcaagaag | tcaacttgag | aaagatcttc 600 |
| caatcccaat | tattcggttt | ggctatgaag | caagccttgg | gtaaagatgt | tgaatccatc 660 |
| tacgttaagg | atttggaaac | caccatgaag | agagaagaaa | tcttcgaagt | tttggttgtc 720 |
| gatccaatga | tgggtgctat | tgaagttgat | tggagagact | ttttcccata | cttgaaatgg 780 |
| gttccaaaca | agtccttcga | aaacatcatc | catagaatgt | acactagaag | agaagctgtt 840 |
| atgaaggcct | tgatccaaga | acacaagaaa | agaattgcct | ccggtgaaaa | cttgaactcc 900 |
| tacattgatt | acttgttgtc | tgaagcccaa | accttgaccg | ataagcaatt | attgatgtct 960 |
| ttgtgggaac | ctattatcga | atcttctgat | accactatgg | ttactactga | atgggctatg 1020 |
| tacgaattgg | ctaagaatcc | aaacatgcaa | gacagattat | acgaagaaat | ccaatccgtt 1080 |
| tgcggttccg | aaaagattac | tgaagaaaac | ttgtcccaat | tgccatactt | gtacgctgtt 1140 |
| ttccaagaaa | ctttgagaaa | gcactgtcca | gttcctatta | tgccattgag | atatgttcac 1200 |
| gaaaacaccg | ttttgggtgg | ttatcatgtt | ccagctggta | ctgaagttgc | tattaacatc 1260 |
| tacggttgca | acatggataa | gaaggtctgg | gaaaatccag | aagaatggaa | tccagaaaga 1320 |
| ttcttgtccg | aaaaagaatc | catggacttg | tacaaaacta | tggcttttgg | tggtggtaaa 1380 |
| agagtttgcg | ctggttcttt | acaagccatg | gttatttctt | gcattggtat | cggtagattg 1440 |
| gtccaagatt | ttgaatggaa | gttgaaggat | gatgccgaag | aagatgttaa | cactttgggt 1500 |
| ttgactaccc | aaaagttgca | tccattattg | gccttgatta | acccaagaaa | gtaactcgag 1560 |
| ccgcgg | | | | | 1566 |

SEQ ID NO: 56

| | | | | | |
|---|---|---|---|---|---|
| atggccaccc | tccttgagca | tttccaagct | atgcccttttg | ccatccctat | tgcactggct 60 |
| gctctgtctt | ggctgttcct | cttttacatc | aaagtttcat | tcttttccaa | caagagtgct 120 |
| caggctaagc | tccctcctgt | gccagtggtt | cctgggctgc | cggtgattgg | gaatttactg 180 |
| caactcaagg | agaagaaacc | ctaccagact | tttacaaggt | gggctgagga | gtatggacca 240 |
| atctattcta | tcaggactgg | tgcttccacc | atggtcgttc | tcaataccac | ccaagttgca 300 |
| aaagaggcca | tggtgaccag | atatttatcc | atctcaacca | gaaagctatc | aaacgcacta 360 |
| aagattctta | ctgctgataa | atgtatggtt | gcaataagtg | actacaacga | ttttcacaag 420 |
| atgataaagc | gatacatact | ctcaaatgtt | cttggaccta | gtgctcagaa | gcgtcaccgg 480 |
| agcaacagag | ataccttgag | agctaatgtc | tgcagccgat | tgcattctca | agtaaagaac 540 |
| tctcctcgag | aagctgtgaa | tttcagaaga | gttttttgagt | gggaactctt | tggaattgca 600 |

TABLE 13-continued

Sequences disclosed herein.

| | | | | |
|---|---|---|---|---|
|ttgaagcaag|cctttggaaa|ggacatagaa|aagcccattt|atgtggagga acttggcact 660|
|acactgtcaa|gagatgagat|ctttaaggtt|ctagtgcttg|acataatgga gggtgcaatt 720|
|gaggttgatt|ggagagattt|cttcccttac|ctgagatgga|ttccgaatac gcgcatggaa 780|
|acaaaaattc|agcgactcta|tttccgcagg|aaagcagtga|tgactgccct gatcaacgag 840|
|cagaagaagc|gaattgcttc|aggagaggaa|atcaactgtt|atatcgactt cttgcttaag 900|
|gaagggaaga|cactgacaat|ggaccaaata|agtatgttgc|tttgggagac ggttattgaa 960|
|acagcagata|ctacaatggt|aacgacagaa|tgggctatgt|atgaagttgc taaagactca 1020|
|aagcgtcagg|atcgtctcta|tcaggaaatc|caaaaggttt|gtggatcgga gatggttaca 1080|
|gaggaatact|tgtcccaact|gccgtacctg|aatgcagttt|tccatgaaac gctaaggaag 1140|
|cacagtccgg|ctgcgttagt|tccttttaaga|tatgcacatg|aagatacccca actaggaggt 1200|
|tactacattc|cagctggaac|tgagattgct|ataaacatat|acgggtgtaa catggacaag 1260|
|catcaatggg|aaagccctga|ggaatggaaa|ccggagagat|ttttggaccc gaaatttgat 1320|
|cctatggatt|tgtacaagac|catggctttt|ggggctggaa|agagggtatg tgctggttct 1380|
|cttcaggcaa|tgttaatagc|gtgcccgacg|attggtaggc|tggtgcagga gtttgagtgg 1440|
|aagctgagag|atggagaaga|agaaaatgta|gatactgttg|ggctcaccac tcacaaacgc 1500|
|tatccaatgc|atgcaatcct|gaagccaaga|agtta| 1535|

SEQ ID NO: 57

| | | | | |
|---|---|---|---|---|
|aagcttacta|gtaaaatggc|ctccatcacc|catttcttac|aagattttca agctactcca 60|
|ttcgctactg|cttttgctgt|tggtggtgtt|tctttgttga|tattcttctt cttcatccgt 120|
|ggtttccact|ctactaagaa|aaacgaatat|tacaagttgc|caccagttcc agttgttcca 180|
|ggtttgccag|ttgttggtaa|tttgttgcaa|ttgaaagaaa|agaagccata caagactttc 240|
|ttgagatggg|ctgaaattca|tggtccaatc|tactctatta|gaactggtgc ttctaccatg 300|
|gttgttgtta|actctactca|tgttgccaaa|gaagctatgg|ttaccagatt ctcttcaatc 360|
|tctaccagaa|agttgtccaa|ggctttggaa|ttattgacct|ccaacaaatc tatggttgcc 420|
|acctctgatt|acaacgaatt|tcacaagatg|gtcaagaagt|acatcttggc cgaattattg 480|
|ggtgctaatg|ctcaaaagag|acacagaatt|catagagaca|ccttgatcga aaacgtcttg 540|
|aacaaattgc|atgcccatac|caagaattct|ccattgcaag|ctgttaactt cagaaagatc 600|
|ttcgaatctg|aattattcgg|tttggctatg|aagcaagcct|tgggttatga tgttgattcc 660|
|ttgttcgttg|aagaatttgggg|tactaccttg|tccagagaag|aaatctacaa cgttttggtc 720|
|agtgacatgt|tgaagggtgc|tattgaagtt|gattggagag|acttttttccc atacttgaaa 780|
|tggatcccaa|acaagtcctt|cgaaatgaag|attcaaagat|tggcctctag aagacaagcc 840|
|gttatgaact|ctattgtcaa|agaacaaaag|aagtccattg|cctctggtaa gggtgaaaac 900|
|tgttacttga|attacttgtt|gtccgaagct|aagactttga|ccgaaaagca aatttccatt 960|
|ttggcctggg|aaaccattat|tgaaactgct|gatacaactg|ttgttaccac tgaatgggct 1020|
|atgtacgaat|tggctaaaaa|cccaaagcaa|caagacagat|tatacaacga aatccaaaac 1080|
|gtctgcggta|ctgataagat|taccgaagaa|catttgtcca|agttgcctta cttgtctgct 1140|
|gttttttcacg|aaaccttgag|aaagtattct|ccatctccat|tggttccatt gagatacgct 1200|
|catgaagata|ctcaattggg|tggttattat|gttccagccg|gtactgaaat tgctgttaat 1260|
|atctacggtt|gcaacatgga|caagaatcaa|tgggaaactc|cagaagaatg gaagccagaa 1320|

TABLE 13-continued

Sequences disclosed herein.

| | | | | |
|---|---|---|---|---|
| agatttttgg | acgaaaagta | cgatccaatg | gacatgtaca | agactatgtc ttttggttcc 1380 |
| ggtaaaagag | tttgcgctgg | ttctttacaa | gctagtttga | ttgcttgtac ctccatcggt 1440 |
| agattggttc | aagaatttga | atggagattg | aaagacggtg | aagttgaaaa cgttgatacc 1000 |
| ttgggtttga | ctacccataa | gttgtatcca | atgcaagcta | tcttgcaacc tagaaactga 1560 |
| ctcgagccgc | gg | | | 1572 |

SEQ ID NO: 58

| | | | | |
|---|---|---|---|---|
| atgatttcct | tgttgttggg | ttttgttgtc | tcctccttct | tgtttatctt cttcttgaaa 60 |
| aaattgttgt | tcttcttcag | tcgtcacaaa | atgtccgaag | tttctagatt gccatctgtt 120 |
| ccagttccag | gttttccatt | gattggtaac | ttgttgcaat | tgaaagaaaa gaagccacac 180 |
| aagactttca | ccaagtggtc | tgaattatat | ggtccaatct | actctatcaa gatgggttcc 240 |
| tcttctttga | tcgtcttgaa | ctctattgaa | accgccaaag | aagctatggt cagtagattc 300 |
| tcttcaatct | ctaccagaaa | gttgtctaac | gctttgactg | ttttgacctg caacaaatct 360 |
| atggttgcta | cctctgatta | cgatgacttt | cataagttcg | tcaagagatg cttgttgaac 420 |
| ggtttgttgg | gtgctaatgc | tcaagaaaga | aaaagacatt | acagagatgc cttgatcgaa 480 |
| aacgttacct | ctaaattgca | tgcccatacc | agaaatcatc | cacaagaacc agttaacttc 540 |
| agagccattt | tcgaacacga | attattcggt | gttgctttga | acaagccttt cggtaaagat 600 |
| gtcgaatcca | tctatgtaaa | agaattgggt | gtcaccttgt | ccagagatga aatttttcaag 660 |
| gttttggtcc | acgacatgat | ggaaggtgct | attgatgttg | attggagaga tttcttccca 720 |
| tacttgaaat | ggatcccaaa | caactctttc | gaagccagaa | ttcaacaaaa gcacaagaga 780 |
| agattggctg | ttatgaacgc | cttgatccaa | gacagattga | atcaaaacga ttccgaatcc 840 |
| gatgatgact | gctacttgaa | tttcttgatg | tctgaagcta | agaccttgac catggaacaa 900 |
| attgctattt | tggtttggga | aaccattatc | gaaactgctg | ataccacttt ggttactact 960 |
| gaatgggcta | tgtacgaatt | ggccaaacat | caatctgttc | aagatagatt attcaaagaa 1020 |
| atccaatccg | tctgcggtgg | tgaaaagatc | aagaagaac | aattgccaag attgccttac 1080 |
| gtcaatggtg | ttttcacga | aaccttgaga | aagtattctc | cagctccatt ggttccaatt 1140 |
| agatacgctc | atgaagatac | ccaaattggt | ggttatcata | ttccagccgg ttctgaaatt 1200 |
| gccattaaca | tctacggttg | caacatggat | aagaagagat | gggaaagacc tgaagaatgg 1260 |
| tggccagaaa | gattttttgga | agatagatac | gaatcctccg | acttgcataa gactatggct 1320 |
| tttggtgctg | gtaaaagagt | ttgtgctggt | gctttacaag | ctagtttgat ggctggtatt 1380 |
| gctatcggta | gattggttca | agaattcgaa | tggaagttga | gagatggtga agaagaaaac 1440 |
| gttgatactt | acggtttgac | ctcccaaaag | ttgtatccat | tgatggccat tatcaaccca 1500 |
| agaagatctt | aa | | | 1512 |

SEQ ID NO: 59

| | | | | |
|---|---|---|---|---|
| atggatgctg | tgacgggttt | gttaactgtc | ccagcaaccg | ctataactat tggtggaact 60 |
| gctgtagcat | tggcggtagc | gctaatcttt | tggtacctga | atcctacac atcagctaga 120 |
| agatcccaat | caaatcatct | tccaagagtg | cctgaagtcc | caggtgttcc attgttagga 180 |
| aatctgttac | aattgaagga | gaaaaagcca | tacatgactt | ttacgagatg ggcagcgaca 240 |
| tatggaccta | tctatagtat | caaaactggg | gctacaagta | tggttgtggt atcatctaat 300 |
| gagatagcca | aggaggcatt | ggtgaccaga | ttccaatcca | tatctacaag gaacttatct 360 |

TABLE 13-continued

Sequences disclosed herein.

```
aaagccctga aagtacttac agcagataag acaatggtcg caatgtcaga ttatgatgat  420
tatcataaaa cagttaagag acacatactg accgccgtct tgggtcctaa tgcacagaaa  480
aagcatagaa ttcacagaga tatcatgatg gataacatat ctactcaact tcatgaattc  540
gtgaaaaaca acccagaaca ggaagaggta gaccttagaa aaatctttca atctgagtta  600
ttcggcttag ctatgagaca agccttagga aaggatgttg aaagtttgta cgttgaagac  660
ctgaaaatca ctatgaatag agacgaaatc tttcaagtcc ttgttgttga tccaatgatg  720
ggagcaatcg atgttgattg gagagacttc tttccatacc taaagtgggt cccaaacaaa  780
aagttcgaaa atactattca acaaatgtac atcagaagag aagctgttat gaaatcttta  840
atcaaagagc acaaaaagag aatagcgtca ggcgaaaagc taaatagtta tatcgattac  900
cttttatctg aagctcaaac tttaaccgat cagcaactat tgatgtcctt gtgggaacca  960
atcattgaat cttcagatac aacaatggtc acaacagaat gggcaatgta cgaattagct 1020 aaaaaccta aattgcaaga taggttgtac agagacatta agtccgtctg tggatctgaa 1080
aagataaccg aagagcatct atcacagctg ccttacatta cagctatttt ccacgaaaca 1140
ctgagaagac actcaccagt tcctatcatt cctctaagac atgtacatga agataccgtt 1200
ctaggcggct accatgttcc tgctggcaca gaacttgccg ttaacatcta cggttgcaac 1260
atggacaaaa acgtttggga aaatccagag gaatggaacc agaaagatt catgaaagag 1320 aatgagacaa ttgattttca aaagacgatg gccttcggtg gtggtaagag agtttgtgct 1380
ggttccttgc aagccctttt aactgcatct attgggattg ggagaatggt tcaagagttc 1440
gaatggaaac tgaaggatat gactcaagag gaagtgaaca cgataggcct aactacacaa 1500
atgttaagac cattgagagc tattatcaaa cctaggatct aa                    1542
```

SEQ ID NO: 60

```
aagcttacta gtaaaatgga catgatgggt attgaagctg ttccatttgc tactgctgtt   60
gttttgggtg gtatttcctt ggttgttttg atcttcatca gaagattcgt ttccaacaga  120
aagagatccg ttgaaggttt gccaccagtt ccagatattc caggtttacc attgattggt  180
aacttgttgc aattgaaaga aaagaagcca cataagacct tgctagatgg gctgaaaact  240
tacggtccaa tttctctat tagaactggt gcttctacca tgatcgtctt gaattcttct  300
gaagttgcca agaagctat ggtcactaga ttctcttcaa tctctaccag aaagttgtcc  360
aacgccttga agattttgac cttcgataag tgtatggttg ccacctctga ttacaacgat  420

CtCcacaaaa tggtcaaggg tttcatcttg agaaacgttt taggtgctcc agcccaaaaa  480
agacatagat gtcatagaga taccttgatc gaaaacatct taagtactt gcatgccat   540 gttaagactt ctccattgga accagttgtc ttgaagaaga ttttcgaatc cgaaattttc  600
ggtttggctt tgaacaagc cttgggtaag gatatcgaat ccatctatgt tgaagaattg  660
ggtactacct tgtccagaga agaaattttt gccgttttgg ttgttgatcc aatggctggt  720
gctattgaag ttgattggag agatttttc ccatacttgt cctggattcc aaacaagtct  780
atggaaatga agatccaaag aatggatttt agaagaggtg ctttgatgaa ggccttgatt  840
ggtgaacaaa agaaaagaat cggttccggt gaagaaaaga actcctacab tgatttcttg  900
ttgtctgaag ctaccacttt gaccgaaaag caaattgcta tgttgatctg ggaaaccatc  960
atcgaaattt ccgatacaac tttggttacc tctgaatggg ctatgtacga attggctaaa 1020
gacccaaata gacaagaaat cttgtacaga gaaatccaca aggtttgcgg tbctaacaag 1080
```

TABLE 13-continued

Sequences disclosed herein.

| | | | | |
|---|---|---|---|---|
| ttgactgaag | aaaacttgtc | caagttgcca | tacttgaact | ctgttttcca cgaaaccttg 1140 |
| agaaagtatt | ctccagctcc | aatggttcca | gttagatatg | ctcatgaaga tactcaattg 1200 |
| ggtggttacc | atattccagc | tggttctcaa | attgccatta | acatctacgg ttgcaacatg 1260 |
| aacaaaaagc | aatgggaaaa | tcctgaagaa | tggaagccag | aaagattctt ggacgaaaag 1320 |
| tatgacttga | tggacttgca | taagactatg | gcttttggtg | gtggtaaaag agtttgtgct 1380 |
| ggtgctttac | aagcaatgtt | gattgcttgc | acttccatcg | gtagattcgt tcaagaattt 1440 |
| gaatggaagt | tgatgggtgg | tgaagaagaa | aacgttgata | ctgttgcttt gacctcccaa 1500 |
| aaattgcatc | caatgcaagc | cattattaag | gccagagaat | gactcgagcc gcgg      1554 |

SEQ ID NO: 61

| | | | | |
|---|---|---|---|---|
| atgcaatcag | attcagtcaa | agtctctcca | tttgatttgg | tttccgctgc tatgaatggc   60 |
| aaggcaatgg | aaaagttgaa | cgctagtgaa | tctgaagatc | caacaacatt gcctgcacta  120 |
| aagatgctag | ttgaaaatag | agaattgttg | acactgttca | caacttcctt cgcagttctt  180 |
| attgggtgtc | ttgtatttct | aatgtggaga | cgttcatcct | ctaaaaagct ggtacaagat  240 |
| ccagttccac | aagttatcgt | tgtaaagaag | aaagagaagg | agtcagaggt tgatgacggg  300 |
| aaaaagaaag | tttctatttt | ctacggcaca | caaacaggaa | ctgccgaagg ttttgctaaa  360 |
| gcattagtcg | aggaagcaaa | agtgagatat | gaaaagacct | ctttcaaggt tatcgatcta  420 |
| gatgactacg | ctgcagatga | tgatgaatat | gaggaaaaac | tgaaaaagga atccttagcc  480 |
| ttcttcttct | tggccacata | cggtgatggt | gaacctactg | ataatgctgc taacttctac  540 |
| aagtggttca | cagaaggcga | cgataaaggt | gaatggctga | aaaagttaca atacggagta  600 |
| tttggtttag | gtaacagaca | atatgaacat | ttcaacaaga | tcgctattgt agttgatgat  660 |
| aaacttactg | aaatgggagc | caaaagatta | gtaccagtag | gattagggga tgatgatcag  720 |
| tgtatagaag | atgacttcac | cgcctggaag | gaattggtat | ggccagaatt ggatcaactt  780 |
| ttaagggacg | aagatgatac | ttctgtgact | accccataca | ctgcagccgt attggagtac  840 |
| agagtggttt | accatgataa | accagcagac | tcatatgctg | aagatcaaac ccatacaaac  900 |
| ggtcatgttg | tcatgatgc | acagcatcct | tcaagatcta | atgtggcttt caaaaaggaa  960 |
| ctacacacct | ctcaatcaga | taggtcttgt | actcacttag | aattcgatat ttctcacaca 1020 |
| ggactgtctt | acgaaactgg | cgatcacgtt | ggcgtttatt | ccgagaactt gtccgaagtt 1080 |
| gtcgatgaag | cactaaaaact | gttagggtta | tcaccagaca | catacttctc agtccatgct 1140 |
| gataaggagg | atgggacacc | tatcggtggt | gcttcactac | caccacctt tcctccttgc 1200 |
| acattgagag | acgctctaac | cagatacgca | gatgtcttat | cctcacctaa aaaggtagct 1260 |
| ttgctggcat | tggctgctca | tgctagtgat | cctagtgaag | ccgataggtt aaagttcctg 1320 |
| gcttcaccag | ccggaaaaga | tgaatatgca | caatggatcg | tcgccaacca acgttctttg 1380 |
| ctagaagtga | tgcaaagttt | tccatctgcc | aagcctccat | taggtgtgtt cttcgcagca 1440 |
| gtagctccac | gtttacaacc | aagatactac | tctatcagtt | catctcctaa gatgtctcct 1500 |
| aacagaatac | atgttacatg | tgctttggtg | tacgagacta | ctccagcagg cagaattcac 1560 |
| agaggattgt | gttcaacctg | gatgaaaaat | gctgtcccctt | taacgagtc acctgattgc 1620 |
| tctcaagcat | ccatttttcgt | tagaacatca | aatttcagac | ttccagtgga tccaaaagtt 1680 |
| ccagtcatta | tgataggacc | aggcactggt | cttgccccat | tcagggggctt tcttcaagag 1740 |
| agattggcct | tgaaggaatc | tggtacagaa | ttgggttctt | ctatctttt ctttggttgc 1800 |

TABLE 13-continued

Sequences disclosed herein.

cgtaatagaa aagttgactt tatctacgag gacgagctta acaattttgt tgagacagga 1860
gcattgtcag aattgatcgt cgcattttca agagaaggga ctgccaaaga gtacgttcag 1920
cacaagatga gtcaaaaagc ctccgatata tggaaacttc taagtgaagg tgcctatctt 1980
tatgtctgtg gcgatgcaaa gggcatggcc aaggatgtcc atagaactct gcatacaatt 2040
gttcaggaac aagggagtct ggattcttcc aaggctgaat tgtacgtcaa aaacttacag 2100
atgtctggaa gatacttaag agatgtttgg taa                               2133

SEQ ID NO: 62 atgaaggtca gtccattcga attcatgtcc gctattatca agggtagaat ggacccatct   60
aactcctcat ttgaatctac tggtgaagtt gcctccgtta tctttgaaaa cagagaattg  120
gttgccatct tgaccacttc tattgctgtt atgattggtt gcttcgttgt cttgatgtgg  180 agaagagctg qttctaqaaa ggttaagaat gtcgaattgc caaaqccatt gattgtccat  240 gaaccagaac ctgaagttga agatggtaag aagaaggttt ccatcttctt cggtactcaa  300
actggtactg ctgaaggttt tgctaaggct ttggctgatg aagctaaagc tagatacgaa  360
aaggctacct tcagagttgt tgatttggat gattatgctg ccgatgatga ccaatacgaa  420
gaaaaattga gaacgaatc cttcgccgtt ttcttgttgg ctacttatgg tgatggtgaa  480
cctactgata atgctgctag attttacaag tggttcgccg aaggtaaaga aagaggtgaa  540
tggttgcaaa acttgcacta tgctgttttt ggtttgggta acagacaata cgaacacttc  600
aacaagattg ctaaggttgc cgacgaatta ttggaagctc aaggtggtaa tagattggtt  660
aaggttggtt taggtgatga cgatcaatgc atcgaagatg attttctgc ttggagagaa  720 tctttgtggc cagaattgga tatgttgttg agagatgaag atgatgctac tactgttact  780
actccatata ctgctgctgt cttggaatac agagttgtct ttcatgattc tgctgatgtt  840
gctgctgaag ataaqtcttg gattaacgct aatggtcatg ctgttcatga tgctcaacat  900
ccattcagat ctaacgttgt cgtcagaaaa gaattgcata cttctgcctc tgatagatcc  960
tgttctcatt tggaattcaa catttccggt tccgctttga attacgaaac tggtgatcat 1020
gttggtgCcC actgtgaaaa cttgactgaa actgttgatg aagccttgaa cttgttgggt 1080
ttgtctccag aaacttactt ctctatctac accgataacg aagatggtac tccattgggt 1140
ggttcttcat tgccaccacc atttccatca tgtactttga gaactgcttt gaccagatac 1200
gctgatttgt tgaactctcc aaaaaagtct gctttgttgg ctttagctgc tcatgcttct 1260
aatccagttg aagctgatag attgagatac ttggcttctc cagctggtaa agatgaatat 1320
gcccaatctg ttatcggttc ccaaaagtct ttgttggaag ttatggctga attcccatct 1380
gctaaaccac cattaggtgt ttttttttgct gctgttgctc caagattgca acctagattc 1440
tactccattt catcctctcc aagaatggct ccatctagaa tccatgttac ttgtgctttg 1500
gtttacgata agatgccaac tggtagaatt cataagggtg tttgttctac ctggatgaag 1560
aattctgttc aatggaaaaa gtcccatgaa tgttcttggg ctccaatttt cgttagacaa 1620
tccaatttta agttgccagc cgaatccaag gttccaatta tcatggttgg tccaggtact 1680
ggtttggctc ctttttagagg tttttttacaa gaaagattgg ccttgaaaga atccggttgtt 1740 gaattgggtc catccatttt gttttttcggt tgcagaaaca gaagaatgga ttacatctac 1800
gaagatgaat tgaacaactt cgttgaaacc ggtgctttgt ccgaattggt tattgctttt 1860
tctagagaag gtcctaccaa agaatacgtc caacataaga tggctgaaaa ggcttctgat 1920

TABLE 13-continued

Sequences disclosed herein.

atctggaact tgatttctga aggtgcttac ttgtacgttt gtggtgatgc taaaggtatg 1980
gctaaggatg ttcatagaac cttgcatacc atcatgcaag aacaaggttc tttggattct 2040
tccaaagctg aatccatggt caagaacttg caaatgaatg gtagatactt aagagatgtt 2100
tggtaa 2106

SEQ ID NO: 63 aagcttaaaa tgagtaagtc taatagtatg aattctacat cacacgaaac ccttttttcaa  60 caattggtct tgggtttgga ccgtatgcca ttgatggatg ttcactggtt gatctacgtt 120
gctttcggcg catggttatg ttcttatgtg atacatgttt tatcatcttc ctctacagta 180
aaagtgccag ttgttggata caggtctgta ttcgaaccta catggttgct tagacttaga 240
ttcgtctggg aaggtggctc tatcataggt caagggtaca ataagtttaa agactctatt 300
ttccaagtta ggaaattggg aactgatatt gtcattatac cacctaacta tattgatgaa 360
gtgagaaaat tgtcacagga caagactaga tcagttgaac ctttcattaa tgattttgca 420
ggtcaataca caagaggcat ggttttcttg caatctgact acaaaaccg tgttatacaa 480 caaagactaa ctccaaaatt ggtttccttg accaaggtca tgaaggaaga gttggattat 540
gctttaacaa aagagatgcc tgatatgaaa atgacgaat gggtagaagt agatatcagt 600
agtataatgg tgagattgat ttccaggatc tccgccagag tctttctagg gcctgaacac 660
tgtcgtaacc aggaatggtt gactactaca gcagaatatt cagaatcact tttcattaca 720
gggtttatct taagagttgt acctcatatc ttaagaccat tcatcgcccc tctattacct 780
tcatacagga ctctacttag aaacgtttca agtggtagaa gagtcatcgg tgacatcata 840
agatctcagc aaggggatgg taacgaagat atactttcct ggatgagaga tgctgccaca 900
ggagaggaaa agcaaatcga taacattgct cagagaatgt taattctttc tttagcatca 960
atccacacta ctgcgatgac catgacacat gccatgtacg atctatgtgc ttgccctgag 1020
tacattgaac cattaagaga tgaagttaaa tctgttgttg gggcttctgg ctgggacaag 1080
acagcgttaa acagatttca taagttggac tccttcctaa aagagtcaca aagattcaac 1140
ccagtattct tattgacatt caatagaatc taccatcaat ctatgacctt atcagatggc 1200
actaacattc catctggaac acgtattgct gttccatcac acgcaatgtt gcaagattct 1260
gcacatgtcc caggtccaac cccacctact gaatttgatg gattcagata tagtaagata 1320
cgttctgata gtaactacgc acaaaagtac ctattctcca tgaccgattc ttcaaacatg 1380
gctttcggat acggcaagta tgcttgtcca ggtagatttt acgcgtctaa tgagatgaaa 1440
ctaacattag ccattttgtt gctacaattt gagttcaaac taccagatgg taaaggtcgt 1500
cctagaaata tcactatcga ttctgatatg attccagacc caagagctag actttgcgtc 1560
agaaaaagat cacttagaga tgaatgaccg cgg 1593

SEQ ID NO: 64 aagcttaaaa tggaagatcc tactgtctta tatgcttgtc ttgccattgc agttgcaact  60
ttcgttgtta gatggtacag agatccattg agatccatcc aacagttgg tggttccgat 120 ttgcctattc tatcttacat cggcgcacta agatggacaa gacgtggcag agagatactt 180
caagagggat atgatggcta cagaggatct acattcaaaa tcgcgatgtt agaccgttgg 240
atcgtgatcg caaatggtcc taaactagct gatgaagtca gacgtagacc agatgaagag 300
ttaaacttta tggacggatt aggagcattc gtccaaacta gtacacctt aggtgaagct 360

TABLE 13-continued

Sequences disclosed herein.

```
attcataacg atccatacca tgtcgatatc ataagagaaa aactaacaag aggccttcca  420
gccgtgcttc ctgatgtcat tgaagagttg acacttgcgg ttagacagta cattccaaca  480
gaaggtgatg aatgggtgtc cgtaaactgt tcaaaggccg caagagatat tgttgctaga  540
gcttctaata gagtctttgt aggtttgcct gcttgcagaa accaaggtta cttagatttg  600
gcaatagact ttacattgtc tgttgtcaag gatagagcca tcatcaatat gtttccagaa  660
ttgttgaagc caatagttgg cagagttgta ggtaacgcca ccagaaatgt tcgtagagct  720
gttccttttg ttgctccatt ggtggaggaa agacgtagac ttatggaaga gtacggtgaa  780
gactggtctg aaaaacctaa tgatatgtta cagtggataa tggatgaagc tgcatccaga  840
gatagttcag tgaaggcaat cgcagagaga ttgttaatgg tgaacttcgc ggctattcat  900
acctcatcaa acactatcac tcatgctttg taccaccttg ccgaaatgcc tgaaactttg  960
caaccactta gagaagagat cgaaccatta gtcaaagagg agggctggac caaggctgct 1020
atgggaaaaa tgtggtggtt agattcattt ctaagagaat ctcaaagata caatggcatt 1080
aacatcgtat cttaactag aatggctgac aaagatatta cattgagtga tgcacatttt 1140
ttgccaaaag gtactctagt ggccgttcca gcgtattcta ctcatagaga tgatgctgtc 1200
tacgctgatg cctagtatt cgatccttc agattctcac gtatgagagc gagagaaggt 1260
gaaggtacaa agcaccagtt cgttaatact tcagtcgagt acgttccatt tggtcacgga 1320
aagcatgctt gtccaggaag attcttcgcc gcaaacgaat tgaaagcaat gttggcttac 1380
attgttctaa actatgatgt aaagttgcct ggtgacggta aacgtccatt gaacatgtat 1440
tggggtccaa cagttttgcc tgcaccagca ggccaagtat tgttcagaaa gagacaagtt 1500
agtctataac cgcgg                                                  1515
```

SEQ ID NO: 65

```
atggctacct tgttggaaca ttttcaagct atgccattcg ctattccaat tgctttggct   60
gctttgtctt ggttgttttt gttctacatc aaggtttctt tcttctccaa caaatccgct  120
caagctaaat tgccaccagt tccagttgtt ccaggtttgc cagttattgg taatttgttg  180
caattgaaag aaaagaagcc ataccaaacc ttcactagat gggctgaaga atatggtcca  240
atctactcta ttagaactgg tgcttctact atggttgtct tgaacactac tcaagttgcc  300
aaagaagcta tggttaccag atacttgtct atctctacca gaaagttgtc caacgccttg  360
aaaattttga ccgctgataa gtgcatggtt gccatttctg attacaacga tttccacaag  420
atgatcaaga gatatatctt gtctaacgtt ttgggtccat ctgcccaaaa aagacataga  480
tctaacagag ataccttgag agccaacgtt tgttctagat tgcattccca agttaagaac  540
tctccaagag aagctgtcaa ctttagaaga gttttcgaat gggaattatt cggtatcgct  600
ttgaaacaag ccttcggtaa ggatattgaa aagccaatct acgtcgaaga attgggtact  660
actttgtcca gagatgaaat cttcaaggtt ttggtcttgg acattatgga aggtgccatt  720
gaagttgatt ggagagattt ttccccatac ttgcgttgga ttccaaacac cagaatggaa  780
actaagatcc aaagattata ctttagaaga aaggccgtta tgaccgcctt gattaacgaa  840
caaaagaaaa gaattgcctc cggtgaagaa atcaactgct acatcgattt cttgttgaaa  900
gaaggtaaga ccttgaccat ggaccaaatc tctatgttgt tgtgggaaac cgttattgaa  960
actgctgata ccacaatggt tactactgaa tgggctatgt acgaagttgc taaggattct 1020
aaaagacaag acagattata ccaagaaatc caaaaggtct gcggttctga aatggttaca 1080
```

TABLE 13-continued

Sequences disclosed herein.

```
gaagaatact tgtcccaatt gccatacttg aatgctgttt tccacgaaac tttgagaaaa 1140
cattctccag ctgctttggt tccattgaga tatgctcatg aagatactca attgggtggt 1200
tattacattc cagccggtac tgaaattgcc attaacatct acggttgcaa catggacaaa 1260
caccaatggg aatctccaga agaatggaag ccagaaagat ttttggatcc taagtttgac 1320
ccaatggact tgtacaaaac tatggctttt ggtgctggta aaagagtttg cgctggttct 1380
ttacaagcta tgttgattgc ttgtccaacc atcggtagat tggttcaaga atttgaatgg 1440
aagttgagag atggtgaaga agaaaacgtt gatactgttg gtttgaccac ccataagaga 1500
tatccaatgc atgctatttt gaagccaaga tcttaa                            1536
```

SEQ ID NO: 66

```
atggcagaat tagatacact tgatatagta gtattaggtg ttatcttttt gggtactgtg   60
gcatacttta ctaagggtaa attgtggggt gttaccaagg atccatacgc taacggattc  120
gctgcaggtg gtgcttccaa gcctggcaga actagaaaca tcgtcgaagc tatggaggaa  180
tcaggtaaaa actgtgttgt tttctacggc agtcaaacag gtacagcgga ggattacgca  240
tcaagacttg caaggaagg aaagtccaga ttcggtttga acactatgat cgccgatcta  300
gaagattatg acttcgataa cttagacact gttccatctg ataacatcgt tatgtttgta  360
ttggctactt acggtgaagg cgaaccaaca gataacgccg tggatttcta tgagttcatt  420
actggcgaag atgcctcttt caatgagggc aacgatcctc cactaggtaa cttgaattac  480
gttgcgttcg gtctgggcaa caatacctac gaacactaca actcaatggt caggaacgtt  540
aacaaggctc tagaaaagtt aggagctcat agaattggag aagcaggtga gggtgacgac  600
ggagctggaa ctatggaaga ggactttttta gcttggaaag atccaatgtg gaagccttg  660 gctaaaaaga tgggcttgga ggaaagagaa gctgtatatg aacctatttt cgctatcaat  720
gagagagatg atttgacccc tgaagcgaat gaggtatact tgggagaacc taataagcta  780
cacttggaag gtacagcgaa aggtccattc aactcccaca acccatatat cgcaccaatt  840
gcagaatcat acgaacttt ctcagctaag gatagaaatt gtctgcatat ggaaattgat  900
atttctggta gtaatctaaa gtatgaaaca ggcgaccata tcgcgatctg gcctaccaac  960
ccaggtgaag aggtcaacaa atttcttgac attctagatc tgtctggtaa gcaacattcc 1020
gtcgtaacag tgaaagcctt agaacctaca gccaaagttc cttttccaaa tccaactacc 1080
tacgatgcta tattgagata ccatctggaa atatgcgctc cagtttctag acagtttgtc 1140
tcaactttag cagcattcgc ccctaatgat gatatcaaag ctgagatgaa ccgtttggga 1200
tcagacaaag attacttcca cgaaaagaca ggaccacatt actacaatat cgctagattt 1260
ttggcctcag tctctaaagg tgaaaaatgg acaaagatac cattttctgc tttcatagaa 1320
ggccttacaa aactacaacc aagatactat tctatctctt cctctagttt agttcagcct 1380
aaaaagatta gtattactgc tgttgtcgaa tctcagcaaa ttccaggtag atgaccca 1440 ttcagaggtg tagcgactaa ctacttgttc gctttgaagc agaaacaaaa cggtgatcca 1500
aatccagctc cttttggcca atcatacgag ttgacaggac caaggaataa gtatgatggt 1560
atacatgttc cagtccatgt aagacattct aactttaagc taccatctga tccaggcaaa 1620
cctattatca tgatcggtcc aggtaccggt gttgcccctt ttagaggctt cgtccaagag 1680
agggcaaaac aagccagaga tggtgtagaa gttggtaaaa cactgctgtt ctttggatgt 1740
agaaagagta cagaagattt catgtatcaa aaagagtggc aagagtacaa ggaagctctt 1800
```

TABLE 13-continued

Sequences disclosed herein.

ggcgacaaat tcgaaatgat tacagcttt tcaagagaag gatctaaaaa ggtttatgtt 1860
caacacagac tgaaggaaag atcaaaggaa gtttctgatc ttctatccca aaaagcatac 1920
ttctacgttt gcggagacgc cgcacatatg gcacgtgaag tgaacactgt gttagcacag 1980
atcatagcag aaggccgtgg tgtatcagaa gccaagggtg aggaaattgt caaaaacatg 2040
agatcagcaa atcaatacca agtgtgttct gatttcgtaa cttacactg taaagagaca 2100 acatacgcga attcagaatt gcaagaggat gtctggagtt aa 2142

SEQ ID NO: 67 atggccgaat tggatacctt ggatatcgtt gttttgggtg ttatcttctt gggtactgtt 60
gcttacttca ccaaaggtaa attgtggggt gttactaagg atccatacgc taatggtttt 120
gctgctggtg gtgcttctaa accaggtaga actagaaata tcgttgaagc catggaagaa 180
tctggtaaga actgtgttgt tttctacggt tctcaaactg gtactgctga agattatgct 240
tccagattgg ctaaagaagg taagagtaga ttcggtttga acaccatgat tgccgatttg 300
gaagattacg atttcgataa cttggatacc gtcccatctg ataacatcgt tatgtttgtt 360
ttggctacct acggtgaagg tgaacctact gataatgctg ttgacttcta cgaattcatt 420
accggtgaag atgcttcttt caacgaaggt aatgatccac cattgggtaa cttgaattac 480
gttgcttttg gtttgggtaa caacacctac gaacattaca actccatggt tagaaacgtc 540
aacaaggctt ggaaaaatt gggtgctcat agaattggtg aagctggtga aggtgatgat 600
ggtgctggta ctatggaaga agattttttg gcttggaaag acccaatgtg ggaagccttg 660
gctaaaaaga tgggtttgga agaaagagaa gctgtctacg aacctatttt cgccattaac 720
gaaagagatg atttgacccc tgaagccaat gaagtttatt tgggtgaacc taacaagttg 780
cacttggaag gtactgctaa aggtccattc aattctcaca acccatatat gctccaatc 840 gccgaatctt acgaattatt ctctgctaag gatagaaact gcttgcacat ggaaattgac 900
atctctggtt ctaatttgaa gtacgaaacc ggtgatcata ttgccatttg gccaactaat 960
ccaggtgaag aagttaacaa gttcttggac atcttggact tgtccggtaa acaacattct 1020
gttgttactg ttaaggcctt ggaacctaca gctaaagttc cttttccaaa tccaactacc 1080
tacgatgcca ttttgagata ccatttggaa atttgcgctc agtctctag acaattcgtt 1140 tctactttgg ctgcttttgc tccaaacgat gatattaagg ctgaaatgaa cagattgggt 1200
tccgataagg attacttcca cgaaaaaact ggtccacact actacaacat tgctagattt 1260
ttggcctctg tctctaaagg tgaaagtgg actaagattc cattctccgc tttcattgaa 1320
ggtttgacta agttgcaacc tagatattac tccatctcct cctcatcttt ggttcaacct 1380
aagaagatct ctattaccgc cgttgttgaa tcccaacaaa ttccaggtag agatgatcct 1440
tttagaggtg ttgctaccaa ttacttgttc gccttgaaac aaaagcaaaa cggtgatcca 1500
aatcctgctc catttggtca atcttatgaa ttgactggtc caagaaacaa gtacgatggt 1560
attcatgttc cagttcacgt tagacactct aactttaagt tgccatctga tccaggtaag 1620
ccaattatca tgattggtcc aggtactggt gttgctccat tcagaggttt tgttcaagaa 1680
agagctaagc aagctagaga tggtgttgaa gttggtaaaa ccttgttgtt cttcggttgt 1740
agaaagtcca ctgaagattt catgtaccaa aaagaatggc aagaatacaa agaagcctta 1800
ggtgacaagt tcgaaatgat tactgccttc tcaagagaag gttctaagaa ggtttacgtc 1860
caacacagat tgaaagaaag atccaaagaa gtctccgatt tgttgtctca aaaggcctac 1920

TABLE 13-continued

Sequences disclosed herein.

```
ttttacgttt gtggtgatgc tgctcatatg gccagagaag ttaatactgt tttggcccaa 1980
attatcgctg aaggtagagg tgtatctgaa gctaagggtg aagaaatcgt taagaacatg 2040
agatccgcca atcaatacca agtttgctct gattttgtta ccttgcactg taaagaaacc 2100
acctacgcta attccgaatt gcaagaagat gtttggtcct aa                   2142
```

SEQ ID NO: 68

```
MEASYLYISI LLLLASYLFT TQLRRKSANL PPTVFPSIPI IGHLYLLKKP LYRTLAKIAA  60
KYGPILQLQL GYRRVLVISS PSAAEECFTN NDVIFANRPK TLFGKIVGGT SLGSLSYGDQ 120
WRNLRRVASI EILSVHRLNE FHDIRVDENR LLIRKLRSSS SPVTLITVFY ALTLNVIMRM 180
ISGKRYFDSG DRELEEEGKR FREILDETLL LAGASNVGDY LPILNWLGVK SLEKKLIALQ 240
KKRDDFFQGL IEQVRKSRGA KVGKGRKTMI ELLLSLQESE PEYYTDAMIR SFVLGLLAAG 300
SDTSAGTMEW AMSLLVNHPH VLKKAQAEID RVIGNNRLID ESDIGNIPYI GCIINETLRL 360
YPAGPLLFPH ESSADCVISG YNIPRGTMLI VNQWAIHHDP KVWDDPETFK PERFQGLEGT 420
RDGFKLMPFG SGRRGCPGEG LAIRLLGMTL GSVIQCFDWE RVGDEMVDMT EGLGVTLPKA 480
VPLVAKCKPR SEMTNLLSEL                                             500
```

SEQ ID NO: 69

```
MQSESVEAST IDLMTAVLKD TVIDTANASD NGDSKMPPAL AMMFEIRDLL LILTTSVAVL  60
VGCFVVLVWK RSSGKKSGKE LEPPKIVVPK RRLEQEVDDG KKKVTIFFGT QTGTAEGFAK 120
ALFEEAKARY EKAAFKVIDL DDYAADLDEY AEKLKKETYA FFFLATYGDG EPTDNAAKFY 180
KWFTEGDEKG VWLQKLQYGV FGLGNRQYEH FNKIGIVVDD GLTEQGAKRI VPVGLGDDDQ 240
SIEDDFSAWK ELVWPELDLL LRDEDDKAAA TPYTAAIPEY RVVFHDKPDA FSDDHTQTNG 300
HAVHDAQHPC RSNVAVKKEL HTPESDRSCT HLEFDISHTG LSYETGDHVG VYCENLIEVV 360
EEAGKLLGLS TDTYFSLHID NEDGSPLGGP SLQPPFPPCT LRKALTNYAD LLSSPKKSTL 420
LALAAHASDP TEADRLRFLA SREGKDEYAE WVVANQRSLL EVMEAFPSAR PPLGVFFAAV 480
APRLQPRYYS ISSSPKMEPN RIHVTCALVY EKTPAGRIHK GICSTWMKNA VPLTESQDCS 540
WAPIFVRTSN FRLPIDPKVP VIMIGPGTGL APFRGFLQER LALKESGTEL GSSILFFGCR 600
NRKVDYIYEN ELNNFVENGA LSELDVAFSR DGPTKEYVQH KMTQKASEIW NMLSEGAYLY 660
VCGDAKGMAK DVHRTLHTIV QEQGSLDSSK AELYVKNLQM SGRYLRDVW              709
```

SEQ ID NO: 70

```
MASITHFLQD FQATPFATAF AVGGVSLLIF FFFIRGFHST KKNEYYKLPP VPVVPGLPVV  60
GNLLQLKEKK PYKTFLRWAE IHGPIYSIRT GASTMVVVNS THVAKEAMVT RFSSISTRKL 120
SKALELLTSN KSMVATSDYN EFHKMVKKYI LAELLGANAQ KRHRIHRDTL IENVLNKLHA 180
HTKNSPLQAV NFRKIFESEL FGLAMKQALG YDVDSLFVEE LGTTLSREEI YNVLVSDMLK 240
GAIEVDWRDF FPYLKWIPNK SFEMKIQRLA SRRQAVMNSI VKEQKKSIAS GKGENCYLNY 300
LLSEAKTLTE KQISILAWET IIETADTTVV TTEWAMYELA KNPKQQDRLY NEIQNVCGTD 360
KITEEHLSKL PYLSAVFHET LRKYSPSPLV PLRYAHEDTQ LGGYYVPAGT EIAVNIYGCN 420
MDKNQWETPE EWKPERFLDE KYDPMDMYKT MSFGSGKRVC AGSLQASLIA CTSIGRLVQE 480
FEWRLKDGEV ENVDTLGLTT HKLYPMQAIL QPRN                            514
```

TABLE 13-continued

Sequences disclosed herein.

SEQ ID NO: 71

```
MASM1SLLLG FVVSSFLFIF FLKKLLFFFS RHKMSEVSRL PSVPVPGFPL IGNLLQLKEK  60
KPHKTFTKWS ELYGPIYSIK MGSSSLIVLN SIETAKEAMV SRFSSISTRK LSNALTVLTC 120
NKSMVATSDY DDFHKFVKRC LLNGLLGANA QERKRHYRDA LIENVTSKLH AHTRNHPQEP 180
VNFRAIFEHE LFGVALKQAF CKDVESIYVK ELGVTLSRDE IFKVLVHDMM EGAIDVDWRD 240
FFPYLKWIPN NSFEARIQQK HKRRLAVMNA LIQDRLNQND SESDDDCYLN FLMSEAKTLT 300
MEQIAILVWE T1IETADTTL VTTEWAMYEL AKHQSVQDRL FKE1QSVCGG EK1KEEQLPR 360
LPYVNGVFHE TLRKYSPAPL VPIRYAHEDT QIGGYHIPAG SE1AIN1YGC NMDKKRWERP 420
EEWWPERFLE DRYESSDLHK TMAFGAGKRV CAGALQASLM AGIAIGRLVQ EFEWKLRDGE 480
EENVDTYGLT SQKLYPLMAI INPRRS                                    506
```

SEQ ID NO: 72

```
MDMMG1EAVP FATAVVLGGI SLVVLIFIRR FVSNRKRSVE GLPPVPDIPG LPLIGNLLQL  60
KEKKPHKTFA RWAETYGPIF S1RTGASTMI VLNSSEVAKE AMVTRFSS1S TRKLSNALK1 120
LTFDKCMVAT SDYNDFHKMV KGFILRNVLG APAQKRHRCH RDTLIENISK YLHAHVKISP 180
LEPVVLKKIF ESEIFGLALK QALGKDIESI YVEELGTTLS REEIFAVLVV DPMAGAIEVD 240
WRDFFPYLSW IPNKSMEMKI QRMDFRRGAL MKALIGEQKK RIGSGEEKNS YIDFLLSEAT 300
TLTEKQIAML IWETIIEISD TTLVTSEWAM YELAKDPNRQ EILYREIHKV CGSNKLTBEN 360
LSKLPYLNSV FHETLRKYSP APMVPVRYAH EDTQLGGYHI PAGSQIAINI YGCNMNKKQW 420
ENPEEWKPER FLDEKYDLMD LHKTMAFGGG KRVCAGALQA MLIACTSIGR FVQEFEWKLM 480
GGEEENVDTV ALTSQKLHPM QAIIKARE                                  508
```

SEQ ID NO: 73

```
MAELDTLDIV VLGVIFLGTV AYFTKGKLWC VTKDPYANGF AAGGASKPGR TRNIVEAMEE  60
SGKNCVVFYG SQTGTAEDYA SRLAKEGKSR FGLNTMIADL EDYDFDNLDT VPSDN1VMtV 120
LATYGEGEPT DNAVDFYEFI TGEDASFNEG NDPPLGNLNY VAFGLGNNTY EHYNSMVRNV 180
NKALEKLGAH RIGEAGEGDD GAGTMEEDFL AWKDPMWEAL AKKMGLEERE AVYEPIFAIN 240
ERDDLTPEAN EVYLGEPNKL HLEGTAKGPF NSHNPYIAPI AESYELFSAK DRNCLHMEID 300
ISCSNLKYEr CDHIAIWPTN PCEEVNKFLD ILDLSCKQHS VVTVKALEPT AKVPFPNPTT 360
YDAILRYHLE ICAPVSRQFV STLAAFAPND DIKAEMNRLG SDKDYFHEKT GPHYYNIARF 420
LASVSKGEKW TKIPFSAFIE GLTKLQPRYY S1SSSSLVQP KKISITAVVE SQQIPGRDDP 480
FRGVATNYLF ALKQKQNGDP NPAPFGQSYE LTGPRNKYDG IHVPVHVRHS NFKLPSDPGK 540
P1IM1GPGTG VAPFRGFVQE RAKQARDGVE VGKTLLFFGC RKSTEDFMYQ KEWQEYKEAL 600
GDKFEMITAF SREGSKKVYV QHRLKERSKE VSDLLSQKAY FYVCGDAAHM AREVNTVLAQ 660
IIAEGRGVSE AKGEEIVKNM RSANQYQVCS DFVTLHCKET TYANSELQED VWS        713
```

SEQ ID NO: 74

```
MKVSPFEFMS AIIKGRMDPS NSSFESTGEV ASVIFENREL VA1LTTSIAV MIGCFVVLMW  60
RRAGSRKVKN VELPKPLIVH EPEPEVEDGK KKVSIFFGTQ TGTAEGFAKA LADEAKARYE 120
KATFRVVDLD DYAADDDQYE EKLKNESFAV FLLATYGDGE PTDNAARFYK WFAEGKERGE 180
WLQNLHYAVF GLGNRQYEHF HKIAKVADEL LEAQGGNRLV KVGLGDDDQC IEDDFSAWRE 240
SLWPELDMLL RDEDDATTVT TPYTAAVLEY RVVFHDSADV AAEDKSWINA NGHAVHDAQH 300
```

TABLE 13-continued

Sequences disclosed herein.

| | | | | | |
|---|---|---|---|---|---|
| PFRSNVVRK | ELHTSASDRS | CSHLEFNISG | SALNYETGDH | VGVYCENLTE | TVDEALNLLG 360 |
| LSPETYFSIY | TDNEDGTPLG | GSSLPPPFPS | CTLRTALTRY | ADLLNSPKKS | ALLALAAHAS 420 |
| NPVEADRLRY | LASPAGKDEY | AQSVIGSQKS | LLEVMAEFPS | AKPPLGVFFA | AVAPRLQPRF 480 |
| YSISSSPRMA | PSRIHVTCAL | VYDKMPTGRI | HKGVCSTWMK | NSVPMEKSHE | CSWAPIFVRQ 540 |
| SNFKLPAESK | VPIIMVGPGT | GLAPFRGFLQ | ERLALKESGV | ELGPSILFFG | CRMRRMDYIY 600 |
| EDELNNFVET | GALSELVIAF | SREGPTKEYV | QHKMAEKASD | IWNLISEGAY | LYVCGDAKGM 660 |
| AKDVHRTLHT | IMQEQGSLDS | SKAESMVKNL | QMNGRYLRDV | W | 701 |

SEQ ID NO: 75

| | | | | | |
|---|---|---|---|---|---|
| MATLLEHFQA | MPFAXPIALA | ALSWLFLFYI | KVSFFSNKSA | QAKLPPVPVV | PGLPVIGNLL 60 |
| QLKEKKPYQT | FTRWAEEYGP | IYSIRTGAST | MVVLNTTQVA | KEAMVTRYLS | ISTRKLSNAL 120 |
| KILTADKCMV | AISDYNDFHK | MIKRYILSNV | LGPSAQKRHR | SNRDTLRANV | CSRLHSQVKN 180 |
| SPREAVNFRR | VFEWELFGIA | LKQAFGKDIE | KPIYVEELGT | TLSRDEIFKV | LVLDIMEGAI 240 |
| EVDWRDFFPY | LRWIPNTRME | TKIQRLYFRR | KAVMTALINE | QKKRIASGEE | INCYIDFLLK 300 |
| EGKTLTMDQI | SMLLWETVIE | TADTTMVTTE | WAMYEVAKDS | KRQDRLYQEI | QKVCGSEMVT 360 |
| EEYLSQLPYL | NAVFHETLRK | HSPAALVPLR | YAHEDTQLGG | YYIPAGTEIA | INIYGCNMDK 420 |
| HQWESPEEWK | PERFLDPKFD | PMDLYKTMAF | GAGKRVCAGS | LQAMLIACPT | IGRLVQEFEW 480 |
| KLRDGEEENV | DTVGLITHKR | YPMHAILKPR | S | | 511 |

SEQ ID NO: 76

| | | | | | |
|---|---|---|---|---|---|
| MQSDSVKVSP | FDLVSAAMNG | KAMEKLNASE | SEDPTTLPAL | KMLVENRELL | TLFTTSFAVL 60 |
| IGCLVFLMWR | RSSSKKLVQD | PVPQVIVVKK | KEKESEVDDG | KKKVSIFYGT | QTGTAEGFAK 120 |
| ALVEEAKVRY | EKTSFKVIDL | DDYAADDDEY | EEKLKKESLA | FFFLATYGDG | EPTDNAANFY 180 |
| KWFTEGDDKG | EWLKKLQYGV | FGLGNRQYEH | FNKIAIVVDD | KLTEMGAKRL | VPVGLGDDDQ 240 |
| CIEDDFTAWK | ELVWPELDQL | LRDEDDTSVT | TPYTAAVLEY | RVVYHDKPAD | SYAEDQTHTN 300 |
| GHVVHDAQHP | SRSNVAFKKE | LHTSQSDRSC | THLEFDISHT | GLSYETGDHV | GVYSENLSEV 360 |
| VDEALKLLGL | SPDTYFSVHA | DKEDGTPIGG | ASLPPPFPPC | TLRDALTRYA | DVLSSPKKVA 420 |
| LLALAAHASD | PSEADRLKFL | ASPAGKDEYA | QWIVANQRSL | LEVMQSFPSA | KPPLGVFFAA 480 |
| VAPRLQPRYY | SISSSPKMSP | NRIHVTCALV | YETTPAGRIH | RGLCSTWMKN | AVPLTESPDC 540 |
| SQASIFVRTS | NFRLPVDPKV | PVIMIGPGTG | LAPFRGFLQE | RLALKESGTE | LGSSIFFFGC 600 |
| RRRKVDFIYE | DELNNFVETG | ALSELIVAFS | RECTAKEYVQ | HKMSQKASDI | WKLLSEGAYL 660 |
| YVCGDAKGMA | KDVHRTLHTI | VQEQGSLDSS | KAELYVKNLQ | MSGRYLRDVW | 710 |

SEQ ID NO: 77

| | | | | | |
|---|---|---|---|---|---|
| MSKSNSMNST | SHETLFQQLV | LGLDRMPLMD | VHWLIYVAFG | AWLCSYVIHV | LSSSSTVKVP 60 |
| VVGYRSVFEP | TWLLRLRFVW | EGGSIIGQGY | MKFKDSIFQV | RKLGTDIVII | PPNYIDEVRK 120 |
| LSQDKTRSVE | PFINDFAGQY | TRGMVFLQSD | LQNRVIQQRL | TPKLVSLTKV | MKEELDYALT 180 |
| KEMPDMKNDE | WVEVDISSIM | VRLISRISAR | VFLGPEHCRN | QEWLITTAEY | SESLFITGFI 240 |
| LRVVPHILRP | FIAPLLPSYR | TLLRNVSSGR | RVIGDIIRSQ | QGDGNEDILS | WMRDAATGEE 300 |
| KQIDNIAQRM | LILSLASIHP | TAMTMTHAMY | DLCACPEYIE | PLRDEVKSVV | GASGWDKTAL 360 |

TABLE 13-continued

Sequences disclosed herein.

NRFHKLDSFL KESQRFNPVF LLTFNRIYHQ SMTLSDGTNI PSGTRIAVPS HAMLQDSAHV 420

PGPTPPTEFD GFRYSKIRSD SNYAQKYLFS MTDSSNMAFG YGKYACPGRF YASNEMKLTL 480

AILLLQFEFK LPDGKGRPRN ITIDSDMIPD PRARLCVRKR SLRDE 525

SEQ ID NO: 78

MEDPTVLYAC LAIAVATFVV RWYRDPLRSI PTVGGSDLPI LSYIGALRWT RRGREILQEG 60

YDGYRGSTFK IAMLDRWIVI ANGPKLADEV RRRPDEELNF MDGLGAFVQT KYTLGEAIHN 120

DPYHVDIIRE KLTRGLPAVL PDVIEELTLA VRQYIPTEGD EWVSVNCSKA ARDIVARASN 180

RVFVGLPACR NQGYLDLAID FTLSVVKDRA IINMFPELLK PIVGRVVGNA TRNVRRAVPF 240

VAPLVEERRR LMEEYGEDWS EKPNDMLQWI MDEAASRDSS VKAIAERLLM VNFAAIHTSS 300

NTITHALYHL AEMPETLQPL REEIEPLVKE EGWTKAAMGK MWWLDSFLRE SQRYNGINIV 360

SLTRMADKDI TLSDGTFLPK GTLVAVPAYS THRDDAVYAD ALVFDPFRFS RMRAREGEGT 420

KHQFVNTSVE YVPFGHGKHA CPGRFFAANE LKAMLAYIVL NYDVKLPGDG KRPLNMYWGP 480

TVLPAPAGQV LFRKRQVSL 499

SEQ ID NO: 79

MDAVTGLLTV PATAITIGGT AVALAVALIF WYLKSYTSAR RSQSNHLPRV PEVPGVPLLG 60

NLLQLKEKKP YMTFTRWAAT YGPIYSIKTC ATSMVVVSSN EIAKEALVTR FQSISTRNLS 120

KALKVLTADK TMVAMSDYDD YHKTVKRHIL TAVLGPNAQK KHRIHRDIMM DNISTQLHEF 180

VKNNPEQEEV DLRKIFQSEL FGLAMRQALG KDVESLYVED LKITMNRDEI FQVLVVDPMM 240

GAIDVDWRDF FPYLKWVPNK KFENTIQQMY IRREAVMKSL IKEHKKRIAS GEKLNSYIDY 300

LLSEAQTLTD QQLLMSLWEP IIESSDTTMV TTEWAMYELA KNPKLQDRLY RDIKSVCGSE 360

KITEEHLSQL PYITAIFHET LRRHSPVPII PLRHVHEDTV LGGYHVPAGT ELAVNIYGCN 420

MDKNVWENPE EWNPERFMKE NETIDFQKTM AFGGGKRVCA GSLQALLTAS IGIGRMVQEF 480

EWKLKDMTQE EVNTIGLTTQ MLRPLRAIIK PRI 513

SEQ ID NO: 80 atggaagtaa cagtagctag tagtgtagcc ctgagcctgg tctttattag catagtagta 60
agatgggcat ggagtgtggt gaattgggtg tggtttaagc cgaagaagct ggaaagattt 120
ttgagggagc aaggccttaa aggcaattcc tacaggtttt tatatggaga catgaaggag 180
aactctatcc tgctcaaaca agcaagatcc aaacccatga acctctccac ctcccatgac 240
atagcacctc aagtcacccc ttttgtcgac caaaccgtga agcttacgg taagaactct 300 tttaattggg ttggccccat accaagggtg aacataatga atccagaaga tttgaaggac 360
gtcttaacaa aaaatgttga ctttgttaag ccaatatcaa acccacttat caagttgcta 420
gctacaggta ttgcaatcta tgaaggtgag aaatggacta acacagaag gattatcaac 480 ccaacattcc attcggagag gctaaagcgt atgttacctt catttcacca agttgtaat 540 gagatggtca aggaatggga gagcttggtg tcaaaagagg gttcatcatg tgagttggat 600
gtctggcctt ttcttgaaaa tatgtcggca gatgtgatct cgagaacagc atttggaact 660
agctacaaaa aaggacagaa aatctttgaa ctccttgagag agcaagtaat atatgtaacg 720
aaaggctttc aaagttttta cattccagga tggaggtttc tcccaactaa gatgaacaag 780
aggatgaatg agattaacga agaaataaaa ggattaatca ggggtattat aattgacaga 840
gagcaaatca ttaaggcagg tgaagaaacc aacgatgact tattaggtgc acttatggag 900

TABLE 13-continued

Sequences disclosed herein.

| | |
|---|---|
| tcaaacttga aggacattcg ggaacatggg aaaaacaaca aaaatgttgg gatgagtatt | 960 |
| gaagatgtaa ttcaggagtg taagctgttt tactttgctg ggcaagaaac cacttcagtg | 1020 |
| ttgctggctt ggacaatggt tttacttggt caaaatcaga actggcaaga tcgagcaaga | 1080 |
| caagaggttt tgcaagtctt tggaagcagc aagccagatt tgatggtct agctcacctt | 1140 |
| aaagtcgtaa ccatgatttt gcttgaagtt cttcgattat acccaccagt cattgaactt | 1200 |
| attcgaacca ttcacaagaa aacacaactt gggaagctct cactaccaga aggagttgaa | 1260 |
| gtccgcttac caacactgct cattcaccat gacaaggaac tgtggggtga tgatgcaaac | 1320 |
| cagttcaatc cagagaggtt ttcggaagga gtttccaaag caacaaagaa ccgactctca | 1380 |
| ttcttcccct tcggagccgg tccacgcatt tgcattggac agaacttttc tatgatggaa | 1440 |
| gcaaagttgg ccttagcatt gatcttgcaa cacttcacct ttgagctttc tccatctcat | 1500 |
| gcacatgctc cttcccatcg tataacccctt caaccacagt atggtgttcg tatcatttta | 1560 |
| catcgacgtt ag | 1572 |

SEQ ID NO: 81

| | |
|---|---|
| atggaagtca ctgtcgcctc ttctgtcgct ttatccttag tcttcatttc cattgtcgtc | 60 |
| agatgggctt ggtccgttgt caactgggtt tggttcaaac caagaagtt ggaaagattc | 120 |
| ttgagagagc aaggtttgaa gggtaattct tatagattct tgtacggtga catgaaggaa | 180 |
| aattctattt tgttgaagca agccagatcc aaaccaatga acttgtctac ctctcatgat | 240 |
| attgctccac aagttactcc attcgtcgat caaactgtta aagcctacgg taagaactct | 300 |
| ttcaattggg ttggtccaat tcctagagtt aacatcatga acccagaaga tttgaaggat | 360 |
| gtcttgacca agaacgttga cttcgttaag ccaatttcca acccattgat taaattgttg | 420 |
| gctactggta ttgccatttta cgaaggtgaa aagtggacta agcatagaag aatcatcaac | 480 |
| cctaccttcc actctgaaag attgaagaga atgttaccat ctttccatca atcctgtaat | 540 |
| gaaatggtta aggaatggga atccttggtt tctaaagaag gttcttcttg cgaattggat | 600 |
| gtttggccat tcttggaaaa tatgtctgct gatgtcattt ccagaaccgc tttcggtacc | 660 |
| tcctacaaga agggtcaaaa gattttcgaa ttgttgagag agcaagttat ttacgttacc | 720 |
| aagggttttcc aatccttcta catcccaggt tggagattct tgccaactaa aatgaacaag | 780 |
| cgtatgaacg agatcaacga agaaattaaa ggtttgatca gaggtattat tatcgacaga | 840 |
| gaacaaatta ttaaagctgg tgaagaaacc aacgatgatt tgttgggtgc tttgatggag | 900 |
| tccaacttga aggatattag agaacatggt aagaacaaca agaatgttgg tatgtctatt | 960 |
| gaagatgtta ttcaagaatg taagttattc tacttcgctg gtcaagagac cacttctgtt | 1020 |
| ttgttagcct ggactatggt cttgttaggt caaaaccaaa attggcaaga tagagctaga | 1080 |
| caagaagttt tgcaagtctt cggttcttcc aagccagact tgatggttt ggcccacttg | 1140 |
| aaggttgtta ctatgatttt gttagaagtt ttgagattgt acccaccagt cattgagtta | 1200 |
| atcagaacca ttcataaaaa gactcaattg ggtaaattat cttttgccaga aggtgttgaa | 1260 |
| gtcagattac caaccttgtt gattcaccac gataaggaat tatggggtga cgacgctaat | 1320 |
| caatttaatc cagaaagatt ttccgaaggt gtttccaagg ctaccaaaaa ccgtttgtcc | 1380 |
| ttcttcccat ttggtgctgg tccacgtatt tgtatcggtc aaaactttttc catgatggaa | 1440 |
| gccaagttgg ctttggcttt aatcttgcaa cacttcactt tcgaattgtc tccatcccat | 1500 |
| gcccacgctc cttctcatag aatcacttta caaccacaat acggtgtcag aatcatctta | 1560 |

TABLE 13-continued

Sequences disclosed herein.

```
cacagaagat aa                                                        1572
```

SEQ ID NO: 82

```
MEVTVASSVA LSLVFISIVV RWAWSVVNWV WFKPKKLERF LREQGLKGNS YRFLYGDMKE   60
NSILLKQARS KPMNLSTSHD IAPQVTPFVD QTVKAYGKNS FNWVGPIPRV NIMNPEDLKD  120
VLTKNVDFVK PISNPLIKLL ATGIAIYEGE KWTKHRRIIN PTFHSERLKR MLPSFHQSCN  180
EMVKEWESLV SKEGSSCELD VWPFLENMSA DVISRTAFGT SYKKGQKIFE LLREQVIYVT  240
KGFQSFYIPG WRFLPTKMNK RMNEINEEIK GLIRGIIIDR EQIIKAGEET NDDLLGALME  300
SNLKDIREHG KNNKNVGMSI EDVIQECKLF YFAGQETTSV LLAWTMVLLG QNQNWQDRAR  360
QEVLQVFCSS KPDFDCLAHL KVVTMILLEV LRLYPPVIEL IRTIHKKTQL GKLSLPEGVE  420
VRLPTLLIHH DKELWGDDAN QFNPERFSEG VSKATKNRLS FFPFGAGPRI CICQNFSMME  480
AKLALALILQ HFTFELSPSH AHAPSHRITL QPQYGVRIIL HRR                    523
```

SEQ ID NO: 83

```
MENKTETTVR RRRRIILFPV PFQGHINPIL QLANVLYSKG FSITIFHTNF NKPKTSNYPH   60
FTFRFILDND PQDERISNLP THGPLAGMRI PIINEHGADE LRRELELLML ASEEDEEVSC  120
LITDALWYFA QSVADSLNLR RLVLMTSSLF NFHAHVSLPQ FDELGYLDPD DKTRLEEQAS  180
GFPMLKVKDI KSAYSNWQIL KEILGKMIKQ TKASSGVIWN SFKELEESEL ETVIREIPAP  240
SFLIPLPKHL TASSSSLLDH DRTVFQWLDQ QPPSSVLYVS FGSTSEVDEK DFLEIARGLV  300
DSKQSFLWVV RPGFVKGSTW VEPLPDGFLG ERGRIVKWVP QQEVLAHGAI GAFWTHSGWN  360
STLESVCEGV PMIFSDFGLD QPLNARYMSD VLKVGVYLEN GWERGEIANA IRRVMVDEEG  420
EYIRQNARVL KQKADVSLMK GGSSYESLES LVSYISSL                          458
```

SEQ ID NO: 84

```
MDAMATTEKK PHVIFIPFPA QSHIKAMLKL AQLLHHKGLQ ITFVNTDFIH NQFLESSGPH   60
CLDGAPGFRF ETIPDGVSHS PEASIPIRES LLRSIETNFL DRFIDLVTKL PDPPTCIISD  120
GFLSVFTIDA AKKLGIPVMM YWTLAACGFM GFYHIHSLIE KGFAPLKDAS YLTNGYLDTV  180
IDWVPGMEGI RLKDFPLDWS TDLNDKVLMF TTEAPQRSHK VSHHIFHTFD ELEPSIIKTL  240
SLRYNHIYTI GPLQLLLDQI PEEKKQTGIT SLHGYSLVKE EPECFQWLQS KEPNSVVYVN  300
FGSTTVMSLE DMTEFGWGLA NSNHYFLWII RSNLVIGENA VLPPELEEHI KKRGFIASWC  360
SQEKVLKHPS VGGFLTHCGW GSTIESLSAG VPMICWPYSW DQLTNCRYIC KEWEVGLEMG  420
TKVKRDEVKR LVQELMGEGG HKMRNKAKDW KEKARIAIAP NGSSSLNIDK MVKEITVLAR  480
```

SEQ ID NO: 85

```
MATSDSIVDD RKQLHVATFP WLAFGHILPY LQLSKLIAEK GHKVSFLSTT RNIQRLSSHI   60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG LVLKGSDCLL SKCYHEFGTQ WLPLLETLHQ  240
VPVVPVGLLP PEIPGDEKDE TWVSIKKWLD GKQKGSVVYV ALGSEVLVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGEIPRNE EDGCLTKESV ARSLRSVVVE KEGEIYKANA  420
RELSKIYNDT KVEKEYVSQF VDYLEKNARA VAIDHES                           457
```

TABLE 13-continued

Sequences disclosed herein.

SEQ ID NO: 86

```
MDSGYSSSYA AAAGMHVVIC PWLAFGHLLP CLDLAQRLAS RGHRVSFVST PRNISRLPPV  60
RPALAPLVAF VALPLPRVEG LPDGAESTND VPHDRPDMVE LHRRAFDGLA APFSEFLGTA 120
CADWVIVDVF HHWAAAAALE HKVPCAMMLL GSAHMIASIA DRRLERAETE SPAAAGQGRP 180
AAAPTFEVAR MKLIRTKGSS GMSLAERFSL TLSRSSLVVG RSCVEFEPET VPLLSTLRGK 240
PITFLGLMPP LHEGRREDGE DATVRWLDAQ PAKSVVYVAL GSEVPLGVEK VHELALGLEL 300
AGTRFLWALR KPTGVSDADL LPAGFEERTR GRGVVATRWV PQMSILAHAA VGAFLTHCGW 360
NSTIEGLMFG HPLIMLPIFG DQGPNARLIE AKNAGLQVAR NDGDGSFDRE GVAAAIRAVA 420
VEEESSKVFQ AKAKKLQEIV ADMACHERYI DGFIQQLRSY KD               462
```

SEQ ID NO: 87

```
MSSSSSSSTS MIDLMAAIIK GEPVIVSDPA NASAYESVAA ELSSMLIENR QFAMIVTTSI  60
AVLIGCIVML VWRRSGSGNS KRVEPLKPLV IKPREEEIDD GRKKVTIFFG TQTGTAEGFA 120
KALGEEAKAR YEKTRFKIVD LDDYAADDDE YEEKLKKEDV AFFFLATYGD GEPTDNAARF 180
YKWFTEGNDR GEWLKNLKYG VFGLGNRQYE HFNKVAKVVD DILVEQGAQR LVQVGLGDDD 240
QCIEDDFTAW REALWPELDT ILREEGDTAV ATPYTAAVLE YRVSIHDSED AKFNDITLAN 300
GNGYTVFDAQ HPYKANVAVK RELHTPESDR SCIHLEFDIA GSGLTMKLGD HVGVLCDNLS 360
ETVDEALRLL DMSPDTYFSL HAEKEDGTPI SSSLPPPFPP CNLRTALTRY ACLLSSPKKS 420
ALVALAAHAS DPTEAERLKH LASPAGKDEY SKWVVESQRS LLEVMAEFPS AKPPLGVFFA 480
GVAPRLQPRF YSISSSPKIA ETRIHVTCAL VYEKMPTGRI HKGVCSTWMK NAVPYEKSEK 540
LFLGRPIFVR QSNFKLPSDS KVPIIMIGPG TGLAPFRGFL QERLALVESG VELGPSVLFF 600
GCRNRRMDFI YEEELQRFVE SGALAELSVA FSREGPTKEY VQHKMMDKAS DIWNMISQGA 660
YLYVCGDAKG MARDVHRSLH TIAQEQGSMD STKAEGFVKN LQTSGRYLRD VW         712
```

SEQ ID NO: 88

```
MATSDSIVDD RKQLHVATFP WLAFGHILPY LQLSKLIAEK GHKVSFLSTT RNIQRLSSHI  60
SPLINVVQLT LPRVQELPED AEATTDVHPE DIPYLKKASD GLQPEVTRFL EQHSPDWIIY 120
DYTHYWLPSI AASLGISRAH FSVTTPWAIA YMGPSADAMI NGSDGRTTVE DLTTPPKWFP 180
FPTKVCWRKH DLARLVPYKA PGISDGYRMG MVLKGSDCLL SKCYHEFGTQ WLPLLETLHQ 240
VPVVPVGLLP PEIPGDEKDE TWVSIKKWLD GKQKGSVVYV ALGSEALVSQ TEVVELALGL 300
ELSGLPFVWA YRKPKGPAKS DSVELPDGFV ERTRDRGLVW TSWAPQLRIL SHESVCGFLT 360
HCGSGSIVEG LMFGHPLIML PIFGDQPLNA RLLEDKQVGI EPPRNEEDGC LTKESVARSL 420
RSVVVEKEGE IYKANARELS KIYNDTKVEK EYVSQFVDYL EKNARAVAID HES        473
```

SEQ ID NO: 89

```
atggctactt ctgattccat cgttgacgat agaaagcaat tgcatgttgc tacttttcca  60
tggttggctt tcggtcatat tttgccatac ttgcaattgt ccaagttgat tgctgaaaag 120
ggtcacaagg tttcattctt gtctaccacc agaaacatcc aaagattgtc ctctcatatc 180
tccccattga tcaacgttgt tcaattgact ttgccaagag tccaagaatt gccagaagat 240
gctgaagcta ctactgatgt tcatccagaa gatatccctt acttgaaaaa ggcttccgat 300
ggtttacaac cagaagttac tagattcttg gaacaacatt ccccagattg gatcatctac 360
gattatactc attactggtt gccatccatt gctgcttcat tgggtatttc tagagcccat 420
```

TABLE 13-continued

Sequences disclosed herein.

| | | | | | |
|---|---|---|---|---|---|
| ttctctgtta | ctactccatg | ggctattgct | tatatgggtc | catctgctga | tgctatgatt 480 |
| aacggttctg | atggtagaac | taccgttgaa | gatttgacta | ctccaccaaa | gtggtttcca 540 |
| tttccaacaa | aagtctgttg | gagaaaacac | gatttggcta | gattggttcc | atacaaagct 600 |
| ccaggtattt | ctgatggtta | cagaatgggt | atggttttga | aaggttccga | ttgcttgttg 660 |
| tctaagtgct | atcatgaatt | cggtactcaa | tggttgcctt | tgttggaaac | attgcatcaa 720 |
| gttccagttg | ttccagtagg | tttgttgcca | ccagaaattc | caggtgacga | aaaagacgaa 780 |
| acttgggttt | ccatcaaaaa | gtggttggat | ggtaagcaaa | agggttctgt | tgtttatgtt 840 |
| gctttgggtt | ccgaagcttt | ggtttctcaa | accgaagttg | ttgaattggc | tttgggtttg 900 |
| gaattgtctg | gtttgccatt | tgtttgggct | tacagaaaac | ctaaaggtcc | agctaagtct 960 |
| gattctgttg | aattgccaga | tggtttcgtt | gaaagaacta | gagatagagg | tttggtttgg 1020 |
| acttcttggg | ctccacaatt | gagaattttg | tctcatgaat | ccgtctgtgg | tttcttgact 1080 |
| cattgtggtt | ctggttctat | cgttgaaggt | ttgatgtttg | gtcacccatt | gattatgttg 1140 |
| ccaatctttg | gtgaccaacc | attgaacgct | agattattgg | aagataagca | agtcggtatc 1200 |
| gaaatcccaa | gaaatgaaga | agatggttgc | ttgaccaaag | aatctgttgc | tagatctttg 1260 |
| agatccgttc | tcgttgaaaa | agaaggtgaa | atctacaagg | ctaacgctag | agaattgtcc 1320 |
| aagatctaca | acgataccaa | ggtcgaaaaa | gaatacgttt | cccaattcgt | tgactacttg 1380 |
| gaaaagaatg | ctagagctgt | tgccattgat | catgaatctt | ga | 1422 |

SEQ ID NO: 90

| | | | | | |
|---|---|---|---|---|---|
| atggaagctt | ctagagcatc | ttgtgttgct | ttgtgtgttg | tttgggtttc | catcgttatt 60 |
| actttggctt | ggagagtttt | gaattgggtc | tggttaagac | caaaaaagtt | ggaaagatgc 120 |
| ttgagagaac | aaggtttgac | tggtaactct | tacagattgt | tgttcggtga | taccaaggac 180 |
| ttgtctaaga | tgttggaaca | aactcaatcc | aagcctatca | agttgtctac | ctctcatgat 240 |
| attgctccaa | gagttactcc | attcttccat | agaactgtta | actccaacgg | taagaactct 300 |
| tttgtttgga | tgggtccaat | tccaagagtc | catattatga | accctgaaga | tttgaaggac 360 |
| gctttcaaca | gacatgatga | tttccataag | accgtcaaga | acccaattat | gaagtctcca 420 |
| ccaccaggta | tagttggtat | tgaaggtgaa | caatgggcca | acatagaaa | gattattaac 480 |
| ccagccttcc | acttggaaaa | gttgaaaggt | atggttccaa | tcttctacca | atcctgctct 540 |
| gaaatgatta | caagtgggga | atccttggtt | tccaaagaat | cttcctgtga | attggatgtc 600 |
| tggccatatt | tggaaaactt | cacctccgat | gttatttcca | gagctgcttt | tggttcttct 660 |
| tacgaagaag | gtagaaagat | cttccaatta | ttgagagaag | aagccaaggt | ttactccgtt 720 |
| gctttgagat | ctgtttacat | tccaggttgg | agattcttgc | caactaagca | aaacaaaag 780 |
| accaaagaaa | tccacaacga | aatcaagggt | tgttgaagg | gtatcatcaa | caagagaa 840 |
| gaagctatga | aggctggtga | agctacaaaa | gatgatttgt | tgggtatctt | gatggaatcc 900 |
| aacttcagag | aaatccaaga | acacggtaac | aacaagaatg | ccggtatgtc | tattgaagat 960 |
| gttatcggtg | aatgcaagtt | gttctacttt | gctggtcaag | aaactacctc | cgttttgttg 1020 |
| gtttggacca | tgattttgtt | gtcccaaaat | caagattggc | aagctagagc | tagagaagaa 1080 |
| gtcttgaaag | ttttcggttc | taacatccca | acctacgaag | aattgtctca | cttgaaggtt 1140 |
| gtcactatga | tcttgttgga | agtattgaga | ttataccat | ccgttgttgc | attgccaaga 1200 |
| actactcata | agaaaactca | attgggtaaa | ttgtccttgc | cagctggtgt | tgaagtttct 1260 |

TABLE 13-continued

Sequences disclosed herein.

```
ttgccaattt tgttagtcca ccacgacaaa gaattgtggg gtgaagatgc taatgaattc 1320
aagccagaaa gattctccga aggtgtttct aaagctacca agaacaagtt cacttacttg 1380
ccatttggtg gtggtccaag aatatgtatt ggtcaaaatt tcgctatggt cgaagctaaa 1440
ttggctttgg ctttgatctt gcaacatttc gctttcgaat tgtcaccatc ttatgctcat 1500
gctccatctg ctgttattac attgcaacca caatttggtg cccatatcat cttgcataag 1560
agataac                                                          1567
```

SEQ ID NO: 91

```
MEASRASCVA LCVVWVSIVI TLAWRVLNWV WLRPKKLERC LREQGLTGNS YRLLFGDTKD  60
LSKMLEQTQS KPIKLSTSHD IAPRVTPFFH RTVNSNGKNS FVWMGPIPRV HIMNPEDLKD 120
AFNRHDDFHK TVKNPIMKSP PPGIVGIEGE QWAKHRKIIN PAFHLEKLKG MVPIFYQSCS 180
EMINKWESLV SKESSCELDV WPYLENFTSD VISRAAFGSS YEEGRKIFQL LREEAKVYSV 240
ALRSVYIPGW RFLPTKQNKK TKEIHNEIKG LLKGIINKRE EAMKAGEATK DDLLGILMES 300
NFREIQEHGN NKNAGMSIED VIGECKLFYF AGQETTSVLL VWTMILLSQN QDWQARAREE 360
VLKVFGSNIP TYEELSHLKV VTMILLEVLR LYPSVVALPR TTHKKTQLGK LSLPAGVEVS 420
LPILLVHHDK ELWGEDANEF KPERFSEGVS KATKNKFTYL PFGGGPRICI GQNFAMVEAK 480
LALALILQHF AFELSPSYAH APSAVITLQP QFGAHIILHK R                    521
```

SEQ ID NO: 92

```
ASWVAVLSVV WVSMVIAWAW RVLNWVWLRP KKLEKCLREQ GLAGNSYRLL FGDTKDLSKM  60
LEQTQSKPIK LSTSHDIAPH VTPFFHQTVN SYGKNSFVWM GPIPRVHIMN PEDLKDTFNR 120
HDDFHKVVKN PIMKSLPQGI VGIEGEQWAK HRKIINPAFH LEKLKGMVPI FYRSCSEMIN 180
KWESLVSKES SCELDVWPYL ENFTSDVISR AAFGSSYEEG RKIFQLLREE AKIYTVAMRS 240
VYIPGWRFLP TKQNKKAKEI HNEIKGLLKG IINKREEAMK AGEArKDDLL GILMEGNFRE 300
IQEHGNNKNA GMSIEDVIGE CKLFYFAGQE TTSVLLVWTM VLLSQNQDWQ ARAREEVLQV 360
FGSNIPTYEE LSQLKVVTMI LLEVLRLYPS VVALPRTTHK KTQLGKLSLP AGVEVSLPIL 420
LVHHDKELWG EDANEFKPER FSEGVSKATK NQFTYFPFGG GPRICIGQNF AMMEAKLALS 480
LILRHFALEL SPLYAHAPSV TITLQPQYGA HIILHKR                         517
```

SEQ ID NO: 93

```
MEASRPSCVA LSVVLVSIVI AWAWRVLNWV WLRPNKLERC LREQGLTGNS YRLLFGDTKE  60
ISMMVEQAQS KPIKLSTTHD IAPRVIPFSH QIVYTYGRNS FVWMGPTPRV TIMNPEDLKD 120
AFNKSDEFQR AISNPIVKSI SQGLSSLEGE KWAKHRKIIN PAFHLEKLKG MLPTFYQSCS 180
EMINKWESLV FKEGSREMDV WPYLENLTSD VISRAAFGSS YEEGRKIFQL LREEAKFYTI 240
AARSVYIPGW RFLPTKQNKR MKEIHKEVRG LLKGIINKRE DAIKAGEAAK GNLLGILMES 300
NFREIQEHGN NKNAGMSIED VIGECKLFYF AGQErTSVLL VWTLVLLSQN QDWQARAREE 360
VLQVFGTNIP TYDQLSHLKV VTMILLEVLR LYPAVVELPR TTYKKTQLGK FLLPAGVEVS 420
LHIMLAHHDK ELWGEDAKEF KPERFSEGVS KATKNQFTYF PFGAGPRICI GQNFAMLEAK 480
LALSLILQHF TFELSPSYAH APSVTITLHP QFGAHFILHK R                    521
```

SEQ ID NO: 94

```
CVALSVVLVS IVIAWAWRVL NWVWLRPNKL ERCLREQGLT CNSYRLLFGD TKEISMMVEQ  60
AQSKPIKLST THDIAPRVIP FSHQIVYTYG RNStVWMGPT PRVTlMNPED LKDAFNKSDE 120
```

TABLE 13-continued

Sequences disclosed herein.

| | | | | | |
|---|---|---|---|---|---|
|FQRAISNPIV|KSISQGLSSL|EGEKWAKHRK|IINPAFHLEK|LKGMLPTFYQ|SCSEMINKWE 180|
|SLVFKEGSRE|MDVWPYLENL|TSDVISRAAF|GSSYEEGRKI|FQLLREEAKF|YTIAARSVYI 240|
|PGWRFLPTKQ|NKRMKEIHKE|VRGLLKGIIN|KREDAIKAGE|AAKGNLLGIL|MESNFREIQE 300|
|HCNNKNAGMS|IEDVIGECKL|FYFAGQETTS|VLLVWTLVLL|SQNQDWQARA|REEVLQVFGT 360|
|NIPTYDQLSH|LKVVTMILLE|VLRLYPAVVE|LPRTTYKKTQ|LGKFLLPAGV|EVSLHIMLAH 420|
|HDKELWGEDA|KEFKPERFSE|GVSKATKNQF|TYFPFGAGPR|ICIGQNFAML|EAKLALSLIL 480|
|QHFTFELSPS|YAHAPSVTIT|LHPQFGAHFI|LHKR| | 514|

SEQ ID NO: 95

| | | | | | |
|---|---|---|---|---|---|
|MGPIPRVHIM|NPEDLKDTFN|RHDDFHKVVK|NPIMKSLPQG|IVGIEGDQWA|KHRKIINPAF 60|
|HLEKLKGMVP|IFYQSCSEMI|NIWKSLVSKE|SSCELDVWPY|LENFTSDVIS|RAAFGSSYEE 120|
|GRKIFQLLRE|EAKVYTVAVR|SVYIPGWRFL|PTKQNKKTKE|IHNEIKGLLK|GIINKREEAM 180|
|KAGEATKDDL|LGILMESNFR|EIQEHGNNKN|AGMSIEDVIG|ECKLFYFAGQ|ETTSVLLVWT 240|
|MVLLSQNQDW|QARAREEVLQ|VFGSNIPTYE|ELSHLKVVTM|ILLEVLRLYP|SVVALPRTTH 300|
|KKTQLGKLSL|PAGVEVSLPI|LLVHHDKELW|GEDANEFKPE|RFSEGVSKAT|KNQFTYPFPG 360|
|GGPRICIGQN|FAMMEAKLAL|SLILQHFTFE|LSPQYSHAPS|VTITLQPQYG|AHLILHKR 418|

SEQ ID NO: 96

| | | | | | |
|---|---|---|---|---|---|
|atggaagcat|caagggctag|ttgtgttgcg|ctatgtgttg|tttgggtgag|catagtaatt 60|
|acattggcat|ggagggtgct|gaattgggtg|tggttgaggc|caaagaaact|agaaagatgc 120|
|ttgagggagc|aaggccttac|aggcaattct|tacaggcttt|tgtttggaga|caccaaggat 180|
|ctctcgaaga|tgctggaaca|aacacaatcc|aaacccatca|aactctccac|ctcccatgat 240|
|atagcgccac|gagtcacccc|attttccat|cgaactgtga|actctaatgg|caagaattct 300|
|tttgtttgga|tgggccctat|accaagagtg|cacatcatga|atccagaaga|tttgaaagat 360|
|gccttcaaca|gacatgatga|ttttcataag|acagtaaaaa|atcctatcat|gaagtctcca 420|
|ccaccgggca|ttgtaggcat|tgaaggtgag|caatgggcta|acacagaaa|gattatcaac 480|
|ccagcattcc|atttagagaa|gctaaagggt|atggtaccaa|tattttacca|aagttgtagc 540|
|gagatgatta|acaaatggga|gagcttggtg|tccaaagaga|gttcatgtga|gttggatgtg 600|
|tggccttatc|ttgaaaattt|taccagcgat|gtgatttccc|gagctgcatt|tggaagtagc 660|
|tatgaagagg|gaaggaaaat|atttcaacta|ctaagagagg|aagcaaaagt|ttattcggta 720|
|gctctacgaa|gtgtttacat|tccaggatgg|aggtttctac|caaccaagca|gaacaagaag 780|
|acgaaggaaa|ttcacaatga|aattaaaggc|ttacttaagg|gcattataaa|taaaagggaa 840|
|gaggcgatga|aggcagggga|agccactaaa|gatgacttac|taggaatact|tatggagtcc 900|
|aacttcaggg|aaattcagga|acatgggaac|aacaaaaatg|ctggaatgag|tattgaagat 960|
|gtaattggag|agtgtaagtt|gttttacttt|gctgggcaag|agaccacttc|ggtgttgctt 1020|
|gtttggacaa|tgattttact|aagccaaaat|caggattggc|aagctcgtgc|aagagaagag 1080|
|gtcttgaaag|tctttggaag|caacatccca|acctatgaag|agctaagtca|cctaaaagtt 1140|
|gtgaccatga|ttttacttga|agttcttcga|ttatacccat|cagtcgttgc|gcttcctcga 1200|
|accactcaca|agaaaacaca|gcttggaaaa|ttatcattac|cagctggagt|ggaagtctcc 1260|
|ttgcccatac|tgcttgttca|ccatgacaaa|gagttgtggg|gtgaggatgc|aaatgagttc 1320|
|aagccagaga|ggttttcaga|gggagtttca|aaggcaacaa|agaacaaatt|tacatactta 1380|

TABLE 13-continued

Sequences disclosed herein.

```
cctttcggag ggggtccaag gatttgcatt ggacaaaact tgccatggt ggaagctaaa 1440 ttggccttgg ccctgatttt acaacacttt gcctttgagc tttctccatc ctatgctcat 1500
gctccttctg cagttataac ccttcaacct caatttggtg ctcatatcat tttgcataaa 1560
cgttga                                                             1566
```

SEQ ID NO: 97

```
atgtcctcca actccgattt ggtcagaaga ttggaatctg ttttgggtgt ttctttcggt   60
ggttctgtta ctgattccgt tgttgttatt gctaccacct ctattgcttt ggttatcggt  120
gttttggttt tgttgtggag aagatcctct gacagatcta gagaagttaa gcaattggct  180
gttccaaagc cagttactat cgttgaagaa gaagatgaat tcgaagttgc ttctggtaag  240
accagagttt ctatttttcta cggtactcaa actggtactg ctgaaggttt tgctaaggct  300
ttggctgaag aaatcaaagc cagatacgaa aaagctgccg ttaaggttat tgatttggat  360
gattacacag ccgaagatga caaatacggt gaaaagttga agaaagaaac tatggccttc  420
ttcatgttgg ctacttatgg tgatggtgaa cctactgata tgctgctag attttacaag  480 tggttcaccg aaggtactga tagaggtgtt tggttggaac atttgagata cggtgtattc  540
ggtttgggta acagacaata cgaacacttc aacaagattg ccaaggttgt tgatgatttg  600
ttggttgaac aaggtgccaa gagattggtt actgttggtt tgggtgatga tgatcaatgc  660
atcgaagatg atttctccgc ttggaaagaa gccttgtggc cagaattgga tcaattattg  720
caagatgata ccaacaccgt ttctactcca tacactgctg ttattccaga atacagagtt  780
gttatccacg atccatctgt tacctcttat gaagatccat actctaacat ggctaacggt  840
aatgcctctt acgatattca tcatccatgt agagctaacg ttgccgtcca aaaagaattg  900
cataagccag aatctgacag aagttgcatc catttggaat tcgatatttt cgctactggt  960
ttgacttacg aaaccggtga tcatgttggt gtttacgctg ataattgtga tgatactgta 1020
gaagaagccg ctaagttgtt gggtcaacca ttggatttgt tgttctccat tcataccgat 1080
aacaacgacg gtacttcttt gggttcttct ttgccaccac catttccagg tccatgtact 1140
ttgagaactg ctttggctag atatgccgat ttgttgaatc caccaaaaaa ggctgctttg 1200
attgctttag ctgctcatgc tgatgaacca tctgaagctg aaagattgaa gttcttgtca 1260
tctccacaag gtaaggacga atattctaaa tgggttgtcg gttcccaaag atccttggtt 1320
gaagttatgg ctgaatttcc atctgctaaa ccaccattgg gtgtattttt tgctgctgtt 1380
gttcctagat tgcaacctag atattactcc atctcttcca gtccaagatt tgctccacat 1440
agagttcatg ttacttgcgc tttggtttat ggtccaactc caactggtag aattcacaga 1500
ggtgtatgtt cattctggat gaagaatgtt gtcccattgg aaaagtctca aaactgttct 1560
tgggccccaa ttttcatcag acaatctaat ttcaagttgc cagccgatca ttctgttcca 1620
atagttatgg ttggtccagg tactggttta gctccttttta gaggtttctt acaagaaaga 1680
ttggccttga agaagaaagg tgctcaagtt ggtcctgctt tgttgttttt tggttgcaga 1740
aacagacaaa tggacttcat ctacgaagtc gaattgaaca ctttgtcga caaggtgct 1800 ttgtccgaat tgatcgttgc ttttttcaaga gaaggtccat ccaaagaata cgtccaacat 1860
aagatggttg aaaaggcagc ttacatgtgg aacttgattt ctcaaggtgg ttacttctac 1920
```

TABLE 13-continued

Sequences disclosed herein.

gtttgtggtg atgctaaagg tatggctaga gatgttcata gaacattgca taccatcgtc 1980
caacaagaag aaaaggttga ttctaccaag gccgaatcca tcgttaagaa attgcaaatg 2040
gacggtagat acttgagaga tgtttggtga 2070

SEQ ID NO: 98

MSSNSDLVRR LESVLGVSFG GSVTDSVVVI ATTSIALVIG VLVLLWRRSS DRSREVKQLA 60

VPKPVTIVEE EDEFEVASGK TRVSIFYGTQ TGTAEGFAKA LAEEIKARYE KAAVKVIDLD 120

DYTAEDDKYG EKLKKETMAF FMLATYGDGE PTDNAARFYK WFTEGTDRGV WLEHLRYGVF 180

GLCNRQYEHF NKIAKVVDDL LVEQGAKRLV TVGLGDDDQC IEDDFSAWKE ALWPELDQLL 240

QDDTNTVSTP YTAVIPEYRV VIHDPSVTSY EDPYSNMANG NASYDIHHPC RANVAVQKEL 300

HKPESDRSCI HLEFDIFATG LTYETGDHVG VYADNCDDTV EEAAKLLGQP LDLLFSIHTD 360

NNDGTSLGSS LPPPFPGPCT LRTALARYAD LLNPPKKAAL IALAAHADEP SEAERLKFLS 420

SPQGKDEYSK WVVGSQRSLV EVMAEFPSAK PPLGVFFAAV VPRLQPRYYS ISSSPRFAPH 480

RVHVTCALVY GPTPTGRIHR GVCSFWMKNV VPLEKSQNCS WAPIFIRQSN FKLPADHSVP 540

IVMVGPGTGL APFRGFLQER LALKEEGAQV CPALLFFGCR NRQMDFIYEV ELNNFVEQGA 600

LSELIVAFSR EGPSKEYVQH KMVEKAAYMW NLISQGGYFY VCGDAKGMAR DVHRTLHTIV 660

QQEEKVDSTK AESIVKKLQM DGRYLRDVW 689

SEQ ID NO: 99 atggatgctg tgacgggttt gttaactgtc ccagcaaccg ctataactat tggtggaact 60
gctgtagcat tggcggtagc gctaatcttt tggtacctga atcctacac atcagctaga 120 agatcccaat caaatcatct tccaagagtg cctgaagtcc caggtgttcc attgttagga 100
aatctgttac aattgaagga gaaaaagcca tacatgactt ttacgagatg ggcagcgaca 240 tatgaccta tctatagtat caaaactggg gctacaagta tggttgtggt atcatctaat 300
gagatagcca aggaggcatt ggtgaccaga ttccaatcca tatctacaag gaacttatct 360
aaagccctga agtacttac agcagataag acaatggtcg caatgtcaga ttatgatgat 420
tatcataaaa cagttaagag acacatactg accgccgtct tgggtcctaa Igcacagaaa 480 aagcatagaa ttcacagaga tatcatgatg gataacatat ctactcaact tcatgaattc 540
gtgaaaaaca acccagaaca ggaagaggta gaccttagaa aaatctttca atctgagtta 600
ttcggcttag ctatgagaca agccttagga aaggatgttg aaagtttgta cgttgaagac 660
ctgaaaatca ctatgaatag agacgaaatc tttcaagtcc ttgttgttga tccaatgatg 720
ggagcaatcg atgttgattg gagagacttc tttccatacc taaagtgggt cccaaacaaa 780
aagttcgaaa atactattca aeaaatgtac atcagaagag aagctgttat gaaatcttta 840
atcaaagagc acaaaaagag aatagcgtca ggcgaaaagc taaatagtta tatcgattac 900
cttttatctg aagctcaaac tttaaccgat cagcaactat tgatgtcctt gtgggaacca 960
atcattgaat cttcagatac aacaatggtc acaacagaat gggcaatgta cgaattagct 1020 aaaaaccta aattgcaaga taggttgtac agagacatta agtccgtctg tggatctgaa 1080
aagataaccg aagagcatct atcacagctg ccttacatta cagctatttt ccacgaaaca 1140
ctgagaagac actcaccagt tcctatcatt cctctaagac atgtacatga agataccgtt 1200
ctaggcggct accatgttcc tgctggcaca gaacttgccg ttaacatcta cggttgcaac 1260
atggacaaaa acgtttggga aaatccagag gaatggaacc cagaaagatt catgaaagag 1320

TABLE 13-continued

Sequences disclosed herein.

```
aatgagacaa ttgattttca aaagacgatg gccttcggtg gtggtaagag agtttgtgct 1380
ggttccttgc aagccctttt aactgcatct attgggattg ggagaatggt tcaagagttc 1440
gaatggaaac tgaaggatat gactcaagag gaagtgaaca cgataggcct aactacacaa 1500
atgttaagac cattgagagc tattatcaaa cctaggatcc catcaagacc aagtcctagt 1560
accgaacaat ctgcaaaaaa agttagaaaa aaagcagaaa atgcacacaa tactccattg 1620
ctagttcttt atggttctaa tatgggaaca gcggaaggaa cggccaggga tctagctgac 1680
atagctatgt ccaagggatt tgccccgcaa gtagcaaccc tggattccca tgcaggtaac 1740
ctgccaagag aaggtgctgt tctaatagtt accgctagct acaatgggca ccctccagat 1800
aatgcgaagc agttcgtcga ttggttagat caagcatcag cagatgaagt taagggtgtt 1860
agatactctg tttttggatg tggagataag aattgggcca ccacatatca gaaggttccg 1920
gctttcatcg atgaaatgct tgctgcaaaa ggggctgaaa atatagcaga tcgtggtgag 1980
gccgacgcaa gcgacgattt tgagggtacc tatgaggagt ggagagagca catgtggtct 2040
gatgttgccg cgtattttaa tctagacata gaaaattctg aagacaataa aagtgcctta 2100
cttcttcaat tcgtcgatag tgctgcggac atgcccttag caaagatgca tggagccttt 2160
tcaacgaacg tagtagccag taaggaactt caacaaccag gtagtgccag aagtacacgt 2220
cacttggaaa ttgaattacc aaaagaggca tcctaccaag aaggtgacca tcttggtgta 2280
atcccaagaa actacgaagg tatagtcaat agggtaacgg caagatttgg gctggatgca 2340
agccaacaga taagactaga agcagaagaa gaaaaattgg cgcaccttcc actagcgaag 2400
acagtatccg ttgaagaatt attgcaatac gtggaattgc aggatcccgt cactagaacg 2460
caattgagag ctatggcagc aaagactgtt tgtccacctc acaaggttga acttgaagct 2520
ctacttgaaa aacaagcata caaagagcaa gtgctagcaa agagactaac catgttagaa 2580
ttgctggaaa aatacccggc atgcgaaatg gaattctccg aatttatcgc gttgttgcca 2640
agtattcgtc ccaggtatta ctcaatttca tcttcaccaa gggttgacga gaaacaggca 2700
tctattaccg tatctgtggt ctctggagaa gcttggagtg ttacggaga atacaagggt 2760 attgcttcca attatcttgc agaactgcag gaaggggata caattacctg ctttatttct 2820
actcctcaat cagaatttac tcttccgaag gatccagaaa ctccgttaat tatggtaggt 2880
ccgggaacag gagtcgcccc tttcagaggc tttgtgcaag caaggaagca actaaaagaa 2940
cagggacaaa gtctgggtga ggcacatcta tatttcggtt gcagatctcc gcatgaggat 3000
tacttatacc aagaagaact tgaaaacgcc aatcagaag gtattatcac cttgcatact 3060
gcattcagta gaatgccaaa ccagccgaaa acttacgtac agcatgttat ggagcaagat 3120
ggtaagaagt taattgagct tttggataag ggcgcccact tctacatttg cggcgacgga 3180
tcccaaatgg cgcctgccgt tgaagccacc ttgatgaaat catatgcaga tgttcatcaa 3240
gtttcagaag cggacgcccg tctttggtta caacaactag aggagaaagg aaggtatgca 3300
aaagatgttt ggtaa                                                  3315
```

SEQ ID NO: 100

```
MDAVTGLLTV PATAITIGGT AVALAVALIF WYLKSYTSAR RSQSNHLPRV PEVPGVPLLG  60

NLLQLKEKKP YMTFTRWAAT YGPIYSIKTG ATSMVVVSSN EIAKEALVTR FQSISTRNLS 120

KALKVLTADK TMVAMSDYDD YHKTVKRHIL TAVLGPNAQK KHRIHRDIMM DNISTQLHEF 180

VKNNPEQEEV DLRKIFQSEL FGLAMRQALG KDVESLYVED LKITMNRDEI FQVLVVDPMM 240
```

TABLE 13-continued

Sequences disclosed herein.

```
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRIPSRPSPS TEQSAKKVRK KAENAHNTPL  540
LVLYGSNMGT AEGTARDLAD IAMSKGFAPQ VATLDSHAGN LPREGAVLIV TASYNGHPPD  600
NAKQFVDWLD QASADEVKGV RYSVFGCGDK NWATTYQKVP AFIDEMLAAK GAENIADRCE  660
ADASDDFEGT YEEWREHMWS DVAAYFNLDI ENSEDNKSAL LLQFVDSAAD MPLAKMHGAF  720
STNVVASKEL QQPGSARSTR HLEIELPKEA SYQEGDHLGV IPRNYEGIVN RVTARFGLDA  780
SQQIRLEAEE EKLAHLPLAK TVSVEELLQY VELQDPVTRT QLRAMAAKTV CPPHKVELEA  840
LLEKQAYKEQ VLAKRLTMLE LLEKYPACEM EFSEFIALLP SIRPRYYSIS SSPRVDEKQA  900
SITVSVVSGE AWSGYGEYKG IASNYLAELQ EGDTITCFIS TPQSEFTLPK DPETPLIMVG  960
PGTGVAPFRG FVQARKQLKE QGQSLGEAHL YFGCRSPHED YLYQEELENA QSEGIITLHT 1020
AFSRMPNQPK TYVQHVMEQD GKKLIELLDK GAHFYICGDG SQMAPAVEAT LMKSYADVHQ 1080
VSEADARLWL QQLEEKGRYA KDVW                                       1104
```

SEQ ID NO: 101

```
atggatgctg tgacgggttt gttaactgtc ccagcaaccg ctataactat tggtggaact   60
gctgtagcat tggcggtagc gctaatcttt tggtacctga atcctacac atcagctaga   120
agatcccaat caaatcatct tccaagagtg cctgaagtcc caggtgttcc attgttagga  180
aatctgttac aattgaagga gaaaaagcca tacatgactt tacgagatg ggcagcgaca   240
tatggaccta tctatagtat caaaactggg gctacaagta tggttgtggt atcatctaat  300
gagatagcca aggaggcatt ggtgaccaga ttccaatcca tatctacaag gaacttatct   360
aaagccctga agtacttac agcagataag acaatggtcg caatgtcaga ttatgatgat   420
tatcataaaa cagttaagag acacatactg accgccgtct gggtcctaa tgcacagaaa    480
aagcatagaa ttcacagaga tatcatgatg gataacatat ctactcaact tcatgaattc   540
gtgaaaaaca acccagaaca ggaagaggta gaccttagaa aaatctttca atctgagtta   600
ttcggcttag ctatgagaca agccttagga aaggatgttg aaagtttgta cgttgaagac   660
ctgaaaatca ctatgaatag agacgaaatc tttcaagtcc ttgttgttga tccaatgatg   720
ggagcaatcg atgttgattg gagagacttc tttccatacc taaagtgggt cccaaacaaa  780
aagttcgaaa atactattca acaaatgtac atcagaagag aagctgttat gaaatcttta  840
atcaaagagc acaaaaagag aatagcgtca ggcgaaaagc taaatagtta tatcgattac   900
cttttatctg aagctcaaac tttaaccgat cagcaactat tgatgtcctt gtgggaacca   960
atcattgaat cttcagatac aacaatggtc acaacagaat gggcaatgta cgaattagct  1020
aaaaaccta aattgcaaga taggttgtac agagacatta gtccgtctg tggatctgaa   1080
aagataaccg aagagcatct atcacagctg ccttacatta cagctatttt ccacgaaaca  1140
ctgagaagac actcaccagt tcctatcatt cctctaagac atgtacatga gataccgtt   1200
ctaggcggct accatgttcc tgctggcaca gaacttgccg ttaacatcta cggttgcaac  1260
atggacaaaa acgtttggga aaatccagag aatggaacc cagaaagatt catgaaagag   1320
aatgagacaa ttgattttca aaagacgatg gccttcggtg gtggtaagag agtttgtgct  1380
```

TABLE 13-continued

Sequences disclosed herein.

```
ggttccttgc aagcccttt aactgcatct attgggattg ggagaatggt tcaagagttc 1440
gaatggaaac tgaaggatat gactcaagag gaagtgaaca cgataggcct aactacacaa 1500
atgttaagac cattgagagc tattatcaaa cctaggatcc catcaagacc aagtcctagt 1560
accgaacaat ctgcaaaaaa agttagaaaa aaagcagaaa atgcacacaa tactccattg 1620
ctagttcttt atggttctaa tatgggaaca gcggaaggaa cggccaggga tctagctgac 1680
atagctatgt ccaagggatt tgccccgcaa gtagcaaccc tggattccca tgcaggtaac 1740
ttgccaagag aaggtgctgt tctaatagtt accgctagct acaatgggca ccctccagat 1800
aatgcgaagc agttcgtcga ttggttagat caagcatcag cagatgaagt taagggtgtt 1860
agatactctg tttttggatg tggagataag aattgggcca ccacatatca gaaggttccg 1920
gctttcatcg atgaaatgct tgctgcaaaa ggggctgaaa atatagcaga tcgtggtgag 1980
gccgacgcaa gcgacgattt tgagggtacc tatgaggagt ggagagagca catgtggtct 2040
gatgttgccg cgtattttaa tctagacata gaaaattctg aagacaataa agtgcctta 2100
cttcttcaat tcgtcgatag tgctgcggac atgcccttag caaagatgca tggagccttt 2160
tcaacgaacg tagtagccag taaggaactt caacaaccag gtagtgccag aagtacacgt 2220
cacttggaaa ttgaattacc aaaagaggca tcctaccaag aaggtgacca tcttggtgta 2280
atcccaagaa actacgaagg tatagtcaat agggtaacgg caagatttgg gctggatgca 2340
agccaacaga taagactaga agcagaagaa gaaaaattgg cgcaccttcc actagcgaag 2400
acagtatccg ttgaagaatt attgcaatac gtggaattgc aggatcccgt cactagaacg 2460
caattgagag ctatggcagc aaagactgtt tgtccacctc acaaggttga acttgaagct 2520
ctacttgaaa acaagcata caaagagcaa gtgctagcaa agagactaac catgttagaa 2580
ttgctggaaa ataccccggc atgcgaaatg gaattctccg aatttatcgc gttgttgcca 2640
agtattcgtc ccaggtatta ctcaatttca tcttcaccaa gggttgacga gaaacaggca 2700
tctattaccg tatctgtggt ctctggagaa gcttggagtg gttacggaga atacaagggt 2760
attgcttcca attatcttgc agaactgcag gaaggggata caattacctg ctttatttct 2820
actcctcaat cagaatttac tcttccgaag gatccagaaa ctccgttaat tatggtaggt 2880
ccgggaacag gagtcgcccc tttcagaggc tttgtgcaag caaggaagca actaaaagaa 2940
cagggacaaa gtctgggtga ggcacatcta tatttcggtt gcagatctcc gcatgaggat 3000
tacttatacc aagaagaact tgaaaacgcc caatcagaag gtattatcac cttgcatact 3060
gcattcagta gaatgccaaa ccagccgaaa acttacgtac agcatgttat ggagcaagat 3120
ggtaagaagt taattgagct tttggataag gcgcccact tctacatttg cggcgacgga 3180
tcccaaatgg cgcctgccgt tgaagccacc ttgatgaaat catatgcaga tgttcatcaa 3240
gtttcagaag cggacgcccg tctttggtta caacaactag aggagaaagg aaggtatgca 3300
aaagatgttg cttaa                                                    3315
```

SEQ ID NO: 102

```
MDAVTGLLTV PATAITIGGT AVALAVALIF WYLKSYTSAR RSQSNHLPRV PEVPGVPLLG   60
NLLQLKEKKP YMTFTRWAAT YGP1YSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKHNPEQEEV DLRKIFQSEL FGLAMRQALG KDVESLYVED LKITMNRDEI FQVLVVDPMM  240
GAIDVDWRDF FPYLKWVPNK KFENTIQQHY IRREAVMKSL IKEHKKRIAS GEKLNSYIDY  300
```

TABLE 13-continued

Sequences disclosed herein.

```
LLSEAQTLTD QQLLMSLWEP IIESSDTTMV TTEWAMYELA KNPKLQDRLY RDIKSVCGSE  360

K1TEEHLSQL PYITAIFHET LRRHSPVPII PLRHVHEDIV LGGYHVPAGT ELAVNIYGCN  420

MDKNVWENPE EWNPERFMKE NEriDFQKTM AFGGGKRVCA GSLQALLTAS IGXGRMVQEF  480

EWKLKDMTQE EVNTIGLTTQ MLRPLRAIIK PRIPSRPSPS TEQSAKKVRK KAENAHNTPL  540

LVLYGSNHGT AEGTARDLAD IAMSKGFAPQ VATLDSHAGN LPREGAVLIV TASYNGHPPD  600

NAKQFVDWLD QASADEVKGV RYSVFGCGDK NWATTYQKVP AFIDEMLAAK GAENIADRGE  660

ADASDDFEGr YEEWREHMWS DVAAYFNLDI ENSEDNKSAL LLQFVDSAAD MPLAKMHGAF  720

STNVVASKEL QQPGSARSTR HLE1ELPKEA SYQEGDHLGV IPRNYEGIVN RVTARFGLDA  780

SQQ1RLEAEE EKLAHLPLAK TVSVEELLQY VELQDPVTRT QLRAMAAKTV CPPHKVELEA  840

LLEKQAYKEQ VLAKRLTMLE LLEKYPACEM EFSEFIALLP SIRPRYYSIS SSPRVDEKQA  900

SITVSVVSGE AWSGYGEYKG IASNYLAELQ EGDTITCFIS TPQSEFTLPK DPETPLIMVG  960

PGTGVAPFRG FVQARKQLKE QGQSLGEAHL YFGCRSPHED YLYQEELENA QSEGIITLHT 1020

AFSRMPNQPK TYVQHVMEQD GKKLIELLDK GAHFYICGDG SQMAPAVEAT LMKSYADVHQ 1080

VSEADARLWL QQLEEKGRYA KDVA                                        1104
```

SEQ ID NO: 103

```
atgccaagag tgcctgaagt cccaggtgtt ccattgttag gaaatctgtt acaattgaag   60 gagaaaagc catacatgac ttttacgaga tgggcagcga catatggacc tatctatagt  120
atcaaaactg gggctacaag tatggttgtg gtatcatcta atgagatagc caaggaggca  180
ttggtgacca gattccaatc catatctaca aggaacttat ctaaagccct gaaagtactt  240
acagcagata agacaatggt cgcaatgtca gattatgatg attatcataa aacagttaag  300
agacacatac tgaccgccgt cttgggtcct aatgcacaga aaaagcatag aattcacaga  360
gatatcatga tggataacat atctactcaa cttcatgaat tcgtgaaaaa caacccagaa  420
caggaagagg tagaccttag aaaaatcttt caatctgagt tattcggctt agctatgaga  480
caagccttag gaaggatgt tgaaagtttg tacgttgaag acctgaaaat cactatgaat  540
agagacgaaa tctttcaagt ccttgttgtt gatccaatga tgggagcaat cgatgttgat  600
tggagagact tctttccata cctaaagtgg gtcccaaaca aaagttcga aaatactatt  660 caacaaatgt acatcagaag agaagctgtt atgaaatctt taatcaaaga gcacaaaaag  720
agaatagcgt caggcgaaaa gctaaatagt tatatcgatt accttttatc tgaagctcaa  780 acttttaaccg atcagcaact attgatgtcc ttgtgggaac caatcattga atcttcagat  840
acaacaatgt tcacaacaga atgggcaatg tacgaattag ctaaaaaccc taaattgcaa  900
gataggttgt acagagacat taagtccgtc tgtggatctg aaaagataac cgaagagcat  960
ctatcacagc tgccttacat tacagctatt ttccacgaaa cactgagaag acactccacca 1020 gttcctatca ttcctctaag acatgtacat gaagataccg ttctaggcgg ctaccatgtt 1080
cctgctggca cagaacttgc cgttaacatc tacggttgca acatggacaa aaacgtttgg 1140
gaaaatccag aggaatggaa cccagaaaga ttcatgaaag agatgagac aattgatttt 1200 caaaagacga tggccttcgg tggtggtaag agagtttgtg ctggttcctt gcaagcctt 1260 ttaactgcat ctattgggat tgggagaatg gttcaagagt tcgaatggaa actgaaggat 1320
atgactcaag aggaagtgaa cacgataggc ctaactacac aaatgttaag accattgaga 1380
gctattatca aacctaggat cccatcaaga ccaagtccta gtaccgaaca atctgcaaaa 1440
```

TABLE 13-continued

Sequences disclosed herein.

```
aaagttagaa aaaaagcaga aaatgcacac aatactccat tgctagttct ttatggttct 1500
aatatgggaa cagcggaagg aacggccagg gatctagctg acatagctat gtccaaggga 1560
tttgccccgc aagtagcaac cctggattcc catgcaggta acttgccaag agaaggtgct 1620
gttctaatag ttaccgctag ctacaatggg caccctccag ataatgcgaa gcagttcgtc 1680
gattggttag atcaagcatc agcagatgaa gttaagggtg ttagatactc tgttttttgga 1740 tgtggagata agaattgggc caccacatat cagaaggttc cggctttcat cgatgaaatg 1800
cttgctgcaa aaggggctga aaatatagca gatcgtggtg aggccgacgc aagcgacgat 1860
tttgagggta cctatgagga gtggagagag cacatgtggt ctgatgttgc cgcgtatttt 1920
aatctagaca tagaaaattc tgaagacaat aaaagtgcct tacttcttca attcgtcgat 1980
agtgctgcgg acatgcccct agcaaagatg catggagcct tttcaacgaa cgtagtagcc 2040
agtaaggaac ttcaacaacc aggtagtgcc agaagtacac gtcacttgga aattgaatta 2100
ccaaaagagg catcctacca agaaggtgac catcttggtg taatcccaag aaactacgaa 2160
ggtatagtca atagggtaac ggcaagattt gggctggatg caagccaaca gataagacta 2220
gaagcagaag aagaaaaatt ggcgcacctt ccactagcga agacagtatc cgttgaagaa 2280
ttattgcaat acgtggaatt gcaggatccc gtcactagaa cgcaattgag agctatggca 2340
gcaaagactg tttgtccacc tcacaaggtt gaacttgaag ctctacttga aaacaagca 2400 tacaaagagc aagtgctagc aaagagacta accatgttag aattgctgga aaaatacccg 2460
gcatgcgaaa tggaattctc cgaatttatc gcgttgttgc caagtattcg tcccaggtat 2520
tactcaattt catcttcacc aagggttgac gagaaacagg catctattac cgtatctgtg 2580
gtctctggag aagcttggag tggttacgga gaatacaagg gtattgcttc caattatctt 2640
gcagaactgc aggaagggga tacaattacc tgctttattt ctactcctca atcagaattt 2700
actcttccga aggatccaga aactccgtta attatggtag gtccgggaac aggagtcgcc 2760
cctttcagag gctttgtgca agcaaggaag caactaaaag aacagggaca aagtctgggt 2820
gaggcacatc tatatttcgg ttgcagatct ccgcatgagg attacttata ccaagaagaa 2880
cttgaaaacg cccaatcaga aggtattatc accttgcata ctgcattcag tagaatgcca 2940
aaccagccga aaacttacgt acagcatgtt atggagcaag atggtaagaa gttaattgag 3000
cttttggata agggcgccca cttctacatt tgcggcgacg gatcccaaat ggcgcctgcc 3060
gttgaagcca ccttgatgaa atcatatgca gatgttcatc aagtttcaga gcggacgcc 3120 cgtctttggt tacaacaact agaggagaaa ggaaggtatg caaaagatgt ttggtaa    3177
```

SEQ ID NO: 104

```
MPRVPEVPGV PLLGNLLQLK EKKPYMTFTR WAATYCPIYS IKTGATSMVV VSSNEIAKEA  60

LVTRFQSIST RULSKALKVL TADKTMVAMS DYDDYHKTVK RHILTAVLGP NAQKKHRIHR 120

DIMMDNISTQ LHEFVKNNPE QEEVDLRKIF QSELFGLAMR QALGKDVESL YVEDLKITMN 180

RDEIFQVLVV DPMMGAIDVD WRDFFPYLKW VPNKKFENTI QQMYIRREAV MKSLIKEHKK 240

RIASGEKLNS YIDYLLSEAQ TLTDQQLLMS LWEPIIESSD TTMVTTEWAM YELAKNPKLQ 300

DRLYRDIKSV CGSEKITEEH LSQLPYITAI FHETLRRHSP VPIIPLRHVH EDTVLGGYHV 360

PAGTELAVNI YGCNMDKNVW ENPEEWNPER FMKENETIDF QKTMAFCGCK RVCAGSLQAL 420

LTASIGIGRM VQEFEWKLKD MTQEEVNTIC LTTQMLRPLR AIIKPRIPSR PSPSTEQSAK 480

KVRKKAENAH NTPLLVLYGS NMGTAEGTAR DLADIAMSKG FAPQVATLDS HAGNLPREGA 540
```

TABLE 13-continued

Sequences disclosed herein.

| | | | | | |
|---|---|---|---|---|---|
|VLIVTASYNG|HPPDNAKQFV|DWLDQASADE|VKGVRYSVFG|CGDKNWATTY|QKVPAFIDEM 600|
|LAAKGAENIA|DRGEADASDD|FEGTYEEWRE|HMWSDVAAYF|NLDIENSEDN|KSALLLQFVD 660|
|SAADMPLAKM|HGAFSTNVVA|SKELQQPGSA|RSTRHLEIEL|PKEASYQEGD|HLGVIPRNYE 720|
|GIVNRVTARF|GLDASQQIRL|EAEEEKLAHL|PLAKTVSVEE|LLQYVELQDP|VTRTQLRAMA 780|
|AKTVCPPHKV|ELEALLEKQA|YKEQVLAKRL|TMLELLEKYP|ACEMEFSEFI|ALLPSIRPRY 840|
|YSISSSPRVD|EKQASITVSV|VSGEAWSGYG|EYKGIASNYL|AELQEGDTIT|CFISTPQSEF 900|
|TLPKDPETPL|IMVGPGTGVA|PFRGFVQARK|QLKEQGQSLG|EAHLYFGCRS|PHEDYLYQEE 960|
|LENAQSEGII|TLHTAFSRMP|NQPKTYVQHV|MEQDGKKLIE|LLDKGAHFYI|CGDGSQMAPA 1020|
|VEATLMKSYA|DVHQVSEADA|RLWLQQLEEK|GRYAKDVW| |1058|

SEQ ID NO: 105

```
atgccaagag tgcctgaagt cccaggtgtt ccattgttag aaatctgtt acaattgaag   60
gagaaaaagc catacatgac ttttacgaga tgggcagcga catatggacc tatctatagt  120
atcaaaactg gggctacaag tatggttgtg gtatcatcta atgagatagc caaggaggca  180
ttggtgacca gattccaatc catatctaca aggaacttat ctaaagccct gaaagtactt  240
acagcagata agacaatggt cgcaatgtca gattatgatg attatcataa acagttaag   300
agacacatac tgaccgccgt cttgggtcct aatgcacaga aaaagcatag aattcacaga  360
gatatcatga tggataacat atctactcaa cttcatgaat cgtgaaaaa caacccagaa   420
caggaagagg tagaccttag aaaaatcttt caatctgagt tattcggctt agctatgaga  480
caagccttag gaaaggatgt tgaaagtttg tacgttgaag acctgaaaat cactatgaat  540
agagacgaaa tctttcaagt ccttgttgtt gatccaatga tgggagcaat cgatgttgat  600
tggagagact tctttccata cctaaagtgg gtcccaaaca aaagttcga aatactatt    660
caacaaatgt acatcagaag agaagctgtt atgaaatctt taatcaaaga gcacaaaaag  720
agaatagcgt caggcgaaaa gctaaatagt tatatcgatt accttttatc tgaagctcaa  780
actttaaccg atcagcaact attgatgtcc ttgtgggaac caatcattga atcttcagat  840
acaacaatgg tcacaacaga atgggcaatg tacgaattag ctaaaaaccc taaattgcaa  900
gataggttgt acagagacat taagtccgtc tgtggatctg aaaagataac cgaagagcat  960
ctatcacagc tgccttacat tacagctatt ttccacgaaa cactgaagaag cactcacca 1020
gttcctatca ttcctctaag acatgtacat gaagataccg ttctaggcgg ctaccatgtt 1080
cctgctggca cagaacttgc cgttaacatc tacggttgca acatggacaa aaacgtttgg 1140
gaaaatccag aggaatggaa cccagaaaga ttcatgaaag agaatgagac aattgatttt 1200
caaaagacga tggccttcgg tggtggtaag agagtttgtg ctggttcctt gcaagccctt 1260
ttaactgcat ctattgggat tgggagaatg gttcaagagt tcgaatggaa actgaaggat 1320
atgactcaag aggaagtgaa cacgataggc ctaactacac aaatgttaag accattgaga 1380
gctattatca aacctaggat cccatcaaga ccaagtccta gtaccgaaca atctgcaaaa 1440
aaagttagaa aaaaagcaga aaatgcacac aatactccat tgctagttct ttatggttct 1500
aatatgggaa cagcggaagg aacggccagg gatctagctg acatagctat gtccaaggga 1560
tttgccccgc aagtagcaac cctggattcc catgcaggta acttgccaag agaaggtgct 1620
gttctaatag ttaccgctag ctacaatggg caccctccag ataatgcgaa gcagttcgtc 1680
gattggttag atcaagcatc agcagatgaa gttaagggtg ttagatactc tgtttttgga 1740
```

TABLE 13-continued

Sequences disclosed herein.

```
tgtggagata agaattgggc caccacatat cagaaggttc cggctttcat cgatgaaatg 1800
cttgctgcaa aaggggctga aaatatagca gatcgtggtg aggccgacgc aagcgacgat 1860
tttgagggta cctatgagga gtggagagag cacatgtggt ctgatgttgc cgcgtatttt 1920
aatctagaca tagaaaattc tgaagacaat aaaagtgcct tacttcttca attcgtcgat 1980
agtgctgcgg acatgccctt agcaaagatg catggagcct tttcaacgaa cgtagtagcc 2040
agtaaggaac ttcaacaacc aggtagtgcc agaagtacac gtcacttgga aattgaatta 2100
ccaaaagagg catcctacca agaaggtgac catcttggtg taatcccaag aaactacgaa 2160
ggtatagtca atagggtaac ggcaagattt gggctggatg caagccaaca gataagacta 2220
gaagcagaag aagaaaaatt ggcgcacctt ccactagcga agacagtatc cgttgaagaa 2280
ctattgcaat acgtggaatt gcaggatccc gtcactagaa cgcaattgag agctatggca 2340
gcaaagactg tttgtccacc tcacaaggtt gaacttgaag ctctacttga aaacaagca 2400
tacaaagagc aagtgctagc aaagagacta accatgttag aattgctgga aaaatacccg 2460
gcatgcgaaa tggaattctc cgaatttatc gcgttgttgc caagtattcg tcccaggtat 2520
tactcaattt catcttcacc aagggttgac gagaaacagg catctattac cgtatctgtg 2580
gtctctggag aagcttggag tggttacgga gaatacaagg gtattgcttc caattatctt 2640
gcagaactgc aggaagggga tacaattacc tgctttattt ctactcctca atcagaattt 2700
actcttccga aggatccaga aactccgtta attatggtag gtccgggaac aggagtcgcc 2760
cctttcagag gctttgtgca agcaaggaag caactaaaag aacagggaca aagtctgggt 2820
gaggcacatc tatatttcgg ttgcagatct ccgcatgagg attacttata ccaagaagaa 2880
cttgaaaacg cccaatcaga aggtattatc accttgcata ctgcattcag tagaatgcca 2940
aaccagccga aaacttacgt acagcatgtt atggagcaag atggtaagaa gttaattgag 3000
cttttggata agggcgccca cttctacatt tgcggcgacg gatcccaaat ggcgcctgcc 3060
gttgaagcca ccttgatgaa atcatatgca gatgttcatc aagtttcaga agcggacgcc 3120
cgtctttggt tacaacaact agaggagaaa ggaaggtatg caaagatgt tgcttaa   3177
```

SEQ ID NO: 106

```
MPRVPEVPGV PLLGNLLQLK EKKPYMTFTR WAATYGPIYS IKTGATSMVV VSSNEIAKEA  60
LVTRFQSIST RWLSKALKVL TADKIMVAMS DYDDYHKTVK RHILTAVLGP NAQKKHRIHR 120
DIMMDNISTQ LHEFVKNNPE QEEVDLRKIF QSELFGLAMR QALGKDVESL YVEDLKITMN 180
RDEIFQVLVV DPMMGAIDVD WRDFFPYLKW VPNKKFENTI QQMYIRREAV MKSLIKEHKK 240
RiASCEKLNS YIDYLLSEAQ TLTDQQLLHS LWEPIIESSD TTMVTTEWAM YELAKNPKLQ 300
DRLYRDIKSV CGSEKITEEH LSQLPYITAI FHETLRRHSP VPIIPLRHVH EDTVLGGYHV 360
PAGTELAVNI YGCNMDKNVW ENPEEWNPER FMKENEPIDF QKTMAFGGGK RVCAGSLQAL 420
LTASIGIGRM VQEFEWKLKD MTQEEVNTIG LTTQMLRPLR AIIKPRIPSR PSPSTEQSAK 480
KVRKKAENAH NTPLLVLYGS NMGTAEGTAR DLADIAMSKG FAPQVATLDS HAGNLPREGA 540
VLIVTASYNG HPPDNAKQFV DWLDQASADE VKGVRYSVFG CGDKNWATTY QKVPAFIDEM 600
LAAKGAENIA DRGEADASDD FEGTYEEWRE HMWSDVAAYF NLDIENSEDN KSALLLQFVD 660
SAADMPLAKM HGAFSTNVVA SKELQQPGSA RSTRHLEIEL PKEASYQEGD HLGVIPRNYE 720
GIVNRVTARF GLDASQQIRL EAEEEKLAHL PLAKTVSVEE LLQYVELQDP VTRTQLRAMA 780
AKTVCPPHKV ELEALLEKQA YKEQVLAKRL TMLELLEKYP ACEMEFSEFI ALLPSIRPRY 840
```

TABLE 13-continued

Sequences disclosed herein.

| | | | | | |
|---|---|---|---|---|---|
| YSISSSPRVD | EKQASITVSV | VSGEAWSGYG | EYKGIASNYL | AELQEGDTIT | CFISTPQSEF 900 |
| TLPKDPETPL | IMVGPGTGVA | PFRGFVQARK | QLKEQGQSLG | EAHLYFGCRS | PHEDYLYQEE 960 |
| LENAQSEGII | TLHTAFSRMP | NQPKTYVQHV | MEQDGKKLIE | LLDKCAHFYI | CCDGSQMAPA 1020 |
| VEATLMKSYA | DVHQVSEADA | RLWLQQLEEK | GRYAKDVA | | 1058 |

SEQ ID NO: 107

| | | | | | |
|---|---|---|---|---|---|
| atggctacct | tgttggaaca | ttttcaagct | atgccattcg | ctattccaat | tgctttggct   60 |
| gctttgtctt | ggttgttttt | gttctacatc | aaggtttctt | tcttctccaa | caaatccgct  120 |
| caagctaaat | tgccaccagt | tccagttgtt | ccaggtttgc | cagttattgg | taatttgttg  180 |
| caattgaaag | aaaagaagcc | ataccaaacc | ttcactagat | gggctgaaga | atatggtcca  240 |
| atctactcta | ttagaactgg | tgcttctact | atggttgtct | gaacactac | tcaagttgcc  300 |
| aaagaagcta | tggttaccag | atacttgtct | atctctacca | gaaagttgtc | caacgccttg  360 |
| aaaattttga | ccgctgataa | gtgcatggtt | gccatttctg | attacaacga | tttccacaag  420 |
| atgatcaaga | gatatatctt | gtctaacgtt | ttgggtccat | ctgcccaaaa | agacataga  480 |
| tctaacagag | ataccttgag | agccaacgtt | tgttctagat | gcattccca | agttaagaac  540 |
| tctccaagaa | aagctgtcaa | ctttagaaga | gttttcgaat | gggaattatt | cggtatcgct  600 |
| ttgaaacaag | ccttcggtaa | ggatattgaa | agccaatct | acgtcgaaga | attgggtact  660 |
| actttgtcca | gagatgaaat | cttcaaggtt | ttggtcttgg | acattatgga | aggtgccatt  720 |
| gaagttgatt | ggagagattt | ttcccatac | ttgcgttgga | ttccaaacac | cagaatggaa  780 |
| actaagatcc | aaagattata | ctttagaaga | aaggccgtta | tgaccgcctt | gattaacgaa  840 |
| caaaagaaaa | gaattgcctc | cggtgaagaa | atcaactgct | catcgattt | cttgttgaaa  900 |
| gaaggtaaga | ccttgaccat | ggaccaaatc | tctatgttgt | tgtgggaaac | cgttattgaa  960 |
| actgctgata | ccacaatggt | tactactgaa | tgggctatgt | acgaagttgc | taaggattct 1020 |
| aaaagacaag | acagattata | ccaagaaatc | caaaaggtct | gcggttctga | aatggttaca 1080 |
| gaagaatact | tgtcccaatt | gccatacttg | aatgctgttt | tccacgaaac | tttgagaaaa 1140 |
| cattctccag | ctgctttggt | tccattgaga | tatgctcatg | aagatactca | attgggtggt 1200 |
| tattacattc | cagccggtac | tgaaattgcc | attaacatct | acggttgcaa | catggacaaa 1260 |
| caccaatggg | aatctccaga | agaatggaag | ccagaaagat | ttttggatcc | taagtttgac 1320 |
| ccaatggact | tgtacaaaac | tatggcttt | ggtgctggta | aaagagtttg | cgctggttct 1380 |
| ttacaagcta | tgttgattgc | ttgtccaacc | atcggtagat | ggttcaaga | atttgaatgg 1440 |
| aagttgagag | atggtgaaga | agaaaacgtt | gatactgttg | gtttgaccac | ccataagaga 1500 |
| tatccaatgc | atgctatttt | gaagccaaga | tctccatcaa | gaccaagtcc | tagtaccgaa 1560 |
| caatctgcaa | aaaagttag | aaaaaaagca | gaaaatgcac | acaatactcc | attgctagtt 1620 |
| ctttatggtt | ctaatatggg | aacagcggaa | ggaacggcca | gggatctagc | tgacatagct 1680 |
| atgtccaagg | gatttgcccc | gcaagtagca | accctggatt | cccaugcagg | taacttgcca 1740 |
| agagaaggtg | ctgttctaat | agttaccgct | agctacaatg | gcaccctcc | agataatgcg 1800 |
| aagcagttcg | tcgattggtt | agatcaagca | tcagcagatg | aagttaaggg | tgttagatac 1860 |
| tctgttttg | gatgtggaga | taagaattgg | gccaccacat | atcagaaggt | tccggctttc 1920 |
| atcgatgaaa | tgcttgctgc | aaaagggct | gaaaatatag | cagatcgtgg | tgaggccgac 1980 |
| gcaagcgacg | attttgaggg | tacctatgag | gagtggagag | agcacatgtg | gtctgatgtt 2040 |

TABLE 13-continued

Sequences disclosed herein.

```
gccgcgtatt ttaatctaga catagaaaat tctgaagaca ataaaagtgc cttacttctt 2100
caattcgtcg atagtgctgc ggacatgccc ttagcaaaga tgcatggagc cttttcaacg 2160
aacgtagtag ccagtaagga acttcaacaa ccaggtagtg ccagaagtac acgtcacttg 2220
gaaattgaat taccaaaaga ggcatcctac caagaaggtg accatcttgg tgtaatccca 2280
agaaactacg aaggtatagt caatagggta acggcaagat ttgggctgga tgcaagccaa 2340
cagataagac tagaagcaga agaagaaaaa ttggcgcacc ttccactagc gaagacagta 2400
tccgttgaag aattattgca atacgtgaaa ttgcaggatc ccgtcactag aacgcaattg 2460
agagctatgg cagcaaagac tgtttgtcca cctcacaagg ttgaacttga agctctactt 2520
gaaaaacaag catacaaaga gcaagtgcta gcaaagagac taaccatgtt agaattgctg 2580
gaaaaatacc cggcatgcga aatggaattc tccgaattta tcgcgttgtt gccaagtatt 2640
cgtcccaggt attactcaat ttcatcttca ccaagggttg acgagaaaca ggcatctatt 2700
accgtatctg tggtctctgg agaagcttgg agtggttacg gagaatacaa gggtattgct 2760
tccaattatc ttgcagaact gcaggaaggg gatacaatta cctgctttat ttctactcct 2820
caatcagaat ttactcttcc gaaggatcca gaaactccgt taattatggt aggtccggga 2880
acaggagtcg cccctttcag aggctttgtg caagcaagga agcaactaaa agaacaggga 2940
caaagtctgg gtgaggcaca tctatatttc ggttgcagat ctccgcatga ggattactta 3000
taccaagaag aacttgaaaa cgcccaatca gaaggtatta tcaccttgca tactgcattc 3060
agtagaatgc caaaccagcc gaaaacttac gtacagcatg ttatggagca agatggtaag 3120
aagttaattg agcttttgga taagggcgcc cacttctaca tttgcggcga cggatcccaa 3180
atggcgcctg ccgttgaagc caccttgatg aaatcatatg cagatgttca tcaagtttca 3240
gaagcggacg cccgtctttg gttacaacaa ctagaggaga aaggaaggta tgcaaaagat 3300
gtttggtaa                                                        3309
```

SEQ ID NO: 108

```
MATLLEHFQA MPFAIPIALA ALSWLFLFYI KVSFFSNKSA QAKLPPVPVV PGLPVIGNLL  60

QLKEKKPYQT FTRWAEEYGP IYSIRTGAST MVVLNTTQVA KEAMVTRYLS ISTRKLSNAL 120

KILTADKCMV AISDYNDFHK MIKRYILSNV LGPSAQKRHR SNRDTLRANV CSRLHSQVKN 180

SPREAVNFRR VFEWELFGIA LKQAFGKDIE KPIYVEELGT TLSRDE1FKV LVLDIMEGAI 240

EVDWRDFFPY LRWIPNTRME TKIQRLYFRR KAVMTALINE QKKRIASGEE INCYIDFLLK 300

ECKTLTMDQI SMLLWETVIE TADTTMVTTE WAMYEVAKDS KRQDRLYQEI QKVCGSEMVT 360

EEYLSQLPYL NAVFHETLRK HSPAALVPLR YAHEDTQLCG YYIPACTEIA INIYGCNMDK 420

HQWESPEEWK PERFLDPKFD PMDLYKTMAF GAGKRVCAGS LQAMLIACPT IGRLVQEFEW 480

KLRDGEEENV DTVGLTTHKR YPMHAILKPR SPSRPSPSTE QSAKKVRKKA ENAHNTPLLV 540

LYGSNMGTAE GTARDLADIA MSKGFAPQVA TLDSHAGNLP REGAVLIVTA SYNGHPPDNA 600

KQFVDWLDQA SADEVKGVRY SVFGCGDKNW ATTYQKVPAF IDEMLAAKGA ENIADRGEAD 660

ASDDFEGTYE EWREHMWSDV AAYFNLDIEN SEDNKSALLL QFVDSAADMP LAKMHGAFST 720

NVVASKELQQ PGSARSTRHL EIELPKEASY QECDHLCVIP RNYEGIVNRV TARFGLDASQ 780

QIRLEAEEEK LAHLPLAKTV SVEELLQYVE LQDPVTRTQL RAMAAKTVCP PHKVELEALL 840

EKQAYKEQVL AKRLTMLELL EKYPACEMEF SEFIALLPSI RPRYYSISSS PRVDEKQASI 900

TVSVVSGEAW SGYGEYKGIA SNYLAELQEG DTITCFISTP QSEFTLPKDP ETPLIMVGPG 960
```

TABLE 13-continued

Sequences disclosed herein.

```
TGVAPFRGFV QARKQLKEQG QSLGEAHLYF GCRSPHEDYL YQEELENAQS EGIITLHTAF 1020
SRMPNQPKTY VQHVMEQDGK KLIELLDKGA HFYICGDGSQ MAPAVEATLM KSYADVHQVS 1080
EADARLWLQQ LEEKGRYAKD VW                                         1102
```

SEQ ID NO: 109

```
atggctacct tgttggaaca ttttcaagct atgccattcg ctattccaat tgctttggct   60
gctttgtctt ggttgttttt gttctacatc aaggtttctt tcttctccaa caaatccgct  120
caagctaaat tgccaccagt tccagttgtt ccaggtttgc cagttattgg taatttgttg  180
caattgaaag aaaagaagcc ataccaaacc ttcactagat gggctgaaga atatggtcca  240
atctactcta ttagaactgg tgcttctact atggttgtct gaacactac tcaagttgcc  300
aaagaagcta tggttaccag atacttgtct atctctacca gaaagttgtc caacgccttg  360
aaaattttga ccgctgataa gtgcatggtt gccatttctg attacaacga tttccacaag  420
atgatcaaga gatatatctt gtctaacgtt ttgggtccat ctgcccaaaa aagacataga  480
tctaacagag ataccttgag agccaacgtt tgttctagat gcattccca agttaagaac  540
tctccaagag aagctgtcaa ctttagaaga gttttcgaat gggaattatt cggtatcgct  600
ttgaaacaag ccttcggtaa ggatattgaa aagccaatct acgtcgaaga attgggtact  660
actttgtcca gagatgaaat cttcaaggtt ttggtcttgg acattatgga aggtgccatt  720
gaagttgatt ggagagattt tttcccatac ttgcgttgga ttccaaacac cagaatggaa  780
actaagatcc aaagattata ctttagaaga aaggccgtta tgaccgcctt gattaacgaa  840
caaaagaaaa gaattgcctc cggtgaagaa atcaactgct acatcgattt cttgttgaaa  900
gaaggtaaga ccttgaccat ggaccaaatc tctatgttgt tgtgggaaac cgttattgaa  960
actgctgata ccacaatggt tactactgaa tgggctatgt acgaagttgc taaggattct 1020
aaaagacaag acagattata ccaagaaatc caaaaggtct gcggttctga atggttaca 1080
gaagaatact tgtcccaatt gccatacttg aatgctgttt ccacgaaac tttgagaaaa 1140
cattctccag ctgctttggt tccattgaga tatgctcatg aagatactca attgggtggt 1200
tattacattc cagccggtac tgaaattgcc attaacatct acggttgcau catggacaaa 1260
caccaatggg aatctccaga agaatggaag ccagaaagat ttttggatcc taagtttgac 1320
ccaatggact tgtacaaaac tatggctttt ggtgctggta aaagagtttg cgctggttct 1380
ttacaagcta tgttgattgc ttgtccaacc atcggtagat tggttcaaga atttgaatgg 1440
aagttgagag atggtgaaga agaaaacgtt gatactgttg gtttgaccac ccataagaga 1500
tatccaatgc atgctatttt gaagccaaga tctccatcaa gaccaagtcc tagtaccgaa 1560
caatctgcaa aaaagttag aaaaaaagca gaaaatgcac acaatactcc attgctagtt 1620
ctttatggtt ctaatatggg aacagcggaa ggaacggcca gggatctagc tgacatagct 1680
atgtccaagg gatttgcccc gcaagtagca accctggatt cccatgcagg taacttgcca 1740
agagaaggtg ctgttctaat agttaccgct agctacaatg gcaccctcc agataatgcg 1800
aagcagttcg tcgattggtt agatcaagca tcagcagatg aagttaaggg tgttagatac 1860
tctgtttttg gatgtggaga taagaattgg gccaccacat atcagaaggt tccggctttc 1920
atcgatgaaa tgcttgctgc aaaaggggct gaaaatatag cagatcgtgg tgaggccgac 1980
gcaagcgacg atttgaggg tacctatgag gagtggagag agcacatgtg gtctgatgtt 2040
gccgcgtatt ttaatctaga catagaaaat tctgaagaca taaaagtgc cttacttctt 2100
```

TABLE 13-continued

Sequences disclosed herein.

```
caattcgtcg atagtgctgc ggacatgccc ttagcaaaga tgcatggagc ctttcaacg 2160 aacgtagtag ccagtaagga acttcaacaa ccaggtagtg ccagaagtac acgtcacttg 2220
gaaattgaat taccaaaaga ggcatcctac caagaaggtg accatcttgg tgtaatccca 2280
agaaactacg aaggtatagt caatagggta acggcaagat ttgggctgga tgcaagccaa 2340
cagataagac tagaagcaga agaagaaaaa ttggcgcacc ttccactagc gaagacagta 2400
tccgttgaag aattattgca atacgtggaa ttgcaggatc ccgtcactag aacgcaattg 2460
agagctatgg cagcaaagac tgtttgtcca cctcacaagg ttgaacttga agctctactt 2520
gaaaaacaag catacaaaga gcaagtgcta gcaaagagac taaccatgtt agaattgctg 2580
gaaaaatacc cggcatgcga aatggaattc tccgaattta tcgcgttgtt gccaagtatt 2640
cgtcccaggt attactcaat ttcatcttca ccaagggttg acgagaaaca ggcatctatt 2700
accgtatctg tggtctctgg agaagcttgg agtggttacg gagaatacaa gggtattgct 2760
tccaattatc ttgcagaact gcaggaaggg gatacaatta cctgctttat ttctactcct 2820
caatcagaat ttactcttcc gaaggatcca gaaactccgt taattatggt aggtccggga 2880
acaggagtcg ccccttttcag aggctttgtg caagcaagga agcaactaaa agaacaggga 2940
caaagtctgg gtgaggcaca tctatatttc ggttgcagat ctccgcatga ggattactta 3000
taccaagaag aacttgaaaa cgcccaatca gaaggtatta tcaccttgca tactgcattc 3060
agtagaatgc caaaccagcc gaaaacttac gtacagcatg ttatggagca agatggtaag 3120
aagttaattg agcttttgga taagggcgcc cacttctaca tttgcggcga cggatcccaa 3180
atggcgcctg ccgttgaagc caccttgatg aaatcatatg cagatgttca tcaagtttca 3240
gaagcggacg cccgtctttg gttacaacaa ctagaggaga aggaaggta tgcaaaagat 3300 gttgcttaa                                                       3309
```

SEQ ID NO: 110

```
MATLLEHFQA MPFAIPIALA ALSWLFLFYI KVSFFSNKSA QAKLPPVPVV PGLPVIGNLL    60

QLKEKKPYQT FTRWAEEYGP IYSIRTGAST MVVLNTTQVA KEAMVTRYLS ISTRKLSNAL   120

KILTADKCMV AISDYNDFHK MIKRYILSNV LGPSAQKRHR SNRDTLRANV CSRLHSQVKN   180

SPREAVNFRR VFEWELFGIA LKQAFGKDIE KPIYVEELGT TLSRDEIFKV LVLDIMEGAI   240

EVDWRDFFPY LRWIPNTRME TKIQRLYFRR KAVMTALINE QKKRIASGEE INCYIDFLLK   300

EGKPLrMDQI SMLLWETVIE TADTTMVTrE WAMYEVAKDS KRQDRLYQEI QKVCGSEMVT   360

EEYLSQLPYL NAVFHETLRK HSPAALVPLR YAHEDTQLGG YYIPAGTEIA INIYGCNMDK   420

HQWESPEEWK PERFLDPKFD PMDLYKTMAF GAGKRVCAGS LQAMLIACPT IGRLVQEFEW   480

KLRDGEEENV DTVGLTTHKR YPMHAILKPR SPSRPSPSPE QSAKKVRKKA ENAHNTPLLV   540

LYGSNMGTAE GTARDLADIA MSKGFAPQVA TLDSHAGNLP REGAVLIVTA SYNGHPPDNA   600

KQFVDWLDQA SADEVKGVRY SVFGCGDKNW ATTYQKVPAF IDEMLAAKGA ENIADRGEAD   660

ASDDFEGPYE EWREHMWSDV AAYFNLDIEM SEDNKSALLL QFVDSAADMP LAKMHGAFST   720

NVVASKELQQ PGSARSTRHL EIELPKEASY QEGDHLGVIP RNYEGIVNRV TARFGLDASQ   780

QIRLEAEEEK LAHLPLAKTV SVEELQYVE LQDPVTRTQL RAMAAKTVCP PHKVELEALL   840

EKQAYKEQVL AKRLTMLELL EKYPACEMEF SEFIALLPSI RPRYYSISSS PRVDEKQASI   900

TVSVVSGEAW SGYGEYKGIA SNYLAELQEG DTITCFISTP QSEFTLPKDP ETPLIMVGPG   960

TGVAPFRGFV QARKQLKEQG QSLGEAHLYF GCRSPHEDYL YQEELENAQS EGIITLHTAF  1020
```

TABLE 13-continued

Sequences disclosed herein.

SRMPNQPKTY VQHVMEQDGK KLIELLDKGA HFYICCDCSQ MAPAVEATLM KSYADVHQVS 1080

EADARLWLQQ LEEKGRYAKD VA 1102

SEQ ID NO: 111

| | | | | | |
|---|---|---|---|---|---|
| atggttccag | gtttgccagt | tattggtaat | ttgttgcaat | tgaaagaaaa | gaagccatac 60 |
| caaaccttca | ctagatgggc | tgaagaatat | ggtccaatct | actctattag | aactggtgct 120 |
| tctactatgg | ttgtcttgaa | cactactcaa | gttgccaaag | aagctatggt | taccagatac 180 |
| ttgtctatct | ctaccagaaa | gttgtccaac | gccttgaaaa | ttttgaccgc | tgataagtgc 240 |
| atggttgcca | tttctgatta | caacgatttc | cacaagatga | tcaagagata | tatcttgtct 300 |
| aacgttttgg | gtccatctgc | ccaaaaaaga | catagatcta | acagagatac | cttgagagcc 360 |
| aacgtttgtt | ctagattgca | ttcccaagtt | aagaactctc | aagagaagc | tgtcaacttt 420 |
| agaagagttt | tcgaatggga | attattcggt | atcgctttga | acaagcctt | cggtaaggat 480 |
| attgaaaagc | caatctacgt | cgaagaattg | gtactactt | tgtccagaga | tgaaatcttc 540 |
| aaggttttgg | tcttggacat | tatggaaggt | gccattgaag | ttgattggag | agatttttc 600 |
| ccatacttgc | gttggattcc | aaacaccaga | atggaaacta | agatccaaag | attatacttt 660 |
| agaagaaagg | ccgttatgac | cgccttgatt | aacgaacaaa | agaaaagaat | tgcctccggt 720 |
| gaagaaatca | actgctacat | cgatttcttg | ttgaaagaag | gtaagacctt | gaccatggac 780 |
| caaatctcta | tgttgttgtg | ggaaaccgtt | attgaaactg | ctgataccac | aatggttact 840 |
| actgaatggg | ctatgtacga | agttgctaag | gattctaaaa | gacaagacag | attataccaa 900 |
| gaaatccaaa | aggtctgcgg | ttctgaaatg | gttacagaag | aatacttgtc | ccaattgcca 960 |
| tacttgaatg | ctgttttcca | cgaaactttg | agaaaacatt | ctccagctgc | tttggttcca 1020 |
| ttgagatatg | ctcatgaaga | tactcaattg | ggtggttatt | acattccagc | cggtactgaa 1080 |
| attgccatta | acatctacgg | ttgcaacatg | gacaaacacc | aatgggaatc | tccagaagaa 1140 |
| tggaagccag | aaagattttt | ggatcctaag | tttgacccaa | tggacttgta | caaaactatg 1200 |
| gcttttggtg | ctggtaaaag | agtttgcgct | ggttctttac | aagctatgtt | gattgcttgt 1260 |
| ccaaccatcg | gtagattggt | tcaagaattt | gaatggaagt | tgagagatgg | tgaagaagaa 1320 |
| aacgttgata | ctgttggttt | gaccacccat | aagagatatc | caatgcatgc | tatttttgaag 1380 |
| ccaagatctc | catcaagacc | aagtcctagt | accgaacaat | ctgcaaaaaa | agttagaaaa 1440 |
| aaagcagaaa | atgcacacaa | tactccattg | ctagttcttt | atggttctaa | tatgggaaca 1500 |
| gcggaaggaa | cggccaggga | tctagctgac | atagctatgt | ccaagggatt | gccccgcaa 1560 |
| gtagcaaccc | tggattccca | tgcaggtaac | ttgccaagag | aaggtgctgt | tctaatagtt 1620 |
| accgctagct | acaatgggca | ccctccagat | aatgcgaagc | agttcgtcga | ttggttagat 1680 |
| caagcatcag | cagatgaagt | taagggtgtt | agatactctg | tttttggatg | tggagataag 1740 |
| aattgggcca | ccacatatca | gaaggttccg | gctttcatcg | atgaaatgct | tgctgcaaaa 1800 |
| ggggctgaaa | atatagcaga | tcgtggtgag | gccgacgcaa | gcgacgattt | tgagggtacc 1860 |
| tatgaggagt | ggagagagca | catgtggtct | gatgttgccg | cgtattttaa | tctagacata 1920 |
| gaaaattctg | aagacaataa | aagtgcctta | cttcttcaat | cgtcgatag | tgctgcggac 1980 |
| atgcccttag | caaagatgca | tggagccttt | tcaacgaacg | tagtagccag | taaggaactt 2040 |
| caacaaccag | gtagtgccag | aagtacacgt | cacttggaaa | ttgaattacc | aaaagaggca 2100 |
| tcctaccaag | aaggtgacca | tcttggtgta | atcccaagaa | actacgaagg | tatagtcaat 2160 |

TABLE 13-continued

Sequences disclosed herein.

| | | | | | |
|---|---|---|---|---|---|
| agggtaacgg | caagatttgg | gctggatgca | agccaacaga | taagactaga | agcagaagaa 2220 |
| gaaaaattgg | cgcaccttcc | actagcgaag | acagtatccg | ttgaagaatt | attgcaatac 2280 |
| gtggaattgc | aggatcccgt | cactagaacg | caattgagag | ctatggcagc | aaagactgtt 2340 |
| tgtccacctc | acaaggttga | acttgaagct | ctacttgaaa | aacaagcata | caaagagcaa 2400 |
| gtgctagcaa | agagactaac | catgttagaa | ttgctggaaa | atacccggc | atgcgaaatg 2460 |
| gaattctccg | aatttatcgc | gttgttgcca | agtattcgtc | ccaggtatta | ctcaatttca 2520 |
| tcttcaccaa | gggttgacga | gaaacaggca | tctattaccg | tatctgtggt | ctctggagaa 2580 |
| gcttggagtg | gttacggaga | atacaagggt | attgcttcca | attatcttgc | agaactgcag 2640 |
| gaagggata | caattacctg | ctttatttct | actcctcaat | cagaatttac | tcttccgaag 2700 |
| gatccagaaa | ctccgttaat | tatggtaggt | ccgggaacag | gagtcgcccc | tttcagaggc 2760 |
| tttgtgcaag | caaggaagca | actaaaagaa | cagggacaaa | gtctgggtga | ggcacatcta 2820 |
| tatttcggtt | gcagatctcc | gcatgaggat | tacttatacc | aagaagaact | tgaaaacgcc 2880 |
| caatcagaag | gtattatcac | cttgcatact | gcattcagta | gaatgccaaa | ccagccgaaa 2940 |
| acttacgtac | agcatgttat | ggagcaagat | ggtaagaagt | taattgagct | tttggataag 3000 |
| ggcgcccact | tctacatttg | cggcgacgga | tcccaaatgg | cgcctgccgt | tgaagccacc 3060 |
| ttgatgaaat | catatgcaga | tgttcatcaa | gtttcagaag | cggacgcccg | tctttggtta 3120 |
| caacaactag | aggagaaagg | aaggtatgca | aaagatgttg | cttaa | 3165 |

SEQ ID NO: 112

| | | | | |
|---|---|---|---|---|
| MVPGLPVIGN | LLQLKEKKPY | QTFTRWAEEY | GPIYSIRTGA | STMVVLNTTQ VAKEAMVTRY 60 |
| LSISTRKLSN | ALKILTADKC | MVAISDYNDF | HKMIKRYILS | NVLGPSAQKR HRSNRDTLRA 120 |
| NVCSRLHSQV | KNSPREAVNF | RRVFEWELFG | IALKQAFGKD | IEKPIYVEEL GTTLSRDEIF 180 |
| KVLVLDIMEG | AIEVDWRDFF | PYLRWIPNTR | METKIQRLYF | RRKAVMTALI NEQKKRIASG 240 |
| EEINCYIDFL | LKEGKTLTMD | QISMLLWETV | IETADTTMVT | TEWAMYEVAK DSKRQDRLYQ 300 |
| EIQKVCGSEM | VTEEYLSQLP | YLNAVFHETL | RKHSPAALVP | LRYAHEDTQL GGYYIPAGTE 360 |
| IAINIYGCNM | DKHQWESPEE | WKPERFLDPK | FDPMDLYKTM | AFGAGKRVCA GSLQAMLIAC 420 |
| PTIGRLVQEF | EWKLRDGEEE | NVDTVGLTTH | KRYPMHAILK | PRSPSRPSPS TEQSAKKVRK 480 |
| KAENAHNTPL | LVLYGSNMGT | AEGTARDLAD | IAMSKGFAPQ | VATLDSHAGN LPREGAVLIV 540 |
| TASYNGHPPD | NAKQFVDWLD | QASADEVKGV | RYSVFGCGDK | NWATTYQKVP AFIDEMLAAK 600 |
| GAENIADRGE | ADASDDFEGT | YEEWREHMWS | DVAAYFNLDI | ENSEDNKSAL LLQFVDSAAD 660 |
| MPLAKMHGAF | STNVVASKEL | QQPGSARSTR | HLEIELPKEA | SYQEGDHLGV IPRNYEGIVN 720 |
| RVTARFGLDA | SQQIRLEAEE | EKLAHLPLAK | TVSVEELLQY | VELQDPVTRT QLRAMAAKTV 780 |
| CPPHKVELEA | LLEKQAYKEQ | VLAKRLTMLE | LLEKYPACEM | EFSEFIALLP SIRPRYYSIS 840 |
| SSPRVDEKQA | SITVSVVSGE | AWSGYGEYKG | IASNYLAELQ | EGDTITCFIS TPQSEFTLPK 900 |
| DPETPLIMVG | PGTGVAPFRG | FVQARKQLKE | QGQSLGEAHL | YFGCRSPHED YLYQEELENA 960 |
| QSEGIITLHT | AFSRMPNQPK | TYVQHVMEQD | GKKLIELLDK | GAHFYICGDG SQMAPAVEAT 1020 |
| LMKSYADVHQ | VSEADARLWL | QQLEEKGRYA | KDVA | 1054 |

SEQ ID NO: 113

| | | | | | |
|---|---|---|---|---|---|
| atgaccagtt | tgtccaaaag | cttcatgcag | agtggacgaa | tctgcgcagc | atgtttctat 60 |
| ctgttattca | cactactttc | aattccaatc | tcgtttaaag | ttggtggttt | ggaatgcggg 120 |

TABLE 13-continued

Sequences disclosed herein.

```
ctttccttca cggtgacact gttcacttta tatttcataa ctacgactct taacgtgttg  180
gcaagacgac atggaggaag actatacatt ttttttacca actgtctgta ttactcacaa  240
cattttatca ttgcatcttt gctatacctg tttttgtctg gattttctaa tgatgagtta  300
ggaaacgttc tgaaaaataa atataatgag tcggagtcgt tcctggaagc tttgaaaaat  360
agcttgaatt ccaatcaaat taactacgtc ttatattatt actactatcg atttgttgta  420
caaccgtggc aattcgtgct taccaagtcc acaccttttt ttactctatc ggaaggtttt  480
ttcactattt tagccattca ggccgtcggg gaaactaata tggttatc aaatgacttg  540
aattcaaaca cgtggattat ttcctcattg ttaacctccg gaggtgtgat taccgcatcg  600
ctgtactatt tgtatcggat ttatgtcacc cccatatggc cgttatccat ccaaacggcg  660
tccttattag gacttgtttt gtctatggta tgtggactgg ggttgtatgg tattgtgagt  720
caaaaaggat ccgtcataga gagctctta ttttttgcgt atattgttcg ttgtatttat  780
gaaatttccc ccaaattagc tactaccgcg actgatgaaa tttaaattt gttcaaagac  840
gtctggcaga aacatcaaag aaatctgccc acagctgaca atcttttgtg ctactttcat  900
aatgtcatat tgaaaaatgc agaggtgtta tgggggtcct ttattcctag aggaagaaag  960
aaaaccggtg attttcatga taaactcatt agcattctat cattcgaaaa agtatccttg 1020
atatctaaac cattttggaa atttttcaag aatttcacct ttagtgttcc gctatccatt 1080
aatgaatttt gtcaagttac aattaagatg caagcgaat cagttccccc agctatagta 1140
atcaatttat gctttagagt tctgatgttt tactcggcaa agaggattat tccagcatta 1200
caaagaaaaa atgacaaaca gttgcgcaag agtcgcagga tcatgaaggg attgtattgg 1260
tacagtcctt gcatattaat tgctatgtat actcacctga ttttacaata ttcaggtgag 1320
ctaaagaaag acctgtgcat atggggttgc agtgaaaagt ggtttggcgt agatcaacca 1380
gaaattatag tagattcatg gggattttgg aactggtgca acattttctg tactattttg 1440
gtatacgcta cagaattaat aggttctggt agttga                            1476
```

SEQ ID NO: 114

```
MTSLSKSFMQ SGRICAACFY LLFTLLSIPI SFKVGGLECG LSFTVTLFTL YFITTTLNVL   60
ARRHGGRLYI FFTSCLYYSQ HFIIASLLYL FLSGFSNDEL GNVLKNKYNE SESFLEALKN  120
SLNSNQINYV LYYYYRFVV QPWQFVLTKS TPFFTLSEGF FTILAIQAVG ETNRWLSNDL  180
NSNTWIISSL LTSGGVITAS LYYLYRIYVT PIWPLSIQTA SLLGFVLSMV CGLGLYGIVS  240
QKGSVIESSL FFAYIVRCIY EPSPKLATTA TDEILNLFKD VWQKHQRNLP TADNLLCYFH  300
NVILKNAEVL WGSFIPRGRK KTGDFHDKLI SILSFEKVSL ISKPFWKFFK NFTFSVPLSI  360
NEFCQVTIKM ASESVSPAIV INLCFRVLMF YSATRIIPAL QRKNDKQLRK SRRIMKGLYW  420
YSPCILIAMY THLILQYSGE LKKDLCIWGC SEKWFGVDQP EIIVDSWGFW NWCNIFCTIL  480
VYATELIGSG S                                                      491
```

SEQ ID NO: 115

```
agatctttat gaagacatag ctgcagaaga aaaagcaaga gctacatatc aatggttaat   60
tgatatatca gatgatcccg atttaaacga cagcttacga ttttttacgag aaagagagat  120
tgttcactca cagcggttcc gcgaggccgt ggagatttta aaagatgaca gagacaggaa  180
gaaaatcttt taactagtaa aaaaacatcc cccttggcga atgcaaacga aaggagggat  240
gttttttgtt gtgactgcgt tgattatgcg ctagaactgc agtgacaaga aacaaccttt  300
```

TABLE 13-continued

Sequences disclosed herein.

```
aatttccctt caacatcttt ccaaactcgc gtataactgt attcacctcc aatagattca  360
ccggttgcca gtgccccatt taacgctact tttgtaacgg taacggcaag ttcttgaaac  420
agtttaactt cttgttccaa cacttccatg cccgctatat caagactttt tgaacgatga  480
acatttatat cttcttcttt tgacaaccat tgcccaaggt gattcacaaa aataagctca  540
tctgaaagta attcttctaa tagctctatg ttattagaaa gcatggctga gcgaagcatt  600
tcttcgtatt ctataactct tgcttgattc atttttaatc ctcctttacg ccttgtgtaa  660
ctcttttcta tttccacgtt gcttttcctt taaacttctt tcattaataa ttcgtgctaa  720
attatgttaa tagaggggat aagtggacta attttctgta agcactaaat attctgaaat  780
actctgttaa ttacctttaa atggtataaa attagaatga aagaaccttt tctttccact  840
tttctagtta tctttttact attaagatgc agttttttat acttgtaatt gtageggaat  900
gaacgttcat tccgttttg aaaagaggtg ataaagtgga atctactcca acaaaacaaa  960
aagcgatttt ttctgcttcg cttctgctgt ttgcagaaag agggtttgat gcaaccacga 1020
tgccaatgat tgcagagaat gccaaagtag gagcaggaac aatttatcgc tactttaaaa 1080
ataaagaaag ccttgtaaat gaattattcc aacagcacgt aaacgagttt ttacagtgca 1140
ttgaaagcgg tctggcaaac gagagagatg gataccgaga tgggtttcat catatctttg 1200
aaggtatggt gacatttact aaaaaccatc ctcgtgctct tggatttatt aaaactcata 1260
gccaaggaac ttttttaaca gaagagagcc gcttagcata tcaaaagctg gtggaatttg 1320
tttgtacgtt cttcagagaa ggacaaaagc aaggtgtgat tagaaatctt cctgaaaatg 1380
cgctaattgc tattttattt ggaagtttca tggaagtata tgaaatgatt gaaaatgact 1440
acttatcttt aactgatgaa cttcttaccg gtgtagaaga gagtctgtgg gcagcactta 1500
gcagacaatc atgaaactta acaagtgaaa gagggataac atgacaatta aagaaatgcc 1560
tcagccaaaa acgtttggag agcttaaaaa tttaccgtta ttaaacacag ataaaccggt 1620
tcaagctttg atgaaaattg cggatgaatt aggagaaatc tttaaattcg aggcgcctgg 1680
tcgtgtaacg cgctacttat caagtcagcg tctaattaaa gaagcatgcg atgaatcacg 1740
ctttgataaa aacttaagtc aagcgcttaa atttgtacgt gattttgcag gagacgggtt 1800
atttacaagc tggacgcatg aaaaaaattg gaaaaaagcg cataatatct tacttccaag 1860
cttcagtcag caggcaatga aaggctatca tgcgatgatg gtcgatatcg ccgtgcagct 1920
tgttcaaaag tgggagcgtc taaatgcaga tgagcatatt gaagtaccgg aagacatgac 1980
acgtttaacg cttgatacaa ttggtctttg cggctttaac tatcgcttta acagcttta  2040
ccgagatcag cctcatccat ttattacaag tatggtccgt gcactggatg aagcaatgaa 2100
caagctgcag cgagcaaatc cagacgaccc agcttatgat gaaaacaagc gccagtttca 2160
agaagatatc aaggtgatga acgacctagt agataaaatt attgcagatc gcaaagcaag 2220
cggtgaacaa agcgatgatt tattaacgca tatgctaaac ggaaaagatc cagaaacggg 2280
tgagccgctt gatgacgaga acattcgcta tcaaattatt acattcttaa ttgcgggaca 2340
cgaaacaaca agtggtcttt tatcatttgc gctgtatttc ttagtgaaaa atccacatgt 2400
attacaaaaa gcagcagaag aagcagcacg agttctagta gatcctgttc caagctacaa 2460
acaagtcaaa cagcttaaat atgtcggcat ggtcttaaac gaagcgctgc gcttatggcc 2520
aactgctcct gcgttttccc tatatgcaaa agaagatacg gtgcttggag gagaatatcc 2580
tttagaaaaa ggcgacgaac taatggttct gattcctcag cttcaccgtg ataaaacaat 2640
```

TABLE 13-continued

Sequences disclosed herein.

```
ttggggagac gatgtggaag agttccgtcc agagcgtttt gaaaatccaa gtgcgattcc 2700
gcagcatgcg tttaaaccgt ttggaaacgg tcagcgtgcg tgtatcggtc agcagttcgc 2760
tcttcatgaa gcaacgctgg tacttggtat gatgctaaaa cactttgact ttgaagatca 2820
tacaaactac gagctggata ttaaagaaac tttaacgtta aaacctgaag gctttgtggt 2880
aaaagcaaaa tcgaaaaaaa ttccgcttgg cggtattcct tcacctagca ctgaacagtc 2940
tgctaaaaaa gtacgcaaaa aggcagaaaa cgctcataat acgccgctgc ttgtgctata 3000
cggttcaaat atgggaacag ctgaaggaac ggcgcgtgat ttagcagata ttgcaatgag 3060
caaaggattt gcaccgcagg tcgcaacgct tgattcacac gccggaaatc ttccgcgcga 3120
aggagctgta ttaattgtaa cggcgtctta taacggtcat ccgcctgata acgcaaagca 3180
atttgtcgac tggttagacc aagcgtctgc tgatgaagta aaaggcgttc gctactccgt 3240
atttggatgc ggcgataaaa actgggctac tacgtatcaa aaagtgcctg cttttatcga 3300
tgaaacgctt gccgctaaag gggcagaaaa catcgctgac cgcggtgaag cagatgcaag 3360
cgacgacttt gaaggcacat atgaagaatg gcgtgaacat atgtggagtg acgtagcagc 3420
ctactttaac ctcgacattg aaaacagtga agataataaa tctactcttt cacttcaatt 3480
tgtcgacagc gccgcggata tgccgcttgc gaaaatgcac ggtgcgtttt caacgaacgt 3540
cgtagcaagc aaagaacttc aacagccagg cagtgcacga agcacgcgac atcttgaaat 3600
tgaacttcca aaagaagctt cttatcaaga aggagatcat ttaggtgtta ttcctcgcaa 3660
ctatgaagga atagtaaacc gtgtaacagc aaggttcggc ctagatgcat cacagcaaat 3720
ccgtctggaa gcagaagaag aaaaattagc tcatttgcca ctcgctaaaa cagtatccgt 3780
agaagagctt ctgcaatacg tggagcttca agatcctgtt acgcgcacgc agcttcgcgc 3840
aatggctgct aaaacggtct gcccgccgca taaagtagag cttgaagcct tgcttgaaaa 3900
gcaagcctac aaagaacaag tgctggcaaa acgtttaaca atgcttgaac tgcttgaaaa 3960
atacccggcg tgtgaaatga aattcagcga atttatcgcc cttctgccaa gcatacgccc 4020
gcgctattac tcgatttctt catcacctcg tgtcgatgaa aaacaagcaa gcatcacggt 4080
cagcgttgtc tcaggagaag cgtggagcgg atatggagaa tataaaggaa ttgcgtcgaa 4140
ctatcttgcc gagctgcaag aaggagatac gattacgtgc tttatttcca caccgcagtc 4200
agaatttacg ctgccaaaag accctgaaac gccgcttatc atggtcggac cgggaacagg 4260
cgtcgcgccg tttagaggct ttgtgcaggc gcgcaaacag ctaaaagaac aaggacagtc 4320
acttggagaa gcacatttat acttcggctg ccgttcacct catgaagact atctgtatca 4380
agaagagctt gaaacgcccc aaagcgaagg catcattacg cttcataccg ctttttctcg 4440
catgccaaat cagccgaaaa catacgttca gcacgtaatg gaacaagacg gcaagaaatt 4500
gattgaactt cttgatcaag gagcgcactt ctatatttgc ggagacggaa gccaaatggc 4560
acctgccgtt gaagcaacgc ttatgaaaag ctatgctgac gttcaccaag tgagtgaagc 4620
agacgctcgc ttatggctgc agcagctaga agaaaaaggc cgatacgcaa aagacgtgtg 4680
ggctgggtaa attaaaaaga ggctaggata aaagtagttt agttggttga aggaagatcc 4740
gaacgatgaa tcgttcggat ctttttattg gtagagtaaa cgtagatttc atctatttag 4800
tgacttgtag cggttgattg gagggcaagg tgaagactcc aatcaaccgc ggtgtcacat 4860
gcaagccata cgaaattcat ttctcccatt tattcgtctt ttgtccccac ttaattttta 4920
tagcgcctta acgtttcttc tgcgtgacag cagatct                         4957
```

TABLE 13-continued

Sequences disclosed herein.

SEQ ID NO: 116

MTIKEMPQPK TFGELKNLPL LNTDKPVQAL MKIADELGEI FKFEAPGRVT RYLSSQRLIK 60
EACDESRFDK NLSQALKFVR DFAGDGLFTS WTHEKNWKKA HNILLPSFSQ QAMKGYHAMM 120
VDIAVQLVQK WERLNADEHI EVPEDMTRLT LDTIGLCGFN YRFNSFYRDQ PHPFITSMVR 180
ALDEAMNKLQ RANPDDPAYD EMKRQFQEDI KVMWDLVDKI IADRKASGEQ SDDLLTHMLM 240
GKDPETGEPL DDENIRYQII TFLIAGHETT SGLLSFALYF LVKNPHVLQK AAEEAARVLV 300
DPVPSYKQVK QLKYVGMVLN EALRLWPTAP AFSLYAKEDT VLGGEYPLEK GDELMVLIPQ 360
LHRDKriWGD DVEEFRPERF ENPSAIPQHA FKPFGNGQRA CIGQQFALHE ATLVLGMMLK 420
HFDFEDHTNY ELDIKETLTL KPEGFVVKAK SKKIPLGGIP SPSTEQSAKK VRKKAENAHN 480
TPLLVLYGSN MGTAEGTARD LADIAMSKGF APQVATLDSH AGNLPREGAV LIVTASYNGH 540
PPDNAKQFVD WLDQASADEV KGVRYSVFGC GDKNWATTYQ KVPAFIDErL AAKGAENIAD 600
RGEADASDDF EGTYEEWREH MWSDVAAYFN LDIENSEDNK STLSLQFVDS AADMPLAKMH 660
GAFSTNVVAS KELQQPCSAR STRHLEIELP KEASYQEGDH LCVIPRNYEG IVNRVTARFG 720
LDASQQIRLE AEEEKLAHLP LAKTVSVEEL LQYVELQDPV TRTQLRAMAA KTVCPPHKVE 780
LEALLEKQAY KEQVLAKRLT MLELLEKYPA CEMKFSEFIA LLPSIRPRYY SISSSPRVDE 840
KQASITVSVV SGEAWSGYGE YKGIASNYLA ELQEGDTITC F1STPQSEFT LPKDPETPLI 900
MVGPGTGVAP FRGFVQARKQ LKEQGQSLGE AHLYFGCRSP HEDYLYQEEL ENAQSEGIIT 960
LHTAFSRMPN QPKTYVQHVM EQDGKKLIEL LDQGAHFYIC GDSQMAPAV EATLMKSYAD 1020
VHQVSEADAR LWLQQLEEKG RYAKDVWAG 1049

SEQ ID NO: 117 ccaagtccta gtaccgaaca atctgcaaaa aaagttagaa aaaaagcaga aaatgcacac 60
aatactccat tgctagttct ttatggttct aatatgggaa cagcggaagg aacggccagg 120
gatctagctg acatagctat gtccaaggga tttgccccgc aagtagcaac cctggattcc 180
catgcaggta acttgccaag agaaggtgct gttctaatag ttaccgctag ctacaatggg 240
caccctccag ataatgcgaa gcagttcgtc gattggttag atcaagcatc agcagatgaa 300
gttaagggtg ttagatactc tgtttttgga tgtggagata agaattgggc caccacatat 360
cagaaggttc cggctttcat cgatgaaatg cttgctgcaa aggggctgaa aaatatagca 420
gatcgtggtg aggccgacgc aagcgacgat tttgagggta cctatgagga gtggagagag 480
cacatgtggt ctgatgttgc cgcgtatttt aatctagaca tagaaaattc tgaagacaat 540
aaaagtgcct tacttcttca attcgtcgat agtgctgcgg acatgccctt agcaaagatg 600
catggagcct tttcaacgaa cgtagtagcc agtaaggaac ttcaacaacc aggtagtgcc 660
agaagtacac gtcacttgga aattgaatta ccaaaagagg catcctacca agaaggtgac 720
catcttggtg taatcccaag aaactacgaa ggtatagtca atagggtaac ggcaagattt 780
gggctggatg caagccaaca gataagacta gaagcagaag aagaaaaatt ggcgcacctt 840
ccactagcga agacagtatc cgttgaagaa ttattgcaat acgtggaatt gcaggatccc 900
gtcactagaa cgcaattgag agctatggca gcaaagactg tttgtccacc tcacaaggtt 960
gaacttgaug ctctacttga aaaacaagca tacaaagagc aagtgctagc aaagagacta 1020
accatgttag aattgctgga aaaatacccg catgcgaaa tggaattctc cgaatttatc 1080
gcgttgttgc caagtattcg tcccaggtat tactcaattt catcttcacc aagggttgac 1140

TABLE 13-continued

Sequences disclosed herein.

```
gagaaacagg catctattac cgtatctgtg gtctctggag aagcttggag tggttacgga 1200
gaatacaagg gtattgcttc caattatctt gcagaactgc aggaagggga tacaattacc 1260
tgctttattt ctactcctca atcagaattt actcttccga aggatccaga aactccgtta 1320
attatggtag gtccgggaac aggagtcgcc cctttcagag gctttgtgca agcaaggaag 1380
caactaaaag aacagggaca aagtctgggt gaggcacatc tatatttcgg ttgcagatct 1440
ccgcatgagg attacttata ccaagaagaa cttgaaaacg cccaatcaga aggtattatc 1500
accttgcata ctgcattcag tagaatgcca aaccagccga aaacttacgt acagcatgtt 1560
atggagcaag atggtaagaa gttaattgag cttttggata agggcgccca cttctacatt 1620
tgcggcgacg gatcccaaat ggcgcctgcc gttgaagcca ccttgatgaa atcatatgca 1680
gatgttcatc aagtttcaga agcggacgcc cgtctttggt tacaacaact agaggagaaa 1740
ggaaggtatg caaaagatgt ttggtaa                                  1767
```

SEQ ID NO: 118

```
PSPSTEQSAK KVRKKAENAH NTPLLVLYGS NMGTAECTAR DLADIAMSKC FAPQVATLDS  60

HAGNLPREGA VLIVTASYNG HPPDNAKQFV DWLDQASADE VKGVRYSVFG CGDKNWATTY 120

QKVPAFIDEM LAAKGAENIA DRGEADASDD FEGTYEEWRE HMWSDVAAYF NLDIENSEDN 180

KSALLLQtVD SAADMPLAKM HGAFSTNVVA SKELQQPGSA RSTRHLEIEL PKEASYQEGD 240

HLGVIPRNYE GIVNRVTARF GLDASQQIRL EAEEEKLAHL PLAKTVSVEE LLQYVELQDP 300

VTRTQLRAMA AKTVCPPHKV ELEALLEKQA YKEQVLAKRL TMLELLEKYP ACEMEFSEFI 360

ALLPSIRPRY YSISSSPRVD EKQASITVSV VSGEAWSGYG EYKGIASNYL AELQEGDTIT 420

CFISTPQSEF TLPKDPETPL IMVGPGTGVA PFRGFVQARK QLKEQGQSLG EAHLYFGCRS 480

PHEDYLYQEE LENAQSEGII TLHTAFSRMP NQPKTYVQHV MEQDGKKLIE LLDKGAHFYI 540

CGDGSQMAPA VEATLMKSYA DVHQVSEADA RLWLQQLEEK GRYAKDVW               588
```

SEQ ID NO: 119

```
ccaagtccta gtaccgaaca atctgcaaaa aaagttagaa aaaaagcaga aaatgcacac   60
aatactccat tgctagttct ttatggttct aatatgggaa cagcggaagg aacggccagg  120
gatctagctg acatagctat gtccaaggga tttgccccgc aagtagcaac cctggattcc  180
catgcaggta acttgccaag agaaggtgct gttctaatag ttaccgctag ctacaatggg  240
caccctccag ataatgcgaa gcagttcgtc gattggttag atcaagcatc agcagatgaa  300
gttaagggtg ttagatactc tgtttttgga tgtggagata agaattgggc caccacatat  360
cagaaggttc cggctttcat cgatgaaatg cttgctgcaa aaggggctga aaatatagca  420
gatcgtggtg aggccgacgc aagcgacgat tttgagggta cctatgagga gtggagagag  480
cacatgtggt ctgatgttgc cgcgtatttt aatctagaca tagaaaattc tgaagacaat  540
aaaagtgcct tacttcttca attcgtcgat agtgctgcgg acatgccctt agcaaagatg  600
catggagcct tttcaacgaa cgtagtagcc agtaaggaac ttcaacaacc aggtagtgcc  660
agaagtacac gtcacttgga aattgaatta ccaaaagagg catcctacca agaaggtgac  720
catcttggtg taatcccaag aaactacgaa ggtatagtca atagggtaac ggcaagattt  780
gggctggatg caagccaaca gataagacta gaagcagaag aagaaaaatt ggcgcacctt  840
ccactagcga agacagtatc cgttgaagaa ttattgcaat acgtggaatt gcaggatccc  900
gtcactagaa cgcaattgag agctatggca gcaaagactg tttgtccacc tcacaaggtt  960
```

TABLE 13-continued

Sequences disclosed herein.

```
gaacttgaag ctctacttga aaacaagca tacaaagagc aagtgctagc aaagagacta 1020
accatgttag aattgctgga aaaatacccg gcatgcgaaa tggaattctc cgaatttatc 1080
gcgttgttgc caagtattcg tcccaggtat tactcaattt catcttcacc aagggttgac 1140
gagaaacagg catctattac cgtatctgtg gtctctggag aagcttggag tggttacgga 1200
gaatacaagg gtattgcttc caattatctt gcagaactgc aggaagggga tacaattacc 1260
tgctttattt ctactcctca atcagaattt actcttccga aggatccaga aactccgtta 1320
attatggtag gtccgggaac aggagtcgcc ccttttcagag gctttgtgca agcaaggaag 1380
caactaaaag aacagggaca aagtctgggt gaggcacatc tatatttcgg ttgcagatct 1440
ccgcatgagg attacttata ccaagaagaa cttgaaaacg cccaatcaga aggtattatc 1500
accttgcata ctgcattcag tagaatgcca aaccagccga aaacttacgt acagcatgtt 1560
atggagcaag atggtaagaa gttaattgag cttttggata agggcgccca cttctacatt 1620
tgcggcgacg gatcccaaat ggcgcctgcc gttgaagcca ccttgatgaa atcatatgca 1680
gatgttcatc aagtttcaga agcggacgcc cgtctttggt acaacaact agaggagaaa 1740
ggaaggtatg caaaagatgt tgcttaa                                 1767
```

SEQ ID NO: 120

```
PSPSTEQSAK KVRKKAENAH NTPLLVLYCS NMGTAEGTAR DLADIAMSKG FAPQVATLDS  60
HACNLPREGA VLIVTASYNG HPPDNAKQFV DWLDQASADE VKGVRYSVFG CGDKNWATTY 120
QKVPAFIDEM LAAKGAENIA DRGEADASDD IEGTYEEWRE HMWSDVAAYF NLDIENSEDN 180
KSALLLQFVD SAADMPLAKM HGAFSTNVVA SKELQQPGSA RSTRHLEIEL PKEASYQEGD 240
HLGVIPRNYE GIVNRVTARF GLDASQQIRL EAEEEKLAHL PLAKTVSVEE LLQYVELQDP 300
VTRTQLRAMA AKTVCPPHKV ELEALLEKQA YKEQVLAKRL TMLELLEKYP ACEMEFSEFI 360
ALLPSIRPRY YSISSSPRVD EKQASITVSV VSGEAWSGYG EYKGIASNYL AELQEGDTIT 420
CFISTPQSEF TLPKDPETPL IMVGPGTGVA PFRGFVQARK QLKEQGQSLG EAHLYFGCRS 480
PHEDYLYQEE LENAQSEGII TLHTAFSRMP MQPKTYVQHV MEQDGKKLIE LLDKGAHFYI 540
CGDGSQMAPA VEATLMKSYA DVHQVSEADA RLWLQQLEEK GRYAKDVA           588
```

SEQ ID NO: 121

```
ccatcaaga                                                        9
```

SEQ ID NO: 122

```
PSR                                                              3
```

---

What is claimed is:

1. A recombinant host, comprising:
   (a) a gene encoding a cytochrome P450 reductase (CPR) polypeptide;
      wherein the CPR polypeptide comprises a CPR polypeptide having at least 90% sequence identity to the amino acid sequence set forth in SEQ ID NO:98; and
   (b) a gene encoding an ent-kaurenoic acid hydroxylase (KAH) polypeptide;
      wherein the KAH polypeptide comprises a KAH polypeptide having at least 90% sequence identity to the amino acid sequence set forth in SEQ ID NO:82;
   wherein at least one of the genes is a recombinant gene;
   wherein the recombinant host produces a steviol or a steviol glycoside precursor; and
   wherein the recombinant host cell is a fungal cell.

2. The recombinant host of claim 1, further comprising:
   (c) a gene encoding an ent-kaurene oxidase (KO) polypeptide;
      wherein the KO polypeptide has at least 90% sequence identity to the amino acid sequence set forth in SEQ ID NO: 54, 70, 71, 72, 75, 77, 78, or 79; and
   wherein at least one of the genes is a recombinant gene.

3. The recombinant host of claim 2, further comprising:
   (d) a gene encoding a geranylgeranyl diphosphate synthase (GGPPS) polypeptide;
   (e) a gene encoding an ent-copalyl diphosphate synthase (CDPS) polypeptide; and
   (f) a gene encoding an ent-kaurene synthase (KS) polypeptide;
   wherein at least one of the genes is a recombinant gene.

4. The recombinant host of claim 2, comprising:
   (a) the gene encoding the CPR polypeptide having at least 90% sequence identity to the amino acid sequence set forth in SEQ ID NO:98;
   (b) the gene encoding the KAH polypeptide having at least 90% (b) sequence identity to the amino acid sequence set forth in SEQ ID NO:82; and
   (c) the gene encoding the KO polypeptide having at least 90% sequence identity to the amino acid sequence set forth in SEQ ID NO:75;
   wherein at least one of the genes is a recombinant gene; and
   wherein the recombinant host produces a steviol glycoside precursor.

5. The recombinant host of claim 3, wherein:
   (a) the GGPPS polypeptide comprises a polypeptide having at least 90% sequence identity to the amino acid sequence set forth in SEQ ID NO:49;
   (b) the CDPS polypeptide comprises a polypeptide having at least 90% sequence identity to the amino acid sequence set forth in SEQ ID NO:37; and
   (c) the KS polypeptide comprises a polypeptide having at least 90% sequence identity to the amino acid sequence set forth in SEQ ID NO:6.

6. The recombinant host of claim 1, wherein the host further comprises a gene encoding an endoplasmic reticulum membrane polypeptide.

7. The recombinant host of claim 2, wherein the host further comprises one or more of:
   (a) a gene encoding a polypeptide that glycosylates steviol or a steviol glycoside at its C-13 hydroxyl group thereof;
   (b) a gene encoding a polypeptide that beta 1,3 glycosylates the C3' of the 13-O-glucose, 19-O-glucose, or both 13-O-glucose and 19-O-glucose of a steviol glycoside;
   (c) a gene encoding a polypeptide that glycosylates steviol or a steviol glycoside at its C-19 carboxyl group thereof;

(d) a first gene encoding a first polypeptide that beta 1,2 glycosylates the C2' of the 13-O-glucose, 19-O-glucose, or both 13-O-glucose and 19-O— glucose of a steviol glycoside; and/or (e) a second gene encoding a second polypeptide that beta 1,2 glycosylates the C2' of the 13-O-glucose, 19-O-glucose, or both 13-O-glucose and 19-O-glucose of a steviol glycoside;

wherein at least one of the genes is a recombinant gene; and wherein the host produces one or more steviol glycoside.

8. The recombinant host of claim 7, wherein:

(a) the polypeptide that glycosylates steviol or the steviol glycoside at its C-13 hydroxyl group thereof comprises a polypeptide having at least 90% sequence identity to the amino acid sequence set forth in SEQ ID NO:30;

(b) the polypeptide that beta 1,3 glycosylates the C3' of the 13-O-glucose, 19-O-glucose, or both 13-O-glucose and 19-O-glucose of the steviol glycoside comprises a polypeptide having at least 90% sequence identity to the amino acid sequence set forth in SEQ ID NO:83;

(c) the polypeptide that glycosylates steviol or the steviol glycoside at its C-19 carboxyl group comprises a polypeptide having at least 90% sequence identity to the amino acid sequence set forth in SEQ ID NO:29;

(d) the first polypeptide that beta 1,2 glycosylates the C2' of the 13-O-glucose, 19-O-glucose, or both 13-O-glucose and 19-O-glucose of the steviol glycoside comprises a polypeptide having at least 90% sequence identity to the amino acid sequence set forth in SEQ ID NO:84 or 88; and/or (e) the second polypeptide that beta 1,2 glycosylates the C2' of the 13-O— glucose, 19-O-glucose, or both 13-O-glucose and 19-O-glucose of the steviol glycoside comprises a polypeptide having at least 90% sequence identity to the amino acid sequence set forth in SEQ ID NO:86.

9. The recombinant host of claim 1, wherein the fungal cell comprises a yeast cell.

10. The recombinant host of claim 9, wherein the yeast cell is a cell from *Saccharomyces cerevisiae*.

11. A method of producing a steviol glycoside or a steviol glycoside precursor, comprising:

(a) growing the recombinant host of claim 1 in a culture medium, under conditions wherein any of the genes are expressed;

wherein the steviol glycoside or the steviol glycoside precursor is produced by the host; and/or (b) quantifying the steviol glycoside or the steviol glycoside precursor; and/or (c) isolating the steviol glycoside or the steviol glycoside precursor.

12. The method of claim 11, wherein the steviol glycoside comprises steviol-13-O-glucoside (13-SMG), steviol-1,2-bioside, steviol-1,3-bioside, steviol-19-O-glucoside (19-SMG), stevioside, 1,3-stevioside, rubusoside, Rebaudioside A (RebA), Rebaudioside B (RebB), Rebaudioside C (RebC), Rebaudioside D (RebD), Rebaudioside E (RebE), Rebaudioside F (RebF), Rebaudioside M (RebM), Rebaudioside Q (RebQ), Rebaudioside I (RebI), dulcoside A, di-glycosylated steviol, tri-glycosylated steviol, tetra-glycosylated steviol, penta-glycosylated steviol, hexa-glycosylated steviol, hepta-glycosylated steviol, or isomers thereof.

13. A steviol glycoside composition produced by the recombinant host of claim 1, wherein the composition has a steviol glycoside composition enriched for RebD or RebM relative to the steviol glycoside composition of a wild-type *Stevia* plant.

* * * * *

SEQUENCE LISTING

```
Sequence total quantity: 122
SEQ ID NO: 1           moltype = AA  length = 784
FEATURE                Location/Qualifiers
source                 1..784
                       mol_type = protein
                       organism = Stevia rebaudiana
SEQUENCE: 1
MNLSLCIASP LLTKSNRPAA LSAIHTASTS HGGQTNPTNL IIDTTKERIQ KQFKNVEISV  60
SSYDTAWVAM VPSPNSPKSP CFPECLNWLI NNQLNDGSWG LVNHTHNHNH PLLKDSLSST 120
LACIVALKRW NVGEDQINKG LSFIESNLAS ATEKSQPSPI GFDIIFPGLL EYAKNLDINL 180
LSKQTDFSLM LHKRELEQKR CHSNEMDGYL AYISEGLGNL YDWNMVKKYQ MKNGSVFNSP 240
SATAAAFINH QNPGCLNYLN SLLDKFGNAV PTVYPHDLFI RLSMVDTIER LGISHHFRVE 300
IKNVLDETYR CWVERDEQIF MDVVTCALAF RLLRINGYEV SPDPLAEITN ELALKDEYAA 360
```

```
LETYHASHIL YQEDLSSGKQ ILKSADFLKE IISTDSNRLS KLIHKEVENA LKFPINTGLE    420
RINTRRNIQL YNVDNTRILK TTYHSSNISN TDYLRLAVED FYTCQSIYRE ELKGLERWVV    480
ENKLDQLKFA RQKTAYCYFS VAATLSSPEL SDARISWAKN GILTTVVDDF FDIGGTIDEL    540
TNLIQCVEKW NVDVDKDCCS EHVRILFLAL KDAICWIGDE AFKWQARDVT SHVIQTWLEL    600
MNSMLREAIW TRDAYVPTLN EYMENAYVSF ALGPIVKPAI YFVGPKLSEE IVESSEYHNL    660
FKLMSTQGRL LNDIHSFKRE FKEGKLNAVA LHLSNGESGK VEEEVVEEMM MMIKNKRKEL    720
MKLIFEENGS IVPRACKDAF WNMCHVLNFF YANDDGFTGN TILDTVKDII YNPLVLVNEN    780
EEQR                                                                784

SEQ ID NO: 2             moltype = AA   length = 784
FEATURE                  Location/Qualifiers
source                   1..784
                         mol_type = protein
                         organism = Stevia rebaudiana
SEQUENCE: 2
MNLSLCIASP LLTKSSRPTA LSAIHTASTS HGGQTNPTNL IIDTTKERIQ KLFKNVEISV     60
SSYDTAWVAM VPSPNSPKSP CFPECLNWLI NNQLNDGSWG LVNHTHNHNH PLLKDSLSST    120
LACIVALKRW NVGEDQINKG LSFIESNLAS ATDKSQPSPI GFDIIFPGLL EYAKNLDINL    180
LSKQTDFSLM LHKRELEQKR CHSNEIDGYL AYISEGLGNL YDWNMVKKYQ MKNGSVFNSP    240
SATAAAFINH QNPGCLNYLN SLLDKFGNAV PTVYPLDLYI RLSMVDTIER LGISHHFRVE    300
IKNVLDETYR CWVERDEQIF MDVVTCALAF RLLRIHGYKV SPDQLAEITN ELAFKDEYAA    360
LETYHASQIL YQEDLSSGKQ ILKSADFLKG ILSTDSNRLS KLIHKEVENA LKFPINTGLE    420
RINTRRNIQL YNVDNTRILK TTYHSSNISN TYYLRLAVED FYTCQSIYRE ELKGLERWVV    480
QNKLDQLKFA RQKTAYCYFS VAATLSSPEL SDARISWAKN GILTTVVDDF FDIGGTIDEL    540
TNLIQCVEKW NVDVDKDCCS EHVRILFLAL KDAICWIGDE AFKWQARDVT SHVIQTWLEL    600
MNSMLREAIW TRDAYVPTLN EYMENAYVSF ALGPIVKPAI YFVGPKLSEE IVESSEYHNL    660
FKLMSTQGRL LNDIHSFKRE FKEGKLNAVA LHLSNGESGK VEEEVVEEMM MMIKNKRKEL    720
MKLIFEENGS IVPRACKDAF WNMCHVLNFF YANDDGFTGN TILDTVKDII YNPLVLVNEN    780
EEQR                                                                784

SEQ ID NO: 3             moltype = AA   length = 590
FEATURE                  Location/Qualifiers
source                   1..590
                         mol_type = protein
                         organism = Zea mays
SEQUENCE: 3
MAMPVKLTPA SLSLKAVCCR FSSGGHALRF GSSLPCWRRT PTQRSTSSST TRPAAEVSSG     60
KSKQHDQEAS EATIRQQLQL VDVLENMGIS RHFAAEIKCI LDRTYRSWLQ RHEEIMLDTM    120
TCAMAFRILR LNGYNVSSDE LYHVVEASGL HNSLGGYLND TRTLLELHKA STVSISEDES    180
ILDSIGSRSR TLLREQLESG GALRKPSLFK EVEHALDGPF YTTLDRLHHR WNIENFNIIE    240
QHMLETPYLS NQHTSRDILA LSIRDFSSSQ FTYQQELQHL ESWVKECRLD QLQFARQKLA    300
YFYLSAAGTM FSPELSDART LWAKNGVLTT IVDDFFDVAG SKEELENLVM LVEMWDEHHK    360
VEFYSEQVEI IFSSIYDSVN QLGEKASLVQ DRSITKHLVE IWLDLLKSMM TEVEWRLSKY    420
VPTEKEYMIN ASLIFGLGPI VLPALYFVGP KISESIVKDP EYDELFKLMS TCGRLLNDVQ    480
TFEREYNEGK LNSVSLLVLH GGPMSISDAK RKLQKPIDTC RRDLLSLVLR EESVVPRPCK    540
ELFWKMCKVC YFFYSTTDGF SSQVERAKEV DAVINEPLKL QGSHTLVSDV               590

SEQ ID NO: 4             moltype = AA   length = 775
FEATURE                  Location/Qualifiers
source                   1..775
                         mol_type = protein
                         organism = Populus trichocarpa
SEQUENCE: 4
MSCIRPWFCP SSISATLTDP ASKLVTGEFK TTSLNFHGTK ERIKKMFDKI ELSVSSYDTA     60
WVAMVPSPDC PETPCFPECT KWILENQLGD GSWSLPHGNP LLVKDALSST LACILALKRW    120
GIGEEQINKG LRFIELNSAS VTDNEQHKPI GFDIIFPGMI EYAKDLDLNL PLKPTDINSM    180
LHRRALELTS GGGKNLEGRR AYLAYVSEGI GKLQDWEMAM KYQRKNGSLF NSPSTTAAAF    240
IHIQDAECLH YIRSLLQKFG NAVPTIYPLD IYARLSMVDA LERLGIDRHF RKERKFVLDE    300
TYRFWLQGEE EIFSDNATCA LAFRILRLNG YDVSLEDHFS NSLGGYLKDS GAALELYRAL    360
QLSYPDESLL EKQNSRTSYF LKQGLSNVSL CGDRLRKNII GEVHDALNFP DHANLQRLAI    420
RRRIKHYATD DTRILKTSYR CSTIGNQDFL KLAVEDFNIC QSIQREEFKH IERWVVERRL    480
DKLKFARQKE AYCYFSAAAT LFAPELSDAR MSWAKNGVLT TVVDDFFDVG GSEEELVNLI    540
ELIERWDVNG SADFCSEEVE IIYSAIHSTI SEIGDKSFGW QGRDVKSHVI KIWLDLLKSM    600
LTEAQWSSNK SVPTLDEYMT TAHVSFALGP IVLPALYFVG PKLSEEVAGH PELLNLYKVM    660
STCGRLLNDW RSFKRESEEG KLNAISLYMI HSGGASTEEE TIEHFKGLID SQRRQLLQLV    720
LQEKDSIIPR PCKDLFWNMI KLLHTFYMKD DGFTSNEMRN VVKAIINEPI SLDEL         775

SEQ ID NO: 5             moltype = DNA   length = 2506
FEATURE                  Location/Qualifiers
source                   1..2506
                         mol_type = other DNA
                         organism = Arabidopsis thaliana
SEQUENCE: 5
cgtcagtcat caaggctaat tcgtcgcgag ttgctacgac gccgtttcgg ttgcttctgg     60
tttctttatg tctatcaacc ttcgctcctc cggttgttcg tctccgatct cagctacttt    120
ggaacgagga tttggactca gaagtacgac aagagctaac aatgtgagct ttgagcaaac    180
aaaggagaag attaggaaga tgttggaaga agtggagctt tctgtttcgg cctacgatac    240
tagttgggta gcaatggttc catcaccgag ctcccaaaat gctccacttt tcccacagtg    300
tgtgaaatgg ttattggata tcaacatgag agatggatct tggggacttg ataaccatga    360
```

```
ccatcaatct cttaagaagg atgtgttatc atctcactg gctagtatcc tcgcgttaaa    420
gaagtgggga attggtgaaa gacaaataaa caagggtctc cagtttattg agctgaattc    480
tgcattagtc actgatgaaa ccatacagaa accaacaggg tttgatatta tatttcctgg    540
gatgattaaa tatgctagag atttgaatct gacgattcca ttgggctcag aagtggtgga    600
tgacatgata cgaaaaagag atctggatct taaatgtagt agtgaaaagt tttcaaaggg    660
aagagaagca tatctggcct atgttttaga ggggacaaga aacctaaaag attgggattt    720
gatagtcaaa tatcaaagga aaaatgggtc actgtttgat tctccagcca caacagcagc    780
tgcttttact cagtttggga atgatggttg tctccgttat ctctgttctc tccttcgaa    840
attcgaggct gcagttcctt cagtttatcc atttgatata tatgcacgcc ttagtataat    900
tgtcactctt gaaagcttag gaattgatag agattcaaa accgaaatca aaagcatatt    960
ggatgaaacc tatagatatt ggcttcgtgg ggatgaagaa atatgtttgg acttggccac   1020
ttgtgctttg gctttccgat tattgcttgc tcatggctat gatgtgtctt acgatccgct   1080
aaaaccattt gcagaagaat ctggtttctc tgatactttg gaaggatatg ttaagaatac   1140
gttttctgtg ttagaattat ttaaggctgc tcaaagttat ccacatgaat cagctttgaa   1200
gaagcagtgt tgttggacta aacaatatct ggagatggaa ttgtccagct gggttaagac   1260
ctctgttcga gataaatacc tcaagaaaga ggtcgaggat gctcttgctt ttccctccta   1320
tgcaagccta gaaagatcag atcacaggag aaaaatactc aatggttctg ctgtggaaaa   1380
caccgagtt acaaaaacct catatcgttt gcacaatatt tgcacctctg atatcctgaa   1440
gttagctgtg gatgacttca atttctgcca gtccatacac cgtgaagaaa tggaacgtct   1500
tgataggtgg attgtggaga atagattgca ggaactgaaa tttgccagac agaagctggc   1560
ttactgttat ttctctgggg ctgcaacttt attttctcca gaactatctg atgctcgtat   1620
atcgtgggcc aaaggtggag tacttacaac ggttgtagac gacttctttg atgttggagg   1680
gtccaaagaa gaactggaaa acctcataca cttggtcgaa aagtgggatt tgaacgtgtt   1740
tcctgagtac agctcagaac atgttgagat catattctca gttctaaggg acaccattct   1800
cgaaacagga gacaaagcat tcacctatca aggacgcaat gtgacacacc acattgtgaa   1860
aatttggttg gatctgctca gtcatgttg gagagaagcc gagtggtcca gtcaagtc    1920
aacaccaagc ttggaggatt acatgaaaa tgcgtacata tcatttgcat taggaccaat   1980
tgtcctccca gctaccatc tgatcggacc tccacttcca gagaagacag tcgatagcca   2040
ccaatataat cagctctaca agctcgtgag cactatgggt cgtcttctaa atgacataca   2100
aggttttaag agagaaagcg cggaagggaa gctgaatcgg gtttcattgc acatgaaaca   2160
cgagagagac aatcgcagca aagaagtgat catagaatcg atgaaaggtt tagcagagag   2220
aaaagaggga gaattgcata agctagtttt ggaggagaaa ggaagtgtgg ttccaaggga   2280
atgcaaagaa gcgttcttga aaatgagcaa agtgttgaac ttattttaca ggaaggacga   2340
tggattcaca tcaaatgatc tgatgagtct tgttaaatca gtgatctacg agcctgttag   2400
cttacaggaa gaatctttaa cttgatccaa gttgatctgg caggtaaact cagtaaatga   2460
aaataagact ttggtcttct tctttgttgc ttcagaacaa gaagag              2506

SEQ ID NO: 6            moltype = AA   length = 785
FEATURE                 Location/Qualifiers
source                  1..785
                        mol_type = protein
                        organism = Arabidopsis thaliana
SEQUENCE: 6
MSINLRSSGC SSPISATLER GLDSEVQTRA NNVSFEQTKE KIRKMLEKVE LSVSAYDTSW    60
VAMVPSPSSQ NAPLFPQCVK WLLDNQHEDG SWGLDNHDHQ SLKKDVLSST LASILALKKW   120
GIGERQINKG LQFIELNSAL VTDETIQKPT GFDIIFPGMI KYARDLNLTI PLGSEVVDDM   180
IRKRDLDLKC DSEKFSKGRE AYLAYVLEGT RNLKDWDLIV KYQRKNGSLF DSPATTAAAF   240
TQFGNDGCLR YLCSLLQKFE AAVPSVYPFD QYARLSIIVT LESLGIDRDF KTEIKSILDE   300
TYRYWLRGDE EICLDLATCA LAFRLLLAHG YDVSYDPLKP FAEESGFSDT LEGYVKNTFS   360
VLELFKAAQS YPHESALKKQ CCWTKQYLEM ELSSWVKTSV RDKYLKKEVE DALAFPSYAS   420
LERSDHRRKI LNGSAVENTR VTKTSYRLHN ICTSDILKLA VDDFNFCQSI HREEMERLDR   480
WIVENRLQEL KFARQKLAYC YFSGAATLFS PELSDARISW AKGGVLTTVV DDFFDVGGSK   540
EELENLIHLV EKWDLNGVPE YSSEHVEIIF SVLRDTILET GDKAFTYQGR NVTHHIVKIW   600
LDLLKSMLRE AEWSSDKSTP SLEDYMENAY ISFALGPIVL PATYLIGPPL PEKTVDSHQY   660
NQLYKLVSTM GRLLNDIQGF KRESAEGKLN AVSLHMKHER DNRSKEVIIE SMKGLAERKR   720
EELHKLVLEE KGSVVPRECK EAFLKMSKVL NLFYRKDDGF TSNDLMSLVK SVIYEPVSLQ   780
KESLT                                                             785

SEQ ID NO: 7            moltype = AA   length = 513
FEATURE                 Location/Qualifiers
source                  1..513
                        mol_type = protein
                        organism = Arabidopsis thaliana
SEQUENCE: 7
MDAVTGLLTV PATAITIGGT AVALAVALIF WYLKSYTSAR RSQSNHLPRV PEVPGVPLLG    60
NLLQLKEKKP YMTFTRWAAT YGPIYSIKTG ATSMVVVSSN EIAKEALVTR FQSISTRNLS   120
KALKVLTADK TMVAMSDYDD YHKTVKRHIL TAVLGPNAQK KHRIHRDIMM DNISTQLHEF   180
VKNNPEQEEV DLRKIFQSEL FGLAMRQALG KDVESLYVED LKITMNRDEI FQVLVVDPMM   240
GAIDVDWRDF FPYLKWVPNK KFENTIQQMY IRREAVMKSL IKEHKKRIAS GEKLNSYIDY   300
LLSEAQTLTD QQLLMSLWEP IIESSDTTMV TTEWAMYELA KNPKLQDRLY RDIKSVCGSE   360
KITEEHLSQL PYITAIFHET LRRHSPVPII PLRHVHEDTV LGGYHVPAGT ELAVNIYGCN   420
MDKNVWENPE EWNPERFMKE NETIDFQKTM AFGGGKRVCA GSLQALLTAS IGIGRMVQEF   480
EWKLKDMTQE EVNTIGLTTQ MLRPLRAIIK PRI                               513

SEQ ID NO: 8            moltype = AA   length = 509
FEATURE                 Location/Qualifiers
source                  1..509
                        mol_type = protein
                        organism = Arabidopsis thaliana
```

```
SEQUENCE: 8
MAFFSMISIL LGFVISSFIF IFFFKKLLSF SRKNMSEVST LPSVPVVPGF PVIGNLLQLK    60
EKKPHKTFTR WSEIYGPIYS IKMGSSSLIV LNSTETAKEA MVTRFSSIST RKLSNALTVL   120
TCDKSMVATS DYDDFHKLVK RCLLNGLLGA NAQKRKRHYR DALIENVSSK LHAHARDHPQ   180
EPVNFRAIFE HELFGVALKQ AFGKDVESIY VKELGVTLSK DEIFKVLVHD MMEGAIDVDW   240
RDFFPYLKWI PNKSFEARIQ QKHKRRLAVM NALIQDRLKQ NGSESDDDCY LNFLMSEAKT   300
LTKEQIAILV WETIIETADT TLVTTEWAIY ELAKHPSVQD RLCKEIQNVC GGEKFKEEQL   360
SQVPYLNGVF HETLRKYSPA PLVPIRYAHE DTQIGGYHVP AGSEIAINIY GCNMDKKRWE   420
RPEDWWPERF LDDGKYETSD LHKTMAFGAG KRVCAGALQA SLMAGIAIGR LVQEFEWKLR   480
DGEEENVDTY GLTSQKLYPL MAIINPRRS                                    509

SEQ ID NO: 9              moltype = AA  length = 525
FEATURE                   Location/Qualifiers
source                    1..525
                          mol_type = protein
                          organism = Fusarium fujikuroi
SEQUENCE: 9
MSKSNSMNST SHETLFQQLV LGLDRMPLMD VHWLIYVAFG AWLCSYVIHV LSSSSTVKVP    60
VVGYRSVFEP TWLLRLRFVW EGGSIIGQGY NKFKDSIFQV RKLGTDIVII PPNYIDEVRK   120
LSQDKTRSVE PFINDFAGQY TRGMVFLQSD LQNRVIQQRL TPKLVSLTKV MKEELDYALT   180
KEMPDMKNDE WVEVDISSIM VRLISRISAR VFLGPEHCRN QEWLTTTAEY SESLFITGFI   240
LRVVPHILRP FIAPLLPSYR TLLRNVSSGR RVIGDIIRSQ QGDGNEDILS WMRDAATGEE   300
KQIDNIAQRM LILSLASIHT TAMTMTHAMY DLCACPEYIE PLRDEVKSVV GASGWDKTAL   360
NRFHKLDSFL KESQRFNPVF LLTFNRIYHQ SMTLSDGTNI PSGTRIAVPS HAMLQDSAHV   420
PGPTPPTEFD GFRYSKIRSD SNYAQKYLFS MTDSSNMAFG YGKYACPGRF YASNEMKLTL   480
AILLLQFEFK LPDGKGRPRN ITIDSDMIPD PRARLCVRKR SLRDE                   525

SEQ ID NO: 10             moltype = AA  length = 499
FEATURE                   Location/Qualifiers
source                    1..499
                          mol_type = protein
                          organism = Trametes versicolor
SEQUENCE: 10
MEDPTVLYAC LAIAVATFVV RWYRDPLRSI PTVGGSDLPI LSYIGALRWT RRGREILQEG    60
YDGYRGSTFK IAMLDRWIVI ANGPKLADEV RRRPDEELNF MDGLGAFVQT KYTLGEAIHN   120
DPYHVDIIRE KLTRGLPAVL PDVIEELTLA VRQYIPTEGD EWVSVNCSKA ARDIVARASN   180
RVFVGLPACR NQGYLDLAID FTLSVVKDRA IINMFPELLK PIVGRVVGNA TRNVRRAVPF   240
VAPLVEERRS LMEEYGEDWS EKPNDMLQWI MDEAASRDSS VKAIAERLLM VNFAAIHTSS   300
NTITHALYHL AEMPETLQPL REEIEPLVKE EGWTKAAMGK MWWLDSFLRE SQRYNGINIV   360
SLTRMADKDI TLSDGTFLPK GTLVAVPAYS THRDDAVYAD ALVFDPFRFS RMRAREGEGT   420
KHQFVNTSVE YVPFGHGKHA CPGRFFAANE LKAMLAYIVL NYDVKLPGDG KRPLNMYWGP   480
TVLPAPAGQV LFRKRQVSL                                               499

SEQ ID NO: 11             moltype = DNA  length = 1678
FEATURE                   Location/Qualifiers
source                    1..1678
                          mol_type = other DNA
                          organism = Stevia rebaudiana
SEQUENCE: 11
aaacaaagaa tgattcaagt tctaacaccg atccttctct tcctcatttt cttcgttttc    60
tggaaggttt acaagcacca gaaaaccaaa atcaatcttc caccgggaag cttcggatgg   120
ccatttctgg gcgaaactct ggcactccta cgtgcaggtt gggactcaga gccgagaga   180
tttgttcgtg aacggatcaa gaaacacgga agtcctctag tgtttaagac gtcgttgttt   240
ggcgaccgtt ttgcggtgtt gtgtggacct gccggaaaca agttcctgtt ctgcaacgag   300
aacaagctgg tggcgtcgtg gtggccggtt ccggtgagga agcttttcgg caagtctctg   360
ctcacgattc gtggtgatga agctaagtgg atgaggaaga tgttgttatc gtatctcggt   420
cctgatgctt tcgcaactca ttatgccggt ccatgacg tcgtcacccg tcggcatatc    480
gacgttcatt ggcgagggaa ggaagaggtg aacgtattcc aaaccgttaa gttatatgcc   540
tttgagcttg catgtcgttt attcatgaac ctagacgacc caaaccacat tgcaaaactc   600
ggttccttgt tcaacatttt cttgaaaggc atcattgagc ttccaatcga cgtcccaggg   660
acacgatttt atagctccaa aaaagcagca gcagctatca ggattgaact aaaaaaaatg   720
attaaagcaa gaaaactgga actgaaagaa gggaaggcat catcttcaca agacctctta   780
tcacatttgc ttacatctcc agatgaaaat ggtatgtttc taaccgaaga agagattgta   840
gacaacatct tgttactact ctttgcgggt catgataccc cggctctttc aatcactttg   900
ctcatgaaga ctcttggcga acattctgat gtttatgaca aggtgttaaa agagcaacta   960
gagatatcga agacgaaaga agcatggagt ccctgaaat gggaggacat acaaaagatg  1020
aaatactcct ggagtgttat atgtgaagtc atgagactaa atccacctgt tataggaacc  1080
tatagagagg cccttgtgga tattgattat gcgggttata ccatcccaa aggatggaa   1140
ctgcactgga gtgctgtatc gacacaaagg gacgaggcta actttgaaga cgtaacacgt  1200
tttgacccat cacggtttga aggcgcagga ccgactccat tcacctttgt tccgtttgga  1260
gggggggccta gaatgtgttt agggaaagaa tttgctcgat tggaagtact tgcgtttctt  1320
cacaatattg tcaccaattt caaatgggac ctgttgatac ctgatgagaa aatagaatat  1380
gatcccatgg ctacccccagc aaaggggctt ccaattcgtc ttcatcccca tcaagtttga  1440
ttacttcaag catgaatcag tgatgtgaag gtaaccatga tggatcttta ttggtagtta  1500
cagattatgt gttttatatgg catgaagaag ttatgataaa taaaattgtg ttattctaca  1560
acttatgtaa tttgtgcctg taagtaactg aatcttataa tgtttatgt gacatgaaac  1620
ataaatgtat aattagtaaa ttttctgctc aaaaaaaaaa aaaaaaaaa aaaaaaa     1678

SEQ ID NO: 12             moltype = AA  length = 476
```

```
FEATURE                 Location/Qualifiers
source                  1..476
                        mol_type = protein
                        organism = Stevia rebaudiana
SEQUENCE: 12
MIQVLTPILL FLIFFVFWKV YKHQKTKINL PPGSFGWPFL GETLALLRAG WDSEPERFVR   60
ERIKKHGSPL VFKTSLFGDR FAVLCGPAGN KFLFCNENKL VASWWPVPVR KLFGKSLLTI  120
RGDEAKWMRK MLLSYLGPDA FATHYAVTMD VVTRRHIDVH WRGKEEVNVF QTVKLYAFEL  180
ACRLFMNLDD PNHIAKLGSL FNIFLKGIIE LPIDVPGTRF YSSKKAAAAI RIELKKLIKA  240
RKLELKEGKA SSSQDLLSHL LTSPDENGMF LTEEEIVDNI LLLLFAGHDT SALSITLLMK  300
TLGEHSDVYD KVLKEQLEIS KTKEAWESLK WEDIQKMKYS WSVICEVMRL NPPVIGTYRE  360
ALVDIDYAGY TIPKGWKLHW SAVSTQRDEA NFEDVTRFDP SRFEGAGPTP FTFVPFGGGP  420
RMCLGKEFAR LEVLAFLHNI VTNFKWDLLI PDEKIEYDPM ATPAKGLPIR LHPHQV     476

SEQ ID NO: 13           moltype = AA length = 522
FEATURE                 Location/Qualifiers
source                  1..522
                        mol_type = protein
                        organism = Stevia rebaudiana
SEQUENCE: 13
MGLFPLEDSY ALVFEGLAIT LALYYLLSFI YKTSKKTCTP PKASGEHPIT GHLNLLSGSS   60
GLPHLALASL ADRCGPIFTI RLGIRRVLVV SNWEIAKEIF TTHDLIVSNR PKYLAAKILG  120
FNYVSFSFAP YGPYWVGIRK IIATKLMSSS RLQKLQFVRV FELENSMKSI RESWWKEKKDE 180
EGKVLVEMKK WFWELNMNIV LRTVAGKQYT GTVDDADAKR ISELFREWFH YTGRFVVGDA  240
FPPFLGWLDLG GYKKTMELVA SRLDSMVSKW LDEHRKKQAN DDKKEDMDFM DIMISMTEAN  300
SPLEGYGTDT IIKTTCMTLI VSGVDTTSIV LTWALSLLLN NRDTLKKAQE ELDMCVGKGR  360
QVNESDLVNL IYLEAVLKEA LRLYPAAFLG GPRAFLEDCT VAGYRIPKGT CLLINMWKLH  420
RDPNIWSDPC EFKPERFLTP NQKDVDVIGM DFELIPFGAG RRYCPGTRLA LQMLHIVLAT  480
LLQNFEMSTP NDAPVDMTAS VGMTNAKASP LEVLLSPRVK WS                    522

SEQ ID NO: 14           moltype = AA length = 476
FEATURE                 Location/Qualifiers
source                  1..476
                        mol_type = protein
                        organism = Stevia rebaudiana
SEQUENCE: 14
MIQVLTPILL FLIFFVFWKV YKHQKTKINL PPGSFGWPFL GETLALLRAG WDSEPERFVR   60
ERIKKHGSPL VFKTSLFGDR FAVLCGPAGN KFLFCNENKL VASWWPVPVR KLFGKSLLTI  120
RGDEAKWMRK MLLSYLGPDA FATHYAVTMD VVTRRHIDVH WRGKEEVNVF QTVKLYAFEL  180
ACRLFMNLDD PNHIAKLGSL FNIFLKGIIE LPIDVPGTRF YSSKKAAAAI RIELKKLIKA  240
RKLELKEGKA SSSQDLLSHL LTSPDENGMF LTEEEIVDNI LLLLFAGHDT SALSITLLMK  300
TLGEHSDVYD KVLKEQLEIS KTKEAWESLK WEDIQKMKYS WSVICEVMRL NPPVIGTYRE  360
ALVDIDYAGY TIPKGWKLHW SAVSTQRDEA NFEDVTRFDP SRFEGAGPTP FTFVPFGGGP  420
RMCLGKEFAR LEVLAFLHNI VTNFKWDLLI PDEKIEYDPM ATPAKGLPIR LHPHQV     476

SEQ ID NO: 15           moltype = AA length = 525
FEATURE                 Location/Qualifiers
source                  1..525
                        mol_type = protein
                        organism = Arabidopsis thaliana
SEQUENCE: 15
MESLVVHTVN AIWCIVIVGI FSVGYHVYGR AVVEQWRMRR SLKLQGVKGP PPSIFNGNVS   60
EMQRIQSEAK HCSGDNIISH DYSSSLFPHF DHWRKQYGRI YTYSTGLKQH LYINHPEMVK  120
ELSQTNTLNL GRITHITKRL NPILGNGIIT SNGPHWAHQR RIIAYEFTHD KIKGMVGLMV  180
ESAMPMLNKW EEMVKRGGEM GCDIRVDEDL KDVSADVIAK ACFGSSFSKG KAIFSMIRDL  240
LTAITKRSVL FRFNGFTDMV FGSKKHGDVD IDALEMELES SIWETVKERE IECKDTHKKD  300
LMQLILEGAM RSCDGNLWDK SAYRRFVVDN CKSIYFAGHD STAVSWCL MLLALNPSWQ   360
VKIRDEILSS CKNGIPDAES IPNLKTVTMV IQETMRLYPP APIVGREASK DIRLGDLVVP  420
KGVCIWTLIP ALHRDPEIWG PDANDFKPER FSEGISKACK YPQSYIPFGL GPRTCVGKNF  480
GMMEVKVLVS LIVSKFSFTL SPTYQHSPSH KLLVEPQHGV VIRVV                 525

SEQ ID NO: 16           moltype = AA length = 526
FEATURE                 Location/Qualifiers
source                  1..526
                        mol_type = protein
                        organism = Vitis vinifera
SEQUENCE: 16
MYFLLQYLNI TTGVPATLF LSYCLLLWRS RAGNKKIAPE AAAAWPIIGH LHLLAGGSHQ    60
LPHITLGNMA DKYGPVFTIR IGLHRAVVVS SWEMAKECST ANDQVSSSRP ELLASKLLGY  120
NYAMFGFSPY GSYWREMRKI ISLELLSNSR LELLKDVRAS EVVTSIKELY KLWAEKKNES  180
GLVSVEMKQW FGDLTLNVIL RMVAGKRYFS ASDASENKQA QRCRRVFREF FHLSGLFVVA  240
DAIPFLGWLD WGRHEKTLKK TAIEMDSIAQ EWLEEHRRRK DSGDDNSTQD FMDVMQSVLD  300
GKNLGGYDAD TINKATCLTL ISGGSDTTVV SLTWALSLVL NNRDTLKKAQ EELDIQVGKE  360
RLVNEQDISK LVYLQAIVKE TLRLYPPGPL GGLRQFTEDC TLGGYHVSKG TRLIMNLSKI  420
QKDPRIWSDP TEFQPERFLT THKDVDPRGK HFEFIPFGAG RRACPGITFG LQVLHLTLAS  480
FLHAFEFSTP SNEQVNMRES LGLTNMKSTP LEVLISPRLS SCSLYN                526

SEQ ID NO: 17           moltype = AA length = 479
FEATURE                 Location/Qualifiers
```

```
source                    1..479
                          mol_type = protein
                          organism = Medicago truncatula
SEQUENCE: 17
MEPNFYLSLL LLFVTFISLS LFFIFYKQKS PLNLPPGKMG YPIIGESLEF LSTGWKGHPE    60
KFIFDRMRKY SSELFKTSIV GESTVVCCGA ASNKFLFSNE NKLVTAWWPD SVNKIFPTTS   120
LDSNLKEESI KMRKLLPQFF KPEALQRYVG VMDVIAQRHF VTHWDNKNEI TVYPLAKRYT   180
FLLACRLFMS VEDENHVAKF SDPFQLIAAG IISLPIDLPG TPFNKAIKAS NFIRKELIKI   240
IKQRRVDLAE GTASPTQDIL SHMLLTSDEN GKSMNELNIA DKILGLLIGG HDTASVACTF   300
LVKYLGELPH IYDKVYQEQM EIAKSKPAGE LLNWDDLKKM KYSWNVACEV MRLSPPLQGG   360
FREAITDFMF NGFSIPKGWK LYWSANSTHK NAECFPMPEK FDPTRFEGNG PAPYTFVPFG   420
GGPRMCPGKE YARLEILVFM HNLVKRFKWE KVIPDEKIIV DPFPIPAKDL PIRLYPHKA    479

SEQ ID NO: 18             moltype = DNA  length = 1503
FEATURE                   Location/Qualifiers
misc_feature              1..1503
                          note = Codon-optimized Stevia rebaudiana KAHe1
source                    1..1503
                          mol_type = other DNA
                          organism = synthetic construct
SEQUENCE: 18
atggaagcct cttacctata catttctatt ttgcttttac tggcatcata cctgttcacc    60
actcaactta gaaggaagag cgctaatcta ccaccaaccg tgtttccatc aataccaatc   120
attggacact tatacttact caaaaagcct ctttatagaa ctttagcaaa aattgccgct   180
aagtacggac caatactgca attacaactc ggctacagac gtgttctggt gatttcctca   240
ccatcagcag cagaagagtg cttttaccaa tacgatgtaa tcttcgcaaa tagacctaag   300
acattgtttg gcaaaatagt gggtggaaca tcccttggca gtttatccta cggcgatcaa   360
tggcgtaatc taaggagagt agcttctatc gaaatcctat cagttcatag ttgaacgaa    420
tttcatgata tcagagtgga tgagaacaga ttgttaatta gaaaacttag aagttcatct   480
tctcctgtta ctcttataac agtctttat gctctaacat tgaacgtcat tatgagaatg   540
atctctggca aaagatattt cgacagtggg gatagagaat tggaggagga aggtaagaga   600
tttcgagaaa tcttagacga aacgttgctt ctagccggtg cttctaatgt tggcgactac   660
ttaccaatat tgaactggtt gggagttaag tctcttgaaa agaaattgat cgctttgcag   720
aaaaagagag atgactttt ccagggtttg attgaacagg ttagaaaatc tcgtggtgct   780
aaagtaggca aaggtagaaa gactatgatc gaactcttat tatctttgca aagtcagaa    840
cctgagtact atacagatgc tatgataaga tctttttgtcc taggtctgct ggctgcaggt   900
agtgatactc cagcgggcac tatggaatgg gccatgagct actggtcaa tcacccacat   960
gtattgaaga aagctcaagc tgaaatcgat agagttatcg gtaataacag attgattgac  1020
gagtcagaca ttggaaatat cccttacatc ggtgtatta tcaatgaaac tctaagactc  1080
tatccagcag ggccattgtt gtttcccact gaaagttctg ccgactgcgt tatttccggt  1140
tacaatatac ctagaggtac aatgttaatc gtaaaccaat gggcgattca tcacgatcct  1200
aaagtctggg atgatcctga aacctttaaa cctgaaagat tcaaggatt agaaggaact  1260
agagatggtt tcaaacttat gccattcggt tctgggagaa gaggatgtcc aggtgaaggt  1320
ttggcaataa ggctgttagg gatgacacta ggccagtga tccaatgttt tgattgggag  1380
agagtaggag atgagatggt tgacatgaca gaaggtttgg gtgtcacact tcctaaggcc  1440
gttccattag ttgccaaatg taagccacgt tccgaaatga ctaatctcct atccgaactt  1500
taa                                                                 1503

SEQ ID NO: 19             moltype = AA  length = 500
FEATURE                   Location/Qualifiers
source                    1..500
                          mol_type = protein
                          organism = Stevia rebaudiana
SEQUENCE: 19
MEASYLYISI LLLLASYLFT TQLRRKSANL PPTVFPSIPI IGHLYLLKKP LYRTLAKIAA    60
KYGPILQLQL GYRRVLVISS PSAAEECFTN NDVIFANRPK TLFGKIVGGT SLGSLSYGDQ   120
WRNLRRVASI EILSVHRLNE FHDIRVDENR LLIRKLRSSS SPVTLITVFY ALTLNVIMRM   180
ISGKRYFDSG DRELEEEGKR FREILDETLL LAGASNVGDY LPILNWLGVK SLEKKLIALQ   240
KKRDDFPQGL IEQVRKSRGA KVGKGRKTMI ELLLSLQESE PEYYTDAMIR SFVLGLLAAG   300
SDTSAGTMEW AMSLLVNHPH VLKKAQAEID RVIGNNRLID ESDIGNIPYI GCIINETLRL   360
YPAGPLLFPH ESSADCVISG YNIPRGTMLI VNQWAIHHDP KVWDDPETFK PERFQGLEGT   420
RDGFKLMPFG SGRRGCPGEG LAIRLLGMTL GSVIQCFDWE RVGDEMVDMT EGLGVTLPKA   480
VPLVAKCKPR SEMTNLLSEL                                               500

SEQ ID NO: 20             moltype = AA  length = 710
FEATURE                   Location/Qualifiers
source                    1..710
                          mol_type = protein
                          organism = Stevia rebaudiana
SEQUENCE: 20
MQSDSVKVSP FDLVSAAMNG KAMEKLNASE SEDPTTLPAL KMLVENRELL TLFTTSFAVL    60
IGCLVFLMWR RSSSKKLVQD PVPQVIVVKK KEKESEVDDG KKKVSIFYGT QTGTAEGFAK   120
ALVEEAKVRY EKTSFKVIDL DDYAADDDEY EEKLKKESLA FFFLATYGDG EPTDNAANFY   180
KWFTEGDDKG EWLKKLQYGV FGLGNRQYEH FNKIAIVVDD KLTEMGAKRL VPVGLGDDDQ   240
CIEDDFTAWK ELVWPELDQL LRDEDDTSVT TPYTAAVLEY RVVYHDKPAD SYAEDQTHTN   300
GHVVHDAQHP SRSNVAFKKE LHTSQSDRSC THLEFDISHT GLSYETGDHV GVYSENLSEV   360
VDEALKLLGL SPDTYFSVHA DKEDGTPIGG ASLPPPFPPC TLRDALTRYA DVLSSPKKVA   420
LLALAAHASD PSEADRLKFL ASPAGKDEYA QWIVANQRSL LEVMQSFPSA KPPLGVFFAA   480
VAPRLQPRYY SISSSPKMSP NRIHVTCALV YETTPAGRIH RGLCSTWMKN AVPLTESPDC   540
```

```
SQASIFVRTS NFRLPVDPKV PVIMIGPGTG LAPFRGFLQE RLALKESGTE LGSSIFFFGC  600
RNRKVDFIYE DELNNFVETG ALSELIVAFS REGTAKEYVQ HKMSQKASDI WKLLSEGAYL  660
YVCGDAKGMA KDVHRTLHTI VQEQGSLDSS KAELYVKNLQ MSGRYLRDVW            710

SEQ ID NO: 21            moltype = AA  length = 692
FEATURE                  Location/Qualifiers
source                   1..692
                         mol_type = protein
                         organism = Arabidopsis thaliana
SEQUENCE: 21
MTSALYASDL FKQLKSIMGT DSLSDDVVLV IATTSLALVA GFVVLLWKKT TADRSGELKP   60
LMIPKSLMAK DEDDDLDLGS GKTRVSIFFG TQTGTAEGFA KALSEEIKAR YEKAAVKVID  120
LDDYAADDDQ YEEKLKKETL AFFCVATYGD GEPTDNAARF YKWFTEENER DIKLQQLAYG  180
VFALGNRQYE HFNKIGIVLD EELCKKGAKR LIEVGLGDDD QSIEDDFNAW KESLWSELDK  240
LLKDEDDKSV ATPYTAVIPE YRVVTHDPRF TTQKSMESNV ANGNTTIDIH HPCRVDVAVQ  300
KELHTHESDR SCIHLEFDIS RTGITYETGD HVGVYAENHV EIVEEAGKLL GHSLDLVFSI  360
HADKEDGSPL ESAVPPPFPG PCTLGTGLAR YADLLNPPRK SALVALAAYA TEPSEAEKLK  420
HLTSPDGKDE YSQWIVASQR SLLEVMAAFP SAKPPLGVFF AAIAPRLQPR YYSISSSPRL  480
APSRVHVTSA LVYGPTPTGR IHKGVCSTWM KNAVPAEKSH ECSGAPIFIR ASNFKLPSNP  540
STPIVMVGPG TGLAPFRGFL QERMALKEDG EELGSSLLFF GCRNRQMDFI YEDELNNFVD  600
QGVISELIMA FSREGAQKEY VQHKMMEKAA QVWDLIKEEG YLYVCGDAKG MARDVHRTLH  660
TIVQEQEGVS SSEAEAIVKK LQTEGRYLRD VW                               692

SEQ ID NO: 22            moltype = AA  length = 713
FEATURE                  Location/Qualifiers
source                   1..713
                         mol_type = protein
                         organism = Fusarium fujikuroi
SEQUENCE: 22
MAELDTLDIV VLGVIFLGTV AYFTKGKLWG VTKDPYANGF AAGGASKPGR TRNIVEAMEE   60
SGKNCVVFYG SQTGTAEDYA SRLAKEGKSR FGLNTMIADL EDYDFDNLDT VPSDNIVMFV  120
LATYGEGEPT DNAVDFYEFI TGEDASFNEG NDPPLGNLNY VAFGLGNNTY EHYNSMVRNV  180
NKALEKLGAH RIGEAGEGDD GAGTMEEDFL AWKDPMWEAL AKKMGLEERE AVYEPIFAIN  240
ERDDLTPEAN EVYLGEPNKL HLEGTAKGPF NSHNPYIAPI AESYELFSAK DRNCLHMEID  300
ISGSNLKYET GDHIAIWPTN PGEEVNKFLD ILDLSGKQHS VVTVKALEPT AKVPFPNPTT  360
YDAILRYHLE ICAPVSRQFV STLAAFAPND DIKAEMNRLG SDKDYFHEKT GPHYYNIARF  420
LASVSKGEKW TKIPFSAFIE GLTKLQPRYY SISSSSLVQP KKISITAVVE SQQIPGRDDP  480
FRGVATNYLF ALKQKQNGDP NPAPFGQSYE LTGPRNKYDL IHVPVHVRHS NFKLPSDPGK  540
PIIMIGPGTG VAPFRGFVQE RAKQARDGVE VGKTLLFFGC RKSTEDFMYQ KEWQEYKEAL  600
GDKFEMITAF SREGSKKVYV QHRLKERSKE VSDLLSQKAY FYVCGDAAHM AREVNTVLAQ  660
IIAEGRGVSE AKGEEIVKNM RSANQYQVCS DFVTLHCKET TYANSELQED VWS         713

SEQ ID NO: 23            moltype = DNA  length = 2130
FEATURE                  Location/Qualifiers
source                   1..2130
                         mol_type = other DNA
                         organism = Stevia rebaudiana
SEQUENCE: 23
atgcaatcgg aatccgttga agcatcgacg attgatttga tgactgctgt tttgaaggac   60
acagtgatcg atacagcgaa cgcatctgat aacggagact caaagatgcc gccggcgttg  120
gcgatgatgt tcgaaattcg tgatctgttg ctgattttga ctacgtcagt tgctgtttta  180
gtcggatgtt tcgttgtttt ggtgtgaaag agatcgtccg ggaagaagtc cggcaaggaa  240
ttggagccgc cgaagatcgt tgtgccgaag aggcggctgg agcaggaggt tgatgatggt  300
aagaagaagg ttacgatttt cttcggaaca caaactggaa cggctgaagg tttcgctaag  360
gcacttttcg aaagagcgaa agcgcgatat gaaaaggcac cgtttaaagt gattgatttg  420
gatgattatg ctgctgattt ggatgagtat gcagagaagc tgaagaagga aacatatgct  480
ttcttcttct tggctacata tggagatggt gagccaactg ataatgctgc caaatttat   540
aaatggttta ctgagggaga cgagaaaggc gtttggcttc aaaaacttca atatggagta  600
tttggtcttg gcaacagaca atatgaacat tcaacaagaa ttggaatagt ggttgatgat  660
ggtctcaccg agcagggtgc aaaacgcatt gttccgttgg tcttggagag cgacgatcaa  720
tcaattgaag acgattttc ggcatggaaa gagttagtgt ggcccgaatt ggatctattg  780
cttcgcgatg aagatgacaa agctgctgca actccttaca cagctgcaat ccctgaatac  840
cgcgtcgtat tcatgacaaa cccgatgcg ttttctgatg atcatactca aaccaatggt  900
catgctgttc atgatgctca acatccatgc agatccaatg tggctgttaa aaaagagtct  960
catactcctg aatccgatcg ttcatgcaca catcttgaat ttgacatttc tcacactgga 1020
ttatcttatg aaactgggga tcatgttggt gtatactgtg aaaacctaat gaagtagtg  1080
gaagaagctg ggaaattgtt aggattatca acagatactt atttctcgtt acatattgat 1140
aacgaagatg gttcaccact tggtggacct tcattacaac ctccttttcc tccttgtact 1200
ttaagaaaag cattgactaa ttatgcagat ctgttaagct ctcccaaaaa gtcaactttg 1260
cttgctctag ctgctcatgc ttccgatccc actgaagctg atcgtttaag atttcttgca 1320
tctcgcgagg gcaaggatga atatgctgaa tgggttgttg caaaccaaag aagtcttctt 1380
gaagtcatgg aagctttccc gtcagctaga ccgccacttg tgttttctt tgcagcggtt 1440
gcaccgcgtt tacagcctcg ttactactct atttcttcct ccccaaagat ggaaccaaac 1500
aggattcatg ttacttcgcg gttggtttat gaaaaaatcc cgacgtcg tatccacaaa 1560
ggaatctgct caacctggat gaagaacgct gtaccttgaa ccgaaagtca agattcagt  1620
tgggcaccga tttttgttag aacatcaaac ttcagacttc caattgaccc gaaagtcccg 1680
gttatcatga ttggtcctgg aacgggttg ctccatttta ggggttttct tcaagaaaga 1740
ttggctctta agaatccgg aaccgaactc gggtcatcta tttattcttc ggttgtaga  1800
aaccgcaaag tggattacat atatgagaat gaactcaaca actttgttga aaatggtgcg 1860
```

-continued

```
ctttctgagc ttgatgttgc tttctcccgc gatggcccga cgaaagaata cgtgcaacat 1920
aaaatgaccc aaaaggcttc tgaaatatgg aatatgcttt ctgagggagc atatttatat 1980
gtatgtggtg atgctaaagg catggctaaa gatgtacacc gtacacttca caccattgtg 2040
caagaacagg aagtttggga ctcgtctaaa gcggagttgt atgtgaagaa tctacaaatg 2100
tcaggaagat acctccgtga tgtttggtaa             2130

SEQ ID NO: 24           moltype = DNA  length = 2124
FEATURE                 Location/Qualifiers
source                  1..2124
                        mol_type = other DNA
                        organism = Stevia rebaudiana
SEQUENCE: 24
atgcaatcta actccgtgaa gatttcgccg cttgatctgg taactgcgct gtttagcggc 60
aaggttttgg acacatcgaa cgcatcggaa tcgggagaat ctgctatgct gccgactata 120
gcgatgatta tggagaatcg tgagctgttg atgatactca aacgtcggt tgctgtattg 180
atcggatgcg ttgtcgtttt ggtgtggcgg agatcgtcta cgaagaagtc ggcgttggag 240
ccaccggtga ttgtggttcc gaagagagtg caagaggagg aagttgatga tggtaagaag 300
aaagttacgg ttttcttcgg cacccaaact ggaacagtcg aaggcttcgc taaggcactt 360
gttgaggaag ctaaagctcg atatgaaaag gctgtcttta agtaattgaa tttggatgat 420
tatgctgctg atgacgatga gtatgaggag aaactaaaga aagaatcttt ggcctttttc 480
tttttggcta cgtatggaga tggtgagcca acagataatg ctgccagatt ttataaatgg 540
tttactgagg gagatcgaa aggagaatgg cttaataagc ttcaatatgg agtatttggt 600
ttgggtaaca gacaatatga acatttttaac aagatcgcaa agtggttgaa tgatggtctt 660
gtagaacagg gtgcaaagcg tcttgttcct gttggacttg agatgatga tcaatgtatt 720
gaagatgact tcaccgcatg gaaagagtta gtatggccgg agttggatca attacttcgt 780
gatgaggatg acacaactgt tgctactcca tacacagctg ctgttgcaga atatcgcgtt 840
gttttcatg aaaaaccaga cgcgcttttct gaagattata gttatacaaa tggccatgct 900
gttcatgatg ctcaacatcc atgcagatcc aacgtggctg tcaaaaagga acttcatagt 960
cctgaatctg accggtcttg cactcatctt gaatttgaca tctcgaacac cggactatca 1020
tatgaaactg gggaccatgt tggagtttac tgtgaaaact tgagtgaagt tgtgaatgat 1080
gctgaaagat tagtaggatt accaccagac acttactcct ccatccacac tgatagtgaa 1140
gacgggtcgc cacttggcgg agcctcattg ccgcctcctt tcccgccatg cactttaagg 1200
aaagcattga cgtgttatgc tgatgttttg agttctccca agaagtcggc tttgcttgca 1260
ctagctgctc atgccaccga tcccagtgaa gctgatagat tgaaatttct tgcatcctcc 1320
gccggaaagg atgaattatc tcaatggata gttgcaagcc aaagaagtct ccttgaagtc 1380
atggaagcat tcccgtcagc taagccttca cttggtgttt tctttgcatc tgttgccccg 1440
cgcttacaac caagatacta ctctatttct tcctcaccca agatggcacc ggataggatt 1500
catgttacat gtgcattagt ctatgagaaa acacctgcag gccgcatcca caaggagtt 1560
tgttcaactt ggatgaagaa cgcagttgcc atgaccgaga gtcaagattg cagttgggcc 1620
ccaatatacg tccgaacatc caatttcaga ctaccatctg accctaaggt cccggttatc 1680
atgattggac ctgcactgg tttggctcct tttagaggtt tccttcaaga gcggttagct 1740
ttaaaggaag ccgaactga cctcggttta tccattttat tcttcggatg taggaatcgc 1800
aaagtggatt tcatatatga aaacgagctt aacaacttcg tggagactgg tgtctcttta 1860
gagcttattg ttgcttttctc ccgtgaaggc ccgactaagg aatatgtgca acacaagatg 1920
agtgagaagg cttcggatat ctggaacttg ctttctgaag gagcatattt atacgtatgt 1980
ggtgatgcca aaggcatggc caagatgta catcgaaccc tccacacaat gtgtcaagaa 2040
cagggatctc ttgactcgtc aaaggcagaa ctctacgtga agaatctaca aatgtcagga 2100
agatacctcc gtgacgtttg gtaa               2124

SEQ ID NO: 25           moltype = AA  length = 692
FEATURE                 Location/Qualifiers
source                  1..692
                        mol_type = protein
                        organism = Arabidopsis thaliana
SEQUENCE: 25
MTSALYASDL FKQLKSIMGT DSLSDDVVLV IATTSLALVA GFVVLLWKKT TADRSGELKP 60
LMIPKSLMAK DEDDDLDLGS GKTRVSIFFG TQTGTAEGFA KALSEEIKAR YEKAAVKVID 120
LDDYAADDDQ YEEKLKKETL AFFCVATYGD GEPTDNAARF YKWFTEENER DIKLQQLAYG 180
VFALGNRQYE HFNKIGIVLD EELCKKGAKR LIEVGLGDDD QSIEDDFNAW KESLWSELDK 240
LLKDEDDKSV ATPYTAVIPE YRVVTHDPRF TTQKSMESNV ANGNTTIDIH HPCRVDVAVQ 300
KELHTHESDR SCIHLEFDIS RTGITYETGD HVGVYAENHV EIVEEAGKLL GHSLDLVFSI 360
HADKEDGSPL ESAVPPPFPG PCTLGTGLAR YADLLNPPRK SALVALAAYA TEPSEAEKLK 420
HLTSPDGKDE YSQWIVASQR SLLEVMAAFP SAKPPLGVFF AAIAPRLQPR YYSISSSPRL 480
APSRVHVTSA LVYGPTPTGR IHKGVCSTWM KNAVPAEKSH ECSGAPIFIR ASNFKLPSNP 540
STPIVMVGPG TGLAPFRGFL QERMLKEDG EELGSSLLFF GCRNRQMDFI YEDELNNFVD 600
QGVISELIMA FSREGAQKEY VQHKMMEKAA QVWDLIKEEG YLYVCGDAKG MARDVHRTLH 660
TIVQEQEGVS SSEAEAIVKK LQTEGRYLRD VW          692

SEQ ID NO: 26           moltype = AA  length = 712
FEATURE                 Location/Qualifiers
source                  1..712
                        mol_type = protein
                        organism = Arabidopsis thaliana
SEQUENCE: 26
MSSSSSSSTS MIDLMAAIIK GEPVIVSDPA NASAYESVAA ELSSMLIENR QFAMIVTTSI 60
AVLIGCIVML VWRRSGSGNS KRVEPLKPLV IKPREEEIDD GRKKVTIFFG TQTGTAEGFA 120
KALGEEAKAR YEKTRFKIVD LDDYAADDDE YEEKLKKEDV AFFFLATYGD GEPTDNAARF 180
YKWFTEGNDR GEWLKNLKYG VFGLGNRQYE HFNKVAKVVD DILVEQGAQR LVQVGLGDDD 240
QCIEDDFTAW REALWPELDT ILREEGDTAV ATPYTAAVLE YRVSIHDSED AKFNDITLAN 300
```

```
GNGYTVFDAQ HPYKANVAVK RELHTPESDR SCIHLEFDIA GSGLTMKLGD HVGVLCDNLS    360
ETVDEALRLL DMSPDTYFSL HAEKEDGTPI SSSLPPPFPP CNLRTALTRY ACLLSSPKKS    420
ALVALAAHAS DPTEAERLKH LASPAGKDEY SKWVVESQRS LLEVMAEFPS AKPPLGVFFA    480
GVAPRLQPRF YSISSSPKIA ETRIHVTCAL VYEKMPTGRI HKGVCSTWMK NAVPYEKSEK    540
LFLGRPIFVR QSNFKLPSDS KVPIIMIGPG TGLAPFRGFL QERLALVESG VELGPSVLFF    600
GCRNRRMDFI YEEELQRFVE SGALAELSVA FSREGPTKEY VQHKMMDKAS DIWNMISQGA    660
YLYVCGDAKG MARDVHRSLH TIAQEQGSMD STKAEGFVKN LQTSGRYLRD VW            712

SEQ ID NO: 27              moltype = AA   length = 709
FEATURE                    Location/Qualifiers
source                     1..709
                           mol_type = protein
                           organism = Stevia rebaudiana
SEQUENCE: 27
MQSESVEAST IDLMTAVLKD TVIDTANASD NGDSKMPPAL AMMFEIRDLL LILTTTSVAVL    60
VGCFVVLVWK RSSGKKSGKE LEPPKIVVPK RRLEQEVDDG KKKVTIFFGT QTGTAEGFAK    120
ALFEEAKARY EKAAFKVIDL DDYAADLDEY AEKLKKETYA FFFLATYGDG EPTDNAAKFY    180
KWFTEGDEKG VWLQKLQYGV FGLGNRQYEH FNKIGIVVDD GLTEQGAKRI VPVGLGDDDQ    240
SIEDDFSAWK ELVWPELDLL LRDEDDKAAA TPYTAAIPEY RVVFHDKPDA FSDDHTQTNG    300
HAVHDAQHPC RSNVAVKKEL HTPESDRSCT HLEFDISHTG LSYETGDHVG VYCENLIEVV    360
EEAGKLLGLS TDTYFSLHID NEDGSPLGGP SLQPPFPPCT LRKALTNYAD LLSSPKKSTL    420
LALAAHASDP TEADRLRFLA SREGKDEYAE WVVANQRSLL EVMEAFPSAR PPLGVFFAAV    480
APRLQPRYYS ISSSPKMEPN RIHVTCALVY EKTPAGRIHK GICSTWMKNA VPLTESQDCS    540
WAPIFVRTSN FRLPIDPKVP VIMIGPGTGL APFRGFLQER LALKESGTEL GSSILFFGCR    600
NRKVDYIYEN ELNNFVENGA LSELDVAFSR DGPTKEYVQH KMTQKASEIW NMLSEGAYLY    660
VCGDAKGMAK DVHRTLHTIV QEQGSLDSSK AELYVKNLQM SGRYLRDVW                709

SEQ ID NO: 28              moltype = AA   length = 707
FEATURE                    Location/Qualifiers
source                     1..707
                           mol_type = protein
                           organism = Stevia rebaudiana
SEQUENCE: 28
MQSNSVKISP LDLVTALFSG KVLDTSNASE SGESAMLPTI AMIMENRELL MILTTTSVAVL    60
IGCVVVLVWR RSSTKKSALE PPVIVVPKRV QEEEVDDGKK KVTVFFGTQT GTAEGFAKAL    120
VEEEAKARYEK AVFKVIDLDD YAADDDEYEE KLKKESLAFF FLATYGDGEP TDNAARFYKW    180
FTEGDAKGEW LNKLQYGVFG LGNRQYEHFN KIAKVVDDGL VEQGAKRLVP VGLGDDDQCI    240
EDDFTAWKEL VWPELDQLLR DEDDTTVATP YTAAVAEYRV VPHEKPDALS EDYSYTNGHA    300
VHDAQHPCRS NVAVKKELHS PESDRSCTHL EFDISNTGLS YETGDHVGVY CENLSEVVND    360
AERLVGLPPD TYSSIHTDSE DGSPLGGASL PPPPFPPCTLR KALTCYADVL SSPKKSALLA    420
LAAHATDPSE ADRLKFLASP AGKDEYSQWI VASQRSLLEV MEAFPSAKPS LGVFFASVAP    480
RLQPRYYSIS SSPKMAPDRI HVTCALVYEK TPAGRIHKGV CSTWMKNAVP MTESQDCSWA    540
PIYVRTSNFR LPSDPKVPVI MIGPGTGLAP FRGFLQERLA LKEAGTDLGL SILFFGCRNR    600
KVDFIYENEL NNFVETGALS ELIVAFSREG PTKEYVQHKM SEKASDIWNL LSEGAYLYVC    660
GDAKGMAKDV HRTLHTIVQE QGSLDSSKAE LYVKNLQMSG RYLRDVW                  707

SEQ ID NO: 29              moltype = AA   length = 460
FEATURE                    Location/Qualifiers
source                     1..460
                           mol_type = protein
                           organism = Stevia rebaudiana
SEQUENCE: 29
MAEQQKIKKS PHVLLIPFPL QGHINPFIQF GKRLISKGVK TTLVTTIHTL NSTLNHSNTT    60
TTSIEIQAIS DGCDEGGFMS AGESYLETFK QVGSKSLADL IKKLQSEGTT IDAIIYDSMT    120
EWVLDVAIEF GIDGGSFFTQ ACVVNSLYYH VHKGLISLPL GETVSVPGFP VLQRWETPLI    180
LQNHEQIQSP WSQMLFGQFA NIDQARWVFT NSFYKLEEEV IEWTRKIWNL KVIGPTLPSM    240
YLDKRLDDDK DNGFNLYKAN HHECMNWLDD KPKESVVYVA FGSLVKHGPE QVEEITRALI    300
DSDVNFLWVI KHKEEGKLPE NLSEVIKTGK GLIVAWCKQL DVLAHESVGC FVTHCGFNST    360
LEAISLGVPV VAMPQFSDQT TNAKLLDEIL GVGVRVKADE NGIVRRGNLA SCIKMIMEEE    420
RGVIIRKNAV KWKDLAKVAV HEGGSSDNDI VEFVSELIKA                         460

SEQ ID NO: 30              moltype = AA   length = 481
FEATURE                    Location/Qualifiers
source                     1..481
                           mol_type = protein
                           organism = Stevia rebaudiana
SEQUENCE: 30
MDAMATTEKK PHVIFIPFPA QSHIKAMLKL AQLLHHKGLQ ITFVNTDPIH NQFLESSGPH    60
CLDGAPGFRF ETIPDGVSHS PEASIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                   481

SEQ ID NO: 31              moltype = DNA   length = 1586
FEATURE                    Location/Qualifiers
```

```
source                      1..1586
                            mol_type = other DNA
                            organism = Stevia rebaudiana
SEQUENCE: 31
atggatgcaa tggctacaac tgagaagaaa ccacacgtca tcttcatacc atttccagca   60
caaagccaca ttaaagccat gctcaaacta gcacaacttc tccaccacaa aggactccag  120
ataaccttcg tcaacaccga cttcatccac aaccagtttc ttgaatcatc gggcccacat  180
tgtctagacg gtgcaccggg tttccggttc gaaaccattc cggatggtgt ttctcacagt  240
ccggaagcga gcatcccaat cagagaatca ctcttgagat ccattgaaac caacttcttg  300
gatcgtttca ttgatcttgt aaccaaactt ccggatcctc cgacttgtat tatctcagat  360
gggttcttgt cggttttcac aattgacgct gcaaaaaagc ttggaattcc ggtcatgatg  420
tattggacac ttgctgcctg tgggttcatg gttttttacc atattcattc tctcattgag  480
aaaggatttg caccacttaa agatgcaagt tacttgacaa atgggtattt ggacaccgtc  540
attgattggg ttccgggaat ggaaggcatc cgtctcaatg atttccccgct ggactggagc  600
actgacctca atgacaaagt tttgatgttc actacgaagc ctcctcaaag gtcacacaag  660
gtttcacatc atattttcca cacgttcgat gagttggagc ctagtattat aaaaaacttg  720
tcattgaggt ataatcacat ttacaccatc ggcccactgc aattacttct tgatcaaata  780
cccgaagaga aaaagcaaac tggaattacg agtctccatg gatacagttt agtaaaagaa  840
gaaccagagt gtttccagtg gcttcagtct aaagaaccaa attccgtcgt ttatgtaaat  900
tttggaagta ctacagtaat gtctttagaa gacatgacgg aatttggttg gggacttgct  960
aatagcaacc attatttcct ttggatcatc cgatcaaact tggtgatagg ggaaaatgca 1020
gttttgcccc ctgaacttga ggaacatata aagaaaagg gctttattgc tagctggtgt 1080
tcacaagaaa aggtcttgaa gcaccccttcg gttggagggt tcttgactca ttgtgggtgg 1140
ggatcgacca tcgagagctt gtctgctggg gtgccaatga tatgctgcc ttattcgtgg 1200
gaccagctga ccaactgtag gtatatatgc aaagaatggg aggttgggct cgagatggga 1260
accaaagtga aacgagatga agtcaagagg cttgtacaag gttgatggg agaaggaggt 1320
cacaaaaatg ggaacaaggc taaagattgg aaagaaaagg ctcgcattgc aatagctcct 1380
aacggttcat cttctttgaa catagacaaa atggtcaagg aaatcaccgt gctagcaaga 1440
aactagttac aaagttgttt cacattgtgc tttctattta agatgtaact ttgttctaat 1500
ttaatattgt ctagatgtat tgaaccataa gtttagttgg tctcaggaat tgattttttaa 1560
tgaaataatg gtcattaggg gtgagt                                      1586

SEQ ID NO: 32              moltype = DNA  length = 1446
FEATURE                    Location/Qualifiers
misc_feature               1..1446
                           note = Codon optimized nucleotide sequence encoding Stevia
                            rebaudiana UGT85C2
source                     1..1446
                           mol_type = other DNA
                           organism = synthetic construct
SEQUENCE: 32
atggatgcaa tggcaactac tgagaaaaag cctcatgtga tcttcattcc atttcctgca   60
caatctcaca taaaggcaat gctaaagtta cacaactata caccataag gggattacag  120
ataactttcg tgaataccga cttcatccat aatcaatttc tggaatctag tggcccctcat  180
tgtttggacg gagcccccagg gtttagattc gaaacaattc ctgacggtgt ttcacattcc  240
ccagaggcct ccatcccaat aagagagagt tactgaggt caatagaaac caacttttg  300
gatcgtttca ttgacttggt cacaaaactt ccagacccac caacttgcat aatctctgat  360
ggctttctgt cagtgtttac tatcgacgct gccaaaaagt ggtgtatccc agttatgatg  420
tactggactc ttgctgcatg cggtttcatg gttctatc acatccattc tcttatcgaa  480
aagggttttg ctccactgaa agatgcatca tacttaacca acggctacct ggatactgtt  540
attgactggg taccaggtat ggaaggtata agacttaag attttccttt tggattggtct  600
acagaccta atgataaagt attgatgttt actacagaag ctccacaaag atctcataag  660
gtttcacatc atatctttca caccttttgat gaattggaac catcaatcat caaaaccttg  720
tctctaagat acaatcatat ctacactatt ggtccattac aattacttct agatcaaatt  780
cctgaagaa aaaagcaaac tggtattaca tccttacacg gctactcttt agtgaaagag  840
gaaccagaat gttttcaatg gctacaagt aaagagccta attctgtggt ctacgtcaac  900
ttcggaagta acagtcat gtccttggaa gatatgactg aatttggttg gggccttgct  960
aattcaaatc attactttct atggatattc aggtccaatt tggtaatagg gaaaacgcc 1020
gtattacctc cagaattgga ggaacacatc aaaaagagaa gttcattgc ttcctggtgt 1080
tctcaggaaa aggtattgaa acatcccttct gttggtggtt tccttactca ttgcggttgg 1140
ggctctacaa tcgaatcact aagtgcagga gttccaatga tttgttgcc atattcatgg 1200
gaccaactta caaattgtag gtatatctgt aaagagtggg aagttggatt agaaatggga 1260
acaaaggtta acgtgatga agtgaaaaga ttggttcagg agttgatggg ggaaggtggc 1320
cacaagatga gaaacaaggc caagattgg aaggaaaaag ccagaattgc tattgctcct 1380
aacgggtcat cctctctaaa cattgataag atggtcaaag agattacagt cttagccaga 1440
aactaa                                                             1446

SEQ ID NO: 33             moltype = AA  length = 787
FEATURE                   Location/Qualifiers
source                    1..787
                          mol_type = protein
                          organism = Stevia rebaudiana
SEQUENCE: 33
MKTGFISPAT VFHHRISPAT TFRHHLSPAT TNSTGIVALR DINFRCKAVS KEYSDLLQKD   60
EASFTKWDDD KVKDHLDTNK NLYPNDEIKE FVESVKAMFG SMNDGEINVS AYDTAWVALV  120
QDVDGSGSPQ FPSSLEWIAN NQLSDGSWGD HLLFSAHDRI INTLACVIAL TSWNVHPSKC  180
EKGLNFLREN ICKLEDENAE HMPIGFEVTF PSLIDIAKKL NIEVPEDTPA LKEIYARRDI  240
KLTKIPMEVL HKVPTTLLHS LEGMPDLEWE KLLKLQCKDG SFLFSPSSTA FALMQTKDEK  300
CLQYLTNIVT KFNGGVPNVY PVDLFEHIWV VDRLQRLGIA RYFKSEIKDC VEYINKYWTK  360
```

```
NGICWARNTH VQDIDDTAMG FRVLRAHGYD VTPDVFRQFE KDGKFVCFAG QSTQAVTGMF   420
NVYRASQMLF PGERILEDAK KFSYNYLKEK QSTNELLDKW IIAKDLPGEV GYALDIPWYA   480
SLPRLETRYY LEQYGGEDDV WIGKTLYRMG YVSNNTYLEM AKLDYNNYVA VLQLEWYTIQ   540
QWYVDIGIEK FESDNIKSVL VSYYLAAASI FEPERSKERI AWAKTTILVD KITSIFDSSQ   600
SSKEDITAFI DKFRNKSSSK KHSINGEPWH EVMVALKKTL HGFALDALMT HSQDIHPQLH   660
QAWEMWLTKL QDGVDVTAEL MVQMINMTAG RWVSKELLTH PQYQRLSTVT NSVCHDITKL   720
HNFKENSTTV DSKVQELVQL VFSDTPDDLD QDMKQTFLTV MKTFYYKAWC DPNTINDHIS   780
KVFEIVI                                                             787

SEQ ID NO: 34           moltype = AA   length = 527
FEATURE                 Location/Qualifiers
source                  1..527
                        mol_type = protein
                        organism = Streptomyces clavuligerus
SEQUENCE: 34
MPDAHDAPPP QIRQRTLVDE ATQLLTESAE DAWGEVSVSE YETARLVAHA TWLGGHATRV    60
AFLLERQHED GSWGPPGGYR LVPTLSAVHA LLTCLASPAQ DHGVPHDRLL RAVDAGLTAL   120
RRLGTSDSPP DTIAVELVIP SLLEGIQHLL DPAHPHSRPA FSQHRGSLVC PGGLDGRTLG   180
ALRSHAAAGT PVPGKVWHAS ETLGLSTEAA SHLQPAQGII GGSAAATATW LTRVAPSQQS   240
DSARRYLEEL QHRYSGPVPS ITPITYFERA WLLNNFAAAG VPCEAPAALL DSLEAALTPQ   300
GAPAGAGLPP DADDTAAVLL ALATHGRGRR PEVLMDYRTD GYFQCFIGER TPSISTNAHV   360
LETLGHHVAQ HPQDRARYGS AMDTASAWLL AAQKQDGSWL DKWHASPYYA TVCCTQALAA   420
HASPATAPAR QRAVRWVLAT QRSDGGWGLW HSTVEETAYA LQILAPPSGG GNIPVQQALT   480
RGRARLCGAL PLTPLWHDKD LYTPVRVVRA ARAAALYTTR DLLLPPL                 527

SEQ ID NO: 35           moltype = AA   length = 516
FEATURE                 Location/Qualifiers
source                  1..516
                        mol_type = protein
                        organism = Bradyrhizobium diazoefficiens
SEQUENCE: 35
MNALSEHILS ELRRLLSEMS DGGSVGPSVY DTAQALRFHG NVTGRQDAYA WLIAQQQADG    60
GWGSADFPLF RHAPTWAALL ALQRADPLPG AADAVQTATR FLQRQPDPYA HAVPEDAPIG   120
AELILPQFCG EAAWLLGGVA FPRHPALLPL RQACLVKLGA VAMLPSGHPL LHSWEAWGTS   180
PTTACPDDDG SIGIGSPAATA AWRAQAVTRG STPQVGRADA YLQMASRATR SGIEGVFPNV   240
WPINVFEPCW SLYTLHLAGL FAHPALAEAV RVIVAQLEAR LGVHGLGPAL HFAADADDTA   300
VALCVLHLAG RDPAVDALRH FEIGELFVTF PGERNASVST NIHALHALRL LGKPAAGASA   360
YVEANRNPHG LWDNEKWHVS WLYPTAHAVA ALAQGKPQWR DERALAALLQ AQRDDGGWGA   420
GRGSTFEETA YALFALHVMD GSEEATGRRR IAQVVARALE WMLARHAAHG LPQTPLWIGK   480
ELYCPTRVVR VAELAGLWLA LRWGRRVLAE GAGAAP                              516

SEQ ID NO: 36           moltype = DNA   length = 4577
FEATURE                 Location/Qualifiers
source                  1..4577
                        mol_type = other DNA
                        organism = Zea mays
SEQUENCE: 36
gacctgacca ccaccccccg gccggcccctt tcattctttc cttactttct tcctcctgct    60
gctcttgccg tttcagtgat tattagctgc tgtacgtgcg tgcgtacatt gttctctctg   120
ctgacaccca tacacgctgt agcttctaca catacccagtt cgatcgcaag ctatagcatg   180
gggcttcaat catcgcccat gctgctgcca gcgccgacgg caacgcggc cggcagcggg   240
tcacagtggc gcacggctgt ggcgggtaat ggtaactcgt ttatcttctt ctacacgtaa   300
tctctattat atacctagat tttctccaca ggcagatcag attctttaca cagctgtatt   360
ctcaaaaaaa actcatagaa aaaaagaaa aaactaaacc aaaggagcga cctcaacctg   420
taccagtgcc cctgctagca gtagcttcgt tctgtccctt tttttttcatt tggatcctct   480
acataaaatgc tggatggtgg tgtcctttca cgcacacatc cgcagatagc gcccccagcag   540
catttatgtg gggacgacgg ctctgaaatg aattactagt cagtttcatg cgtttcagtg   600
cgagtattat agtagtagat ctcttctccg atatatccgg ccaaaggaag aagagaagag   660
aaaccacaca tctcattctc aactagtagt agaaaagtaa aaacgtacta caagcgcaag   720
cgcaaagatg gttcttttcat cgtcttgcac aacagttcct cacctttctt cccttgcgcg t   780
cgttcaacta ggcccatgga gttcccgcat caagaagaag acggatacag tcgccgtccc   840
cgcggccgcc ggcggtgga ggagggccact ggcgcgggcc cagcacacca gcgaatcccg c   900
cgccgtcgcc aaaggtacgg gtgatcgcta gctttgatag ctccaaatct gagcagcaaa   960
ttaaatagct aggtttgtaa cgcacgcacg catgcaggtt cgtccctaac gccatcccgg  1020
agaaccgatg ccgaaagccg ccgcacgaga tggcctacgg acgacgacga cgctgagccg  1080
ctggtcgacg agatcagggc aatgctgacg tcgatgagcg acgggacat cagcgtgtcg  1140
gcgtacgaca ccgcctgggt gggtcttgtg cccaggctgg acggcggcga gggcccgcag  1200
ttcccggccg ccgtgcggtg gatccggaac aaccagctcc ccgacggctc gtggggcgac  1260
gcggccctgt tctccggcta cgaccgcctg atcaacacgc tggcctgcgt cgtcacgctc  1320
accaggtggt cgctgagcc cgagatgcgc ggcagaggta cgtaattact gtgtgctggc  1380
cgatcgagag aacacacgac ggcagtgtac ctcgacagaa aacggcgtt gctgaagact  1440
caagtgtgtg tgtgtgtgtg ttcacagggc tctcttcct cggccggaac atgtggaagc  1500
tagcgacgga ggacgaggag tccatgccga tagggttcga gctcgcgttc ccttctctca  1560
tcgaactagc caagagtctg ggcgtccacg acttcccgta cgaccaccag gtctgcagg  1620
gaatatactc gagcagggag atcaagatga agaggattcc taaggaagtg atgcacacgg  1680
ttcccacatc cattctccac agcctggaag ggatgcccgg gctagactgg gcgaagctgc  1740
tgaaactgca gtcgagcgac gggtccttcc tcttctctcc cgcggccacc gcgtacgctc  1800
tcatgaacac cggcgacgac aggtgcttca gctacatcga caggacagtc aagaaattca  1860
acggaggagg tacgcaagca gtagcgtaga tacatgggca tagcatgcat gcatgcaatg  1920
```

-continued

```
cagcgttgcc cactgcatgc gccttccttc cttccttctc gtctcttcaa cggttcgtct    1980
tctctcgccg tttctcgcag tgcccaacgt ctacccgtg gacctttcg agcacatatg    2040
ggctgtcgat cgcctggagc gtctcgggat ctcccgctac ttccagaaag agattgagca    2100
gtgcatggac tacgtgaaca ggcactggac tgaggacggg atctgctggg cgaggaactc    2160
cgacgtgaag gaggtggacg acacggccat ggctttccgc ctgctacggc tgcacggata    2220
cagcgtctcg ccaggtacgt aacaaacaca aaaaaaaaaa acgcgcagac aacagagatc    2280
gtcacgtcat acacacgcgt gtcctgaaca tttttcattt ggtctcccac ccatcgtacg    2340
taataataat aaaaaaaaac gtgcttctgc cctgcctgtg tacgtgtaga tgtgttcaag    2400
aacttcgaga aggacgggga gttcttcgcc ttcgtggggc agtcgaacca ggcggtgacg    2460
gggatgtaca acctcaacag ggcctcccag ataagcttcc cggggagga cgtcctgcac    2520
cgtgcagggg ctttctcgta cgagtttctc aggcggaaag aggccgaggg agcgctccgt    2580
gacaaatgga tcatatctaa ggacctgcct ggggaggtag tgtacaccct ggacttccct    2640
tggtatggga acctgccgcg cgtggaggcg agagactatc tggaacagta cggcggcggc    2700
gacgatgtct ggatcgggaa gacgctctac aggtagatag atcttttag ctattaattg    2760
gtttcagatc gaccagataa aatttgcatt attggttctt ttgatgcatg taattgaaag    2820
ccaataaaata acctcagtat gcgtgatggc tgacttttgc attggcagga tgcctcttgt    2880
gaataacgat gtgtatcttg agctggctag gatggacttc aaccattgcc aagccctaca    2940
tcagcttgag tggcaaggcc tgaaaaggta tgtatgttac tatatatata cagcccggtt    3000
gttgagtttt tttttatt tattttttc gcgattacca tttcttctcg atgcaaata    3060
aatctgcaca gatcatcata tatatccttg atgatatata agggcttctc gtatatatat    3120
cttatcacct atatatacat aggtggtaca ctgagaaccg gctcatggat ttcggagtgg    3180
cgcaaggga tgctctgcga gcgtatttcc tggccgccgc ttccgtctac gagccgtgcc    3240
gagccgcgga gcggcttgcg tgggccagag cggcgatact tgccaacgcc gtctctaccc    3300
atctccgtaa cagcccctca ttcagagaac gcttggaaca ctccttgcgt tgccgcccca    3360
gtgaagaaac ggatggatca tggtaataag ctgatcgatg gaaattaaa aatttaagtt    3420
ttttttttct tttttgttgc cattatctga gaccaatgca atgtggtgca tatatatcca    3480
ggttcaactc atcaagtgga agtgacgctg ttcttgtgaa ggcagttctg cggcttaccg    3540
actcgttagc gcgagaagcg cagccgattc atggcggtga tccggaggac atcatccaca    3600
agctactgag atcagctgta agttaaacgt aacgttcaga agaagatttt tttttttt    3660
tgcagttaac aagtactacg acatctatcg tttttgttca gcatgcacag tcatcctgc    3720
tactaatacc attattcttc tgtgaacttg tgtagtgggc tgaatgggtc agggagaagg    3780
cagatgcagc agacagcgtg tgtaatggat ccagtgctgt ggaacaagaa gggtcgcgca    3840
tggttcatga caagcaaacg tgtctgcttt tagctcgaat gatcgagatc agcgctgggc    3900
gagctgcagg tgaggctgcg agcgaagatg gtgaccgtcg gattatccag ctcactgggt    3960
ctatatgtga cagtctcaag cagaagatgc tagtatctca ggtatagcac atatatacta    4020
cagaaagttt gtgcgtagtt attatttccc tttttcatg tgacgaacat gatgacctat    4080
tgatgcatgt atatgcttc ataaggacc ccgagaagaa cgaagagatg atgagccatg    4140
tcgatgacga attgaagctg cgtatacgag agttcgttca gtatcttctg agactcggtg    4200
agaagaaaac cggcagcagc gagacaaggc agacctttct ggcatcgtg aaaagctgtt    4260
actacgctgc tcactgcccg ccgcatgtgg tagacaggca tatttccaga gttattttg    4320
aacctgtttc cgccgcaaaa taatggtaat ggtagatgtg aatgtgatat ggagataaga    4380
gagagagaaa atgttgatag tggaaattgg cgttgatgtc gcctcacat tctttacgca    4440
aaagtagcgt ctgttttgga taaaaaaat ccagtttctg taaattatag aataaaatcaa    4500
tcgctgtgtc ccaaactcta aaatgttatt ctgtgaagta tggaataaac cggtcactat    4560
acctatcttg tggatgc                                                  4577
```

SEQ ID NO: 37    moltype = AA  length = 827
FEATURE       Location/Qualifiers
source        1..827
            mol_type = protein
            organism = Zea mays
SEQUENCE: 37

```
MVLSSSCTTV PHLSSLAVVQ LGPWSSRIKK KTDTVAVPAA AGRWRRALAR AQHTSESAAV     60
AKGSSLTPIV RTDAESRRTR WPTDDDDAEP LVDEIRAMLT SMSDGDISVS AYDTAWVGLV    120
PRLDGGEGPQ FPAAVRWIRN NQLPDGSWGD AALFSAYDRL INTLACVVTL TRWSLEPEMR    180
GRGLSFLGRN MWKLATEDEE SMPIGFELAF PSLIELAKSL GVHDFPYDHQ ALQGIYSSRE    240
IKMKRIPKEV MHTVPTSILH SLEGMPGLDW AKLLKLQSSD GSFLFSPAAT AYALMNTGDD    300
RCFSYIDRTV KKFNGGVPNV YPVDLFEHIW AVDRLERLGI SRYFQKEIEQ CMDYVNRHWT    360
EDGICWARNS DVKEVDDTAM AFRLLRLHGY SVSPDVFKNF EKDGEFFAFV GQSNQAVTGM    420
YNLNRASQIS FPGEDVLHRA GAFSYEFLRR KEAEGALRDK WIISKDLPGE VVYTLDFPWY    480
GNLPRVEARD YLEQYGGGDD VWIGKTLYRM PLVNNDVYLE LARMDFNHCQ ALHQLEWQGL    540
KRWYTENRLM DFGVAQEDAL RAYFLAAASV YEPCRAAERL AWARAAILAN AVSTHLRNSP    600
SFRERLEHSL RCRPSEETDG SWFNSSSGSD AVLVKAVLRL TDSLAREAQP IHGGDPEDII    660
HKLLRSAWAE WVREKADAAD SVCNGSSAVE QEGSRMVHDK QTCLLLARMI EISAGRAAGE    720
AASEDGDRRI IQLTGSICDS LKQKMLVSQD PEKNEEMMSH VDDELKLRIR EFVQYLLRLG    780
EKKTGSSETR QTFLSIVKSC YYAAHCPPHV VDRHISRVIF EPVSAAK                  827
```

SEQ ID NO: 38    moltype = DNA length = 2570
FEATURE       Location/Qualifiers
source        1..2570
            mol_type = other DNA
            organism = Arabidopsis thaliana
SEQUENCE: 38

```
cttcttcact aaaatacttag acagagaaaa cagagctttt taaagccatg tctcttcagt     60
atcatgttct aaaactccatt ccaagtacaa ccttttctcag ttctactaaa acaacaatat    120
cttcttcttt cctaccatc tcaggatctc tctcaatgt cgctagagac aaatccagaa    180
gcggttccat acattgttca aagcttgaa ctcaagaata cattaattct caagaggttc    240
aacatgattt gcctctaata catgagtggc aacagcttca aggagaagat gctcctcaga    300
ttagtgttgg aagtaatagt aatgcattca aagaagcagt gaagagtgtg aaaacgatct    360
```

```
tgagaaacct aacggacggg gaaattacga tatcggctta cgatacagct tgggttgcat    420
tgatcgatgc cggagataaa actccggcgt ttccctccgc cgtgaaatgg atcgccgaga    480
accaactttc cgatggttct tggggagatg cgtatctctt ctcttatcat gatcgtctca    540
tcaatacccg tgcatgcgtc gttgctctaa gatcatggaa tctctttcct catcaatgca    600
acaaaggaat cacgttttc cgggaaaata ttgggaagct agaagacgaa aatgatgagc     660
atatgccaat cggattcgaa gtagcattcc catcgttgct tgagatagct cgaggaataa    720
acattgatgt accgtacgat tctccggtct aaaagatat atacgccaag aaagagctaa     780
agcttacaag gataccaaaa gagataatgc acaagatacc aacaacattg ttgcatagtt    840
tggaggggat gcgtgattta gattgggaaa agctcttgaa acttcaatct caagacgtat    900
cttcctctt ctctccttcc tctaccgctt ttgcattcat gcagacccga gacagtaact      960
gcctcgagta tttgcgaaat gccgtcaaac gtttcaatgg aggagttccc aatgtctttc   1020
ccgtggatct tttcgagcac atatggatag tggatcggtt acaacgttta gggatatcga   1080
gatactttga agaagagatt aaagagtgtc ttgactatgt ccacagatat tggaccgaca   1140
atggcatatg ttgggctaga tgttcccatg tccaagacat cgatgataca gccatggcat   1200
ttaggctctt aagacaacat ggataccaag tgtccgcaga tgtattcaag aactttgaga   1260
aagagggaga gttttctgc tttgtggggc aatcaaacca agcagtaacc ggtatgttca     1320
acctataccg ggcatcacaa ttggcgtttc aagggaaga gatattgaaa aacgccaaag     1380
agttttctta taattatctg ctagaaaaac gggagagaga ggagttgatt gataagtgaa   1440
ttataatgaa agacttacct ggcgagattg ggtttgcgtt agagattcca tggtacgcaa   1500
gcttgcctcg agtagagacg agattctata ttgatcaata tggtgagaa aacgacgttt      1560
ggattggcaa gactctttat aggatgccat acgtgaacaa taatggatat ctggaattag   1620
caaaacaaga ttacaacaat tgccaagctc agcatcgact cgaatgggac atattccaaa   1680
agtggtatga agaaaatagg ttaagtgagt ggggtgtgcg cagaagtgag cttctcgagt   1740
gttactactt agcggctgca actatatttg aatcagaaag gtcacatgag agaatggttt   1800
gggctaagtc aagtgtattg gttaaagcca tttcttcttc ttttgggaa tcctctgact      1860
ccagaagaag cttctccgat cagtttcatg aatacattgc caagtctcga cgaagtgatc   1920
atcactttaa tgacaggaac atgagattgg accgaccagg atcggttcag gccagtcggc   1980
ttgccggagt gttaatcggg actttgaatc aaatgtcttt tgacctttc atgtctcatg       2040
gccgtgacgt taacaatctc ctctatctat cgtggggaga ttggatgaa aaatggaaac     2100
tatatggaga tgaaggagaa ggagagctca tggtgaagat gataattcta attgaagaaca   2160
atgacctaac taacttcttc acccacactc acttcgttcg tctcgcggaa atcatcaatc    2220
gaatctgtct tcctcgccaa tacttaaagg caaggagaaa cgatgagaag gagaagacaa   2280
taaagagtat ggagaaggag atggggaaaa tggttgagtt agcattgtcg gagagtgaca   2340
catttcgtga cgtcagcatc acgttttctg atgtagcaaa agcattttac tactttgctt    2400
tatgtggcga tcatctccaa actcacatct ccaaagtctt gtttcaaaaa gtctagtaac    2460
ctcatcatca tcatcgatcc attaacaatc agtggatcga tgtatccata gatgcgtgaa    2520
taatatttca tgtagagaag gagaacaaat tagatcatgt agggttatca                    2570
```

SEQ ID NO: 39           moltype = AA   length = 802
FEATURE                 Location/Qualifiers
source                  1..802
                        mol_type = protein
                        organism = Arabidopsis thaliana
SEQUENCE: 39
MSLQYHVLNS IPSTTFLSST KTTISSSFLT ISGSPLNVAR DKSRSGSIHC SKLRTQEYIN    60
SQEVQHDLPL IHEWQQLQGE DAPQISVGSN SNAFKEAVKS VKTILRNLTD GEITISAYDT   120
AWVALIDAGD KTPAFPSAVK WIAENQLSDG SWGDAYLFSY HDRLINTLAC VVALRSWNLF   180
PHQCNKGITF FRENIGKLED ENDEHMPIGF EVAFPSLLEI ARGINIDVPY DSPVLKDIYA   240
KKELKLTRIP KEIMHKIPTT LLHSLEGMRD LDWEKLLKLQ SQDGSFLFSP SSTAFAFMQT   300
RDSNCLEYLR NAVKRFNGGV PNVFPVDLFE HIWIVDRLQR LGISRYFEEE IKECLDYVHR   360
YWTDNGICWA RCSHVQDIDD TAMAFRLLRQ HGYQVSADVF KNFEKEGEFF CFVGQSNQAV   420
TGMFNLYRAS QLAFPREEIL KNAKEFSYNY LLEKREREEL IDKWIIMKDL PGEIGFALEI   480
PWYASLPRVE TRFYIDQYGG ENDVWIGKTL YRMPYVNNNG YLELAKQDYN NCQAHQLEW    540
DIFQKWYEEN RLSEWGVRRS ELLECYYLAA ATIFESERSH ERMVWAKSSV LVKAISSSFG   600
ESSDSRRSFS DQFHEYIANA RRSDHHFNDR NMRLDRPGSV QASRLAGVLI GTLNQMSFDL   660
FMSHGRDVNN LLYLSWGDWM EKWKLYGDEG EGELMVKMII LMKNNDLTNF FTHTHFVRLA   720
EIINRICLPR QYLKARRNDE KEKTIKSMEK EMGKMVELAL SESDTFRDVS ITFLDVAKAF   780
YYFALCGDHL QTHISKVLFQ KV                                          802

SEQ ID NO: 40           moltype = AA   length = 983
FEATURE                 Location/Qualifiers
source                  1..983
                        mol_type = protein
                        organism = Diaporthe amygdali
SEQUENCE: 40
MEFDEPLVDE ARSLVQRTLQ DYDDRYGFGT MSCAAYDTAW VSLVTKTVDG RKQWLFPECF    60
EFLLETQSDA GGWEIGNSAP IDGILNTAAS LLALKRHVQT EQIIQPQHDH KDLAGRAERA   120
AASLRAQLAA LDVSTTEHVG FEIIVPAMLD PLEAEDPSLV FDPPARKPLM KIHDAKMSRF   180
RPEYLYGKQP MTALHSLEAF IGKKIDFDKVR HHRTHGSMMG SPSSTAAYLM HASQWDGDSE   240
AYLRHVIKHA AGQGTGAVPS AFPSTHFESS WILTTLFRAG FSASHLACDE LNKLVEILEG   300
SPFEKEGGAIG YAPGFQADVD DTAKTISTLA VLGRDATPRQ MIKVFEANTH FRTYPGERDP   360
SLTANCNALS ALLHQPDAAM YGSQIQKITK FVCDYWWKSD GKIKDWNTC YLYPSVLLVE    420
VLVDLVSLLE QGKLPDVLDQ ELQYRVAITL FQACLRPLLD QDAEGSWNKS IEATAYGILI   480
LTEARRVCFF DRLSEPLNEA IRRGIAFADS MSGTEAQLNY IWIEKVSYAP ALLTKSYLLA   540
ARWAAKSPLG ASVGSSLWTP PREGLDKHVR LFHQAELFRS LPEWELRASM IEAALFTPLL   600
RAHRLDVFPR QDVGEDKYLD VVPFFWTAAN NRDRTYASTL FLYDMCFIAM LNFQLDEFME   660
ATAGILFRDH MDDLRQLIHD LLAEKTSPKS SGRSSQGTKD ADSGIEEDVS MSDSASDSQD   720
RSPEYDLVFS ALSTFTKHVL QHPSIQSASV WDRKLLAREM KAYLLAHIQQ AEDSTPLSEL   780
KDVPQKTDVT RVSTSTTTFF NWVRTTSADH ISCPYSFHFV ACHLGAALSP KGSNGDCYPS   840

```
AGEKFLAAAV CRHLATMCRM YNDLGSAERD SDEGNLNSLD FPEFADSAGN GGIEIQKAAL    900
LRLAEFERDS YLEAFRRLQD ESNRVHGPAG GDEARLSRRR MAILEFFAQQ VDLYGQVYVI    960
RDISARIPKN EVEKKRKLDD AFN                                           983

SEQ ID NO: 41           moltype = AA   length = 881
FEATURE                 Location/Qualifiers
source                  1..881
                        mol_type = protein
                        organism = Physcomitrella patens
SEQUENCE: 41
MASSTLIQNR SCGVTSSMSS FQIFRGQPLR FPGTRTPAAV QCLKKRRCLR PTESVLESSP    60
GSGSYRIVTG PSGINPSSNG HLQEGSLTHR LPIPMEKSID NFQSTLYVSD IWSETLQRTE    120
CLLQVTENVQ MNEWIEEIRM YFRNMTLGEI SMSPYDTAWV ARVPALDGSH GPQFHRSLQW    180
IIDNQLPDGD WGEPSLFLGY DRVCNTLACV IALKTWGVGA QNVERGIQFL QSNIYKMEED    240
DANHMPIGFE IVFPAMMEDA KALGLDLPYD ATILQQISAE REKKMKKIPM AMVYKYPTTL    300
LHSLEGLHRE VDWNKLLQLQ SENGSFLYSP ASTACALMYT KDVKCFDYLN QLLIKFDHAC    360
PNVYPVDLFE RLWMVDRLQR LGISRYFERE IRDCLQYVYR YWKDCGIGWA SNSSVQDVDD    420
TAMAFRLLRT HGFDVKEDCF RQFFKDGEFF CFAGQSSQAV TGMFNLSRAS QTLFPGESLL    480
KKARTFSRNF LRTKHENNEC FDKWIITKDL AGEVEYNLTF PWYASLPRLE HRTYLDQYGI    540
DDIWIGKSLY KMPAVTNEVF LKLAKADFNM CQALHKKELE QVIKWNASCQ FRDLEFARQK    600
SVECYFAGAA TMFEPEMVQA RLVWARCCVL TTVLDDYFDH GTPVEELRVF VQAVRTWNPE    660
LINGLPEQAK ILFMGLYKTV NTIAEEEAFMA QKRDVHHHLK HYWDKLITSA LKEAEWAESG   720
YVPTFDEYME VAEISVALEP IVCSTLFFAG HRLDEDVLDS YDYHLVMHLV NRVGRILNDI   780
QGMKREASQG KISSVQIYME EHPSVPSEAM AIAHLQELVD NSMQQLTYEV LRFTAVPKSC    840
KRIHLNMAKI MHAFYKDTDG FSSLTAMTGF VKKVLFEPVP E                       881

SEQ ID NO: 42           moltype = AA   length = 952
FEATURE                 Location/Qualifiers
source                  1..952
                        mol_type = protein
                        organism = Fusarium fujikuroi
SEQUENCE: 42
MPGKIENGTP KDLKTGNDFV SAAKSLLDRA FKSHHSYYGL CSTSCQVYDT AWVAMIPKTR    60
DNVKQWLFPE CFHYLLKTQA ADGSWGSLPT TQTAGILDTA SAVLALLCHA QEPLQILDVS    120
PDEMGLRIEH GVTSLKRQLA VWNDVEDTNH IGVEFIIPAL LSMLEKEDV  PSFEFPCRSI    180
LERMHGEKLG HFDLEQVYGK PSSLLHSLEA FLGKLDFDRL SHHLYHGSMM ASPSSTAAYL    240
IGATKWDDEA EDYLRHVMRN GAGHGNGGIS GTFPTTHFEC SWIIATLLKV GFTLKQIDGD    300
GLRGLSTILL EALRDENGVI GFAPRTADVD DTAKALLALS LVNQPVSPDI MIKVFEGKDH    360
FTTFGSERDP SLTSNLHVLL SLLKQSNLSQ YHPQILKTTL FTCRWWWGSD HCVKDKWNLS    420
HLYPTMLLVE AFTEVLHLID GGELSSLFDE SFKCKIGLSI FQAVLRIILT QDNDGSWRGY    480
REQTCYAILA LVQARHVCFF THMVDRLQSC VDRGFSWLKS CSFHSQDLTW TSKTAYEVGF    540
VAEAYKLAAL QSASLEVPAA TIGHSVTSAV PSSDLEKYMR LVRKTALFSP LDEWGLMASI    600
IESSFFVPLL QAQRVEIYPR DNIKVDEDKY LSIIPFTWVG CNNRSRTFAS NRWLYDMMYL    660
SLLGYQTDEY MEAVAGPVFG DVSLLHQTID KVIDNTMGNL ARANGTVHSG NGHQHESPNI    720
GQVEDTLTRF TNSVLNHKDV LNSSSSDQDT LRREFRTFMH AHITQIEDNS RFSKQASSDA    780
FSSPEQSYFQ WVNSTGGSHV ACAYSFAFSN CLMSANLLQG KDAFPSGTQK YLISSVMRHA    840
TNMCRMYNDF GSIARDNAER NVNSIHFPEF TLCNGTSQNL DERKERLLKI ATYEQGYLDR    900
ALEALERQSR DDAGDRAGSK DMRKLKIVKL FCDVTDLYDQ LYVIKDLSSS MK            952

SEQ ID NO: 43           moltype = AA   length = 361
FEATURE                 Location/Qualifiers
source                  1..361
                        mol_type = protein
                        organism = Stevia rebaudiana
SEQUENCE: 43
MALVNPTALF YGTSIRTRPT NLLNPTQKLR PVSSSSLPSF SSVSAILTEK HQSNPSENNN    60
LQTHLETPFN FDSYMLEKVN MVNEALDASV PLKDPIKIHE SMRYSLLAGG KRIRPMMCIA    120
ACEIVGGNIL NAMPAACAVE MIHTMSLVHD DLPCMDNDDF RRGKPISHKV YGEEMAVLTG    180
DALLSLSFEH IATATKGVSK DRIVRAIGEL ARSVGSEGLV AGQVVDILSE GADVGLDHLE    240
YIHIHKTAML LESSVVIGAI MGGGSDQQIE KLRKFARSIG LLFQVVDDIL DVTKSTEELG    300
KTAGKDLLTD KTTYPKLLGI EKSREFAEKL NKEAQEQLSG FDRRKAAPLI ALANYNAYRQ    360
N                                                                   361

SEQ ID NO: 44           moltype = AA   length = 342
FEATURE                 Location/Qualifiers
source                  1..342
                        mol_type = protein
                        organism = Fusarium fujikuroi
SEQUENCE: 44
MAEQQISNLL SMFDASHASQ KLEITVQMMD TYHYRETPPD SSSSEGGSLS RYDERRVSLP    60
LSHNAASPDI VSQLCFSTAM SSELNHRWKS QRLKVADSPY NYILTLPSKG IRGAFIDSLN    120
VWLEVPEDET SVIKEVIGML HNSSLIIDDF QDNSPLRRGK PSTHTVFGPA QAINTATYVI    180
VKAIEKIQDI VGHDALADVT GTITTIFQGQ AMDLWWTANA IVPSIQEYLL MVNDKTGALF    240
RLSLELLALN SEASISDSAL ESLSSAVSLL GQYFQIRDDY MNLIDNKYTD QKGFCEDLDE    300
GKYSLTLIHA LQTDSSDLLT NILSMRRVQG KLTAQKRCWF WK                      342

SEQ ID NO: 45           moltype = AA   length = 300
FEATURE                 Location/Qualifiers
source                  1..300
```

```
                        mol_type = protein
                        organism = Mus musculus
SEQUENCE: 45
MEKTKEKAER ILLEPYRYLL QLPGKQVRSK LSQAFNHWLK VPEDKLQIII EVTEMLHNAS  60
LLIDDIEDSS KLRRGFPVAH SIYGVPSVIN SANYVYFLGL EKVLTLDHPD AVKLFTRQLL 120
ELHQGQGLDI YWRDTYTCPT EEEYKAMVLQ KTGGLFGLAV GLMQLFSDYK EDLKPLLDTL 180
GLFFQIRDDY ANLHSKEYSE NKSFCEDLTE GKFSFPTIHA IWSRPESTQV QNILRQRTEN 240
IDIKKYCVQY LEDVGSFAYT RHTLRELEAK AYKQIEACGG NPSLVALVKH LSKMFTEENK 300

SEQ ID NO: 46           moltype = AA  length = 339
FEATURE                 Location/Qualifiers
source                  1..339
                        mol_type = protein
                        organism = Thalassiosira pseudonana
SEQUENCE: 46
MARFYFLNAL LMVISLQSTT AFTPAKLAYP TTTTALNVAS AETSFSLDEY LASKIGPIES  60
ALEASVKSRI PQTDKICESM AYSLMAGGKR IRPVLCIAAC EMFGGSQDVA MPTAVALEMI 120
HTMSLIHDDL PSMDNDDLRR GKPTNHVVFG EDVAILAGDS LLSTSFEHVA RETKGVSAEK 180
IVDVIARLGK SVGAEGLAGG QVMDLECEAK PGTTLDDLKW IHIHKTATLL QVAVASGAVL 240
GGATPEEVAA CELFAMNIGL AFQVADDILD VTASSEDLGK TAGKDEATDK TTYPKLLGLE 300
ESKAYARQLI DEAKESLAPF GDRAAPLLAI ADFIIDRKN                        339

SEQ ID NO: 47           moltype = AA  length = 355
FEATURE                 Location/Qualifiers
source                  1..355
                        mol_type = protein
                        organism = Streptomyces clavuligerus
SEQUENCE: 47
MHLAPRRVPR GRRSPPDRVP ERQGALGRRR GAGSTGCARA AAGVHRRRGG GEADPSAAVH  60
RGWQAGGGTG LPDEVVSTAA ALEMFHAFAL IHDDIMDDSA TRRGSPTVHR ALADRLGAL 120
DPDQAGQLGV STAILVGDLA LTWSDELLYA PLTPHRLAAV LPLVTAMRAE TVHGQYLDIT 180
SARRPGTDTS LALRIARYKT AAYTMERPLH IGAALAGARP ELLAGLSAYA LPAGEAFQLA 240
DDLLGVFGDP RRTGKPDLDD LRGGKHTVLV ALAREHATPE QRHTLDTLLG TPGLDRQGAS 300
RLRCVLVATG ARAEAERLIT ERRDQALTAL NALTLPPPLA EALARLTLGS TAHPA      355

SEQ ID NO: 48           moltype = AA  length = 330
FEATURE                 Location/Qualifiers
source                  1..330
                        mol_type = protein
                        organism = Sulfolobus acidocaldarius
SEQUENCE: 48
MSYFDNYFNE IVNSVNDIIK SYISGDVPKL YEASYHLFTS GGKRLRPLIL TISSDLFGGQ  60
RERAYYAGAA IEVLHTFTLV HDDIMDQDNI RRGLPTVHVK YGLPLAILAG DLLHAKAFQL 120
LTQALRGLPS ETIIKAFDIF TRSIIIISEG QAVDMEFEDR IDIKEQEYLD MISRKTAALF 180
SASSSIGALI AGANDNDVRL MSDFGTNLGI AFQIVDDILG LTADEKELGK PVFSDIREGK 240
KTILVIKTLE LCKEDEKKIV LKALGNKSAS KEELMSSADI IKKYSLDYAY NLAEKYYKNA 300
IDSLNQVSSK SDIPGKALKY LAEFTIRRRK                                  330

SEQ ID NO: 49           moltype = AA  length = 297
FEATURE                 Location/Qualifiers
source                  1..297
                        mol_type = protein
                        organism = Synechococcus sp.
SEQUENCE: 49
MVAQTFNLDT YLSQRQQQVE EALSAALVPA YPERIYEAMR YSLLAGGKRL RPILCAACE   60
LAGGSVEQAM PTACALEMIH TMSLIHDDLP AMDNDDFRRG KPTNHKVFGE DIAILAGDAL 120
LAYAFEHIAS QTRGVPPQLV LQVIARIGHA VAATGLVGGQ VVDLESEGKA ISLETLEYIH 180
SHKTGALLEA SVVSGGILAG ADEELLARLS HYARDIGLAF QIVDDILDVT ATSEQLGKTA 240
GKDQAAAKAT YPSLLGLEAS RQKAEELIQS AKEALRPYGS QAEPLLALAD FITRRQH    297

SEQ ID NO: 50           moltype = AA  length = 371
FEATURE                 Location/Qualifiers
source                  1..371
                        mol_type = protein
                        organism = Arabidopsis thaliana
SEQUENCE: 50
MASVTLGSWI VVHHHNHHHP SSILTKSRSR SCPITLTKPI SFRSKRTVSS SSSIVSSSVV  60
TKEDNLRQSE PSSFDPMSYI ITKAELVNKA LDSAVPLREP LKIHEAMRYS LLAGGKRVRP 120
VLCIAACELV GGEESTAMPA ACAVEMIHTM SLIHDDLPCM DNDDLRRGKP TNHKVFGEDV 180
AVLAGDALLS FAFEHLASAT SSDVVSPVRV VRAVGELAKA IGTEGLVAGQ VVDISSEGLD 240
LNDVGLEHLE FIHLHKTAAL LEASAVLGAI VGGGSDDEIE RLRKFARCIG LLFQVVDDIL 300
DVTKSSKELG KTAGKDLIAD KLTYPKIMGL EKSREFAEKL NREARDQLLG FDSDKVAPLL 360
ALANYIAYRQ N                                                      371

SEQ ID NO: 51           moltype = DNA  length = 2139
FEATURE                 Location/Qualifiers
misc_feature            1..2139
                        note = Codon optimized nucleotide seqeunce encoding A.
                        thaliana ATR2
```

```
source                  1..2139
                        mol_type = other DNA
                        organism = synthetic construct
SEQUENCE: 51
atgtcttcct cttcctcttc cagtaccctct atgattgatt tgatggctgc tattattaaa    60
ggtgaaccag ttatcgtctc cgacccagca aatgcctctg cttatgaatc agttgctgca   120
gaattgtctt caatgttgat cgaaaacaga caattcgcca tgatcgtaac tacatcaatc   180
gctgttttga tcggttgtat tgtcatgttg gtatggagaa gatccggtag tggtaattct   240
aaaagagtcg aacctttgaa accattagta attaagcgaa gagaagaaga aatagatgac   300
ggtagaaaga aagttacaat attttttcggt acccaaactg gtacagctga aggttttgca   360
aaagccttag gtgaagaagc taaggcaaga tacgaaaaga ctagattcaa gatagtcgat   420
ttggatgact atgccgctga tgacgatgaa tacgaagaaa agttgaagaa agaagatgtt   480
gcattttttct ttttggcaac ctatggtgac ggtgaaccaa ctgacaatgc agccagattc   540
tacaaatggt ttacagaggg taatgatcgt ggtgaatggt tgaaaaactt aaagtacgagt   600
gttttcggtt tgggtaacag acaatacgaa catttcaaca aagttgcaaa ggttgtcgac   660
gatattttgt cgaacaagg tgctcaaaga ttagtccaag taggtttggg tgacgatgac   720
caatgtatag aagatgactt tactgcctgg agagaagctt gtggcctgaa attagacaca   780
atcttgagag aagaaggtga caccgccgtt gctaccccat atactgctgc agtattagaa   840
tacagagttt ccatccatga tagtgaagac gcaaagttta atgatatcac tttggccaat   900
ggtaacggtt atacagtttt cgatgcacaa caccccttaca aagctaacgt tgcagtcaag   960
agagaattac atacaccaga atccgacaga agttgtatac acttggaatt tgatatcgct  1020
ggttccggtt taaccatgaa gttgggtgac catgtaggtg tttatgcga caatttgtct  1080
gaaactgttg atgaagcatt gagattgttg gatatgtccc ctgacactta ttttagtttg  1140
cacgctgaaa aagaagatgg tacaccaatt tccagttctt taccacctcc attccctcca  1200
tgtaacttaa gaacagcctt gaccagatac gcttgcttgt tatcatcccc taaaaagtcc  1260
gccttggttg ctttagccgc tcatgctagt gatcctactg aagcagaaga attgaaacac  1320
ttagcatctc cagccggtaa agataatat tcaaagtggg tagttgaatc tcaaagatca  1380
ttgttagaag ttatggcaga atttccatct gccaagcctc cattaggtgt cttctttgct  1440
ggtgtagcac ctagattgca accaagattc tactcaatca gttcttcacc taagatcgct  1500
gaaactagaa ttcatgttac atgtcatta gtctacgaaa ggccaac cggtagaatt  1560
cacaagggtg tatgctctac ttggatgaaa aatgctgttc cttacgaaaa atcagaaaag  1620
ttgttcttag gtagaccaat cttcgtaaga caatcaaact tcaagttgcc ttctgattca  1680
aaggttccaa taatcatgat aggtcctggt acaggtttag ccccattcag aggtttcttg  1740
caagaaagat tggctttagt tgaatctggt gtcgaattag gtccttcagt tttgttcttt  1800
ggttgtagaa acagaagaat ggatttcatc tatgaagaag aattgcaaag attcgtcgaa  1860
tctggtgcat tggccgaatt atctgtagct ttttcaagag aaggtccaac taaggaatac  1920
gttcaacata agatgatgga taaggcatcc gacatatgga acatgatcag tcaaggtgct  1980
tatttgtacg tttgcggtga cgcaaagggt atggccagag atgtccatag atctttgcac  2040
acaattgctc aagaacaagg ttccatggat agtaccaaag ctgaaggttt cgtaaagaac  2100
ttacaaactt ccggtagata cttgagagat gtctggtga                         2139

SEQ ID NO: 52            moltype = DNA   length = 1555
FEATURE                  Location/Qualifiers
source                   1..1555
                         mol_type = other DNA
                         organism = Stevia rebaudiana
SEQUENCE: 52
atggcggaac aacaaaagat caagaaatca ccacacgttc tactcatccc attcccttta    60
caaggccata taaaccccttt catccagttt ggcaaacgat taatctccaa aggtgtcaaa   120
acaacacttg ttaccaccat ccacacctta aactcaaccc taaccacag taacaccacc   180
accacctcca tcgaaatcca agcaatttcc gatggttgtg atgaaggcgg tttttatgag   240
gcaggagaat catatttgga aacattcaaa caagttgggt ctaaatcact agctgactta   300
atcaagaagc ttcaaagtga aggaaccaca attgatgcaa tcatttatga ttctatgact   360
gaatgggttt tagatgttgc aattgagttt ggaatcgatg tggttcgtt tttcactcaa   420
gcttgttgtg taaacagctt atattatcat gttcataagg gtttgattc tttgccattg   480
ggtgaaactg tttcggttcc tggattttcca gtgcttcaac ggtgggagac accgttaatt   540
ttgcagaatc atgagcaaat acagagccct ggtctcaga tgttgtttgg tcagtttgct   600
aatattgatc aagcacgttg gtcttcaca aatagttttt acaagctcga ggaagaggta   660
atagagtgga cgagaaagat atggaacttg aaggtaatcg ggccaacact tccatccatg   720
taccttgaca aacgacttga tgatgataaa gataaccggt ttaatctcta caaagcaaac   780
catcatgagt gcatgaactg gttagacgat aagccaaaag aatcagttgt ttacgtagca   840
tttggtagcc tggtgaaaca tggacccgaa caagtgaag aaatcacacg gctttaata   900
gatagtgatg tcaacttctt gtgggttatc aaacataaag aagagggaaa gctcccagaa   960
aatcttctgg aagtaataaa aaccggaaag gtttgattg tagcatgcga caattgttt  1020
gatgtgttag cacacgaatc agtaggatgc tttgttacaa attgtgggtt caactcaact  1080
cttgaagcaa taagtcttgg agtcccgtt ttgcaatgc tcaatttttc ggatcaaact  1140
acaaatgcca agcttctaga tgaaatttgg ggtgttggaa ttagagttaa ggctgatgag  1200
aatggatagt gagaaagagg aaattctttg tcatgtatta atagattatt ggaggaggaa  1260
agaggagtaa taatccgaaa gaatgcggta aaatggaagg atttggctaa agtagccgtt  1320
catgaaggtg gtagctcaga caatgatatt gtcgaatttg taagtgagct aattaaggct  1380
taaatttttg ttgctttgta ttttatgtgt tatggttttt tgatttagat gtattcaatt  1440
aatattgaat cataactaaa ttcaagatta ttgtttgtaa tattctttgt cctaaaattt  1500
tgcgacttaa aaccttttagt tttataaaag aaattgaaaa atactattgc acgga      1555

SEQ ID NO: 53            moltype = DNA   length = 1377
FEATURE                  Location/Qualifiers
misc_feature             1..1377
                         note = Codon-optimized S. rebaudiana UGT76G1
source                   1..1377
```

```
                        mol_type = other DNA
                        organism = synthetic construct
SEQUENCE: 53
atggaaaaca agaccgaaac aacagttaga cgtaggcgta gaatcattct gtttccagta    60
cctttcaag  ggcacatcaa tccaatacta caactagcca acgttttgta tctctaaaggt  120
ttttctatta caatctttca caccaatttc aacaaaccaa aaacatccaa ttacccacat   180
ttcacattca gattcatact tgataatgat ccacaagatg aacgtatttc aaacttacct   240
acccacggtc ctttagctgg aatgagaatt ccaatcatca atgaacatgg tgccgatgag   300
cttagaagag aattagagtt acttatgttg gcatccgaaa aggacgagga agtctcttgt   360
ctgattactg acgctctatg gtactttgcc caatctgtgg ctgatagttt gaatttgagg   420
agattggtac taatgacatc cagtctgttt aactttcacg ctcatgttag tttaccacaa   480
tttgacgaat tgggatactt ggaccctgat gacaagacta ggttagagga acaggcctct   540
ggttttccta tgttgaaagt caaagatatc aagtctgcct attctaattg gcaaatcttg   600
aaagagatct taggaaagat gatcaaacag acaaaggctt catctggagt gatttggaac   660
agtttcaaag agttagaaga gtctgaattg gagactgtaa tcagagaaat tccagccct   720
tcattcctga taccattacc aaaacatttg actgcttcct cttcctcttt gttggatcat   780
gacagaacag tttttcaatg gttggaccaa caaccaccta gttctgtttt gtacgtgtca   840
tttggtagta cttctgaagt cgatgaaaag gacttccttg aaatcgcaag aggcttagtc   900
gatagtaagc agtcattcct ttgggtcgtg cgtccaggtt tcgtgaaagg ctcaacatgg   960
gtcgaaccac ttccagatgg ttttctaggc gaaagaggta gaatagtcaa atgggttcct  1020
caacaggaag ttttagctca tggcgctatt ggggcattct ggactcattc cggatggaat  1080
tcaactttag aatcagtatg cgaagggta  cctatgatct tttcagattt tggtcttgat  1140
caaccactga acgcaagata catgtctgat gttttgaaag tgggtgtata tctagaaaat  1200
ggctgggaaa ggggtgaaat agctaatgca ataagacgtg ttatggttga tgaagagggg  1260
gagtatatca gacaaaacgc aagagtgctg aagcaaaagg ccgacgtttc tctaatgaag  1320
ggaggctctt catacgaatc cttagaatct cttgtttcct acatttcatc actgtaa     1377

SEQ ID NO: 54              moltype = AA  length = 512
FEATURE                    Location/Qualifiers
source                     1..512
                           mol_type = protein
                           organism = Lactuca sativa
SEQUENCE: 54
MDGVIDMQTI PLRTAIAIGG TAVALVVALY FWFLRSYASP SHHSNHLPPV PEVPGVPVLG    60
NLLQLKEKKP YMTFTKWAEM YGPIYSIRTG ATSMVVVSSN EIAKEVVVTR FPSISTRKLS   120
YALKVLTEDK SMVAMSDYHD YHKTVKRHIL TAVLGPNAQK KFRAHRDTMM ENVSNELHAF   180
FEKNPNQEVN LRKIFQSQLF GLAMKQALGK DVESIYVKDL ETTMKREEIF EVLVVDPMMG   240
AIEVDWRDFF PYLKWVPNKS FENIIHRMYT RREAVMKALI QEHKKRIASG ENLNSYIDYL   300
LSEAQTLTDK QLLMSLWEPI IESSDTTMVT TEWAMYELAK NPNMQDRLYE EIQSVCGSEK   360
ITEENLSQLP YLYAVFQETL RKHCPVPIMP LRYVHENTVL GGYHVPAGTE VAINIYGCNM   420
DKKVWENPEE WNPERFLSEK ESMDLYKTMA FGGGKRVCAG SLQAMVISCI GIGRLVQDFE   480
WKLKDDAEED VNTLGLTTQK LHPLLALINP RK                                 512

SEQ ID NO: 55              moltype = DNA  length = 1566
FEATURE                    Location/Qualifiers
misc_feature               1..1566
                           note = Codon-optimized KO
source                     1..1566
                           mol_type = other DNA
                           organism = synthetic construct
SEQUENCE: 55
aagcttacta gtaaaatgga cggtgtcatc gatatgcaaa ccattccatt gagaaccgct    60
attgctattg gtggtactgc tgttgctttg gttgttgcat atacttttg  gttcttgaga   120
tcctacgctt ccccatctca tcattctaat catttgccac cagtacctga agttccaggt   180
gttccagttt tgggtaattt gttgcaattg aaagaaaaa  agccttacat gaccttcacc   240
aagtgggctg aaatgtatgg tccaatctac tctattgaa  ctggtgctac ttccatggtt   300
gttgtctctt ctaacgaaat cgccaaagaa gttgttgtta ccagattccc atctatctct   360
accagaaaat tgtcttacgc cttgaaggtt ttgaccgaag ataagtctat ggttgccatg   420
tctgattatc acgattacca taagaccgtc aagagacata tttgactgc  tgttttgggt   480
ccaaacgccc aaaaaaagtt tagagcacat agagaccaca tgatggaaaa cgttccaat   540
gaattgcatg ccttcttcga aaagaaccca aatcaagaag tcaacttgag aaagatcttc   600
caatcccaat tattcggttt ggctatgaag caagccttgg gtaaagatgt tgaatccatc   660
tacgttaagg atttggaaac caccatgaag agagaagaaa tcttcgaagt tttggttgtc   720
gatccaatga tgggtgctat tgaagttgat tggagagatt tttccata  cttgaaatgt   780
gttccaaaca agtccttcga aaacatcatc catagaatgt acactgtaag agaagctgtt   840
atgaaggcct tgatccaaga acacaagaaa agaattgcct ccggtgaaaa cttgaactcc   900
tacattgatt acttgttgtc tgaagcccaa accttgaccg ataagcaatt attgatgtct   960
ttgtgggaaa ctattatcga atcttctgat accactactg ttactactga atggctatg  1020
tacgaattgg ctaagaatcc aaacatgcaa gacagattat acgaagaaat ccaatccgtt  1080
tgcggttccg aaaagattac tgaagaaaac ttgtcccaat gccatactt  gtacgctgtt  1140
ttccaagaaa ctttgagaaa gcactgtcca gttcctatta tgccattgag atatgttcac  1200
gaaaacaccg ttttgggtgg ttatcatgtt ccagctggta ctgaagttgc tattaacatc  1260
tacggttgca acatggataa gaaggtctgg gaaaatccag aagaatggaa tccagaagag  1320
ttcttgtccg aaaaagaatc tatggacttg tacaaaacta tggccttcgg tggtggtaaa  1380
agagtttgcg ctggttcttt acaagccatg gttattcttt gcattggtat cggtagattg  1440
gtccaagatt ttgaatggaa gttgaaggat gatgccgaag aagatgttaa cactttgggt  1500
ttgactaccc aaaagttgca tccattattg gccttgatta acccaagaaa gtaactcgag  1560
ccgcgg                                                              1566
```

| SEQ ID NO: 56 | moltype = DNA  length = 1535 |
| --- | --- |
| FEATURE | Location/Qualifiers |
| source | 1..1535 |
| | mol_type = other DNA |
| | organism = Rubus suavissimus |

SEQUENCE: 56

```
atggccaccc tccttgagca tttccaagct atgcccttg ccatccctat tgcactggct    60
gctctgtctt ggctgttcct cttttacatc aaagtttcat tcttttccaa caagagtgct   120
caggctaagc tccctcctgt gccagtggtt cctgggctgc cggtgattgg gaatttactg   180
caactcaagg agaagaaacc ctaccagact tttacaaggt gggcgagga gtatggacca   240
atctattcta tcaggactgg tgcttccacc atggtcgttc tcaataccac ccaagttgca   300
aaagaggcca tggtgaccag atatttatcc atctcaacca gaaagctatc aaacgcacta   360
aagattctta ctgctgataa atgtatggtt gcaataagtg actacaacga ttttcacaag   420
atgataaagc gatacatact ctcaaatgtt cttggaccta gtgctcagaa gcgtcaccgg   480
agcaacagag ataccttgag agctaatgtc tgcagccgat tgcattctca agtaaagaac   540
tctcctcgag aagctgtgaa tttcagaaga gtttttgagt gggaactctt tggaattgca   600
ttgaagcaag cctttggaaa ggacatagaa aagcccattt atgtggagga acttggcact   660
acactgtcaa gagatgagat cttaaggttt ctagtgcttg acataatgga gggtgcaatt   720
gaggttgatt ggagagattt cttcccttac ctgagatgga ttccgaatac gcgcatggaa   780
acaaaaattc agcgactcta tttccgcagg aaagcagtga tgactgccct gatcaacgag   840
cagaagaagc gaattgcttc aggagaggaa atcaactgtt atatcgactt cttgcttaag   900
gaagggaaga cactgacaat ggaccaaata agtatgttgc tttgggagac ggttattgaa   960
acagcagata ctacaatggt aacgacagaa tgggctatgt atgaagttgc taaagactca  1020
aagcgtcagg atcgtctcta tcaggaaatc caaaaggttt gtggatcgga gatggttaca  1080
gaggaatact tgtcccaact gccgtacctg aatgcagttt ccatgaaaac gctaaggaag  1140
cacagtccgg ctgcgttagt tccttaagat atgcacataa aagataccca actaggaggt  1200
tactacattc cagctggaac tgagattgct ataaacatat acgggtgtaa catggacaag  1260
catcaatggg aaagccctga ggaatggaaa ccggagagat ttttggaccc gaaatttgat  1320
cctatggatt tgtacaagac catggctttt ggggctggaa agagggtatg tgctggttct  1380
cttcaggcaa tgttaatagc gtgcccgacg attggtaggc tggtgcagga gtttgagtgg  1440
aagctgagag atggagaaga agaaaatgta gatactgttg ggctcaccac tcacaaacgc  1500
tatccaatgc atgcaatcct gaagccaaga agtta                              1535
```

| SEQ ID NO: 57 | moltype = DNA  length = 1572 |
| --- | --- |
| FEATURE | Location/Qualifiers |
| misc_feature | 1..1572 |
| | note = Codon-optimized KO |
| source | 1..1572 |
| | mol_type = other DNA |
| | organism = synthetic construct |

SEQUENCE: 57

```
aagcttacta gtaaaatggc ctccatcacc catttcttac aagattttca agctactcca    60
ttcgctactg cttttgctgt tggtggtgtt tctttgttga tattcttctt cttcatccga   120
ggtttccact ctactaagaa aaacgaatat tacaagttgc caccagttcc agttgttcca   180
ggtttgccag ttgttggtaa tttgttgcaa ttgaaagaaa agaagccata caagactttc   240
ttgagatggg ctgaaattca tggtccaatc tactctatta gaactggtgc ttctaccatg   300
gttgttgtta actctactca tgttgccaaa gaagctatgg ttaccagatt ctcttcaatc   360
tctaccagaa agttgtccaa ggctttggaa ttattgacct ccaacaaatc tatggttgcc   420
acctctgatt acaacgaatt tcacaagatg gtcaagaagt acatcttggc cgaattattg   480
ggtgctaatg ctcaaaagag acacagaatt catagagaca ccttgatcga aacgtcttg   540
aacaaattgc atgccataca caagaattct ccattgcaac tgttaacttt cagaaagatc   600
ttcgaatctg aattattcgg tttggcatg aagcaagccc tgggttatga tgttgattcc   660
ttgttcgttg aagaattggg tactaccttg tccagaagaa aatctacaa cgttttggtc   720
agtgacatgt tgaagggtgc tattgaagtt gattggagag acttttttccc atacttgaaa   780
tggatcccaa acaagtcctt cgaaatgaag attcaaagat tggcctctag aagacaagcc   840
gttatgaact ctattgtcaa agaacaaaag aagtccattg cctctggtaa gggtgaaaac   900
tgttacttga attacttgtt gtccgaagct aagactttga ccgaaaagca aatttccatt   960
ttggcctggg aaaccattat tgaaactgct gatacaactg ttgttaccac tgaatgggct  1020
atgtacgaat tggctaaaaa cccaaagcaa caagacagat tatacaacga aatccaaaac  1080
gtctgcggta ctgataagat taccgaagaa catttgtcca agttgcctta cttgtctgct  1140
gtttttcacg aaaccttgag aaagtattct ccatctccat tggttccatt gagatacgct  1200
catgaagata ctcaattggg tggttattat gttccagccg gtactgaaat tgctgttaat  1260
atctacggtt gcaacatgga caagaatcaa tgggaaactc cagaagaatg gaagccagaa  1320
agatttttgg acgaaaagta cgatccaatg gacatgtaca agctatgtc ttttggttca  1380
ggtaaaagag tttgcgctgg ttctttacaa gctagtttga ttgcttgtac ctccatcggt  1440
agattggttc aagaatttga atggagattg aagacggtg aagttgaaaa cgttgatacc  1500
tgggtttga ctacccataa gttgtatcca atgcaagcta tcttgcaacc tagaaactga  1560
ctcgagccgc gg                                                       1572
```

| SEQ ID NO: 58 | moltype = DNA  length = 1512 |
| --- | --- |
| FEATURE | Location/Qualifiers |
| misc_feature | 1..1512 |
| | note = Codon-optimized KO |
| source | 1..1512 |
| | mol_type = other DNA |
| | organism = synthetic construct |

SEQUENCE: 58

```
atgatttcct gttgttggg ttttgttgtc tcctccttct tgtttatctt cttcttgaaa    60
aaattgttgt tcttcttcag tcgtcacaaa atgtccgaag tttctagatt gccatctgtt   120
```

```
ccagttccag gttttccatt gattggtaac ttgttgcaat tgaaagaaaa gaagccacac   180
aagactttca ccaagtggtc tgaattatat ggtccaatct actctatcaa gatgggttcc   240
tcttctttga tcgtcttgaa ctctattgaa accgccaaag aagctatggt cagtagattc   300
tcttcaatct ctaccagaaa gttgtctaac gctttgactg ttttgacctg caacaaatct   360
atggttgcta cctctgatta cgatgacttt cataagttcg tcaagagatg cttgttgaac   420
ggtttgttgg gtgctaatgc tcaagaaaga aaaagacatt acagagatgc cttgatcgaa   480
aacgttacct ctaaattgca tgcccatacc agaaatcatc cacaagaacc agttaacttc   540
agagccattt tcgaacacga attattcggt gttgctttga acaagccttt cggtaaagat   600
gtcgaatcca tctatgtaaa agaattgggt gtcaccttgt ccagagatga aattttcaag   660
gttttggtcc acgacatgat ggaaggtgct attgatgttg attggagaga tttcttccca   720
tacttgaaat ggatcccaaa caactctttc gaagccagaa ttcaacaaaa gcacaagaga   780
agattggctt tatgaacgc cttgatccaa gacagattga atcaaaacga ttccgaatcc   840
gatgatgact gctacttgaa tttcttgatg tctgaagcta agaccttgac catgaacaa   900
attgctattt tggtttggga aaccattatc gaaactgctt ataccacttt ggttactact   960
gaatgggcta tgtacgaatt ggccaaacat caatctgttc aagatagatt attcaaagaa  1020
atccaatccg tctgcggtgg tgaaaagatc aagaagaac aattgccaag attgccttac  1080
gtcaatggtg ttttttcacga aaccttgaga agtattctc cagctccatt ggttccaatt  1140
agatacggta atgaagatac ccaaattggt ggttatcata ttccagccgg ttctgaaatt  1200
gccattaaca tctacggttg caacatggat aagaagagat gggaaagacc tgaagaatgg  1260
tggccagaaa gattttttgga agatagatac gaatcctccg acttgcataa gactatggct  1320
tttggtgctg gtaaaagagt ttgtgctggt gcttacaag ctagtttgat ggctggtatt  1380
gctatcggta gattggttca agaattcgaa tggaagttga gagatggtga agaagaaac  1440
gttgatactt acggtttgac ctcccaaaag ttgtatccat tgatggccat tatcaaccca  1500
agaagatctt aa                                                       1512

SEQ ID NO: 59          moltype = DNA  length = 1542
FEATURE                Location/Qualifiers
misc_feature           1..1542
                       note = Codon-optimized KO
source                 1..1542
                       mol_type = other DNA
                       organism = synthetic construct
SEQUENCE: 59
atggatgctg tgacgggttt gttaactgtc ccagcaaccg ctataactat tggtggaact   60
gctgtagcat tggcggtagc gctaatcttt tggtacctga atcctacac atcagctaga  120
agatcccaat caaatcatct tccaagagtg cctgaagtcc aggtgttcc attgttagga  180
aatctgttac aattgaagga gaaaagcca tacatgactt tacgagatg ggcagcgaca  240
tatggaccta tctatagtat caaaactggg gctacaagta tggttgtggt atcatctaat  300
gagatagcca aggaggcatt ggtgaccaga ttccaatcca tatctacaag gaacttatct  360
aaagccctga agtacttac agcagataag acaatggtcg caatgtcaga ttatgatgat  420
tatcataaaa cagttaagag acacatactg accgccgtct tgggtcctaa tgcacagaaa  480
aagcatagaa ttcacagaga tatcatgatg gataacatat tactcaact tcatgaattc  540
gtgaaaaaca acccagaaca ggaagaggta gaccttagaa aaatctttca atctgagtta  600
ttcggcttag ctatgagaca agccttagga aaggatgttg aaagtttgta cgttgaagac  660
ctgaaaatca ctatgaatag agacgaaatc tttcaagtcc ttgttgttga tccaatgatg  720
ggagcaatcg atgttgattg gagagacttc tttccatacc taaagtgggt cccaaacaaa  780
aagttcgaaa atactattca acaaaatgtca atcagaagag aagctgttat gaaatcttta  840
atcaaagagc acaaaagag aatagctcca gcgaaaagc taaatagta tatccgattac  900
cttttatctg aagctcaaac tttaaccgat cagcaactat tgatgtcctt gtgggaacca  960
atcattgaat cttcagatac aacaatggtc acaacgaat gggcaatgta cgaattagct 1020
aaaaccccta aattgcaaga taggttgtac agagacatta agtccgtctg tggatcgtaa 1080
aagataaccg aagagcatct atcacagctg ccttacatta cagctatttt ccacgaaaca 1140
ctgagaagac actcaccagt tcctatcatt cctctaagac atgtacatga agataccgtt 1200
ctaggcggct accatgttcc tgctggcaca gaacttgccg ttaacatcta cggttgcaac 1260
atggcaaaaa acgtttggga aaatccagag gaatggaacc cagaaagatt catgaaagag 1320
aatgagacaa ttgattttca aaagacgatg gccttcggtg gtggtaagag agtttgtgct 1380
ggttccttgc aagcccttt aactgcatct attgggattg ggagatgg tcaagagttc 1440
gaatggaaac tgaaggatat gactcaagag gaagtgaaca cgataggcct aactacaca 1500
atgttaagac cattgagagc tattatcaaa cctaggatct aa                    1542

SEQ ID NO: 60          moltype = DNA  length = 1554
FEATURE                Location/Qualifiers
misc_feature           1..1554
                       note = Codon-optimized KO
source                 1..1554
                       mol_type = other DNA
                       organism = synthetic construct
SEQUENCE: 60
aagcttactag gtaaaatgga catgatgggt attgaagctg ttccatttgc tactgctgtt   60
gttttgggtg gtatttcctt ggttgttttg atcttcatca gaagattcgt ttccaacaga  120
aagagatccg ttgaaggttt gccaccagtt ccagatattc caggtttacc attgattggt  180
aacttgttgc aattgaaaga aaagaagcca cataagacct tgctagatg ggctgaaact  240
tacggtccaa ttttctctat tagaactggt gcttctacca tgatcgtctt gaattcttct  300
gaagttgcca aagaagctat ggtcactaga ttctcttcaa tctctaccag aaagttgtcc  360
aacgccttga gattttgac cttcgataag tgtatggttg ccacctctga ttacaacgat  420
tttcacaaaa tggtcaaggg tttcatcttg agaaacgttt aggtgctccc agcccaaaaa  480
agacatagat gtcatagaga taccttgatc gaaaacatct taagtactt gcatgccat  540
gttaagactt ctccattgga accagttgtc ttgaagaaga tttcgaatc cgaaattttc  600
ggtttggctt tgaaacaagc cttgggtaag gatatcgaat ccatctatgt tgaagaattg  660
```

```
ggtactacct tgtccagaga agaaattttt gccgttttgg ttgttgatcc aatggctggt    720
gctattgaag ttgattggag agattttttc ccatacttgt cctggattcc aaacaagtct    780
atggaaatga agatccaaag aatggatttt agaagaggtg ctttgatgaa ggccttgatt    840
ggtgaacaaa agaaaagaat cggttccggt gaagaaaaga actcctacat tgatttcttg    900
ttgtctgaag ctaccacttt gaccgaaaag caaattgcta tgttgatctg ggaaacccatc    960
atcgaaattt ccgatacaac tttggttacc tctgaatggg ctatgtacga attggctaaa   1020
gacccaaata gacaagaaat cttgtacaga gaaatccaca aggttgcgg ttctaacaag    1080
ttgactgaag aaaacttgtc caagttgcca tacttgaact ctgttttcca cgaaaccttg   1140
agaaagtatt ctccagctcc aatggttcca gttagatatg ctcatgaaga tactcaattg   1200
ggtggttacc atattccagc tggttctcaa attgccatta acatctacgg ttgcaacatg   1260
aacaaaaagc aatgggaaaa tcctgaagaa tggaagccag aaagattctt ggacgaaaag   1320
tatgacttga tggacttgca taagactatg gcttttggtg tggtaaaag agtttgtgct   1380
ggtgctttac aagcaatgtt gattgcttgc acttccatcg tagattcgt tcaagaattt   1440
gaatggaagt tgatgggtgg tgaagaagaa aacgttgata ctgttgcttt gacctcccaa   1500
aaattgcatc caatgcaagc cattattaag gccagaagaa gactcgagcc gcgg           1554

SEQ ID NO: 61              moltype = DNA   length = 2133
FEATURE                    Location/Qualifiers
misc_feature               1..2133
                           note = Codon-optimized CPR
source                     1..2133
                           mol_type = other DNA
                           organism = synthetic construct
SEQUENCE: 61
atgcaatcag attcagtcaa agtctctcca tttgatttgg tttccgctgc tatgaatggc     60
aaggcaatgg aaaagttgaa cgctagtgaa tctgaagatc caacaacatt gcctgcacta    120
aagatgctag ttgaaaatag agaattgttg acactgttca caacttcctt cgcagttctt    180
attgggtgtc ttgtatttct aatgtggaga cgttcatcct ctaaaaagct ggtacaagat    240
ccagttccac aagttatcgt tgtaaagaag aagagaagg agtcagaggt tgatgacggg    300
aaaaagaaag tttctatttt ctacggcaca caaacggaa ctgccgaagg ttttgctaaa    360
gcattagtcg aggaagcaaa agtgacatat gaaaagacct cttttcaaggt tatcgatcta    420
gatgactacg ctgcagatga tgatgaatat gaggaaaaac tgaaaaagga tccttagcc     480
ttcttcttct tggccacata cggtgatggt gaacctactg ataatgctgc taacttctac    540
aagtggttca cagaaggcga cgataaaggt gaatggctga aaaagttaca atacggagta    600
tttggtttag gtaacagaca agaacat ttcaacagaa tcgctattgt agttgatgat    660
aaacttactg aaatgggagc caaaagatta gtaccagtag gattaggga tgatgatcag    720
tgtatagaag atgacttcac cgcctggaag gaattggtat ggccagaatt ggatcaactt    780
ttaagggacg aagatgatac ttctgtgact accccataca ctgcagccgt attggagtac    840
agagtgtttt accatgataa accagcagac tcatatgctg aagtcaaac ccatacaaac    900
ggtcatgttg ttcatgatgc acagcatcct tcaagatcta atgtggcttt caaaaaggaa    960
ctacacacct tcaatcaga taggtcttgt actcacttag aattcgatat ttctcacaca   1020
ggactgtctt acgaaactgg cgatcacgtt ggcgttatt ccgagaactt gtccgaagtt   1080
gtcgataag cactaaaact gttagggtta tcaccagaca catcttctc agtccatgct   1140
gataaggagg atgggacac tatcggtggt gcttcactac caccacctttt cctcccttgc   1200
acattgagag acgctctaac cagatacgca gatgtcttat cctcacctaa aaaggtagct   1260
ttgctggcat tggctgctca tgctagtgat cctagtgaag ccgataggtt aaagttcctg   1320
gcttcaccgg ccgaaaaga tgaatatgca caatggattg tgccaacca acgttctttg   1380
ctagaagtga tgcaaagttt tccatctgcc aagcctccat taggtgtgtt cttcgcagca   1440
gtagctccac gttacaacc aagatactac tctatcagtt catctcctaa gatgtctcct   1500
aacagaatac atgttacatg tgctttggtg tacgagacta ctccagcagg cagaattcac   1560
agaggattgt gttcaacctg gatgaaaaat gctgtcccct taacagagtc acctgattgc   1620
tctcaagcat ccatttttcgt tagaacatca aatttcagac ttccagtgga tccaaaagtt   1680
ccagtcatta tgataggacc aggcactggt cttgccccat tcaggggctt tcttcaagag   1740
agattggcct tgaaggaatc tggtacagaa ttgggttctt ctatcttttt ctttggttgc   1800
cgtaatagaa aagttgactt tatctacgag gacgagctta acaattttgt tgagacagga   1860
gcattgtcag aattgatcgt cgcattttca agagaaggga ctgccaaaga gtacgttcag   1920
cacaagatga gtcaaaaagc ctccgatata tggaaacttc aagtgaagg tgcctatctt   1980
tatgtctgtg gcgatgcaaa gggcatggcc aaggatgtcc atagaactct gcatacaatt   2040
gttcaggaac aagggagtct ggattcttcc aaggctgaat tgtacgtcaa aaacttacag   2100
atgtctggaa gatacttaag agatgtttgg taa                                2133

SEQ ID NO: 62              moltype = DNA   length = 2106
FEATURE                    Location/Qualifiers
source                     1..2106
                           mol_type = other DNA
                           organism = Siraitia grosvenorii
SEQUENCE: 62
atgaaggtca gtccattcga attcatgtcc gctattatca agggtagaat ggacccatct     60
aactcctcat ttgaatctac tggtgaagtt gcctccgtta tcttgaaaa cagagaattg    120
gttgccatct tgaccacttc tattgctgtt atgattggtt gcttcgttgt cttgatgtgg    180
agaagagctg ttctagaaa ggttaagaat gtcgaattgc aaagccatt gattgtccat    240
gaaccagaac tgaagttga agatggtaag aagaaggttt ccatcttctt cggtactcaa    300
actggtactg ctgaaggttt tgctaaggct ttggctgatg aagctaaagc tagatacgaa    360
aaggctacct tcagagttgt tgatttggat gattatgctg ccgatgatga ccaatacgaa    420
gaaaaattga agaacgaatc cttcgccgtt tccttgttgg ctacttatgg tgatggtgaa    480
cctactgata tgctgctag attttacaag tggttcgccg aagtaaaga aagaggtgaa    540
tggttgcaaa acttgcacta tgctgttttt ggtttgggta acagacaata cgaacacttc    600
aacaagattg ctaaggttgc cgacgaatta ttggaagctc aaggtggtaa tagattggtt    660
aaggttggtt aggtgatga cgatcaatgc atcgaagatg attttttctgc ttggagagaa    720
```

```
tctttgtggc cagaattgga tatgttgttg agagatgaag atgatgctac tactgttact    780
actccatata ctgctgctgt cttggaatac agagttgtct ttcatgattc tgctgatgtt    840
gctgctgaag ataagtcttg gattaacgct aatggtcatg ctgttcatga tgctcaacat    900
ccattcagat ctaacgttgt cgtcagaaaa gaattgcata cttctgcctc tgatagatcc    960
tgttctcatt tggaattcaa catttccggt tccgcttttg attacgaaac tggtgatcat   1020
gttggtgtct actgtgaaaa cttgactgaa actgttgatg aagccttgaa cttgttgggt   1080
ttgtctccag aaacttactt ctctatctac accgataacg aagatggtac tccattgggt   1140
ggttcttcat tgccaccacc atttccatca tgtactttga gaactgcttt gaccagatac   1200
gctgatttgt tgaactctcc aaaaaagtct gctttgttgg ctttagctgc tcatgcttct   1260
aatccagttg aagctgatag attgagatac ttggcttctc cagctggtaa agatgaatat   1320
gcccaatctg ttatcggttc ccaaaagtct tgttggaag ttatggctga attcccatct   1380
gctaaaccac cattaggtgt ttttttttgct gctgttgctc aagattgca acctagattc   1440
tactccattt catcctctcc aagaatggct ccatctagaa tccatgttac ttgtgctttg   1500
gtttacgata agatgccaac tggtagaatt cataagggtg tttgttctac ctggatgaat   1560
aattctgttc caatggaaaa gtcccatgaa tgttcttggg ctccaatttt cgttagacaa   1620
tccaatttta agttgccagc cgaatccaag gttccaatta tcatggttgg tccaggtact   1680
ggtttggctc cttttagagg ttttttacaa gaaagattgg ccttgaaaga atccggtgtt   1740
gaattgggtc catccatttt gttttcggt tgcagaaaca gaagaatgga ttacatctac   1800
gaagatgaat tgaacaactt cgttgaaacc ggtgctttgt ccgaattggt tattgctttt   1860
tctagagaag gtcctaccaa agaatacgtc aacataaga tggctgaaaa ggcttctgat   1920
atctggaact tgatttctga aggtgcttac ttgtacgttt tggtgatgc taaaggtatg   1980
gctaaggatg ttcatagaac cttgcatacc atcatgcaag aacaaggttc tttgattct   2040
tccaaagctg aatccatggt caagaacttg caaatgaatg tagatactt aagagatgtt   2100
tggtaa                                                              2106

SEQ ID NO: 63              moltype = DNA  length = 1593
FEATURE                    Location/Qualifiers
misc_feature               1..1593
                           note = Codon-optimized KO
source                     1..1593
                           mol_type = other DNA
                           organism = synthetic construct
SEQUENCE: 63
aagcttaaaa tgagtaagtc taatagtatg aattctacat cacacgaaac ccttttttcaa    60
caattggtct tgggtttgga ccgtatgcca ttgatggatg ttcactggtt gatctacgtt   120
gctttcggcg catggttatg ttcttatgtg atacatgttt tatcatcttc ctctacagta   180
aaagtgccag ttgttggata caggtctgta ttcgaaccta catggttgct tagacttaga   240
ttcgtctggg aaggtggctc tatcataggt caagggtaca ataagtttaa agactctatt   300
ttccaagtta ggaaattggg aactgatatt gtcattatac cacctaacta tattgatgaa   360
gtgagaaaaat tgtcacagga caagactaga tcagttgaac cttcattaa tgattttgca   420
ggtcaataca caagaggcat ggttttcttg caatctgact tacaaaaaccg tgttatacaa   480
caaagactaa ctccaaaatt ggtttccttg accaaggtca tgaaggaaga gttggattat   540
gctttaacaa aagagatgcc tgatatgaaa aatgacgaat aggtagaagt agatatcagt   600
agtataatgg tgagattgat ttccaggatc tccgccagag tctttctagg gcctgaacac   660
tgtcgtaacc aggaatggtt gactactaca gcagaatatt cagaatcact tttcattaca   720
gggtttatct taagagttgt accctcatatc ttaagaccat tcatcgcccc tctattacct   780
tcatacagga ctctacttag aaacgttttca agtggtagga gagtcatcgg tgacatcata   840
agatctcagc aaggggatgg taacgaagat atactttcct ggatgagaga tgctgccaca   900
ggagaggaaa agcaaatcga taacattgct cagagaatgt taattctttc tttagcatca   960
atccacacta ctgcgatgac catgacacat gccatgtacg atctatgtgc ttgccctgag  1020
tacattgaac cattaagaga tgaagttaaa tctgttgttg gggcttctgg ctgggacaag  1080
acagcgttaa acagatttca taagttggac tccttcctaa aagagtcaca aagattcaac  1140
ccagtattct tattgacatt caatagaatc taccatcaat ctatgacctt atcagatggc  1200
actaacattc catctggaac acgtattgct gttccatcac acgcaatgtt gcaagattct  1260
gcacatgtcc caggtccaac cccacctact gaatttgatg gattcagata tagtaagata  1320
cgttctgata gtaactacgc acaaaagtac ctattctcca tgaccgattc ttcaaacatg  1380
gctttcggat acgcaagta tgcttgtcca ggtagatttt acgcgtctaa tgagatgaaa  1440
ctaacattag ccatttttgtt gctacaattt gagttcaaac taccgatgg taaaggtcgt  1500
cctagaaata tcactatcga ttctgatatg attccagacc caagagctag actttgcgtc  1560
agaaaaagat cacttagaga tgaatgaccg cgg                                1593

SEQ ID NO: 64              moltype = DNA  length = 1515
FEATURE                    Location/Qualifiers
misc_feature               1..1515
                           note = Codon-optimized KO
source                     1..1515
                           mol_type = other DNA
                           organism = synthetic construct
SEQUENCE: 64
aagcttaaaa tggaagatcc tactgtctta tatgcttgtc ttgccattgc agttgcaact    60
ttcgttgtta gatggtacag agatccattg agatccatcc aacagttgg tggttccgat   120
ttgcctattc tatcttacat cggcgcacta agatggacaa gacgtggcag agagatactt   180
caagagggat atgatggcta cagaggatct acattcaaaa tcgcgatgtt agaccgttgg   240
atcgtgatcg caaatggtcc taaactagct gatgaagtca gactgagaag atgaagaag   300
ttaaactttta tggacggatt aggagcattc gtccaaacta agtacacctt aggtgaagct   360
attcataacg atccataccc a tgtcgatatc ataagagaaa aactaacaag aggccttcca   420
gccgtgcttc ctgatgtcat tgaagagttg acacttgcgg ttagacagta cattccaaca   480
gaaggtgatg aatgggtgtc cgtaaactgt tcaaaggccg caagagatat tgttgctaga   540
gcttctaata gagtctttgt aggtttgcct gcttgcagaa accaaggtta cttagatttg   600
```

```
gcaatagact ttacattgtc tgttgtcaag gatagagcca tcatcaatat gttccagaa   660
ttgttgaagc caatagttgg cagagttgta ggtaacgcca ccagaaatgt tcgtagagct   720
gttcctttg ttgctccatt ggtggaggaa agacgtagac ttatggaaga gtacggtgaa   780
gactggtctg aaaaacctaa tgatatgtta cagtggataa tggatgaagc tgcatccaga   840
gatagttcag tgaaggcaat cgcagagaga ttgttaatgg tgaacttcgc ggctattcat   900
acctcatcaa acactatcac tcatgctttg taccaccttg ccgaaatgcc tgaaactttg   960
caaccactta gagaagagat cgaaccatta gtcaaagagg agggctggac caaggctgct  1020
atgggaaaaa tgtggtggtt agattcattt ctaagagaat ctcaaagata caatggcatt  1080
aacatcgtat ctttaactag aatggctgac aaagatatta cattgagtga tggcacattt  1140
ttgccaaaag gtactctagt ggccgttcca gcgtattcta ctcatagaga tgatgctgtc  1200
tacgctgatg cctagtatt cgatcctttc agattctcac gtatgagagc gagagaaggt  1260
gaaggtacaa agcaccagtt cgttaatact tcagtcgagt acgttccatt tggtcacgga  1320
aagcatgctt gtccaggaag attcttcgcc gcaaacgaat tgaaagcaat gttggcttac  1380
attgttctaa actatgatgt aaagttgcct ggtgacggta acgtccatt gaacatgtat  1440
tggggtccaa cagttttgcc tgcaccagca ggccaagtat tgttcagaaa gagacaagtt  1500
agtctataac cgcgg                                                    1515

SEQ ID NO: 65          moltype = DNA  length = 1536
FEATURE                Location/Qualifiers
misc_feature           1..1536
                       note = Codon-optimized KO
source                 1..1536
                       mol_type = other DNA
                       organism = synthetic construct
SEQUENCE: 65
atggctacct tgttggaaca ttttcaagct atgccattcg ctattccaat tgctttggct    60
gctttgtctt ggttgttttt gttctacatc aaggtttctt tcttctccaa caaatccgct   120
caagctaaat tgccaccagt tccagttgtt ccaggtttgc cagttattgg taatttgttg   180
caattgaaag aaaagaagcc ataccaaacc ttcactagat gggctgaaga atatggtcca   240
atctactcta ttagaactgg tgcttctact atggttgtct gaacactac tcaagttgcc   300
aaagaagcta tggttaccag atacttgtct atctctacca gaaagttgtc caacgccttg   360
aaaattttga ccgctgataa gtgcatggtt gccattctg attacaacga tttccacaag   420
atgatcaaga gatatatctt gtctaacgtt ttgggtccat ctgcccaaaa aagacataga   480
tctaacagag ataccttgag agccaacgtt tgttctagat tgcattccca agttaagaac   540
tctccaagag aagctgtcaa cttagaaga gttttcgaat gggaattatt cggtatcgct   600
ttgaaacaag cctcggtaa ggatattgaa aagccaatct acgtcgaaga attgggtact   660
actttgtcca gagatgaaat cttcaaggtt ttggtcttgg acattatgga aggtgccatt   720
gaagttgatt ggagagattt ttttcccatac ttgcgttgga ttccaaacac cagaatggaa   780
actaagatcc aaagattata cttagaaga aaggccgtta tgaccgcctt gattaacgaa   840
caaaagaaaa gaattgcctc cggtgaagaa atcaactgct acatcgattt cttgttgaaa   900
gaaggtaaga ccttgaccat ggaccaaatc tctatgttgt tgtgggaaac cgttattgaa   960
actgctgata ccacaatggt tactactgaa tgggctatgt acgaagttgc taaggattct  1020
aaaagacaag acagattata ccaagaaatc caaaaggtct gcggttctga aatggttaca  1080
gaagaatact tgtcccaatt gcctacttgg aatgctgttt ccacgaaac tttgagaaaa  1140
cattctccag ctgctttggt tccattgaga tatgctcatg aagatactca attgggtggt  1200
tattacattc cagccggtac tgaaattgcc attaacatca cgttgcaa catggacaaa  1260
caccaatgga aatctccaga agaatggaag ccagaaaact ttttggatcc taagtttgac  1320
ccaatggact tgtacaaaac tatggctttt ggtgctggta aaagagtttg cgctggttct  1380
ttacaagcta tgttgattgc ttgtccaacc atcggtagat tggttcaaga atttgaatgg  1440
aagttgagag atggtgaaga agaaaacgtt gatactgttg gtttgaccac ccataagaga  1500
tatccaatgc atgctatttt gaagccaaga tcttaa                            1536

SEQ ID NO: 66          moltype = DNA  length = 2142
FEATURE                Location/Qualifiers
misc_feature           1..2142
                       note = Codon-optimized CPR
source                 1..2142
                       mol_type = other DNA
                       organism = synthetic construct
SEQUENCE: 66
atggcagaat tagatacact tgatatagta gtattaggtg ttatctttt gggtactgtg    60
gcatacttta ctaagggtaa attgtggggt gttaccaagg atccatacg taacggattc   120
gctgcaggtg gtgcttccaa gcctggcaga actagaaaca tcgtcgaagc tatggaggaa   180
tcaggtaaaa actgtgttgt tttctacggc agtcaaacag gtacagcggg ggattacgca   240
tcaagacttg caaaggaagg aaagtccaga ttcggtttga acactatgat cgccgatcta   300
gaagattatg acttcgataa cttagacact gttccatctg ataacatcgt tatgtttgta   360
ttggctactt acggtgaagg cgaaccaaca gataacgccg tggatttcta tgagttcatt   420
actggcgaag atgcctcttt caatgagggc aacgatcctc cactaggtaa cttgaattac   480
gttgcgttcg gtctgggcaa caatacctac gaacactaca actcaatggt caggaacgtc   540
aacaaggctc tagaaaagtt aggagctcat gaattggag aagcaggtga gggtgacgac   600
ggagctggaa ctatggaaga ggactttta gcttggaaag atcaatgtg gaagccttg    660
gctaaaaaga tgggcttgga ggaaagagaa gctgtatatg aacctatttt cgctatcaat   720
gagagagatg atttgacccc tgaagcgaat gaggtatact gggagaacc taataagcta   780
cacttggaag gtacagcgaa aggtcattc aactcccaaa gccaccaatt gcaccaatt    840
gcagaatcat acgaactttt ctcagctaag gatagaaatt gtctgcatat ggaaattgat   900
atttctggta gtaatctaaa gtatgaaaca ggcgaccata tcgcgatctg gcctaccaac   960
ccaggtgaag aggtcaacaa atttcttgac attctagatc tgtctggtaa gcaacattcc  1020
gtcgtaacag tgaaagcctt agaacctaca gccaaagttc ttttccaaa tccaactacc  1080
tacgatgcta tattgagata ccatctggaa atatgcgctc cagtttctag acagtttgtc  1140
```

```
tcaactttag cagcattcgc ccctaatgat gatatcaaag ctgagatgaa ccgtttggga  1200
tcagacaaag attacttcca cgaaaagaca ggaccacatt actacaatat cgctagattt  1260
ttggcctcag tctctaaagg tgaaaaatgg acaaagatac catttctgc tttcatagaa   1320
ggccttacaa aactacaacc aagatactat tctatctctt cctctagttt agttcagcct  1380
aaaaagatta gtattactgc tgtttgtcgaa tctcagcaaa ttccaggtag agatgaccca  1440
ttcagaggtg tagcgactaa ctacttgttc gctttgaagc agaaacaaaa cggtgatcca  1500
aatccagctc cttttggcca atcatacgag ttgacaggac caaggaataa gtatgatggt  1560
atacatgttc cagtccatgt aagacattct aactttaagc taccatctga tccaggcaaa  1620
cctattatca tgatcggtcc aggtaccggt gttgcccctt ttagaggcct cgtccaagag  1680
agggcaaaac aagccagaga tggtgtagaa gttggtaaaa cactgctgtt ctttggatgt  1740
agaaagagta cagaagattt catgtatcaa aaagagtggc aagagtacaa ggaagctctt  1800
ggcgacaaat cgaaatgat tacagctttt caagagaag gatctaaaaa ggtttatgtt   1860
caacacagac tgaaggaaag atcaaaggaa gtttctgatc ttctatccca aaaagcatac  1920
ttctacgttt gcggagacgc cgcacatatg gcacgtgaag tgaacactgt gttagcacag  1980
atcatagcag aaggccgtgg tgtatcagaa gccaagggtg aggaaattgt caaaaacatg  2040
agatcagcaa atcaatacca agtgtgttct gatttcgtaa ctttacactg taaagagaca  2100
acatacgcga attcagaatt gcaagaggat gtctggagtt aa                     2142

SEQ ID NO: 67           moltype = DNA   length = 2142
FEATURE                 Location/Qualifiers
misc_feature            1..2142
                        note = Codon-optimized CPR
source                  1..2142
                        mol_type = other DNA
                        organism = synthetic construct
SEQUENCE: 67
atggccgaat tggatacctt ggatatcgtt gttttgggtg ttatcttctt gggtactgtt  60
gcttacttca ccaaaggtaa attgtggggt gttactaagg atccatacgc taatggtttt  120
gctgctggtg gtgcttctaa accaggtaga actagaaata tcgttgaagc catggaagaa  180
tctgtaaga actgtgttgt tttctacggt tctcaaactg gatatgctga agattatgct  240
tccagattgg ctaaagaagg taagagtaga ttcggtttga acaccatgat tgccgatttg  300
gaagattacg atttcgataa cttggatacc gtcccatctg ataacatcgt tatgtttgtt  360
ttggctacct acggtgaagg tgaacctact gataatgctg ttgacttcta cgaattcatt  420
accggtgaag atgcttcttt caacgaaggt aatgaattcac cattgggtaa cttgaattac  480
gttgcttttg gtttgggtaa caacacctac gaacattaca actccagtgt tagaaacgtc  540
aacaaggctt tggaaaaatt gggtgctcat agaattggtg aagctggtga aggtgatgat  600
ggtgctggta ctatgaaga gattttttg gcttggaaag acccaatgtg ggaagccttg  660
gctaaaaaga tgggtttgga agaaagaga gctgtctacg aacctatttt cgccattaac  720
gaaaagatga atttgacccc tgaagccaat gaagttttat tgggtgaacc taacaagttg  780
cacttggaag gtactgctaa aggtccattc aattctcaca cccatatat tgctccaatc  840
gccgaatctt acgaattatt ctctgctaag gatagaaact gcttgcacat ggaaattgac  900
atctctggtt ctaaatttga agtacgaaacc ggtgatcata ttgccatttg gccaactaat  960
ccaggtgaag aagttaacaa gttcttggac atcttggact tgtccggtaa acaacattct  1020
gttgttactg ttaaggcctt ggaacctaca gctaaagttc cttttccaaa tccaactacc  1080
tacgatgcca ttttgagata ccatttgaaa atttgcgctc cagtctctag acaattcgtt  1140
tctactttgg ctgcttttgc tccaaacgat gatattaagg ctgaaatgaa cagattgggt  1200
tccgataagg attacttcca cgaaaaaact ggtccacact actacaaatc tgctagattt  1260
ttggcctctg tctctaaagg tgaaagtgg actaagattc cattctccgc tttcattgaa  1320
ggtttgacta agttgcaacc tagatattac tccatctcct cctcatcttt ggttcaacct  1380
aagaagatct ctattaccgc cgttgttgaa tcccaacaaa ttccaggtag agatgatcct  1440
tttagagtg ttgctaccaa ttacttgttc gccttgaaac aaaagcaaaa cggtgatcca  1500
aatcctgctc catttggtca atcttatgaa ttgactggtc caagaaacaa gtacgatggt  1560
attcatgttc cagttcacgt tagacactct aactttaagt tgccatctga tccaggtaag  1620
ccaattatca tgattggtcc aggtactggt gttgctccat tcagaggttt tgttcaagaa  1680
agagctaagc aagctagaga tggtgttgaa gttggtaaaa ccttgttgtt cttcggttgt  1740
agaaagtcca ctgaagattt catgtaccaa aaagaatggc aagaatacaa agaagcctta  1800
ggtgacaagt cgaaatgat tactgccttc tcaagagaag ttctaagaa ggtttacgtc   1860
caacacagat tgaagaaag atccaaagaa gtctccgatt tgttgtctca aaaggcctac  1920
ttctacgttt gtggtgatgc tgctcatatg gccagagaa ttaatactgt tttggcccaa   1980
attatcgctg aagtagagg tgtatctgaa gctaagggtg aagaaatcgt taagaacatg  2040
agatccgcca atcaatacca gtttgctct gattttgtta ccttgcactg taaagaaacc  2100
acctacgcta attccgaatt gcaagaagat gtttggtcct aa                    2142

SEQ ID NO: 68           moltype = AA   length = 500
FEATURE                 Location/Qualifiers
source                  1..500
                        mol_type = protein
                        organism = Stevia rebaudiana
SEQUENCE: 68
MEASYLYISI LLLLASYLFT TQLRRKSANL PPTVFPSIPI IGHLYLLKKP LYRTLAKIAA  60
KYGPILQLQL GYRRVLVISS PSAAEECFTN NDVIFANRPK TLFGKIVGGT SLGSLSYGDQ  120
WRNLRRVASI EILSVHRLNE FHDIRVDENR LLIRKLRSSS SPVTLITVFY ALTLNVIMRM  180
ISGKRYFDSG DRELEEEGKR FREILDETLL LAGASNVGDY LPILNWLGVK SLEKKLIALQ  240
KKRDDFFQGL IEQVRKSRGA KVGKGRKTMI ELLLSLQESE PEYYTDAMIR SFVLGLLAAG  300
SDTSAGTMEW AMSLLVNHPH VLKKAQAEID RVIGNNRLID ESDIGNIPYI GCIINETLRL  360
YPAGPLLFPH ESSADCVISG YNIPRGTMLI VNQWAIHHDP KVWDDPETFK PERFQGLEGT  420
RDGFKLMPFG SGRRGCPGEG LAIRLLGMTL GSVIQCFDWE RVGDEMVDMT EGLGVTLPKA  480
VPLVAKCKPR SEMTNLLSEL                                              500
```

```
SEQ ID NO: 69             moltype = AA  length = 709
FEATURE                   Location/Qualifiers
source                    1..709
                          mol_type = protein
                          organism = Stevia rebaudiana
SEQUENCE: 69
MQSESVEAST IDLMTAVLKD TVIDTANASD NGDSKMPPAL AMMFEIRDLL LILTTSVAVL    60
VGCFVVLVWK RSSGKKSGKE LEPPKIVVPK RRLEQEVDDG KKKVTIFFGT QTGTAEGFAK   120
ALFEEAKARY EKAAFKVIDL DDYAADLDEY AEKLKKETYA FFFLATYGDG EPTDNAAKFY   180
KWFTEGDEKG VWLQKLQYGV FGLGNRQYEH FNKIGIVVDD GLTEQGAKRI VPVGLGDDDQ   240
SIEDDFSAWK ELVWPELDLL LRDEDDKAAA TPYTAAIPEY RVVFHDKPDA FSDDHTQTNG   300
HAVHDAQHPC RSNVAVKKEL HTPESDRSCT HLEFDISHTG LSYETGDHVG VYCENLIEVV   360
EEAGKLLGLS TDTYFSLHID NEDGSPLGGP SLQPPFPPCT LRKALTNYAD LLSSPKKSTL   420
LALAAHASDP TEADRLRFLA SREGKDEYAE WVVANQRSLL EVMEAFPSAR PPLGVFFAAV   480
APRLQPRYYS ISSSPKMEPN RIHVTCALVY EKTPAGRIHK GICSTWMKNA VPLTESQDCS   540
WAPIFVRTSN FRLPIDPKVP VIMIGPGTGL APFRGFLQER LALKESGTEL GSSILFFGCR   600
NRKVDYIYEN ELNNFVENGA LSELDVAFSR DGPTKEYVQH KMTQKASEIW NMLSEGAYLY   660
VCGDAKGMAK DVHRTLHTIV QEQGSLDSSK AELYVKNLQM SGRYLRDVW              709

SEQ ID NO: 70             moltype = AA  length = 514
FEATURE                   Location/Qualifiers
source                    1..514
                          mol_type = protein
                          organism = Castanea mollissima
SEQUENCE: 70
MASITHFLQD FQATPFATAF AVGGVSLLIF FFFIRGFHST KKNEYYKLPP VPVVPGLPVV    60
GNLLQLKEKK PYKTFLRWAE IHGPIYSIRT GASTMVVVNS THVAKEAMVT RFSSISTRKL   120
SKALELLTSN KSMVATSDYN EFHKMVKKYI LAELLGANAQ KRHRIHRDTL IENVLNKLHA   180
HTKNSPLQAV NFRKIFESEL FGLAMKQALG YDVDSLFVEE LGTTLSREEI YNVLVSDMLK   240
GAIEVDWRDF FPYLKWIPNK SFEMKIQRLA SRRQAVMNSI VKEQKKSIAS GKGENCYLNY   300
LLSEAKTLTE KQISILAWET IIETADTTVV TTEWAMYELA KNPKQQDRLY NEIQNVCGTD   360
KITEEHLSKL PYLSAVFHET LRKYSPSPLV PLRYAHEDTQ LGGYYVPAGT EIAVNIYGCN   420
MDKNQWETPE EWKPERFLDE KYDPMDMYKT MSFGSGKRVC AGSLQASLIA CTSIGRLVQE   480
FEWRLKDGEV ENVDTLGLTT HKLYPMQAIL QPRN                              514

SEQ ID NO: 71             moltype = AA  length = 506
FEATURE                   Location/Qualifiers
source                    1..506
                          mol_type = protein
                          organism = Eutrema halophilum
SEQUENCE: 71
MASMISLLLG FVVSSFLFIF FLKKLLFFFS RHKMSEVSRL PSVPVPGFPL IGNLLQLKEK    60
KPHKTFTKWS ELYGPIYSIK MGSSSLIVLN SIETAKEAMV SRFSSISTRK LSNALTVLTC   120
NKSMVATSDY DDFHKFVKRC LLNGLLGANA QERKRHYRDA LIENVTSKLH AHTRNHPQEP   180
VNFRAIFEHE LFGVALKQAF GKDVESIYVK ELGVTLSRDE IFKVLVHDMM EGAIDVDWRD   240
FFPPYLKWIPN NSFEARIQQK HKRRLAVMNA LIQDRLNQND SESDDDCYLN FLMSEAKTLT   300
MEQIAILVWE TIIETADTTL VTTEWAMYEL AKHQSVQDRL FKEIQSVCGG EKIKEEQLPR   360
LPYVNGVFHE TLRKYSPAPL VPIRYAHEDT QIGGYHIPAG SEIAINIYGC NMDKKRWERP   420
EEWWPERFLE DRYESSDLHK TMAFGAGKRV CAGALQASLM AGIAIGRLVQ EFEWKLRDGE   480
EENVDTYGLT SQKLYPLMAI INPRRS                                       506

SEQ ID NO: 72             moltype = AA  length = 508
FEATURE                   Location/Qualifiers
source                    1..508
                          mol_type = protein
                          organism = Vitis vinifera
SEQUENCE: 72
MDMMGIEAVP FATAVVLGGI SLVVLIFIRR FVSNRKRSVE GLPPVPDIPG LPLIGNLLQL    60
KEKKPHKTFA RWAETYGPIF SIRTGASTMI VLNSSEVAKE AMVTRFSSIS TRKLSNALKI   120
LTFDKCMVAT SDYNDFHKMV KGFILRNVLG APAQKRHRCH RDTLIENISK YLHAHVKTSP   180
LEPVVLKKIF ESEIFGLALK QALGKDIESI YVEELGTTLS REEIFAVLVV DPMAGAIEVD   240
WRDFFPYLSW IPNKSMEMKI QRMDFRRGAL MKALIGEQKK RIGSGEEKNS YIDFLLSEAT   300
TLTEEQIAML IWETIIEISD TTLVTSEWAM YELAKDPNRQ EILYREIHKV CGSNKLTEEN   360
LSKLPYLNSV FHETLRKYSP APMVPVRYAH EDTQLGGYHI PAGSQIAINI YGCNMNKKQW   420
ENPEEWKPER FLDEKYDLMD LHKTMAFGGG KRVCAGALQA MLIACTSIGR FVQEFEWKLM   480
GGEEENVDTV ALTSQKLHPM QAIIKARE                                     508

SEQ ID NO: 73             moltype = AA  length = 713
FEATURE                   Location/Qualifiers
source                    1..713
                          mol_type = protein
                          organism = Fusarium fujikuroi
SEQUENCE: 73
MAELDTLDIV VLGVIFLGTV AYFTKGKLWG VTKDPYANGF AAGGASKPGR TRNIVEAMEE    60
SGKNCVVFYG SQTGTAEDYA SRLAKEGKSR FGLNTMIADL EDYDFDNLDT VPSDNIVMFV   120
LATYGEGEPT DNAVDFYEFI TGEDASFNEG NDPPLGNLNY VAFGLGNNTY EHYNSMVRNV   180
NKALEKLGAH RIGEAGEGDD GAGTMEEDFL AWKDPMWEAL AKKMGLEERE AVYEPIFAIN   240
ERDDLTPEAN EVYLGEPNKL HLEGTAKGPF NSHNPYIAPI AESYELFSAK DRNCLHMEID   300
ISGSNLKYET GDHIAIWPTN PGEEVNKFLD ILDLSGKQHS VVTVKALEPT AKVPFPNPTT   360
```

```
YDAILRYHLE ICAPVSRQFV STLAAFAPND DIKAEMNRLG SDKDYFHEKT GPHYYNIARF   420
LASVSKGEKW TKIPFSAFIE GLTKLQPRYY SISSSSLVQP KKISITAVVE SQQIPGRDDP   480
FRGVATNYLF ALKQKQNGDP NPAPFGQSYE LTGPRNKYDG IHVPVHVRHS NFKLPSDPGK   540
PIIMIGPGTG VAPFRGFVQE RAKQARDGVE VGKTLLFFGC RKSTEDFMYQ KEWQEYKEAL   600
GDKFEMITAF SREGSKKVYV QHRLKERSKE VSDLLSQKAY FYVCGDAAHM AREVNTVLAQ   660
IIAEGRGVSE AKGEEIVKNM RSANQYQVCS DFVTLHCKET TYANSELQED VWS          713

SEQ ID NO: 74             moltype = AA  length = 701
FEATURE                   Location/Qualifiers
source                    1..701
                          mol_type = protein
                          organism = Siraitia grosvenorii
SEQUENCE: 74
MKVSPFEFMS AIIKGRMDPS NSSFESTGEV ASVIFENREL VAILTTSIAV MIGCFVVLMW    60
RRAGSRKVKN VELPKPLIVH EPEPEVEDGK KKVSIFFGTQ TGTAEGFAKA LADEAKARYE   120
KATFRVVDLD DYAADDDQYE EKLKNESFAV FLLATYGDGE PTDNAARFYK WFAEGKERGE   180
WLQNLHYAVF GLGNRQYEHF NKIAKVADEL LEAQGGNRLV KVGLGDDDQC IEDDFSAWRE   240
SLWPELDMLL RDEDDATTVT TPYTAAVLEY RVVFHDSADV AAEDKSWINA NGHAVHDAQH   300
PFRSNVVVRK ELHTSASDRS CSHLEFNISG SALNYETGDH VGVYCENLTE TVDEALNLLG   360
LSPETYFSIY TDNEDGTPLG GSSLPPPFPS CTLRTALTRY ADLLNSPKKS ALLALAAHAS   420
NPVEADRLRY LASPAGKDEY AQSVIGSQKS LLEVMAEFPS AKPPLGVFFA AVAPRLQPRF   480
YSISSSPRMA PSRIHVTCAL VYDKMPTGRI HKGVCSTWMK NSVPMEKSHE CSWAPIFVRQ   540
SNFKLPAESK VPIIMVGPGT GLAPFRGFLQ ERLALKESGV ELGPSILFFG CRNRRMDYIY   600
EDELNNFVET GALSELVIAF SREGPTKEYV QHKMAEKASD IWNLISEGAY LYVCGDAKGM   660
AKDVHRTLHT IMQEQGSLDS SKAESMVKNL QMNGRYLRDV W                       701

SEQ ID NO: 75             moltype = AA  length = 511
FEATURE                   Location/Qualifiers
source                    1..511
                          mol_type = protein
                          organism = Rubus suavissimus
SEQUENCE: 75
MATLLEHFQA MPFAIPIALA ALSWLFLFYI KVSFFSNKSA QAKLPPVPVV PGLPVIGNLL    60
QLKEKKPYQT FTRWAEEYGP IYSIRTGAST MVVLNTTQVA KEAMVTRYLS ISTRKLSNAL   120
KILTADKCMV AISDYNDFHK MIKRYILSNV LGPSAQKRHR SNRDTLRANV CSRLHSQVKN   180
SPREAVNFRR VFEWELFGIA LKQAFGKDIE KPIYVEELGT TLSRDEIFKV LVLDIMEGAI   240
EVDWRDFFPY LRWIPNTRME TKIQRLYFRR KAVMTALINE QKKRIASGEE INCYIDFLLK   300
EGKTLTMDQI SMLLWETVIE TADTTMVTTE WAMYEVAKDS KRQDRLYQEI QKVCGSEMVT   360
EEYLSQLPYL NAVFHETLRK HSPAALVPLR YAHEDTQLGG YYIPAGTEIA INIYGCNMDK   420
HQWESPEEWK PERFLDPKFD PMDLYKTMAF GAGKRVCAGS LQAMLIACPT IGRLVQEFEW   480
KLRDGEEENV DTVGLTTHKR YPMHAILKPR S                                  511

SEQ ID NO: 76             moltype = AA  length = 710
FEATURE                   Location/Qualifiers
source                    1..710
                          mol_type = protein
                          organism = Stevia rebaudiana
SEQUENCE: 76
MQSDSVKVSP FDLVSAAMNG KAMEKLNASE SEDPTTLPAL KMLVENRELL TLFTTSFAVL    60
IGCLVFLMWR RSSSKKLVQD PVPQVIVVKK KEKESEVDDG KKKVSIFYGT QTGTAEGFAK   120
ALVEEAKVRY EKTSFKVIDL DDYAADDDEY EEKLKKESLA FFFLATYGDG EPTDNAANFY   180
KWFTEGDDKG EWLKKLQYGV FGLGNRQYEH FNKIAIVVDD KLTEMGAKRL VPVGLGDDDQ   240
CIEDDFTAWK ELVWPELDQL LRDEDDTSVT TPYTAAVLEY RVVYHDKPAD SYAEDQTHTN   300
GHVVHDAQHP SRSNVAFKKE LHTSQSDRSC THLEFDISHT GLSYETGDHV GVYSENLSEV   360
VDEALKLLGL SPDTYFSVHA DKEDGTPIGG ASLPPPFPSC TLRDALTRYA DVLSSPKKVA   420
LLALAAHASD PSEADRLKFL ASPAGKDEYA QWIVANQRSL LEVMQSFPSA KPPLGVFFAA   480
VAPRLQPRYY SISSSPKMSP NRIHVTCALV YETTPAGRIH RGLCSTWMKN AVPLTESPDC   540
SQASIFVRTS NFRLPVDPKV PVIMIGPGTG LAPFRGFLQE RLALKESGTE LGSSIFFFGC   600
RNRKVDFIYE DELNNFVETG ALSELIVAFS REGTAKEYVQ HKMSQKASDI WKLLSEGAYL   660
YVCGDAKGMA KDVHRTLHTI VQEQGSLDSS KAELYVKNLQ MSGRYLRDVW              710

SEQ ID NO: 77             moltype = AA  length = 525
FEATURE                   Location/Qualifiers
source                    1..525
                          mol_type = protein
                          organism = Fusarium fujikuroi
SEQUENCE: 77
MSKSNSMNST SHETLFQQLV LGLDRMPLMD VHWLIYVAFG AWLCSYVIHV LSSSSTVKVP    60
VVGYRSVFEP TWLLRLRFVW EGGSIIGQGY NKFKDSIFQV RKLGTDIVII PPNYIDEVRK   120
LSQDKTRSVE PFINDFAGQY TRGMVFLQSD LQNRVIQQRL TPKLVSLTKV MKEELDYALT   180
KEMPDMKNDE WVEVDISSIM VRLISRISAR VFLGPEHCRN QEWLTTTAEY SESLFITGFI   240
LRVVPHILRP FIAPLLPSYR TLLRNVSSGR RVIGDIIRSQ QGDGNEDILS WMRDAATGEE   300
KQIDNIAQRM LILSLASIHT TAMTMTHAMY DLCACPEYIE PLRDEVKSVV GASGKDTAL   360
NRFHKLDSFL KESQRFNPVF LLTFNRIYHQ SMTLSDGTNI PSGTRIAVPS HAMLQDSAHV   420
PGPTPPTEFD GFRYSKIRSD SNYAQKYLFS MTDSSNMAFG YGKYACPGRF YASNEMKLTL   480
AILLLQFEFK LPDGKGRPRN ITIDSDMIPD PRARLCVRKR SLRDE                   525

SEQ ID NO: 78             moltype = AA  length = 499
FEATURE                   Location/Qualifiers
```

```
source                  1..499
                        mol_type = protein
                        organism = Trametes versicolor
SEQUENCE: 78
MEDPTVLYAC LAIAVATFVV RWYRDPLRSI PTVGGSDLPI LSYIGALRWT RRGREILQEG    60
YDGYRGSTFK IAMLDRWIVI ANGPKLADEV RRRPDEELNF MDGLGAFVQT KYTLGEAIHN   120
DPYHVDIIRE KLTRGLPAVL PDVIEELTLA VRQYIPTEGD EWVSVNCSKA ARDIVARASN   180
RVFVGLPACR NQGYLDLAID FTLSVVKDRA IINMFPELLK PIVGRVVGNA TRNVRRAVPF   240
VAPLVEERRR LMEEYGEDWS EKPNDMLQWI MDEAASRDSS VKAIAERLLM VNFAAIHTSS   300
NTITHALYHL AEMPETLQPL REEIEPLVKE EGWTKAAMGK MWWLDSFLRE SQRYNGINIV   360
SLTRMADKDI TLSDGTFLPK GTLVAVPAYS THRDDAVYAD ALVFDPFRFS RMRAREGEGT   420
KHQFVNTSVE YVPFGHGKHA CPGRFFAANE LKAMLAYIVL NYDVKLPGDG KRPLNMYWGP   480
TVLPAPAGQV LFRKRQVSL                                                499

SEQ ID NO: 79           moltype = AA  length = 513
FEATURE                 Location/Qualifiers
source                  1..513
                        mol_type = protein
                        organism = Stevia rebaudiana
SEQUENCE: 79
MDAVTGLLTV PATAITIGGT AVALAVALIF WYLKSYTSAR RSQSNHLPRV PEVPGVPLLG    60
NLLQLKEKKP YMTFTRWAAT YGPIYSIKTG ATSMVVVSSN EIAKEALVTR FQSISTRNLS   120
KALKVLTADK TMVAMSDYDD YHKTVKRHIL TAVLGPNAQK KHRIHRDIMM DNISTQLHEF   180
VKNNPEQEEV DLRKIFQSEL FGLAMRQALG KDVESLYVED LKITMNRDEI FQVLVVDPMM   240
GAIDVDWRDF FPYLKWVPNK KFENTIQQMY IRREAVMKSL IKEHKKRIAS GEKLNSYIDY   300
LLSEAQTLTD QQLLMSLWEP IIESSDTTMV TTEWAMYELA KNPKLQDRLY RDIKSVCGSE   360
KITEEHLSQL PYITAIFHET LRRHSPVPII PLRHVHEDTV LGGYHVPAGT ELAVNIYGCN   420
MDKNVWENPE EWNPERFMKE NETIDFQKTM AFGGGKRVCA GSLQALLTAS IGIGRMVQEF   480
EWKLKDMTQE EVNTIGLTTQ MLRPLRAIIK PRI                                513

SEQ ID NO: 80           moltype = DNA  length = 1572
FEATURE                 Location/Qualifiers
source                  1..1572
                        mol_type = other DNA
                        organism = Rubus suavissimus
SEQUENCE: 80
atggaagtaa cagtgctag tagtgtagcc ctgagcctgg tctttattag catagtagta     60
agatgggcat ggagtgtggt gaattgggtg tggtttaagc cgaagaagct ggaaagattt   120
ttgagggagc aaggccttaa aggcaattcc tacaggtttt tatatggaga catgaaggag   180
aactctatcc tgctcaaaca agcaagatcc aaacccatga acctctccac ctcccatgac   240
atagcacctc aagtcacccc ttttgtcgac caaaccgtga agcttacgg taagaactct    300
tttaattggg ttggcccat accaaggtg aacataatga atccagaaga tttgaaggac     360
gtcttaacaa aaaatgttga ctttgttaag ccaatatcaa acccacttat caagttgtca   420
gctacaggta ttgcaatcta tgaaggtgag aaatggacta acacagaag gattatcaac    480
ccaacattcc attcggagag gctaaagcgt atgttacctt catttcacca aagttgtaat   540
gagatggtca aggaatggga gagcttgtg tcaaagagg gttcatcatg tgagttggat     600
gtctggcctt ttcttgaaaa tatgtcggca gatgtgatct cgagaacgac atttggaact   660
agctacaaaa aaggacagaa aatctttgaa ctcttgagag agcaagtaat atatgtaacg   720
aaaggctttc aaagttttta cattccagga tggaggtttc tcccaactaa gatgaacaag   780
aggatgaatg agattaacga agaaataaaa ggattaatca ggtgtattat aattgacaga   840
gagcaaatca ttaaggcagg tgaagaaacc aacgatgact tattaggtgc acttatggag   900
tcaaacttga aggacattcg ggaacatggg aaaaacaaca aaaatgttgg gatgagtatt   960
gaagatgtaa tcaggagtg taagctgttt tactttgctg ggcaagaaac cacttcagtg  1020
ttgctggctt ggacaatggt tttacttggt caaaatcaga actggcaaga tcgagcaaga 1080
caagaggttt tgcaagtctt tggaagcagc aagccaagtt ttgatgtcct agctcaccct 1140
aaagtcgtaa ccatgatttt gcttgaagtt cttcgattat acccaccagt cattgaactt 1200
attcgaacca ttcacaagaa aacacaactt gggaagctct cactaccaga aggagttgaa 1260
gtccgcttac caacactgct cattcaccat gacaaggaac tgtggggtga tgatgcaaac 1320
cagttcaatc cagagaggtt tcggaagga gtttccaaag caacaaagaa ccgactctca  1380
ttcttcccct tcggagccgg tccacgcatt tgcattggac agaacttttc tatgatggaa 1440
gcaaagttgg ccttagcatt gatcttgcaa cacttcacct ttgagctttc tccatctcat 1500
gcacatgctc cttcccatcg tataacccct caaccacagt atggtgttcg tatcatttta 1560
catcgacgtt ag                                                      1572

SEQ ID NO: 81           moltype = DNA  length = 1572
FEATURE                 Location/Qualifiers
misc_feature            1..1572
                        note = Codon-optimized KAH
source                  1..1572
                        mol_type = other DNA
                        organism = synthetic construct
SEQUENCE: 81
atggaagtca ctgtcgcctc ttctgtcgct ttatccttag tcttcattc cattgtcgtc     60
agatgggcat ggtccgttgt caactgggtt tggttcaaac caagagaagtt ggaaagattc  120
ttgagagagc aaggttttga gggtaattct tatagattct tgtacggtga catgaaggaa  180
aattctattt tgttgaagca agccagatcc aaaccaatga acttgtctac ctctcatgat  240
attgctccac aagttactcc attcgtcgat caaactgtta agcctacgg taagaactct   300
ttcaattggg ttggtccaat tcctagagtt aacatcatga cccagaaga tttgaaggat    360
gtcttggacca gaacgttga cttcgttaag ccaatttcca acccattgat taaattgtg    420
```

```
gctactggta ttgccattta cgaaggtgaa aagtggacta agcatagaag aatcatcaac    480
cctaccttcc actctgaaag attgaagaga atgttaccat cttcccatca atcctgtaat    540
gaaatggtta aggaatggga atccttggtt tctaaagaag ttcttcttg  cgaattggat    600
gtttggccta tcttggaaaa tatgtctgct gatgtcattt ccagaaccgc tttcggtacc    660
tcctacaaga agggtcaaaa gattttcgaa ttgttgagaa agcaagttat ttacgttacc    720
aagggtttcc aatccttcta catcccaggt tggagattct tgccaactaa aatgaacaag    780
cgtatgaacg agatcaacga agaaattaaa ggtttgatca gaggtattat tatcgacaga    840
gaacaaatta ttaaagctgg tgaagaaacc aacgatgatt tgttgggtgc tttgatggag    900
tccaacttga aggatattag agaacatggt aagaacaaca agaatgttgg tatgtctatt    960
gaagatgtta ttcaagaatg taagttattc tacttcgctg gtcaagagac cacttctgtt   1020
ttgttagcct ggactatggt cttgttaggt caaaaccaaa attggcaaga tagagctaga   1080
caagaagttt tgcaagtctt cggttcttcc aagccagact tgatggtttt ggcccacttg   1140
aaggttgtta ctatgatttt gttagaagtt ttgagattgt acccaccagt cattgagtta   1200
atcagaacca ttcataaaaa gactcaattg ggtaaattat ctttgccaga aggtgttgaa   1260
gtcagattac caaccttgtt gattcaccac gataaggaat tatggggtga cgacgctaat   1320
caattaatc  cagaaagatt ttccgaaggt gtttccaagg ctaccaaaaa ccgtttgtcc   1380
ttcttcccat ttggtgctgg tccacgtatt tgtatcggtc aaaactttc  catgatggaa   1440
gccaagttgg ctttggcttt aatcttgcaa cacttcactt tcgaattgtc tccatcccat   1500
gcccacgctc cttctcatag aatcacttta caaccacaat acggtgtcag aatcatctta   1560
cacagaagat aa                                                        1572

SEQ ID NO: 82            moltype = AA  length = 523
FEATURE                  Location/Qualifiers
source                   1..523
                         mol_type = protein
                         organism = Rubus suavissimus
SEQUENCE: 82
MEVTVASSVA LSLVFISIVV RWAWSVVNWV WFKPKKLERF LREQGLKGNS YRFLYGDMKE     60
NSILLKQARS KPMNLSTSHD IAPQVTPFVD QTVKAYGKNS FNWVGPIPRV NIMNPEDLKD    120
VLTKNVDFVK PISNPLIKLL ATGIAIYEGE KWTKHRRIIN PTFHSERLKR MLPSFHQSCN    180
EMVKEWESLV SKEGSSCELD VWPFLENMSA DVISRTAFGT SYKKGQKIFE LLREQVIYVT    240
KGFQSFYIPG WRFLPTKMNK RMNEINEEIK GLIRGIIIDR EQIIKAGEET NDDLLGALME    300
SNLKDIREHG KNNKNVGMSI EDVIQECKLF YFAGQETTSV LLAWTMVLLG QNQNWQDRAR    360
QEVLQVFGSS KPDFDGLAHL KVVTMILLEV LRLYPPVIEL IRTIHKKTQL GKLSLPEGVE    420
VRLPTLLIHH DKELWGDDAN QFNPERFSEG VSKATKNRLS FFPFGAGPRI CIGQNFSMME    480
AKLALALILQ HFTFELSPSH AHAPSHRITL QPQYGVRIIL HRR                      523

SEQ ID NO: 83            moltype = AA  length = 458
FEATURE                  Location/Qualifiers
source                   1..458
                         mol_type = protein
                         organism = Stevia rebaudiana
SEQUENCE: 83
MENKTETTVR RRRRIILFPV PFQGHINPIL QLANVLYSKG FSITIFHTNF NKPKTSNYPH     60
FTFRFILDND PQDERISNLP THGPLAGMRI PIINEHGADE LRRELELLML ASEEDEEVSC    120
LITDALWYFA QSVADSLNLR RLVLMTSSLF NFHAHVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSSLLDH DRTVFQWLDQ QPPSSVLYVS FGSTSEVDEK DFLEIARGLV    300
DSKQSFLWVV RPGFVKGSTW VEPLPDGFLG ERGRIVKWVP QQEVLAHGAI GAFWTHSGWN    360
STLESVCEGV PMIFSDFGLD QPLNARYMSD VLKVGVYLEN GWERGEIANA IRRVMVDEEG    420
EYIRQNARVL KQKADVSLMK GGSSYESLES LVSYISSL                            458

SEQ ID NO: 84            moltype = AA  length = 480
FEATURE                  Location/Qualifiers
source                   1..480
                         mol_type = protein
                         organism = Stevia rebaudiana
SEQUENCE: 84
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES LLRSIETNFL DRFIDLVTKL PDPPTCIISD    120
GFLSVFTIDA AKKLGIPVMM YWTLAACGFM GFYIHSLIE  KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVFE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480

SEQ ID NO: 85            moltype = AA  length = 457
FEATURE                  Location/Qualifiers
source                   1..457
                         mol_type = protein
                         organism = Stevia rebaudiana
SEQUENCE: 85
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDRTTVE  DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
```

```
HCGSGSIVEG LMFGHPLIML PIFGEIPRNE EDGCLTKESV ARSLRSVVVE KEGEIYKANA  420
RELSKIYNDT KVEKEYVSQF VDYLEKNARA VAIDHES                          457

SEQ ID NO: 86           moltype = AA  length = 462
FEATURE                 Location/Qualifiers
source                  1..462
                        mol_type = protein
                        organism = Oryza sativa
SEQUENCE: 86
MDSGYSSSYA AAAGMHVVIC PWLAFGHLLP CLDLAQRLAS RGHRVSFVST PRNISRLPPV   60
RPALAPLVAF VALPLPRVEG LPDGAESTND VPHDRPDMVE LHRRAFDGLA APFSEFLGTA  120
CADWVIVDVF HHWAAAAALE HKVPCAMMLL GSAHMIASIA DRRLERAETE SPAAAGQGRP  180
AAAPTFEVAR MKLIRTKGSS GMSLAERFSL TLSRSSLVVG RSCVEFEPET VPLLSTLRGK  240
PITFLGLMPP LHEGRREDGE DATVRWLDAQ PAKSVVYAL GSEVPLGVEK VHELALGLEL  300
AGTRFLWALR KPTGVSDADL LPAGFEERTR GRGVVATRWV PQMSILAHAA VGAFLTHCGW  360
NSTIEGLMFG HPLIMLPIFG DQGPNARLIE AKNAGLQVAR NDGDGSFDRE GVAAAIRAVA  420
VEEESSKVFQ AKAKKLQEIV ADMACHERYI DGFIQQLRSY KD                    462

SEQ ID NO: 87           moltype = AA  length = 712
FEATURE                 Location/Qualifiers
source                  1..712
                        mol_type = protein
                        organism = Arabidopsis thaliana
SEQUENCE: 87
MSSSSSSSTS MIDLMAAIIK GEPVIVSDPA NASAYESVAA ELSSMLIENR QFAMIVTTSI   60
AVLIGCIVML VWRRSGSGNS KRVEPLKPLV IKPREEEIDD GRKKVTIFFG TQTGTAEGFA  120
KALGEEAKAR YEKTRFKIVD LDDYAADDDE YEEKLKKEDV AFFFLATYGD GEPTDNAARF  180
YKWFTEGNDR GEWLKNLKYG VFGLGNRQYE HFNKVAKVVD DILVEQGAQR LVQVGLGDDD  240
QCIEDDFTAW REALWPELDT ILREEGDTAV ATPYTAAVLE YRVSIHDSED AKFNDITLAN  300
GNGYTVFDAQ HPYKANVAVK RELHTPESDR SCIHLEFDIA GSGLTMKLGD HVGVLCDNLS  360
ETVDEALRLL DMSPDTYFSL HAEKEDGTPI SSSLPPPFPP CNLRTALTRY ACLLSSPKKS  420
ALVALAAHAS DPTEAERLKH LASPAGKDEY SKWVVESQRS LLEVMAEFPS AKPPLGVFFA  480
GVAPRLQPRF YSISSSPKIA ETRIHVTCAL VYEKMPTGRI HKGVCSTWMK NAVPYEKSEK  540
LFLGRPIFVR QSNFKLPSDS KVPIIMIGPG TGLAPFRGFL QERLALVESG VELGPSVLFF  600
GCRNRRMDFI YEEELQRFVE SGALAELSVA FSREGPTKEY VQHKMMDKAS DIWNMISQGA  660
YLYVCGDAKG MARDVHRSLH TIAQEQGSMD STKAEGFVKN LQTSGRYLRD VW          712

SEQ ID NO: 88           moltype = AA  length = 473
FEATURE                 Location/Qualifiers
REGION                  1..473
                        note = Synthetic polypeptide
source                  1..473
                        mol_type = protein
                        organism = synthetic construct
SEQUENCE: 88
MATSDSIVDD RKQLHVATFP WLAFGHILPY LQLSKLIAEK GHKVSFLSTT RNIQRLSSHI   60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG MVLKGSDCLL SKCYHEFGTQ WLPLLETLHQ  240
VPVVPVGLLP PEIPGDEKDE TWVSIKKWLD GKQKGSVVYV ALGSEALVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNARAVAID HES         473

SEQ ID NO: 89           moltype = DNA  length = 1422
FEATURE                 Location/Qualifiers
misc_feature            1..1422
                        note = Synthetic oligonucleotide
source                  1..1422
                        mol_type = other DNA
                        organism = synthetic construct
SEQUENCE: 89
atggctactt ctgattccat cgttgacgat agaaagcaat tgcatgttgc tacttttcca   60
tggttggctt tcggtcatat tttgccatac ttgcaattgt ccaagttgat tgctgaaaag  120
ggtcacaagg tttcattctt gtctaccacc agaaacatcc aaagattgtc ctctcatatc  180
tccccattga tcaacgttgt caattgact tgccaagag tccaagaatt gccagaagat  240
gctgaagcta ctactgatgt tcatccagaa gatatccctt acttgaaaaa ggcttccgat  300
ggtttacaac cagaagttac tagattcttg gaacaacatt ccccagattg gatcatctac  360
gattatactc attactggtt gccatccatt gctgcttcat tgggtatttc tagagccat  420
ttctctgtta ctactccatg ggctattgct tatatgggtc catctgctga tgctatgatt  480
aacggttctg atggtagaac taccgttgaa gatttgacta ctccaccaaa gtggtttcca  540
tttccaacaa aagtctgttg gagaaaacac gatttggcta gattggttcc atacaaagct  600
ccaggtattt ctgatggtta cagaatgggt atggttttga aggttccga ttgcttgttg  660
tctaagtgct atcatgaatt cggtactcaa tggttgcctt tgttggaaac attgcatcaa  720
gttccagttg ttccagtagg tttgttgcca ccagaaattc caggtgacga aaaagacgaa  780
acttgggttt ccatcaaaaa gtggttggat ggtaagcaaa agggttctgt tgtttatgtt  840
gctttggttt ccgaagcttt ggtttctcaa accgaagttg ttgaattggc tttgggtttg  900
gaattgtctg gtcttgccatt tgtttgggct tacagaaaac ctaaaggtcc agctaagtct  960
gattctgttg aattgccaga tggtttcgtt gaaagaacta gagatagagg tttggtttgg 1020
```

```
acttcttggg ctccacaatt gagaattttg tctcatgaat ccgtctgtgg tttcttgact  1080
cattgtggtt ctggttctat cgttgaaggt ttgatgtttg gtcacccatt gattatgttg  1140
ccaatctttg gtgaccaacc attgaacgct agattattgg aagataagca agtcggtatc  1200
gaaatcccaa gaaatgaaga agatggttgc ttgaccaaag aatctgttgc tagatctttg  1260
agatccgttg tcgttgaaaa agaaggtgaa atctacaagg ctaacgctag agaattgtcc  1320
aagatctaca acgataccaa ggtccgaaaaa gaatacgttt cccaattcgt tgactacttg  1380
gaaaagaatg ctagagcttgt tgccattgat catgaatctt ga                    1422
```

```
SEQ ID NO: 90           moltype = DNA  length = 1567
FEATURE                 Location/Qualifiers
misc_feature            1..1567
                        note = Synthetic oligonucleotide
source                  1..1567
                        mol_type = other DNA
                        organism = synthetic construct
SEQUENCE: 90
atggaagctt ctagagcatc ttgtgttgct ttgtgtgttg tttgggtttc catcgttatt   60
actttggttt ggagagtttt gaattgggtc tggttaagac caaaaaagtt ggaaagatgc  120
ttgagagaac aaggtttgac tggtaactct tacagattgt tgttcggtga taccaaggac  180
ttgtctaaga tgttggaaca aactcaatcc aagcctatca agttgtctac ctctcatgat  240
attgctccaa gagttactcc attcttccat agaactgtta actccaacgg taagaactct  300
tttgtttgga tgggtccaat tccaagagtc catatattga accctgaaga tttgaaggac  360
gctttcaaca gacatgatga tttccataag accgtcaaga ccccaattat gaagtctcca  420
ccaccaggta tagttggtat tgaaggtgaa caatgggcca acatagaaa gattattaac   480
ccagccttcc acttggaaaa gttgaaaggt atggttccaa tcttctacca atcctgctct  540
gaaatgatta caagtgggga atccttggtt tccaaagaat cttcctgtga attggatgtc  600
tggccatatt tggaaaactt cacctccgat gttatttcca gagctgcttt tggttcttcc  660
tacgaagaag gtagaaagat cttccaatta ttgagagaag aagccaaggt ttactccgtt  720
gctttgagat ctgtttacat tccaggttgg agattcttgc caactaagca aaacaaaaag  780
accaaagaaa tccacaacga aatcaagggt ttgttgaagg gtatcatcaa caagagagaa  840
gaagctatga aggctggtga agctacaaaa gatgatttgt tgggtatctt gatggaatcc  900
aacttcagag aaatccaaga aacacggtaac aacaagaatg ccggtatgtc tattgaagat  960
gttatcggtg aatgcaagtt gttctacttt gctggtcaag aaactacctc cgttttgttg 1020
gtttggacca tgattttgtt gtcccaaaat caagattggc aagctagagc tagaagaaga 1080
gtcttgaaag ttttcggttc taacatccca acctacgaag aattgtctca cttgaaggtt 1140
gtcactatga tcttgttgga agtattgaga ttatacccat ccgttgttgc attgccaaga 1200
actactcata gaaaaactca attgggtaaa ttgtccttgc cagctggtgt tgaagtttct 1260
ttgccaattt tgttagtcca ccacgacaaa gaattgtggg gtgaagatgc taatgaattc 1320
aagccagaaa gattccgaa aggtgtttct aaagctacca acttacttg 1380
ccatttggtg gtggtccaag aatatgtatt ggtcaaaatt tcgctatggt cgaagctaaa 1440
ttggctttgg ctttgatctt gcaacatttc gctttcgaat tgtccacatc ttatgctcat 1500
gctccatctg ctgttattac attgcaacca caatttggtg cccatatcat cttgcataag 1560
agataac                                                           1567
```

```
SEQ ID NO: 91           moltype = AA  length = 521
FEATURE                 Location/Qualifiers
source                  1..521
                        mol_type = protein
                        organism = Prunus avium
SEQUENCE: 91
MEASRASCVA LCVVWVSIVI TLAWRVLNWV WLRPKKLERC LREQGLTGNS YRLLFGDTKD   60
LSKMLEQTQS KPIKLSTSHD IAPRVTPFFH RTVNSNGKNS FVWMGPIPRV HIMNPEDLKD  120
AFNRHDDFHK TVKNPIMKSP PPGIVGIEGE QWAKHRKIIN PAFHLEKLKG MVPIFYQSCS  180
EMINKWESLV SKESSCELDV WPYLENFTSD VISRAAFGSS YEEGRKIFQL LREEAKVYSV  240
ALRSVYIPGW RFLPTKQNKK TKEIHNEIKG LLKGIINKRE EAMKAGEATK DDLLGILMES  300
NFREIQEHGN NKNAGMSIED VIGECKLFYF AGQETTSVLL VWTMILLSQN QDWQARAREE  360
VLKVFGSNIP TYEELSHLKV VTMILLEVLR LYPSVVALPR TTHKKTQLGK LSLPAGVEVS  420
LPILLVHHDK ELWGEDANEF KPERFSEGVS KATKNKFTYL PFGGGPRICI GQNFAMVEAK  480
LALALILQHF AFELSPSYAH APSAVITLQP QFGAHIILHK R                      521
```

```
SEQ ID NO: 92           moltype = AA  length = 517
FEATURE                 Location/Qualifiers
source                  1..517
                        mol_type = protein
                        organism = Prunus mume
SEQUENCE: 92
ASWVAVLSVV WVSMVIAWAW RVLNWVWLRP KKLEKCLREQ GLAGNSYRLL FGDTKDLSKM   60
LEQTQSKPIK LSTSHDIAPH VTPFFHQTVN SYGKNSFVWM GPIPRVHIMN PEDLKDTFNR  120
HDDFHKVVKN PIMKSLPQGI VGIEGEQWAK HRKIINPAFH LEKLKGMVPI FYRSCSEMIN  180
KWESLVSKES SCELDVWPYL ENFTSDVISR AAFGSSYEEG RKIFQLLREE AKIYTVAMRS  240
VYIPGWRFLP TKQNKKAKEI HNEIKGLLKG IINKREEAMK AGEATKDDLL GILMESNFRE  300
IQEHGNNKNA GMSIEDVIGE CKLFYFAGQE TTSVLLVWTM VLLSQNQDWQ ARAREEVLQV  360
FGSNIPTYEE LSQLKVVTMI LLEVLRLYPS VVALPRTTHK KTQLGKLSLP AGVEVSLPIL  420
LVHHDKELWG EDANEFKPER FSEGVSKATK NQFTYFPFGG GPRICIGQNF AMMEAKLALS  480
LILRHFALEL SPLYAHAPSV TITLQPQYGA HIILHKR                           517
```

```
SEQ ID NO: 93           moltype = AA  length = 521
FEATURE                 Location/Qualifiers
source                  1..521
```

```
                        mol_type = protein
                        organism = Prunus mume
SEQUENCE: 93
MEASRPSCVA LSVVLVSIVI AWAWRVLNWV WLRPNKLERC LREQGLTGNS YRLLFGDTKE    60
ISMMVEQAQS KPIKLSTTHD IAPRVIPFSH QIVYTYGRNS FVWMGPTPRV TIMNPEDLKD   120
AFNKSDEFQR AISNPIVKSI SQGLSSLEGE KWAKHRKIIN PAFHLEKLKG MLPTFYQSCS   180
EMINKWESLV FKEGSREMDV WPYLENLTSD VISRAAFGSS YEEGRKIFQL LREEAKFYTI   240
AARSVYIPGW RFLPTKQNKR MKEIHKEVRG LLKGIINKRE DAIKAGEEAK GNLLGILMES   300
NFREIQEHGN NKNAGMSIED VIGECKLFYF AGQETTSVLL VWTLVLLSQN QDWQARAREE   360
VLQVFGTNIP TYDQLSHLKV VTMILLEVLR LYPAVVELPR TTYKKTQLGK FLLPAGVEVS   420
LHIMLAHHDK ELWGEDAKEF KPERFSEGVS KATKNQFTYF PFGAGPRICI GQNFAMLEAK   480
LALSLILQHF TFELSPSYAH APSVTITLHP QFGAHFILHK R                      521

SEQ ID NO: 94           moltype = AA  length = 514
FEATURE                 Location/Qualifiers
source                  1..514
                        mol_type = protein
                        organism = Prunus mume
SEQUENCE: 94
CVALSVVLVS IVIAWAWRVL NWVWLRPNKL ERCLREQGLT GNSYRLLFGD TKEISMMVEQ    60
AQSKPIKLST THDIAPRVIP FSHQIVYTYG RNSFVWMGPT PRVTIMNPED LKDAFNKSDE   120
FQRAISNPIV KSISQGLSSL EGEKWAKHRK IINPAFHLEK LKGMLPTFYQ SCSEMINKWE   180
SLVFKEGSRE MDVWPYLENL TSDVISRAAF GSSYEEGRKI FQLLREEAKF YTIAARSVYI   240
PGWRFLPTKQ NKRMKEIHKE VRGLLKGIIN KREDAIKAGE AAKGNLLGIL MESNFREIQE   300
HGNNKNAGMS IEDVIGECKL FYFAGQETTS VLLVWTLVLL SQNQDWQARA REEVLQVFGT   360
NIPTYDQLSH LKVVTMILLE VLRLYPAVVE LPRTTYKKTQ LGKFLLPAGV EVSLHIMLAH   420
HDKELWGEDA KEFKPERFSE GVSKATKNQF TYFPFGAGPR ICIGQNFAML EAKLALSLIL   480
QHFTFELSPS YAHAPSVTIT LHPQFGAHFI LHKR                              514

SEQ ID NO: 95           moltype = AA  length = 418
FEATURE                 Location/Qualifiers
source                  1..418
                        mol_type = protein
                        organism = Prunus persica
SEQUENCE: 95
MGPIPRVHIM NPEDLKDTFN RHDDFHKVVK NPIMKSLPQG IVGIEGDQWA KHRKIINPAF    60
HLEKLKGMVP IFYQSCSEMI NIWKSLVSKE SSCELDVWPY LENFTSDVIS RAAFGSSYEE   120
GRKIFQLLRE EAKVYTVAVR SVYIPGWRFL PTKQNKKTKE IHNEIKGLLK GIINKREEAM   180
KAGEATKDDL LGILMESNFR EIQEHGNNKN AGMSIEDVIG ECKLFYFAGQ ETTSVLLVWT   240
MVLLSQNQDW QARAREEVLQ VFGSNIPTYE ELSHLKVVTM ILLEVLRLYP SVVALPRTTH   300
KKTQLGKLSL PAGVEVSLPI LLVHHDKELW GEDANEFKPE RFSEGVSKAT KNQFTYFPFG   360
GGPRICIGQN FAMMEAKLAL SLILQHFTFE LSPQYSHAPS VTITLQPQYG AHLILHKR    418

SEQ ID NO: 96           moltype = DNA  length = 1566
FEATURE                 Location/Qualifiers
source                  1..1566
                        mol_type = other DNA
                        organism = Prunus avium
SEQUENCE: 96
atggaagcat caagggctag ttgtgttgcg ctatgtgttg tttgggtgag catagtaatt    60
acattggcat ggagggtgct gaattgggtg tggttgagac caaagaaact agaaagatgc   120
ttgagggagc aaggccttac aggcaattct tacaggcttt tgtttggaga caccaaggat   180
ctctcgaaga tgctggaaca aacacaatcc aaacccatca aactctccac ctcccatgat   240
atagcgccac gagtcacccc atttttccat cgaactgtga actctaatgg caagaattct   300
tttgtttgga tgggccctat accaagagtg cacatcatga atccagaaga tttgaaagat   360
gccttcaaca gacatgatga tttccataag acagtaaaaa atcctatcat gaagtctcca   420
ccaccgggca ttgtaggcat tgaaggtgag caatgggcta acacagaaa gattatcaac   480
ccagcattcc atttagagaa gctaaagggt atggtaccaa tattttacca aagttgtagc   540
gagatgatta acaaatggga gagcttggtg tccaaagaga gttcatgtga gttggatgtg   600
tggccttatc ttgaaaattt taccagcgat gtgatttccc gagctgcatt tggaagtagc   660
tatgaagagg gaaggaaaat atttcaacta ctaagagagg aagcaaagt tattccggta   720
gctctacgaa gtgtttacat tccaggatgg aggtttctac caaccaagca gaacaagaag   780
acgaaggaaa ttcacaatga aattaaaggc ttacttaagg gcattataaa taaaagggaa   840
gaggcgatga aggcagggga agccactaaa gatgacttac taggaatact tatggagtcc   900
aacttcaggg aaattcagga acatgggaac aacaaaatg ctggaatgag tattgaagat   960
gtaattggag agtgtaagtt gttttacttt gctgggcaag agaccacttc ggtgttgctt  1020
gtttggacaa tgattttact aagccaaaat caggattggc aagctcgtgc aagagaagag  1080
gtcttgaaag tctttggaag caacatccca acctatgaag agctaagtca cctaaaagtt  1140
gtgaccatga ttttacttga agttcttcga ttatacccat cagtcgttgc gcttcctcga  1200
accactcaca agaaaacaca gcttggaaaa ttatcattac cagctggagt ggaagtctcc  1260
ttgcccatac tgcttgttca ccatgacaaa gagttgtggg gtgaggatgc aaatgagttc  1320
aagccagaga ggttttcaga gggagtttca aggcaacaa gaacaaatt tacatactta  1380
ccttttcggag ggggtccaag gatttgcatt ggacaaaact tgccatggt ggaagctaaa  1440
ttggccttag ccctgatttt acaacacttt gccttgagc tttctccatc ctatgctcat  1500
gctccttctg cagttataac ccttcaacct caatttggtg ctcatatcat tttgcataaa  1560
cgttga                                                            1566

SEQ ID NO: 97           moltype = DNA  length = 2070
FEATURE                 Location/Qualifiers
```

-continued

```
misc_feature           1..2070
                       note = Synthetic oligonucleotide
source                 1..2070
                       mol_type = other DNA
                       organism = synthetic construct
SEQUENCE: 97
atgtcctcca actccgattt ggtcagaaga ttggaatctg ttttgggtgt ttcttcggt    60
ggttctgtta ctgattccgt tgttgttatt gctaccacct ctattgcttt ggttatcggt  120
gttttggttt tgttgtggag aagatcctct gacagatcta gagaagttaa gcaattggct  180
gttccaaagc cagttactat cgttgaagaa gaagatgaat tcgaagttgc ttctggtaag  240
accagagttt ctattttcta cggtactcaa actggtactg ctgaaggttt tgctaaggct  300
ttggctgaag aaatcaaagc cagatacgaa aaagctgccg ttaaggttat tgatttggat  360
gattacacag ccgaagatga caaatacggt gaaaagttga agaaagaaac tatggccttc  420
ttcatgttgg ctacttatgg tgatgtgaa cctactgata atgctgctag attttacaag  480
tggttcaccg aagtactga tagaggtgtt tggttgaaac atttgagata cggtgtattc  540
ggtttgggta acagacaata cgaacacttc aacaagattg ccaaggttgt tgatgatttg  600
ttggttgaac aaggtgccaa gagattggtt actgttggtt tgggtgatga tgatcaatgc  660
atcgaagatg atttctccgc ttggaaagaa gccttgtgga tcgatttt cgctactgt    720
caagatgata ccaacaccgt ttctactcca tacactgctg ttattccaga atacagagtt  780
gttatccacg atccatctgt tacctcttat gaagatccat actctaacat ggctaacggt  840
aatgcctctt acgatattca tccatgt agagctaacg ttgccgtcca aaagaattg    900
cataagccag aatctgacag aagttgcatc catttgaat tcgatatttt cgctactggt  960
ttgacttacg aaaccggtga tcatgttggt gttacgctg ataattgtga tgatactgta 1020
gaagaagccg ctaagttgtt gggtcaacca ttggatttgt tgttctccat tcataccgat 1080
aacaacgacg gtacttcttt gggttcttct ttgccaccac catttccagg tccatgtact 1140
tgagaactg ctttggctag atatgccgat ttgttgaatc caccaaaaaa ggctgctttg 1200
attgctttag ctgctcatgc tgatgaacca tctgaagctg aaagattgaa gttcttgtca 1260
tctccacaag gtaaggacga atattctaaa tgggttgtcg gttcccaaag atccttggtt 1320
gaagttatgc ctgaatttcc atctgctaaa ccaccattgg gtgtattttt tgctgctgtt 1380
gttcctagat tgcaacctag atattactcc atctcttcca gtccaagatt tgctccacat 1440
agagttcatg ttacttgcgc tttggttat ggtccaactc caactggtag aattcacaga 1500
ggtgtatgtt cattctggat gaagaatgtt gtcccattgg aaaagtctca aaactgttct 1560
tgggccccaa ttttcatcag acaatctaat ttcaagttgc cagccgatca ttctgttcca 1620
atagttatgg ttggtccagg tactggttta gctcctttta gaggttttctt acaagaaaga 1680
ttggccttga aagaagaagg tgctcaagtt ggtcctgctt tgttgttttt tggttgcaga 1740
aacagacaaa tggacttcat ctacgaagtc gaattgaaca actttgtcga acaaggtgct 1800
ttgtccgaat tgatcgttgc ttttttcaaga gaaggtccat ccaaagaata cgtccaacat 1860
aagatggttg aaaaggcagc ttacatgtgg aacttgattt ctcaaggtgg ttacttctac 1920
gtttgtggtg atgctaaagg tatggctaga gatgttcata gaacattgca taccatcgtc 1980
caacaagaag aaaaggttga ttctaccaag gccgaatcca tcgttaagaa attgcaaatg 2040
gacggtagat acttgagaga tgttggtga                                   2070

SEQ ID NO: 98         moltype = AA  length = 689
FEATURE               Location/Qualifiers
source                1..689
                      mol_type = protein
                      organism = Rubus suavissimus
SEQUENCE: 98
MSSNSDLVRR LESVLGVSFG GSVTDSVVVI ATTSIALVIG VLVLLWRRSS DRSREVKQLA   60
VPKPVTIVEE EDEFEVASGK TRVSIFYGTQ TGTAEGFAKA LAEEIKARYE KAAVKVIDLD  120
DYTAEDDKYG EKLKKETMAF FMLATYGDGE PTDNAARFYK WFTEGTDRGV WLEHLRYGVF  180
GLGNRQYEHF NKIAKVVDDL LVEQGAKRLV TVGLGDDDQC IEDDFSAWKE ALWPELDQLL  240
QDDTNTVSTP YTAVIPEYRV VIHDPSVTSY EDPYSNMANG NASYDIHPC RANVAVQKEL   300
HKPESDRSCI HLEFDIFATG LTYETGDHVG VYADNCDDTV EEAAKLLGQP LDLLFSIHTD  360
NNDGTSLGSS LPPPFPGPCT LRTALARYAD LLNNPPKKAAL IALAAHADEP SEAERLKFLS  420
SPQGKDEYSK WVVGSQRSLV EVMAEFPSAK PPLGVFFAAV VPRLQPRYYS ISSSPRFAPH  480
RVHVTCALVY GPTPTGRIHR GVCSFWMKNV VPLEKSQNCS WAPIFIRQSN FKLPADHSVP  540
IVMVGPGTGL APFRGFLQER LALKEEGAQV GPALLFFGCR NRQMDFIYEV ELNNFVEQGA  600
LSELIVAFSR EGPSKEYVQH KMVEKAAYMW NLISQGGYFY VCGDAKGMAR DVHRTLHTIV  660
QQEEKVDSTK AESIVKKLQM DGRYLRDVW                                    689

SEQ ID NO: 99         moltype = DNA  length = 3315
FEATURE               Location/Qualifiers
misc_feature          1..3315
                      note = KO-BMR fusion construct
source                1..3315
                      mol_type = other DNA
                      organism = synthetic construct
SEQUENCE: 99
atggatgctg tgacgggttt gttaactgtc ccagcaaccg ctataactat tggtggaact    60
gctgtagcat tggcggtagc gctaatcttt ggtacctga atcctacac atcagctaga   120
agatcccaat caaatcatct tccaagagtg cctgaagtcc aggtgttcc attgttagga   180
aatctgttac aattgaagga gaaaaagcca tacatgactt ttacgagatg ggcagcgaca   240
tatggaccta tctatagtat caaaactggg tggttgtgt atcatctaat                300
gagatagcca aggaggcatt ggtgaccaga ttccaatcca tatctacaag gaacttatct   360
aaagccctga agtacttac agcagataag acaatggtcg caatgtcaga ttatgatgat   420
tatcataaaa cagttaagag acacatactg accgccgtct gggtcctaa tgcacagaaa   480
aagcatagaa ttcacagaga tatcatgatg gataacatat ctactcaact tcatgaattc   540
gtgaaaaaca acccagaaca ggaagaggta gaccttagaa aaatctttca atctgagtta   600
```

```
ttcggcttag ctatgagaca agccttagga aaggatgttg aaagtttgta cgttgaagac  660
ctgaaaatca ctatgaatag agacgaaatc tttcaagtcc ttgttgttga tccaatgatg  720
ggagcaatcg atgttgattg gagagacttc tttccatacc taaagtgggt cccaaacaaa  780
aagttcgaaa atactattca acaaatgtac atcagaagag aagctgttat gaaatcttta  840
atcaaagagc acaaaaagag aatagcgtca ggcgaaaagc taaatagtta tatcgattac  900
cttttatctg aagctcaaac tttaaccgat cagcaactat tgatgtcctt gtgggaacca  960
atcattgaat cttcagatac aacaatggtc acaacagaat gggcaatgta cgaattagct 1020
aaaaaccct a aattgcaaga taggttgtac agagacatta gtccgtctg tggatctgaa 1080
aagataaccg aagagcatct atcacagctg ccttacatta cagctatttt ccacgaaaca 1140
ctgagaagac actcaccagt tcctatcatt cctctaagac atgtacatga agataccgtt 1200
ctaggcggct accatgttcc tgctggcaca gaacttgccg ttaacatcta cggttgcaac 1260
atggacaaaa acgtttggga aaatccagag aatggaacc cagaaagatt catgaaagag 1320
aatgagacaa ttgattttca aaagacgatg gccttcggtg gtggtaagag agttgtgct 1380
ggttccttgc aagccttttt aactgcatct attgggattg ggagaatggt tcaagagttc 1440
gaatggaaac tgaaggatat gactcaagag gaagtgaaca cgataggcct aactacacaa 1500
atgttaagac cattgagagc tattatcaaa cctaggatcc catcaagacc aagtcctagt 1560
accgaacaat ctgcaaaaaa agttagaaaa aaagcagaaa atgcacacaa tactccattg 1620
ctagttcttt atggttctaa tatgggaaca gcggaaggaa cggccaggga tctagctgac 1680
atagctatgt ccaagggatt tgccccgcaa gtagcaaccc tggattccca tgcaggtaac 1740
ttgccaagag aaggtgctgt tctaatagtt accgctagct acaatgggca ccctccagat 1800
aatgcgaagc agttcgtcga ttggttagat caagcatcag cagatgaagt taagggtgtt 1860
agatactctg tttttggatg tggagataag aattgggcac cacatatcca gaaggttccg 1920
gctttcatcg atgaaatgct tgctgcaaaa ggggctgaaa atatagcaga tcgtggtgag 1980
gccgacgcaa gcgacgattt tgagggtacc tatgaggagt ggagagagca catgtggtct 2040
gatgttgccg cgtatttaa tctagacata gaaaattctg aagacaataa aagtgcctta 2100
cttcttcaat tcgtcgatag tgctgcggac mpccctt caaagatgca tggagccttt 2160
tcaacgaacg tagtagccag taggaacttc aacaaccag gtagtgccag aagtacacgt 2220
cacttggaaa ttgaattacc aaaagaggca tcctaccaag aagtgacca tcttggtgta 2280
atcccaagaa actacgaagg tatagtcaat agggtaacgg caagatttgg gctgatgca 2340
agccaacaga taagactaga agcagaagaa gaaaaattgg cgcaccttcc actagcgaag 2400
acagtatccg ttgaagaatt attgcaatac gtggaattgc aggatcccgt cactagaacg 2460
caattgagag ctatgcagc aaagactgtt tgtccacctc acaaggttga acttgaagct 2520
ctacttgaaa aacaagcata caagagcaa gtgctagcaa agactaac catgttagaa 2580
ttgctggaaa aatacccggc atgcgaaatg gaattctccg aatttatcgc gttgttgcca 2640
agtattcgtc ccaggtatta ctcaatttca tcttccacaa gggttgacga gaaacaggca 2700
tctattaccg tatctgtggt ctctggagaa gcttggagtg gttacggaga atacaagggt 2760
attgcttcca attatcttgc agaactgcag gaagggata caattacctg ctttatttct 2820
actcctcaat cagaatttac tcttccgaag gatccgaaaa ctccgttaat tatggtaggt 2880
ccgggaacag gagtcgcccc tttcagaggc tttgtgcaag caagaagca actaaaagaa 2940
cagggacaaa gtctgggtga ggcacatcta tatttcggtt gcagatcctcc gcatgaggat 3000
tacttatacc aagaagaact tgaaaacgcc aatcagaag gtattatcac cttgcatact 3060
gcattcagta gaatgccaaa ccagccgaaa acttacgtac agcatgttat ggagcaagat 3120
ggtaagaagt taattgagct tttggataag ggcgcccact tctacatttg cggcgacgga 3180
tcccaaatgg cgcctgccgt tgaagccacc ttgatgaaat catatgcaga tgttcatcaa 3240
gtttcagaag cggacgcccg tcttttggtta caacaactag aggagaaagg aaggtatgca 3300
aaagatgttt ggtaa                                                 3315

SEQ ID NO: 100         moltype = AA   length = 1104
FEATURE                Location/Qualifiers
REGION                 1..1104
                       note = KO-BMR fusion construct
source                 1..1104
                       mol_type = protein
                       organism = synthetic construct
SEQUENCE: 100
MDAVTGLLTV PATAITIGGT AVALAVALIF WYLKSYTSAR RSQSNHLPRV PEVPGVPLLG   60
NLLQLKEKKP YMTFTRWAAT YGPIYSIKTG ATSMVVVSSN EIAKEALVTR FQSISTRNLS  120
KALKVLTADK TMVAMSDYDD YHKTVKRHIL TAVLGPNAQK KHRIHRDIMM DNISTQLHEF  180
VKNNPEQEEV DLRKIFQSEL FGLAMRQALG KDVESLYVED LKITMNRDEI FQVLVVDPMM  240
GAIDVDWRDF FPYLKWVPNK KFENTIQQMY IRREAVMKSL IKEHKKRIAS GEKLNSYIDY  300
LLSEAQTLTD QQLLMSLWEP IIESSDTTMV TTEWAMYELA KNPKLQDRLY RDIKSVCGSE  360
KITEEHLSQL PYITAIFHET LRRHSPVPII PLRHVHEDTV LGGYHVPAGT ELAVNIYGCN  420
MDKNVWENPE EWNPERFMKE NETIDFQKTM AFGGGKRVCA GSLQALLTAS IGIGRMVQEF  480
EWKLKDMTQE EVNTIGLTTQ MLRPLRAIIK PRIPSRPSPS TEQSAKKVRK KAENAHNTPL  540
LVLYGSNMGT AEGTARDLAD IAMSKGFAPQ VATLDSHAGN LPREGAVLIV TASYNGHPPD  600
NAKQFVDWLD QASADEVKGV RYSVFGCGDK NWATTYQKVP AFIDEMLAAK GAENIADRGE  660
ADASDDFEGT YEEWREHMWS DVAAYFNLDI ENSEDNKSAL LLQFVDSAAD MPLAKMHGAF  720
STNVVASKEL QQPGSARSTR HLEIELPKEA SYQEGDHLGV IPRNYEGIVN RVTARFGLDA  780
SQQIRLEAEE EKLAHLPLAK TVSVEELLQY VELQDPVTRT QLRAMAAKTV CPPHKVELEA  840
LLEKQAYKEQ VLAKRLTMLE LLEKYPACEM EFSEFIALLP SIRPRYYSIS SSPRVDEKQA  900
SITVSVVSGE AWSGYGEYKG IASNYLAELQ EGDTITCFIS TPQSEFTLPK DPETPLIMVG  960
PGTGVAPFRG FVQARKQLKE QGQSLGEAHL YFGCRSPHED YLYQEELENA QSEGIITLHT 1020
AFSRMPNQPK TYVQHVMEQD GKKLIELLDK GAHFYICGDG SQMAPAVEAT LMKSYADVHQ 1080
VSEADARLWL QQLEEKGRYA KDVW                                       1104

SEQ ID NO: 101         moltype = DNA   length = 3315
FEATURE                Location/Qualifiers
misc_feature           1..3315
                       note = KO-BMR fusion construct
```

```
source                  1..3315
                        mol_type = other DNA
                        organism = synthetic construct
SEQUENCE: 101
atggatgctg tgacgggttt gttaactgtc ccagcaaccg ctataactat tggtggaact    60
gctgtagcat tggcggtagc gctaatcttt tggtacctga atcctacac atcagctaga   120
agatcccaat caaatcatct tccaagagtg cctgaagtcc caggtgttcc attgttagga   180
aatctgttac aattgaagga gaaaaagcca tacatgactt ttacgagatg ggcagcgaca   240
tatggaccta tctatagtat caaaactggg gctacaagta tggttgtggt atcatctaat   300
gagatagcca aggaggcatt ggtgaccaga ttccaatcca tatctacaag gaacttatct   360
aaagccctga agtacttac agcagataag acaatggtcg caatgtcaga ttatgatgat   420
tatcataaaa cagttaagag acacatactg accgccgtct tgggtcctaa tgcacagaaa   480
aagcatagaa ttcacagaga tatcatgatg gataacatat ctactcaact tcatgaattc   540
gtgaaaaaca acccagaaca ggaagaggta gaccttagaa aaatcttca atctgagtta   600
ttcggcttag ctatgagaca agccttagga aaggatgttg aaagtttgta cgttgaagac   660
ctgaaaatca ctatgaatag agacgaaatc tttcaagtcc ttgttgttga tccaatgatg   720
ggagcaatcg atgttgattg gagagacttc tttccatacc taaagtgggt cccaaacaaa   780
aagttcgaaa atactattca acaaatgtac atcagaagga agctgttaat gaaatcttta   840
atcaaagagc acaaaagag aatagcgtca ggcgaaaagc taaatagtta tatcgattac   900
cttttatctg aagctcaaac tttaaccgat cagcaactat tgatgtcctt gtgggaacca   960
atcattgaat cttcagatac aacaatggtc acaacagaat gggcaatgta cgaattagct  1020
aaaaaccta aattgcaaga taggttgtac agagacatta agtccgtctg tggatctgaa  1080
aagataaccg aagagcatct atcacagctg ccttacatta cagctatttt ccacgaaaca  1140
ctgagaagac actcaccagt tcctatcatt cctctaagac atgtacatga agataccgtt  1200
ctaggcggct accatgttcc tgctggcaca gaacttgccg ttaacatcta cggttgcaac  1260
atggacaaca acgtttggga aaatccagag gaatggaacc cagaaagatt catgaaagag  1320
aatgagacaa ttgattttca aaagacgatg gccttcggtg gtggtaagag agtttgtgct  1380
ggttccttgc aagccctttt aactgcatct attgggattg ggagaatggt tcaagagttc  1440
gaatggaaac tgaaggatat gactcaagag gaagtgaaca cgataggcct aactacacaa  1500
atgttaagac cattgagagc tattatcaaa cctaggatcc catcaagacc aagtcctagt  1560
accgaacaat ctgcaaaaaa agttagaaaa aaagcagaaa atgcacacaa tactccattg  1620
ctagttcttt atggttctaa tatgggaaca gcggaaggaa cggccaggga tctagctgac  1680
atagctatgt ccaagggatt tgccccgcaa gtagcaaccc tggattccca tgcaggtaac  1740
ttgccaagag aaggtgctgt tctaatagtt accgctagct acaatgggca ccctccagat  1800
aatgcgaagc agttcgtcga ttggttagat caagcatcag cagtagatta taagggtgtt  1860
agatactctg tttttggatg tggagataag aattgggcca ccacatatca gaaggttccg  1920
gctttcatcg atgaaatgct tgctgcaaaa ggggctgaaa atatagcaga tcgtggtgag  1980
gccgacgcaa gcgacgattt tgagggtacc tatgaggagt ggagagagca catgtggtct  2040
gatgttgccg cgtattttaa tctagacata gaaaattcta aagcaataaa aagtgcctta  2100
cttcttcaat tcgtcgatag tgctgcggac atgcccttag caaagatgca tggagccttt  2160
tcaacgaacg tagtagccag taaggaactt caacaaccag gtagtgccag aagtacacgt  2220
cacttggaaa ttgaattacc aaaagaggca tcctaccaag aaggtgacca tcttggtgta  2280
atcccaagaa actacgaagg tatagtcaat agggtaacgg aagatttgg gctgatgcaa  2340
agccaacaga taagactaga agcagaagaa gaaaaattgg cgcaccttcc actagcgaag  2400
acagtatccg ttgaagaatt attgcaatac gtggaattgc aggatcccgt cactagaacg  2460
caattgagag ctatggcagc aaagactgtt tgtccacctc acaaggttga acttgaagct  2520
ctacttgaaa aacaagcata caaagagcaa gtgctagcaa aggagactaac catgttagaa  2580
ttgctgaaaa ataccccggc atgcgaaatg gaattctccg aatttatcgc gttgttgcca  2640
agtattcgtc ccaggtatta ctcaatttca tcttcaccaa gggttgacga gaaacaggca  2700
tctattaccg tatctgtggt ctctggagaa gcttggagtg ttacggaga atacaagggt  2760
attgcttcca attatcttgc agaactgcag gaagggata caattacctg ctttattct  2820
actcctcaat cagaatttac tcttccgaag gatccagaaa ctccgttaat tatggtaggt  2880
ccgggaacag gagtcgcccc tttcagaggc tttgtgcaag caaggaagca actaaaagaa  2940
cagggacaaa gtctgggtga ggcacatcta tatttcggtt gcagatcctcc gcatgaggat  3000
tacttatacc aagaagaact tgaaaacgcc caatcagaag gtattatcac cttgcatact  3060
gcattcagta gaatgccaaa ccagccgaaa acttacgtac agcatgttat ggagcaagat  3120
ggtaagaagt taattgagct tttggataag gcgccccact tctacatttg cggcgacgga  3180
tcccaaatgg cgcctgccgt tgaagccacc ttgatgaaat catatgcaga tgttcatcaa  3240
gtttcagaag cggacgcccg tctttggtta caacaactag aggagaaagg aaggtatgca  3300
aaagatgttg cttaa                                                  3315

SEQ ID NO: 102          moltype = AA  length = 1104
FEATURE                 Location/Qualifiers
REGION                  1..1104
                        note = KO-BMR fusion construct
source                  1..1104
                        mol_type = protein
                        organism = synthetic construct
SEQUENCE: 102
MDAVTGLLTV PATAITIGGT AVALAVALIF WYLKSYTSAR RSQSNHLPRV PEVPGVPLLG    60
NLLQLKEKKP YMTFTRWAAT YGPIYSIKTG ATSMVVVSSN EIAKEALVTR FQSISTRNLS   120
KALKVLTADK TMVAMSDYDD YHKTVKRHIL TAVLGPNAQK KHRIHRDIMM DNISTQLHEF   180
VKNNPEQEEV DLRKIFQSEL FGLAMRQALG KDVESLYVED LKITMNRDEI FQVLVVDPMM   240
GAIDVDWRDF FPYLKWVPNK KFENTIQQMY IRREAVMKSL IKEHKKRIAS GEKLNSYIDY   300
LLSEAQTLTD QQLLMSLWEP IIESSDTTMV TTEWAMYELA KNPKLQDRLY RDIKSVCGSE   360
KITEEHLSQL PYITAIFHET LRRHSPVPII PLRHVHEDTV LGGYHVPAGT ELAVNIYGCN   420
MDKNVWENPE EWNPERFMKE NETIDFQKTM AFGGGKRVCA GSLQALLTAS IGIGRMVQEF   480
EWKLKDMTQE EVNTIGLTTQ MLRPLRAIIK PRIPSRPSPS TEQSAKKVRK KAENAHNTPL   540
LVLYGSNMGT AEGTARDLAD IAMSKGFAPQ VATLDSHAGN LPREGAVLIV TASYNGHPPD   600
```

```
NAKQFVDWLD QASADEVKGV RYSVFGCGDK NWATTYQKVP AFIDEMLAAK GAENIADRGE  660
ADASDDFEGT YEEWREHMWS DVAAYFNLDI ENSEDNKSAL LLQFVDSAAD MPLAKMHGAF  720
STNVVASKEL QQPGSARSTR HLEIELPKEA SYQEGDHLGV IPRNYEGIVN RVTARFGLDA  780
SQQIRLEAEE EKLAHLPLAK TVSVEELLQY VELQDPVTRT QLRAMAAKTV CPPHKVELEA  840
LLEKQAYKEQ VLAKRLTMLE LLEKYPACEM EFSEFIALLP SIRPRYYSIS SSPRVDEKQA  900
SITVSVVSGE AWSGYGEYKG IASNYLAELQ EGDTITCFIS TPQSEFTLPK DPETPLIMVG  960
PGTGVAPFRG FVQARKQLKE QGQSLGEAHL YFGCRSPHED YLYQEELENA QSEGIITLHT 1020
AFSRMPNQPK TYVQHVMEQD GKKLIELLDK GAHFYICGDG SQMAPAVEAT LMKSYADVHQ 1080
VSEADARLWL QQLEEKGRYA KDVA                                       1104

SEQ ID NO: 103          moltype = DNA  length = 3177
FEATURE                 Location/Qualifiers
misc_feature            1..3177
                        note = KO-BMR fusion construct
source                  1..3177
                        mol_type = other DNA
                        organism = synthetic construct
SEQUENCE: 103
atgccaagag tgcctgaagt cccaggtgtt ccattgttag gaaatctgtt acaattgaag   60
gagaaaaagc catacatgac ttttacgaga tgggcagcga catatggacc tatctatagt  120
atcaaaactg gggctacaag tatggttgtg gtatcatcta atgagatagc caaggaggca  180
ttggtgacca gattccaatc catatctaca aggaacttat ctaaagccct gaaagtactt  240
acagcagata agacaatggt cgcaatgtca gattatgatg attatcataa aacagttaag  300
agacacatac tgaccgccgt cttgggtcct aatgcacaga aaaagcatag aattcacaga  360
gatatcatga tggataacat atctactcaa cttcatgaat tcgtgaaaaa caacccagaa  420
caggaagagg tagacccttag aaaaatcttt caatctgatt tattcggctt agctatgaga  480
caagccttag gaaaggatgt tgaaagtttt tacgttgaag acctgaaaat cactatgaat  540
agagacgaaa tctttcaagt ccttgttgtt gatccaatga tgggagcaat cgatgttgat  600
tggagagact tctttccata cctaaagtgg gtcccaaaca aaagttcga aaatactatt   660
caacaaatgt acatcagaag gaaagctgtt atgaaatctt taatcaaaga gcacaaaaag  720
agaatagcgt caggcgaaaa gctaaatagt tatatcgatt acctttatc tgaagctcaa  780
actttaaccg atcagcaact attgatgtcc ttgtgggaac caatcattga atcttcagat  840
acaacaatgt tcacaacaga atgggcaatg tacgaattag ctaaaaaccc taaattgcaa  900
gataggttgt acagagacat taagtccgtc tgtggatctg aaaagataac cgaagagcat  960
ctatcacagc tgccttacat tacagctatt tcccacgaa cactgagaag acactccacca 1020
gttcctatca ttcctctaag acatgtacat gaagataccg ttctaggcgg ctaccatgtt 1080
cctgctggca cagaacttgc cgttaacatc tacggttgca acatggacaa aaacgtttgg 1140
gaaaatccag aggaatggaa cccagaaaga ttcatgaaag agaatgagac aattgattt 1200
caaaagacga tggcctcgg tggtgtaag agagtttgta ctggttcctt gcaagccgtt 1260
ttaactgcat ctattgggat tgggagaatg gttcaagagt tcgaatgaa actgaaggat 1320
atgactcaag aggaagtgaa cacgatagc ctaactacac aaatgttaag accattgaga 1380
gctattatca aacctaggat cccatcaaga ccaagtccta gtaccgaaca atctgcaaaa 1440
aaagttagaa aaaaagcaga aaatgcacac aatactccat tctagttct ttatggttct 1500
aatatgggaa cagcggaagg aacggccagg gatctagctg acatagctat gtccaaggga 1560
tttgccccgc aagtagcaac cctggattcc catgcaggta acttgccaag agaaggtgct 1620
gttctaatag ttaccgctag ctacaatggg caccctccag ataatgcgaa gcagttcgtc 1680
gattggttag atcaagcatc acagatgaa gttaaggtg ttagatactc tgtttttga 1740
tgtggagata agaattgggc caccacatat cagaaggttc cggctttcat cgatgaaatg 1800
cttgctgcaa aagggctga aaatatagca gatcgtggtg aggccgacgc aagcgacgat 1860
tttgagggta cctatgagga gtggagagag cacatgtggt ctgatgttgc cgcgtatttt 1920
aatctagaca tagaaaattc tgaagacaat aaaagtgcct tacttcttca attcgtcgat 1980
agtgctgcgg acatgccctt agcaaagatg catggagcct tttcaacgaa cgtagtagcc 2040
agtaaggaac ttcaacaacc aggtagtgcc agaagtacac gtcacttgga aattgaatta 2100
ccaaaagagg catcctacca agaaggtgac catcttggtg taatcccaag aaactacgaa 2160
ggtatagtca atagggtaac ggcaagattt gggctggatg caagccaaca gataagacta 2220
gaagcagaag aagaaaaatt ggcgcaccct ccactagcga agacagtatc cgttgaagaa 2280
ttattgcaat acgtggaatt gcaggatccc gtcactagaa cgcaattgag agctatggca 2340
gcaaagactg tttgtccacc tcacaaggtt gaacttgaag ctctacttga aaacaagca 2400
tacaaagagc aagtgctagc aaagagacta accatgttag aattgctgaa aaaataccg 2460
gcatgcgaaa tggaattctc cgaatttatc gcgttgttgc caagtattcg tcccaggtat 2520
tactcaattt catcttccacc aaggttgac gagaaacagg catctattac cgtatctgtg 2580
gtctctggaa aagcttggag tggttacgga gaatacaagg gtattgcttc caattatctt 2640
gcagaactgc aggaagggga tacaattacc tgctttattt ctactcctca atcagaattt 2700
actcttccga aggatccaga aactccgtta attatgttag gtccggaaac aggagtcgcc 2760
cctttcagag gctttgtgca agcaaggaag caactaaaag aacgggaca aagtctgggt 2820
gaggcacatc tatatttcgg ttgcagatct ccgcatgagg attacttata ccaagaagaa 2880
cttgaaaacg cccaatcaga aggtattatc accttgcata ctgcattcag tagaatgcca 2940
aaccagccga aaacttacgt acagcatgtt atggagcaag atggtaagaa gttaattgag 3000
cttttggata agggcgccca cttctacatt tgcggcgacg gatcccaaat ggcgcctgcc 3060
gttgaagcca ccttgatgaa atcatatgca gatgttcatc aagtttcaga agcggacgcc 3120
cgtcttttggt tacaacaact agaggagaaa ggaaggtatg caaaagatgt ttggtaa    3177

SEQ ID NO: 104          moltype = AA  length = 1058
FEATURE                 Location/Qualifiers
REGION                  1..1058
                        note = KO-BMR fusion construct
source                  1..1058
                        mol_type = protein
                        organism = synthetic construct
```

```
SEQUENCE: 104
MPRVPEVPGV PLLGNLLQLK EKKPYMTFTR WAATYGPIYS IKTGATSMVV VSSNEIAKEA    60
LVTRFQSIST RNLSKALKVL TADKTMVAMS DYDDYHKTVK RHILTAVLGP NAQKKHRIHR   120
DIMMDNISTQ LHEFVKNNPE QEEVDLRKIF QSELFGLAMR QALGKDVESL YVEDLKITMN   180
RDEIFQVLVV DPMMGAIDVD WRDFFPYLKW VPNKKFENTI QQMYIRREAV MKSLIKEHKK   240
RIASGEKLNS YIDYLLSEAQ TLTDQQLLMS LWEPIIESSD TTMVTTEWAM YELAKNPKLQ   300
DRLYRDIKSV CGSEKITEEH LSQLPYITAI FHETLRRHSP VPIIPLRHVH EDTVLGGYHV   360
PAGTELAVNI YGCNMDKNVW ENPEEWNPER FMKENETIDF QKTMAFGGGK RVCAGSLQAL   420
LTASIGIGRM VQEFEWKLKD MTQEEVNTIG LTTQMLRPLR AIIKPRIPSR PSPSTEQSAK   480
KVRKKAENAH NTPLLVLYGS NMGTAEGTAR DLADIAMSKG FAPQVATLDS HAGNLPREGA   540
VLIVTASYNG HPPDNAKQFV DWLDQASADE VKGVRYSVFG CGDKNWATTY QKVPAFIDEM   600
LAAKGAENIA DRGEADASDD FEGTYEEWRE HMWSDVAAYF NLDIENSEDN KSALLLQFVD   660
SAADMPLAKM HGAFSTNVVA SKELQQPGSA RSTRHLEIEL PKEASYQEGD HLGVIPRNYE   720
GIVNRVTARF GLDASQQIRL EAEEEKLAHL PLAKTVSVEE LLQYVELQDP VTRTQLRAMA   780
AKTVCPPHKV ELEALLEKQA YKEQVLAKRL TMLELLEKYP ACEMEFSEFI ALLPSIRPRY   840
YSISSSPRVD EKQASITVSV VSGEAWSGYG EYKGIASNYL AELQEGDTIT CFISTPQSEF   900
TLPKDPETPL IMVGPGTGVA PFRGFVQARK QLKEQGQSLG EAHLYFGCRS PHEDYLYQEE   960
LENAQSEGII TLHTAFSRMP NQPKTYVQHV MEQDGKKLIE LLDKGAHFYI CGDGSQMAPA  1020
VEATLMKSYA DVHQVSEADA RLWLQQLEEK GRYAKDVW                          1058

SEQ ID NO: 105          moltype = DNA  length = 3177
FEATURE                 Location/Qualifiers
misc_feature            1..3177
                        note = KO-BMR fusion construct
source                  1..3177
                        mol_type = other DNA
                        organism = synthetic construct
SEQUENCE: 105
atgccaagag tgcctgaagt cccaggtgtt ccattgttag gaaatctgtt acaattgaag    60
gagaaaaagc catacatgac ttttacgaga tgggcagcac catatggcat tatctatagt   120
atcaaaactg gggctacaag tatggttgtg gtatcatcta atgagatagc caaggaggca   180
ttggtgacca gattccaatc catatctaca aggaacttat ctaaagccct gaaagtactt   240
acagcagata agacaatggt cgcaatgtca gattatgatg attatcataa aacagttaag   300
agacacatac tgaccgccgt cttgggtcct aatgcacaga aaagcatag aattcacaga   360
gatatcatga tggataacat atctactcaa cttcatgaat cgtgaaaaa caacccagaa   420
caggaagagg tagaccttag aaaaatcttt caatctgagt tattcggctt agctatgaga   480
caagccttag gaaggatgt tgaaagtttg tacgttgaag acctgaaaat cactatgaat   540
agagacgaaa tctttcaagt ccttgttgtt gatccaatga tgggagcaat cgatgttgat   600
tggagagact tctttccata cctaaagtgg gtcccaaaca aaagttcga aaatactatt   660
caacaaatgt acatcagaag agaagctgtt atgaaatctt taatcaaaga gcacaaaaag   720
agaatagcgt caggcgaaaa gctaaatagt tatatcgatt accttttatc tgaagctcaa   780
actttaaccg atcagcaact attgatgtcc ttgtgggaac caatcattga atcttcagat   840
acaacaatgg tcacaacaga atgggcaatg tacgaattag ctaaaaaccc taaattgcaa   900
gataggttgt acagagacat taagtccgtc tgtggatctg aaaagataac cgaagagcat   960
ctatcacagc tgccttacat tacagctatt ttccacgaaa cactgagaag acactcacca  1020
gttcctatca ttcctctaag acatgtacat gaagataccg ttctaggcgg ctaccatgtt  1080
cctgctggca cagaacttgc cgttaacatc tacggttgca acatgacaaa aacgtttgg   1140
gaaaatccag aggaatggaa cccagaaaga ttcatgaaag agaatgagac aattgatttt  1200
caaaagacga tggccttcgg tggtggtaag agagtttgtg ctggttcctt gcaagccctt  1260
ttaactgcat ctattgggat tgggagaatg gttcaagagt tcgaatggaa actgaaggat  1320
atgactcaag aggaagtgaa cacgataggc ctaactacac aaatgttaag accattgaga  1380
gctattatca aacctaggat cccatcaaga ccagtcccta gtaccgaaca atctgcaaaa  1440
aaagttagaa aaaagcaga aaatgcacac aatactccat gctagtgttct ttatggttct  1500
aatatgggaa cagcggaagg aacggccagg atctagctg acatagctat gtccaaggga  1560
tttgcccgc aagtagcaac cctgattcc catgcaggta acttgccaag agaaggtgct  1620
gttctaatag ttaccgctag ctacaatggg caccctccag ataatgcgaa gcagttcgtc  1680
gattggttag atcaagcatc agcagatgaa gttaagggtg ttagatactc tgttttggga  1740
tgtggagata agaattgggc caccacatat cagaaggttc cggctttcat cgatgaaatg  1800
cttgctgcaa aaggggctga aaatatagca gatcgtggtg aggccgacgc aagcgacgat  1860
tttgagggtt cctatgagga gtggagagag cacatggtt ctgatgttgc cgcgtatttt  1920
aatctagaca tagaaaattc tgaagacaat aaaagtgcct tacttcttca attcgtcgat  1980
agtgctgcgg acatgccctt agcaaagatg catggagcct tttcaacgaa cgtagtagcc  2040
agtaaggaac ttcaacaacc aggtagtgcc agaagtacac gtcacttgga aattgaatta  2100
ccaaaagagg catcctacca agaaggtgac catcttggtg taatcccaag aaactacgaa  2160
ggtatagtca ataggggtaac ggcaagattt gggctggatg caagccaaca gataagacta  2220
gaagcagaag aagaaaaatt ggcgcaccct ccactagcga agacagtatc cgttgaagaa  2280
ttattgcaat acgtggaatt gcaggatccc gtcactagaa cgcaattgag agctatggca  2340
gcaaagactg tttgtccacc tcacaaggtt gaacttgaag ctcttacttga aaaacaagca  2400
tacaaagagc aagtgctagc aaagagacta accatgttag aattgctgga aaaatacccg  2460
gcatgcgaaa tggaattctc gaatttatc gcgttgttgc caagtattcg tcccaggtat  2520
tactcaattt catcttcacc aagggttgac gagaaacagg catctattac cgtatctgtg  2580
gtctctggaa gcttggagtg gttacgga gaatacaagg gtattgcttc caattatctt  2640
gcagaactgc aggaagggga tacaattacc tgctttattt ctactcctca atcagaattt  2700
actcttccga aggatccaga aactccgtta attatgtgg tcccggagtg gagtgcc    2760
cctttcagag ctttgtgca agcaaggaag caactaaaag aacgggaca aagtctggtt  2820
gaggcacatc tatatttcgg ttgcagatct ccgcatgagg attcttata ccaagaagaa  2880
cttgaaaacg cccaatcaga aggtattatc accttgcata ctgcattcag tagaatgcca  2940
aaccagccga aacttacgt acagcatgtt atggagcaag atggtaagaa gttaattgag  3000
cttttggata agggcgccca cttctacatt tgcggcgacg gatcccaaat ggcgcctgcc  3060
```

```
gttgaagcca ccttgatgaa atcatatgca gatgttcatc aagtttcaga agcggacgcc   3120
cgtctttggt tacaacaact agaggagaaa ggaaggtatg caaaagatgt tgcttaa      3177
```

| SEQ ID NO: 106 | moltype = AA  length = 1058 |
|---|---|
| FEATURE | Location/Qualifiers |
| REGION | 1..1058 |
| | note = KO-BMR fusion construct |
| source | 1..1058 |
| | mol_type = protein |
| | organism = synthetic construct |

SEQUENCE: 106

```
MPRVPEVPGV PLLGNLLQLK EKKPYMTFTR WAATYGPIYS IKTGATSMVV VSSNEIAKEA    60
LVTRFQSIST RNLSKALKVL TADKTMVAMS DYDDYHKTVK RHILTAVLGP NAQKKHRIHR   120
DIMMDNISTQ LHEFVKNNPE QEEVDLRKIF QSELFGLAMR QALGKDVESL YVEDLKITMN   180
RDEIFQVLVV DPMMGAIDVD WRDFFPYLKW VPNKKFENTI QQMYIRREAV MKSLIKEHKK   240
RIASGEKLNS YIDYLLSEAQ TLTDQQLLMS LWEPIIESSD TTMVTTEWAM YELAKNPKLQ   300
DRLYRDIKSV CGSEKITEEH LSQLPYITAI FHETLRRHSP VPIIPLRHVH EDTVLGGYHV   360
PAGTELAVNI YGCNMDKNVW ENPEEWNPER FMKENETIDF QKTMAFGGGK RVCAGSLQAL   420
LTASIGIGRM VQEFEWKLKD MTQEEVNTIG LTTQMLRPLR AIIKPRIPSR PSPSTEQSAK   480
KVRKKAENAH NTPLLVLYGS NMGTAEGTAR DLADIAMSKG FAPQVATLDS HAGNLPREGA   540
VLIVTASYNG HPPDNAKQFV DWLDQASADE VKGVRYSVFG CGDKNWATTY QKVPAFIDEM   600
LAAKGAENIA DRGEADASDD FEGTYEEWRE HMWSDVAAYF NLDIENSEDN KSALLLQFVD   660
SAADMPLAKM HGAFSTNVVA SKELQQPGSA RSTRHLEIEL PKEASYQEGD HLGVIPRNYE   720
GIVNRVTARF GLDASQQIRL EAEEEKLAHL PLAKTVSVEE LLQYVELQDP VTRTQLRAMA   780
AKTVCPPHKV ELEALLEKQA YKEQVLAKRL TMLELLEKYP ACEMEFSEFI ALLPSIRPRY   840
YSISSSPRVD EKQASITVSV VSGEAWSGYG EYKGIASNYL AELQEGDTIT CFISTPQSEF   900
TLPKDPETPL IMVGPGTGVA PFRGFVQARK QLKEQGQSLG EAHLYFGCRS PHEDYLYQEE   960
LENAQSEGII TLHTAFSRMP NQPKTYVQHV MEQDGKKLIE LLDKGAHFYI CGDGSQMAPA  1020
VEATLMKSYA DVHQVSEADA RLWLQQLEEK GRYAKDVA                         1058
```

| SEQ ID NO: 107 | moltype = DNA  length = 3309 |
|---|---|
| FEATURE | Location/Qualifiers |
| misc_feature | 1..3309 |
| | note = KO-BMR fusion construct |
| source | 1..3309 |
| | mol_type = other DNA |
| | organism = synthetic construct |

SEQUENCE: 107

```
atggctacct tgttggaaca ttttcaagct atgccattcg ctattccaat tgctttggct     60
gctttgtctt ggttgttttt gttctacatc aaggttctt tcttctccaa caaatccgct    120
caagctaaat tgccaccagt tccagttgtt ccaggtttgc cagttattgg taatttgttg    180
caattgaaag aaaagaagcc ataccaaacc ttcactagat gggctgaaga atatggtcca    240
atctactcta ttagaactgg tgcttctact atggttgtca tgaacactac tcaagttgcc    300
aaagaagcta tggttaccag atacttgtct atctctacca gaaagttgtc caacgccttg    360
aaaattttga ccgctgataa gtgcatggtt gccattctg attacaacga tttccacaag    420
atgatcaaga gatatatctt gtctaacgtt ttgggtccat ctgccaaaa aagacataga    480
tctaacagag ataccttgag agccaacgtt tgttctagat tgcattccca agttaagaac    540
tctccaagag aagctgtcaa ctttagaaga gttttcgaat gggaattatt cggtatcgct    600
ttgaaacaag ccttcggtaa ggatattgaa aagccaatct acgtcgaaga attgggtact    660
actttgtcca gagatgaaat cttcaaggtt ttggtcttgg acattatgga aggtgccatt    720
gaagttgatt ggagagattt tttcccatac ttgcgttgga ttcaaacac cagaatgcaa    780
actaagatcc aaagattata ctttagaaga aaggccgtta tgaccgcctt gattaacgaa    840
caaaagaaaa gaattgcctc cggtgaagaa atcaactgct acatcgattt cttgttgaaa    900
gaaggtaaga ccttgaccat ggaccaaatc tctatgttgt tgtgggaaac cgttattgaa    960
actgctgata ccacaatggt tactactgaa tgggctatgt acgaagttgc taaggattct   1020
aaaaagacaa acagattata ccaagaaatc caaaaggtct gcggttctga aatggttaca   1080
gaagaatact tgtcccaatt gccatacttg aatgctgttt tccacgaaac tttgagaaaa   1140
cattctccag ctgctttggt tccattgaga tatgctcatg aagatactca attgggtggt   1200
tattacattc cagccggtac tgaaattgcc attaacatct acggttgcaa catggacaaa   1260
caccaatggg aatctgcaga agaatggaag ccagaaagat ttttggatcc taagtttgac   1320
ccaatggact tgtacaaaac tatggctttt ggtgctggta aaagagtttg cgctggttct   1380
ttacaagcta tgttgattgc ttgtccaacc atcggtagat ggttcaaga atttgaatgg   1440
aagttgagag atggtgaaga gaaaacgtt gatactgttg gtttgaccac ccataagaga   1500
tatccaatgc atgctatttt gaagccaaga tctccatcaa gccaagtcc tagtaccgaa   1560
caatctgcaa aaaagttag aaaaaagca gaaaatgcac acaatactcc attgctagtt   1620
ctttatggtt ctaatatggg aacagcggaa ggaacggcca gggatctagc tgacatagct   1680
atgtccaagg gatttgcccc gcaagtagca acctgggatt cccatgcagg taacttgcca   1740
agagaaggtg ctgttctaat agttaccgct agctacaatg gcaccctcc agataatgcg   1800
aagcagttcg tcgattggtt agatcaagca tcagcagatg aagttaagtg tgttagatac   1860
tctgtttttg gatgtggaga taagaattgg gccaccacat atcagaaggt tccggctttc   1920
atcgatgaaa tgcttgctgc aaaaggggct gaaaatatag cagatcgtgg tgaggccgac   1980
gcaagcgacg attttgaggg tacctatgag gagtggagag agcacatgtg gtctgatgtt   2040
gccgcgtatt ttaatctaga catagaaaat tctgaagaca taaaagtgc cttacttctt   2100
caattcgtcg atagtcctgg gacatgcc ttagcaaag ctggaggc cttttcaacg   2160
aacgtagtag ccagtaagga acttcaacaa ccaggtagtg ccagaagtac acgtcacttg   2220
gaaattgaat taccaaaaga ggcatcctac caagaaggtg accatcttgg tgtaatccca   2280
agaaactacg aaggtatagt caataggta acggcaagat tgggctgga tgcaagccaa   2340
cagataagac tagaagcaga agaagaaaa ttggcgcacc ttccactagc gaagacagta   2400
tccgttgaag aattattgca atacgtgaa ttgcaggatc ccgtcactag aacgcaattg   2460
```

```
agagctatgg cagcaaagac tgtttgtcca cctcacaagg ttgaacttga agctctactt   2520
gaaaaacaag catacaaaga gcaagtgcta gcaaagagac taaccatgtt agaattgctg   2580
gaaaaatacc cggcatgcga aatggaattc tccgaattta tcgcgttgtt gccaagtatt   2640
cgtcccaggt attactcaat ttcatcttca ccaagggttg acgagaaaca ggcatctatt   2700
accgtatctg tggtctctgg agaagcttgg agtggttacg gagaatacaa gggtattgct   2760
tccaattatc ttgcagaact gcaggaaggg gatacaatta cctgctttat ttctactcct   2820
caatcagaat ttactcttcc gaaggatcca gaaactccgt taattatggt aggtccggga   2880
acaggagtcg cccctttcag aggctttgtg caagcaagga agcaactaaa gaacaggga   2940
caaagtctgg gtgaggcaca tctatatttc ggttgcagat ctccgcatga ggattactta   3000
taccaagaag aacttgaaaa cgcccaatca gaaggtatta tcaccttgca tactgcattc   3060
agtagaatgc caaccagcc gaaaacttac gtacagcatg ttatggagca agatggtaag   3120
aagtaattg agcttttgga taagggcgcc cacttctaca tttgcggcga cggatcccaa   3180
atggcgcctc ccgttgaagc caccttgatg aaatcatatg cagatgttca tcaagtttca   3240
gaagcggacg cccgtctttg gttacaacaa ctagaggaga aggaaggta tgcaaaagat   3300
gtttggtaa                                                          3309

SEQ ID NO: 108           moltype = AA  length = 1102
FEATURE                  Location/Qualifiers
REGION                   1..1102
                         note = KO-BMR fusion construct
source                   1..1102
                         mol_type = protein
                         organism = synthetic construct
SEQUENCE: 108
MATLLEHFQA MPFAIPIALA ALSWLFLFYI KVSFFSNKSA QAKLPPVPVV PGLPVIGNLL     60
QLKEKKPYQT FTRWAEEYGP IYSIRTGAST MVVLNTTQVA KEAMVTRYLS ISTRKLSNAL    120
KILTADKCMV AISDYNDFHK MKRYILSNV LGPSAQKRHR SNRDTLRANV CSRLHSQVKN    180
SPREAVNFRR VFEWELFGIA LKQAFGKDIE KPIYVEELGT TLSRDEIFKV LVLDIMEGAI    240
EVDWRDFFPY LRWIPNTRME TKIQRLYFRR KAVMTALINE QKKRIASGEE INCYIDFLLK    300
EGKTLTMDQI SMLLWETVIE TADTTMVTTE WAMYEVAKDS KRQDRLYQEI QKVCGSEMVT    360
EEYLSQLPYL NAVFHETLRK HSPAALVPLR YAHEDTQLGG YYIPAGTEIA INIYGCNMDK    420
HQWESPEEWK PERFLDPKFD PMDLYKTMAF GAGKRVCAGS LQAMLIACPT IGRLVQEFEW    480
KLRDGEEENV DTVGLTTHKR YPMHAILKPR SPSRPSPSTE QSAKKVRKKA ENAHNTPLLV    540
LYGSNMGTAE GTARDLADIA MSKGFAPQVA TLDSHAGNLP REGAVLIVTA SYNGHPPDNA    600
KQFVDWLDQA SADEVKGVRY SVFGCGDKNW ATTYQKVPAF IDEMLAAKGA ENIADRGEAD    660
ASDDFEGTYE EWREHMWSDV AAYFNLDIEN SEDNKSALLL QFVDSAADMP LAKMHGAFST    720
NVVASKELQQ PGSARSTRHL EIELPKEASY QEGDHLGVIP RNYEGIVNRV TARFGLDASQ    780
QIRLEAEEEK LAHLPLAKTV SVEELLQYVE LQDPVTRTQL RAMAAKTVCP PHKVELEALL    840
EKQAYKEQVL AKRLTMLELL EKYPACEMEF SEFIALLPSI RPRYYSISSS PRVDEKQASI    900
TVSVVSGEAW SGYGEYKGIA SNYLAELQEG DTITCFISTP QSEFTLPKDP ETPLIMVGPG    960
TGVAPFRGFV QARKQLKEQG QSLGEAHLYF GCRSPHEDYL YQEELENAQS EGIITLHTAF   1020
SRMPNQPKTY VQHVMEQDGK KLIELLDKGA HFYICGDGSQ MAPAVEATLM KSYADVHQVS   1080
EADARLWLQQ LEEKGRYAKD VW                                           1102

SEQ ID NO: 109           moltype = DNA  length = 3309
FEATURE                  Location/Qualifiers
misc_feature             1..3309
                         note = KO-BMR fusion construct
source                   1..3309
                         mol_type = other DNA
                         organism = synthetic construct
SEQUENCE: 109
atggctacct tgttggaaca ttttcaagct atgccattcg ctattccaat tgctttggct     60
gctttgtctt ggttgttttt gttctacatc aaggtttctt tcttctccaa caaatccgct    120
caagctaaat tgccaccagt tccagttgtt ccaggtttgc cagttattgg taatttgttg    180
caattgaaag aaaagaagcc ataccaaacc ttcactagat gggctgaaga atatggtcca    240
atctactcta ttagaactgg tgcttctact atggttgtct tgaacactac tcaagttgcc    300
aaagaagcta tggttaccag atacttgtct atctctacca gaaagttgtc caacgccttg    360
aaaattttga ccgctgataa gtgcatggtt gccatttgta attacaacga tttccacaag    420
atgatcaaga gatatatctt gtctaacgtt ttgggtccat ctgcccaaaa aagacataga    480
tctaacagag ataccttgag agccaacgtt tgttctagat gcattccca gttaagaac    540
tctccaagag aagctgtcaa ctttagaaga gttttcgaat gggaattatt cggtatcgct    600
ttgaaacaag ccttcggtaa ggatattgaa aagccaatct acgtcgaaga attgggtact    660
actttgtcca gagatgaaat cttcaaggtt ttggtcttgg acattatgga aggtgccatt    720
gaagttgatt ggagagattt tttcccatac ttgcgtttgga ttccaaacac cagaatggaa    780
actaagatcc aaagattata ctttagaaga aaggccgtta tgaccgcctt gattaacgaa    840
caaaagaaaa gaattgcctc cggtgaagaa atcaactgct catcgatttt cttgttgaaa    900
gaaggtaaga cccttgacca tggaccaaatc tctatgttgt tgtgggaaac cgttattgaa    960
actgctgata ccacaatggt tactactgaa tgggctatgt acgaagttgc taaggattcc   1020
aaaagacaag acagattata ccaagaaatc caaaaggtct gcggttctga atggttaca   1080
gaagaatact tgtcccaatt gccatacttg aatgctgttt tccacgaaac tttgagaaaa   1140
cattctccaa ctgctttggt tccattgaga tatgctcatg aagatactca attgggtggt   1200
tattacattc cagccggtac tgaaattgcc attaacatct acggttgcaa catggacaaa   1260
caccaatggg aatctccaga agaatggaag ccagaaaagt ttttcgatcc taagtttgaa   1320
ccaatggact tgtacaaaac tatggctttt ggtgctggta aaagagtttg cgctggttct   1380
ttacaagcta tgttgattgc ttgtccaacc atcggtagat ggttcaagag atttgaatgg   1440
aagttgagag atggtgaaga agaaaacgtt gatactgttg gtttgaccac ccataagaga   1500
tatccaatgc atgctatttt gaagccaaga tctccatcaa gaccagtcc tagtaccgaa   1560
caatctgcaa aaaagtttag aaaaaaagca gaaaatgcac acaatactcc attgctagtt   1620
```

```
ctttatggtt ctaatatggg aacagcggaa ggaacggcca gggatctagc tgacatagct    1680
atgtccaagg gatttgcccc gcaagtagca accctggatt cccatgcagg taacttgcca    1740
agagaaggtg ctgttctaat agttaccgct agctacaatg gcaccctcc agataatgcg     1800
aagcagttcg tcgattggtt agatcaagca tcagcagata agttaaggg tgttagatac     1860
tctgtttttg gatgtggaga taagaattgg gccaccaat atcagaaggt tccggctttc    1920
atcgatgaaa tgcttgctgc aaaaggggct gaaaatatag cagatcgtgg tgaggccgac    1980
gcaagcgacg attttgaggg tacctatgag gagtggagag agcacatgtg gtctgatgtt    2040
gccgcgtatt ttaatctaga catagaaaat tctgaagaca ataaaagtgc cttacttctt    2100
caattcgtcg atagtgctgc ggacatgccc ttagcaatga tgcatggacc cttttcaacg    2160
aacgtagtag ccagtaagga acttcaacaa ccaggtagtg ccagaagtac acgtcacttg    2220
gaaattgaat taccaaaaga ggcatcctac caagaaggtg accatcttgg tgtaatccca    2280
agaaactacg aaggtatagt caataggta acggcaagat ttgggctgga tgcaagccaa     2340
cagataagac tagaagcaga agaagaaaaa ttggcgcacc ttccactagc gaagacagta    2400
tccgttgaag aattattgca atacgtggaa ttgcaggatc ccgtcactag aacgcaattg    2460
agagctatgg cagcaaagac tgtttgtcca cctcacaagg ttgaacttga agctctactt    2520
gaaaaacaag catacaaaga gcaagtgcta gcaaagagac taaccatgtt agaattgctg    2580
gaaaaatacc cggcatgcga aatggaattc tccgaattta tcgcgttgtt gccaagtatt    2640
cgtcccaggt attactcaat ttcatcttca ccaagggttg acgagaaaca ggcatctatt    2700
accgtatctg tggtctctgg agaagcttgg agtggttacg gagaaatacaa gggtattgct    2760
tccaattatc ttgcagaact gcaggaaggg gatacaatta cctgctttat ttctactcct    2820
caatcagaat ttactcttcc gaaggatcca gaaactccgt taattatggt aggtccggga    2880
acaggagtcg ccccctttcag aggctttgtg caagcaagga agcaactaaa agctttggga    2940
caaagtctgg gtgaggcaca tctatatttc ggttgcagat ctccgcatga ggattactta    3000
taccaagaag aacttgaaaa cgcccaatca gaaggtatta tcaccttgca tactgcattc    3060
agtagaatgc caaccagcc gaaaacttac gtacagcatg ttatgagca agatggtaag     3120
aagttaattg agcttttgga taagggcgcc cacttctata tttgcggcga cggatcccaa    3180
atggcgcctg ccgttgaagc caccttgatg aaatcatatg cagatgttca tcaagtttca    3240
gaagcggacg cccgtctttg gttacaacaa ctagaggaga aggaaggta tgcaaaagat    3300
gttgcttaa                                                            3309

SEQ ID NO: 110           moltype = AA   length = 1102
FEATURE                  Location/Qualifiers
REGION                   1..1102
                         note = KO-BMR fusion construct
source                   1..1102
                         mol_type = protein
                         organism = synthetic construct
SEQUENCE: 110
MATLLEHFQA MPFAIPIALA ALSWLFLFYI KVSFFSNKSA QAKLPPVPVV PGLPVIGNLL      60
QLKEKKPYQT FTRWAEEYGP IYSIRTGAST MVVLNTTQVA KEAMVTRYLS ISTRKLSNAL    120
KILTADKCMV AISDYNDFHK MIKRYILSNV LGPSAQKRHR SNRDTLRANV CSRLHSQVKN    180
SPREAVNFRR VFEWELFGIA LKQAFGKDIE KPIYVEELGT TLSRDEIFKV LVLDIMEGAI    240
EVDWRDFFPY LRWIPNTRME TKIQRLYFRR KAVMTALINE QKKRIASGEE INCYIDFLLK    300
EGKTLTMDQI SMLLWETVIE TADTTMVTTE WAMYEVAKDS KRQDRLYQEI QKVCGSEMVT    360
EEYLSQLPYL NAVFHETLRK HSPAALVPLR YAHEDTQLGG YYIPAGTEIA INIYGCNMDK    420
HQWESPEEWK PERFLDPKFD PMDLYKTMAF GAGKRVCAGS LQAMLIACPT IGRLVQEFEW    480
KLRDGEEENV DTVGLTTHKR YPMHAILKPR SPSRPSPSTE QSAKKVRKKA ENAHNTPLLV    540
LYGSNMGTAE GTARDLADIA MSKGFAPQVA TLDSHAGNLP REGAVLIVTA SYNGHPPDNA    600
KQFVDWLDQA SADEVKGVRY SVFGCGDKNW ATTYQKVPAF IDEMLAAKGA ENIADRGEAD    660
ASDDFEGTYE EWREHMWSDV AAYFNLDIEN SEDNKSALLL QFVDSAADMP LAKMHGAFST    720
NVVASKELQQ PGSARSTRHL EIEELPKEASY QEGDHLGVIP RNYEGIVNRV TARFGLDASQ    780
QIRLEAEEEK LAHLPLAKTV SVEELLQYVE LQDPVTRTQL RAMAAKTVCP PHKVELEALL    840
EKQAYKEQVL AKRLTMLELL EKYPACEMEF SEFIALLPSI RPRYYSISSS PRVDEKQASI    900
TVSVVSGEAW SGYGEYKGIA SNYLAELQEG DTITCFISTP QSEFTLPKDP ETPLIMVGPG    960
TGVAPFRGFV QARKQLKEQG QSLGEAHLYF GCRSPHEDYL YQEELENAQS EGIITLHTAF   1020
SRMPNQPKTY VQHVMEQDGK KLIELLDKGA HFYICGDGSQ MAPAVEATLM KSYADVHQVS   1080
EADARLWLQQ LEEKGRYAKD VA                                            1102

SEQ ID NO: 111           moltype = DNA   length = 3165
FEATURE                  Location/Qualifiers
misc_feature             1..3165
                         note = KO-BMR fusion construct
source                   1..3165
                         mol_type = other DNA
                         organism = synthetic construct
SEQUENCE: 111
atggttccag gttgccagt tattggtaat tgttgcaat tgaaagaaaa gaagccatac        60
caaaccttca ctagatgggc tgaagaatat ggtccaatct actctattag aactggtgct    120
tctactatgg ttgtcttgaa cactactcaa gttgccaaca aagctatgt taccagatac    180
ttgtctatct ctaccagaaa gttgtccaac gccttgaaaa ttttgaccgc tgataagtgc    240
atggttgcca tttctgatta caacgatttc cacaagatga tcaagagata tatcttgtct    300
aacgttttgg gtccatctgc ccaaaaaaga catagatcta cagagatac cttgagagcc    360
aacgtttgtt ctagattgca ttcccaagtt aagaactctc caagagaagc tgtcaacttt    420
agaagagttt tcgaatggga attattcggt atcgctttga acaagcctt cggtaaggat    480
attgaaaagc caatctacgt tgaagaattg gtactactt tgtccagaga tgaaatcttc    540
aaggttttgg tcttggacat tatggaaggt gccattgaag ttgattggag agatttttttc    600
ccatacttgc gttggattcc aaacaccaga atggaaacta gatcaaag attatacttt    660
agaagaaagg ccgttatgac cgccttgatt aacgaacaaa gaaaagaat tgcctccggt    720
gaagaaatca actgctacat cgatttcttg ttgaaagaag gtaagacctt gaccatggac    780
```

```
caaatctcta tgttgttgtg ggaaaccgtt attgaaactg ctgataccac aatggttact  840
actgaatggg ctatgtacga agttgctaag gattctaaaa gacaagacag attataccaa  900
gaaatccaaa aggtctgcgg ttctgaaatg gttacagaag aatacttgtc ccaattgcca  960
tacttgaatg ctgttttcca cgaaactttg agaaaacatt ctccagctgc tttggttcca 1020
ttgagatatg ctcatgaaga tactcaattg ggtggttatt acattccagc cggtactgaa 1080
attgccatta acatctacgg ttgcaacatg gacaaacacc aatgggaatc tccagaagaa 1140
tggaagccag aaagattttt ggatcctaag tttgacccaa tggacttgta caaaactatg 1200
gcttttggtg ctggtaaaag agtttgcgct ggttctttac aagctatgtt gattgcttgt 1260
ccaaccatcg gtagattggt tcaagaattt gaatggaagt tgagagatgg tgaagaagaa 1320
aacgttgata ctgttggttt gaccacccat aagagatatc caatgcatgc tattttgaag 1380
ccaagatctc catcaagacc aagtcctagt accgaacaat ctgcaaaaaa agttagaaaa 1440
aaagcagaaa atgcacacaa tactccattg ctagttcttt atggttctaa tatgggaaca 1500
gcggaaggaa cggccaggga tctagctgac atagctatgt ccaagggatt tgccccgcaa 1560
gtagcaaccc tggattccca tgcaggtaac ttgccaagag aaggtgctgt tctaatagtt 1620
accgctagct acaatgggca ccctccagat aatgcgaagc agttcgtcga ttggttagat 1680
caagcatcag cagatgaagt taagggtgtt agatactctg ttttttggatg tggagataag 1740
aattgggcca ccacatatca gaaggttccg gctttcatcg atgaaatgct tgctgcaaaa 1800
ggggctgaaa atatagcaga tcgtggtgag gccgacgcaa gcgacgattt tgagggtacc 1860
tatgaggagt ggagagagca catgtggtct gatgttgccg cgtatttaa tctagacata 1920
gaaaattctg aagacaataa aagtgcctta cttcttcaat cgtcgatag tgctgcggac 1980
atgcccttag caaagatgca tggagccttt tcaacgaacg tagtagccag taggaacttt 2040
caacaaccag gtagtgccag aagtacacgt cacttgaaa ttgaattacc aaaagaggca 2100
tcctaccaag aaggtgacca tcttggtgta atcccaagaa actacgaagg tatagtcaat 2160
agggtaacgg caagatttgg gctggatgca agccaacaga taagactaga agcagaagaa 2220
gaaaaattgg cgcaccttcc actagcgaag acagtatccg ttgaagaatt attgcaatac 2280
gtggaattgc aggatcccgt cactagaacg caattgcaag ctatggcagc aaagactgtt 2340
tgtccaccctc acaaggttga acttgaagct ctacttgaaa aacaagcata caaagagcaa 2400
gtgctagcaa agagactaac catgttagaa ttgctggaaa atacccggc atgcgaaatg 2460
gaattctccg aatttatcgc gttgttgcca agtattcgtc ccaggtatta ctcaatttca 2520
tcttcaccaa gggttgacga gaaacaggca tctattaccg tatctgtggt ctctggagaa 2580
gcttggagtg gttacggaga atacaagggt attgcttcca attatcttgc agaactgcag 2640
gaagggata caattacctg ctttatttct actcctcaat cagaatttac tcttccgaag 2700
gatccagaaa ctccgttaat tatggtaggt ccgggaacag gagtcgcccc tttcagaggc 2760
tttgtgcaag caaggaagca actaaaagaa caggcacac gtcgggtga ggcacatcta 2820
tattcggtt gcagatctcc gcatgaggat tacttatacc aagaggaact tgaaaacgcc 2880
caatcagaag gtattatcac cttgcatact gcattcagta aatgccaaa ccagccgaaa 2940
acttacgtac agcatgttat ggagcaagat ggtaagaagt taattgagct tttggataag 3000
ggcgcccact tctacatttg cggcgacgga tcccaaatgg cgcctgccgt tgaagccacc 3060
ttgatgaaat catatgcaga tgttcatcaa gtttcagaag cggacgcccg tctttggtta 3120
caacaactag aggagaaagg aagtatgca aagatgttg cttaa       3165
SEQ ID NO: 112      moltype = AA  length = 1054
FEATURE             Location/Qualifiers
REGION              1..1054
                    note = KO-BMR fusion construct
source              1..1054
                    mol_type = protein
                    organism = synthetic construct
SEQUENCE: 112
MVPGLPVIGN LLQLKEKKPY QTFTRWAEEY GPIYSIRTGA STMVVLNTTQ VAKEAMVTRY   60
LSISTRKLSN ALKILTADKC MVAISDYNDF HKMIKRYILS NVLGPSAQKR HRSNRDTLRA  120
NVCSRLHSQV KNSPREAVNF RRVFEWELFG IALKQAFGKD IEKPIYVEEL GTTLSRDEIF  180
KVLVLDIMEG AIEVDWRDFF PYLRWIPNTR METKIQRLYF RRKAVMTALI NEQKKRIASG  240
EEIINCYIDFL LKEGKTLTMD QISMLLWETV IETADTTMVT TEWAMYEVAK DSKRQDRLYQ  300
EIQKVCGSEM VTEEYLSQLP YLNAVFHETL RKHSPAALVP LRYAHEDTQL GGYYIPAGTE  360
IAINIYGCNM DKHQWESPEE WKPERFLDPK FDPMDLYKTM AFGAGKRVCA GSLQAMLIAC  420
PTIGRLVQEF EWKLRDGEEE NVDTVGLTTH KRYPMHAILK PRSPSRPSPS TEQSAKKVRK  480
KAENAHNTPL LVLYGSNMGT AEGTARDLAD IAMSKGFAPQ VATLDSHAGN LPREGAVLIV  540
TASYNGHPPD NAKQFVDWLD QASADEVKGV RYSVFGCGDK NWATTYQKVP AFIDEMLAAK  600
GAENIADRGE ADASDDFEGT YEEWREHMWS DVAAYFNLDI ENSEDNKSAL LLQFVDSAAD  660
MPLAKMHGAF STNVVASKEL QQPGSARSTR HLEIELPKEA SYQEGDHLGV IPRNYEGIVN  720
RVTARFGLDA SQQIRLEAEE EKLAHLPLAK TVSVEELLQY VELQDPVTRT QLRAMAAKTV  780
CPPHKVELEA LLEKQAYKEQ VLAKRLTMLE LLEKYPACEM EFSEFIALLP SIRPRYYSIS  840
SSPRVDEKQA SITVSVVSGE AWSGYGEYKG IASNYLAELQ EGDTITCFIS TPQSEFTLPK  900
DPETPLIMVG PGTGVAPFRG FVQARKQLKE QGQSLGEAHL YFGCRSPHED YLYQEELENA  960
QSEGIITLHT AFSRMPNQPK TYVQHVMEQD GKKLIELLDK GAHFYICGDG SQMAPAVEAT 1020
LMKSYADVHQ VSEADARLWL QQLEEKGRYA KDVA                             1054

SEQ ID NO: 113      moltype = DNA  length = 1476
FEATURE             Location/Qualifiers
source              1..1476
                    mol_type = other DNA
                    organism = Saccharomyces cerevisiae
SEQUENCE: 113
atgaccagtt tgtccaaaag cttcatgcag agtggacgaa tctgcgcagc atgtttctat   60
ctgttattca cactactttc aattccaatc tcgtttaaag ttggtggttt ggaatgcggg  120
cttccttca cggtgacact gttcacttta tatttcataa ctacgactct taacgttgtta  180
gcaagacgac atgaggaag actatacatt ttttttacca actgtctgta ttactcacaa  240
catttttatca ttgcatcttt gctataccctg ttttttgtctg gatttctaa tgatgagttg  300
```

-continued

```
ggaaacgttc tgaaaaataa atataatgag tcggagtcgt tcctggaagc tttgaaaaat    360
agcttgaatt ccaatcaaat taactacgtc ttatattatt actactatcg atttgttgta    420
caaccgtggc aattcgtgct taccaagtcc acaccttttt ttactctatc ggaaggtttt    480
ttcactattt tagccattca ggccgtcggg gaaactaata gatggttatc aaatgacttg    540
aattcaaaca cgtggattat ttcctcattg ttaacctccg gaggtgtgat taccgcatcg    600
ctgtactatt tgtatcggat ttatgtcacc cccatggcc cgttatccat ccaaacggcg    660
tcctttattag gacttgtttt gtctatggta tgtggactgg ggttgtatgg tattgtgagt    720
caaaaaggat ccgtcataga gagctcttta ttttttgcgt atattgttcg ttgtatttat    780
gaaatttccc ccaaattagc tactaccgcg actgatgaaa ttttaaattt gttcaaagac    840
gtctggcaga aacatcaaag aaatctgccc acagcgtgaca atcttttgtg ctactttcat    900
aatgtcatat tgaaaaatgc agaggtgtta tgggggtcct ttattcctag aggaagaaag    960
aaaaccggtg attttcatga taaactcatt agcattctat cattcgaaaa agtatccttg   1020
atatctaaac cattttggaa attttttcaag aatttcacct ttagtgttcc gctatccatt   1080
aatgaatttt gtcaagttac aattaagatg gcaagcgaat cagtttcccc agctatagta   1140
atcaatttat gctttagagt tctgatgttt tactcggcaa cgaggattat tccagcatta   1200
caaagaaaaa atgacaaaca gttgcgcaag agtcgcagga tcatgaaggg attgtattgg   1260
tacagtcctt gcatattaat tgctatgtat actcacctga ttttacaata ttcaggtgag   1320
ctaaagaaag acctgtgca tggggttgc agtgaaaagt ggttggcgt agatcaacca   1380
gaaattatag tagattcatg gggattttgg aactggtgca acattttctg tactattttg   1440
gtatacgcta cagaattaat aggttctggt agttga                             1476

SEQ ID NO: 114         moltype = AA   length = 491
FEATURE                Location/Qualifiers
source                 1..491
                       mol_type = protein
                       organism = Saccharomyces cerevisiae
SEQUENCE: 114
MTSLSKSFMQ SGRICAACFY LLFTLLSIPI SFKVGGLECG LSFTVTLFTL YFITTTLNVL     60
ARRHGGRLYI FFTSCLYYSQ HFIIASLLYL FLSGFSNDEL GNVLKNKYNE SESFLEALKN    120
SLNSNQINYV LYYYYYRFVV QPWQFVLTKS TPFFTLSEGF FTILAIQAVG ETNRWLSNDL    180
NSNTWIISSL LTSGGVITAS LYYLYRIYVT PIWPLSIQTA SLLGFVLSMV CGLGLYGIVS    240
QKGSVIESSL FFAYIVRCIY EISPKLATTA TDEILNLFKD VWQKHQRNLP TADNLLCYFH    300
NVILKNAEVL WGSFIPRGRK KTGDFHDKLI SILSFEKVSL ISKPFWKFFK NFTFSVPLSI    360
NEFCQVTIKM ASESVSPAIV INLCFRVLMF YSATRIIPAL QRKNDKQLRK SRRIMKGLYW    420
YSPCILIAMY THLILQYSGE LKKDLCIWGC SEKWFGVDQP EIIVDSWGFW NWCNIFCTIL    480
VYATELIGSG S                                                        491

SEQ ID NO: 115         moltype = DNA   length = 4957
FEATURE                Location/Qualifiers
source                 1..4957
                       mol_type = other DNA
                       organism = Bacillus megaterium
SEQUENCE: 115
agatctttat gaagacatag ctgcagaaga aaaagcaaga gctacatatc aatggttaat     60
tgatatatca gatgatcccg atttaaacga cagcttacga ttttttacgag aaagagagat    120
tgttcactca cagcggttcc gcgaggccgt ggagatttta aagatgacaga gacaggaa    180
gaaaattctt taactagtaa aaaaacatcc ccttggcga atgcaaacga aaggagggat    240
gttttttgtt gtgactgcgt tgattatgcg ctagaactgc agtgacaaga acaacccttt    300
aatttccctt caacatcttt ccaaactcgc gtataactgt attcacctcc aatagattca    360
ccggttgcca gtgccccatt taacgctact tttgtaacgg taacggcaag ttcttgaaac    420
agtttaactt cttgttccaa cacttccatg cccgctatat caagacttttt tgaacgatga    480
acatttatat cttcttcttt tgacaaccat tgcccaaggt gattcacaaa ataagctca    540
tctgaaagta attcttctaa tagctctatg ttattagaaa gcatggctga gcgaagcatt    600
tcttcgtatt ctataactct tgcttgattc attttttaatc ctcctttacg ccttgtgtaa    660
ctcttttcta tttccacgtt gcttttcctt taaacttctt tcattaataa ttcgtgctaa    720
attatgttaa tagaggggat aagtggacta attttctgta agcactaaat attctgaaat    780
actctgttaa ttaccttttaa atggtataaa attagaatga agaacctttt tctttccact    840
tttctagtta tcttttttact attaagatgc agttttttat acttgtaatt gtagcggaat    900
gaacgttcat tccgtttttg aaaagaggtg ataaagtgga atctactcca acaaaacaaa    960
aagcgatttt ttctgcttcg cttctgctgt ttgcagaaag agggtttgat gcaaccacga   1020
tgccaatgat tgcagagaat gccaagtag gagcaggaac aatttatcgc tactttaaaa   1080
ataaagaaag ccttgtaaat gaattattcc aacagcacgt aaacgagttt ttacagtgca   1140
ttgaaagcgg tctggcaaac gagagagatg gataccgaga tgggtttcat catatctttg   1200
aaggtatggt gacatttact aaaaaccatc ctcgtgctct tgatttattt aaaactcata   1260
gccaaggaac tttttttaaca gaagagagcc gcttagcata tcaaaagctg gtggaattgt   1320
ttttgtacgtt cttcagagaa ggacaaaagc aaggtgtgat tagaaatctt cctgaaaatg   1380
cgctaattgc tattttattt ggaagtttca tggaagtata tgaaatgatt gaaaatgact   1440
acttatcttt aactgatgaa cttccttaccg gtgtagaaga gagtctgtgg gcagcactta   1500
gcagacaatc atgaaactta acaagtgaaa gagggataac atgacaatta aagaaatgcc   1560
tcagccaaaa acgtttggag agcttaaaaa tttaccgtta ttaaacacag ataaaccggt   1620
tcaagctttg atgaaaattg cggatgaatt aggagaaatc tttaaattcg aggcgcctgg   1680
tcgtgtaacg cgctacttat caagtcagcg tctaattaaa aagcatgcg atgaatcacg   1740
ctttgataaa aacttaagtc aagcgcttaa atttgtacgt gattttgcag agagcgggtt   1800
atttacagg tggacgcatg aaaaaaattg gaaaaaagtg cataatatct tacttccaag   1860
cttcagtcag caggcaatga aaggctatca tgcgatgatg gtcgatatcg ccgtgcagct   1920
tgttcaaaaa tgggagcgtc taaatgcaga tgagcatatt gaagtaccgg aagacatgac   1980
acgtttaacg cttgatacaa ttggtctttg cggctttaac tatcgcttta acagctttta   2040
ccgagatcag cctcatccat ttattacaag tatggtccgt gcactggatg aagcaatgaa   2100
caagctgcag cgagcaaatc cagacgaccc agcttatgat gaaaacaagc gccagtttca   2160
```

```
agaagatatc aaggtgatga acgacctagt agataaaatt attgcagatc gcaaagcaag   2220
cggtgaacaa agcgatgatt tattaacgca tatgctaaac ggaaaagatc cagaaacggg   2280
tgagccgctt gatgacgaga acattcgcta tcaaattatt acattcttaa ttgcgggaca   2340
cgaaacaaca agtggtcttt tatcatttgc gctgtatttc ttagtgaaaa atccacatgt   2400
attacaaaaa gcagcagaag aagcagcacg agttctagta gatcctgttc caagctacaa   2460
acaagtcaaa cagcttaaat atgtcggcat ggtcttaaac gaagcgctgc gcttatggcc   2520
aactgctcct gcgttttccc tatatgcaaa agaagatacg gtgcttggag agaatatcc    2580
tttagaaaaa ggcgacgaac taatggttct gattcctcag cttcaccgtg ataaaacaat   2640
ttggggagac gatgtggaag agttccgtcc agagcgtttt gaaaatccaa gtgcgattcc   2700
gcagcatgcg tttaaaccgt ttggaaacgg tcagcgtgcg tgtatcggtc agcagttcgc   2760
tcttcatgaa gcaacgctgg tacttggtat gatgctaaaa cactttgact ttgaagatca   2820
tacaaactac gagctggata ttaagaaac tttaacgtta aaacctgaag ctttgtggt     2880
aaaagcaaaa tcgaaaaaaa ttccgcttgg cggtattcct tcacctagca ctgaacagtc   2940
tgctaaaaaa gtacgcaaaa aggcagaaaa cgctcataat agccgctgc ttgtgctata    3000
cggttcaaat atgggaacag ctgaaggaac ggccgcgtga ttagcagata ttgcaatgag   3060
caaaggattt gcaccgcagg tcgcaacgct tgattcacac gccggaaatc ttccgcgcga   3120
aggagctgta ttaattgtaa cggcgtctta taacggtcat ccgcctgata acgcaaagca   3180
atttgtcgac tggttagacc aagcgctctg tgatgaagta aaaggcgttc gctactccgt   3240
atttggatgc ggcgataaaa actgggctac tacgtatcaa aaagtgcctg ctttatcga    3300
tgaaacgctt gccgctaaag gggcagaaaa catcgctgac cgcggtgaag cagatctcaag  3360
cgacgacttt gaaggcacat atgaagaatg gcgtgaacat atgtggagtg acgtagcagc   3420
ctactttaac ctcgacattg aaacagtga agataatataa tctactcttt cacttcaatt   3480
tgtcgacagc gccgcggata tgccgcttgc gaaaatgcac ggtgcgtttt caacgaacgt   3540
cgtagcaagc aaagaacttc aacagccagg cagtgcacga agcacgcgac atcttgaaat   3600
tgaacttcca aaagaagctt cttatcaaga aggagatcat ttaggtgtta ttcctcgcaa   3660
ctatgaagga atagtaaacc gtgtaacagc aaggttcgcc ctagatgcat cacagcaaat   3720
ccgtctggaa gcagaagaag aaaaattagc tcatttgcca ctcgctaaaa cagtatccgt   3780
agaagagctt ctgcaatacg tggagcttca agatcctgtt acgcgcacgc agcttcgcgc   3840
aatggctgct aaaacggtct gcccgccgca taaagtagag cttgaagcct tgcttgaaaa   3900
gcaagcctac aaagaacaag tgctggcaaa acgtttaaca atgcttgaac tgcttgaaaa   3960
ataccgggcg tgtgaaatga aattcagcga atttatcgcc cttctgccaa gcatacgccc   4020
gcgctattac tcgatttctt catcacctcg tgtcgatgaa aaacaagcaa gcatcacggt   4080
cagcgttgtc tcaggagaag cgtggagcgg atatggagaa tataaaggaa ttgcgtcgaa   4140
ctatcttgcc gagctgcaag aaggagatac gattacgtgc ttttatttcca caccgcagtc   4200
agaatttacg ctgccaaaag accctgaaac gccgcttatc atggtcggac cgggaacagg   4260
cgtcgcgccg tttagaggct ttgtgcaggc gcgcaaacag ctaaaagaac aaggacagtc   4320
acttggagaa gcacatttat acttcggctg ccgttcacct catgaagact atctgtatca   4380
agaagagctt gaaaacgccc aaagcgaagg catcattacg cttcataccg ctttttctcg   4440
catgccaaat cagccgaaaa catacgttca gcacgtaatg gaacaagacg gcaagaaatt   4500
gattgaactt cttgatcaag agcgcacttt ctatatttgc ggagacggaa gccaaatggc   4560
acctgccgtt gaagcaacgc ttatgaaaag ctatgctgac gttcaccaag tgagtgaagc   4620
agacgctcgc ttatggctgc agcagctaga agaaaaggc cgatacgcaa aagacgtgtg   4680
ggctgggtaa attaaaaaga ggctaggata aagtagttt agttggttga aggaagatcc   4740
gaacgatgaa tcgttcggat cttttttattg gtagagtaaa cgtagatttc atctatttag   4800
tgacttgtag cggttgattg gagggcaagg tgaagactcc aatcaaccgc ggtgtcacat   4860
gcaagccata cgaaattcat ttctcccatt tattcgtctt ttgtccccac ttaatttta    4920
tagcgcctta acgtttcttc tgcgtgacag cagatct                            4957

SEQ ID NO: 116        moltype = AA   length = 1049
FEATURE               Location/Qualifiers
source                1..1049
                      mol_type = protein
                      organism = Bacillus megaterium
SEQUENCE: 116
MTIKEMPQPK TFGELKNLPL LNTDKPVQAL MKIADELGEI FKFEAPGRVT RYLSSQRLIK    60
EACDESRFDK NLSQALKFVR DFAGDGLFTS WTHEKNWKKA HNILLPSFSQ QAMKGYHAMM   120
VDIAVQLVQK WERLNADEHI EVPEDMTRLT LDTIGLCGFN YRFNSFYRDQ PHPFITSMVR   180
ALDEAMNKLQ RANPDDPAYD ENKRQFQEDI KVMNDLVDKI IADRKASGEQ SDDLLTHMLN   240
GKDPETGEPL DDENIRYQII TFLIAGHETT SGLLSFALYF LVKNPHVLQK AAEEAARVLV   300
DPVPSYKQVK QLKYVGMVLN EALRLWPTAP AFSLYAKEDT VLGGEYPLEK GDELMVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPV TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPAV EATLMKSYAD  1020
VHQVSEADAR LWLQQLEEKG RYAKDVWAG                                    1049

SEQ ID NO: 117        moltype = DNA   length = 1767
FEATURE               Location/Qualifiers
misc_feature          1..1767
                      note = Codon-optimized BMR
source                1..1767
                      mol_type = other DNA
```

```
                        organism = synthetic construct
SEQUENCE: 117
ccaagtccta gtaccgaaca atctgcaaaa aaagttagaa aaaaagcaga aaatgcacac    60
aatactccat tgctagttct ttatggttct aatatgggaa cagcggaagg aacggccagg   120
gatctagctg acatagctat gtccaaggga tttgccccgc aagtagcaac cctggattcc   180
catgcaggta acttgccaag agaaggtgct gttctaatag ttaccgctag ctacaatggg   240
cacccctcca gataatgcgaa gcagttcgtc gattggttag atcaagcatc agcagatgaa   300
gttaagggtg ttagatactc tgttttttga tgtggagata agaattgggc caccacatat   360
cagaaggttc cggctttcat cgatgaaatg cttgctgcaa aaggggctga aaatatagca   420
gatcgtggtg aggccgacgc aagcgacgat tttgagggta cctatgagga gtggagagag   480
cacatgtggt ctgatgttgc cgcgtatttt aatctagaca tagaaaattc tgaagacaat   540
aaaagtgcct tacttcttca attcgtcgat agtgctgcgg acatgccctt agcaaagatg   600
catggagcct tttcaacgaa cgtagtagcc agtaaggaac ttcaacaacc aggtagtgcc   660
agaagtacac gtcacttgga aattgaatta ccaaaagagg catcctacca agaaggtgac   720
catcttggtg taatcccaag aaactacgaa ggtatagtca atagggtaac ggcaagattt   780
gggctggatg caagccaaca gataagacta gaagcagaag aagaaaaatt ggcgcacctt   840
ccactagcga agacagtatc cgttgaagaa ttattgcaat acgtggaatt gcaggatccc   900
gtcactagaa cgcaattgag agctatggca gcaaagacta tttgtcccac tcacaaggtt   960
gaacttgaag ctctacttga aaaacaagca tacaaagagc aagtgctagc aaagagacta  1020
accatgttag aattgctgga aaaatacccg gcatgcgaaa tggaattctc gaatttatc   1080
gcgttgttgc caagtattcg tcccaggtat tactcaattt catcttcacc aagggttgac  1140
gagaaacagg catctattac cgtatctgtg gtctctggag aagcttggag tggttacgga  1200
gaatacaagg gtattgcttc caattatctt gcagaactgc aggaagggga tacaattacc  1260
tgctttattt ctactcctca atcagaattt actcttccga aggatccaga aactccgtta  1320
attatggtag gtccgggaac aggagtcgcc ccttttcagag gctttgtgca agcaaggaag  1380
caactaaaag aacaggggaca aagtctgggt gaggcacatc tatatttcgg ttgcagatct  1440
ccgcatgagg attacttata ccaagaagaa cttgaaaacg cccaatcaga aggtattatc  1500
accttgcata ctgcattcag tagaatgcca aaccagccga aaacttacgt acagcatgtt  1560
atggagcaag atggtaagaa gttaattgag cttttggata agggcgccca cttctacatt  1620
tgcggcgacg gatcccaaat ggcgcctgcc gttgaagcca ccttgatgaa atcatatgca  1680
gatgttcatc aagtttcaga agcggacgcc cgtctttggt acaacaact agaggagaaa  1740
ggaaggtatg caaaagatgt ttggtaa                                      1767

SEQ ID NO: 118          moltype = AA  length = 588
FEATURE                 Location/Qualifiers
source                  1..588
                        mol_type = protein
                        organism = Bacillus megaterium
SEQUENCE: 118
PSPSTEQSAK KVRKKAENAH NTPLLVLYGS NMGTAEGTAR DLADIAMSKG FAPQVATLDS    60
HAGNLPREGA VLIVTASYNG HPPDNAKQFV DWLDQASADE VKGVRYSVFG CGDKNWATTY   120
QKVPAFIDEM LAAKGAENIA DRGEADASDD FEGTYEEWRE HMWSDVAAYF NLDIENSEDN   180
KSALLLQFVD SAADMPLAKM HGAFSTNVVA SKELQQPGSA RSTRHLEIEL PKEASYQEGD   240
HLGVIPRNYE GIVNRVTARF GLDASQQIRL EAEEEKLAHL PLAKTVSVEE LLQYVELQDP   300
VTRTQLRAMA AKTVCPPHKV ELEAALLEKQA YKEQVLAKRL TMLELLEKYP ACEMEFSEFI   360
ALLPSIRPRY YSISSSPRVD EKQASITVSV VSGEAWSGYG EYKGIASNYL AELQEGDTIT   420
CFISTPQSEF TLPKDPETPL IMVGPGTGVA PFRGFVQARK QLKEQGQSLG EAHLYFGCRS   480
PHEDYLYQEE LENAQSEGII TLHTAFSRMP NQPKTYVQHV MEQDGKKLIE LLDKGAHFYI   540
CGDGSQMAPA VEATLMKSYA DVHQVSEADA RLWQQLEEK GRYAKDVW                588

SEQ ID NO: 119          moltype = DNA  length = 1767
FEATURE                 Location/Qualifiers
misc_feature            1..1767
                        note = Codon-optimized BMR W1046A
source                  1..1767
                        mol_type = other DNA
                        organism = synthetic construct
SEQUENCE: 119
ccaagtccta gtaccgaaca atctgcaaaa aaagttagaa aaaaagcaga aaatgcacac    60
aatactccat tgctagttct ttatggttct aatatgggaa cagcggaagg aacggccagg   120
gatctagctg acatagctat gtccaaggga tttgccccgc aagtagcaac cctggattcc   180
catgcaggta acttgccaag agaaggtgct gttctaatag ttaccgctag ctacaatggg   240
cacccctcca gataatgcgaa gcagttcgtc gattggttag atcaagcatc agcagatgaa   300
gttaagggtg ttagatactc tgttttttga tgtggagata agaattgggc caccacatat   360
cagaaggttc cggctttcat cgatgaaatg cttgctgcaa aaggggctga aaatatagca   420
gatcgtggtg aggccgacgc aagcgacgat tttgagggta cctatgagga gtggagagag   480
cacatgtggt ctgatgttgc cgcgtatttt aatctagaca tagaaaattc tgaagacaat   540
aaaagtgcct tacttcttca attcgtcgat agtgctgcgg acatgccctt agcaaagatg   600
catggagcct tttcaacgaa cgtagtagcc agtaaggaac ttcaacaacc aggtagtgcc   660
agaagtacac gtcacttgga aattgaatta ccaaaagagg catcctacca agaaggtgac   720
catcttggtg taatcccaag aaactacgaa ggtatagtca atagggtaac ggcaagattt   780
gggctggatg caagccaaca gataagacta gaagcagaag aagaaaaatt ggcgcacctt   840
ccactagcga agacagtatc cgttgaagaa ttattgcaat acgtggaatt gcaggatccc   900
gtcactagaa cgcaattgag agctatggca gcaaagacta tttgtcccac tcacaaggtt   960
gaacttgaag ctctacttga aaaacaagca tacaaagagc aagtgctagc aaagagacta  1020
accatgttag aattgctgga aaaatacccg gcatgcgaaa tggaattctc gaatttatc   1080
gcgttgttgc caagtattcg tcccaggtat tactcaattt catcttcacc aagggttgac  1140
gagaaacagg catctattac cgtatctgtg gtctctggag aagcttggag tggttacgga  1200
gaatacaagg gtattgcttc caattatctt gcagaactgc aggaagggga tacaattacc  1260
```

-continued

```
tgctttattt ctactcctca atcagaattt actcttccga aggatccaga aactccgtta 1320
attatggtag gtccgggaac aggagtcgcc cctttcagag gctttgtgca agcaaggaag 1380
caactaaaag aacagggaca aagtctgggt gaggcacatc tatatttcgg ttgcagatct 1440
ccgcatgagg attacttata ccaagaagaa cttgaaaacg cccaatcaga aggtattatc 1500
accttgcata ctgcattcag tagaatgcca aaccagccga aaacttacgt acagcatgtt 1560
atggagcaag atggtaagaa gttaattgag cttttggata agggcgccca cttctacatt 1620
tgcggcgacg gatcccaaat ggcgcctgcc gttgaagcca ccttgatgaa atcatatgca 1680
gatgttcatc aagtttcaga agcggacgcc cgtctttggt tacaacaact agaggagaaa 1740
ggaaggtatg caaaagatgt tgcttaa                                    1767

SEQ ID NO: 120         moltype = AA  length = 588
FEATURE                Location/Qualifiers
REGION                 1..588
                       note = BMR W1046A
source                 1..588
                       mol_type = protein
                       organism = synthetic construct
SEQUENCE: 120
PSPSTEQSAK KVRKKAENAH NTPLLVLYGS NMGTAEGTAR DLADIAMSKG FAPQVATLDS  60
HAGNLPREGA VLIVTASYNG HPPDNAKQFV DWLDQASADE VKGVRYSVFG CGDKNWATTY 120
QKVPAFIDEM LAAKGAENIA DRGEADASDD FEGTYEEWRE HMWSDVAAYF NLDIENSEDN 180
KSALLLQFVD SAADMPLAKM HGAFSTNVVA SKELQQPGSA RSTRHLEIEL PKEASYQEGD 240
HLGVIPRNYE GIVNRVTARF GLDASQQIRL EAEEEKLAHL PLAKTVSVEE LLQYVELQDP 300
VTRTQLRAMA AKTVCPPHKV ELEALLEKQA YKEQVLAKRL TMLELLEKYP ACEMEFSEFI 360
ALLPSIRPRY YSISSSPRVD EKQASITVSV VSGEAWSGYG EYKGIASNYL AELQEGDTIT 420
CFISTPQSEF TLPKDPETPL IMVGPGTGVA PFRGFVQARK QLKEQGQSLG EAHLYFGCRS 480
PHEDYLYQEE LENAQSEGII TLHTAFSRMP NQPKTYVQHV MEQDGKKLIE LLDKGAHFYI 540
CGDGSQMAPA VEATLMKSYA DVHQVSEADA RLWLQQLEEK GRYAKDVA             588

SEQ ID NO: 121         moltype =    length =
SEQUENCE: 121
000

SEQ ID NO: 122         moltype =    length =
SEQUENCE: 122
000
```